United States Patent
De Bettignies et al.

(10) Patent No.: US 12,275,942 B2
(45) Date of Patent: Apr. 15, 2025

(54) METHOD FOR PRODUCING DNA VECTORS FROM MOLECULAR BRICKS CONTAINING SEQUENCES OF INTEREST

(71) Applicants: Universite de Lille, Lille (FR); CENTRE NATIONAL DE LA RECHERCHE SCIENTIFIQUE, Paris (FR)

(72) Inventors: Geoffroy De Bettignies, Houplin-ancoisne (FR); Carine De Bettignies, Houplin-ancoisne (FR); Sylvain Julien, Croix (FR)

(73) Assignees: Universite de Lille, Lille (FR); Centre National de la Recherche Scientifique (CNRS), Paris (FR)

( * ) Notice: Subject to any disclaimer, the term of this patent is extended or adjusted under 35 U.S.C. 154(b) by 1440 days.

(21) Appl. No.: 15/549,848

(22) PCT Filed: Feb. 10, 2016

(86) PCT No.: PCT/FR2016/050305
§ 371 (c)(1),
(2) Date: Aug. 9, 2017

(87) PCT Pub. No.: WO2016/128679
PCT Pub. Date: Aug. 18, 2016

(65) Prior Publication Data
US 2019/0040397 A1  Feb. 7, 2019

(30) Foreign Application Priority Data

Feb. 10, 2015 (FR) .................................. 15/51075

(51) Int. Cl.
| | |
|---|---|
| *C12N 15/66* | (2006.01) |
| *C12N 9/22* | (2006.01) |
| *C12N 15/10* | (2006.01) |
| *C12N 15/63* | (2006.01) |
| *C12N 15/64* | (2006.01) |

(52) U.S. Cl.
CPC .............. *C12N 15/66* (2013.01); *C12N 9/22* (2013.01); *C12N 15/1031* (2013.01); *C12N 15/63* (2013.01); *C12N 15/64* (2013.01); *C12Y 301/21004* (2013.01); *C12N 2800/10* (2013.01); *C12N 2800/101* (2013.01); *C12N 2800/80* (2013.01)

(58) Field of Classification Search
None
See application file for complete search history.

(56) References Cited

U.S. PATENT DOCUMENTS

2014/0038240 A1    2/2014  Temme et al.

FOREIGN PATENT DOCUMENTS

| | | |
|---|---|---|
| EP | 2395087 A1 | 12/2011 |
| WO | WO 98/38326 * | 9/1998 |
| WO | 2008/095927 A1 | 8/2008 |

OTHER PUBLICATIONS

New England Biolabs, retrieved from the Internet <<https://www.neb.com/tools-and-resources/selection-charts/type-iis-restriction-enzymes>> and <<https://www.neb.com/protocols/2012/12/07/optimizing-restriction-endonuclease-reactions>>, retrieved on Mar. 31, 2022).*
Morbitzer et al. (Assembly of custom TALE-type DNA binding domains by modular cloning, Nucleic Acids Research, 2011, vol. 39, No. 13, pp. 5790-5799).*
New England Biolabs, retrieved from the Internet << https://www.neb.com/tools-and-resources/feature-articles/everything-you-ever-wanted-to-know-about-type-ii-restriction-enzymes>>, retrived on Oct. 5, 2022.*
Engler et al. (Combinatorial DNA Assembly Using Golden Gate Cloning, Methods Mol Biol. 2013; 1073: pp. 141-156) (Year: 2013).*
Weber et al. (Assembly of Designer TAL Effectors by Golden Gate Cloning. PLoS One 6(5): e19722, 2011) (Year: 2011).*
New England Biolabs, retrieved from the Internet << https://www.neb.com/tools-and-resources/feature-articles/everything-you-ever-wanted-to-know-about-type-ii-restriction-enzymes>>, retrieved on Oct. 5, 2022 (Year: 2022).*
Weber, E., et al., "A Modular Cloning System for Standardized Assembly of Multigene Constructs," PLOS One, vol. 6, Issue 2, 2011, pp. 1-11.
Werner, S., et al., "Fast Track Assembly of Multigene Constructs Using Golden Gate Cloning and the MoClo System," Bioengineered Bugs, vol. 3, No. 1, 2012, pp. 38-43.
Wang, T., et al., "Available Methods for Assembling Expression Cassettes for Synthetic Biology," Appl Microbiol Biotechnol, vol. 93, 2012, pp. 1853-1863.
Sarrion-Perdigones, A., et al., "GoldenBraid: An Iterative Cloning System for Standardized Assembly of Reusable Genetic Modules," PLOS One, vol. 6, Issue 7, 2011, pp. 1-11.
Engler, C., et al., "Golden Gate Shuffling: A One-Pot DNA Shuffling Method Based on Type IIs Restriction Enzymes," PLOS One, vol. 4, Issue 5, pp. 1-9.
"SnapFast Plasmids," Oxford Genetics (https://www.oxfordgenetics.com/SiteContent/TeamResources/snapfast-plasmids?complex=True) retrieved Sep. 18, 2017, pp. 1-5.

(Continued)

*Primary Examiner* — Suzanne M Noakes
*Assistant Examiner* — Jae W Lee
(74) *Attorney, Agent, or Firm* — Morgan, Lewis & Bockius LLP

(57) ABSTRACT

Disclosed is a method for producing, in one step, "made to measure" double-stranded DNA vectors from molecular bricks including sequences of interest in the presence of a one and only type IIs restriction enzyme.

14 Claims, 24 Drawing Sheets

Figure 1:
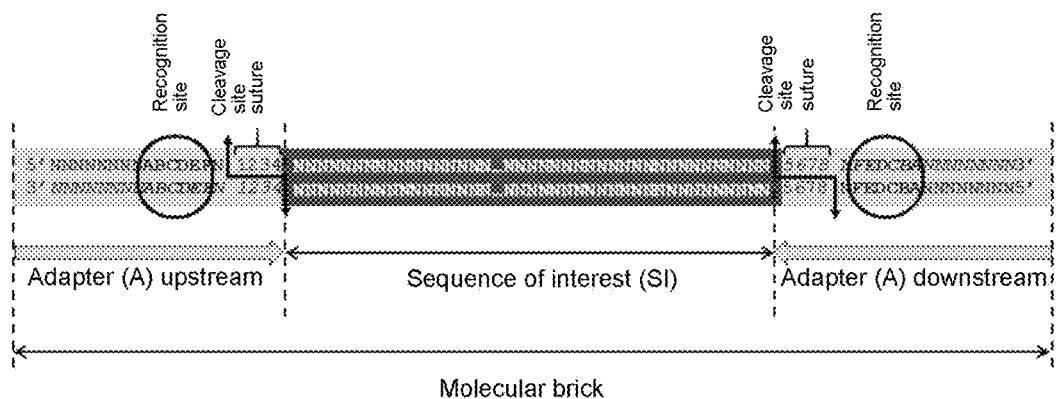
Figure 1:
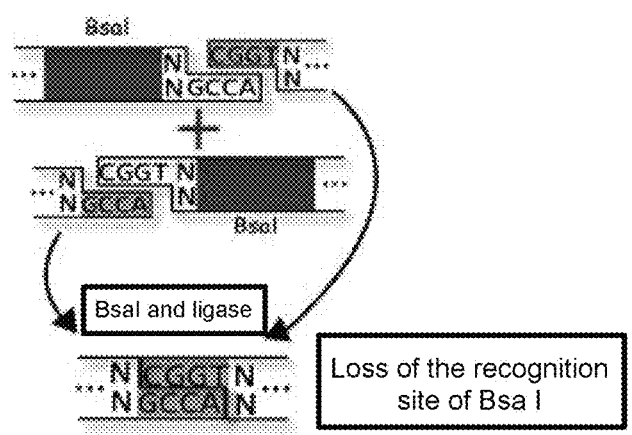

Specification includes a Sequence Listing.

(56) References Cited

OTHER PUBLICATIONS

Lippow, S., et al., "Creation of a Type IIS Restriction Endonuclease with a Long Recognition Sequence," Nucleic Acids Research, vol. 37, No. 9, 2009, pp. 3061-3073.
Wang, Z., et al., "Classification of Plasmid Vectors Using Replication Origin, Selection Marker and Promoter as Criteria," Plasmid, vol. 61, 2009, pp. 47-51.
Engler, C., et al., "A One Pot, One Step, Precision Cloning Method with High Throughput Capability," PLOS One, vol. 3, Issue 11, 2008, pp. 1-7.
Cormack, B., et al., "Directed Mutagenesis Using the Polymerase Chain Reaction," Current Protocols in Molecular Biology, 1997, pp. 8.5.1-8.5.10.
Prober, J., et al., "A System for Rapid DNA Sequencing with Fluorescent Chain-Terminating Dideoxynucleotides," Science, vol. 238, pp. 336-341.
Langer-Safer, P., et al., "Immunological Method for Mapping Genes on *Drosophila* Polytene Chromosomes," Proc. Natl. Acad. Sci., vol. 79, 1982, pp. 4381-4385.
Prigodich, A., et al., "Multiplexed Nan-Flares: mRNA Detection in Live Cells," Anal. Chem, vol. 84, No. 4, 2012, 11 pages.
International Search Report issued in Application No. PCT/FR2016/050305, dated Apr. 22, 2016.

\* cited by examiner

A

B

METHOD FOR PRODUCING DNA VECTORS FROM MOLECULAR BRICKS CONTAINING SEQUENCES OF INTEREST

The material in the text file named SEQ LISTING, which was created on Nov. 8, 2017, and is sized 256, 830 bytes, is hereby incorporated by reference in its entirety.

TECHNICAL FIELD

The present invention relates to a method for producing "tailor-made" double-stranded DNA vectors from molecular building blocks comprising sequences of interest.

PRIOR ART

At present, DNA manipulations are still widely based on the use of cloning or expression vectors. The insertion or extraction of DNA fragments corresponding to functional elements (antibiotic resistance genes, cloning sites, molecular labels, promoters, origins of replication in other organisms, selection cassettes, etc.) in/from plasmids (circular DNA molecules naturally present in some bacteria) has enabled the development of a multitude of different vectors, suitable for various uses, each vector being developed for an especial and specific application. The end user therefore selects a vector adapted to his needs and introduces into it his own DNA fragment of interest by DNA cloning methods. These methods are traditionally based on the use of, on the one hand, restriction enzymes, most often of type IIp (that is to say enzymes which recognise and cleave DNA at short palindromic sequences) and, on the other hand, DNA ligases, which are capable of putting back together DNA fragments produced by the restriction enzymes. These methods require multiple steps, of which the number increases the risk of exposure to exogenous contaminants that could degrade the DNA, and also the risk of self-pairing or incorrect pairings. Similarly, these methods require the use of multiple enzymes, which are effective to a greater or lesser extent, which constitutes a disadvantage that is difficult to overcome. Difficulties can also be encountered depending on the compatibility of the donor and acceptor plasmids. Indeed, a very large number of vectors differing in terms of their functional components are commercially available to meet the wide range of possible uses. However, each vector is not necessarily compatible with the others, and especially the presence or absence of restriction sites in the plasmid sequence can make the sequence transfers from one vector to another relatively complex. The transfer of DNA fragments from one plasmid to another plasmid has a certain number of disadvantages and results in a sharp reduction in reaction yields and a high cost in terms of time and reagents.

The cloning activities based on the ligation restriction methods and the methods deriving therefrom are based on the use of an entry vector, usually of commercial origin, which causes a lack of control over the nature and number of functional components of the entry vectors. In addition, the use of the ligation restriction method requires the provision of usable restriction sites on either side of the fragment to be inserted into the vector and also requires the provision of these same sites in the vector itself. It must therefore be ensured, in order to be able to introduce a DNA fragment by restriction ligation, that none of the enzymes used cleaves within the DNA fragment of interest and that each of these enzymes cleaves at just one location in the vector, this being the location at which the fragment must be inserted. It is for this reason that the developed vectors contain multiple cloning sites (MCS). The presence and use of these MCSs for inserting fragments of DNA into vectors leaves traces in the hybrid DNA sequence obtained, these being sequences ranging from a few nucleotides to several tens of nucleotides before and after the insert. These 'scar' nucleotides are not necessary for the function of the plasmid and are sometimes even detrimental (for example in the case of two sequences containing proteins that are to be fused).

The Gateway system is presented as a solution to the problems of transferring an insert from one plasma to the other. However, the Gateway system can also be perceived as a closed system, incompatible with the other molecular tools available. Moreover, in the Gateway system, the recombination sequence is fixed and will always leave traces in the final vector. The Golden Gate assembly is also based on a donor plasmid and a receiver plasmid, very similarly to the Gateway system.

Some of the methods described in the prior art are proposed as solutions for overcoming these limitations. For example, methods of ligation independent cloning or sequence location independent cloning (LIC/SLIC) or Gibson Assembly allow users to not have to use multiple restriction enzymes and thereby remove a certain number of technical limitations associated therewith (compatibility, presence of sites in the sequences or plasmids of interest). However, they do not allow greater control of the functionalities of the final vector, this still being dependent on the molecular tools commercially available.

In order to move away from a starting vector and a final vector, Wang T. et al. (2012), Appl Microbiol Biotechnol 93:1853-1863, and also Weber E. (201 1), PLOS ONE 6 (2): e16765 and EP2395087, and Sarrion-Perdigones A. (2012), PLOS ONE 6 (7): e21622) have proposed new modular cloning methods, such as the GoldenBraid (or Golden Gate. The Golden Gate is described in document WO 2008/095927 incorporated herein, in its entirety, by reference as well as the article by Engler et al. PLOS ONE 4 (2009) e5553. This method is compatible with numerous molecular tools (plasmids) commercially available and is based on the use of a type of restriction enzyme available from numerous providers. The users of this method therefore are not captive to a range of dedicated products. The drawback of this versatility is the work to be performed in order to verify that all the elements of the desired constructions are compatible with the method. In other words, they must be naturally devoid of a restriction site of type IIs enzymes, or must be modified in order to eliminate the sites potentially present.

In order to produce a vector according to needs, a 'modular' plasmid backbone was developed by the company Oxford Genetics. This backbone, named SnapFast®, contains restriction sites introduced into the sequence so as to flank the functional components of the plasmid. Thus, each component can be replaced by another of the same category (for example: promoter, label) by applying the restriction-ligation method for each modification desired by the experimenter. However, this technique requires a relatively large amount of DNA. Although the SnapFast® system is probably the molecular biology tool that offers users the greatest flexibility with regard to the control of the functionalities of the entry vector, it is not without its faults. This alternative has the disadvantages inherent to the use of multiple restriction enzymes (for example: possible presence of sites in the sequences of interest, nucleotide scars) and a high cost of provision. Another limitation is that the modularity remains restricted to the substitutions made possible by the defined backbone of this vector.

Other approaches have been developed in order to overcome this limitation. These relate especially to cloning based on recombinase activity. This technique reduces the problems originating from the presence of multiple restriction sites in the large constructions, but is limited by the fact that the recombination sites are left in the final assembly product, which hinders assembly without joining of sequences coding for proteins (Weber E. (2011), PLOS ONE 6 (2): e16765 and EP2395087). In addition, only a small number of fragments can be assembled in a construction in accordance with this method. Furthermore, total control of the composition of the final vector (sequence of interest and functional modules) is not achieved.

Gene synthesis technology would allow this. However, this technology requires its user to provide a complete design of the vector before preparation thereof, with the slightest mistake being synonymous with total and irreversible loss of the investment. In addition, this custom manufacture is very costly and a long process.

Document US 2014 0038240 describes an assembly method performed in a number of successive steps. This method requires the use of either a single-stranded DNA staple or an adapter. The disadvantages associated with the staples are that they can adopt a secondary structure, can self-pair, or can be masked by proteins. This can lead to assembly-related difficulties and low yields. In accordance with another embodiment, document US2014 0038240 describes an assembly method performed with the aid of an adapter. This embodiment requires the use of a number of restriction enzymes in order to produce single-stranded ends.

All cloning techniques by recombination generally leave unwanted sequences in the final vector, these being the sequences used for the recombination.

None of the existing methods or techniques allows users to produce entirely modular custom expression vectors easily (in a single step), at low cost (in the presence of a single enzyme) and within a short space of time.

There is thus a real need to propose a method making it possible to assemble complex DNA molecules and to easily obtain, with a good yield and without error, a construction that has been entirely chosen, that is to say a construction of which the nature and number of the components, especially functional components, can be controlled.

It is therefore necessary to develop a new method making it possible to overcome all of the above problems which is more effective, more economical, and quicker.

The present invention proposes to address these problems.

DISCLOSURE OF THE INVENTION

The present invention relates to a method for producing a circular double-stranded DNA vector comprising at least two sequences of interest, said method comprising:
a) a step of simultaneously contacting at least two molecular building blocks, which are different from one another, in the presence of a single restriction enzyme, said single restriction enzyme being a type IIs restriction enzyme, each molecular building block being a linear double-stranded DNA molecule and containing:
  (i) a sequence of interest with no specific recognition site of the aforementioned type IIs restriction enzyme and comprising at least one unit, said unit being a functional unit or a non-functional unit, said unit comprising at least one module, said module being a functional module or a non-functional module,
  (ii) two double-stranded DNA adapters, flanked upstream and downstream of said sequence of interest, each double-stranded DNA adapter consisting of a sequence of at least 12 nucleotides, which sequence contains a single and only recognition site of the aforementioned type IIs restriction enzyme,
the recognition site of the aforementioned type IIs restriction enzyme of the adapter upstream of said sequence of interest and the recognition site of the aforementioned type IIs restriction enzyme of the adapter downstream of said specific sequence being convergent, which step leads:
  to the elimination by cleaving of the recognition sites of the type IIs restriction enzyme used,
  to the formation of a cohesive single-stranded suture of at least 2 nucleotides at each of the ends of said sequence of interest,
said cohesive single-stranded suture of at least 2 nucleotides upstream of one of the at least two sequences of interest being complementary to said cohesive single-stranded suture of at least 2 nucleotides downstream of another sequence of interest, said step of the method according to the invention leading:
  to the pairing by nucleotide complementarity of the aforementioned cohesive single-stranded sutures of at least 2 nucleotides and
  to the positioning of the sequences of interest contiguously with one another in an order and a single and defined direction, said method also comprising
b) a step of ligation of the aforementioned cohesive single-stranded sutures of at least 2 nucleotides,
so as to obtain a circular double-stranded DNA vector.

In accordance with one embodiment, the method according to the invention relates to a method for producing a circular double-stranded DNA vector comprising at least two sequences of interest, said method comprising:
a) a step of simultaneously contacting at least two molecular building blocks, which are different from one another, in the presence of a single restriction enzyme, said single restriction enzyme being a type IIs restriction enzyme,
each molecular building block being a linear double-stranded DNA molecule with non-cohesive ends and containing:
  (i) a sequence of interest with no specific recognition site of the aforementioned type IIs restriction enzyme and comprising at least one unit, said unit being a functional unit or a non-functional unit, said unit comprising at least one module, said module being a functional module or a non-functional module,
  (ii) two double-stranded DNA adapters, flanked upstream and downstream of said sequence of interest, each double-stranded DNA adapter consisting of a sequence of at least 12 nucleotides, which sequence contains a single and only recognition site of the aforementioned type IIs restriction enzyme,
the recognition site of the aforementioned type IIs restriction enzyme of the adapter upstream of said sequence of interest and the recognition site of the aforementioned type IIs restriction enzyme of the adapter downstream of said specific sequence being convergent, which step leads:

to the elimination by cleaving of the recognition sites of the type IIs restriction enzyme used, to the formation of a cohesive single-stranded suture of at least 2 nucleotides at each of the ends of said sequence of interest, said cohesive single-stranded suture of at least 2 nucleotides upstream of one of the at least two sequences of interest being complementary to said cohesive single-stranded suture of at least 2 nucleotides downstream of another sequence of interest, to the pairing by nucleotide complementarity of the aforementioned cohesive single-stranded sutures of at least 2 nucleotides and to the positioning of the sequences of interest contiguously with one another in an order and a single and defined direction, b) a step of ligation of the aforementioned cohesive single-stranded sutures of at least 2 nucleotides, so as to obtain a circular double-stranded DNA vector.

The method according to the invention requires the use of just a single restriction enzyme, which is a type IIs restriction enzyme.

In accordance with an especial aspect of the invention, the vectors according to the invention, obtained especially in accordance with the method of the invention, are devoid of a multiple cloning site.

The conventions in accordance with which a double-stranded DNA is read from 5' to 3' are respected in the present invention.

The invention described makes it possible to do away entirely with the use of conventional restriction enzymes in the production of vectors, thus avoiding all the disadvantages thereof. This results in a much shorter time required for production of the vectors and a drastic reduction in the risks of error. The production cost is therefore significantly reduced, and the need to create and maintain a stock of varied restriction enzymes in each laboratory will also be reduced.

The term 'conventional restriction enzyme' means a type IIp restriction enzyme.

The invention makes it possible to do away with the use of entry vectors for sub-cloning techniques. In other words, it is no longer necessary to acquire or maintain a collection of multiple vectors in order to be able to carry out sub-cloning activities. This represents a consequent saving of time (bacterial culture and plasmid purification).

In addition, the method according to the invention makes it possible to design vectors comprising multiple expression cassettes. In a context of genetic modification of cells or an organism, this allows users to use just a single vector, and therefore a single step of selection to transfer a plurality of genes of interest simultaneously into their system of interest.

The invention also makes it possible to restrict the content of the vectors solely to the sequences of interest selected by the user. There is no residual plasmid sequence or nucleotide scar resulting from the use of conventional restriction enzymes and the need to use multiple cloning sites. The invention thus allows users to exert total control over the components of the vector produced.

The invention is suitable for producing chimeric genes by combinations of pairings and is completely compatible with applications based on these approaches (for example: intramolecular labelling or promoter analysis). In these contexts the invention allows the simultaneous creation of numerous, different expression vectors in a single step. It therefore makes it possible to produce quickly (in parallel) a range of vectors differentiating from one another by one or other of the selected components (for example: resistance gene, molecular marker), without modifying the entire architecture of the vector.

For all of these reasons, the invention described constitutes a technically and economically attractive method compared to the most effective known methods.

In accordance with the invention, the term 'vector' means a DNA molecule comprising genetic information and capable of transmitting said genetic information. A vector can also be a molecule of plasmid origin, or can be a plasmid modified by genetic engineering and intended to transfer DNA sequences into a cell or an organism of choice.

In accordance with the invention, a 'plasmid' is a DNA molecule, different from chromosomal DNA, capable of autonomous replication. Plasmids are generally circular and have two strands (double-stranded DNA).

A 'molecule of plasmid origin' according to the invention is a molecule formed at least in part of nucleic acid originating from a plasmid.

The term 'expression vector' means any vector used in order to understand and/or allow the expression of the genetic information of a gene in a cell or an organism of choice.

In accordance with the invention, the functionality of each vector is defined in accordance with the combination of the basic functions possessed by the module(s) constituting the vector and/or the use made thereof.

In general, the term 'sequence of interest' means a sequence of nucleic acids that the experimenter wishes to use and/or assemble with another sequence of interest.

The term 'sequence of interest' in accordance with the invention also means a sequence of nucleic acids which contains the genetic information corresponding to one or more functional modules.

The term 'unit' defines all the information contained in a DNA sequence which provides this sequence with an integrated genetic functionality corresponding to one of the primordial functions of a vector. By definition, a unit is composed of a set of modules of which the combination produces the function of this unit.

A 'bacterial unit' or 'bacteria-maintaining unit' has the function of assuring the replication and selection of the vector in a prokaryotic system.

The 'expression unit' has the function of allowing the expression of a genetic product in a system of interest (eukaryotic or prokaryotic).

The 'unit of integration in a eukaryotic or prokaryotic cell' has the function of making it possible to retain the one or more transgenes in the genome of a system of interest.

A vector must contain, as a minimum, a bacterial functional unit and can also contain one or more expression units and/or one or more integration units.

An expression vector must therefore contain a bacterial functional unit and an expression unit. An expression vector can also contain one or more other expression units and one or more integration units.

From a physical point of view, the vector can be provided with a unit by one or more sequences of interest. If the unit is contained in a single sequence, the unit is, de facto, functional.

In accordance with the invention, a functional unit (bacterial, expression, integration) in general comprises a set of modules (at least one module) necessary for a described function.

A functional unit in accordance with the invention is in itself sufficient to confer a biological function to the vector.

In accordance with the invention, a functional unit comprises at least one module, said module being a functional module or a non-functional module.

In general, a functional module means a sequence of nucleic acids which confers a function to the vector by participating in the function of a functional unit. A functional module is a physical entity, represented by a sequence which participates, in combination with other modules, in the function of the unit.

The term 'module' thus defines information contained in a DNA sequence which confers to this sequence a minimal genetic functionality useful for the function of a vector. The information satisfying this minimal criterion is constituted for example by the following:

the promoters, the coding sequences, the terminators, the non-coding sequences corresponding to functional RNAs (introns, hairpin RNA, non-coding long RNA), the enhancers, the insulators, the IRES sequences, the recombinase target sequences, the origins of replication, the sequences homologous to genetic loci.

In accordance with the invention, a functional module is a sequence containing genetic information necessary and sufficient to produce a basic function involved in the functionality of the vector, especially an origin of replication, a promoter, a terminator, a recombination sequence, a coding or non-coding sequence, a translation regulatory sequence, etc.

A non-functional module according to the invention does not have a function in a specific context (in an especial host cell, for example), but can have a function if it is combined with other functional or non-functional modules or if it is used in an appropriate context.

For example, in an expression functional unit (or expression cassette), the minimum modules necessary are a promoter, a sequence coding an expression product, and a terminator. Other modules can be included in this unit in order to modify the function thereof.

In other words, when the information defined by the module is sufficient in itself to support the functionality, the module is said to be functional: For example, an entire coding sequence (from the ATG to the stop codon) or a defined promoter (recognition site of transcription factor and presence of transcription initiation) constitute functional modules. If the information present does not allow this minimal functionality, the module is said to be non-functional. For example, an incomplete coding sequence (absence of an ATG or a stop codon), or a truncated promoter (absence or mutation of recognition site of transcription factor) are, by definition, "non-functional" modules.

The modules therefore have singular and defined functions which, by combination, produce the biological functions of the units.

An expression vector can contain a plurality of units, including at least one bacterial functional unit and one expression functional unit.

The term 'molecular building block' means a linear double-stranded DNA sequence. In accordance with an advantageous embodiment, a molecular building block is a linear double-stranded DNA sequence having a 3' overhanging nucleotide (adenine) over each of the two DNA strands. In accordance with a more advantageous embodiment, a molecular building block is a linear double-stranded blunt-end DNA sequence.

A molecular building block according to the invention is composed of a sequence of interest flanked on either side by an adapter.

In accordance with the invention, a building block is incapable of forming a vector per se. In other words, a building block alone cannot constitute a vector.

Figure 30:
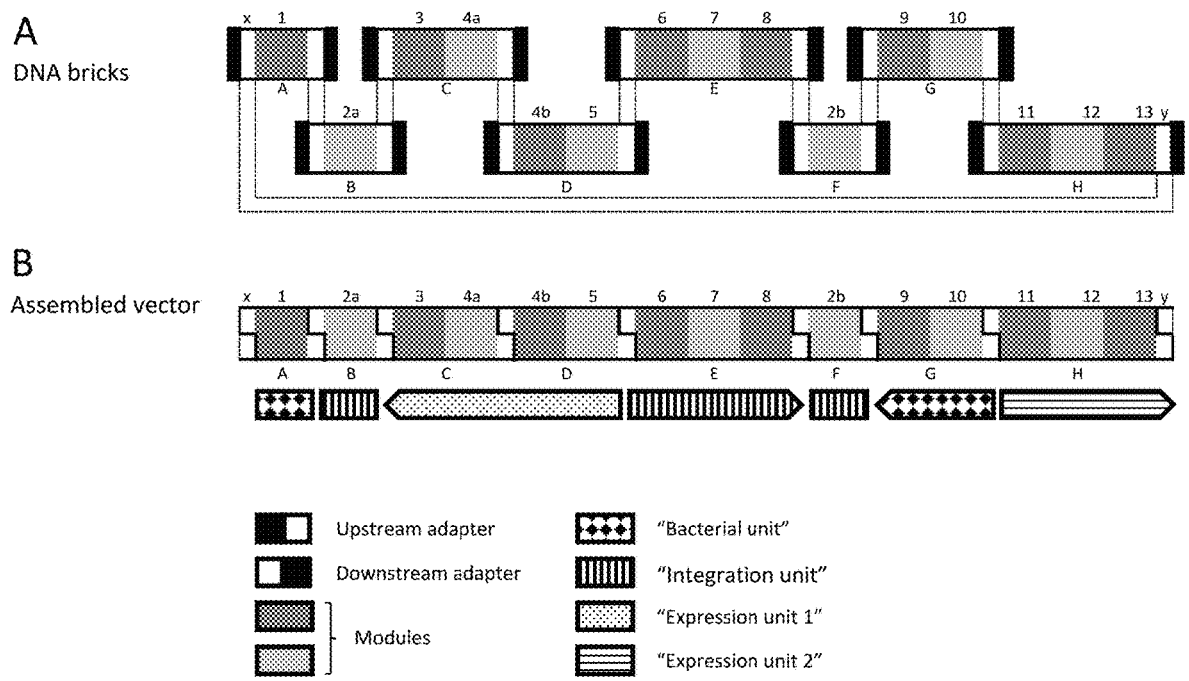

FIG. 30 shows a non-limiting example of a construction according to the invention.

In this example, the ordered assembly of the sequences of interest (SI) produces a vector containing 4 separate functional units:

The bacterial unit is composed of two SIs: A and G. The SI A contains a functional module (1) and the SI G contains two functional modules (9 and 10). By definition, the SIs A and G each contain a (bacterial) non-functional unit.

The integration unit is composed of three SIs: B, E and F. The SIs B and F each contain a non-functional module (2a and 2b respectively). The simultaneous presence of these two non-functional modules in the same vector constitutes a functional module. In the present case this reconstructed functional module allows the integration of the DNA sequence C+D+E in a targeted locus by the sequence B+F. The SI E contains three functional modules (6, 7 and 8), which code a positive selection gene. In the present case this gene makes it possible to select the target cells that will have integrated the sequence C+D+E in a stable manner in their genome by treatment with the antibiotic corresponding to the chosen selection gene. By definition, and in the context described in the example, the SIs B, E and F each contain an integration non-functional unit.

The expression unit 1 is composed of two SIs: C and D. The SIs C and D each contain a functional module and a non-functional module: 3 and 4a for the SI C; 5 and 4b for the SI D. In this example, the assembly produces a functional module from the modules 4a and 4b, which, once connected, constitute a complete coding sequence. By definition, the SIs C and D each contain a non-functional expression unit.

The expression unit 2 is contained by the SI H. The SI H contains three functional modules: 11, 12 and 13. By definition, the SI H contains a (expression) functional unit.

Table 1 presents a non-limiting list of units and modules according to the invention.

TABLE 1

Examples of units and modules according to the invention.

| UNITS | MODULE TYPES | | EXAMPLES |
|---|---|---|---|
| Bacterial functional unit | Bacterial origin of replication | | Origin of replication of plasmids pMB1, pUC, ColE1, p15A, pSC101, R1, RK2, R6K, F1, M13, Lambda, pA81, pRAS3.1, pTi, pBPS1, pUO1, pKH9, pWKS1, pCD1, pMAK3, pBL63.1, pTA1060, p4M, pHT926, pCD6, pJB01, pIME300, pMD5057, pTE44, pDP1, pT38 |
| | Bacterial selection marker | resistance gene to an antibiotic | resistance gene to ampicillin, neomycin, kanamycin, chloramphenicol, streptomycin, gentamicin, tetracycline, erythromycin, vancomycin |
| | | screening gene | lacZα |
| Expression functional unit: | Promoter | RNA polymerase II promoter: | pCMV, pEF1α, pβ-actin, ubiquitin |
| | | Inducible RNA polymerase II promoter: | promoters inducible by tetracycline (for example: pTRE3G), pGAL1, pGAL10 |
| | | RNA polymerase III promoter: | U6, H1 |
| | Sequence coding an expression product | coding or non-coding sequence described in a genome | |
| | | reporter gene | luciferase, β-galactosidase |
| | | Amplifier | HACNS1/CENTG2, GADD45g |
| | Terminator | polyadenylation sequence | BGHpolyA, HSV TKterm, SV40polyA |
| | Tag | tag | HA, Myc, Flag |
| | | affinity protein | GST, MBP, TAPTag |
| | | fluorescent protein | GFP, Mcherry and variants |
| | IRES sequence | | (PPT19)4, KMI1, KMI1, KMI2, KMI2, KMIX, X1, X2. |
| Functional unit of integration in a eukaryotic cell | Selection gene | positive selection gene | Resistance gene to hygromycin B, G418, tetracycline, puromycin, or zeocin |
| | | negative selection gene | Gene coding thymidine kinase |
| | Sequence for retention in a eukaryotic cell | | Yeast origin of replication (ARS), centromere sequence |
| | Homologous sequence of integration | | locus Rosa26 or HRPT (mouse cells) sequences of integration in the genome of yeast |
| | Sequences involved in DNA editing (targeted homologous recombination) | sequence recognised by a recombinase | sequence LoxP or FRT. |

In accordance with an especial embodiment, the present invention relates to a molecular building block comprising a sequence of interest flanked on either side by a single-strand suture.

In accordance with the information contained in the sequence of interest, a molecular building block used in the assembly according to the invention provides the final vector with one or more functions, for example;
- a plurality of functional units
- a functional unit
- a non-functional unit
- a functional module
- a non-functional module
- a plurality of functional modules The term 'restriction enzyme' means a protein that can bind to, and cleave a nucleic acid.

In general, type IIs restriction enzymes are enzymes which bind specifically to double-stranded DNA at a non-palindromic recognition site, and therefore in an oriented manner, and cleave the two strands of the double-stranded DNA at a fixed distance from the recognition site. The nucleotide sequences of the recognition site and of the cleavage site are therefore different.

By convention, the site of a type IIs enzyme is oriented such that its cleavage site is located after its recognition site.

In accordance with the invention, a type IIs enzyme binds to the DNA and cleaves downstream of the binding site.

The length of the produced cohesive end—or the distance between the recognition site of the type IIs enzyme and the cleavage site—is dependent on the type IIs enzyme used.

The nucleotides of the cleavage site do not form part of the recognition site; they can be selected from the 4 nucleotide bases which form the DNA.

The type IIs enzyme used in the method according to the invention is selected from any one of the type IIs enzymes referenced in the REBASE® Restriction Enzyme Database.

Advantageously, type IIs enzymes having a recognition site at a distance of 2, 3, 4, 5, 6, 7, 8, 9, 10, 11, 12, 13, 14, 15, 16, 17 or 18 nucleotides from the cleavage site of one of the DNA strands, as described in Lippow and al, 2009, Nucleic Acides Res, 37: 3061-3073, are used. The cleavage site, according to the invention, is defined as the sequence comprised between the cuts made on each of the two DNA strands.

In accordance with the invention, the sequences of interest are entirely defined and do not contain any restriction site (recognition site) recognised by the type IIs enzyme used in step (a) of the method according to the invention.

In accordance with the invention, 'convergent sites' means sites allowing the type IIs enzyme to generate a single-stranded suture upstream and downstream of the sequence of interest.

In accordance with an advantageous embodiment, 'convergent recognition sites of the type IIs enzyme' are understood to mean two recognition sites of the type IIs enzyme that are convergent and located one on each of the two complementary strands of DNA such that the type IIs enzyme binds on either side of the DNA and cleaves the DNA upstream and downstream of the sequence of interest (see FIG. 1) so as to produce a single-stranded end upstream and downstream.

The term 'adapter' in accordance with the invention means a DNA sequence of at least 8 nucleotides or more, especially 8 to 100 nucleotides, preferably 12 nucleotides, flanking either side of a sequence of interest in a molecular building block.

Especially, an adapter according to the invention is a DNA sequence of at least 12 nucleotides or more, especially 12 to 100 nucleotides, preferably 12 nucleotides, flanking either side of a sequence of interest in a molecular building block.

An adapter contains at least:
  a sequence of 5, 6, 7 or more nucleotides corresponding to the binding site of the used enzyme with type IIs activity for the assembly according to the invention,
  a sequence of 1 to 8 and more nucleotides corresponding to the spacing between the binding site and the cleavage site of the enzyme used. The length of this sequence is dependent on the intrinsic characteristics of the type IIs enzyme used,
  a sequence of 2 to 5 or more nucleotides corresponding to the single-stranded end produced by the action of the type IIs enzyme used. Since this sequence enables the pairing of fragments that are to be assembled, it corresponds de facto to the definition of a suture.

In accordance with the invention, the adapters contain a single restriction site (recognition site) recognised by the type IIs enzyme used in step (a) of the method according to the invention.

The term 'suture' means a single-stranded (or monofilament) sequence of 2 to 5, or more, nucleotides.

In accordance with the invention, a suture is a sequence of 2 to 5, or more, nucleotides corresponding to the single-stranded end produced by the action of the type IIs enzyme used for the assembly, said single-stranded sequence being produced upstream and downstream of the sequence of interest.

This sequence of 2 to 5, or more, nucleotides, paired to its complementary sequence, is present in the adapters, and therefore in the molecular building blocks, as well as in the final reaction product (the vector).

The term 'complementary' or 'complementarity' means that 100% of the nucleotide bases of two sequences are paired with one another. In accordance with the invention, 100% of the sequence of the single-stranded suture downstream of the building block n−1 pairs with 100% of the sequence of the single-stranded suture upstream of the building block n and the sutures are therefore complementary.

The pairing of the two sequences of single-stranded sutures will constitute a double-stranded suture.

The term 'suture' in accordance with the invention also means a single-stranded sequence downstream of the building block n−1 paired with the single-stranded sequence upstream of the building block n.

In accordance with the invention, a suture is a double-stranded DNA sequence in the vector obtained by the method.

The sequence of the sutures produced during the course of the invention is entirely defined so as to allow on the one hand a good ordering of the sequences of interest during the assembly and functioning thereof, and on the other hand an optimum yield. Consequently, the sequence of the sutures produced is a characteristic of each molecular building block (intra-building block selection of the sequence of sutures) and is also dependent on the order in which each of the molecular building blocks are arranged relative to one another (inter-building block selection of the sequence of sutures).

The sutures are not scars, especially scars introducing dysfunctions into the vector.

In accordance with the invention, the sutures are therefore an integral part of each of the molecular building blocks and in addition can form part, entirely or partially, of the genetic information constituting a module.

The sutures are selected in a reasoned manner, with computer assistance, so as to assure a good ordering of the sequences of interest during the assembly and also an optimum yield.

In accordance with the invention, the cohesive single-stranded suture of at least 2 nucleotides produced at each of the upstream and downstream ends of the sequence of interest comprises a sequence selected from "47 possible combinations excluding the z*z combinations resulting in a DNA palindrome, in which z is between 2 and 10 and z is the number of nucleotides of the single-stranded suture".

The method according to the invention comprises an enzymatic reaction combining the action of a type IIs restriction enzyme defined in accordance with the invention and of a ligase defined in accordance with the invention. In accordance with one embodiment, the method according to the invention is an assembly method. The product of the reaction is a DNA molecule, preferably circular and containing the desired number of molecular building blocks, these being assembled in an ordered fashion, based on the complementarities of the sutures. A good ordering of the building blocks assures de facto a good ordering of the modules, whatever the number of modules contained in each building block.

In accordance with an advantageous embodiment, the method according to the invention is an assembly method without scars.

In accordance with one embodiment, the adapter according to the invention comprises at least one other recognition site of a type IIs enzyme, which site is recognised by a type IIs enzyme different from that used in the method according to the invention and is not recognised by the type IIs enzyme used in the method according to the invention.

In accordance with an advantageous embodiment, the adapter according to the invention additionally comprises at least one restriction site, and more advantageously at least one restriction site selected from the rare restriction sites, and even more advantageously a restriction site from the rare restriction sites selected from NotI, PacI, PmeI, SwaI, SmiI, SgsI, SgrDI, SgrAI, SbfI, FseI, AscI, AsiSI, MreI, MssI.

In all the embodiments according to the invention, the recognition site of the type IIs enzyme that is used in the method according to the invention and present in each adapter consists of a single site located solely in the adapters, the sequences of interest according to the invention not comprising any such sites.

The method according to the invention utilises just a single type IIs of enzyme, said type IIs enzyme recognising a DNA sequence, especially a single DNA sequence.

The invention is not limited to a single type IIs enzyme recognising a single sequence.

Any type IIs enzyme having the desired restriction activity, that is to say being able to bind to said single sequence and produce the expected single-stranded DNA sequences, forms part of the present invention.

Likewise, any sequence having a variation not influencing, or hardly influencing the recognition and/or the activity of the type IIs enzyme forms part of the invention.

In accordance with one embodiment, the invention relates to a method for producing a circular double-stranded DNA vector as defined above, comprising a step of simultaneously contacting the molecular building blocks Ori-AmpR BsaI B (SEQ ID NO: 36), pCMV BsaI B (SEQ ID NO: 37), hFUT3 BsaI A (SEQ ID NO: 38), BGHpA BsaI B (SEQ ID NO: 39), and shB3Galt6 BsaI A (SEQ ID NO: 40), so as to obtain the vector V1 (SEQ ID NO: 41).

In accordance with one embodiment, the invention relates to a method for producing a circular double-stranded DNA vector as defined above, comprising a step of simultaneously contacting the molecular building blocks Ori-AmpR BsaI B (SEQ ID NO:36), pCMV BsaI B (SEQ ID NO: 37), hFUT3 BsaI A (SEQ ID NO: 38), BGHpA BsaI B (SEQ ID NO: 39), shB3GALT6 BsaI B (SEQ ID NO: 46), and HygroR BsaI B (SEQ ID NO: 47), so as to obtain the vector V1.1 (SEQ ID NO: 48).

In accordance with one embodiment, the invention relates to a method for producing a circular double-stranded DNA vector as defined above, comprising a step of simultaneously contacting the molecular building blocks Ori-AmpR BsaI B (SEQ ID NO: 36), rosa26-5' BsaI A B (SEQ ID NO: 39), shB3GALT6 BsaI B (SEQ ID NO: 46), HygroR BsaI C (SEQ ID NO: 51), and rosa26-3' BsaI A (SEQ ID NO: 52), so as to obtain the vector V1.2 (SEQ ID NO: 53).

In accordance with one embodiment, the invention relates to a method for producing a circular double-stranded DNA vector as defined above, comprising a step of simultaneously contacting the molecular building blocks Ori-AmpR BsaI B (SEQ ID NO: 36), rosa26-5' BsaI A (SEQ ID NO: 49), pCMV BsaI C (SEQ ID NO: 50), hFUT3 BsaI A (SEQ ID NO: 38), BGHpA BsaI B (SEQ ID NO: 39), shB3GALT6 BsaI B (SEQ ID NO: 46), HygroR BsaI C (SEQ ID NO: 51), rosa26-3' BsaI B (SEQ ID NO: 54), pEF1a BsaI A (SEQ ID NO: 55), TK BsaI A (SEQ ID NO: 56), and Tkter BsaI A (SEQ ID NO: 57), so as to obtain the vector V1.3 (SEQ ID NO: 58).

In accordance with one embodiment, the invention relates to a method for producing a circular double-stranded DNA vector as defined above, comprising a step of simultaneously contacting the molecular building blocks Ori-AmpR BsaI B (SEQ ID NO: 36), pCMV BsaI B (SEQ ID NO: 37), TO3G BsaI A (SEQ ID NO: 59), BGHpA BsaI B (SEQ ID NO: 39), pTRE3G BsaI A (SEQ ID NO: 60), mB3Galt6 BsaI B (SEQ ID NO: 63), and Tkter BsaI A (SEQ ID NO: 57), so as to obtain the vector V2 (SEQ ID NO: 62).

In accordance with one embodiment, the invention relates to a method for producing a circular double-stranded DNA vector as defined above, comprising a step of simultaneously contacting the molecular building blocks Ori-AmpR BsaI B (SEQ ID NO: 36), pCMV BsaI B (SEQ ID NO: 37), TO3G BsaI A (SEQ ID NO: 59), BGHpA BsaI B (SEQ ID NO: 39), pTRE3G BsaI A (SEQ ID NO: 60), mb3GALT6 BsaI B (SEQ ID NO:63), Tkter BsaI B (SEQ ID NO:64), and shB3Galt6 BsaI C (SEQ ID NO:65), so as to obtain the vector V3 (SEQ ID NO: 66).

In accordance with one embodiment, the invention relates to a method for producing a circular double-stranded DNA vector as defined above, comprising a step of simultaneously contacting the molecular building blocks Ori BsaI A (SEQ ID NO: 104), AmpR BsaI A (SEQ ID NO: 105), pCMV BsaI B (SEQ ID NO: 37), TO3G BsaI A (SEQ ID NO: 59), BGHpA BsaI B (SEQ ID NO: 39), pTRE3G BsaI A (SEQ ID NO: 60), mB3Galt6 BsaI B (SEQ ID NO: 63), and Tkter BsaI A (SEQ ID NO: 57), so as to obtain the vector V2b (SEQ ID NO: 149).

In accordance with one embodiment, the invention relates to a method for producing a circular double-stranded DNA vector as defined above, comprising a step of simultaneously contacting the molecular building blocks Ori BsaI A (SEQ ID NO: 104), AmpR BsaI A (SEQ ID NO: 105), pCMV BsaI B (SEQ ID NO: 37), TO3G BsaI A (SEQ ID NO: 59), BGHpA BsaI B (SEQ ID NO: 39), pTRE3G BsaI A (SEQ ID NO: 60), mb3GALT6 BsaI B (SEQ ID NO:63), Tkter BsaI B (SEQ ID NO: 64), and shB3Galt6 BsaI C (SEQ ID NO: 65), so as to obtain the vector V3b (SEQ ID NO: 150).

In accordance with one embodiment, the invention relates to a method for producing a circular double-stranded DNA vector as defined above, comprising a step of simultaneously contacting the molecular building blocks Ori BsaI B (SEQ ID NO: 106), AmpR BsaI B (SEQ ID NO: 107), pEF1aL BsaI B (SEQ ID NO: 108), EGFP-CAAX BsaI A (SEQ ID NO: 109), BGHpA BsaI C (SEQ ID NO: 110), pCMV BsaI D (SEQ ID NO: 111), SiaT BsaI B (SEQ ID NO: 112), mCherry BsaI B (SEQ ID NO: 113), TKter BsaI B (SEQ ID NO: 64) and HygroR BsaI D (SEQ ID NO: 114), so as to obtain the vector V1.1b (SEQ ID NO: 151).

In accordance with one embodiment, the invention relates to a method for producing a circular double-stranded DNA vector as defined above, comprising a step of simultaneously contacting the molecular building blocks Ori-2 BsaI C (SEQ ID NO: 115), AmpR BsaI C (SEQ ID NO: 116), MNN10-Lrec BsaI A (SEQ ID NO: 117), KanMX BsaI A (SEQ ID NO: 119), MNN10-Rrec BsaI A (SEQ ID NO: 118), so as to obtain the vector V4 (SEQ ID NO: 152).

In accordance with one embodiment, the invention relates to a method for producing a circular double-stranded DNA vector as defined above so as to obtain a vector selected from the group of vectors of sequence SEQ ID NO: 30, 31, 32, 33, 34 and 35.

In accordance with one embodiment, the invention relates to a method for producing a circular double-stranded DNA vector as defined above so as to obtain a vector selected from the group of vectors of sequence SEQ ID NO: 41, 48, 53, 58, 62 and 66.

In accordance with one embodiment, the invention relates to a method for producing a circular double-stranded DNA vector as defined above so as to obtain a vector selected from the group of vectors of sequence SEQ ID NO: 149, 150, 151 and 152.

In accordance with one embodiment, the invention relates to a method for producing a circular double-stranded DNA vector as defined above so as to obtain a vector selected from the group of vectors of sequence SEQ ID NO: 30, 31, 32, 33, 34, 35, 41, 48, 53, 58, 62, 66, 149, 150, 151 and 152.

In accordance with an especial aspect, the present invention relates to a method as described above, comprising:
- a) a step of simultaneously contacting n molecular building blocks, each molecular building block being a linear double-stranded DNA molecule, especially a linear double-stranded DNA molecule with non-cohesive ends, and containing: (i) a sequence of interest (SI)i with no specific recognition site of the aforementioned type IIs restriction enzyme and comprising at least one unit, said unit being a functional unit or a non-functional unit, said functional unit comprising at least one module, said module being a functional module or a non-functional module, and (ii) two double-stranded DNA adapters A(i−1,i) and A(i,i+1), which are different from one another, flanked respectively upstream and downstream of said sequence of interest (SI)i, each double-stranded DNA adapter consisting of a sequence of at least 12 nucleotides,
  the sequence of at least 12 nucleotides of the double-stranded DNA adapter A(i−1,i) containing a single and only recognition site of the aforementioned type IIs restriction enzyme, and a suture of at least 2 nucleotides, s(i−1, i) downstream of the recognition site of said type IIs restriction enzyme,
  the sequence of at least 12 nucleotides of the double-stranded DNA adapter A (i+1,i) containing a single and only recognition site of the aforementioned type IIs restriction enzyme, and a suture of at least 2 nucleotides, s(1,i+1) upstream of the recognition site of said type IIs restriction enzyme,
the recognition site of the aforementioned type IIs restriction enzyme of the double-stranded DNA adapter A(i−1,i) upstream of said sequence of interest and the recognition site of the aforementioned type IIs restriction enzyme of the double-stranded DNA adapter A(l,i+1) downstream of said specific sequence being convergent,
  (SI)1 being the sequence of interest (SI)i in which i=1
  (SI) n being the sequence of interest (SI)i in which i=n
n being an integer ranging from 2 to 100, i ranging from 1 to n, i being different from n when i=1 and when i=n then i+1 is 1,
and when i=1, then i−1=n, such that the cohesive single-stranded suture of at least 2 nucleotides produced upstream of (SI)1, si−1, is the complementary sequence of the cohesive single-stranded suture of at least 2 nucleotides produced downstream of (SI)n, sn+1,
and when i=n then the cohesive single-stranded suture of at least 2 nucleotides produced downstream of (SI)n, sn+1, is the complementary sequence of the cohesive single-stranded suture of at least 2 nucleotides produced upstream of (SI)1, si−1, which step leads:
  to the elimination of the recognition sites of the type IIs restriction enzyme used,
  to the formation of a cohesive end formed by a single-stranded suture of at least 2 nucleotides at each of the ends upstream and downstream of the (SI)i and
  to the pairing by nucleotide complementarity of the aforementioned cohesive single-stranded suture of at least 2 nucleotides downstream of (SI)i with the cohesive single-stranded suture of at least 2 nucleotides upstream of the (SI)i+1, and of the aforementioned cohesive single-stranded suture of at least 2 nucleotides upstream of the (SI)i with the aforementioned cohesive single-stranded suture of at least 2 nucleotides downstream of (SI) i−1
and to the positioning of the aforementioned (SI)i contiguously with one another in an order and a single and defined direction,
- b) a step of ligation of the aforementioned cohesive single-stranded sutures of at least 2 nucleotides so as to obtain a circular double-stranded DNA vector.

In accordance with the invention, the recognition site of the type IIs enzyme of the adapter downstream of the sequence of interest is located and oriented such that the enzyme cleaves the DNA in such a way that the recognition site is eliminated and a single-stranded suture is produced (FIG. 1).

In accordance with the invention, the method is carried out in the presence of a ligase.

The term 'ligase' means an enzyme of the class of ligases (EC6) which binds the nucleic acid strands, especially the DNA ligases (EC 6.5.1.1). A ligase according to the invention binds DNA ends, oligonucleotides, RNA, and hybrid RNA-DNA. A ligase according to the invention preferably binds nucleic acid molecules at cohesive ends.

The ligase used in the method according to the invention is a ligase selected from a T3, T4, T7 or Taq ligase, preferably a T3 ligase and more preferably a T7 ligase (T7 DNA ligase) and even more advantageously a T4 ligase.

In accordance with an advantageous embodiment, the method according to the invention is a method in which step (a) of simultaneously contacting at least two molecular building blocks, which are different from one another, in the presence of a single type IIs restriction enzyme is performed at a temperature ranging from 20° C. to a temperature of 55° C., during a period ranging from 2 minutes to a period of 30 minutes,
  step (b) of ligation is performed at a temperature ranging from 10° C. to a temperature of 40° C. during a period ranging from 2 min to a period of 30 min,
  (a) and (b) can be repeated from 1 to 49 times, said method also comprising,
  (c) at least one step of incubation at a temperature from 41 to 60° C. during a period ranging from 0.5 to 15 min and, possibly,
  (d) a step of incubation at a temperature from 61 to 90° C. during a period ranging from 0.5 to 15 minutes.

In accordance with an advantageous embodiment, the method according to the invention is a method in which step (a) of simultaneously contacting at least two molecular building blocks, which are different from one another, in the presence of a single type IIs restriction enzyme is performed at a temperature ranging from 20° C. to a temperature of 55° C., during a period ranging from 2 minutes to a period of 30 minutes,
  step (b) of ligation is performed at a temperature ranging from 10° C. to a temperature of 40° C. during a period ranging from 2 min to a period of 30 min,
  (a) and (b) can be repeated from 1 to 49 times, said method also comprising,
  (c) at least one step of incubation at a temperature from 41 to 60° C. during a period ranging from 0.5 to 15 min and
  (d) a step of incubation at a temperature from 61 to 90° C. during a period ranging from 0.5 to 15 minutes.

In accordance with an especial embodiment, the method according to the invention is a method in which step
  (a) of simultaneously contacting at least two molecular building blocks, which are different from one another, in the presence of a single type IIs restriction enzyme is performed at a temperature ranging from 20° C. to a temperature of 55° C., during a period ranging from 2 minutes to a period of 30 minutes, step (b) of ligation is performed at a temperature greater than 40° C. in the presence of TAq ligase. In accordance with this particular embodiment, step (b) of ligation is carried out at a temperature lower than 95° C., preferably lower than 65° C.

Step (b) of ligation is carried out during a period ranging from 2 min to a period of 30 min, and (b) can be repeated from 1 to 49 times, said method also comprising, (c) at least one step of incubation at a temperature from 41 to 60° C. during a period ranging from 0.5 to 15 min and, possibly, (d) a step of incubation at a temperature from 61 to 90° C. during a period ranging from 0.5 to 15 minutes.

In accordance with an especial embodiment, the method according to the invention is a method in which step (a) of simultaneously contacting at least two molecular building blocks, which are different from one another, in the presence of a single type IIs restriction enzyme, is performed at a temperature ranging from 20° C. to a temperature of 55° C., during a period ranging from 2 minutes to a period of 30 minutes, step (b) of ligation is performed at a temperature greater than 40° C. in the presence of TAq ligase. In accordance with this particular embodiment, step (b) of ligation is carried out at a temperature lower than 95° C., preferably lower than 65° C.

Step (b) of ligation is carried out during a period ranging from 2 min to a period of 30 min, and (b) can be repeated from 1 to 49 times, said method also comprising, (c) at least one step of incubation at a temperature from 41 to 60° C. during a period ranging from 0.5 to 15 min and (d) a step of incubation at a temperature from 61 to 90° C. during a period ranging from 0.5 to 15 minutes.

In accordance with another embodiment, the method for producing a circular double-stranded DNA vector according to the invention is a method in which one of the at least two sequences of interest comprises at least one non-functional unit.

In accordance with another embodiment, the method for producing a circular double-stranded DNA vector is a method comprising at least two sequences of interest, in which said at least two sequences of interest are formed by a non-functional unit and in which the positioning of said sequences of interest contiguously with one another leads to a functional entity of double-stranded DNA.

In accordance with one embodiment, the method for producing a circular double-stranded DNA vector is a method for producing a circular double-stranded DNA vector in which one of the at least two sequences of interest comprises at least one functional unit.

In accordance with the invention, a functional unit can be an expression functional unit or a gene, a functional unit of integration in a eukaryotic or prokaryotic cell, or a bacterial functional unit.

In accordance with the invention, an expression functional unit or a gene comprises a coding sequence and non-coding elements, such as a promoter or a terminator, each of which can be considered individually as a functional module.

A gene according to the invention is a sequence of deoxyribonucleic acid (DNA) which specifies the synthesis of a chain of polypeptides or of a ribonucleic acid (RNA).

A gene can also be defined as a unit of genetic information. A gene comprises a sequence of nucleotides referred to as a promoter, of which the role is to allow the initiation, but above all the regulation of the transcription of DNA into RNA. In the case of coding RNA, the RNA molecule thus produced can be translated into a protein. The DNA sequence corresponding to the information that will be translated into a protein is referred to is referred to as an open reading frame. A non-translated RNA can also be functional (for example: ribosomal RNA, transfer RNA, interfering RNA). A gene can be terminated by a terminating sequence referred to as a terminator, which marks the end of the transcription.

In accordance with one embodiment, the vector according to the invention makes it possible to supply at least one piece of genetic information to the host cell, by allowing the expression or inhibition of at least one gene, or the production or blocking of at least one RNA, of at least one protein.

In accordance with the invention, the method for producing a circular double-stranded DNA is a method in which at least one functional unit is a functional unit selected from the following elements:

(i) a bacterial functional unit, (ii) an expression functional unit, (iii) a functional unit of integration in a eukaryotic or prokaryotic cell, (iv) or a combination.

In accordance with the invention, an expression vector can contain at least three functional elements, 1. Bacterial origin of replication, 2. A bacterial selection marker, 3. An expression cassette.

The method for producing a circular double-stranded DNA vector according to the invention is a method in which one of the at least two sequences of interest comprises at least one non-functional unit.

A bacterial functional unit is understood to mean a functional unit comprising a bacterial origin or replication and a bacterial selection marker.

An origin of replication in accordance with the invention can be of bacterial or artificial origin (also referred to as "ori"). It is a single DNA sequence allowing the initiation of unidirectional or bidirectional replication, especially in a bacterial cell. The replication is the process during which the DNA is synthesised by the DNA polymerase. This mechanism makes it possible to obtain, from a single DNA molecule, two DNA molecules identical to the initial molecule, except for the error of the enzyme. The structure of the origin of replication varies from one species to another. In the functional unit of bacterial replication, the origin of replication is of bacterial origin.

Examples of origin of replication incorporated herein by reference are those described in Table 1 on page 49 of the article by Wang et al., 2009 (Zhijun Wang a, Li Jin a,b, Zhenghong Yuan c, Grzegorz We grzyn d, Alicja We grzyn. Classification of plasmid vectors using origin of replication, selection marker and promoter as criteria. Plasmid, 61 (2009) 47-51).

In accordance with one aspect of the invention, the method for producing a circular double-stranded DNA vector is a method in which the bacterial functional unit contains at least one bacterial origin of replication selected from the elements featuring in the publication by Wang et al., 2009, which is hereby incorporated herein in its entirety by reference.

In accordance with another advantageous aspect of the invention, the method for producing a circular double-stranded DNA vector is a method in which the bacterial functional unit contains at least one origin of replication selected from all the prokaryotic origins of replication in Table 1 of Wang et al., 2009. The plasmids are preferably pMB1, pUC, ColE1, p15A, pSC101, R1, RK2, R6K, pA81, pRAS3.1, pTi, pBPS1, pUO1, pKH9, pWKS1, pCD1, pMAK3, pBL63.1, pTA1060, p4M, pHT926, pCD6, pJB01, pIME300, pMD5057, pTE44, pDP1, or pT38.

A selection marker according to the invention is a gene of which the expression provides its host with a measurable property, such as the ability to produce a pigment or to resist an antibiotic.

A bacterial selection marker is a gene of which the expression provides transformed bacteria (which have incorporated the vector allowing the expression of the marker of interest) with a measurable property.

A bacterial selection marker for example makes it possible to select bacteria in accordance with a defined screen. It can be a resistance gene to an antibiotic, a gene enabling the complementation of an auxotrophy, a gene coding the expression of an optically detectable molecule (dye, chemiluminescent marker, fluorochrome), or any other gene of which the product would make it possible to distinguish the bacterial colonies.

By definition, a bacterial selection marker is therefore for example a resistance gene to an antibiotic, or a screening gene.

In accordance with yet a further aspect of the invention, the method for producing a circular double-stranded DNA vector is a method in which the bacterial functional unit comprises at least one functional module, the functional module being a marker, especially a selection marker, and preferably a selection marker which is a resistance gene to an antibiotic or a screening gene.

Examples of bacterial selection markers are genes coding elements allowing a resistance to an antibiotic, such as:
　　gene bla (AmpR) allowing resistance to ampicillin,
　　gene neo allowing resistance to neomycin,
　　gene aph (kanR) allowing resistance to kanamycin,
　　gene cat allowing resistance to chloramphenicol,
　　gene aadA7 allowing resistance to spectinomycin,
　　gene aacC1 allowing resistance to gentamicin,
　　gene tetA allowing resistance to tetracycline,
　　gene erm allowing resistance to erythromycin,
　　gene van allowing resistance to vancomycin In accordance with the invention, the method for producing a circular double-stranded DNA vector is a method in which the resistance gene to an antibiotic is selected from the genes Ampicillin bla, Ampicillin blaA, Ampicillin blaZ, Kanamycin aph, Neomycin neo, Chloramphenicol cat, Chloramphenicol cmlA, Chloramphenicol catAIII, Chloramphenicol catB2, Chloramphenicol cmx, Gentamycin aacC1, Gentamycin aacC2, Tetracycline tetA(A), Tetracycline tetA(C), Tetracycline tetA(D), Tetracycline tetA(E), Tetracycline tetA(G), Tetracycline tetA(H), Tetracycline tetA(L), Tetracycline tetA(Q), Tetracycline tetA(S), Tetracycline tetA(Y)Tetracycline tetA(Z), Erythromycin erm, Vancomycin van, Spectinomycin aadA7, Streptomycin str. (Table 2, Wang et al., 2009).

The method according to the invention for producing a circular double-stranded DNA vector is preferably a method in which the resistance gene to an antibiotic is selected from the genes allowing a resistance to ampicillin, kanamycin, neomycin, gentamycin, or spectinomycin.

In accordance with the invention, the method for producing a circular double-stranded DNA vector is a method in which the screening gene is the gene lac Zα.

An expression functional unit in accordance with the method of the invention is a unit which comprises at least one functional module, said functional module being formed by one of the following elements.
　　(i) a sequence regulating the expression of genes or a sequence regulating the activity of gene regulatory sequences, selected from:
　　a promoter, a terminator, an "internal ribosome entry site" (IRES) sequence,
　　(ii) a nucleotide sequence coding a product, especially a nucleotide sequence coding an expression product, and more particularly a nucleotide sequence coding a protein,
　　(iii) a sequence coding a molecular label, or
　　(iv) a combination of these elements.

In accordance with the invention, a promoter or promoter sequence is a constituent DNA region of a gene and is indispensable for the transcription of DNA into RNA. The promoter is the zone of the DNA on which the transcription factors and RNA polymerase are initially bound, before starting the RNA synthesis. The promoter sequences are generally situated upstream of the starting site of the transcription. The promoters used in the method according to the invention are constitutive or inducible.

In accordance with the invention, a coding sequence or reading framework is a DNA sequence which, when transcribed by an enzyme which is an RNA polymerase, corresponds to an RNA, especially a messenger RNA (mRNA). Said coding sequence is situated downstream of the promoter and upstream of the terminator in the reading direction of the molecule.

The transcribed mRNA can also correspond, without being limited to one or more open reading phases (RNA transcribable into peptide or protein), to one or more non-coding RNA (for example: small interfering RNA, micro-RNA, catalytic RNA).

In accordance with the invention, a terminator or transcription terminator is a DNA sequence which marks the end of the transcription of an RNA by the enzyme responsible for the transcription. In accordance with the invention, a terminator is a prokaryotic or eukaryotic terminator.

In accordance with the invention, an IRES (internal ribosome entry site) sequence is a sequence which, in the eukaryotic cells, enables the start of the translation of a messenger RNA internally. The conventional process for translation of eukaryotic mRNAs is based on a scanning mechanism by the ribosome from the cap situated at the 5' end, which scans the mRNA as far as the first start codon. The IRES allow the direct recruitment of the ribosome at this start codon, independently of the presence of the cap and the scanning mechanism. The IRES are structured regions of the mRNA that interact directly with the ribosome or with the initiation factors of the translation.

In accordance with the invention, a molecular label is a sequence of DNA, especially coding a peptide or a protein which will be fused to a protein of interest.

The sequence of the label is inserted, or assembled in accordance with the invention, in phase, upstream of the first codon of the protein of interest or downstream of the last codon of the protein of interest, or within the open reading framework of the protein of interest. The intrinsic properties of the label make it possible to visualise and to purify the protein of interest either directly (fluorochrome) or indirectly (epitope recognised by an antibody or by another protein, enzymatic activity, etc.).

In accordance with the invention, the method for producing a circular double-stranded DNA vector is a method in which the expression functional unit comprises at least one functional module, said functional module comprising a promoter, a nucleotide sequence coding a protein, and a terminator.

In accordance with the invention, the method for producing a circular double-stranded DNA vector is a method in which the expression functional unit comprises at least one functional module, said functional module comprising a promoter, a nucleotide sequence coding a protein, or a terminator.

In accordance with the invention, the method for producing a circular double-stranded DNA vector is a method in which the expression functional unit comprises at least one expression functional module, said functional module comprising a promoter, a nucleotide sequence coding a protein, a molecular label, and a terminator.

In accordance with the invention, the method for producing a circular double-stranded DNA vector is a method in which the expression functional unit comprises at least one expression functional module, said functional module comprising a promoter, a nucleotide sequence coding a protein, a molecular label, or a terminator.

In accordance with the invention, a method for producing a circular double-stranded DNA vector is a method in which the expression functional unit comprises at least one expression functional module, said expression functional module comprising a promoter, a nucleotide sequence coding a protein, an IRES sequence, a second nucleotide sequence coding a protein, and a terminator.

In accordance with the invention, the method for producing a circular double-stranded DNA vector is a method in which the expression functional unit comprises at least one expression functional module, said expression functional module comprising a promoter, a nucleotide sequence coding a protein, an IRES sequence, a second nucleotide sequence coding a protein, or a terminator.

In accordance with the invention, the method for producing a circular double-stranded DNA vector is a method in which at least one functional module is an expression functional module containing a nucleotide sequence coding a fusion protein.

In accordance with the invention, the method for producing a circular double-stranded DNA vector is a method in which a functional module is a promoter.

In accordance with the invention, the method for producing a circular double-stranded DNA vector is a method in which a functional module is a promoter and said promoter is a promoter of the cytomegalovirus (CMV), an EF1α promoter, a promoter of the virus SV40, a promoter of beta-actin, or a promoter of ubiquitin C. The promoter according to the invention is preferably a promoter selected from the promoters described in Table 3 of Wang et al., 2009.

In accordance with the invention, the method for producing a circular double-stranded DNA vector is a method in which a functional module is a gene coding an expression product.

In accordance with the invention, the method for producing a circular double-stranded DNA vector is a method in which a functional module is a gene coding an expression product selected from the genes referenced in the "Gene" database of the NCBI (National Center for Biotechnology Information) and said gene coding an expression product is a gene of which the sequence can belong to the species *Homo sapiens, Mus musculus, Rattus norvegicus, Danio rerio, Caenorhabditis elegans, Saccharomyces Cerevisiae, Arabidopsis thaliana, rosophila melanogaster*, or to any other referenced species.

In accordance with the invention, the method for producing a circular double-stranded DNA vector is a method in which a functional module is a terminator.

In accordance with the invention, the method for producing a circular double-stranded DNA vector is a method in which a functional module is a terminator and said terminator is a sequence of polyadenylation.

In accordance with the invention, the method for producing a circular double-stranded DNA vector is a method in which at least one functional module is a marker or molecular label selected from the sequence AviTag, calmodulin-tag, polyglutamate tag, E-tag, FLAG-tag, HA-tag, His-tag, Mc-tag, S-tag, SBP-tag, Softag 1, Softag 3, Strep-tag, TC tag, V5 tag, VSV-tag, Xpress tag, isopeptag, SpyTag, BCCP (biotin carboxyl carrier protein), glutathione-S-transferase-tag, green fluorescent protein-tag, maltose binding protein-tag, Nus-tag, Thioredoxin-tag, Fc-tag, designed intrinsically disordered tags containing disorder promoting amino acids (P,E,S,T,A,Q,G, . . . ) and Ty tag.

In accordance with the invention, the method for producing a circular double-stranded DNA vector is a method in which at least one functional module is a molecular marker (or molecular label), said molecular marker being an affinity protein, selected from the maltose binding protein (MBP), glutathione-S-transferase (GST), the protein tandem affinity purification (TAP)-tag, TAP-Tag, or a sequence coding a fluorescent protein, preferably GFP or one of the numerous variants thereof (BFP, CFP, YFP, mCherry, etc.).

In accordance with the invention, the method for producing a circular double-stranded DNA vector is especially a method in which at least one functional unit is a functional unit of integration in a eukaryotic cell.

In accordance with the invention, the method for producing a circular double-stranded DNA vector is a method in which said functional unit of integration in a eukaryotic cell comprises at least one functional module comprising at least one element selected from:
  a selection gene,
  a sequence for retention in a eukaryotic cell,
  a sequence of integration, especially a sequence of homologous integration
  one or more sequences involved in DNA editing and/or one or more sequences involved in targeted homologous recombination,
  or a combination of these elements.

In accordance with the invention, the method for producing a circular double-stranded DNA vector is a method in which the selection gene is a positive selection gene or a negative selection gene.

In accordance with an advantageous embodiment, a selection gene is a positive selection gene or a negative selection gene and may or may not be dependent on the presence of external substrates.

In accordance with the invention, a positive selection gene is a gene which allows the survival or growth of the cell or the host of which the genome has been genetically modified in the presence of agents that are normally toxic for the cell or the host (for example an antibiotic, a herbicide, or a medicinal product). Some positive selection genes are not conditioned to exterior substrates, but modify physiological processes regulating the development of the cells (bacteria, fungi, animals, or plants as the case may be).

In accordance with the invention, a negative selection gene provokes the death of the cells or host genetically modified under certain conditions, which can be controlled and are known to the experimenter. In accordance with the invention, a sequence for retention in a eukaryotic cell is a DNA sequence that can be used in the case in which the vector is intended to be retained in the cellular descendant of the recipient cell, in the absence of integration in the host genome. It can be an origin of replication specific to the species of the modified cell (example sequence Autonomous Replicating Sequence (ARS) for yeast), or a centromere sequence allowing the segregation of duplicated DNA molecules in each of the daughter cells.

In accordance with the invention, a sequence homologous to the eukaryotic genome is a sequence enabling the integration by homologous recombination. The expression vector can contain DNA sequences corresponding to the genomic DNA of the organism or the targeted cell. These sequences are determined experimentally and can correspond to loci known for their susceptibility to homologous recombination.

In accordance with the invention, a sequence involved in DNA editing is a DNA sequence specifically recognised by a recombinase that allows the targeted modification of the DNA molecule. For example, the sequence LoxP1 recognised by the recombinase Cre, or the sequence FRT recognised by the recombinase Flp.

In accordance with the invention, the method for producing a circular double-stranded DNA vector is a method in which the selection gene is a positive selection gene, especially a positive selection gene in a eukaryotic cell.

In accordance with one embodiment, a positive selection gene is an antibiotic resistance gene selected from: the resistance genes to hygromycin B or derivatives thereof, the resistance genes to G418 or derivatives thereof, the resistance genes to ampicillin or derivatives thereof, the resistance genes to tetracycline or derivatives thereof, the resistance genes to puromycin or derivatives thereof, or the resistance genes to zeocin or derivatives thereof.

In accordance with another embodiment, a positive selection gene in a eukaryotic cell is an antibiotic resistance gene selected from the resistance genes to hygromycin B or derivatives thereof, the resistance genes to G418 or derivatives thereof, the resistance genes to puromycin or derivatives thereof, or the resistance genes to zeocin or derivatives thereof.

In accordance with the invention, the method for producing a circular double-stranded DNA vector is a method in which the negative selection gene is a negative selection gene coding the thymidine kinase in yeast.

In accordance with the invention, the method for producing a circular double-stranded DNA vector is a method in which the sequence for retention in eukaryotic cell is an autonomous replicating sequence (ARS) or a centromere sequence as defined for yeast.

In accordance with the invention, the method for producing a circular double-stranded DNA vector is a method in which the sequence of homologous integration is a Rosa 26 locus or a hypoxanthine phosphoribosyltransferase (HPRT) locus.

In accordance with the invention, the method for producing a circular double-stranded DNA vector is a method in which the sequence involved in the DNA editing and/or the sequence involved in the targeted homologous recombination is a sequence of 34 nucleotides of the bacteriophage P1 "locus of X over P1" (LoxP1) of generic sequence ATAACTTCGTATA-NNNTANNN-TATACGAAGTTAT (SEQ ID NO: 67) in which N is A, T, G or C, preferably a Cre recombinase-LoxP sequence.

In accordance with the invention the method for producing a circular double-stranded DNA vector is a method in which the sequence involved in the DNA editing and/or the sequence involved in the targeted homologous recombination is a sequence FRT Flp-FRT, especially a sequence GAAGTTCCTATTCtctagaaaGtATAGGAACTTC (SEQ ID NO: 68).

In accordance with the invention, the method for producing a circular double-stranded DNA vector is a method in which the type IIs restriction enzyme is a type IIs restriction enzyme selected from BsaI, Eco31I, BbsI, BpiI, BsmBI, Esp3I, BspMI, BfuAI and BveI.

The single type IIs restriction enzyme used in the method according to the invention is preferably BbsI, and more preferably the single type IIs enzyme used in the method according to the invention is BsaI.

In accordance with the invention, the method for producing a circular double-stranded DNA vector is a method in which the double-stranded DNA adapter, downstream or upstream of said sequence of interest, additionally comprises at least one recognition site of a type IIp restriction enzyme, advantageously at least one recognition site of a rare restriction enzyme, such as NotI, PacI, PmeI, SwaI, SmiI, SgsI, SgrDI, SgrAI, SbfI, FseI, AscI, AsiSI, MreI, MssI and more advantageously two sites of recognition of restriction enzymes selected from KpnI, AgeI, EcoRI and BstBI, SalI and MluI.

In general, the method for producing a circular double-stranded DNA vector is a method in which the adapters of double-stranded DNA, upstream and downstream of said sequence of interest, comprise at least one recognition site of a type IIs restriction enzyme, including a single and only recognition site of the type IIs restriction enzyme present in step (a) of simultaneously contacting at least two molecular building blocks, this being an enzyme which cleaves the DNA of the adapters and produces single-stranded ends of at least two nucleotides on either side of the sequences of interest (or the type IIs enzyme used in the method according to the invention in step a).

In accordance with an especial embodiment, the method according to the invention is a method in which the adapters of double-stranded DNA, upstream and downstream of said sequence of interest, do not have a recognition site of a type IIs restriction enzyme other than that of the type IIs restriction enzyme present in the step of simultaneously contacting at least two molecular building blocks, which are different from one another.

In accordance with an advantageous embodiment, the method for producing a circular double-stranded DNA vector according to the invention is a method in which each double-stranded DNA adapter, upstream and downstream of said sequence of interest, comprises just a single (and only) recognition site of the type IIs restriction enzyme present in step (a) of simultaneously contacting at least two molecular building blocks, which are different from one another, and each adapter has no other recognition site of a type IIs restriction enzyme.

More precisely, the method for producing a circular double-stranded DNA vector according to the invention is a method in which each double-stranded DNA adapter, upstream and downstream of said sequence of interest, comprises just a single (and only) recognition site of a single type IIs restriction enzyme which is the type IIs restriction enzyme present in step (a) of simultaneously contacting at least two molecular building blocks, which are different from one another, this being an enzyme which cleaves the DNA of the adapters and produces single-stranded ends of at least two nucleotides on either side of the sequences of interest, or the type IIs enzyme used in the method according to the invention.

In accordance with an advantageous embodiment, the method for producing a circular double-stranded DNA vector according to the invention is a method in which the site of recognition of a type IIs restriction enzyme present in each adapter consists of a single site of recognition of the type IIs enzyme used in the method according to the invention.

Especially, the single site of recognition of the type IIs enzyme used in the method according to the invention is a site recognised by BbsI and more preferably by BsaI.

In accordance with an especial embodiment, the method for producing a circular double-stranded DNA vector is a method in which the double-stranded DNA vectors, upstream and downstream of said sequence of interest, comprise a single (and only) site of recognition of the type IIs restriction enzyme present in step (a) of simultaneously contacting at least two molecular building blocks, which are different from one another, and at least one site of recognition of a type IIs restriction enzyme, said type IIs enzyme being an enzyme other than that present in step a) of simultaneously contacting at least two molecular building blocks, which are different from one another.

In accordance with the invention, the cohesive monostranded suture of at least 2 nucleotides at each of the upstream and downstream ends of the sequence of interest comprises 2 to 10 nucleotides, preferably 2 to 5 nucleotides, and more particularly 4 nucleotides.

The method according to the invention is a method in which the cohesive single-stranded suture of at least 2 nucleotides at each of the upstream and downstream ends of the sequence of interest comprises 2 to 10 nucleotides, preferably 2 to 5 nucleotides, and more particularly 4 nucleotides.

In accordance with an especial embodiment, the method for producing a circular double-stranded DNA vector is a method in which the cohesive single-stranded sutures of at least 2 nucleotides at each of the upstream and downstream ends of the sequence of interest comprise, independently of one another, 2, 3, 4, 5, 6, 7, 8, 9, 10, 11 or 12 nucleotides.

In the method according to the invention, each cohesive single-stranded suture of at least 2 nucleotides produced from a molecular building block pairs with a single cohesive single-stranded suture of at least 2 nucleotides produced from another molecular building block.

In accordance with yet a further aspect of the invention, the method for producing a circular double-stranded DNA vector is a method in which the cohesive single-stranded suture of at least 2 nucleotides can pair only with a single other cohesive single-stranded suture of at least 2 nucleotides present in the reaction mixture.

In accordance with the invention, the reaction medium is a medium in which the method according to the invention is carried out.

In accordance with an especial embodiment, the method for producing a circular double-stranded DNA vector is a method in which the cohesive single-stranded suture of at least 2 nucleotides, upstream and downstream of the sequence of interest, is designed with the aid of a scoring matrix.

In accordance with the invention, the method for producing a circular double-stranded DNA vector is a method in which said type IIs restriction enzyme cleaves the DNA at a distance ranging from 2 to 15 nucleotides, 2 to 14, 2 to 13, 2 to 12, 2 to 11, 2 to 10, 2 to 9, 2 to 8, 2 to 7, 2 to 6, 2 to 5, 2 to 4 or 2 to 3 nucleotides from the specific recognition site of said type IIs enzyme.

Advantageously, said type IIs restriction enzyme cleaves one of the two strands of DNA at a distance of 2 nucleotides, 3, 4, 5, 6, 7, 8, 9, 10, 11, 12, 13, 14 or 15 nucleotides from the specific recognition site of said type IIs enzyme.

In accordance with the method of the invention, the complementary sequence of the cohesive single-stranded suture of at least 2 nucleotides produced upstream is not complementary to the cohesive single-stranded suture of at least 2 nucleotides produced downstream of the same building block, and the complementary sequence of the cohesive single-stranded suture of at least 2 nucleotides produced upstream of (SI)1, (si−1), (of the first building block) is complementary to the cohesive single-stranded suture of at least 2 nucleotides downstream of the sequence (SI)n, (sn+1) (of the last building block).

In accordance with the invention, the method comprises, before the step of simultaneously contacting at least two molecular building blocks, a step of preparing each of the molecular building blocks by chemical synthesis or by a step of amplification by PCR of the sequence of interest contained in a building block with the aid of a forward primer comprising, from 5' to 3', a sequence corresponding to the sequence of the adapter and at least 14 nucleotides of the sequence of interest, and a reverse primer comprising, from 5' to 3', at least 14 nucleotides of the sequence of interest and at least one sequence corresponding to the sequence of the adapter.

In one embodiment, the method comprises, before the step of simultaneously contacting at least two molecular building blocks, a step of preparing each of the molecular building blocks by chemical synthesis or by a step of amplification by PCR of the sequence of interest contained in a building block with the aid of a forward primer comprising, from 5' to 3', a sequence corresponding to the sequence of the adapter and at least 14 to 20 nucleotides of the sequence of interest, and a reverse primer comprising, from 5' to 3', at least 14 to 20 nucleotides of the sequence of interest and at least one sequence corresponding to the sequence of the adapter.

In one embodiment, the method comprises, before the step of simultaneously contacting at least two molecular building blocks, a step of preparing each of the molecular building blocks by chemical synthesis or by a step of amplification by PCR of the sequence of interest contained in a building block with the aid of a forward primer comprising, from 5' to 3', a sequence corresponding to the sequence of the adapter and at least 14, 15, 16, 17, 18, 19 or 20 nucleotides of the sequence of interest, and a reverse primer comprising, from 5' to 3', at least 14, 15, 16, 17, 18, 19 or 20 nucleotides of the sequence of interest and at least one sequence corresponding to the sequence of the adapter.

PCR is a polymerase chain reaction and makes it possible to reproduce DNA in bulk.

The present invention also relates to a method for producing a circular double-stranded DNA vector comprising a step of preparing each of the molecular building blocks, which step is constituted by a step of amplification by polymerase chain reaction (PCR) of a sequence of interest contained in a matrix with the aid of a forward primer comprising, from 5' to 3', at least one sequence corresponding to an adapter and at least 14 nucleotides of the sequence of interest, and a reverse primer comprising, from 5' to 3', at least one sequence corresponding to an adapter and at least 14 nucleotides of the sequence of interest, a step of simultaneously contacting at least two molecular building blocks, which are different from one another, in the presence of a single restriction enzyme, said single restriction enzyme being a type IIs restriction enzyme, each molecular building block being a linear double-stranded DNA molecule with non-cohesive end, and containing:
  (i) a sequence of interest with no specific recognition site of the aforementioned type IIs restriction enzyme and comprising at least one unit, said unit being a functional unit or a non-functional unit, said unit comprising at least one module, said module being a functional module or a non-functional module,
  (ii) two double-stranded DNA adapters, flanked upstream and downstream of said sequence of interest, each double-stranded DNA adapter consisting of a sequence of at least 12 nucleotides, which sequence contains:
    a single and only recognition site of the aforementioned type IIs restriction enzyme,
      the recognition site of the aforementioned type IIs restriction enzyme of the adapter upstream of said sequence of interest and the recognition site of the aforementioned type IIs restriction enzyme of the adapter downstream of said sequence of interest being convergent, which step leads
    to the elimination by cleaving of the recognition sites of the type IIs restriction enzyme used,
    to the formation of a cohesive single-stranded suture of at least 2 nucleotides at each of the ends of said sequence of interest,
  said cohesive single-stranded suture of at least 2 nucleotides upstream of one of the at least two sequences of interest being capable of pairing to said cohesive single-stranded suture of at least 2 nucleotides downstream of another sequence of interest,
    to the pairing by nucleotide complementarity of the aforementioned cohesive single-stranded sutures of at least 2 nucleotides and
    to the positioning of the sequences of interest contiguously with one another in an order and a single and defined direction,
  b) a step of ligation of the aforementioned cohesive single-stranded sutures of at least 2 nucleotides,
  so as to obtain a circular double-stranded DNA vector.

PCR is a polymerase chain reaction and makes it possible to reproduce DNA in bulk.

Particular Embodiments of the Invention

There are numerous potential variants of the invention. A number of restriction enzymes can be used to carry out the assembly. These include type IIs restriction enzymes such as BsaI, BpiI, BsmBI, Esp3I, BspMI. In fact, any type of IIs enzyme that has a cleavage site remote from its recognition site and which produces a sequence having an overhang of 2 or 3 nucleotides or more can be used for the assembly. The incubation conditions for the assembly (buffer, temperature, time, nature of the DNA ligase) can be optimised in accordance with the enzyme used. For each enzyme used in the assembly, a collection of DNA fragments and of sequences of interest with no recognition sites of this enzyme is produced.

1. Preparation of DNA Building Blocks

DNA building blocks are prepared from a matrix by the polymerase chain reaction (PCR) technique, by using carefully selected oligonucleotide primers. The gene synthesis (chemical synthesis) can also be used as an alternative method for obtaining a building block.

By PCR, the primers allow the amplification of the DNA fragment by a high-fidelity polymerase so as to limit, to the greatest possible extent, the number of mutations that could be introduced randomly by the DNA polymerase. On the other hand, these primers make it possible to introduce the adapters containing especially the recognition site(s) of the type IIs enzyme used for the assembly as well as the sutures which will make it possible to obtain an oriented assembly. A building block will thus contain a sequence of interest flanked by two adapters (at 5' and 3' of said sequence of interest). The recognition sites of the type IIs restriction enzyme used for the assembly potentially present in the sequence of interest are undesirable and must be eliminated beforehand by directed mutagenesis or by any other suitable method.

1.1. Definition of Primers

The oligonucleotide primers used for the creation of building blocks contain 2 essential parts.

At part 5', these primers contain the sequence of an adapter. The adapter contains a sequence comprising:
  a sequence of 2 nucleotides minimum, which can contain or participate in 1 or more sites of restriction of type II endonuclease,
  a sequence of 5, 6, 7 or more nucleotides corresponding to the binding site of the enzyme with the type IIs activity used for the assembly,
  a sequence of 1 to 8 and more nucleotides corresponding to the spacing between the binding site and the cleavage site of the enzyme used. The length of this sequence is dependent on the intrinsic characteristics of the type IIs enzyme used,
  a sequence of 2 to 5 or more nucleotides corresponding to the single-stranded end produced by the action of the type IIs enzyme used. This sequence allows the pairing of the fragments to be assembled and corresponds de facto to the definition of a suture.

At part 3', the primers contain a sequence of 14 to 100 nucleotides corresponding to the 5' ends of the sequence of interest, which will enable the hybridisation of the primers at complementary zones of the matrix and the amplification of the sequence of interest. This sequence is of variable size, but greater than or equal to 14 nucleotides. In addition, it is selected so as to i) respect the rather close Tm (fusion temperature) for two primers designed for production of a given building block and ii) where possible finish the primer on at least one G or a C and not more than 2 consecutive Gs or Cs.

In accordance with the invention, 'matrix' means a DNA molecule containing the sequence of interest to be amplified. For example, it can be genomic DNA, or complementary DNA obtained by reverse transcription of an mRNA or a plasmid.

In accordance with another embodiment, supplementary sequences can be inserted between the sequence of the adapter and the complementary sequence of the matrix. A supplementary sequence can be, for example, a sequence coding supplementary amino acids which will be fused to the protein product coded by the sequence of interest.

1.2. PCR (High-Fidelity) with Protocol and Control of the Products Obtained

Each building block is amplified with a high-fidelity DNA polymerase. The phusion taq DNA polymerase (Thermo Scientific) is used in accordance with the manufacturer's protocol, but any high-fidelity DNA polymerase could be used. The amount of matrix used is reduced to a minimum (10 pg to 2 ng/µl, depending on the building block).

The PCR products are purified with the aid of a kit (for example: Macherey Nagel PCR and gel cleanup Kit®) either directly (PCR cleanup) or by running through a step of deposition on an agarose gel in TAE buffer (Tris 40 mM pH8, acetate 20 mM, EDTA 1 mM) or after migration, where the agarose gel pieces containing the PCT products are cleaved and then purified (gel cleanup) and the DNA is then quantified using a nanospectrophotometer (for example: Nanodrop®)

1.3. Strategy for Eliminating Potentially Present Sites of Type IIs Enzyme (for Example BsaI)

So that the building blocks can be assembled and so that the method according to the invention is effective, there should not be any site of the type IIs restriction enzyme used in the method according to the invention (for the assembly) within the sequences of interest. For this, the Golden Gate mutagenesis technique was used, as described by Engler et al., 2008, but any directed mutagenesis technique can be used. (Cormack, B. 2001. Directed Mutagenesis Using the Polymerase Chain Reaction. Current Protocols in Molecular Biology. 37:8.5:8.5.1-8.5.10.) As the case may be, the necessary mutations are introduced so as to conserve the biological function(s) of the sequence of interest (for example: binding sites to the DNA, secondary structures, expression product).

1.4 Method for Choosing Sutures

Due to the use of the adapters according to the invention, the molecular building blocks can be assembled at the nucleotide base. This level of precision makes it possible to eliminate any nucleotide scar.

The term 'scar' means any nucleotide or group of nucleotides of which the presence in the final vector would be made obligatory by the use of the assembly technique, but does not assure any function within the vector itself.

The choice of the sutures is crucial to promote correct assembly. It must satisfy a number of simple criteria. Firstly, a suture must not be palindromic: in fact, a palindromic suture can bind with or to itself, which could lead to difficulties with regard to the assembly and/or could lead to the formation of building block dimers bound head-to-tail.

In accordance with the invention, the suture must not be palindromic (for example: ACGT of which the anti-parallel sequence ACGT is identical) in order to avoid a self-pairing corresponding to an assembly of several examples of the same building block, head-to-tail, so as to form chains.

A palindromic sequence is a sequence that reads the same way from 5' to 3' on each of the two strands of DNA.

In the method according to the invention, there cannot be any "self-circularisation", since the sutures at 5' and 3' are selected so as not to be complementary to one another. The anti-parallel sequence resulting from a cleavage is the non-cohesive end of the freed adapter.

The choice of a suture at one assembly position then eliminates the possibility of using it at another position. Lastly, the choice of sutures that are too similar (differing only by a single nucleotide) in two positions in an assembly is avoided because this could lead to illegitimate assemblies and ligations. In fact, a partially complementary pairing (only 3/4 nucleotides interacting) or 'mismatch' or mispairing can be sufficient for the activity of certain DNA ligases and can therefore lead to the formation of abnormal structures.

This criterion reduces the frequency of obtaining abnormal constructions.

In order to observe these guidelines, a simple program has been developed which, depending on the sutures already selected, eliminates sutures deemed to be incompatible. The programme is based on the use of a matrix of suture combinations: for each 240 possible non-palindromic combinations, a score of compatibility is calculated with each of the 239 others. The method for calculating this score is shown in the schema (FIG. 2):

Consequently, each pairing of two sequences of 4 non-palindromic nucleotides (that is to say 57,600 combinations) is attributed a score ranging from 0 to 10, where 0 corresponds to a total absence of complementarity (0%) and 10 indicates total complementarity (100%).

Figure 3:
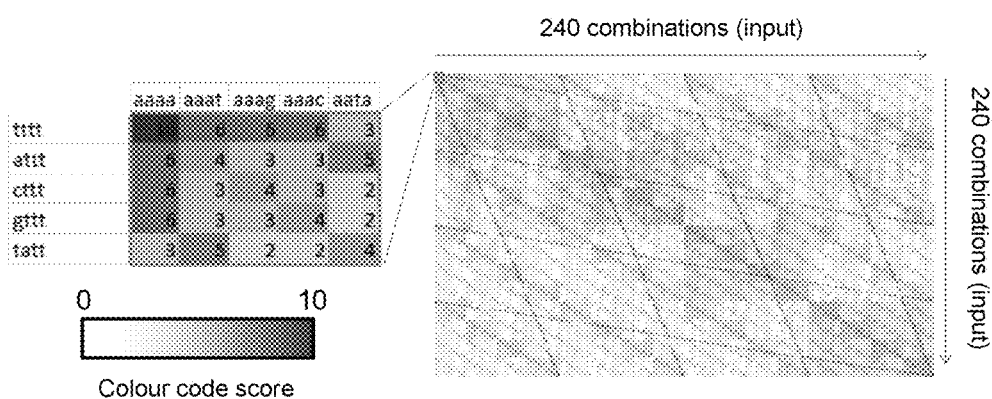

Complementarity means inter-suture complementarities. These scores are integrated in an illustrated matrix (FIG. 3). For a given vector, the necessary totality of sutures is selected such that each suture has a minimal score of complementarity with each of the other sutures necessary for the assembly.

2. General Assembly Protocol

In order to assemble the building blocks with one another in order to obtain the desired vector, it is necessary to mix them at equimolar ratios in the presence of a single type IIs restriction enzyme and a ligase.

Advantageously, the building blocks are mixed at equimolar ratios in the presence of a single type IIs restriction enzyme and a ligase, in a suitable buffer.

The amount in ng of each molecular building block is calculated as follows: $Q_{(ng)} = Size_{(bp)} \times 649_{(ng \cdot nmol^{-1} \cdot bp^{-1})} \times (20$ to $100) \cdot 10 \text{-} 6_{(nmol)}$ and the volume is calculated as follows: $V_{(\mu l)} = Q_{(ng)}/concentration_{(ng \cdot \mu l^{-1})}$.

The mixture is produced at a temperature ranging from 0 to 6° C., preferably at 4° C.

The mixture is then exposed to a temperature of 37° C. during a period ranging from 30' to 6 hours, for a number of molecular building blocks to be assembled of less than 5.

The mixture is subjected to incubation cycles of 2' at 37° C. then 3' at 16° C. (25 to 50 cycles) if the number of molecular building blocks is greater than 4.

The mixture is then incubated at 50° C. for 5' (cutting of the remaining (non-cut) type IIs endonuclease sites)) then at 80° C. for 5' (inactivation of the enzymes).

The reaction mixture is then used to transform competent bacteria, which are then selected.

3. Verifications of the Constructions

Two levels of verification can be considered:
1)—verification of the molecule produced in terms of sequence
2)—verification of the vector in terms of functionality
1)—Parallel to the assembly in vitro, a virtual assembly of the fragments is carried out by computer in order to reconstruct the sequence of the desired vector. This enables the establishment of a restriction map of the vector. In order to verify the clones obtained, the mini preparations of circular DNA are digested by one or more enzymes selected so as to generate at least three fragments of distinct size. The enzymes are preferably chosen such that there is at least one site present in each of the assembled fragments. The analysis of the restriction profile after agarose gel electrophoresis makes it possible to verify that the fragments have all been assembled in the desired order.

Other methods for verifying the obtained clones can be considered, especially a verification by PCR in order to verify the constructions by measuring the size of fragments. In addition, the entire vector or part thereof can be sequenced (Prober J M, Trainor G L, Dam R J, Hobbs F W, Robertson C W, Zagursky R J et al. (16 Oct. 1987). "A system for rapid DNA sequencing with fluorescent chain-terminating dideoxynucleotides". Science 238 (4825): 336-4.).

2)—In accordance with the sequences of interest integrated in the vectors according to the invention, it is also possible to directly or indirectly measure and/or quantify the functionality of the units and/or modules forming the vector. For example, the extraction of a vector from a culture of transformed bacteria produced in the presence of a suitable antibiotic (for example: kanamycin, ampicillin, chlorophenicol) makes it possible to validate the functionality of modules forming the bacterial unit. Similarly, the creation of eukaryotic clones provided by a selection made by an appropriate drug (for example: G418m hygromycin, puromycin) makes it possible to validate the functionality of modules forming a unit of integration in a eukaryotic cell. Lastly, the presence of an expression product (mRNA, micro-RNA, long non-coding RNA) can be detected on the basis of the total RNAs extracted from the target cell having received the vector, by PCR or by any method making it possible to measure the presence of RNA in a cell, such as the RNA-Fish (Langer-Safer P R, Levine M, Ward D C (July 1982). "Immunological method for mapping genes on *Drosophila* polytene chromosomes". *Proc. Natl. Acad. Sci. U.S.A.* 79 (14): 4381-5. doi: 10.1073/pnas.79.14.4381) or the SmartFlare (Prigodich, A. E.; Randeria, P. S.; Briley, W.; Kim, N.; Daniel, W. L.; Giljohann, D. A.; Mirkin, C. A. "Multiplexed Nanoflares: mRNA Detection in Live Cells," Anal. Chem. 2012, 84, 2062-2066, doi: 10.1021/ac202648w). As the case may be, the expression of an interfering RNA can be detected by measuring the reduction of the expression (mRNA) of the endogenous gene targeted by said interfering RNA.

In accordance with an advantageous aspect, the invention relates to a vector selected from a vector V1, V1.1, V1.2, V1.3, V2 and V3.

In accordance with an advantageous vector, the invention relates to a vector selected from a vector V1, V1.1, V1.2, V1.3, V2, V3, V2b, V3b, V1.1b, V4.

Advantageously, the invention relates to a vector without a multiple cloning site and without scar, and even more advantageously a vector without scar and without a site of restriction of the type IIs enzyme having been used for the assembly of said vector.

In accordance with an advantageous aspect, the invention relates to a group of vectors V1, especially a group of vectors V1 obtained in accordance with the method of the invention.

In accordance with an advantageous aspect, the invention relates to a group of vectors V1.1, especially a group of vectors V1.1 obtained in accordance with the method of the invention.

In accordance with an advantageous aspect, the invention relates to a group of vectors V1.2, especially a group of vectors V1.2 obtained in accordance with the method of the invention.

In accordance with an advantageous aspect, the invention relates to a group of vectors V1.3, especially a group of vectors V1.3 obtained in accordance with the method of the invention.

In accordance with an advantageous aspect, the invention relates to a group of vectors V2, especially a group of vectors V2 obtained in accordance with the method of the invention.

In accordance with an advantageous aspect, the invention relates to a group of vectors V3, especially a group of vectors V3 obtained in accordance with the method of the invention.

In accordance with an advantageous aspect, the invention relates to a group of vectors V4, especially a group of vectors V4 obtained in accordance with the method of the invention.

A vector V1 (SEQ ID NO: 41) according to the invention is constructed from a combination of building blocks Ori AmpR BsaI B (SEQ ID NO: 36), pCMV BsaI B (SEQ ID NO: 37), hFUT3 BsaI A (SEQ ID NO: 38), BGHpA BsaI B (SEQ ID NO: 39), and shB3Galt6 BsaI A (SEQ ID NO: 40).

A vector V1.1 (SEQ ID NO: 48) according to the invention is constructed from a combination of building blocks Ori-AmpR BsaI B (SEQ ID NO:36), pCMV BsaI B (SEQ ID NO: 37), hFUT3 BsaI A (SEQ ID NO: 38), BGHpA BsaI B (SEQ ID NO: 39), shB3GALT6 BsaI B (SEQ ID NO: 46), and HygroR BsaI B (SEQ ID NO: 47).

A vector V1.2 (SEQ ID NO: 53) according to the invention is constructed from a combination of building blocks Ori-AmpR BsaI B (SEQ ID NO: 36), rosa26-5' BsaI A (SEQ ID NO: 49), pCMV BsaI C (SEQ ID NO: 50), hFUT3 BsaI A (SEQ ID NO: 38), BGHpA BsaI B (SEQ ID NO: 39), shB3GALT6 BsaI B (SEQ ID NO: 46), HygroR BsaI C (SEQ ID NO: 51), and rosa26-3' BsaI A (SEQ ID NO: 52).

A vector V1.3 (SEQ ID NO: 58) according to the invention is constructed from a combination of building blocks Ori-AmpR BsaI B (SEQ ID NO: 36), rosa26-5' BsaI A (SEQ ID NO: 49), pCMV BsaI C (SEQ ID NO: 50), hFUT3 BsaI A (SEQ ID NO: 38), BGHpA BsaI B (SEQ ID NO: 39), shB3GALT6 BsaI B (SEQ ID NO: 46), HygroR BsaI C (SEQ ID NO: 51), rosa26-3' BsaI B (SEQ ID NO: 54), pEF1a BsaI A (SEQ ID NO: 55), TK BsaI A (SEQ ID NO: 56), and Tkter BsaI A (SEQ ID NO: 57).

A vector V2 (SEQ ID NO: 62) according to the invention is constructed from a combination of building blocks Ori-AmpR BsaI B (SEQ ID NO: 36), pCMV BsaI B (SEQ ID NO: 37), TO3G BsaI A (SEQ ID NO: 59), BGHpA BsaI B (SEQ ID NO: 39), pTRE3G BsaI A (SEQ ID NO: 60), mB3Galt6 BsaI B (SEQ ID NO: 63), and Tkter BsaI A (SEQ ID NO: 57).

A vector V3 (SEQ ID NO: 66) according to the invention is constructed from a combination of building blocks Ori-AmpR BsaI B (SEQ ID NO: 36), pCMV BsaI B (SEQ ID NO: 37), TO3G BsaI A (SEQ ID NO: 59), BGHpA BsaI B (SEQ ID NO: 39), pTRE3G BsaI A (SEQ ID NO: 60), mb3GALT6 BsaI B (SEQ ID NO: 63), Tkter BsaI B (SEQ ID NO:64), and shB3Galt6 BsaI C (SEQ ID NO:65).

A vector V2b (SEQ ID NO: 149) according to the invention is constructed from a combination of building blocks Ori BsaI A (SEQ ID NO: 104), AmpR BsaI A (SEQ ID NO: 105), pCMV BsaI B (SEQ ID NO: 37), TO3G BsaI A (SEQ ID NO: 59), BGHpA BsaI B (SEQ ID NO: 39), pTRE3G BsaI A (SEQ ID NO: 60), mB3Galt6 BsaI B (SEQ ID NO: 63), and Tkter Bsa IA (SEQ ID NO: 57).

A vector V3b (SEQ ID NO: 150) according to the invention is constructed from a combination of building blocks Ori BsaI A (SEQ ID NO: 104), AmpR BsaI A (SEQ ID NO: 105), pCMV BsaI B (SEQ ID NO: 37), TO3G BsaI A (SEQ ID NO: 59), BGHpA BsaI B (SEQ ID NO: 39), pTRE3G BsaI A (SEQ ID NO: 60), mb3GALT6 BsaI B (SEQ ID NO:63), Tkter BsaI B (SEQ ID NO: 64), and shB3Galt6 BsaI C (SEQ ID NO: 65).

A vector V1.1b (SEQ ID NO: 151) according to the invention is constructed from a combination of building blocks Ori BsaI B (SEQ ID NO: 106), AmpR BsaI B (SEQ ID NO: 107), pEF1aL BsaI B (SEQ ID NO: 108), EGFP-CAAX BsaI A (SEQ ID NO: 109), BGHpA BsaI C (SEQ ID NO: 110), pCMV BsaI D (SEQ ID NO: 111), SiaT BsaI B (SEQ ID NO: 112), mCherry BsaI B (SEQ ID NO: 113), TKter BsaI B (SEQ ID NO: 64) and HygroR BsaI D (SEQ ID NO: 114).

A vector V4 (SEQ ID NO: 152) according to the invention is constructed from a combination of building blocks Ori-2 BsaI C (SEQ ID NO: 115), AmpR BsaI C (SEQ ID NO: 116), MNN10-Lrec BsaI A (SEQ ID NO: 117), KanMX BsaI A (SEQ ID NO: 119), and MNN10-Rrec BsaI A (SEQ ID NO: 118).

A vector according to the invention is a vector having a sequence selected from the sequences SEQ ID NO: 41, 48, 53, 58, 62 and 66.

A vector according to the invention is a vector having a sequence selected from the sequences SEQ ID NO: 149, 150, 151 and 152.

A vector according to the invention is a vector having a sequence selected from the sequences SEQ ID NO: 41, 48, 53, 58, 62, 66, 149, 150, 151 and 152.

Another vector according to the invention is a vector having a sequence selected from the sequences SEQ ID NO: 30, 31, 32, 33, 34 and 35.

The vectors obtained in accordance with the method of the invention are the vectors of sequence SEQ ID NO: 30 31, 32, 33, 34 and 35.

The vectors obtained in accordance with the method of the invention are the vectors of sequence SEQ ID NO: 30, 31, 32, 33, 34, 35, 41, 48, 53, 58, 62, 66, 149, 150, 151 and 152.

In accordance with another embodiment, the invention relates to a circular double-stranded DNA vector as obtained by carrying out the method of the invention.

The invention also relates to a double-stranded DNA vector with no multiple cloning site and allowing the simultaneous expression of multiple transgenes and consisting of a sequence comprising the following functional units: U1, nxU2a and mxU2b, U1 representing a bacterial functional unit,
U2a representing an expression functional unit of which the promoter is dependent on RNA polymerase II and of which the expression product is a protein,
U2b representing an expression functional unit of which the promoter is dependent on RNA polymerase III and of which the expression product is a non-coding RNA,
n being greater than or equal to 0,
m being greater than or equal to 0, on the condition that n+m≥2,
the unit U1 possibly being contiguous with the units nxU2a, these in turn possibly being contiguous with the units mxU2b;
the unit U1 preferably being contiguous with the units nxU2a, these in turn preferably being contiguous with the units mxU2b.

These vectors constitute a group of vectors V1.

This group of vectors V1 can be prepared in accordance with the method of the invention.

In accordance with yet a further aspect, the invention relates to a group of vectors V1 as obtained by carrying out the method of the invention.

The invention also relates to a double-stranded DNA vector with no multiple cloning site and allowing selection of the integration of transgenes by non-homologous recombination in the target genome and consisting of a sequence comprising the following functional units: U1, nxU2a, mxU2b and U3a, U1 representing a bacterial functional unit,
U2a representing an expression functional unit of which the promoter is dependent on RNA polymerase II and of which the expression product is a protein,
U2b representing a functional expression unit of which the promoter is dependent on RNA polymerase III and of which the expression product is a non-coding RNA,
n being greater than or equal to 0,
m being greater than or equal to 0, on the condition that n+m≥2,
U3a representing a positive selection cassette,
the unit U1 possibly being contiguous with the units nxU2a, these in turn possibly being contiguous with the units mxU2b, these in turn possibly being contiguous with U3a;
the unit U1 preferably being contiguous with the units nxU2a, these in turn preferably being contiguous with the units mxU2b, these in turn preferably being contiguous with U3a.

These vectors constitute a group of vectors V1.1.

This group of vectors V1.1 can be prepared in accordance with the method of the invention.

In accordance with yet a further aspect, the invention relates to a group of vectors V1.1 as obtained by carrying out the method of the invention.

The invention also relates to a double-stranded DNA vector with no multiple cloning site and allowing selection of the simultaneous integration of multiple transgenes by non-homologous recombination in the target genome and consisting of a sequence comprising the following functional units: U1, U3b, nxU2a, mxU2b, U3a and U3c, U1 representing a bacterial functional unit, U3b representing a motif 5' of a homologous recombination sequence X
U2a representing an expression functional unit of which the promoter is dependent on RNA polymerase II and of which the expression product is a protein,
U2b representing a functional expression unit of which the promoter is dependent on RNA polymerase III and of which the expression product is a non-coding RNA,
n being greater than or equal to 0,
m being greater than or equal to 0, on the condition that n+m≥2,
U3a representing a positive selection cassette,
U3c representing a motif 3' of a homologous recombination sequence X,
the unit U1 being contiguous with U3b, this in turn being contiguous with the units nxU2a, these in turn being contiguous with the units mxU2b, these in turn being contiguous with the unit U3a, this
in turn being contiguous with the unit U3c.

These vectors constitute a group of vectors V1.2.

This group of vectors V1.2 can be prepared in accordance with the method of the invention.

In accordance with yet a further aspect, the invention relates to a group of vectors V1.2 as obtained by carrying out the method of the invention.

The invention also relates to a double-stranded DNA vector with no multiple cloning site and allowing elimination of the host cells having integrated one or more transgenes by non-homologous recombination and consisting of a sequence comprising the following functional units: U1, U3b, nxU2a, mxU2b, U3a, U3c and U3d, U1 representing a bacterial functional unit, U3b representing motif 5' of a homologous recombination sequence X U2a representing an expression functional unit of which the promoter is dependent on RNA polymerase II and of which the expression product is a protein, U2b representing a functional expression unit of which the promoter is dependent on RNA polymerase III and of which the expression product is a non-coding RNA, n being greater than or equal to 0, m being greater than or equal to 0, on the condition that n+m≥2, U3a representing a positive selection cassette, U3c representing motif 3' of a homologous recombination sequence X, U3d representing a negative selection cassette, the unit U1 being contiguous with the unit U3b, this in turn being contiguous with the units nxU2a, these in turn being contiguous with the units mxU2b, these in turn being contiguous with the unit U3a, this in turn being contiguous with the unit U3c, this in turn being contiguous with the unit U3d. These vectors constitute a group of vectors V1.3.

This group of vectors V1.3 can be prepared in accordance with the method of the invention.

In accordance with yet a further aspect, the invention relates to a group of vectors V1.3 as obtained by carrying out the method of the invention.

The invention also relates to a double-stranded DNA vector with no multiple cloning site and allowing expression of one or more transgenes in an inducible manner and consisting of a sequence comprising the following functional units: U1, U2c, nxU2d, and mxU2e, U1 representing a bacterial functional unit, U2c representing a gene coding a transcriptional transactivator, U2d representing a gene of which the promoter is dependent on the transactivator coded by the gene U2c, U2e representing a gene of which the promoter is not dependent on the transactivator coded by the gene U2c, n being greater than or equal to 1, m being greater than or equal to 0, the unit U1 possibly being contiguous with the unit U2c, this in turn possibly being contiguous with the units nxU2d, these in turn possibly being contiguous with the units mxU2e;

the unit U1 preferably being contiguous with the unit U2c, this in turn preferably being contiguous with the units nxU2d, these in turn preferably being contiguous with the units mxU2e.

These vectors constitute a group of vectors V2.

This group of vectors V2 can be prepared in accordance with the method of the invention.

In accordance with yet a further aspect, the invention relates to a group of vectors V2 as obtained by carrying out the method of the invention.

The invention also relates to a double-stranded DNA vector with no multiple cloning site and allowing execution of the genetic complementation under inducible control and consisting of a sequence comprising the following functional units: U1, U2f, U2c, and U2g, U1 representing a bacterial functional unit, U2c representing a gene coding a transcriptional transactivator, U2f representing a gene of which the promoter is an RNA polymerase III promoter and of which the expression product is a short hairpin RNA (shRNA) precursor of a small interfering RNA targeting a gene X, U2g representing a gene of which the promoter is dependent on the transactivator coded by the gene U2c and of which the expression product is a mutated version of the product of the gene X so as to be insensitive to the product of the gene U2f, the unit U1 possibly being contiguous with the unit U2f, this in turn possibly being contiguous with the unit U2c, this in turn possible being contiguous with the unit U2g, the unit U1 preferably being contiguous with the unit U2f, this in turn preferably being contiguous with the unit U2c, this in turn preferably being contiguous with the unit U2g.

These vectors constitute a group of vectors V3.

This group of vectors V3 can be prepared in accordance with the method of the invention.

In accordance with yet a further aspect, the invention relates to a group of vectors V3 as obtained by carrying out the method of the invention.

The invention also relates to a double-stranded DNA vector with no multiple cloning site and allowing selection of the cells of which the genome has been edited by targeted homologous recombination and consisting of a sequence comprising the following functional units: U1, U3a, U3b and U3c, U1 representing a bacterial functional unit, U3a representing a positive selection cassette, U3b representing a motif 5' of a sequence of homologous recombination X U3c representing a motif 3' of a homologous recombination sequence X, the unit U1 being contiguous with the unit U3b, this in turn being contiguous with the unit U3a, this in turn being contiguous with the unit U3c.

These vectors constitute a group of vectors V4.

This group of vectors V4 can be prepared in accordance with the method of the invention.

In accordance with yet a further aspect, the invention relates to a group of vectors V4 as obtained by carrying out the method of the invention.

KEY TO THE FIGURES

FIG. 1

A: Schema showing a molecular building block on which a type IIs enzyme (circle) bound to an adapter (A) on either side of a sequence of interest (SI) is bound to the DNA at its recognition site and cleaves the DNA at a distance form the recognition site (arrow) so as to produce an SI having two single-stranded ends of at least 2 nucleotides (suture) which will allow an ordered assembly.

B. Example of a cut induced by a type IIs enzyme producing a single-stranded end that can pair with another single-stranded end, these being assembled without scar.

Figure 2:
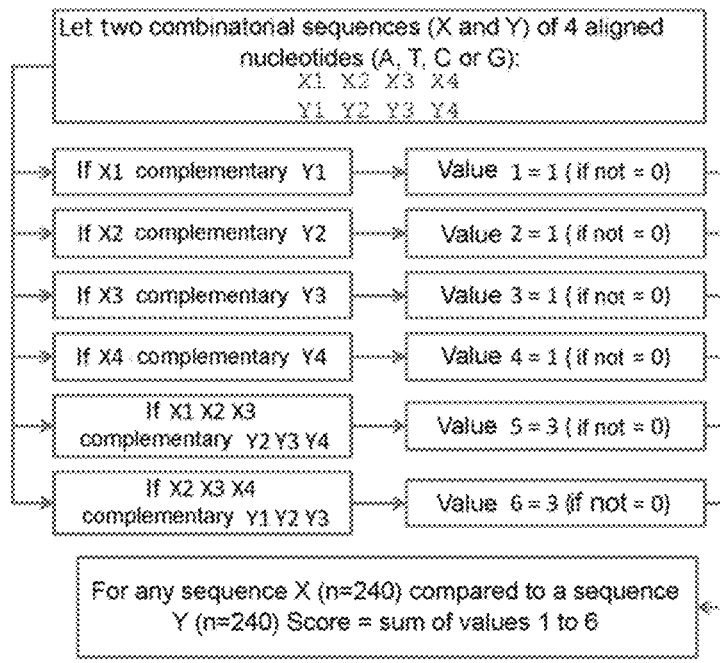

FIG. 2: Schema representing the method for calculating the compatibility score for choosing sutures (inter-suture choice).

FIG. 3: Matrix of the scores obtained for all the possible combinations

Figure 4:
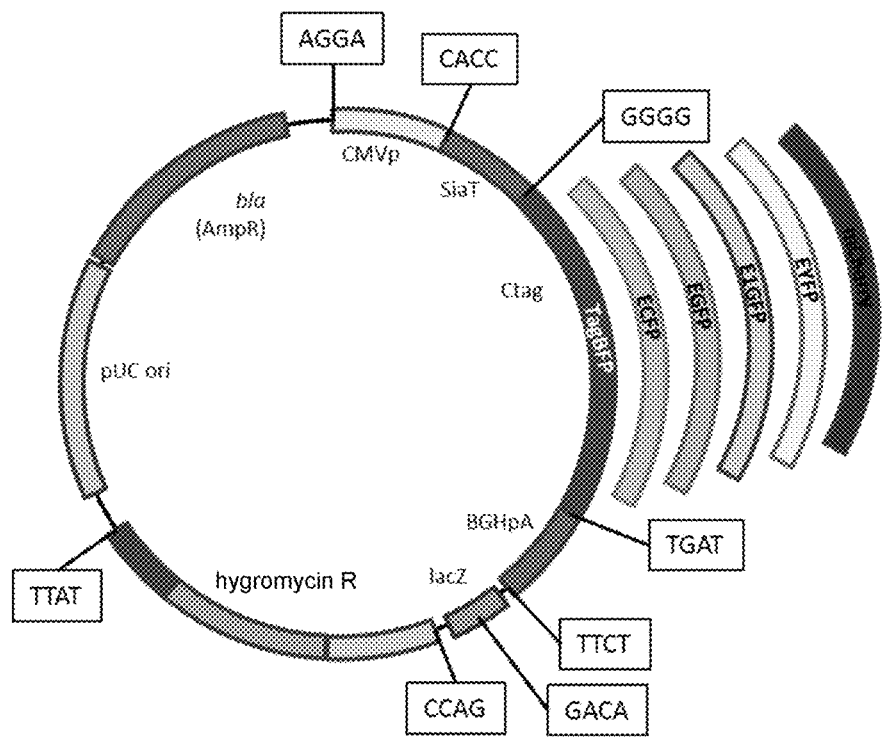

FIG. 4: Schema showing plasmids produced in accordance with the invention (embodiment 1) and sutures for assembly of the building blocks FIG. 5: Restriction map of the plasmid pHCsiaT-EGFP of embodiment 1 and verification of the assembly FIG. 6: Schema of the vector V1 (SEQ ID NO: 41) according to the invention and of the sutures allowing the assembly of the building blocks Ori-AmpR BsaI B (SEQ ID NO: 36), pCMV BsaI B (SEQ ID NO: 37), hFUT3 BsaI A (SEQ ID NO: 38), BGHpA BsaI B (SEQ ID NO: 39), and shB3Galt6 BsaI A (SEQ ID NO: 40).

Where 1=Ori-AmpR BsaI B (SEQ ID NO: 36), 2=pCMV BsaI B (SEQ ID NO: 37), 3=hFUT3 BsaI A (SEQ ID NO: 38), 4=BGHpA BsaI B (SEQ ID NO: 39) and 5=shB3Galt6 BsaI A (SEQ ID NO: 40).

Figure 7:
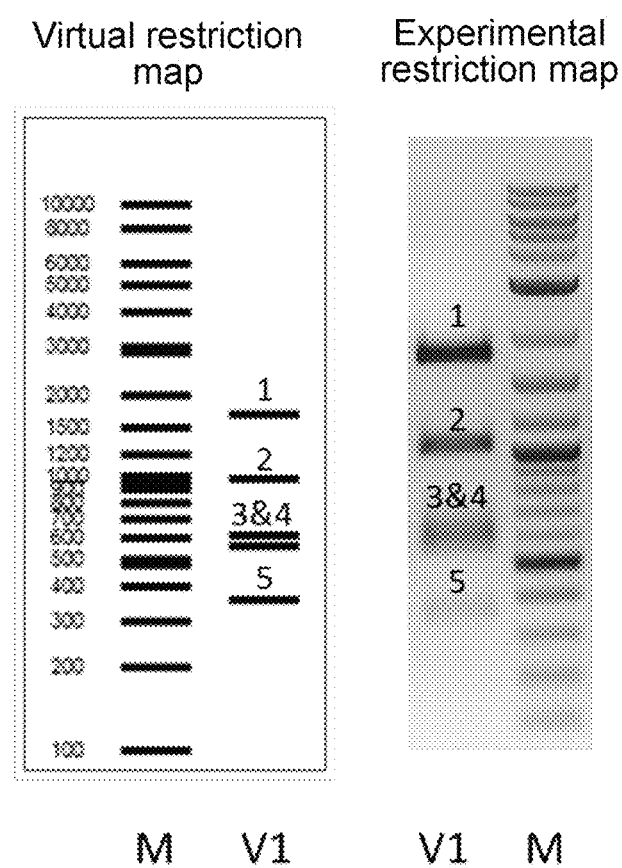

FIG. 7: Restriction fingerprint by triple digestion EcoRV/PvuI/SalI of the vector V1.

The digestion produces 5 fragments of 1705, 992, 602, 561 and 357 base pairs respectively.
- 1: 1705 bp, from SalI [3821] to PvuI [1305]
- 2: 992 bp, from EcoRV [2829] to SalI [3821]
- 3: 606 bp, from SalI [1866] to SalI [2472]
- 4: 561 bp, from PvuI [1305] to SalI [1866]
- 5: 357 bp, from SalI [2472] to EcoRV [2829]

Figure 8:
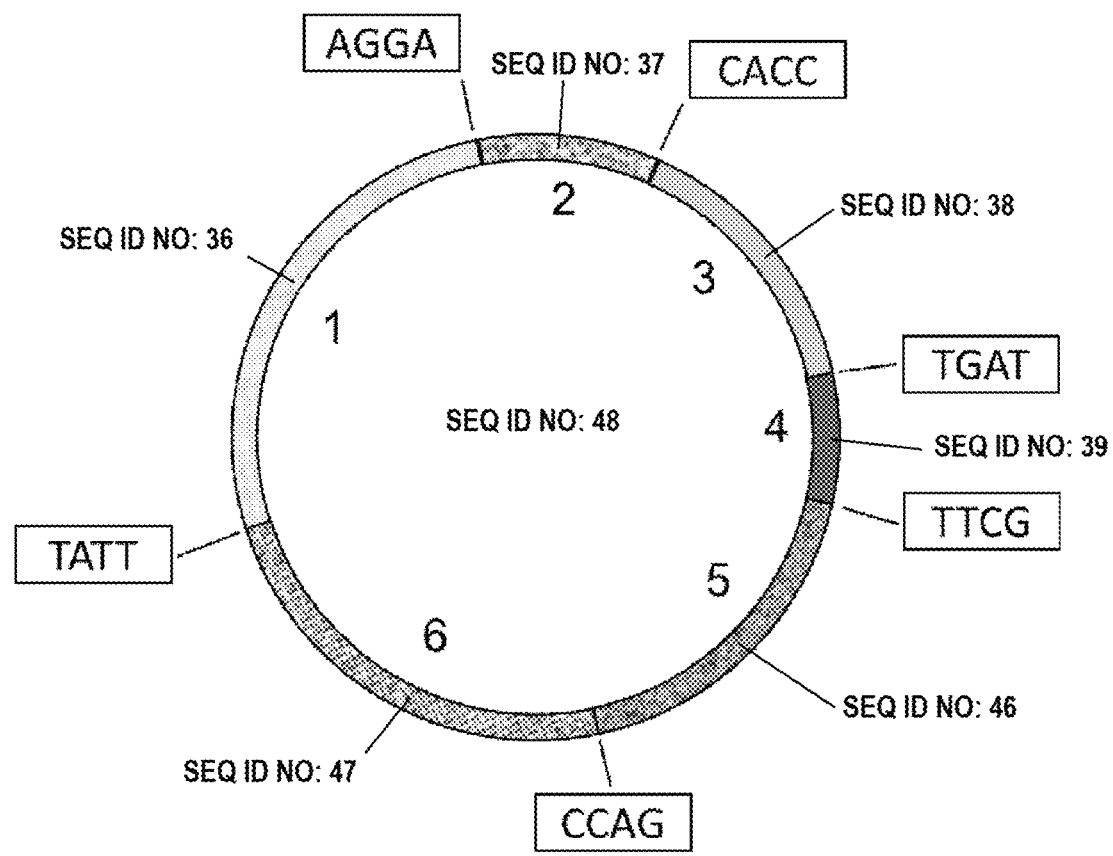

FIG. 8: Schema of the vector V1.1 (SEQ ID NO: 48) according to the invention and of the sutures allowing the assembly of the building blocks Ori-AmpR BsaI B (SEQ ID NO:36), pCMV BsaI B (SEQ ID NO: 37), hFUT3 BsaI A (SEQ ID NO: 38), BGHpA BsaI B (SEQ ID NO: 39), shB3Galt6 BsaI B (SEQ ID NO: 46), and HygroR BsaI B (SEQ ID NO: 47).

Where 1=Ori-AmpR BsaI B (SEQ ID NO: 36), 2=pCMV BsaI B (SEQ ID NO: 37), 3=hFUT3 BsaI A (SEQ ID NO: 38), 4=BGHpA BsaI B (SEQ ID NO: 39), 5=shB3Galt6 BsaI B (SEQ ID NO: 46) and 6=HygroR BsaI B (SEQ ID NO: 47)

Figure 9:
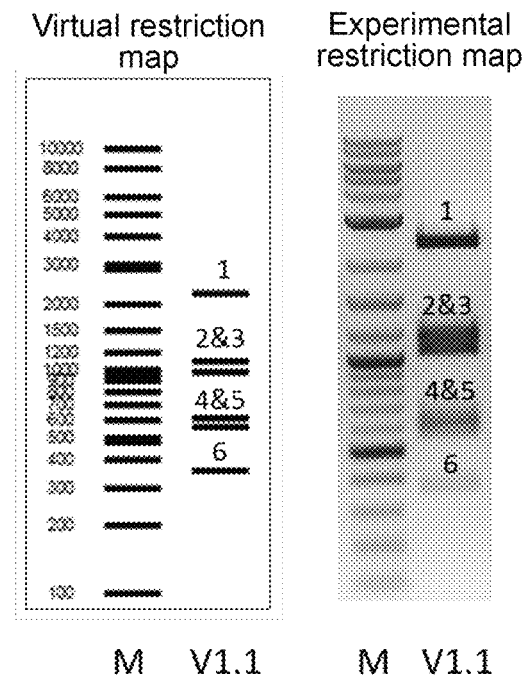

FIG. 9: Restriction fingerprint by triple digestion EcoRV/PvuI/SalI of the vector V1.1.

The digestion produces 6 fragments of 2217, 1104, 992, 606, 561 and 357 base pairs respectively.
- 1: 2 217 bp, from PvuI [4925] to PvuI [1305]
- 2: 1104 bp, from SalI [3821] to PvuI [4925]
- 3: 992 bp, from EcoRV [2829] to SalI [3821]
- 4: 606 bp, from SalI [1866] to SalI [2472]
- 5: 561 bp, from PvuI [1305] to SalI [1866]
- 6: 357 bp, from SalI [2472] to EcoRV [2829]

Figure 10:
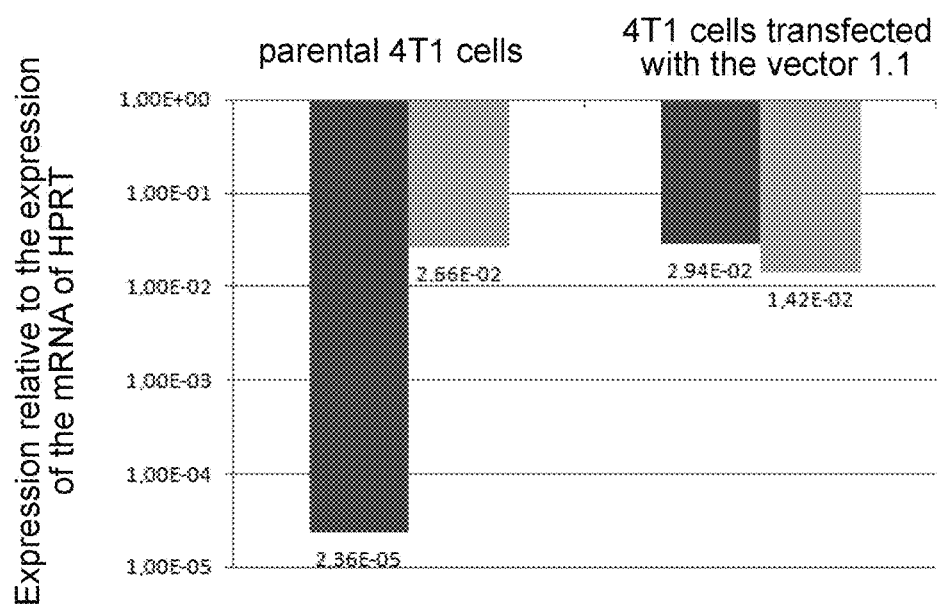

FIG. 10: Functional verification of the vector V1.1 (SEQ ID NO: 48): expression profile of hFUT3 and mB3GALT6 measured by qRT-PCR from total RNAs extracted from a clone of 4T1 mouse cells stably transfected by the vector V1.1.

Figure 11:
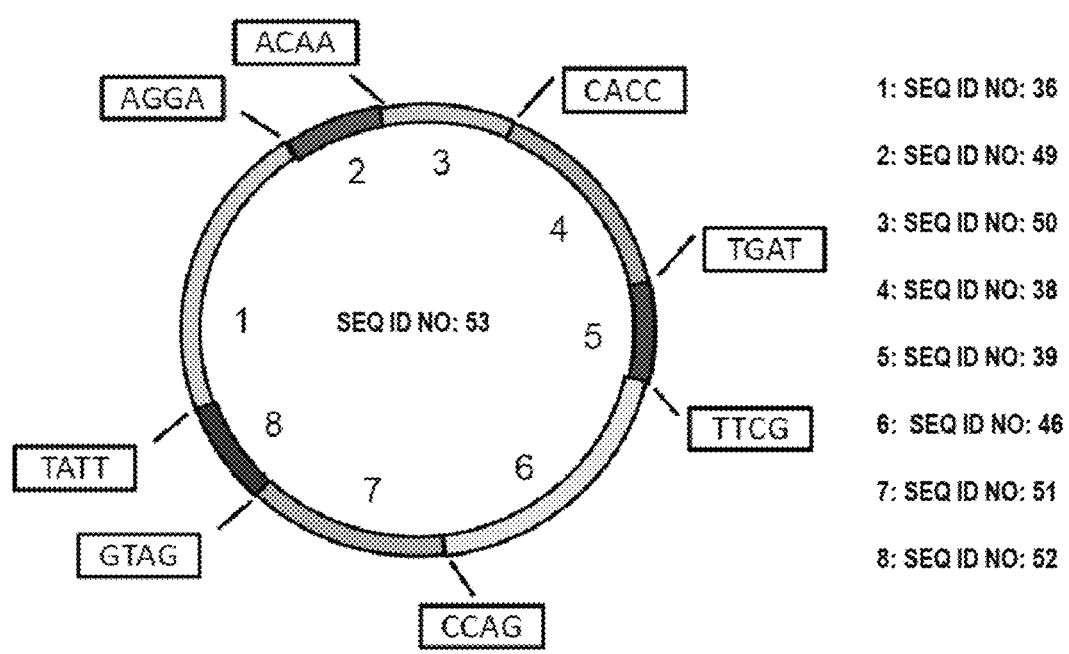

FIG. 11: Schema of the vector V1.2 (SEQ ID NO: 53) according to the invention and of the sutures allowing the assembly of the building blocks Ori-AmpR BsaI B (SEQ ID NO: 36), rosa26-5' BsaI A (SEQ ID NO: 49), pCMV BsaI C (SEQ ID NO: 50), hFUT3 BsaI A (SEQ ID NO: 38), BGHpA BsaI B (SEQ ID NO: 39), shB3Galt6 BsaI B (SEQ ID NO: 46), Hygro BsaI C (SEQ ID NO: 51), and rosa26-3' BsaI A (SEQ ID NO: 52).

Where 1=Ori-AmpR BsaI B (SEQ ID NO: 36), 2=rosa26-5' BsaI A (SEQ ID NO: 49), 3=pCMV BsaI C (SEQ ID NO: 50), 4=hFUT3 BsaI A (SEQ ID NO: 38), 5=BGHpA BsaI B (SEQ ID NO: 39), 6=shB3Galt6 BsaI B (SEQ ID NO: 46), 7=HygroR BsaI C (SEQ ID NO: 51) and 8=rosa26-3' BsaI A (SEQ ID NO: 52).

Figure 12:
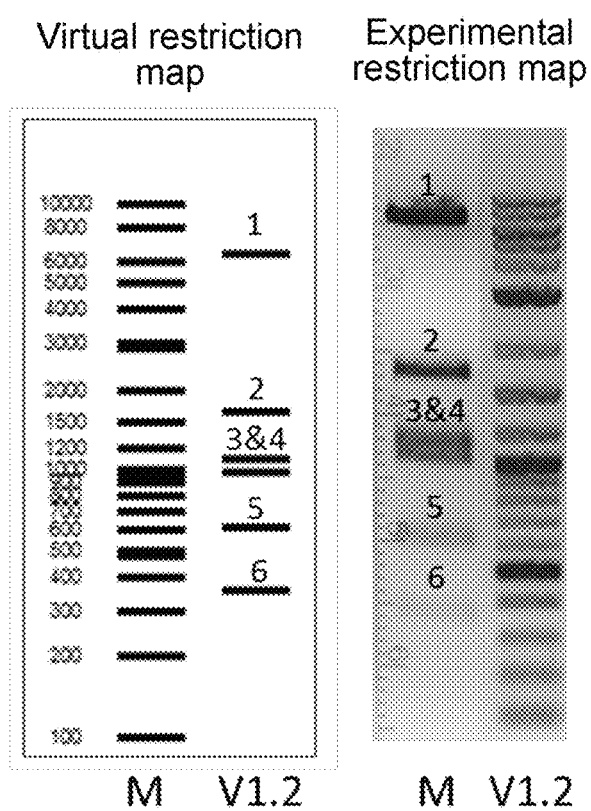

FIG. 12: Restriction fingerprint by triple digestion EcoRV/PvuI/SalI of the vector V1.2.

The digestion produces 6 fragments of 6492, 1649, 1104, 992, 606 and 357 base pairs respectively.
- 1: 6 492 bp, from PvuI [6009] to PvuI [1301]
- 2: 1 649 bp, from PvuI [1301] to SalI [2950]
- 3: 1104 bp, from SalI [4905] to PvuI [6009]
- 4: 992 bp, from EcoRV [3913] to SalI [4905]
- 5: 606 bp, from SalI [2950] to SalI [3556]
- 6: 357 bp, from SalI [3556] to EcoRV [3913]

Figure 13:
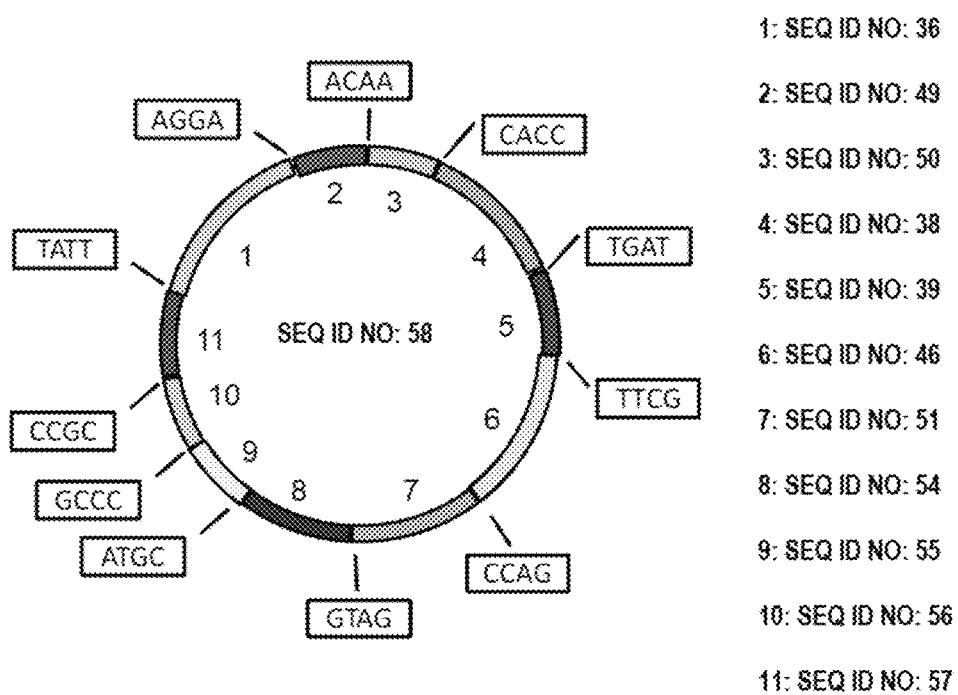

FIG. 13: Schema of the vector V1.3 (SEQ ID NO: 58) according to the invention and of the sutures allowing the assembly of the building blocks Ori-AmpR BsaI B (SEQ ID NO: 36), rosa26-5' BsaI A (SEQ ID NO: 49), pCMV BsaI C (SEQ ID NO: 50), hFUT3 BsaI A (SEQ ID NO: 38), BGHpA BsaI B (SEQ ID NO: 39), shB3Galt6 BsaI B (SEQ ID NO: 46), HygroR BsaI C (SEQ ID NO: 51), rosa26-3' BsaI B (SEQ ID NO: 54), pEF1a BsaI A (SEQ ID NO: 55), TK BsaI A (SEQ ID NO: 56), and Tkter BsaI A (SEQ ID NO: 57).

Where 1=Ori-AmpR BsaI B (SEQ ID NO: 36), 2=rosa26-5' BsaI A (SEQ ID NO: 49), 3=pCMV BsaI C (SEQ ID NO: 50), 4=hFUT3 BsaI A (SEQ ID NO: 38), 5=BGHpA BsaI B (SEQ ID NO: 39), 6=shB3Galt6 BsaI B (SEQ ID NO: 46), 7=HygroR BsaI C (SEQ ID NO: 51), 8=rosa26-3' BsaI B (SEQ ID NO: 54), 9=pEF1a Bsa I A (SEQ ID NO: 55), 10=TK BsaI A (SEQ ID NO: 56) and 11=Tkter BsaI A (SEQ ID NO: 57).

Figure 14:
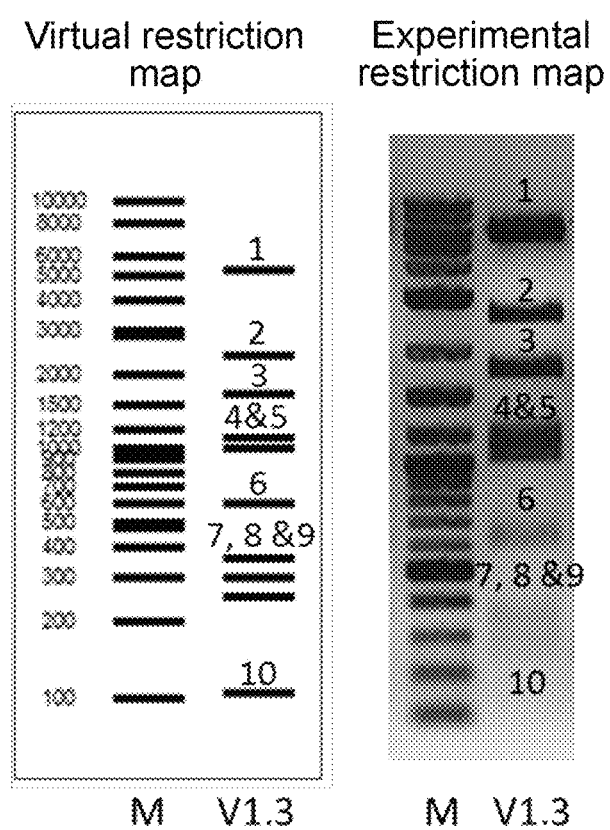

FIG. 14: Restriction fingerprint by triple digestion EcoRV/PvuI/SalI of the vector V1.3.

The digestion produces 10 fragments of 5206, 2379, 1649, 1104, 992, 606, 357, 302, 252 and 104 base pairs respectively.
- 1: 5 206 bp, from PvuI [6009] to SalI [11215]
- 2: 2 379 bp, from EcoRV [11873] to PvuI [1301]
- 3: 1 649 bp, from PvuI [1301] to SalI [2950]
- 4: 1104 bp, from SalI [4905] to PvuI [6009]
- 5: 992 bp, from EcoRV [3913] to SalI [4905]
- 6: 606 bp, from SalI [2950] to SalI [3556]
- 7: 357 bp, from SalI [3556] to EcoRV [3913]
- 8: 302 bp, from SalI [11215] to SalI [11517]
- 9: 252 bp, from SalI [11517] to EcoRV [11769]
- 10: 104 bp, from EcoRV [11769] to EcoRV [11873]

Figure 15:
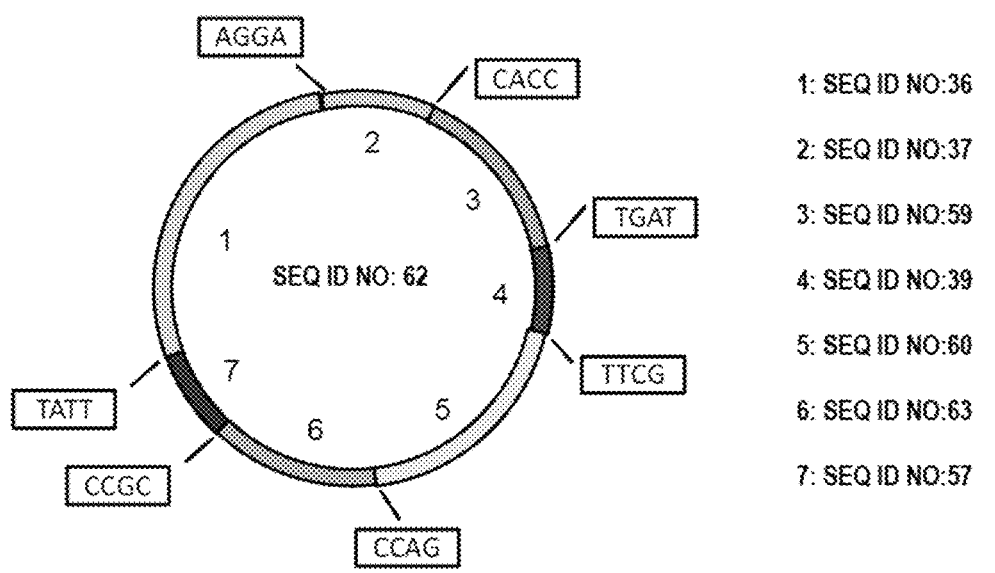

FIG. 15: Schema of the vector V2 (SEQ ID NO: 62) according to the invention and of the sutures allowing the assembly of the building blocks Ori-AmpR BsaI B (SEQ ID NO: 36), pCMV BsaI B (SEQ ID NO: 37), TO3G BsaI A (SEQ ID NO: 59), BGHpA BsaI B (SEQ ID NO: 39), pTRE3G BsaI A (SEQ ID NO: 60), mB3Galt6 BsaI B (SEQ ID NO: 63), and Tkter BsaI A (SEQ ID NO: 57).

Where 1=Ori-AmpR BsaI B (SEQ ID NO: 36), 2=pCMV BsaI B (SEQ ID NO: 37), 3=TO3G BsaI A (SEQ ID NO: 59), 4=BGHpA BsaI B (SEQ ID NO: 39), 5=pTRE3G BsaI A (SEQ ID NO: 60), 6=mB3Galt6 BsaI B (SEQ ID NO: 63) and 7=Tkter BsaI A (SEQ ID NO: 57).

Figure 16:
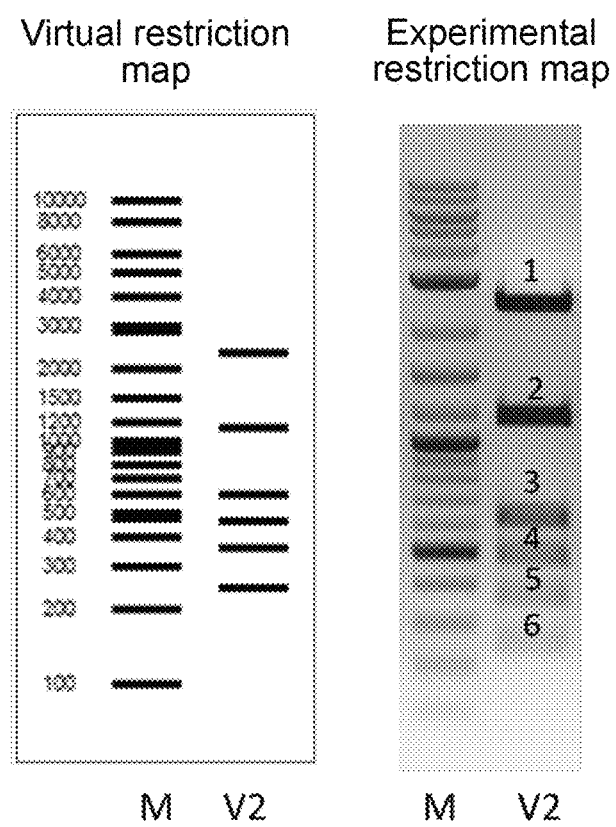

FIG. 16: Restriction fingerprint by triple digestion NdeI/SalI/XhoI of the vector V2.

The digestion produces 6 fragments of 2334, 1132, 602, 472, 361 and 245 base pairs respectively.
- 1: 2 334 bp, from XhoI [4678] to SalI [1866]
- 2: 1132 bp, from NdeI [3074] to XhoI [4206]
- 3: 602 bp, from SalI [2472] to NdeI [3074]
- 4: 472 bp, from XhoI [4206] to XhoI [4678]
- 5: 361 bp, from NdeI [2111] to SalI [2472]
- 6: 245 bp, from SalI [1866] to NdeI [2111]

Figure 17:
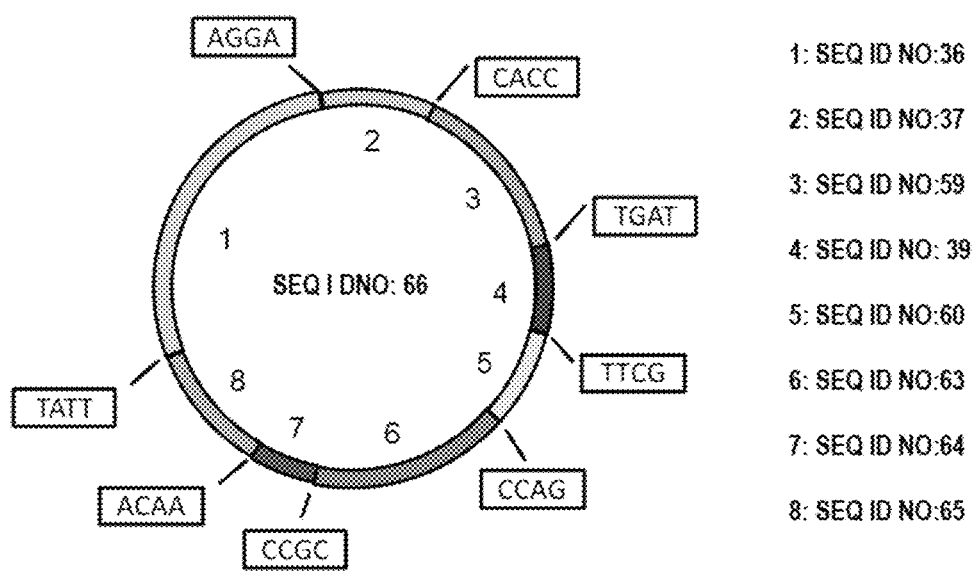

FIG. 17: Schema of the vector V3 (SEQ ID NO: 66) according to the invention and of the sutures allowing the assembly of the building blocks Ori-AmpR BsaI B (SEQ ID NO: 36), pCMV BsaI B (SEQ ID NO: 37), TO3G BsaI A (SEQ ID NO: 59), BGHpA BsaI B (SEQ ID NO: 39), pTRE3G BsaI A (SEQ ID NO: 60), mB3Galt6 BsaI B (SEQ ID NO:63), Tkter BsaI B (SEQ ID NO:64), and shB3Galt6 BsaI C (SEQ ID NO: 65).

Where 1=Ori-AmpR BsaI B (SEQ ID NO: 36), 2=pCMV BsaI B (SEQ ID NO: 37), 3=TO3G BsaI A (SEQ ID NO: 59), 4=BGHpA BsaI B (SEQ ID NO: 39), 5=pTRE3G BsaI A (SEQ ID NO: 60), 6=mB3Galt6 BsaI B (SEQ ID NO: 63), 7=Tkter BsaI B (SEQ ID NO: 64) and 8=shB3Galt6 BsaI C (SEQ ID NO: 65).

Figure 18:
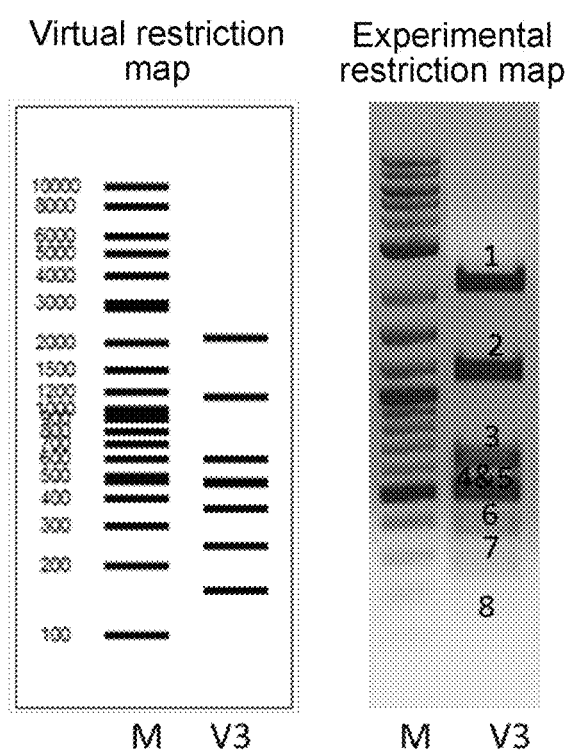

FIG. 18: Restriction fingerprint by triple digestion NdeI/SalI/XhoI of the vector V3.

The digestion produces 8 fragments of 2110, 1107, 602, 478, 472, 361, 245 and 146 base pairs respectively.
1: 2 110 bp, from NdeI [5308] to SalI [1862]
2: 1132 bp, from NdeI [3070] to XhoI [4202]
3: 602 bp, from SalI [2468] to NdeI [3070]
4: 478 bp, from XhoI [4674] to SalI [5152]
5: 472 bp, from XhoI [4202] to XhoI [4674]
6: 361 bp, from NdeI [2107] to SalI [2468]
7: 245 bp, from SalI [1862] to NdeI [2107]
8: 156 bp, from SalI [5152] to NdeI [5308]

Figure 19:
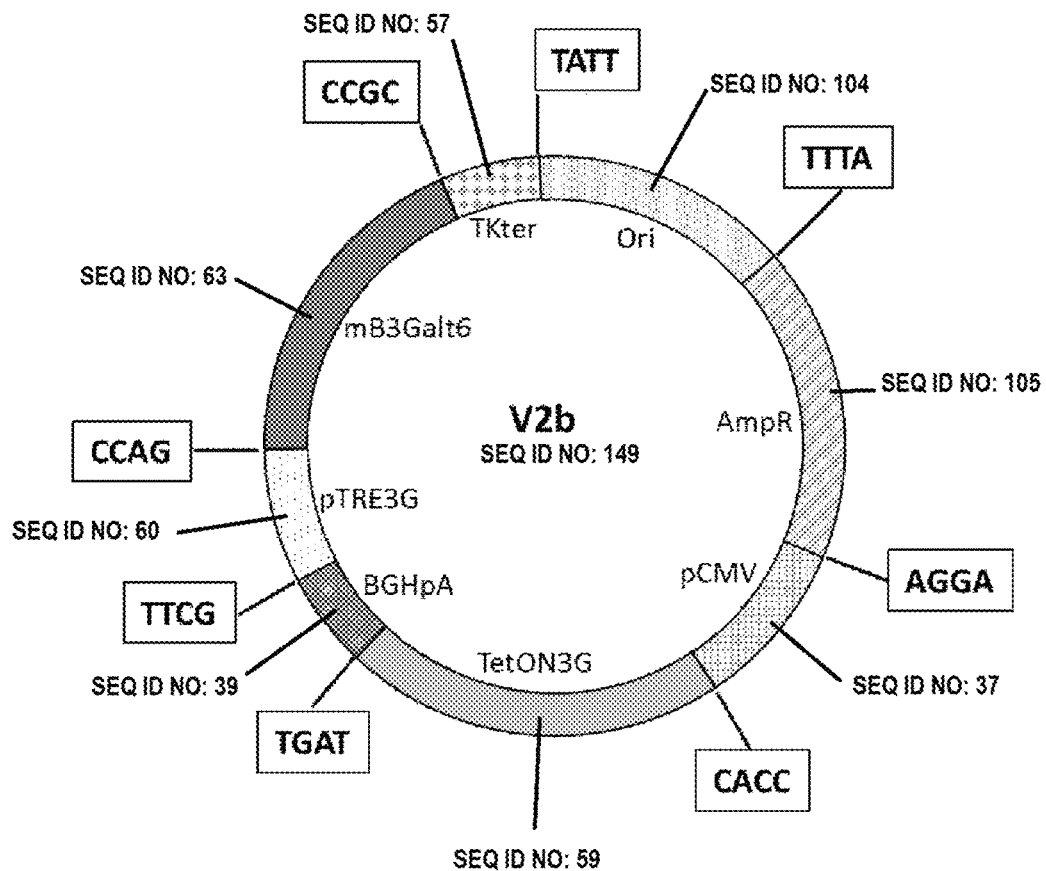

FIG. 19: Schema of the vector V2b (SEQ ID NO: 149) according to the invention and of the sutures allowing the assembly of the building blocks Ori BsaI A (SEQ ID NO: 104), AmpR BsaI A (SEQ ID NO: 105), pCMV BsaI B (SEQ ID NO: 37), TO3G BsaI A (SEQ ID NO: 59), BGHpA BsaI B (SEQ ID NO: 39), pTRE3G BsaI A (SEQ ID NO: 60), mB3Galt6 BsaI B (SEQ ID NO: 63), and Tkter BsaI A (SEQ ID NO: 57)

Figure 20:
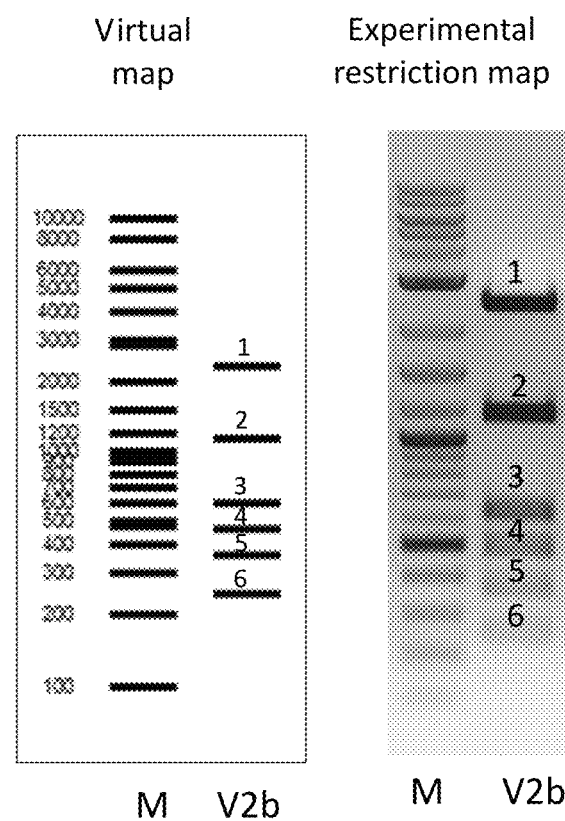

FIG. 20: Restriction fingerprint by triple digestion NdeI/SalI/XhoI of the vector V2b.

Figure 21:
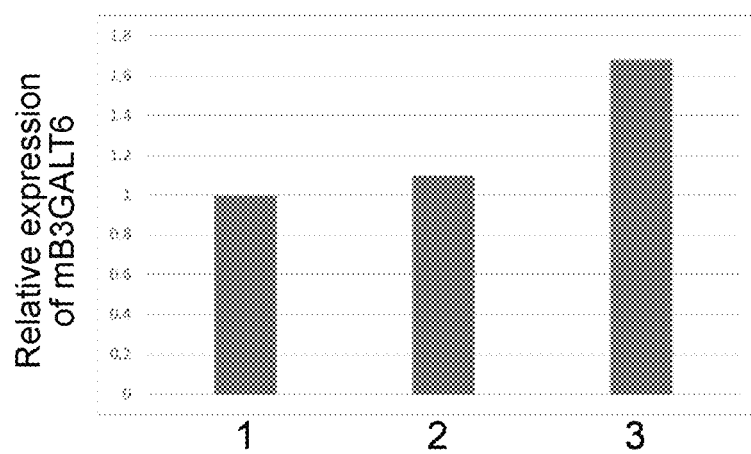

The digestion produces 6 fragments of 2334, 1132, 602, 472, 361 and 245 base pairs respectively.
1:2 334 bp, from XhoI to SalI
2:1 132 bp, from NdeI to XhoI
3:602 bp, from SalI to NdeI
4:472 bp, from XhoI to XhoI
5:361 bp, from NdeI to SalI
6:245 bp, from SalI to NdeI FIG. 21: Relative expression of mB3GALT6 measured by quantitative PCR after transfer of the vector V2b into a 4T1 cell by electroporation. 1: electroporated cells in the absence of a vector. 2: electroporated cells in the presence of V2.b (cells not treated with doxocycline). 3: electroporated cells, then treated for 24 hours with doxocycline. The experiment shows that the expression of the transcript mB3Galt6, coded by the vector V2b, is increased in the 4T1 cell only in the presence of doxocycline, demonstrating the concomitant presence of an inducible transgene and its co-activator in the vector V2b.

Figure 22:
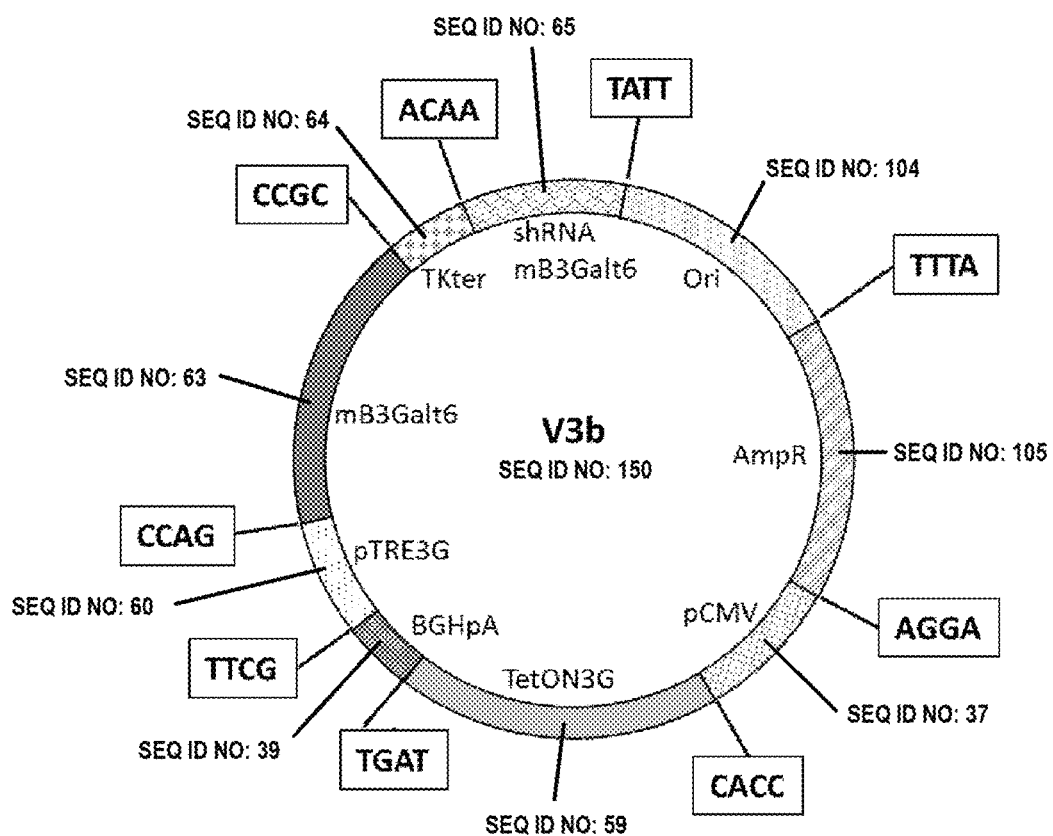

FIG. 22: Schema of the vector V3b (SEQ ID NO: 150) according to the invention and of the sutures allowing the assembly of the building blocks Ori BsaI A (SEQ ID NO: 104), AmpR BsaI A (SEQ ID NO: 105), pCMV BsaI B (SEQ ID NO: 37), TO3G BsaI A (SEQ ID NO: 59), BGHpA BsaI B (SEQ ID NO: 39), pTRE3G BsaI A (SEQ ID NO: 60), mb3Galt6 BsaI B (SEQ ID NO:63), Tkter BsaI B (SEQ ID NO: 64), and shB3Galt6 BsaI C (SEQ ID NO: 65).

Figure 23:
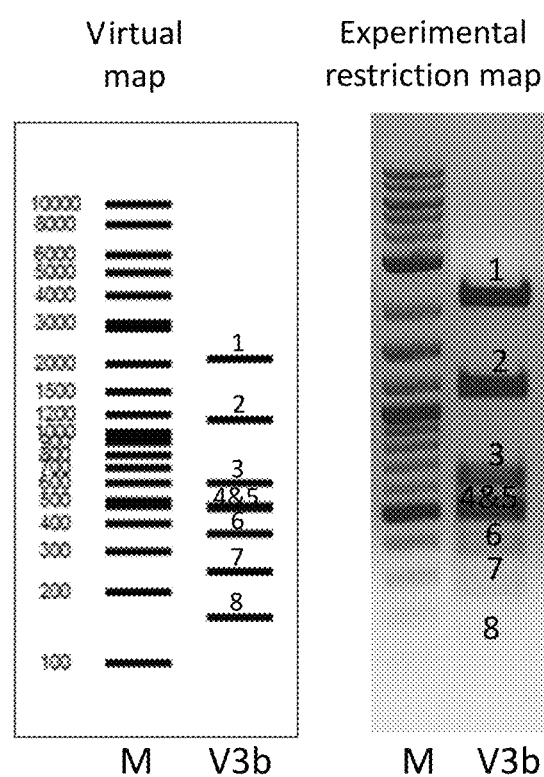

FIG. 23: Restriction fingerprint by triple digestion NdeI/SalI/XhoI of the vector V3b.

The digestion produces 8 fragments of 2110, 1132, 602, 478, 472, 361, 245 and 156 base pairs respectively.
1: 2 110 bp, from NdeI [5312] to SalI [1866]
2: 1132 bp, from NdeI [3074] to XhoI [4206]
3: 602 bp, from SalI [2472] to NdeI [3074]
4:478 bp, from XhoI [4678] to SalI [5156]
5: 472 bp, from XhoI [4206] to XhoI [4678]
6: 361 bp, from NdeI [2111] to SalI [2472]
7: 245 bp, from SalI [1866] to NdeI [2111]
8: 156 bp, from SalI [5156] to NdeI [5312]

Figure 24:
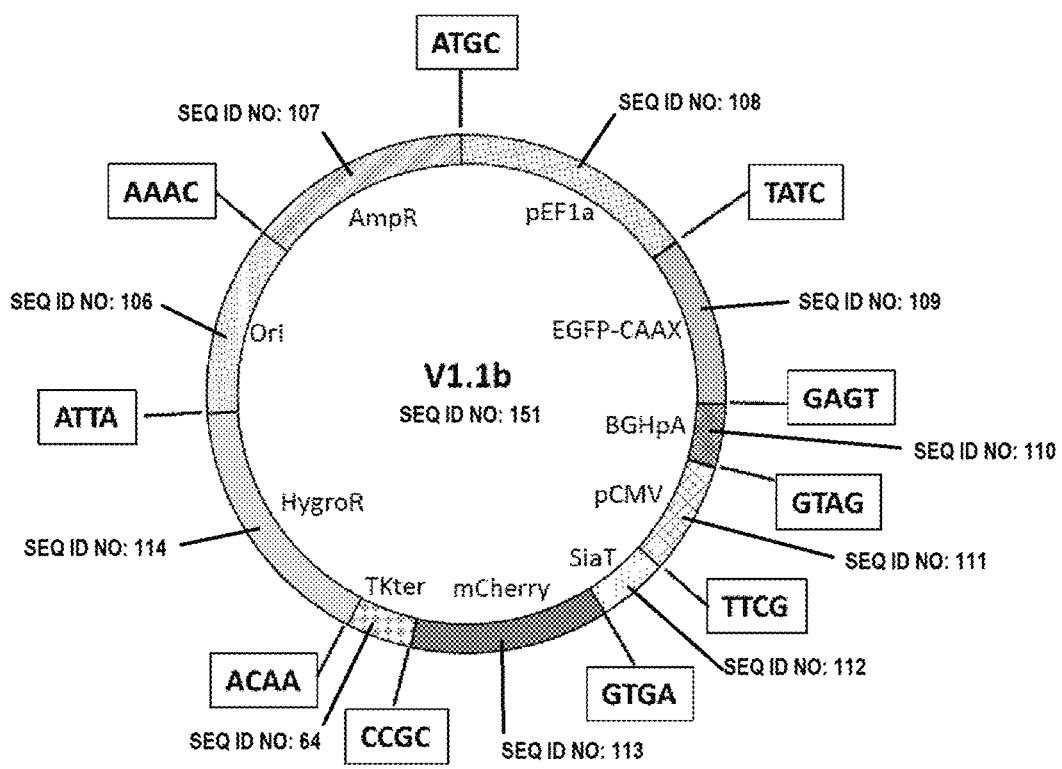

FIG. 24: Schema of the vector V1.1b (SEQ ID NO: 151) according to the invention and of the sutures allowing the assembly of the building blocks Ori BsaI B (SEQ ID NO: 106), AmpR BsaI B (SEQ ID NO: 107), pEF1aL BsaI B (SEQ ID NO: 108), EGFP-CAAX BsaI A (SEQ ID NO: 109), BGHpA BsaI C (SEQ ID NO: 110), pCMV BsaI D (SEQ ID NO: 111), SiaT BsaI B (SEQ ID NO: 112), mCherry BsaI B (SEQ ID NO: 113), TKter BsaI B (SEQ ID NO: 64) and HygroR BsaI D (SEQ ID NO: 114).

Figure 25:
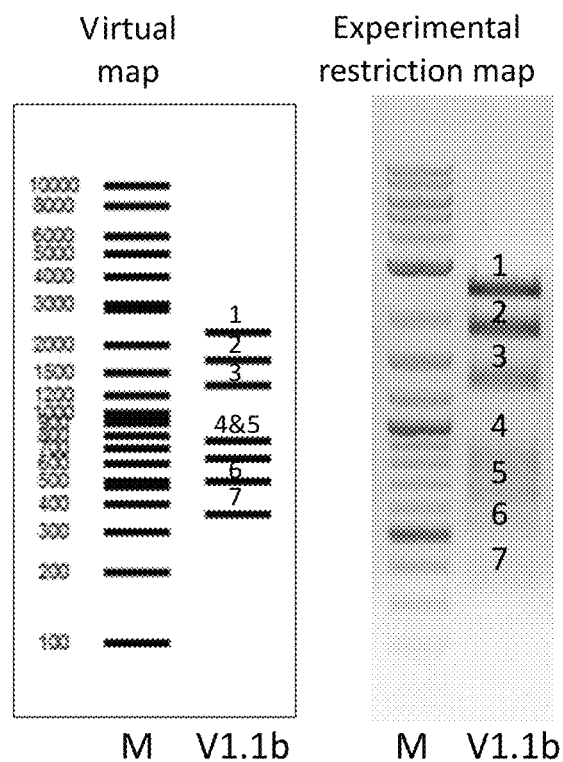

FIG. 25: Restriction fingerprint by triple digestion EcoRV/PstI/ScaI of the vector V1.1b.

The digestion produces 7 fragments of 2281, 1723, 1309, 757, 635, 505 and 360 base pairs respectively.
1: 2 281 bp, from EcoRV [3036] to PstI [5317]
2: 1723 bp, from ScaI [7261] to ScaI [1414]
3: 1309 bp, from PstI [5317] to PstI [6626]
4: 757 bp, from ScaI [1414] to PstI [2171]
5: 635 bp, from PstI [6626] to ScaI [7261]
6: 505 bp, from PstI [2171] to PstI [2676]
7: 360 bp, from PstI [2676] to EcoRV [3036]

Figure 26:
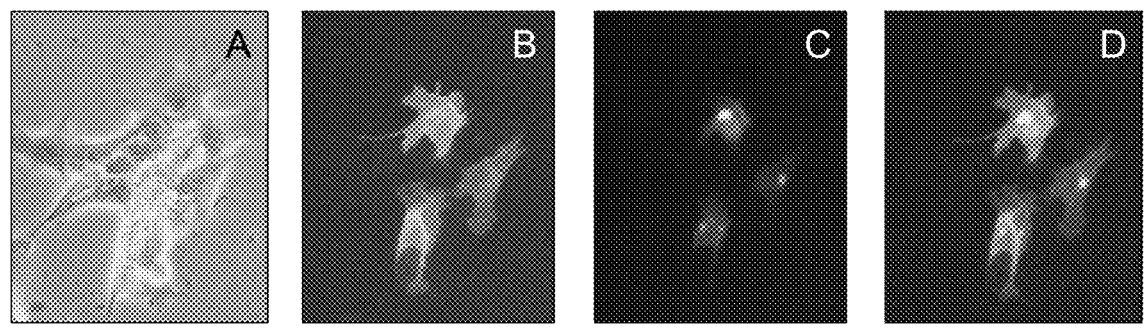

FIG. 26: Observation under microscope of 4T1 cells 24 hours after electroporation with the vector V1.1b.
A: group of cells visible under microscope in white light.
B: same optical field as A observed under microscope with green fluorescence (GFP visualisation).
C: same optical field as A observed under microscope with red fluorescence (mCherry visualisation).
D: superposition of the fields observed in B and C.

Figure 27:
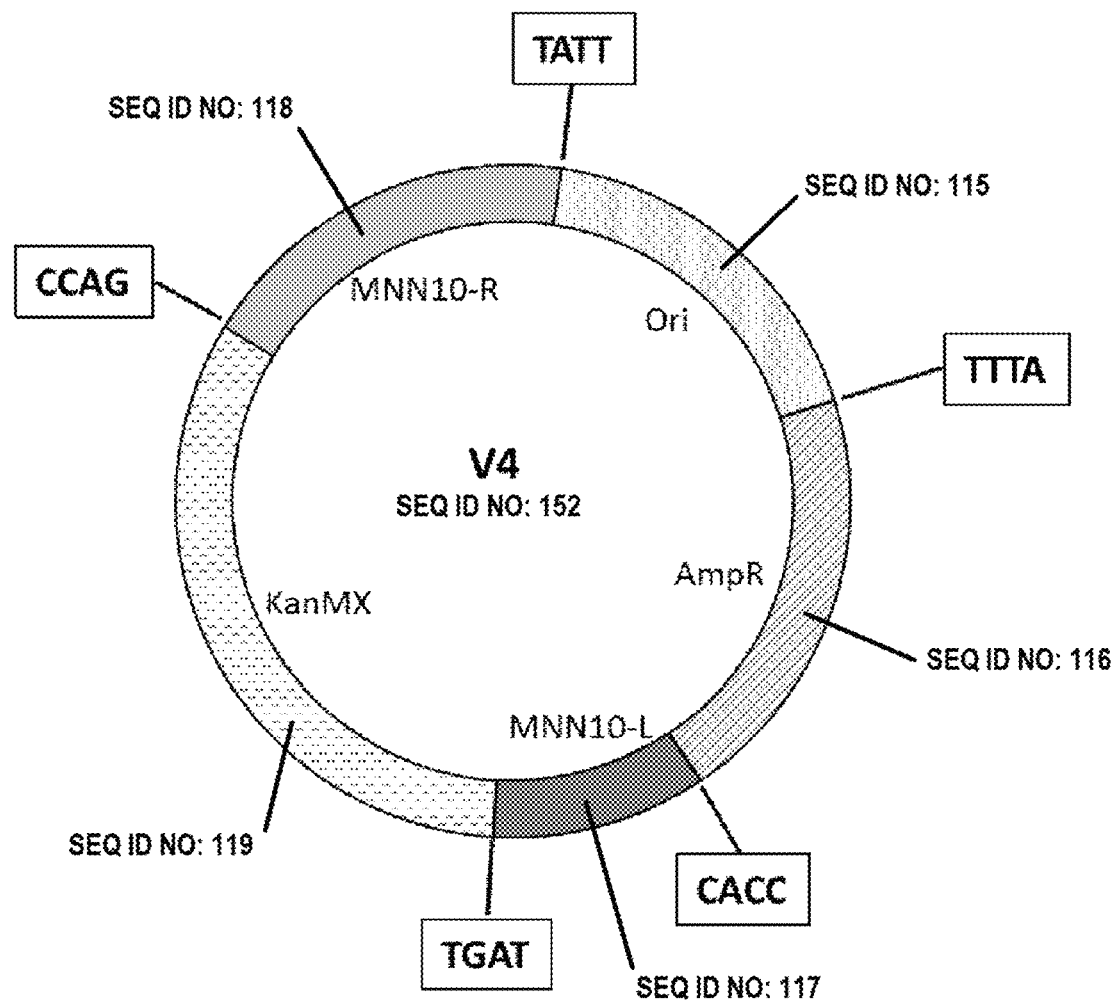

FIG. 27: Schema of the vector V4 (SEQ ID NO: 152) according to the invention and of the sutures allowing the assembly of the building blocks Ori-2 BsaI C (SEQ ID NO: 115), AmpR BsaI C (SEQ ID NO: 116), MNN10-Lrec BsaI A (SEQ ID NO: 117), KanMX BsaI A (SEQ ID NO: 119) and MNN10-Rrec BsaI A (SEQ ID NO: 118).

Figure 28:
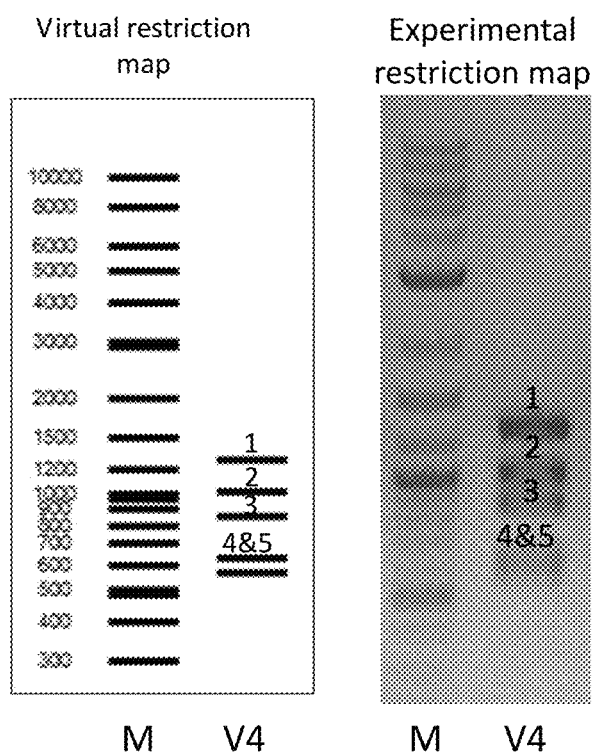

FIG. 28: Restriction fingerprint by double digestion PmeI/HindIII of the vector V4.

Figure 29:
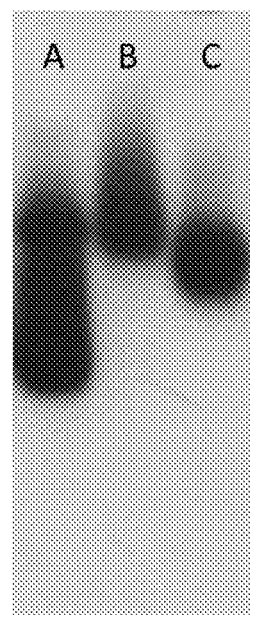

The digestion produces 5 fragments of 1280, 1012, 856, 631 and 567 base pairs respectively.
1:1 280 bp, from PmeI to HindIII
2:1 012 bp, from PmeI to PmeI
3:856 bp, from PmeI to PmeI
4:631 bp, from HindIII to HindIII
5:567 bp, from HindIII to PmeI FIG. 29: Verification of the invalidation of the yeast gene MNN10 by analysis of the profile of invertase glycosylation.
A: profile of migration of a strain inactivated for the gene Pmr1, this being a gene of which the mutation leads to a significant reduction of invertase glycosylation.
B: profile of migration of invertase of a wild-type strain.
C: profile of invertase glycosylation of a strain of which the gene MNN10 has been invalidated by homologous recombination with the deletion cassette of the plasmid V4.

FIG. 30: Schema showing the construction of an expression vector by the described method. A: Illustration of 8 DNA building blocks. Each building block contains a sequence of interest (SI) labelled from A to H (in grey), which sequences can in turn contain a plurality of modules (shades of grey) numbered from 1 to 13. The non-functional modules are labelled a and b in addition to the numbering. The building blocks also contain adapters upstream and downstream of the SIs, of which the 'suture' part is shown in white and the outermost part is shown in black. In this schema, the sutures complementary to one another are connected by dotted lines. B: Linear illustration of a circular vector containing the SIs illustrated in A (x being contiguous with y) obtained in accordance with the described method. The lines in black delimit the SIs which are now contiguous and connected by the sutures (white), of which each of the two cohesive strands has been provided by a neighbouring SI. The structuring of the vector in accordance with the functional units as defined in the text is illustrated in the form of rectangles below the molecule shown. When the combinations of modules constituting the units correspond to a DNA sequence intended to be transcribed, the direction of transcription is shown in the form of an arrow.

In the example shown by Figures A and B, the modules are defined as follows:

Module 1: origin of replication

Module 2a: bipartite sequence of genomic integration, left part

Module 3: transcription terminator

Module 4a: incomplete coding sequence (part 3' which contains a stop codon)

Module 4b: incomplete coding sequence (part 5' which contains an ATG)

Module 5: eukaryotic promoter

Module 6: eukaryotic promoter

Module 7: sequence coding a eukaryotic positive selection marker

Module 8: transcription terminator

Module 2b: bipartite sequence of genomic integration, right part

Module 9: coding sequence of a prokaryotic selection marker

Module 10: bacterial promoter

Module 11: eukaryotic promoter

Module 12: complete coding sequence

Module 13: transcription terminator

EXAMPLES

1. Examples of Building Blocks Produced

TABLE 2

Example of building blocks produced in accordance with the invention, the starting matrices were genetically modified so as to be able to be used in accordance with the method described by the present invention (not shown in the table).

| Building block | Starting matrix | Manufacturer |
|---|---|---|
| OriAmp | pCDNA3.1(+)Hygro | Invitrogen-Life technologies |
| LacZα | pUC19 | Invitrogen-Life technologies |
| ZeocinR | pCDNA3.1(−)Zeo | Invitrogen-Life technologies |
| HygromycinR | pCDNA3.1(+)Hygro | Invitrogen-Life technologies |
| CMVp | pEN_CmiRc2 | ATCC (MBA-284) |
| EF1p | pEN_EmiRc3 | ATCC (MBA-286) |
| Ubi-Cp | pEN_UbmiRc3 | ATCC (MBA-288) |
| EYFP-Ctag | pEYFP-C1 | Clontech disc[d] |
| ECFP-Ctag | pECFP-C1 | Clontech disc[d] |
| EGFP-Ctag | pEGFP-C1 | Clontech disc[d] |
| E1GFP-Ctag | pEGFP-C1 | Clontech disc[d] |
| mCherry-Ctag | pmCherry-C1 | M. Coppey-Moisan |
| TagBFP-Ctag | pTagBFP-C | Evrogen |
| BGHpolyA | pCDNA3.1(+)Hygro | In vitrogen-Life technologies |

BGH-PolyA signal: bovine growth hormone polyadenylation signal
CMV: cytomegalovirus
EGFP: enhanced green fluorescent protein
EYFP: enhanced yellow fluorescent protein

TABLE 3

Building blocks constructed in accordance with the invention.

| BUILDING BLOCK | | MATRIX | |
|---|---|---|---|
| NAME | ID | NAME | ID |
| AmpR BsaI A | SEQ ID NO: 105 | eZ-Ori-AmpR | SEQ ID NO: 153 |
| AmpR BsaI B | SEQ ID NO: 107 | eZ-Ori-AmpR | SEQ ID NO: 153 |
| AmpR BsaI C | SEQ ID NO: 116 | eZ-Ori-AmpR | SEQ ID NO: 153 |
| BGHpA BsaI A | SEQ ID NO: 26 | BGH polyA | SEQ ID NO: 154 |
| BGHpA BsaI B | SEQ ID NO: 39 | BGH polyA | SEQ ID NO: 154 |
| BGHpA BsaI C | SEQ ID NO: 110 | BGH polyA | SEQ ID NO: 154 |
| E1GFP BsaI A | SEQ ID NO: 20 | eZ-E1GFP | SEQ ID NO: 155 |
| ECFP BsaI A | SEQ ID NO: 22 | ECFP | SEQ ID NO: 157 |
| EGFP BsaI A | SEQ ID NO: 21 | EGFP | SEQ ID NO: 156 |

TABLE 3-continued

Building blocks constructed in accordance with the invention.

| | | | |
|---|---|---|---|
| EGFP-CAAX BsaI A | SEQ ID NO: 109 | EGFP | SEQ ID NO: 156 |
| EYFP BsaI A | SEQ ID NO: 23 | EYFP | SEQ ID NO: 158 |
| hFUT3 BsaI A | SEQ ID NO: 38 | hFUT3 cDNA | SEQ ID NO: 160 |
| HygroR BsaI A | SEQ ID NO: 29 | eZ-HygromycinR K7 | SEQ ID NO: 161 |
| HygroR BsaI B | SEQ ID NO: 47 | eZ-HygromycinR K7 | SEQ ID NO: 161 |
| HygroR BsaI C | SEQ ID NO: 51 | eZ-HygromycinR K7 | SEQ ID NO: 161 |
| HygroR BsaI D | SEQ ID NO: 114 | eZ-HygromycinR K7 | SEQ ID NO: 161 |
| KanMX BsaI A | SEQ ID NO: 119 | KanMX4 K7 | SEQ ID NO: 162 |
| LacZα-down BsaI A | SEQ ID NO: 28 | LacZα | SEQ ID NO: 163 |
| LacZα-up BsaI A | SEQ ID NO: 27 | LacZα | SEQ ID NO: 163 |
| mB3Galt6 BsaI A | SEQ ID NO: 61 | mB3Galt6 cDNA | SEQ ID NO: 164 |
| mB3Galt6 BsaI B | SEQ ID NO: 63 | eZ-mB3Galt6 cDNA shins | SEQ ID NO: 165 |
| mCherry BsaI A | SEQ ID NO: 24 | mCherry | SEQ ID NO: 159 |
| mCherry BsaI B | SEQ ID NO: 113 | mCherry | SEQ ID NO: 159 |
| MNN10-Lrec BsaI A | SEQ ID NO: 117 | Yeast MNN10 gene | SEQ ID NO: 166 |
| MNN10-Rrec BsaI A | SEQ ID NO: 118 | Yeast MNN10 gene | SEQ ID NO: 166 |
| Ori BsaI A | SEQ ID NO: 104 | eZ-Ori-AmpR | SEQ ID NO: 153 |
| Ori BsaI B | SEQ ID NO: 106 | eZ-Ori-AmpR | SEQ ID NO: 153 |
| Ori-2 BsaI C | SEQ ID NO: 115 | eZ-Ori-AmpR | SEQ ID NO: 153 |
| Ori-AmpR BsaI A | SEQ ID NO: 17 | eZ-Ori-AmpR | SEQ ID NO: 153 |
| Ori-AmpR BsaI B | SEQ ID NO: 36 | eZ-Ori-AmpR | SEQ ID NO: 153 |
| pCMV BsaI A | SEQ ID NO: 18 | promCMV | SEQ ID NO: 167 |
| pCMV BsaI B | SEQ ID NO: 37 | promCMV | SEQ ID NO: 167 |
| pCMV BsaI C | SEQ ID NO: 50 | promCMV | SEQ ID NO: 167 |
| pCMV BsaI D | SEQ ID NO: 111 | promCMV | SEQ ID NO: 167 |
| pEF1a BsaI A | SEQ ID NO: 55 | promEF1alpha court | SEQ ID NO: 168 |
| pEF1aL BsaI B | SEQ ID NO: 108 | promEF1alpha | SEQ ID NO: 169 |
| pTRE3G BsaI A | SEQ ID NO: 60 | promTRE3G | SEQ ID NO: 170 |
| rosa26-3' BsaI A | SEQ ID NO: 52 | eZ-Rosa26-3' | SEQ ID NO: 171 |
| rosa26-3' BsaI B | SEQ ID NO: 54 | eZ-Rosa26-3' | SEQ ID NO: 171 |
| rosa26-5' BsaI A | SEQ ID NO: 49 | eZ-Rosa26-5' | SEQ ID NO: 172 |

TABLE 3-continued

Building blocks constructed in accordance with the invention.

| | | | |
|---|---|---|---|
| shB3Galt6 BsaI A | SEQ ID NO: 40 | mB3Galt6 shRNA TR506016D | SEQ ID NO: 173 |
| shB3Galt6 BsaI B | SEQ ID NO: 46 | mB3Galt6 shRNA TR506016D | SEQ ID NO: 173 |
| shB3Galt6 BsaI C | SEQ ID NO: 65 | mB3Galt6 shRNA TR506016D | SEQ ID NO: 173 |
| SiaT BsaI A | SEQ ID NO: 19 | eZ-SiaT-TGS-Hook | SEQ ID NO: 174 |
| SiaT BsaI B | SEQ ID NO: 112 | eZ-SiaT-TGS-Hook | SEQ ID NO: 174 |
| TagBFP BsaI A | SEQ ID NO: 25 | TagBFP | SEQ ID NO: 175 |
| TK BsaI A | SEQ ID NO: 56 | Thymidine Kinase cDNA | SEQ ID NO: 176 |
| Tkter BsaI A | SEQ ID NO: 57 | TK term | SEQ ID NO: 177 |
| Tkter BsaI B | SEQ ID NO: 64 | TK term | SEQ ID NO: 177 |
| TO3G BsaI A | SEQ ID NO: 59 | TetON-3G cDNA | SEQ ID NO: 178 |

| FORWARD PRIMER | | REVERSE PRIMER | |
|---|---|---|---|
| NAME | ID | NAME | ID |
| AmpR TTTA BsaI CW | SEQ ID NO: 121 | AmpR-2 TCCT BsaI CCW | SEQ ID NO: 72 |
| AmpR AAAC BsaI CW | SEQ ID NO: 125 | AmpR-2 GCAT BsaI CCW | SEQ ID NO: 124 |
| AmpR AAAC BsaI CW | SEQ ID NO: 125 | AmpR-2 TCAC BsaI CCW | SEQ ID NO: 142 |
| BGHpA TGAT BsaI CW | SEQ ID NO: 1 | BGHpA AGAA BsaI CCW | SEQ ID NO: 2 |
| BGHpA TGAT BsaI CW | SEQ ID NO: 1 | BGHpA CGAA BsaI CCW 2 | SEQ ID NO: 77 |
| BGHpA GAGT BsaI CW | SEQ ID NO: 131 | BGHpA CTAC BsaI CCW 2 | SEQ ID NO: 130 |
| XFP-Ctag GGGG BsaI CW | SEQ ID NO: 15 | XFP-Ctag ATCA BsaI CCW | SEQ ID NO: 16 |
| XFP-Ctag GGGG BsaI CW | SEQ ID NO: 15 | XFP-Ctag ATCA BsaI CCW | SEQ ID NO: 16 |
| XFP-Ctag GGGG BsaI CW | SEQ ID NO: 15 | XFP-Ctag ATCA BsaI CCW | SEQ ID NO: 16 |
| EGFP TATC BsaI CW | SEQ ID NO: 129 | EGFP-CAAX ACTC BsaI CCW | SEQ ID NO: 128 |
| XFP-Ctag GGGG BsaI CW | SEQ ID NO: 15 | XFP-Ctag ATCA BsaI CCW | SEQ ID NO: 16 |
| hFUT3 CACC BsaI CW | SEQ ID NO: 75 | hFUT3 ATCA BsaI CCW | SEQ ID NO: 76 |
| SV40pori CCAG BsaI CW | SEQ ID NO: 7 | SV40term ATAA BsaI CCW | SEQ ID NO: 8 |
| Hygro CCAG BsaI CW | SEQ ID NO: 81 | Hygro AATA BsaI CCW | SEQ ID NO: 82 |
| Hygro CCAG BsaI CW | SEQ ID NO: 81 | Hygro CTAC BsaI CCW | SEQ ID NO: 86 |
| Hygro ACAA BsaI CW | SEQ ID NO: 139 | Hygro TAAT BsaI CCW | SEQ ID NO: 138 |
| KanMX TGCG BsaI CW | SEQ ID NO: 148 | KanMX ACGA BsaI CCW | SEQ ID NO: 147 |
| lacZ-down GACA BsaI CW | SEQ ID NO: 5 | lacZ-down CTGG BsaI CCW | SEQ ID NO: 6 |
| lacZ-up TTCT BsaI CW | SEQ ID NO: 3 | lacZ-up TGTC BsaI CCW | SEQ ID NO: 4 |
| mB3Galt6 CCAG BsaI CW | SEQ ID NO: 100 | mB3Galt6 GCGG BsaI CCW | SEQ ID NO: 101 |

TABLE 3-continued

Building blocks constructed in accordance with the invention.

| | | | | |
|---|---|---|---|---|
| mB3Galt6 CCAG Bsal CW | SEQ ID NO: 100 | mB3Galt6 GCGG Bsal CCW | SEQ ID NO: 101 | |
| XFP-Ctag GGGG Bsal CW | SEQ ID NO: 15 | XFP-Ctag ATCA Bsal CCW | SEQ ID NO: 16 | |
| XFP-Ctag GTGA Bsal CW | SEQ ID NO: 137 | XFP-Ctag GCGG Bsal CCW | SEQ ID NO: 136 | |
| MNN10Lrec GTGA Bsal CW | SEQ ID NO: 144 | MNN10Lrec CGCA Bsal CCW | SEQ ID NO: 143 | |
| MNN10Rrec TCGT Bsal CW | SEQ ID NO: 146 | MNN10Rrec CCCC Bsal CCW | SEQ ID NO: 145 | |
| ColE1-ori 2 TATT Bsal CW | SEQ ID NO: 71 | ColE1-ori TAAA Bsal CCW | SEQ ID NO: 120 | |
| ColE1-ori-2 ATTA Bsal CW | SEQ ID NO: 123 | ColE1-ori GTTT Bsal CCW | SEQ ID NO: 122 | |
| ColE1-ori-2 GGGG Bsal CW | SEQ ID NO: 141 | ColE1-ori-2 GTTT Bsal CCW | SEQ ID NO: 140 | |
| ColE1-ori TTAT Bsal CW | SEQ ID NO: 9 | AmpR TCCT Bsal CCW | SEQ ID NO: 10 | |
| ColE1-ori-2 TATT Bsal CW | SEQ ID NO: 71 | AmpR-2 TCCT Bsal CCW | SEQ ID NO: 72 | |
| pENprom AGGA Bsal CW | SEQ ID NO: 11 | pENprom GGTG Bsal CCW | SEQ ID NO: 12 | |
| CMVp AGGA Bsal CW | SEQ ID NO: 73 | CMVp GGTG Bsal CCW | SEQ ID NO: 74 | |
| CMVp ACAA Bsal CW | SEQ ID NO: 85 | CMVp GGTG Bsal CCW | SEQ ID NO: 74 | |
| CMVp GTAG Bsal CW | SEQ ID NO: 133 | CMVp CGAA Bsal CCW | SEQ ID NO: 132 | |
| EF1ap ATGC Bsal CW | SEQ ID NO: 90 | EF1ap GGGC Bsal CCW | SEQ ID NO: 91 | |
| EF1apL ATGC Bsal CW | SEQ ID NO: 127 | EF1ap GATA Bsal CCW | SEQ ID NO: 126 | |
| pTet3G TTCG Bsal CW | SEQ ID NO: 98 | pTet3G CTGG Bsal CCW | SEQ ID NO: 99 | |
| rosa26-3' GTAG Bsal CW | SEQ ID NO: 87 | rosa26-3' AATA Bsal CCW | SEQ ID NO: 88 | |
| rosa26-3' GTAG Bsal CW | SEQ ID NO: 87 | rosa26-3' GCAT Bsal CCW | SEQ ID NO: 89 | |
| rosa26-5' AGGA Bsal CW | SEQ ID NO: 83 | rosa26-5' TTGT Bsal CCW | SEQ ID NO: 84 | |
| shB3Galt6 TTCG Bsal CW | SEQ ID NO: 78 | shB3Galt6 AATA Bsal CCW | SEQ ID NO: 79 | |
| shB3Galt6 TTCG Bsal CW | SEQ ID NO: 78 | shB3Galt6 CTGG Bsal CCW | SEQ ID NO: 80 | |
| shB3Galt6 ACAA Bsal CW | SEQ ID NO: 103 | shB3Galt6 AATA Bsal CCW | SEQ ID NO: 79 | |
| SiaT CACC Bsal CW | SEQ ID NO: 13 | SiaT CCCC Bsal CCW | SEQ ID NO: 14 | |
| SiaT TTCG Bsal CW | SEQ ID NO: 135 | SiaT TCAC Bsal CCW | SEQ ID NO: 134 | |
| TagBFP-Ctag GGGG Bsal CW | SEQ ID NO: 69 | TagBFP-Ctag ATCA Bsal CCW | SEQ ID NO: 70 | |
| TK GCCC Bsal CW | SEQ ID NO: 92 | TK GCGG Bsal CCW | SEQ ID NO: 93 | |
| HSVTKterm CCGC Bsal CW | SEQ ID NO: 94 | HSVTKterm AATA Bsal CCW | SEQ ID NO: 95 | |
| HSVTKterm CCGC Bsal CW | SEQ ID NO: 94 | HSVTKterm TTGT Bsal CCW | SEQ ID NO: 102 | |
| TetOn3G CACC Bsal CW | SEQ ID NO: 96 | TetOn3G ATCA Bsal CCW | SEQ ID NO: 97 | |

The following examples will better illustrate the invention, without intending to be limiting.

Example of an Assembly Protocol According to the Invention 20 to 100 fmol of each molecular building block selected for production of a vector are mixed in a volume of 20 µl of a solution comprising:

2 µl of ligation buffer 10×,

10 U (1 µl) of type IIs restriction enzyme, for example BsaI,

3 U (1 µl) of ligase if the number of fragments is less than or equal to 4, or 20 U (1 µl) of high-concentration (HC) ligase if the number of fragments is greater than 4.

qsp: ultrapure distilled water

The mixture is produced on ice, that is to say at a temperature of approximately 4° C.

The mixture is then either incubated at 37° C. (30' at 6h), if the number of building blocks to be assembled is less than 5, or is subjected to incubation cycles of 2' at 37° C. and of 3' at 16° C. (25 to 50 cycles) if the number of fragments is greater than 4.

At the end of this incubation period, the reactions are incubated at 50° C. for 5' (cutting of remaining BsaI sites), then at 80° C. for 5' (inactivation of the enzymes).

2 to 10 µl of each assembly are then used to transform 50 to 100 µl of competent bacteria, and all of the bacteria transformed are spread over one or two petri dishes containing an LB agar supplemented with the selection antibiotic (corresponding to the module of antibiotic resistance of the bacterial unit).

Embodiment 1

In this first example, the objective is to produce 6 constructions making it possible to express fluorescent proteins of different colours in the Golgi compartment of mammalian cells (FIG. 4). The vectors must be usable for creation of stable lines, which requires the introduction of a selection module in the integration unit. So as to be able to visually recognise the plasmids where the assembly is correct and to estimate the proportion of contaminants or incorrect clones, a bacterial cassette expressing lac Z is also added.

The desired vectors contain:
A bacterial replication unit:
- a module containing an origin of replication followed by the resistance gene bla (AmpR) a module (in two fragments) enabling blue-white screening by the activity of the gene lacZα

An expression cassette of the fusion proteins, containing:
- a promoter module (CMV),
- a Golgi compartment addressing module (first part of the ORF) formed of the first 111 amino acids coded by the cDNA of the human gene ST6GAL1,
- a module coding a fluorescent protein fused to the addressing sequence at the C-terminal (six interchangeable modules),
- a module corresponding to a transcription terminator (BGHpolyA)

A unit of integration in a eukaryotic cell:
- a module containing the resistance gene to hygromycin B under the control of the promoter SV40.

Each suture was selected in accordance with the invention, and the reconstructed plasmid is shown in FIG. 4.

Preparation of the Molecular Building Blocks

TABLE 4

List of the primers used to amplify the building blocks specified (recognition site BsaI underlined and sutures shown in bold)

| NAME | SEQUENCE | ID |
|---|---|---|
| BGHpA TGAT BsaI CW | GAGGTACC<u>GGTCTC</u>ATGATCGACTGTGCCTTCTAGTTGCC | SEQ ID NO: 1 |
| BGHpA AGAA BsaI CCW | GAGGTACC<u>GGTCTC</u>CAGAAGCCATAGAGCCCACCGC | SEQ ID NO: 2 |
| lacZ-up TTCT BsaI CW | GAGGTACC<u>GGTCTC</u>GTTCTCCCTGCAGGTGCGCCCAATACGCAAACCGCC | SEQ ID NO: 3 |
| lacZ-up TGTC BsaI CCW | GAGGTACC<u>GGTCTC</u>CTGTCCGTAATCATGGTCATAGCTGTTTCC | SEQ ID NO: 4 |
| lacZ-down GACA BsaI CW | GAGGTACC<u>GGTCTC</u>GGACAGCCTGGCCGTCGTTTTACAACG | SEQ ID NO: 5 |
| lacZ-down CTGG BsaI CCW | GAGGTACC<u>GGTCTC</u>ACTGGCCCTGCAGGTCTATGCGGCATCAGAGCAGATTGTAC | SEQ ID NO: 6 |
| SV40pori CCAG BsaI CW | GAGGTACC<u>GGTCTC</u>CCCAGCAGGCAGAAGTATGCAAAGC | SEQ ID NO: 7 |
| SV40term ATAA BsaI CCW | GAGGTACC<u>GGTCTC</u>GATAAGATACATTGATGAGTTTGGAC | SEQ ID NO: 8 |
| ColE1-ori TTAT BsaI CW | GAGGTACC<u>GGTCTC</u>ATTATGCGTCTTCTAGGGTTAAGGTTAGTGTAGAGAAGCAACCG | SEQ ID NO: 9 |
| AmpR TCCT BsaI CCW | GAGGTACC<u>GGTCTC</u>GTCCTTGAGACGCTAGTCCTCGTTCCCGATGCTCTCGTCCTATCC | SEQ ID NO: 10 |
| pENprom AGGA BsaI CW | GAGGTACC<u>GGTCTC</u>AAGGAACCAATTCAGTCGACTGG | SEQ ID NO: 11 |
| pENprom GGTG BsaI CCW | GAGGTACC<u>GGTCTC</u>AGGTGGCGGCCCTGTTATCCCTAGTCGACTAG | SEQ ID NO: 12 |
| SiaT CACC BsaI CW | GAGGTACC<u>GGTCTC</u>CCACCATGATTCACACCAACCTGAAG | SEQ ID NO: 13 |
| SiaT CCCC BsaI CCW | GAGGTACC<u>GGTCTC</u>ACCCCTTTTGCAGCCTAGGGATAAGG | SEQ ID NO: 14 |
| XFP-Ctag GGGG BsaI CW | GAGGTACC<u>GGTCTC</u>CGGGGTCGGGGGTGAGCAAGGGCGAGGAG | SEQ ID NO: 15 |
| XFP-Ctag ATCA BsaI CCW | GAGGTACC<u>GGTCTC</u>CATCACTTGTACAGCTCGTCCATGC | SEQ ID NO: 16 |

TABLE 4-continued

List of the primers used to amplify the building blocks specified
(recognition site BsaI underlined and sutures shown in bold)

| NAME | SEQUENCE | ID |
|---|---|---|
| tagBFP-Ctag GGGG BsaI CW | GAGGTACC<u>GGTCTCC</u>GGGGTCGGGGAGCGAGCTGATTAAGGAGAACATGC | SEQ ID NO: 69 |
| tagBFP-Ctag ATCA BsaI CCW | GAGGTACC<u>GGTCTCC</u>ATCATCCGGAATTAAGCTTGTGCCCCAG | SEQ ID NO: 70 |
| ColE1-ori-2 TATT BsaI CW | GAGGTACC<u>GGTCTCG</u>TATTGTAATACGGTTATCCACAGAATCAGG | SEQ ID NO: 71 |
| Am pR-2 TCCT BsaI CCW | GAGGTACC<u>GGTCTCG</u>TCCTTGGCACTTTTCGGGGAAATGTGC | SEQ ID NO: 72 |
| CMVp AGGA BsaI CW | GAGGTACC<u>GGTCTCA</u>AGGAACCAATTCAGTCGACTGG | SEQ ID NO: 73 |
| CMVp GGTG BsaI CCW | GAGGTACC<u>GGTCTCG</u>GGTGCCCTGTTATCCCTAGTCGACTAG | SEQ ID NO: 74 |
| hFUT3 CACC BsaI CW | GAGGTACC<u>GGTCTCA</u>CACCATGGATCCCTGGGTGCAGC | SEQ ID NO: 75 |
| hFUT3 ATCA BsaI CCW | GAGGTACC<u>GGTCTCG</u>ATCAGGTGAACCAAGCCGCTATGCTG | SEQ ID NO: 76 |
| BGH polyA CGAA BsaI CCW | GAGGTACC<u>GGTCTCG</u>CGAAGCCATAGAGCCCACCGC | SEQ ID NO: 77 |
| shB3Galt6 TTCG BsaI CW | GAGGTACC<u>GGTCTCA</u>TTCGACAGGGTCGACAAGCTTTTCC | SEQ ID NO: 78 |
| shB3Galt6 AATA BsaI CCW | GAGGTACC<u>GGTCTCG</u>AATACAAAACGCACCACGTGACG | SEQ ID NO: 79 |
| shB3Galt6 CTGG BsaI CCW | GAGGTACC<u>GGTCTCG</u>CTGGCAAAACGCACCACGTGACG | SEQ ID NO: 80 |
| Hygro CCAG BsaI CW | GAGGTACC<u>GGTCTCA</u>CCAGCAGGCAGAAGTATGCAAAGC | SEQ ID NO: 81 |
| Hygro AATA BsaI CCW | GAGGTACC<u>GGTCTCG</u>AATAGATACATTGATGAGTTTGGACAAACCAC | SEQ ID NO: 82 |
| rosa26-5' AGGA BsaI CW | GAGGTACC<u>GGTCTCA</u>AGGACCCCGCGGCAGGCCCTCC | SEQ ID NO: 83 |
| rosa26-5' TTGT BsaI CCW | GAGGTACC<u>GGTCTCG</u>TTGTAAGACTGGAGTTGCAGATCACGAG | SEQ ID NO: 84 |
| CMVp ACAA BsaI CW | GAGGTACC<u>GGTCTCA</u>ACAAACCAATTCAGTCGACTGG | SEQ ID NO: 85 |
| Hygro CTAC BsaI CCW | GAGGTACC<u>GGTCTCG</u>CTACGATACATTGATGAGTTTGGACAAACCAC | SEQ ID NO: 86 |
| rosa26-3' GTAG BsaI CW | GAGGTACC<u>GGTCTCA</u>GTAGAGATGGGCGGGAGTCTTCTG | SEQ ID NO: 87 |
| rosa26-3' AATA BsaI CCW | GAGGTACC<u>GGTCTCG</u>AATAGATAAGCTAGATGTCCTAAATATTTCTATC | SEQ ID NO: 88 |
| rosa26-3' GCAT BsaI CCW | GAGGTACC<u>GGTCTCG</u>GCATGATAAGCTAGATGTCCTAAATATTTCTATC | SEQ ID NO: 89 |
| EF1a ATGC BsaI CW | GAGGTACC<u>GGTCTCA</u>ATGCAAGGAACCAATTCAGTCGACTGGATC | SEQ ID NO: 90 |
| EF1a GGGC BsaI CCW | GAGGTACC<u>GGTCTCG</u>GGGCCCCTGTTATCCCTAGTCGACTAG | SEQ ID NO: 91 |
| TK GCCC BsaI CW | GAGGTACC<u>GGTCTCA</u>GCCCATGGCTTCGTACCCCTGC | SEQ ID NO: 92 |
| TK GCGG BsaI CCW | GAGGTACC<u>GGTCTCG</u>GCGGTCAGTTAGCCTCCCCCATCTCC | SEQ ID NO: 93 |
| HSVTKterm CCGC BsaI CW | GAGGTACC<u>GGTCTCA</u>CCGCGGGGAGGCTAACTGAAACAC | SEQ ID NO: 94 |
| HSVTKterm AATA BsaI CCW | GAGGTACC<u>GGTCTCG</u>AATAGGCTATGGCAGGGCCTGC | SEQ ID NO: 95 |

TABLE 4-continued

List of the primers used to amplify the building blocks specified
(recognition site BsaI underlined and sutures shown in bold)

| NAME | SEQUENCE | ID |
|---|---|---|
| TetOn3G CACC BsaI CW | GAGGTACCGGTCTCACACCATGTCTAGACTGGACAAGAGCAAAG | SEQ ID NO: 96 |
| TetOn3G ATCA BsaI CCW | GAGGTACCGGTCTCAATCATTACCCGGGGAGCATGTCAAG | SEQ ID NO: 97 |
| pTet3G TTCG BsaI CW | GAGGTACCGGTCTCATTCGTCTTCAAGAATTCCTCGAGTTTACTCC | SEQ ID NO: 98 |
| pTet3G CTGG BsaI CCW | GAGGTACCGGTCTCGCTGGTTTACGAGGGTAGGAAGTGGTACG | SEQ ID NO: 99 |
| mB3Galt6 CCAG BsaI CW | GAGGTACCGGTCTCACCAGAGCATGAAGGTATTCCGGCGCGCTTG | SEQ ID NO: 100 |
| mB3Galt6 GCGG BsaI CCW | GAGGTACCGGTCTCGGCGGTGACATCAGGGAACGCCCTCCTTG | SEQ ID NO: 101 |
| HSVTKterm TTGT BsaI CCW | GAGGTACCGGTCTCGTTGTGGCTATGGCAGGGCCTGC | SEQ ID NO: 102 |
| shB3Galt6 ACAA BsaI CW | GAGGTACCGGTCTCAACAAACAGGGTCGACAAGCTTTTCC | SEQ ID NO: 103 |
| ColE1-ori TAAA BsaI CCW | GAGGTACCGGTCTCATAAAACTCATATATACTTTAGATTGATTTAAAAC | SEQ ID NO: 120 |
| AmpR TTTA BsaI CW | GAGGTACCGGTCTCTTTTATTGGTCTGACAGTTACCAATGCTTAATC | SEQ ID NO: 121 |
| ColE1-ori GTTT BsaI CCW | GAGGTACCGGTCTCGGTTTACTCATATATACTTTAGATTGATTTAAAAC | SEQ ID NO: 122 |
| ColE1-ori 2 ATTA BsaI CW | GAGGTACCGGTCTCTATTACGGTAATACGGTTATCCACAG | SEQ ID NO: 123 |
| AmpR 2 GCAT BsaI CCW | GAGGTACCGGTCTCAGCATTGGCACTTTTCGGGGAAATGTGC | SEQ ID NO: 124 |
| AmpR AAAC BsaI CW TC | GAGGTACCGGTCTCAAAACTTGGTCTGACAGTTACCAATGCTTAATC | SEQ ID NO: 125 |
| EF1ap GATA BsaI CCW | GAGGTACCGGTCTCGGATATCACGACACCTGAAATGGAAG | SEQ ID NO: 126 |
| EF1apL ATGC BsaI CW | GAGGTACCGGTCTCAATGCGTGAGGCTCCGGTGCCCGTC | SEQ ID NO: 127 |
| EGFP-CAAX ACTC BsaI CCW | GAGGTACCGGTCTCCACTCTTACATAATTACACACTTTGTCTTTGACTTCTTTTTCTTCTTCTTGTACAGCTCGTCCATGC | SEQ ID NO: 128 |
| EGFP TATC BsaI CW | GAGGTACCGGTCTCCTATCATGGTGAGCAAGGGCGAGG | SEQ ID NO: 129 |
| BGHpA CTAC BsaI CCW 2 | GAGGTACCGGTCTCGCTACCCATAGAGCCCACCGCATCC | SEQ ID NO: 130 |
| BGHpA GAGT BsaI CW | GAGGTACCGGTCTCAGAGTCGACTGTGCCTTCTAGTTGCC | SEQ ID NO: 131 |
| CMVp CGAA BsaI CCW | GAGGTACCGGTCTCGCGAAGATCTGACGGTTCACTAAACCAG | SEQ ID NO: 132 |
| CMVp GTAG BsaI CW | GAGGTACCGGTCTCAGTAGTTATTAATAGTAATCAATTACGGGGTC | SEQ ID NO: 133 |
| SiaT TCAC BsaI CCW | GAGGTACCGGTCTCATCACCCCCGACCCCTTTTGCAG | SEQ ID NO: 134 |
| SiaT TTCG BsaI CW | GAGGTACCGGTCTCCTTCGATGATTCACACCAACCTGAAGAAAAAG | SEQ ID NO: 135 |
| XFP-Ctag GCGG BsaI CCW | GAGGTACCGGTCTCAGCGGTTACTTGTACAGCTCGTCCATGC | SEQ ID NO: 136 |
| XFP-Ctag GTGA BsaI CW | GAGGTACCGGTCTCAGTGAGCAAGGGCGAGGAG | SEQ ID NO: 137 |

TABLE 4-continued

List of the primers used to amplify the building blocks specified
(recognition site BsaI underlined and sutures shown in bold)

| NAME | SEQUENCE | ID |
|---|---|---|
| Hygro TAAT BsaI CCW | GAGGTACCGGTCTCGTAATGATACATTGATGAGTTTGGACAAACCAC | SEQ ID NO: 138 |
| Hygro ACAA BsaI CW | GAGGTACCGGTCTCAACAACAGGCAGAAGTATGCAAAGC | SEQ ID NO: 139 |
| ColE1-ori 2 GTTT BsaI CCW | GAGGTACCGGTCTCAGTTTAAACTCATATATACTTTAGATTGATTTAAAAC | SEQ ID NO: 140 |
| ColE1-ori 2 GGGG BsaI CW | GAGGTACCGGTCTCTGGGGCGGTAATACGGTTATCCACAG | SEQ ID NO: 141 |
| AmpR 2 TCAC BsaI CCW | GAGGTACCGGTCTCATCACTGGCACTTTTCGGGGAAATGTGC | SEQ ID NO: 142 |
| MNN10Lrec CGCA BsaI CCW | GAGGTACCGGTCTCACGCAATTGTATAGTTGTACATGCACAATTATTCC | SEQ ID NO: 143 |
| MNN10Lrec GTGA BsaI CW | GAGGTACCGGTCTCTGTGAGTTTAAACATGCATTCAAAGGTCATAATTGCTG | SEQ ID NO: 144 |
| MNN10Rrec CCCC BsaI CCW | GAGGTACCGGTCTCTCCCCGTTTAAACTGCCCAGTTTTTCATTATTAGTGTG | SEQ ID NO: 145 |
| MNN10Rrec TCGT BsaI CW | GAGGTACCGGTCTCTTCGTAATGGAAGTTATCAATATTGTAAAGAGAAGC | SEQ ID NO: 146 |
| KanMX ACGA BsaI CCW | GAGGTACCGGTCTCTACGACACTAGTGGATCTGATATCACC | SEQ ID NO: 147 |
| KanMX TGCG BsaI CW | GAGGTACCGGTCTCGTGCGGTACGCTGCAGGTCGACAACC | SEQ ID NO: 148 |

TABLE 5

Example of the composition of the reaction
mixture for execution of the PCRs

| Compound | volume |
|---|---|
| Matrix (2 ng/μl) | 1 μl |
| 5X HF buffer | 10 μl |
| dNTP (25 mM) | 0.5 μl |
| Oligo_CW_F | 1.25 μl |
| Oligo_CCW_F | 1.25 μl |
| Phusion Taq pol. | 0.5 μl |
| H$_2$O | 35.5 μl |

TABLE 6

Amplification cycles

| Temperature | Duration | Cycle |
|---|---|---|
| 95° C. | 30" | — |
| 95° C. | 10" | X25 |
| ≈Tm + 3° C. | 30" | |
| 72° C. | ≈30"/kb | |
| 72° C. | 5' | — |
| 4° C. | ∞ | — |

* The fluorescent modules were all adjusted to the same concentration

TABLE 7

Characteristics of the building blocks and PCR conditions

| Name of the building block | Size (bp) | Temperature of hybridisation | Extension time | Concentration after purification (ng/μl) |
|---|---|---|---|---|
| Ori-AmpR BsaI A (SEQ ID NO: 17) | 2005 | 60 | 1' | 42 |
| pCMV BsaI A (SEQ ID NO: 18) | 677 | 65 | 20" | 24 |
| SiaT BsaI A (SEQ ID NO: 19) | 370 | 61 | 10" | 104 |
| E1GFP BsaI A (SEQ ID NO: 20) or EGFP BsaI A (SEQ ID NO: 21) or ECFP BsaI A (SEQ ID No: 22) or EYFP BsaI A (SEQ ID NO: 23) or mCherry BsaI A (SEQ ID NO: 24) or TagBFP BsaI A (SEQ ID NO: 25) | 758 | 63 | 20" | 75* |
| BGHpA BsaI A (SEQ ID NO: 26) | 267 | 63 | 8" | 52 |
| LacZα-up BsaI A (SEQ ID NO: 27) | 278 | 67 | 8" | 38 |

TABLE 7-continued

Characteristics of the building blocks and PCR conditions

| Name of the building block | Size (bp) | Temperature of hybridisation | Extension time | Concentration after purification (ng/μl) |
|---|---|---|---|---|
| LacZα-down BsaI A (SEQ ID NO: 28) | 299 | 65 | 8" | 36 |
| HygroR BsaI A (SEQ ID NO: 29) | 1650 | 63 | 45" | 60 |

At the end of the PCR, the products are subjected to agarose gel electrophoresis and the strips cut from the gel are purified and quantified in accordance with the methods well known to a person skilled in the art.

TABLE 8

Composition of an assembly mix:
Protocol for assembly of the different molecular building blocks/construction of the vector

| Building block | Volume (μl) |
|---|---|
| Ori-AmpR BsaI A (SEQ ID NO: 17) | 2.4 |
| pCMV BsaI A (SEQ ID NO: 18) | 1.4 |
| SiaT BsaI A (SEQ ID NO: 19) | 0.2 |
| BGHpA BsaI A (SEQ ID NO: 26) | 0.25 |
| LacZα-up BsaI A (SEQ ID NO: 27) | 0.4 |
| LacZα-down BsaI A (SEQ ID NO: 28) | 0.4 |
| HygroR BsaI A (SEQ ID NO: 29) | 1.4 |
| E1GFP BsaI A (SEQ ID NO: 20) or EGFP BsaI A (SEQ ID NO: 21) or ECFP BsaI A (SEQ ID No: 22) or EYFP BsaI A (SEQ ID NO: 23) or mCherry BsaI A (SEQ ID NO: 24) or TagBFP BsaI A (SEQ ID NO: 25) | 0.5 |
| Ligase HC | 1 |
| BsaI | 1 |
| Ligation10X Br | 2 |
| H2O | 9.05 |

The assembly was performed by 50 incubation cycles at 37° C. for 2', then 16° C. for 3', followed by incubation at 50° C. for 5' and lastly incubation at 80° C. for 5'.

Figure 5:
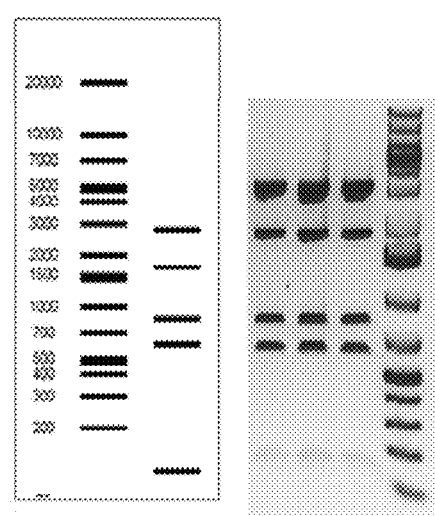

For each construction, the DNA of 3 colonies obtained after transformation was extracted and analysed by restriction by the enzymes PvuIHF and ScaIHF (FIG. 5).

The method according to the invention makes it possible to assemble, in a single step and in the presence of a single enzyme, at least 6 molecular building blocks (and more preferably at least 8 building blocks) without any error.

The method according to the invention makes it possible to assemble, in a single step and in the presence of a single enzyme, at least 6 molecular building blocks with a yield of 100%.

The method according to the invention makes it possible to assemble, in a single step and in the presence of a single enzyme, at least 6 building blocks and up to 30 building blocks.

The present invention thus makes it possible, in accordance with a specific method, to produce a circular double-stranded DNA vector from linear functional modules of double-stranded DNA, said method comprising a single step of assembly of said modules, in the presence of a single restriction enzyme, said single restriction enzyme being a type IIs enzyme.

Sequences of Building Blocks Used for the Different Constructions of Embodiment 1:

```
Building block Ori-AmpR BsaI A (2005 bp)
                                                        (SEQ ID NO: 17)
GAGGTACCGGTCTCATTATGCGTCTTCTAGGGTTAAGGTTAGTGTAGAGAAGCAACCGAAGATTGAGAAGACATG

GCGGTAATACGGTTATCCACAGAATCAGGGGATAACGCAGGAAAGAACATGTGAGCAAAAGGCCAGCAAAAGGC

CAGGAACCGTAAAAAGGCCGCGTTGCTGGCGTTTTTCCATAGGCTCCGCCCCCCTGACGAGCATCACAAAAATCGA

CGCTCAAGTCAGAGGTGGCGAAACCCGACAGGACTATAAAGATACCAGGCGTTTCCCCCTGGAAGCTCCCTCGTGC

GCTCTCCTGTTCCGACCCTGCCGCTTACCGGATACCTGTCCGCCTTTCTCCCTTCGGGAAGCGTGGCGCTTTCTCATA

GCTCACGCTGTAGGTATCTCAGTTCGGTGTAGGTCGTTCGCTCCAAGCTGGGCTGTGTGCACGAACCCCCCGTTCA

GCCCGACCGCTGCGCCTTATCCGGTAACTATCGTCTTGAGTCCAACCCGGTAAGACACGACTTATCGCCACTGGCA

GCAGCCACTGGTAACAGGATTAGCAGAGCGAGGTATGTAGGCGGTGCTACAGAGTTCTTGAAGTGGTGGCCTAAC

TACGGCTACACTAGAAGAACAGTATTTGGTATCTGCGCTCTGCTGAAGCCAGTTACCTTCGGAAAAAGAGTTGGTA

GCTCTTGATCCGGCAAACAAACCACCGCTGGTAGCGGTTTTTTTGTTTGCAAGCAGCAGATTACGCGCAGAAAAAA

AGGATCTCAAGAAGATCCTTTGATCTTTTCTACGGGGTCTGACGCTCAGTGGAACGAAAACTCACGTTAAGGGATT

TTGGTCATGAGATTATCAAAAAGGATCTTCACCTAGATCCTTTTAAATTAAAAATGAAGTTTTAAATCAATCTAAAGT

ATATATGAGTAAACTTGGTCTGACAGTTACCAATGCTTAATCAGTGAGGCACCTATCTCAGCGATCGTCTATTTCG

TTCATCCATAGTTGCCTGACTCCCCGTCGTGTAGATAACTACGATACGGGAGGGCTTACCATCTGGCCCCAGTGCTG

CAATGATACCGCGTGACCCACGCTCACCGGCTCCAGATTTATCAGCAATAAACCAGCCAGCCGGAAGGGCCGAGC

GCAGAAGTGGTCCTGCAACTTTATCCGCCTCCATCCAGTCTATTAATTGTTGCCGGGAAGCTAGAGTAAGTAGTTCG
```

```
CCAGTTAATAGTTTGCGCAACGTTGTTGCCATTGCTACAGGCATCGTGGTGTCACGCTCGTCGTTTGGTATGGCTTC

ATTCAGCTCCGGTTCCCAACGATCAAGGCGAGTTACATGATCCCCATGTTGTGCAAAAAAGCGGTTAGCTCCTTCG

GTCCTCCGATCGTTGTCAGAAGTAAGTTGGCCGCAGTGTTATCACTCATGGTTATGGCAGCACTGCATAATTCTCTT

ACTGTCATGCCATCCGTAAGATGCTTTTCTGTGACTGGTGAGTACTCAACCAAGTCATTCTGAGAATAGTGTATGCG

GCGACCGAGTTGCTCTTGCCCGGCGTCAATACGGGATAATACCGCGCCACATAGCAGAACTTTAAAAGTGCTCATC

ATTGGAAAACGTTCTTCGGGGCGAAAACTCTCAAGGATCTTACCGCTGTTGAGATCCAGTTCGATGTAACCCACTC

GTGCACCCAACTGATCTTCAGCATCTTTTACTTTCACCAGCGTTTCTGGGTGAGCAAAAACAGGAAGGCAAAATGC

CGCAAAAAAGGGAATAAGGGCGACACGGAAATGTTGAATACTCATACTCTTCCTTTTTCAATATTATTGAAGCATTT

ATCAGGGTTATTGTCTCATGAGCGGATACATATTTGAATGTATTTAGAAAAATAAACAAATAGGGGTTCCGCGCAC

ATTTCCCCGAAAAGTGCCACCTATGAGACGTGAGGCTAGGGATAGGACGAGAGCATCGGGAACGAGGACTAGCG

TCTCAAGGACGAGACCGGTACCTC
```

Building block pCMV BsaI A (677 bp)
(SEQ ID NO: 18)

```
GAGGTACCGGTCTCAAGGAACCAATTCAGTCGACTGGATCCTAGTTATTAATAGTAATCAATTACGGGGTCATTAG

TTCATAGCCCATATATGGAGTTCCGCGTTACATAACTTACGGTAAATGGCCCGCCTGGCTGACCGCCCAACGACCCC

CGCCCATTGACGTCAATAATGACGTATGTTCCCATAGTAACGCCAATAGGGACTTTCCATTGACGTCAATGGGTGG

AGTATTTACGGTAAACTGCCCACTTGGCAGTACATCAAGTGTATCATATGCCAAGTACGCCCCCTATTGACGTCAAT

GACGGTAAATGGCCCGCCTGGCATTATGCCCAGTACATGACCTTATGGGACTTTCCTACTTGGCAGTACATCTACGT

ATTAGTCATCGCTATTACCATGGTGATGCGGTTTTGGCAGTACATCAATGGGCGTGGATAGCGGTTTGACTCACGG

GGATTTCCAAGTCTCCACCCCATTGACGTCAATGGGAGTTTGTTTTGGCACCAAAATCAACGGGACTTTCCAAATG

TCGTAACAACTCCGCCCCATTGACGCAAATGGGCGGTAGGCGTGTACGGTGGGAGGTCTATATAAGCAGAGCTGG

TTTAGTGAACCGTCAGATCACTAGTCGACTAGGGATAACAGGGCCGCCACCTGAGACCGGTACCTC
```

Building block SiaT BsaI A (370 bp)
(SEQ ID NO: 19)

```
GAGGTACCGGTCTCCCACCATGATTCACACCAACCTGAAGAAAAAGTTCAGCTGCTGCGTCCTGGTCTTTCTTCTGT

TTGCAGTCATCTGTGTGTGGAAGGAAAAGAAGAAAGGGAGTTACTATGATTCCTTTAAATTGCAAACCAAGGAATT

CCAGGTGTTAAAGAGTCTGGGGAAATTGGCCATGGGGTCTGATTCCCAGTCTGTATCCTCAAGCAGCACCCAGGAC

CCCCACAGGGGCCGCCAGACCCTCGGCAGTCTCAGAGGCCTAGCCAAGGCCAAACCAGAGGCCTCCTTCCAGGTG

TGGAACAAGGACAGCTCTTCCAAAAACCTTATCCCTAGGCTGCAAAAGGGGTGAGACCGGTACCTC
```

Building block EGFP BsaI A (758 bp)
(SEQ ID NO: 20)

```
GAGGTACCGGTCTCCGGGGTCGGGGGTGAGCAAGGGCGAGGAGCTGTTCACCGGGGTGGTGCCCATCCTGGTCG

AGCTGGACGGCGACGTAAACGGCCACAAGTTCAGCGTGTCCGGCGAGGGCGAGGGCGATGCCACCTACGGCAAG

CTGACCCTGAAGTTCATCTGCACCACCGGCAAGCTGCCCGTGCCCTGGCCCACCCTCGTGACCACCCTgtccTACGGC

GTGCAGTGCTTCAGCCGCTACCCCGACCACATGAAGCAGCACGACTTCTTCAAGTCCGCCATGCCCGAAGGCTACG

TCCAGGAGCGCACCATCTTCTTCAAGGACGACGGCAACTACAAGACCCGCGCCGAGGTGAAGTTCGAGGGCGACA

CCCTGGTGAACCGCATCGAGCTGAAGGGCATCGACTTCAAGGAGGACGGCAACATCCTGGGGCACAAGCTGGAG

TACAACTACAACAGCCACAACGTCTATATCATGGCCGACAAGCAGAAGAACGGCATCAAGGTGAACTTCAAGATCC

GCCACAACATCGAGGACGGCAGCGTGCAGCTCGCCGACCACTACCAGCAGAACACCCCCATCGGCGACGGCCCCG

TGCTGCTGCCCGACAACCACTACCTGAGctacCAGTCCGCCCTGAGCAAAGACCCCAACGAGAAGCGCGATCACATG

GTCCTGCTGGAGTTCGTGACCGCCGCCGGGATCACTCTCGGCATGGACGAGCTGTACAAGTGATGGAGACCGGTA

CCTC
```

Building block EGFP BsaI A (758 bp)

(SEQ ID NO: 21)
GAGGTACCGGTCTCCGGGGTCGGGGGTGAGCAAGGGCGAGGAGCTGTTCACCGGGGTGGTGCCCATCCTGGTCG

AGCTGGACGGCGACGTAAACGGCCACAAGTTCAGCGTGTCCGGCGAGGGCGAGGGCGATGCCACCTACGGCAAG

CTGACCCTGAAGTTCATCTGCACCACCGGCAAGCTGCCCGTGCCCTGGCCCACCCTCGTGACCACCCTGACCTACGG

CGTGCAGTGCTTCAGCCGCTACCCCGACCACATGAAGCAGCACGACTTCTTCAAGTCCGCCATGCCCGAAGGCTAC

GTCCAGGAGCGCACCATCTTCTTCAAGGACGACGGCAACTACAAGACCCGCGCCGAGGTGAAGTTCGAGGGCGAC

ACCCTGGTGAACCGCATCGAGCTGAAGGGCATCGACTTCAAGGAGGACGGCAACATCCTGGGGCACAAGCTGGA

GTACAACTACAACAGCCACAACGTCTATATCATGGCCGACAAGCAGAAGAACGGCATCAAGGTGAACTTCAAGAT

CCGCCACAACATCGAGGACGGCAGCGTGCAGCTCGCCGACCACTACCAGCAGAACACCCCCATCGGCGACGGCCC

CGTGCTGCTGCCCGACAACCACTACCTGAGCACCCAGTCCGCCCTGAGCAAAGACCCCAACGAGAAGCGCGATCAC

ATGGTCCTGCTGGAGTTCGTGACCGCCGCCGGGATCACTCTCGGCATGGACGAGCTGTACAAGTGATGGAGACCG

GTACCTC

Building block ECFP BsaI A (758 bp)

(SEQ ID NO: 22)
GAGGTACCGGTCTCCGGGGTCGGGGGTGAGCAAGGGCGAGGAGCTGTTCACCGGGGTGGTGCCCATCCTGGTCG

AGCTGGACGGCGACGTAAACGGCCACAAGTTCAGCGTGTCCGGCGAGGGCGAGGGCGATGCCACCTACGGCAAG

CTGACCCTGAAGTTCATCTGCACCACCGGCAAGCTGCCCGTGCCCTGGCCCACCCTCGTGACCACCCTGACCTGGG

GCGTGCAGTGCTTCAGCCGCTACCCCGACCACATGAAGCAGCACGACTTCTTCAAGTCCGCCATGCCCGAAGGCTA

CGTCCAGGAGCGCACCATCTTCTTCAAGGACGACGGCAACTACAAGACCCGCGCCGAGGTGAAGTTCGAGGGCGA

CACCCTGGTGAACCGCATCGAGCTGAAGGGCATCGACTTCAAGGAGGACGGCAACATCCTGGGGCACAAGCTGG

AGTACAACTACATCAGCCACAACGTCTATATCACCGCCGACAAGCAGAAGAACGGCATCAAGGCCAACTTCAAGAT

CCGCCACAACATCGAGGACGGCAGCGTGCAGCTCGCCGACCACTACCAGCAGAACACCCCCATCGGCGACGGCCC

CGTGCTGCTGCCCGACAACCACTACCTGAGCACCCAGTCCGCCCTGAGCAAAGACCCCAACGAGAAGCGCGATCAC

ATGGTCCTGCTGGAGTTCGTGACCGCCGCCGGGATCACTCTCGGCATGGACGAGCTGTACAAGTGATGGAGACCG

GTACCTC

Building block EYFP BsaI A (758 bp)

(SEQ ID NO: 23)
GAGGTACCGGTCTCCGGGGTCGGGGGTGAGCAAGGGCGAGGAGCTGTTCACCGGGGTGGTGCCCATCCTGGTCG

AGCTGGACGGCGACGTAAACGGCCACAAGTTCAGCGTGTCCGGCGAGGGCGAGGGCGATGCCACCTACGGCAAG

CTGACCCTGAAGTTCATCTGCACCACCGGCAAGCTGCCCGTGCCCTGGCCCACCCTCGTGACCACCTTCGGCTACGG

CCTGCAGTGCTTCGCCCGCTACCCCGACCACATGAAGCAGCACGACTTCTTCAAGTCCGCCATGCCCGAAGGCTAC

GTCCAGGAGCGCACCATCTTCTTCAAGGACGACGGCAACTACAAGACCCGCGCCGAGGTGAAGTTCGAGGGCGAC

ACCCTGGTGAACCGCATCGAGCTGAAGGGCATCGACTTCAAGGAGGACGGCAACATCCTGGGGCACAAGCTGGA

GTACAACTACAACAGCCACAACGTCTATATCATGGCCGACAAGCAGAAGAACGGCATCAAGGTGAACTTCAAGAT

CCGCCACAACATCGAGGACGGCAGCGTGCAGCTCGCCGACCACTACCAGCAGAACACCCCCATCGGCGACGGCCC

CGTGCTGCTGCCCGACAACCACTACCTGAGCTACCAGTCCGCCCTGAGCAAAGACCCCAACGAGAAGCGCGATCAC

ATGGTCCTGCTGGAGTTCGTGACCGCCGCCGGGATCACTCTCGGCATGGACGAGCTGTACAAGTGATGGAGACCG

GTACCTC

Building block mCherry BsaI A (749 bp)

(SEQ ID NO: 24)
GAGGTACCGGTCTCCGGGGTCGGGGGTGAGCAAGGGCGAGGAGGATAACATGGCCATCATCAAGGAGTTCATGC

GCTTCAAGGTGCACATGGAGGGCTCCGTGAACGGCCACGAGTTCGAGATCGAGGGCGAGGGCGAGGGCCGCCCC

TACGAGGGCACCCAGACCGCCAAGCTGAAGGTGACCAAGGGTGGCCCCCTGCCCTTCGCCTGGGACATCCTGTCC

-continued

CCTCAGTTCATGTACGGCTCCAAGGCCTACGTGAAGCACCCCGCCGACATCCCCGACTACTTGAAGCTGTCCTTCCC

CGAGGGCTTCAAGTGGGAGCGCGTGATGAACTTCGAGGACGGCGGCGTGGTGACCGTGACCCAGGACTCCTCCCT

GCAGGACGGCGAGTTCATCTACAAGGTGAAGCTGCGCGGCACCAACTTCCCCTCCGACGGCCCCGTAATGCAGAA

GAAAACCATGGGCTGGGAGGCCTCCTCCGAGCGGATGTACCCCGAGGACGGCGCCCTGAAGGGCGAGATCAAGC

AGAGGCTGAAGCTGAAGGACGGCGGCCACTACGACGCTGAGGTCAAGACCACCTACAAGGCCAAGAAGCCCGTG

CAGCTGCCCGGCGCCTACAACGTCAACATCAAGTTGGACATCACCTCCCACAACGAGGACTACACCATCGTGGAAC

AGTACGAACGCGCCGAGGGCCGCCACTCCACCGGCGGCATGGACGAGCTGTACAAGTGATGGAGACCGGTACCTC

Building block TagBFP BsaI A (746 bp)
(SEQ ID NO: 25)
GAGGTACCGGTCTCCGGGGTCGGGGAGCGAGCTGATTAAGGAGAACATGCACATGAAGCTGTACATGGAGGGCA

CCGTGGACAACCATCACTTCAAGTGCACATCCGAGGGCGAAGGCAAGCCCTACGAGGGCACCCAGACCATGAGAA

TCAAGGTGGTCGAGGGCGGCCCTCTCCCCTTCGCCTTCGACATCCTGGCTACTAGCTTCCTCTACGGCAGCAAGACC

TTCATCAACCACACCCAGGGCATCCCCGACTTCTTCAAGCAGTCCTTCCCTGAGGGCTTCACATGGGAGAGAGTCAC

CACATACGAGGACGGGGGCGTGCTGACCGCTACCCAGGACACCGCCTCCAGGACGGCTGCCTCATCTACAACGT

CAAGATCAGAGGGGTGAACTTCACATCCAACGGCCCTGTGATGCAGAAGAAAACACTCGGCTGGGAGGCCTTCAC

CGAAACGCTGTACCCCGCTGACGGCGGCCTGGAAGGCAGAAACGACATGGCCCTGAAGCTCGTGGGCGGGAGCC

ATCTGATCGCAAACATCAAGACCACATATAGATCCAAGAAACCCGCTAAGAACCTCAAGATGCCTGGCGTCTACTA

TGTGGACTACAGACTGGAAAGAATCAAGGAGGCCAACAACGAAACCTACGTCGAGCAGCACGAGGTGGCAGTGG

CCAGATACTGCGACCTCCCTAGCAAACTGGGGCACAAGCTTAATTCCGGATGATGGAGACCGGTACCTC

Building block BGHpA BsaI A (267 bp)
(SEQ ID NO: 26)
GAGGTACCGGTCTCATGATCGACTGTGCCTTCTAGTTGCCAGCCATCTGTTGTTTGCCCCTCCCCCGTGCCTTCCTTG

ACCCTGGAAGGTGCCACTCCCACTGTCCTTTCCTAATAAAATGAGGAAATTGCATCGCATTGTCTGAGTAGGTGTCA

TTCTATTCTGGGGGGTGGGGTGGGGCAGGACAGCAAGGGGGAGGATTGGGAGGACAATAGCAGGCATGCTGGG

GATGCGGTGGGCTCTATGGCTTCTGGAGACCGGTACCTC

Building block LacZα-up BsaI A (278)
(SEQ ID NO: 27)
GAGGTACCGGTCTCGTTCTCCCTGCAGGTGCGCCCAATACGCAAACCGCCTCTCCCCGCGCGTTGGCCGATTCATTA

ATGCAGCTGGCACGACAGGTTTCCCGACTGGAAAGCGGGCAGTGAGCGCAACGCAATTAATGTGAGTTAGCTCAC

TCATTAGGCACCCCAGGCTTTACACTTTATGCTTCCGGCTCGTATGTTGTGTGGAATTGTGAGCGGATAACAATTTC

ACACAGGAAACAGCTATGACCATGATTACGGACAGGAGACCGGTACCTC

Building block LacZα-down BsaI A (299 bp)
(SEQ ID NO: 28)
GAGGTACCGGTCTCGGACAGCCTGGCCGTCGTTTTACAACGTCGTGACTGGGAAAACCCTGGCGTTACCCAACTTA

ATCGCCTTGCAGCACATCCCCCTTTCGCCAGCTGGCGTAATAGCGAAGAGGCCCGCACCGATCGCCCTTCCCAACA

GTTGCGCAGCCTGAATGGCGAATGGCGCCTGATGCGGTATTTTCTCCTTACGCATCTGTGCGGTATTTCACACCGCA

TATGGTGCACTCTCAGTACAATCTGCTCTGATGCCGCATAGACCTGCAGGGCCAGTGAGACCGGTACCTC

Building block HygroR BsaI A (1650 bp)
(SEQ ID NO: 29)
GAGGTACCGGTCTCCCCAGCAGGCAGAAGTATGCAAAGCATGCATCTCAATTAGTCAGCAACCAGGTGTGGAAAG

TCCCCAGGCTCCCCAGCAGGCAGAAGTATGCAAAGCATGCATCTCAATTAGTCAGCAACCATAGTCCCGCCCCTAA

CTCCGCCCATCCCGCCCCTAACTCCGCCCAGTTCCGCCCATTCTCCGCCCCATGGCTGACTAATTTTTTTTATTTATGC

AGAGGCCGAGGCCGCCTCTGCCTCTGAGCTATTCCAGAAGTAGTGAGGAGGCTTTTTTGGAGGCCTAGGCTTTTGC

AAAAAGCTCCCGGGAGCTTGTATATCCATTTTCGGATCTGATCAGCACGTGATGAAAAAGCCTGAACTCACCGCGA

CGTCTGTCGAGAAGTTTCTGATCGAAAAGTTCGACAGCGTGTCCGACCTGATGCAGCTCTCGGAGGGCGAAGAAT

CTCGTGCTTTCAGCTTCGATGTAGGAGGGCGTGGATATGTCCTGCGGGTAAATAGCTGCGCCGATGGTTTCTACAA

-continued

```
AGATCGTTATGTTTATCGGCACTTTGCATCGGCCGCGCTCCCGATTCCGGAAGTGCTTGACATTGGGGAATTCAGC

GAGAGCCTGACCTATTGCATCTCCCGCCGTGCACAGGGTGTCACGTTGCAAGACTTGCCTGAAACCGAACTGCCCG

CTGTTCTGCAGCCGGTCGCGGAGGCCATGGATGCGATCGCTGCGGCCGATCTTAGCCAGACGAGCGGGTTCGGCC

CATTCGGACCGCAAGGAATCGGTCAATACACTACATGGCGTGATTTCATATGCGCGATTGCTGATCCCCATGTGTAT

CACTGGCAAACTGTGATGGACGACACCGTCAGTGCGTCCGTCGCGCAGGCTCTCGATGAGCTGATGCTTTGGGCC

GAGGACTGCCCCGAAGTCCGGCACCTCGTGCACGCGGATTTCGGCTCCAACAATGTCCTGACGGACAATGGCCGC

ATAACAGCGGTCATTGACTGGAGCGAGGCGATGTTCGGGGATTCCCAATACGAGGTCGCCAACATCTTCTTCTGGA

GGCCGTGGTTGGCTTGTATGGAGCAGCAGACGCGCTACTTCGAGCGGAGGCATCCGGAGCTTGCAGGATCGCCGC

GGCTCCGGGCGTATATGCTCCGCATTGGTCTTGACCAACTCTATCAGAGCTTGGTTGACGGCAATTTCGATGATGC

AGCTTGGGCGCAGGGTCGATGCGACGCAATCGTCCGATCCGGAGCCGGGACTGTCGGGCGTACACAAATCGCCC

GCAGAAGCGCGGCCGTCTGGACCGATGGCTGTGTAGAAGTACTCGCCGATAGTGGAAACCGACGCCCCAGCACTC

GTCCGAGGGCAAAGGAATAGCACGTGCTACGAGATTTCGATTCCACCGCCGCCTTCTATGAAAGGTTGGGCTTCG

GAATCGTTTTCCGGGACGCCGGCTGGATGATCCTCCAGCGCGGGATCTCATGCTGGAGTTCTTCGCCCACCCCAA

CTTGTTTATTGCAGCTTATAATGGTTACAAATAAAGCAATAGCATCACAAATTTCACAAATAAAGCATTTTTTCACT

GCATTCTAGTTGTGGTTTGTCCAAACTCATCAATGTATCTTATCGAGACCGGTACCTC
```

Sequence of the Vectors Obtained in Embodiment 1

A vector pHCsiaT-E₁GFP (SEQ ID NO: 30) according to the invention is constructed from a combination of building blocks Ori-AmpR BsaI A (SEQ ID NO: 17), pCMV BsaI A (SEQ ID NO: 18), SiaT BsaI A (SEQ ID NO: 19), BGHpA BsaI A (SEQ ID NO: 26), LacZα-up BsaI A (SEQ ID NO: 27), LacZα-down BsaI A (SEQ ID NO: 28), HygroR BsaI A (SEQ ID NO: 29) and E1GFP BsaI A (SEQ ID NO: 20).

```
Vector pHCsiaT-E₁GFP
                                    (SEQ ID NO: 30)
TGAGGCTAGGGATAGGACGAGAGCATCGGGAACGAGGACTAGCGTCTCAA

GGAACCAATTCAGTCGACTGGATCCTAGTTATTAATAGTAATCAATTACG

GGGTCATTAGTTCATAGCCCATATATGGAGTTCCGCGTTACATAACTTAC

GGTAAATGGCCCGCCTGGCTGACCGCCCAACGACCCCCGCCCATTGACGT

CAATAATGACGTATGTTCCCATAGTAACGCCAATAGGGACTTTCCATTGA

CGTCAATGGGTGGAGTATTTACGGTAAACTGCCCACTTGGCAGTACATCA

AGTGTATCATATGCCAAGTACGCCCCCTATTGACGTCAATGACGGTAAAT

GGCCCGCCTGGCATTATGCCCAGTACATGACCTTATGGGACTTTCCTACT

TGGCAGTACATCTACGTATTAGTCATCGCTATTACCATGGTGATGCGGTT

TTGGCAGTACATCAATGGGCGTGGATAGCGGTTTGACTCACGGGGATTTC

CAAGTCTCCACCCCATTGACGTCAATGGGAGTTTGTTTTGGCACCAAAAT

CAACGGGACTTTCCAAAATGTCGTAACAACTCCGCCCCATTGACGCAAAT

GGGCGGTAGGCGTGTACGGTGGGAGGTCTATATAAGCAGAGCTGGTTTAG

TGAACCGTCAGATCACTAGTCGACTAGGGATAACAGGGCCGCCACCATGA

TTCACACCAACCTGAAGAAAAAGTTCAGCTGCTGCGTCCTGGTCTTTCTT

CTGTTTGCAGTCATCTGTGTGTGGAAGGAAAAGAAGAAAGGGAGTTACTA

TGATTCCTTTAAATTGCAAACCAAGGAGTTCCAGGTGTTAAAGAGTCTGG

GGAAATTGGCCATGGGGTCTGATTCCCAGTCTGTATCCTCAAGCAGCACC

CAGGACCCCCACAGGGGCCGCCAGACCCTCGGCAGTCTCAGAGGCCTAGC

CAAGGCCAAACCAGAGGCCTCCTTCCAGGTGTGGAACAAGGACAGCTCTT

CCAAAAACCTTATCCCTAGGCTGCAAAAGGGGTCGGGGGTGAGCAAGGGC

GAGGAGCTGTTCACCGGGGTGGTGCCCATCCTGGTCGAGCTGGACGGCGA

CGTAAACGCCACAAGTTCAGCGTGTCCGGCGAGGGCGAGGGCGATGCCA

CCTACGGCAAGCTGACCCTGAAGTTCATCTGCACCACCGGCAAGCTGCCC

GTGCCCTGGCCCACCCTCGTGACCACCCTGTCCTACGGCGTGCAGTGCTT

CAGCCGCTACCCCGACCACATGAAGCAGCACGACTTCTTCAAGTCCGCCA

TGCCCGAAGGCTACGTCCAGGAGCGCACCATCTTCTTCAAGGACGACGGC

AACTACAAGACCCGCGCCGAGGTGAAGTTCGAGGGCGACACCCTGGTGAA

CCGCATCGAGCTGAAGGGCATCGACTTCAAGGAGGACGGCAACATCCTGG

GGCACAAGCTGGAGTACAACTACAACAGCCACAACGTCTATATCATGGCC

GACAAGCAGAAGAACGGCATCAAGGTGAACTTCAAGATCCGCCACAACAT

CGAGGACGGCAGCGTGCAGCTCGCCGACCACTACCAGCAGAACACCCCCA

TCGGCGACGGCCCCGTGCTGCTGCCCGACAACCACTACCTGAGCTACCAG

TCCGCCCTGAGCAAAGACCCCAACGAGAAGCGCGATCACATGGTCCTGCT

GGAGTTCGTGACCGCCGCCGGGATCACTCTCGGCATGGACGAGCTGTACA

AGTGATCGACTGTGCCTTCTAGTTGCCAGCCATCTGTTGTTTGCCCCTCC

CCCGTGCCTTCCTTGACCCTGGAAGGTGCCACTCCCACTGTCCTTTCCTA

ATAAAATGAGGAAATTGCATCGCATTGTCTGAGTAGGTGTCATTCTATTC

TGGGGGGTGGGGTGGGGCAGGACAGCAAGGGGGAGGATTGGGAGGACAAT

AGCAGGCATGCTGGGGATGCGGTGGGCTCTATGGCTTCTCCCTGCAGGTG

CGCCCAATACGCAAACCGCCTCTCCCCGCGCGTTGGCCGATTCATTAATG
```

```
CAGCTGGCACGACAGGTTTCCCGACTGGAAAGCGGGCAGTGAGCGCAACG
CAATTAATGTGAGTTAGCTCACTCATTAGGCACCCCAGGCTTTACACTTT
ATGCTTCCGGCTCGTATGTTGTGTGGAATTGTGAGCGGATAACAATTTCA
CACAGGAAACAGCTATGACCATGATTACGACAGCCTGGCCGTCGTTTTA
CAACGTCGTGACTGGGAAAACCCTGGCGTTACCCAACTTAATCGCCTTGC
AGCACATCCCCCTTTCGCCAGCTGGCGTAATAGCGAAGAGGCCCGCACCG
ATCGCCCTTCCCAACAGTTGCGCAGCCTGAATGGCGAATGGCGCCTGATG
CGGTATTTTCTCCTTACGCATCTGTGCGGTATTTCACACCGCATATGGTG
CACTCTCAGTACAATCTGCTCTGATGCCGCATAGACCTGCAGGGCCAGCA
GGCAGAAGTATGCAAAGCATGCATCTCAATTAGTCAGCAACCAGGTGTGG
AAAGTCCCCAGGCTCCCCAGCAGGCAGAAGTATGCAAAGCATGCATCTCA
ATTAGTCAGCAACCATAGTCCCGCCCCTAACTCCGCCCATCCCGCCCCTA
ACTCCGCCCAGTTCCGCCCATTCTCCGCCCCATGGCTGACTAATTTTTTT
TATTTATGCAGAGGCCGAGGCCGCCTCTGCCTCTGAGCTATTCCAGAAGT
AGTGAGGAGGCTTTTTTGGAGGCCTAGGCTTTTGCAAAAAGCTCCCGGGA
GCTTGTATATCCATTTTCGGATCTGATCAGCACGTGATGAAAAAGCCTGA
ACTCACCGCGACGTCTGTCGAGAAGTTTCTGATCGAAAAGTTCGACAGCG
TGTCCGACCTGATGCAGCTCTCGGAGGGCGAAGAATCTCGTGCTTTCAGC
TTCGATGTAGGAGGGCGTGGATATGTCCTGCGGGTAAATAGCTGCGCCGA
TGGTTTCTACAAAGATCGTTATGTTTATCGGCACTTTGCATCGGCCGCGC
TCCCGATTCCGGAAGTGCTTGACATTGGGGAATTCAGCGAGAGCCTGACC
TATTGCATCTCCCGCCGTGCACAGGGTGTCACGTTGCAAGACTTGCCTGA
AACCGAACTGCCCGCTGTTCTGCAGCCGGTCGCGGAGGCCATGGATGCGA
TCGCTGCGGCCGATCTTAGCCAGACGAGCGGGTTCGGCCCATTCGGACCG
CAAGGAATCGGTCAATACACTACATGGCGTGATTTCATATGCGCGATTGC
TGATCCCCATGTGTATCACTGGCAAACTGTGATGGACGACACCGTCAGTG
CGTCCGTCGCGCAGGCTCTCGATGAGCTGATGCTTTGGGCCGAGGACTGC
CCCGAAGTCCGGCACCTCGTGCACGCGGATTTCGGCTCCAACAATGTCCT
GACGGACAATGGCCGCATAACAGCGGTCATTGACTGGAGCGAGGCGATGT
TCGGGGATTCCCAATACGAGGTCGCCAACATCTTCTTCTGGAGGCCGTGG
TTGGCTTGTATGGAGCAGCAGACGCGCTACTTCGAGCGGAGGCATCCGGA
GCTTGCAGGATCGCCGCGGCTCCGGGCGTATATGCTCCGCATTGGTCTTG
ACCAACTCTATCAGAGCTTGGTTGACGGCAATTTCGATGATGCAGCTTGG
GCGCAGGGTCGATGCGACGCAATCGTCCGATCCGGAGCCGGGACTGTCGG
GCGTACACAAATCGCCCGCAGAAGCGCGGCCGTCTGGACCGATGGCTGTG
TAGAAGTACTCGCCGATAGTGGAAACCGACGCCCCAGCACTCGTCCGAGG
GCAAAGGAATAGCACGTGCTACGAGATTTCGATTCCACCGCCGCCTTCTA
TGAAAGGTTGGGCTTCGGAATCGTTTTCCGGGACGCCGGCTGGATGATCC
TCCAGCGCGGGGATCTCATGCTGGAGTTCTTCGCCCACCCCAACTTGTTT
ATTGCAGCTTATAATGGTTACAAATAAAGCAATAGCATCACAAATTTCAC
AAATAAAGCATTTTTTTCACTGCATTCTAGTTGTGGTTTGTCCAAACTCA
TCAATGTATCTTATGCGTCTTCTAGGGTTAAGGTTAGTGTAGAGAAGCAA
CCGAAGATTGAGAAGACATGGCGGTAATACGGTTATCCACAGAATCAGGG
GATAACGCAGGAAAGAACATGTGAGCAAAAGGCCAGCAAAAGGCCAGGAA
CCGTAAAAAGGCCGCGTTGCTGGCGTTTTTCCATAGGCTCCGCCCCCCTG
ACGAGCATCACAAAAATCGACGCTCAAGTCAGAGGTGGCGAAACCCGACA
GGACTATAAAGATACCAGGCGTTTCCCCCTGGAAGCTCCCTCGTGCGCTC
TCCTGTTCCGACCCTGCCGCTTACCGGATACCTGTCCGCCTTTCTCCCTT
CGGGAAGCGTGGCGCTTTCTCATAGCTCACGCTGTAGGTATCTCAGTTCG
GTGTAGGTCGTTCGCTCCAAGCTGGGCTGTGTGCACGAACCCCCCGTTCA
GCCCGACCGCTGCGCCTTATCCGGTAACTATCGTCTTGAGTCCAACCCGG
TAAGACACGACTTATCGCCACTGGCAGCAGCCACTGGTAACAGGATTAGC
AGAGCGAGGTATGTAGGCGGTGCTACAGAGTTCTTGAAGTGGTGGCCTAA
CTACGGCTACACTAGAAGAACAGTATTTGGTATCTGCGCTCTGCTGAAGC
CAGTTACCTTCGGAAAAAGAGTTGGTAGCTCTTGATCCGGCAAACAAACC
ACCGCTGGTAGCGGTTTTTTTGTTTGCAAGCAGCAGATTACGCGCAGAAA
AAAAGGATCTCAAGAAGATCCTTTGATCTTTTCTACGGGGTCTGACGCTC
AGTGGAACGAAAACTCACGTTAAGGGATTTTGGTCATGAGATTATCAAAA
AGGATCTTCACCTAGATCCTTTTAAATTAAAAATGAAGTTTTAAATCAAT
CTAAAGTATATATGAGTAAACTTGGTCTGACAGTTACCAATGCTTAATCA
GTGAGGCACCTATCTCAGCGATCTGTCTATTTCGTTCATCCATAGTTGCC
TGACTCCCCGTCGTGTAGATAACTACGATACGGGAGGGCTTACCATCTGG
CCCCAGTGCTGCAATGATACCGCGTGACCCACGCTCACCGGCTCCAGATT
TATCAGCAATAAACCAGCCAGCCGGAAGGGCCGAGCGCAGAAGTGGTCCT
GCAACTTTATCCGCCTCCATCCAGTCTATTAATTGTTGCCGGGAAGCTAG
AGTAAGTAGTTCGCCAGTTAATAGTTTGCGCAACGTTGTTGCCATTGCTA
CAGGCATCGTGGTGTCACGCTCGTCGTTTGGTATGGCTTCATTCAGCTCC
GGTTCCCAACGATCAAGGCGAGTTACATGATCCCCCATGTTGTGCAAAAA
AGCGGTTAGCTCCTTCGGTCCTCCGATCGTTGTCAGAAGTAAGTTGGCCG
CAGTGTTATCACTCATGGTTATGGCAGCACTGCATAATTCTCTTACTGTC
ATGCCATCCGTAAGATGCTTTTCTGTGACTGGTGAGTACTCAACCAAGTC
ATTCTGAGAATAGTGTATGCGGCGACCGAGTTGCTCTTGCCCGGCGTCAA
TACGGGATAATACCGCGCCACATAGCAGAACTTTAAAAGTGCTCATCATT
GGAAAACGTTCTTCGGGGCGAAAACTCTCAAGGATCTTACCGCTGTTGAG
ATCCAGTTCGATGTAACCCACTCGTGCACCCAACTGATCTTCAGCATCTT
TTACTTTCACCAGCGTTTCTGGGTGAGCAAAAACAGGAAGGCAAAATGCC
GCAAAAAGGGAATAAGGGCGACACGGAAATGTTGAATACTCATACTCTT
CCTTTTTCAATATTATTGAAGCATTTATCAGGGTTATTGTCTCATGAGCG
GATACATATTTGAATGTATTTAGAAAAATAAACAAATAGGGGTTCCGCGC
ACATTTCCCCGAAAAGTGCCACCTATGAGACG
```

A vector pHCsiaT-EGFP (SEQ ID NO: 31) according to the invention is constructed from a combination of building blocks Ori-AmpR BsaI A (SEQ ID NO: 17), pCMV BsaI A (SEQ ID NO: 18), SiaT BsaI A (SEQ ID NO: 19), BGHpA BsaI A (SEQ ID NO: 26), LacZα-up BsaI A (SEQ ID NO: 27), LacZα-down BsaI A (SEQ ID NO: 28), HygroR BsaI A (SEQ ID NO: 29) and EGFP BsaI A (SEQ ID NO: 21).

```
Vector pHCsiaT-EGFP
                                                                (SEQ ID NO: 31)
TGAGGCTAGGGATAGGACGAGAGCATCGGGAACGAGGACTAGCGTCTCAAGGAACCAATTCAGTCGACTGGATC

CTAGTTATTAATAGTAATCAATTACGGGGTCATTAGTTCATAGCCCATATATGGAGTTCCGCGTTACATAACTTACG

GTAAATGGCCCGCCTGGCTGACCGCCCAACGACCCCCGCCCATTGACGTCAATAATGACGTATGTTCCCATAGTAA

CGCCAATAGGGACTTTCCATTGACGTCAATGGGTGGAGTATTTACGGTAAACTGCCCACTTGGCAGTACATCAAGT

GTATCATATGCCAAGTACGCCCCCTATTGACGTCAATGACGGTAAATGGCCCGCCTGGCATTATGCCCAGTACATG

ACCTTATGGGACTTTCCTACTTGGCAGTACATCTACGTATTAGTCATCGCTATTACCATGGTGATGCGGTTTTGGCA

GTACATCAATGGGCGTGGATAGCGGTTTGACTCACGGGGATTTCCAAGTCTCCACCCCATTGACGTCAATGGGAGT

TTGTTTTGGCACCAAAATCAACGGGACTTTCCAAAATGTCGTAACAACTCCGCCCCATTGACGCAAATGGGCGGTA

GGCGTGTACGGTGGGAGGTCTATATAAGCAGAGCTGGTTTAGTGAACCGTCAGATCACTAGTCGACTAGGGATAA

CAGGGCCGCCACCATGATTCACACCAACCTGAAGAAAAAGTTCAGCTGCTGCGTCCTGGTCTTTCTTCTGTTTGCAG

TCATCTGTGTGTGGAAGGAAAAGAAGAAAGGGAGTTACTATGATTCCTTTAAATTGCAAACCAAGGAATTCCAGGT

GTTAAAGAGTCTGGGGAAATTGGCCATGGGGTCTGATTCCCAGTCTGTATCCTCAAGCAGCACCCAGGACCCCCAC

AGGGGCCGCCAGACCCTCGGCAGTCTCAGAGGCCTAGCCAAGGCCAAACCAGAGGCCTCCTTCCAGGTGTGGAAC

AAGGACAGCTCTTCCAAAAACCTTATCCCTAGGCTGCAAAAGGGGTCGGGGGTGAGCAAGGGCGAGGAGCTGTTC

ACCGGGGTGGTGCCCATCCTGGTCGAGCTGGACGGCGACGTAAACGGCCACAAGTTCAGCGTGTCCGGCGAGGG

CGAGGGCGATGCCACCTACGGCAAGCTGACCCTGAAGTTCATCTGCACCACCGGCAAGCTGCCCGTGCCCTGGCCC

ACCCTCGTGACCACCCTGACCTACGGCGTGCAGTGCTTCAGCCGCTACCCCGACCACATGAAGCAGCACGACTTCTT

CAAGTCCGCCATGCCCGAAGGCTACGTCCAGGAGCGCACCATCTTCTTCAAGGACGACGGCAACTACAAGACCCGC

GCCGAGGTGAAGTTCGAGGGCGACACCCTGGTGAACCGCATCGAGCTGAAGGGCATCGACTTCAAGGAGGACGG

CAACATCCTGGGGCACAAGCTGGAGTACAACTACAACAGCCACAACGTCTATATCATGGCCGACAAGCAGAAGAA

CGGCATCAAGGTGAACTTCAAGATCCGCCACAACATCGAGGACGGCAGCGTGCAGCTCGCCGACCACTACCAGCA

GAACACCCCCATCGGCGACGGCCCCGTGCTGCTGCCCGACAACCACTACCTGAGCACCCAGTCCGCCCTGAGCAAA

GACCCCAACGAGAAGCGCGATCACATGGTCCTGCTGGAGTTCGTGACCGCCGCCGGGATCACTCTCGGCATGGAC

GAGCTGTACAAGTGATCGACTGTGCCTTCTAGTTGCCAGCCATCTGTTGTTTGCCCCTCCCCCGTGCCTTCCTTGACC

CTGGAAGGTGCCACTCCCACTGTCCTTTCCTAATAAAATGAGGAAATTGCATCGCATTGTCTGAGTAGGTGTCATTC

TATTCTGGGGGGTGGGGTGGGGCAGGACAGCAAGGGGGAGGATTGGGAGGACAATAGCAGGCATGCTGGGGAT

GCGGTGGGCTCTATGGCTTCTCCCTGCAGGTGCGCCCAATACGCAAACCGCCTCTCCCCGCGCGTTGGCCGATTCA

TTAATGCAGCTGGCACGACAGGTTTCCCGACTGGAAAGCGGGCAGTGAGCGCAACGCAATTAATGTGAGTTAGCT

CACTCATTAGGCACCCCAGGCTTTACACTTTATGCTTCCGGCTCGTATGTTGTGTGGAATTGTGAGCGGATAACAAT

TTCACACAGGAAACAGCTATGACCATGATTACGGACAGCCTGGCCGTCGTTTTACAACGTCGTGACTGGGAAAACC

CTGGCGTTACCCAACTTAATCGCCTTGCAGCACATCCCCCTTTCGCCAGCTGGCGTAATAGCGAAGAGGCCCGCAC

CGATCGCCCTTCCCAACAGTTGCGCAGCCTGAATGGCGAATGGCGCCTGATGCGGTATTTTCTCCTTACGCATCTGT

GCGGTATTTCACACCGCATATGGTGCACTCTCAGTACAATCTGCTCTGATGCCGCATAGACCTGCAGGGCCAGCAG

GCAGAAGTATGCAAAGCATGCATCTCAATTAGTCAGCAACCAGGTGTGGAAAGTCCCCAGGCTCCCCAGCAGGCA

GAAGTATGCAAAGCATGCATCTCAATTAGTCAGCAACCATAGTCCCGCCCCTAACTCCGCCCATCCCGCCCCTAACT
```

-continued

CCGCCCAGTTCCGCCCATTCTCCGCCCCATGGCTGACTAATTTTTTTTATTTATGCAGAGGCCGAGGCCGCCTCTGCC

TCTGAGCTATTCCAGAAGTAGTGAGGAGGCTTTTTTGGAGGCCTAGGCTTTTGCAAAAAGCTCCCGGGAGCTTGTA

TATCCATTTTCGGATCTGATCAGCACGTGATGAAAAAGCCTGAACTCACCGCGACGTCTGTCGAGAAGTTTCTGATC

GAAAAGTTCGACAGCGTGTCCGACCTGATGCAGCTCTCGGAGGGCGAAGAATCTCGTGCTTTCAGCTTCGATGTAG

GAGGGCGTGGATATGTCCTGCGGGTAAATAGCTGCGCCGATGGTTTCTACAAAGATCGTTATGTTTATCGGCACTT

TGCATCGGCCGCGCTCCCGATTCCGGAAGTGCTTGACATTGGGGAATTCAGCGAGAGCCTGACCTATTGCATCTCC

CGCCGTGCACAGGGTGTCACGTTGCAAGACTTGCCTGAAACCGAACTGCCCGCTGTTCTGCAGCCGGTCGCGGAG

GCCATGGATGCGATCGCTGCGGCCGATCTTAGCCAGACGAGCGGGTTCGGCCCATTCGGACCGCAAGGAATCGGT

CAATACACTACATGGCGTGATTTCATATGCGCGATTGCTGATCCCCATGTGTATCACTGGCAAACTGTGATGGACG

ACACCGTCAGTGCGTCCGTCGCGCAGGCTCTCGATGAGCTGATGCTTTGGGCCGAGGACTGCCCCGAAGTCCGGC

ACCTCGTGCACGCGGATTTCGGCTCCAACAATGTCCTGACGGACAATGGCCGCATAACAGCGGTCATTGACTGGAG

CGAGGCGATGTTCGGGGATTCCCAATACGAGGTCGCCAACATCTTCTTCTGGAGGCCGTGGTTGGCTTGTATGGAG

CAGCAGACGCGCTACTTCGAGCGGAGGCATCCGGAGCTTGCAGGATCGCCGCGGCTCCGGGCGTATATGCTCCGC

ATTGGTCTTGACCAACTCTATCAGAGCTTGGTTGACGGCAATTTCGATGATGCAGCTTGGGCGCAGGGTCGATGCG

ACGCAATCGTCCGATCCGGAGCCGGGACTGTCGGGCGTACACAAATCGCCCGCAGAAGCGCGGCCGTCTGGACCG

ATGGCTGTGTAGAAGTACTCGCCGATAGTGGAAACCGACGCCCCAGCACTCGTCCGAGGGCAAAGGAATAGCACG

TGCTACGAGATTTCGATTCCACCGCCGCCTTCTATGAAAGGTTGGGCTTCGGAATCGTTTTCCGGGACGCCGGCTG

GATGATCCTCCAGCGCGGGGATCTCATGCTGGAGTTCTTCGCCCACCCCAACTTGTTTATTGCAGCTTATAATGGTT

ACAAATAAAGCAATAGCATCACAAATTTCACAAATAAAGCATTTTTTTCACTGCATTCTAGTTGTGGTTTGTCCAAAC

TCATCAATGTATCTTATGCGTCTTCTAGGGTTAAGGTTAGTGTAGAGAAGCAACCGAAGATTGAGAAGACATGGCG

GTAATACGGTTATCCACAGAATCAGGGGATAACGCAGGAAAGAACATGTGAGCAAAAGGCCAGCAAAAGGCCAG

GAACCGTAAAAAGGCCGCGTTGCTGGCGTTTTTCCATAGGCTCCGCCCCCCTGACGAGCATCACAAAAATCGACGC

TCAAGTCAGAGGTGGCGAAACCCGACAGGACTATAAAGATACCAGGCGTTTCCCCCTGGAAGCTCCCTCGTGCGCT

CTCCTGTTCCGACCCTGCCGCTTACCGGATACCTGTCCGCCTTTCTCCCTTCGGGAAGCGTGGCGCTTTCTCATAGCT

CACGCTGTAGGTATCTCAGTTCGGTGTAGGTCGTTCGCTCCAAGCTGGGCTGTGTGCACGAACCCCCCGTTCAGCC

CGACCGCTGCGCCTTATCCGGTAACTATCGTCTTGAGTCCAACCCGGTAAGACACGACTTATCGCCACTGGCAGCA

GCCACTGGTAACAGGATTAGCAGAGCGAGGTATGTAGGCGGTGCTACAGAGTTCTTGAAGTGGTGGCCTAACTAC

GGCTACACTAGAAGAACAGTATTTGGTATCTGCGCTCTGCTGAAGCCAGTTACCTTCGGAAAAAGAGTTGGTAGCT

CTTGATCCGGCAAACAAACCACCGCTGGTAGCGGTTTTTTTGTTTGCAAGCAGCAGATTACGCGCAGAAAAAAAGG

ATCTCAAGAAGATCCTTTGATCTTTTCTACGGGGTCTGACGCTCAGTGGAACGAAAACTCACGTTAAGGGATTTTG

GTCATGAGATTATCAAAAAGGATCTTCACCTAGATCCTTTTAAATTAAAAATGAAGTTTTAAATCAATCTAAAGTAT

ATATGAGTAAACTTGGTCTGACAGTTACCAATGCTTAATCAGTGAGGCACCTATCTCAGCGATCTGTCTATTTCGTT

CATCCATAGTTGCCTGACTCCCCGTCGTGTAGATAACTACGATACGGGAGGGCTTACCATCTGGCCCCAGTGCTGC

AATGATACCGCGTGACCCACGCTCACCGGCTCCAGATTTATCAGCAATAAACCAGCCAGCGGAAGGGCCGAGCG

CAGAAGTGGTCCTGCAACTTTATCCGCCTCCATCCAGTCTATTAATTGTTGCCGGGAAGCTAGAGTAAGTAGTTCGC

CAGTTAATAGTTTGCGCAACGTTGTTGCCATTGCTACAGGCATCGTGGTGTCACGCTCGTCGTTTGGTATGGCTTCA

TTCAGCTCCGGTTCCCAACGATCAAGGCGAGTTACATGATCCCCCATGTTGTGCAAAAAAGCGGTTAGCTCCTTCG

GTCCTCCGATCGTTGTCAGAAGTAAGTTGGCCGCAGTGTTATCACTCATGGTTATGGCAGCACTGCATAATTCTCTT

ACTGTCATGCCATCCGTAAGATGCTTTTCTGTGACTGGTGAGTACTCAACCAAGTCATTCTGAGAATAGTGTATGCG

GCGACCGAGTTGCTCTTGCCCGGCGTCAATACGGGATAATACCGCGCCACATAGCAGAACTTTAAAAGTGCTCATC

ATTGGAAAACGTTCTTCGGGGCGAAAACTCTCAAGGATCTTACCGCTGTTGAGATCCAGTTCGATGTAACCCACTC

```
GTGCACCCAACTGATCTTCAGCATCTTTTACTTTCACCAGCGTTTCTGGGTGAGCAAAAACAGGAAGGCAAAATGC

CGCAAAAAAGGGAATAAGGGCGACACGGAAATGTTGAATACTCATACTCTTCCTTTTTCAATATTATTGAAGCATTT

ATCAGGGTTATTGTCTCATGAGCGGATACATATTTGAATGTATTTAGAAAAATAAACAAATAGGGGTTCCGCGCAC

ATTTCCCCGAAAAGTGCCACCTATGAGACG
```

A vector pHCsiaT-ECFP (SEQ ID NO: 32) according to the invention is constructed from a combination of building blocks Ori-AmpR BsaI A (SEQ ID NO: 17), pCMV BsaI A (SEQ ID NO: 18), SiaT BsaI A (SEQ ID NO: 19), BGHpA BsaI A (SEQ ID NO: 26), LacZα-up BsaI A (SEQ ID NO: 27), LacZα-down BsaI A (SEQ ID NO: 28), HygroR BsaI A (SEQ ID NO: 29) and ECFP BsaI A (SEQ ID NO: 22).

```
Vector pHCsiaT-ECFP
                                                                (SEQ ID NO: 32)
TGAGGCTAGGGATAGGACGAGAGCATCGGGAACGAGGACTAGCGTCTCAAGGAACCAATTCAGTCGACTGGATC

CTAGTTATTAATAGTAATCAATTACGGGGTCATTAGTTCATAGCCCATATATGGAGTTCCGCGTTACATAACTTACG

GTAAATGGCCCGCCTGGCTGACCGCCCAACGACCCCCGCCCATTGACGTCAATAATGACGTATGTTCCCATAGTAA

CGCCAATAGGGACTTTCCATTGACGTCAATGGGTGGAGTATTTACGGTAAACTGCCCACTTGGCAGTACATCAAGT

GTATCATATGCCAAGTACGCCCCCTATTGACGTCAATGACGGTAAATGGCCCGCCTGGCATTATGCCCAGTACATG

ACCTTATGGGACTTTCCTACTTGGCAGTACATCTACGTATTAGTCATCGCTATTACCATGGTGATGCGGTTTTGGCA

GTACATCAATGGGCGTGGATAGCGGTTTGACTCACGGGGATTTCCAAGTCTCCACCCCATTGACGTCAATGGGAGT

TTGTTTTGGCACCAAAATCAACGGGACTTTCCAAAATGTCGTAACAACTCCGCCCCATTGACGCAAATGGGCGGTA

GGCGTGTACGGTGGGAGGTCTATATAAGCAGAGCTGGTTTAGTGAACCGTCAGATCACTAGTCGACTAGGGATAA

CAGGGCCGCCACCATGATTCACACCAACCTGAAGAAAAAGTTCAGCTGCTGCGTCCTGGTCTTTCTTCTGTTTGCAG

TCATCTGTGTGTGGAAGGAAAAGAAGAAAGGGAGTTACTATGATTCCTTTAAATTGCAAACCAAGGAATTCCAGGT

GTTAAAGAGTCTGGGGAAATTGGCCATGGGGTCTGATTCCCAGTCTGTATCCTCAAGCAGCACCCAGGACCCCCAC

AGGGGCCGCCAGACCCTCGGCAGTCTCAGAGGCCTAGCCAAGGCCAAACCAGAGGCCTCCTTCCAGGTGTGGAAC

AAGGACAGCTCTTCCAAAAACCTTATCCCTAGGCTGCAAAAGGGGTCGGGGGTGAGCAAGGGCGAGGAGCTGTTC

ACCGGGGTGGTGCCCATCCTGGTCGAGCTGGACGGCGACGTAAACGGCCACAAGTTCAGCGTGTCCGGCGAGGG

CGAGGGCGATGCCACCTACGGCAAGCTGACCCTGAAGTTCATCTGCACCACCGGCAAGCTGCCCGTGCCCTGGCCC

ACCCTCGTGACCACCCTGACCTGGGGCGTGCAGTGCTTCAGCCGCTACCCCGACCACATGAAGCAGCACGACTTCT

TCAAGTCCGCCATGCCCGAAGGCTACGTCCAGGAGCGCACCATCTTCTTCAAGGACGACGGCAACTACAAGACCCG

CGCCGAGGTGAAGTTCGAGGGCGACACCCTGGTGAACCGCATCGAGCTGAAGGGCATCGACTTCAAGGAGGACG

GCAACATCCTGGGGCACAAGCTGGAGTACAACTACATCAGCCACAACGTCTATATCACCGCCGACAAGCAGAAGA

ACGGCATCAAGGCCAACTTCAAGATCCGCCACAACATCGAGGACGGCAGCGTGCAGCTCGCCGACCACTACCAGC

AGAACACCCCCATCGGCGACGGCCCCGTGCTGCTGCCCGACAACCACTACCTGAGCACCCAGTCCGCCCTGAGCAA

AGACCCCAACGAGAAGCGCGATCACATGGTCCTGCTGGAGTTCGTGACCGCCGCCGGGATCACTCTCGGCATGGA

CGAGCTGTACAAGTGATCGACTGTGCCTTCTAGTTGCCAGCCATCTGTTGTTTGCCCCTCCCCCGTGCCTTCCTTGAC

CCTGGAAGGTGCCACTCCCACTGTCCTTTCCTAATAAAATGAGGAAATTGCATCGCATTGTCTGAGTAGGTGTCATT

CTATTCTGGGGGGTGGGGTGGGCAGGACAGCAAGGGGGAGGATTGGGAAGACAATAGCAGGCATGCTGGGG

ATGCGGTGGGCTCTATGGCTTCTCCCTGCAGGTGCGCCCAATACGCAAACCGCCTCTCCCCGCGCGTTGGCCGATT

CATTAATGCAGCTGGCACGACAGGTTTCCCGACTGGAAAGCGGGCAGTGAGCGCAACGCAATTAATGTGAGTTAG

CTCACTCATTAGGCACCCCAGGCTTTACACTTTATGCTTCCGGCTCGTATGTTGTGTGGAATTGTGAGCGGATAACA
```

-continued

```
ATTTCACACAGGAAACAGCTATGACCATGATTACGGACAGCCTGGCCGTCGTTTTACAACGTCGTGACTGGGAAAA
CCCTGGCGTTACCCAACTTAATCGCCTTGCAGCACATCCCCCTTTCGCCAGCTGGCGTAATAGCGAAGAGGCCCGC
ACCGATCGCCCTTCCCAACAGTTGCGCAGCCTGAATGGCGAATGGCGCCTGATGCGGTATTTTCTCCTTACGCATCT
GTGCGGTATTTCACACCGCATATGGTGCACTCTCAGTACAATCTGCTCTGATGCCGCATAGACCTGCAGGGCCAGC
AGGCAGAAGTATGCAAAGCATGCATCTCAATTAGTCAGCAACCAGGTGTGGAAAGTCCCCAGGCTCCCCAGCAGG
CAGAAGTATGCAAAGCATGCATCTCAATTAGTCAGCAACCATAGTCCCGCCCCTAACTCCGCCCATCCCGCCCCTAA
CTCCGCCCAGTTCCGCCCATTCTCCGCCCCATGGCTGACTAATTTTTTTATTTATGCAGAGGCCGAGGCCGCCTCTG
CCTCTGAGCTATTCCAGAAGTAGTGAGGAGGCTTTTTTGGAGGCCTAGGCTTTTGCAAAAAGCTCCCGGGAGCTTG
TATATCCATTTTCGGATCTGATCAGCACGTGATGAAAAAGCCTGAACTCACCGCGACGTCTGTCGAGAAGTTTCTGA
TCGAAAAGTTCGACAGCGTGTCCGACCTGATGCAGCTCTCGGAGGGCGAAGAATCTCGTGCTTTCAGCTTCGATGT
AGGAGGGCGTGGATATGTCCTGCGGGTAAATAGCTGCGCCGATGGTTTCTACAAAGATCGTTATGTTTATCGGCAC
TTTGCATCGGCCGCGCTCCCGATTCCGGAAGTGCTTGACATTGGGGAATTCAGCGAGAGCCTGACCTATTGCATCT
CCCGCCGTGCACAGGGTGTCACGTTGCAAGACTTGCCTGAAACCGAACTGCCCGCTGTTCTGCAGCCGGTCGCGGA
GGCCATGGATGCGATCGCTGCGGCCGATCTTAGCCAGACGAGCGGGTTCGGCCCATTCGGACCGCAAGGAATCGG
TCAATACACTACATGGCGTGATTTCATATGCGCGATTGCTGATCCCCATGTGTATCACTGGCAAACTGTGATGGACG
ACACCGTCAGTGCGTCCGTCGCGCAGGCTCTCGATGAGCTGATGCTTTGGGCCGAGGACTGCCCCGAAGTCCGGC
ACCTCGTGCACGCGGATTTCGGCTCCAACAATGTCCTGACGGACAATGGCCGCATAACAGCGGTCATTGACTGGAG
CGAGGCGATGTTCGGGGATTCCCAATACGAGGTCGCCAACATCTTCTTCTGGAGGCCGTGGTTGGCTTGTATGGAG
CAGCAGACGCGCTACTTCGAGCGGAGGCATCCGGAGCTTGCAGGATCGCCGCGGCTCCGGGCGTATATGCTCCGC
ATTGGTCTTGACCAACTCTATCAGAGCTTGGTTGACGGCAATTTCGATGATGCAGCTTGGGCGCAGGGTCGATGCG
ACGCAATCGTCCGATCCGGAGCCGGGACTGTCGGGCGTACACAAATCGCCCGCAGAAGCGCGGCCGTCTGGACCG
ATGGCTGTGTAGAAGTACTCGCCGATAGTGGAAACCGACGCCCCAGCACTCGTCCGAGGGCAAAGGAATAGCACG
TGCTACGAGATTTCGATTCCACCGCCGCCTTCTATGAAAGGTTGGGCTTCGGAATCGTTTTCCGGGACGCCGGCTG
GATGATCCTCCAGCGCGGGGATCTCATGCTGGAGTTCTTCGCCCACCCCAACTTGTTTATTGCAGCTTATAATGGTT
ACAAATAAAGCAATAGCATCACAAATTTCACAAATAAAGCATTTTTTTCACTGCATTCTAGTTGTGGTTTGTCCAAAC
TCATCAATGTATCTTATGCGTCTTCTAGGGTTAAGGTTAGTGTAGAGAAGCAACCGAAGATTGAGAAGACATGGCG
GTAATACGGTTATCCACAGAATCAGGGGATAACGCAGGAAAGAACATGTGAGCAAAAGGCCAGCAAAAGGCCAG
GAACCGTAAAAAGGCCGCGTTGCTGGCGTTTTTCCATAGGCTCCGCCCCCTGACGAGCATCACAAAAATCGACGC
TCAAGTCAGAGGTGGCGAAACCCGACAGGACTATAAAGATACCAGGCGTTTCCCCCTGGAAGCTCCCTCGTGCGCT
CTCCTGTTCCGACCCTGCCGCTTACCGGATACCTGTCCGCCTTTCTCCCTTCGGGAAGCGTGGCGCTTTCTCATAGCT
CACGCTGTAGGTATCTCAGTTCGGTGTAGGTCGTTCGCTCCAAGCTGGGCTGTGTGCACGAACCCCCCGTTCAGCC
CGACCGCTGCGCCTTATCCGGTAACTATCGTCTTGAGTCCAACCCGGTAAGACACGACTTATCGCCACTGGCAGCA
GCCACTGGTAACAGGATTAGCAGAGCGAGGTATGTAGGCGGTGCTACAGAGTTCTTGAAGTGGTGGCCTAACTAC
GGCTACACTAGAAGAACAGTATTTGGTATCTGCGCTCTGCTGAAGCCAGTTACCTTCGGAAAAAGAGTTGGTAGCT
CTTGATCCGGCAAACAAACCACCGCTGGTAGCGGTTTTTTTGTTTGCAAGCAGCAGATTACGCGCAGAAAAAAAGG
ATCTCAAGAAGATCCTTTGATCTTTTCTACGGGGTCTGACGCTCAGTGGAACGAAAACTCACGTTAAGGGATTTTG
GTCATGAGATTATCAAAAAGGATCTTCACCTAGATCCTTTTAAATTAAAAATGAAGTTTTAAATCAATCTAAAGTAT
ATATGAGTAAACTTGGTCTGACAGTTACCAATGCTTAATCAGTGAGGCACCTATCTCAGCGATCTGTCTATTTCGTT
CATCCATAGTTGCCTGACTCCCCGTCGTGTAGATAACTACGATACGGGAGGGCTTACCATCTGGCCCCAGTGCTGC
AATGATACCGCGTGACCCACGCTCACCGGCTCCAGATTTATCAGCAATAAACCAGCCAGCCGGAAGGGCCGAGCG
CAGAAGTGGTCCTGCAACTTTATCCGCCTCCATCCAGTCTATTAATTGTTGCCGGGAAGCTAGAGTAAGTAGTTCGC
```

-continued

```
CAGTTAATAGTTTGCGCAACGTTGTTGCCATTGCTACAGGCATCGTGGTGTCACGCTCGTCGTTTGGTATGGCTTCA

TTCAGCTCCGGTTCCCAACGATCAAGGCGAGTTACATGATCCCCCATGTTGTGCAAAAAAGCGGTTAGCTCCTTCG

GTCCTCCGATCGTTGTCAGAAGTAAGTTGGCCGCAGTGTTATCACTCATGGTTATGGCAGCACTGCATAATTCTCTT

ACTGTCATGCCATCCGTAAGATGCTTTTCTGTGACTGGTGAGTACTCAACCAAGTCATTCTGAGAATAGTGTATGCG

GCGACCGAGTTGCTCTTGCCCGGCGTCAATACGGGATAATACCGCGCCACATAGCAGAACTTTAAAAGTGCTCATC

ATTGGAAAACGTTCTTCGGGGCGAAAACTCTCAAGGATCTTACCGCTGTTGAGATCCAGTTCGATGTAACCCACTC

GTGCACCCAACTGATCTTCAGCATCTTTTACTTTCACCAGCGTTTCTGGGTGAGCAAAAACAGGAAGGCAAAATGC

CGCAAAAAAGGGAATAAGGGCGACACGGAAATGTTGAATACTCATACTCTTCCTTTTTCAATATTATTGAAGCATTT

ATCAGGGTTATTGTCTCATGAGCGGATACATATTTGAATGTATTTAGAAAAATAAACAAATAGGGGTTCCGCGCAC

ATTTCCCCGAAAAGTGCCACCTATGAGACG
```

A vector pHCsiaT-EYGFP (SEQ ID NO: 33) according to the invention is constructed from a combination of building blocks Ori-AmpR BsaI A (SEQ ID NO: 17), pCMV BsaI A (SEQ ID NO: 18), SiaT BsaI A (SEQ ID NO: 19), BGHpA BsaI A (SEQ ID NO: 26), LacZα-up BsaI A (SEQ ID NO: 27), LacZα-down BsaI A (SEQ ID NO: 28), HygroR BsaI A (SEQ ID NO: 29) and EYFP BsaI A (SEQ ID NO: 23).

Vector pHCsiaT-EYFP (SEQ ID NO: 33)
```
TGAGGCTAGGGATAGGACGAGAGCATCGGGAACGAGGACTAGCGTCTCAAGGAACCAATTCAGTCGACTGGATC

CTAGTTATTAATAGTAATCAATTACGGGGTCATTAGTTCATAGCCCATATATGGAGTTCCGCGTTACATAACTTACG

GTAAATGGCCCGCCTGGCTGACCGCCCAACGACCCCCGCCCATTGACGTCAATAATGACGTATGTTCCCATAGTAA

CGCCAATAGGGACTTTCCATTGACGTCAATGGGTGGAGTATTTACGGTAAACTGCCCACTTGGCAGTACATCAAGT

GTATCATATGCCAAGTACGCCCCCTATTGACGTCAATGACGGTAAATGGCCCGCCTGGCATTATGCCCAGTACATG

ACCTTATGGGACTTTCCTACTTGGCAGTACATCTACGTATTAGTCATCGCTATTACCATGGTGATGCGGTTTTGGCA

GTACATCAATGGGCGTGGATAGCGGTTTGACTCACGGGGATTTCCAAGTCTCCACCCCATTGACGTCAATGGGAGT

TTGTTTTGGCACCAAAATCAACGGGACTTTCCAAAATGTCGTAACAACTCCGCCCCATTGACGCAAATGGGCGGTA

GGCGTGTACGGTGGGAGGTCTATATAAGCAGAGCTGGTTTAGTGAACCGTCAGATCACTAGTCGACTAGGGATAA

CAGGGCCGCCACCATGATTCACACCAACCTGAAGAAAAAGTTCAGCTGCTGCGTCCTGGTCTTTCTTCTGTTTGCAG

TCATCTGTGTGTGGAAGGAAAAGAAGAAAGGGAGTTACTATGATTCCTTTAAATTGCAAACCAAGGAATTCCAGGT

GTTAAAGAGTCTGGGGAAATTGGCCATGGGGTCTGATTCCCAGTCTGTATCCTCAAGCAGCACCCAGGACCCCCAC

AGGGGCCGCCAGACCCTCGGCAGTCTCAGAGGCCTAGCCAAGGCCAAACCAGAGGCCTCCTTCCAGGTGTGGAAC

AAGGACAGCTCTTCCAAAAACCTTATCCCTAGGCTGCAAAAGGGGTCGGGGTGAGCAAGGGCGAGGAGCTGTTC

ACCGGGGTGGTGCCCATCCTGGTCGAGCTGGACGGCGACGTAAACGGCCACAAGTTCAGCGTGTCCGGCGAGGG

CGAGGGCGATGCCACCTACGGCAAGCTGACCCTGAAGTTCATCTGCACCACCGGCAAGCTGCCCGTGCCCTGGCCC

ACCCTCGTGACCACCTTCGGCTACGGCCTGCAGTGCTTCGCCCGCTACCCCGACCACATGAAGCAGCACGACTTCTT

CAAGTCCGCCATGCCCGAAGGCTACGTCCAGGAGCGCACCATCTTCTTCAAGGACGACGGCAACTACAAGACCCGC

GCCGAGGTGAAGTTCGAGGGCGACACCCTGGTGAACCGCATCGAGCTGAAGGGCATCGACTTCAAGGAGGACGG

CAACATCCTGGGGCACAAGCTGGAGTACAACTACAACAGCCACAACGTCTATATCATGGCCGACAAGCAGAAGAA

CGGCATCAAGGTGAACTTCAAGATCCGCCACAACATCGAGGACGGCAGCGTGCAGCTCGCCGACCACTACCAGCA

GAACACCCCCATCGGCGACGGCCCCGTGCTGCTGCCCGACAACCACTACCTGAGCTACCAGTCCGCCCTGAGCAAA

GACCCCAACGAGAAGCGCGATCACATGGTCCTGCTGGAGTTCGTGACCGCCGCCGGGATCACTCTCGGCATGGAC
```

-continued
```
GAGCTGTACAAGTGATCGACTGTGCCTTCTAGTTGCCAGCCATCTGTTGTTTGCCCCTCCCCCGTGCCTTCCTTGACC

CTGGAAGGTGCCACTCCCACTGTCCTTTCCTAATAAAATGAGGAAATTGCATCGCATTGTCTGAGTAGGTGTCATTC

TATTCTGGGGGGTGGGGTGGGGCAGGACAGCAAGGGGGAGGATTGGGAGGACAATAGCAGGCATGCTGGGGAT

GCGGTGGGCTCTATGGCTTCTCCCTGCAGGTGCGCCCAATACGCAAACCGCCTCTCCCCGCGCGTTGGCCGATTCA

TTAATGCAGCTGGCACGACAGGTTTCCCGACTGGAAAGCGGGCAGTGAGCGCAACGCAATTAATGTGAGTTAGCT

CACTCATTAGGCACCCCAGGCTTTACACTTTATGCTTCCGGCTCGTATGTTGTGTGGAATTGTGAGCGGATAACAAT

TTCACACAGGAAACAGCTATGACCATGATTACGGACAGCCTGGCCGTCGTTTTACAACGTCGTGACTGGGAAAACC

CTGGCGTTACCCAACTTAATCGCCTTGCAGCACATCCCCCTTTCGCCAGCTGGCGTAATAGCGAAGAGGCCCGCAC

CGATCGCCCTTCCCAACAGTTGCGCAGCCTGAATGGCGAATGGCGCCTGATGCGGTATTTTCTCCTTACGCATCTGT

GCGGTATTTCACACCGCATATGGTGCACTCTCAGTACAATCTGCTCTGATGCCGCATAGACCTGCAGGGCCAGCAG

GCAGAAGTATGCAAAGCATGCATCTCAATTAGTCAGCAACCAGGTGTGGAAAGTCCCCAGGCTCCCCAGCAGGCA

GAAGTATGCAAAGCATGCATCTCAATTAGTCAGCAACCATAGTCCCGCCCCTAACTCCGCCCATCCCGCCCCTAACT

CCGCCCAGTTCCGCCCATTCTCCGCCCCATGGCTGACTAATTTTTTTTATTTATGCAGAGGCCGAGGCCGCCTCTGCC

TCTGAGCTATTCCAGAAGTAGTGAGGAGGCTTTTTTGGAGGCCTAGGCTTTTGCAAAAAGCTCCCGGGAGCTTGTA

TATCCATTTTCGGATCTGATCAGCACGTGATGAAAAAGCCTGAACTCACCGCGACGTCTGTCGAGAAGTTTCTGATC

GAAAAGTTCGACAGCGTGTCCGACCTGATGCAGCTCTCGGAGGGCGAAGAATCTCGTGCTTTCAGCTTCGATGTAG

GAGGGCGTGGATATGTCCTGCGGGTAAATAGCTGCGCCGATGGTTTCTACAAAGATCGTTATGTTTATCGGCACTT

TGCATCGGCCGCGCTCCCGATTCCGGAAGTGCTTGACATTGGGGAATTCAGCGAGAGCCTGACCTATTGCATCTCC

CGCCGTGCACAGGGTGTCACGTTGCAAGCTTGCCTGAAACCGAACTGCCCGCTGTTCTGCAGCCGGTCGCGGAG

GCCATGGATGCGATCGCTGCGGCCGATCTTAGCCAGACGAGCGGGTTCGGCCCATTCGGACCGCAAGGAATCGGT

CAATACACTACATGGCGTGATTTCATATGCGCGATTGCTGATCCCCATGTGTATCACTGGCAAACTGTGATGGACG

ACACCGTCAGTGCGTCCGTCGCGCAGGCTCTCGATGAGCTGATGCTTTGGGCCGAGGACTGCCCCGAAGTCCGGC

ACCTCGTGCACGCGGATTTCGGCTCCAACAATGTCCTGACGGACAATGGCCGCATAACAGCGGTCATTGACTGGAG

CGAGGCGATGTTCGGGGATTCCCAATACGAGGTCGCCAACATCTTCTTCTGGAGGCCGTGGTTGGCTTGTATGGAG

CAGCAGACGCGCTACTTCGAGCGGAGGCATCCGGAGCTTGCAGGATCGCCGCGGCTCCGGGCGTATATGCTCCGC

ATTGGTCTTGACCAACTCTATCAGAGCTTGGTTGACGGCAATTTCGATGATGCAGCTTGGGCGCAGGGTCGATGCG

ACGCAATCGTCCGATCCGGAGCCGGGACTGTCGGGCGTACACAAATCGCCCGCAGAAGCGCGGCCGTCTGGACCG

ATGGCTGTGTAGAAGTACTCGCCGATAGTGGAAACCGACGCCCCAGCACTCGTCCGAGGGCAAAGGAATAGCACG

TGCTACGAGATTTCGATTCCACCGCCGCCTTCTATGAAAGGTTGGGCTTCGGAATCGTTTTCCGGGACGCCGGCTG

GATGATCCTCCAGCGCGGGGATCTCATGCTGGAGTTCTTCGCCCACCCCAACTTGTTTATTGCAGCTTATAATGGTT

ACAAATAAAGCAATAGCATCACAAATTTCACAAATAAAGCATTTTTTTCACTGCATTCTAGTTGTGGTTTGTCCAAAC

TCATCAATGTATCTTATGCGTCTTCTAGGGTTAAGGTTAGTGTAGAGAAGCAACCGAAGATTGAGAAGACATGGCG

GTAATACGGTTATCCACAGAATCAGGGGATAACGCAGGAAAGAACATGTGAGCAAAAGGCCAGCAAAAGGCCAG

GAACCGTAAAAAGGCCGCGTTGCTGGCGTTTTTCCATAGGCTCCGCCCCCTGACGAGCATCACAAAAATCGACGC

TCAAGTCAGAGGTGGCGAAACCCGACAGGACTATAAAGATACCAGGCGTTTCCCCCTGGAAGCTCCCTCGTGCGCT

CTCCTGTTCCGACCCTGCCGCTTACCGGATACCTGTCCGCCTTTCTCCCTTCGGGAAGCGTGGCGCTTTCTCATAGCT

CACGCTGTAGGTATCTCAGTTCGGTGTAGGTCGTTCGCTCCAAGCTGGGCTGTGTGCACGAACCCCCCGTTCAGCC

CGACCGCTGCGCCTTATCCGGTAACTATCGTCTTGAGTCCAACCCGGTAAGACACGACTTATCGCCACTGGCAGCA

GCCACTGGTAACAGGATTAGCAGAGCGAGGTATGTAGGCGGTGCTACAGAGTTCTTGAAGTGGTGGCCTAACTAC

GGCTACACTAGAAGAACAGTATTTGGTATCTGCGCTCTGCTGAAGCCAGTTACCTTCGGAAAAAGAGTTGGTAGCT

CTTGATCCGGCAAACAAACCACCGCTGGTAGCGGTTTTTTTGTTTGCAAGCAGCAGATTACGCGCAGAAAAAAGG
```

-continued

```
ATCTCAAGAAGATCCTTTGATCTTTTCTACGGGGTCTGACGCTCAGTGGAACGAAAACTCACGTTAAGGGATTTTG

GTCATGAGATTATCAAAAAGGATCTTCACCTAGATCCTTTTAAATTAAAAATGAAGTTTTAAATCAATCTAAAGTAT

ATATGAGTAAACTTGGTCTGACAGTTACCAATGCTTAATCAGTGAGGCACCTATCTCAGCGATCTGTCTATTTCGTT

CATCCATAGTTGCCTGACTCCCCGTCGTGTAGATAACTACGATACGGGAGGGCTTACCATCTGGCCCCAGTGCTGC

AATGATACCGCGTGACCCACGCTCACCGGCTCCAGATTTATCAGCAATAAACCAGCCAGCCGGAAGGGCCGAGCG

CAGAAGTGGTCCTGCAACTTTATCCGCCTCCATCCAGTCTATTAATTGTTGCCGGGAAGCTAGAGTAAGTAGTTCGC

CAGTTAATAGTTTGCGCAACGTTGTTGCCATTGCTACAGGCATCGTGGTGTCACGCTCGTCGTTTGGTATGGCTTCA

TTCAGCTCCGGTTCCCAACGATCAAGGCGAGTTACATGATCCCCCATGTTGTGCAAAAAAGCGGTTAGCTCCTTCG

GTCCTCCGATCGTTGTCAGAAGTAAGTTGGCCGCAGTGTTATCACTCATGGTTATGGCAGCACTGCATAATTCTCTT

ACTGTCATGCCATCCGTAAGATGCTTTTCTGTGACTGGTGAGTACTCAACCAAGTCATTCTGAGAATAGTGTATGCG

GCGACCGAGTTGCTCTTGCCCGGCGTCAATACGGGATAATACCGCGCCACATAGCAGAACTTTAAAAGTGCTCATC

ATTGGAAAACGTTCTTCGGGGCGAAAACTCTCAAGGATCTTACCGCTGTTGAGATCCAGTTCGATGTAACCCACTC

GTGCACCCAACTGATCTTCAGCATCTTTTACTTTCACCAGCGTTTCTGGGTGAGCAAAAACAGGAAGGCAAAATGC

CGCAAAAAAGGGAATAAGGGCGACACGGAAATGTTGAATACTCATACTCTTCCTTTTTCAATATTATTGAAGCATTT

ATCAGGGTTATTGTCTCATGAGCGGATACATATTTGAATGTATTTAGAAAAATAAACAAATAGGGGTTCCGCGCAC

ATTTCCCCGAAAAGTGCCACCTATGAGACG
```

A vector pHCsiaT-mCherry (SEQ ID NO: 34) according to the invention is constructed from a combination of building blocks Ori-AmpR BsaI A (SEQ ID NO: 17), pCMV BsaI A (SEQ ID NO: 18), SiaT BsaI A (SEQ ID NO: 19), BGHpA BsaI A (SEQ ID NO: 26), LacZα-up BsaI A (SEQ ID NO: 27), LacZα-down BsaI A (SEQ ID NO: 28), HygroR BsaI A (SEQ ID NO: 29) and mCherry BsaI A (SEQ ID NO: 24).

```
Vector pHCsiaT-mCherry
                                                              (SEQ ID NO: 34)
TGAGGCTAGGGATAGGACGAGAGCATCGGGAACGAGGACTAGCGTCTCAAGGAACCAATTCAGTCGACTGGATC

CTAGTTATTAATAGTAATCAATTACGGGGTCATTAGTTCATAGCCCATATATGGAGTTCCGCGTTACATAACTTACG

GTAAATGGCCCGCCTGGCTGACCGCCCAACGACCCCCGCCCATTGACGTCAATAATGACGTATGTTCCCATAGTAA

CGCCAATAGGGACTTTCCATTGACGTCAATGGGTGGAGTATTTACGGTAAACTGCCCACTTGGCAGTACATCAAGT

GTATCATATGCCAAGTACGCCCCCTATTGACGTCAATGACGGTAAATGGCCCGCCTGGCATTATGCCCAGTACATG

ACCTTATGGGACTTTCCTACTTGGCAGTACATCTACGTATTAGTCATCGCTATTACCATGGTGATGCGGTTTTGGCA

GTACATCAATGGGCGTGGATAGCGGTTTGACTCACGGGGATTTCCAAGTCTCCACCCCATTGACGTCAATGGGAGT

TTGTTTTGGCACCAAAATCAACGGGACTTTCCAAAATGTCGTAACAACTCCGCCCCATTGACGCAAATGGGCGGTA

GGCGTGTACGGTGGAGGTCTATATAAGCAGAGCTGGTTTAGTGAACCGTCAGATCACTAGTCGACTAGGGATAA

CAGGGCCGCCACCATGATTCACACCAACCTGAAGAAAAGTTCAGCTGCTGCGTCCTGGTCTTTCTTCTGTTTGCAG

TCATCTGTGTGTGGAAGGAAAAGAAGAAAGGGAGTTACTATGATTCCTTTAAATTGCAAACCAAGGAATTCCAGGT

GTTAAAGAGTCTGGGGAAATTGGCCATGGGGTCTGATTCCCAGTCTGTATCCTCAAGCAGCACCCAGGACCCCCAC

AGGGGCCGCCAGACCCTCGGCAGTCTCAGAGGCCTAGCCAAGGCCAAACCAGAGGCCTCCTTCCAGGTGTGGAAC

AAGGACAGCTCTTCCAAAAACCTTATCCCTAGGCTGCAAAAGGGGTCGGGGGTGAGCAAGGGCGAGGAGGATAA

CATGGCCATCATCAAGGAGTTCATGCGCTTCAAGGTGCACATGGAGGGCTCCGTGAACGGCCACGAGTTCGAGAT

CGAGGGCGAGGGCGAGGGCCGCCCCTACGAGGGCACCCAGACCGCCAAGCTGAAGGTGACCAAGGGTGGCCCC

CTGCCCTTCGCCTGGGACATCCTGTCCCCTCAGTTCATGTACGGCTCCAAGGCCTACGTGAAGCACCCCGCCGACAT

CCCCGACTACTTGAAGCTGTCCTTCCCCGAGGGCTTCAAGTGGGAGCGCGTGATGAACTTCGAGGACGGCGGCGT

GGTGACCGTGACCCAGGACTCCTCCCTGCAGGACGGCGAGTTCATCTACAAGGTGAAGCTGCGCGGCACCAACTT
```

-continued

```
CCCCTCCGACGGCCCCGTAATGCAGAAGAAAACCATGGGCTGGGAGGCCTCCTCCGAGCGGATGTACCCCGAGGA
CGGCGCCCTGAAGGGCGAGATCAAGCAGAGGCTGAAGCTGAAGGACGGCGGCCACTACGACGCTGAGGTCAAG
ACCACCTACAAGGCCAAGAAGCCCGTGCAGCTGCCCGGCGCCTACAACGTCAACATCAAGTTGGACATCACCTCCC
ACAACGAGGACTACACCATCGTGGAACAGTACGAACGCGCCGAGGGCCGCCACTCCACCGGCGGCATGGACGAG
CTGTACAAGTGATCGACTGTGCCTTCTAGTTGCCAGCCATCTGTTGTTTGCCCCTCCCCCGTGCCTTCCTTGACCCTG
GAAGGTGCCACTCCCACTGTCCTTTCCTAATAAAATGAGGAAATTGCATCGCATTGTCTGAGTAGGTGTCATTCTAT
TCTGGGGGGTGGGGTGGGGCAGGACAGCAAGGGGGAGGATTGGGAGGACAATAGCAGGCATGCTGGGGATGC
GGTGGGCTCTATGGCTTCTCCCTGCAGGTGCGCCCAATACGCAAACCGCCTCTCCCCGCGCGTTGGCCGATTCATTA
ATGCAGCTGGCACGACAGGTTTCCCGACTGGAAAGCGGGCAGTGAGCGCAACGCAATTAATGTGAGTTAGCTCAC
TCATTAGGCACCCCAGGCTTTACACTTTATGCTTCCGGCTCGTATGTTGTGTGGAATTGTGAGCGGATAACAATTTC
ACACAGGAAACAGCTATGACCATGATTACGGACAGCCTGGCCGTCGTTTTACAACGTCGTGACTGGGAAAACCCTG
GCGTTACCCAACTTAATCGCCTTGCAGCACATCCCCCTTTCGCCAGCTGGCGTAATAGCGAAGAGGCCCGCACCGA
TCGCCCTTCCCAACAGTTGCGCAGCCTGAATGGCGAATGGCGCCTGATGCGGTATTTTCTCCTTACGCATCTGTGCG
GTATTTCACACCGCATATGGTGCACTCTCAGTACAATCTGCTCTGATGCCGCATAGACCTGCAGGGCCAGCAGGCA
GAAGTATGCAAAGCATGCATCTCAATTAGTCAGCAACCAGGTGTGGAAAGTCCCCAGGCTCCCCAGCAGGCAGAA
GTATGCAAAGCATGCATCTCAATTAGTCAGCAACCATAGTCCCGCCCCTAACTCCGCCCATCCCGCCCCTAACTCCG
CCCAGTTCCGCCCATTCTCCGCCCCATGGCTGACTAATTTTTTTATTTATGCAGAGGCCGAGGCCGCCTCTGCCTCT
GAGCTATTCCAGAAGTAGTGAGGAGGCTTTTTTGGAGGCCTAGGCTTTTGCAAAAAGCTCCCGGGAGCTTGTATAT
CCATTTTCGGATCTGATCAGCACGTGATGAAAAAGCCTGAACTCACCGCGACGTCTGTCGAGAAGTTTCTGATCGA
AAAGTTCGACAGCGTGTCCGACCTGATGCAGCTCTCGGAGGGCGAAGAATCTCGTGCTTTCAGCTTCGATGTAGGA
GGGCGTGGATATGTCCTGCGGGTAAATAGCTGCGCCGATGGTTTCTACAAAGATCGTTATGTTTATCGGCACTTTG
CATCGGCCGCGCTCCCGATTCCGGAAGTGCTTGACATTGGGGAATTCAGCGAGAGCCTGACCTATTGCATCTCCCG
CCGTGCACAGGGTGTCACGTTGCAAGACTTGCCTGAAACCGAACTGCCCGCTGTTCTGCAGCCGGTCGCGGAGGC
CATGGATGCGATCGCTGCGGCCGATCTTAGCCAGACGAGCGGGTTCGGCCCATTCGGACCGCAAGGAATCGGTCA
ATACACTACATGGCGTGATTTCATATGCGCGATTGCTGATCCCCATGTGTATCACTGGCAAACTGTGATGGACGAC
ACCGTCAGTGCGTCCGTCGCGCAGGCTCTCGATGAGCTGATGCTTTGGGCCGAGGACTGCCCCGAAGTCCGGCAC
CTCGTGCACGCGGATTTCGGCTCCAACAATGTCCTGACGGACAATGGCCGCATAACAGCGGTCATTGACTGGAGC
GAGGCGATGTTCGGGGATTCCCAATACGAGGTCGCCAACATCTTCTTCTGGAGGCCGTGGTTGGCTTGTATGGAGC
AGCAGACGCGCTACTTCGAGCGGAGGCATCCGGAGCTTGCAGGATCGCCGCGGCTCCGGGCGTATATGCTCCGCA
TTGGTCTTGACCAACTCTATCAGAGCTTGGTTGACGGCAATTTCGATGATGCAGCTTGGGCGCAGGGTCGATGCGA
CGCAATCGTCCGATCCGGAGCCGGGACTGTCGGGCGTACACAAATCGCCCGCAGAAGCGCGGCCGTCTGGACCGA
TGGCTGTGTAGAAGTACTCGCCGATAGTGGAAACCGACGCCCCAGCACTCGTCCGAGGGCAAAGGAATAGCACGT
GCTACGAGATTTCGATTCCACCGCCGCCTTCTATGAAAGGTTGGGCTTCGGAATCGTTTTCCGGACGCCGGCTGG
ATGATCCTCCAGCGCGGGGATCTCATGCTGGAGTTCTTCGCCCACCCCAACTTGTTTATTGCAGCTTATAATGGTTA
CAAATAAAGCAATAGCATCACAAATTTCACAAATAAAGCATTTTTTTCACTGCATTCTAGTTGTGGTTTGTCCAAACT
CATCAATGTATCTTATGCGTCTTCTAGGGTTAAGGTTAGTGTAGAGAAGCAACCGAAGATTGAGAAGACATGGCG
GTAATACGGTTATCCACAGAATCAGGGGATAACGCAGGAAAGAACATGTGAGCAAAAGGCCAGCAAAAGGCCAG
GAACCGTAAAAAGGCCGCGTTGCTGGCGTTTTTCCATAGGCTCCGCCCCCTGACGAGCATCACAAAAATCGACGC
TCAAGTCAGAGGTGGCGAAACCCGACAGGACTATAAAGATACCAGGCGTTTCCCCCTGGAAGCTCCCTCGTGCGCT
CTCCTGTTCCGACCCTGCCGCTTACCGGATACCTGTCCGCCTTTCTCCCTTCGGGAAGCGTGGCGCTTTCTCATAGCT
CACGCTGTAGGTATCTCAGTTCGGTGTAGGTCGTTCGCTCCAAGCTGGGCTGTGTGCACGAACCCCCCGTTCAGCC
```

-continued

```
CGACCGCTGCGCCTTATCCGGTAACTATCGTCTTGAGTCCAACCCGGTAAGACACGACTTATCGCCACTGGCAGCA

GCCACTGGTAACAGGATTAGCAGAGCGAGGTATGTAGGCGGTGCTACAGAGTTCTTGAAGTGGTGGCCTAACTAC

GGCTACACTAGAAGAACAGTATTTGGTATCTGCGCTCTGCTGAAGCCAGTTACCTTCGGAAAAAGAGTTGGTAGCT

CTTGATCCGGCAAACAAACCACCGCTGGTAGCGGTTTTTTTGTTTGCAAGCAGCAGATTACGCGCAGAAAAAAGG

ATCTCAAGAAGATCCTTTGATCTTTTCTACGGGGTCTGACGCTCAGTGGAACGAAAACTCACGTTAAGGGATTTTG

GTCATGAGATTATCAAAAAGGATCTTCACCTAGATCCTTTTAAATTAAAAATGAAGTTTTAAATCAATCTAAAGTAT

ATATGAGTAAACTTGGTCTGACAGTTACCAATGCTTAATCAGTGAGGCACCTATCTCAGCGATCTGTCTATTTCGTT

CATCCATAGTTGCCTGACTCCCCGTCGTGTAGATAACTACGATACGGGAGGGCTTACCATCTGGCCCCAGTGCTGC

AATGATACCGCGTGACCCACGCTCACCGGCTCCAGATTTATCAGCAATAAACCAGCCAGCCGGAAGGGCCGAGCG

CAGAAGTGGTCCTGCAACTTTATCCGCCTCCATCCAGTCTATTAATTGTTGCCGGGAAGCTAGAGTAAGTAGTTCGC

CAGTTAATAGTTTGCGCAACGTTGTTGCCATTGCTACAGGCATCGTGGTGTCACGCTCGTCGTTTGGTATGGCTTCA

TTCAGCTCCGGTTCCCAACGATCAAGGCGAGTTACATGATCCCCCATGTTGTGCAAAAAAGCGGTTAGCTCCTTCG

GTCCTCCGATCGTTGTCAGAAGTAAGTTGGCCGCAGTGTTATCACTCATGGTTATGGCAGCACTGCATAATTCTCTT

ACTGTCATGCCATCCGTAAGATGCTTTTCTGTGACTGGTGAGTACTCAACCAAGTCATTCTGAGAATAGTGTATGCG

GCGACCGAGTTGCTCTTGCCCGGCGTCAATACGGGATAATACCGCGCCACATAGCAGAACTTTAAAAGTGCTCATC

ATTGGAAAACGTTCTTCGGGGCGAAAACTCTCAAGGATCTTACCGCTGTTGAGATCCAGTTCGATGTAACCCACTC

GTGCACCCAACTGATCTTCAGCATCTTTTACTTTCACCAGCGTTTCTGGGTGAGCAAAAACAGGAAGGCAAAATGC

CGCAAAAAAGGGAATAAGGGCGACACGGAAATGTTGAATACTCATACTCTTCCTTTTTCAATATTATTGAAGCATTT

ATCAGGGTTATTGTCTCATGAGCGGATACATATTTGAATGTATTTAGAAAAATAAACAAATAGGGGTTCCGCGCAC

ATTTCCCCGAAAAGTGCCACCTATGAGACG
```

A vector pHCsiaT-TagBFP (SEQ ID NO: 35) according to the invention is constructed from a combination of building blocks Ori-AmpR BsaI A (SEQ ID NO: 17), pCMV BsaI A (SEQ ID NO: 18), SiaT BsaI A (SEQ ID NO: 19), BGHpA BsaI A (SEQ ID NO: 26), LacZα-up BsaI A (SEQ ID NO: 27), LacZα-down BsaI A (SEQ ID NO: 28), HygroR BsaI A (SEQ ID NO: 29) and TagBFP BsaI A (SEQ ID NO: 25).

```
Vector pHCsiaT-TagBFP
                                                            (SEQ ID NO: 35)
TGAGGCTAGGGATAGGACGAGAGCATCGGGAACGAGGACTAGCGTCTCAAGGAACCAATTCAGTCGACTGGATC

CTAGTTATTAATAGTAATCAATTACGGGGTCATTAGTTCATAGCCCATATATGGAGTTCCGCGTTACATAACTTACG

GTAAATGGCCCGCCTGGCTGACCGCCCAACGACCCCCGCCCATTGACGTCAATAATGACGTATGTTCCCATAGTAA

CGCCAATAGGGACTTTCCATTGACGTCAATGGGTGGAGTATTTACGGTAAACTGCCCACTTGGCAGTACATCAAGT

GTATCATATGCCAAGTACGCCCCCTATTGACGTCAATGACGGTAAATGGCCCGCCTGGCATTATGCCCAGTACATG

ACCTTATGGGACTTTCCTACTTGGCAGTACATCTACGTATTAGTCATCGCTATTACCATGGTGATGCGGTTTTGGCA

GTACATCAATGGGCGTGGATAGCGGTTTGACTCACGGGGATTTCCAAGTCTCCACCCCATTGACGTCAATGGGAGT

TTGTTTTGGCACCAAAATCAACGGGACTTTCCAAAATGTCGTAACAACTCCGCCCCATTGACGCAAATGGGCGGTA

GGCGTGTACGGTGGAGGTCTATATAAGCAGAGCTGGTTTAGTGAACCGTCAGATCACTAGTCGACTAGGGATAA

CAGGGCCGCCACCATGATTCACACCAACCTGAAGAAAAAGTTCAGCTGCTGCGTCCTGGTCTTTCTTCTGTTTGCAG

TCATCTGTGTGTGGAAGGAAAAGAAGAAAGGGAGTTACTATGATTCCTTTAAATTGCAAACCAAGGAATTCCAGGT

GTTAAAGAGTCTGGGGAAATTGGCCATGGGGTCTGATTCCCAGTCTGTATCCTCAAGCAGCACCCAGGACCCCCAC

AGGGGCCGCCAGACCCTCGGCAGTCTCAGAGGCCTAGCCAAGGCCAAACCAGAGGCCTCCTTCCAGGTGTGGAAC
```

-continued

AAGGACAGCTCTTCCAAAAACCTTATCCCTAGGCTGCAAAAGGGGTCGGGGAGCGAGCTGATTAAGGAGAACATG

CACATGAAGCTGTACATGGAGGGCACCGTGGACAACCATCACTTCAAGTGCACATCCGAGGGCGAAGGCAAGCCC

TACGAGGGCACCCAGACCATGAGAATCAAGGTGGTCGAGGGCGGCCCTCTCCCCTTCGCCTTCGACATCCTGGCTA

CTAGCTTCCTCTACGGCAGCAAGACCTTCATCAACCACACCCAGGGCATCCCCGACTTCTTCAAGCAGTCCTTCCCT

GAGGGCTTCACATGGGAGAGAGTCACCACATACGAGGACGGGGGCGTGCTGACCGCTACCCAGGACACCAGCCT

CCAGGACGGCTGCCTCATCTACAACGTCAAGATCAGAGGGGTGAACTTCACATCCAACGGCCCTGTGATGCAGAA

GAAAACACTCGGCTGGGAGGCCTTCACCGAAACGCTGTACCCCGCTGACGGCGGCCTGGAAGGCAGAAACGACAT

GGCCCTGAAGCTCGTGGGCGGGAGCCATCTGATCGCAAACATCAAGACCACATATAGATCCAAGAAACCCGCTAA

GAACCTCAAGATGCCTGGCGTCTACTATGTGGACTACAGACTGGAAAGAATCAAGGAGGCCAACAACGAAACCTA

CGTCGAGCAGCACGAGGTGGCAGTGGCCAGATACTGCGACCTCCCTAGCAAACTGGGGCACAAGCTTAATTCCGG

ATGATCGACTGTGCCTTCTAGTTGCCAGCCATCTGTTGTTTGCCCCTCCCCCGTGCCTTCCTTGACCCTGGAAGGTGC

CACTCCCACTGTCCTTTCCTAATAAAATGAGGAAATTGCATCGCATTGTCTGAGTAGGTGTCATTCTATTCTGGGGG

GTGGGGTGGGGCAGGACAGCAAGGGGGAGGATTGGGAGGACAATAGCAGGCATGCTGGGGATGCGGTGGGCT

CTATGGCTTCTCCCTGCAGGTGCGCCCAATACGCAAACCGCCTCTCCCCGCGCGTTGGCCGATTCATTAATGCAGCT

GGCACGACAGGTTTCCCGACTGGAAAGCGGGCAGTGAGCGCAACGCAATTAATGTGAGTTAGCTCACTCATTAGG

CACCCCAGGCTTTACACTTTATGCTTCCGGCTCGTATGTTGTGTGGAATTGTGAGCGGATAACAATTTCACACAGGA

AACAGCTATGACCATGATTACGGACAGCCTGGCCGTCGTTTTACAACGTCGTGACTGGGAAAACCCTGGCGTTACC

CAACTTAATCGCCTTGCAGCACATCCCCCTTTCGCCAGCTGGCGTAATAGCGAAGAGGCCCGCACCGATCGCCCTTC

CCAACAGTTGCGCAGCCTGAATGGCGAATGGCGCCTGATGCGGTATTTTCTCCTTACGCATCTGTGCGGTATTTCAC

ACCGCATATGGTGCACTCTCAGTACAATCTGCTCTGATGCCGCATAGACCTGCAGGGCCAGCAGGCAGAAGTATGC

AAAGCATGCATCTCAATTAGTCAGCAACCAGGTGTGGAAAGTCCCCAGGCTCCCCAGCAGGCAGAAGTATGCAAA

GCATGCATCTCAATTAGTCAGCAACCATAGTCCCGCCCCTAACTCCGCCCATCCCGCCCCTAACTCCGCCCAGTTCCG

CCCATTCTCCGCCCCATGGCTGACTAATTTTTTTTATTTATGCAGAGGCCGAGGCCGCCTCTGCCTCTGAGCTATTCC

AGAAGTAGTGAGGAGGCTTTTTTGGAGGCCTAGGCTTTTGCAAAAAGCTCCCGGGAGCTTGTATATCCATTTTCGG

ATCTGATCAGCACGTGATGAAAAAGCCTGAACTCACCGCGACGTCTGTCGAGAAGTTTCTGATCGAAAAGTTCGAC

AGCGTGTCCGACCTGATGCAGCTCTCGGAGGGCGAAGAATCTCGTGCTTTCAGCTTCGATGTAGGAGGGCGTGGA

TATGTCCTGCGGGTAAATAGCTGCGCCGATGGTTTCTACAAAGATCGTTATGTTTATCGGCACTTTGCATCGGCCGC

GCTCCCGATTCCGGAAGTGCTTGACATTGGGGAATTCAGCGAGAGCCTGACCTATTGCATCTCCCGCCGTGCACAG

GGTGTCACGTTGCAAGACTTGCCTGAAACCGAACTGCCCGCTGTTCTGCAGCCGGTCGCGGAGGCCATGGATGCG

ATCGCTGCGGCCGATCTTAGCCAGACGAGCGGGTTCGGCCCATTCGGACCGCAAGGAATCGGTCAATACACTACA

TGGCGTGATTTCATATGCGCGATTGCTGATCCCCATGTGTATCACTGGCAAACTGTGATGGACGACACCGTCAGTG

CGTCCGTCGCGCAGGCTCTCGATGAGCTGATGCTTTGGGCCGAGGACTGCCCCGAAGTCCGGCACCTCGTGCACG

CGGATTTCGGCTCCAACAATGTCCTGACGGACAATGGCCGCATAACAGCGGTCATTGACTGGAGCGAGGCGATGT

TCGGGGATTCCCAATACGAGGTCGCCAACATCTTCTTCTGGAGGCCGTGGTTGGCTTGTATGGAGCAGCAGACGC

GCTACTTCGAGCGGAGGCATCCGGAGCTTGCAGGATCGCCGCGGCTCCGGGCGTATATGCTCCGCATTGGTCTTG

ACCAACTCTATCAGAGCTTGGTTGACGGCAATTTCGATGATGCAGCTTGGGCGCAGGGTCGATGCGACGCAATCGT

CCGATCCGGAGCCGGGACTGTCGGGCGTACACAAATCGCCCGCAGAAGCGCGGCCGTCTGGACCGATGGCTGTGT

AGAAGTACTCGCCGATAGTGGAAACCGACGCCCCAGCACTCGTCCGAGGGCAAAGGAATAGCACGTGCTACGAG

ATTTCGATTCCACCGCCGCCTTCTATGAAAGGTTGGGCTTCGGAATCGTTTTCCGGGACGCCGGCTGGATGATCCTC

CAGCGCGGGGATCTCATGCTGGAGTTCTTCGCCCACCCCAACTTGTTTATTGCAGCTTATAATGGTTACAAATAAAG

CAATAGCATCACAAATTTCACAAATAAAGCATTTTTTTCACTGCATTCTAGTTGTGGTTTGTCCAAACTCATCAATGT

-continued

```
ATCTTATGCGTCTTCTAGGGTTAAGGTTAGTGTAGAGAAGCAACCGAAGATTGAGAAGACATGGCGGTAATACGG
TTATCCACAGAATCAGGGGATAACGCAGGAAAGAACATGTGAGCAAAAGGCCAGCAAAAGGCCAGGAACCGTAA
AAAGGCCGCGTTGCTGGCGTTTTTCCATAGGCTCCGCCCCCTGACGAGCATCACAAAAATCGACGCTCAAGTCAG
AGGTGGCGAAACCCGACAGGACTATAAAGATACCAGGCGTTTCCCCCTGGAAGCTCCCTCGTGCGCTCTCCTGTTC
CGACCCTGCCGCTTACCGGATACCTGTCCGCCTTTCTCCCTTCGGGAAGCGTGGCGCTTTCTCATAGCTCACGCTGT
AGGTATCTCAGTTCGGTGTAGGTCGTTCGCTCCAAGCTGGGCTGTGTGCACGAACCCCCCGTTCAGCCCGACCGCT
GCGCCTTATCCGGTAACTATCGTCTTGAGTCCAACCCGGTAAGACACGACTTATCGCCACTGGCAGCAGCCACTGG
TAACAGGATTAGCAGAGCGAGGTATGTAGGCGGTGCTACAGAGTTCTTGAAGTGGTGGCCTAACTACGGCTACAC
TAGAAGAACAGTATTTGGTATCTGCGCTCTGCTGAAGCCAGTTACCTTCGGAAAAAGAGTTGGTAGCTCTTGATCC
GGCAAACAAACCACCGCTGGTAGCGGTTTTTTTGTTTGCAAGCAGCAGATTACGCGCAGAAAAAAAGGATCTCAA
GAAGATCCTTTGATCTTTTCTACGGGGTCTGACGCTCAGTGGAACGAAAACTCACGTTAAGGGATTTTGGTCATGA
GATTATCAAAAAGGATCTTCACCTAGATCCTTTTAAATTAAAAATGAAGTTTTAAATCAATCTAAAGTATATATGAGT
AAACTTGGTCTGACAGTTACCAATGCTTAATCAGTGAGGCACCTATCTCAGCGATCTGTCTATTTCGTTCATCCATAG
TTGCCTGACTCCCCGTCGTGTAGATAACTACGATACGGGAGGGCTTACCATCTGGCCCCAGTGCTGCAATGATACC
GCGTGACCCACGCTCACCGGCTCCAGATTTATCAGCAATAAACCAGCCAGCCGGAAGGGCCGAGCGCAGAAGTGG
TCCTGCAACTTTATCCGCCTCCATCCAGTCTATTAATTGTTGCCGGGAAGCTAGAGTAAGTAGTTCGCCAGTTAATA
GTTTGCGCAACGTTGTTGCCATTGCTACAGGCATCGTGGTGTCACGCTCGTCGTTTGGTATGGCTTCATTCAGCTCC
GGTTCCCAACGATCAAGGCGAGTTACATGATCCCCCATGTTGTGCAAAAAAGCGGTTAGCTCCTTCGGTCCTCCGA
TCGTTGTCAGAAGTAAGTTGGCCGCAGTGTTATCACTCATGGTTATGGCAGCACTGCATAATTCTCTTACTGTCATG
CCATCCGTAAGATGCTTTTCTGTGACTGGTGAGTACTCAACCAAGTCATTCTGAGAATAGTGTATGCGGCGACCGA
GTTGCTCTTGCCCGGCGTCAATACGGGATAATACCGCGCCACATAGCAGAACTTTAAAAGTGCTCATCATTGGAAA
ACGTTCTTCGGGGCGAAAACTCTCAAGGATCTTACCGCTGTTGAGATCCAGTTCGATGTAACCCACTCGTGCACCCA
ACTGATCTTCAGCATCTTTTACTTTCACCAGCGTTTCTGGGTGAGCAAAAACAGGAAGGCAAAATGCCGCAAAAAA
GGGAATAAGGGCGACACGGAAATGTTGAATACTCATACTCTTCCTTTTTCAATATTATTGAAGCATTTATCAGGGTT
ATTGTCTCATGAGCGGATACATATTTGAATGTATTTAGAAAAATAAACAAATAGGGGTTCCGCGCACATTTCCCCGA
AAAGTGCCACCTATGAGACG
```

In the following examples, the objective was to create a vector making it possible to express a human transgene (cDNA) in a stable manner in a cancerous mouse line and/or to inhibit the expression of a second mouse gene (shRNA), again in a stable manner. The series of vectors described below illustrates the implementation of different functional modules making it possible to develop the integration functionalities from an originator architecture (vector V1) characterised by the presence of the two expression units described above and by the absence of a multiple cloning site (inherent to the method described).

The building blocks described below were obtained by PCR in accordance with a conventional protocol as described above for embodiment 1. The assemblies were performed with the aid of the enzyme BsaI (NEB) and the ligase T4 HC (Promega) in the buffer of the ligase T4 HC, in accordance with the protocol described above.

Embodiment 2

Group of vectors V1: vectors allowing the simultaneous expression of multiple transgenes (and not containing a multiple cloning site)

U1+nxU2a+mxU2b

U1: Bacterial functional unit

U2a: Expression functional unit of which the promoter is dependent on RNA polymerase II and of which the expression product is a protein U2b: Expression functional unit of which the promoter is dependent on RNA polymerase III and of which the expression product is a non-coding RNA $n \geq 0$, $m \geq 0$ and $n+m \geq 2$ Example: Vector Allowing the Expression of the Enzyme hFUT3 Whilst Suppressing the Expression of Mb3Galt6

| U1 | ori-Amp |
|---|---|
| U2a | CMV promoter |
| | hFUT3 cDNA |
| | BPA terminator |
| U2b | shRNA mB3Galt6 cassette |

Figure 6:
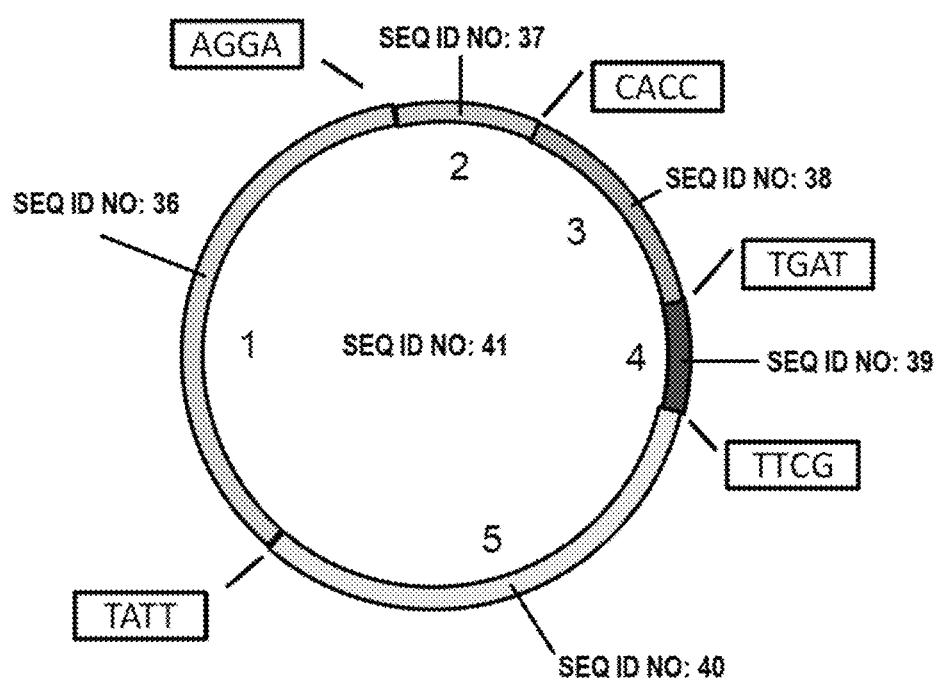

List of building blocks used for the construction of the vector V1 (FIG. 6)

Building block Ori-AmpR BsaI B
(SEQ ID NO: 36)
GAGGTACCGGTCTCATATTGTAATACGGTTATCCACAGAATCAGGGGATA
ACGCAGGAAAGAACATGTGAGCAAAAGGCCAGCAAAAGGCCAGGAACCGT
AAAAAGGCCGCGTTGCTGGCGTTTTTCCATAGGCTCCGCCCCCCTGACGA
GCATCACAAAAATCGACGCTCAAGTCAGAGGTGGCGAAACCCGACAGGAC
TATAAAGATACCAGGCGTTTCCCCCTGGAAGCTCCCTCGTGCGCTCTCCT
GTTCCGACCCTGCCGCTTACCGGATACCTGTCCGCCTTTCTCCCTTCGGG
AAGCGTGGCGCTTTCTCATAGCTCACGCTGTAGGTATCTCAGTTCGGTGT
AGGTCGTTCGCTCCAAGCTGGGCTGTGTGCACGAACCCCCCGTTCAGCCC
GACCGCTGCGCCTTATCCGGTAACTATCGTCTTGAGTCCAACCCGGTAAG
ACACGACTTATCGCCACTGGCAGCAGCCACTGGTAACAGGATTAGCAGAG
CGAGGTATGTAGGCGGTGCTACAGAGTTCTTGAAGTGGTGGCCTAACTAC
GGCTACACTAGAAGAACAGTATTTGGTATCTGCGCTCTGCTGAAGCCAGT
TACCTTCGGAAAAAGAGTTGGTAGCTCTTGATCCGGCAAACAAACCACCG
CTGGTAGCGGTTTTTTTGTTTGCAAGCAGCAGATTACGCGCAGAAAAAA
GGATCTCAAGAAGATCCTTTGATCTTTTCTACGGGGTCTGACGCTCAGTG
GAACGAAAACTCACGTTAAGGGATTTTGGTCATGAGATTATCAAAAAGGA
TCTTCACCTAGATCCTTTTAAATTAAAAATGAAGTTTTAAATCAATCTAA
AGTATATATGAGTAAACTTGGTCTGACAGTTACCAATGCTTAATCAGTGA
GGCACCTATCTCAGCGATCTGTCTATTTCGTTCATCCATAGTTGCCTGAC
TCCCCGTCGTGTAGATAACTACGATACGGGAGGGCTTACCATCTGGCCCC
AGTGCTGCAATGATACCGCGTGACCCACGCTCACCGGCTCCAGATTTATC
AGCAATAAACCAGCCAGCCGGAAGGGCCGAGCGCAGAAGTGGTCCTGCAA
CTTTATCCGCCTCCATCCAGTCTATTAATTGTTGCCGGGAAGCTAGAGTA
AGTAGTTCGCCAGTTAATAGTTTGCGCAACGTTGTTGCCATTGCTACAGG
CATCGTGGTGTCACGCTCGTCGTTTGGTATGGCTTCATTCAGCTCCGGTT
CCCAACGATCAAGGCGAGTTACATGATCCCCCATGTTGTGCAAAAAAGCG
GTTAGCTCCTTCGGTCCTCCGATCGTTGTCAGAAGTAAGTTGGCCGCAGT
GTTATCACTCATGGTTATGGCAGCACTGCATAATTCTCTTACTGTCATGC
CATCCGTAAGATGCTTTTCTGTGACTGGTGAGTACTCAACCAAGTCATTC
TGAGAATAGTGTATGCGGCGACCGAGTTGCTCTTGCCCGGCGTCAATACG
GGATAATACCGCGCCACATAGCAGAACTTTAAAAGTGCTCATCATTGGAA
AACGTTCTTCGGGGCGAAAACTCTCAAGGATCTTACCGCTGTTGAGATCC
AGTTCGATGTAACCCACTCGTGCACCCAACTGATCTTCAGCATCTTTTAC
TTTCACCAGCGTTTCTGGGTGAGCAAAAACAGGAAGGCAAAATGCCGCAA
AAAAGGGAATAAGGGCGACACGGAAATGTTGAATACTCATACTCTTCCTT
TTTCAATATTATTGAAGCATTTATCAGGGTTATTGTCTCATGAGCGGATA
CATATTTGAATGTATTTAGAAAAATAAACAAATAGGGGTTCCGCGCACAT
TTCCCCGAAAAGTGCCAAGGACGAGACCGGTACCTC Building block pCMV BsaI B
(SEQ ID NO: 37)
GAGGTACCGGTCTCAAGGAACCAATTCAGTCGACTGGATCCTAGTTATTA
ATAGTAATCAATTACGGGGTCATTAGTTCATAGCCCATATATGGAGTTCC
GCGTTACATAACTTACGGTAAATGGCCCGCCTGGCTGACCGCCCAACGAC
CCCCGCCCATTGACGTCAATAATGACGTATGTTCCCATAGTAACGCCAAT
AGGGACTTTCCATTGACGTCAATGGGTGGAGTATTTACGGTAAACTGCCC
ACTTGGCAGTACATCAAGTGTATCATATGCCAAGTACGCCCCCTATTGAC
GTCAATGACGGTAAATGGCCCGCCTGGCATTATGCCCAGTACATGACCTT
ATGGGACTTTCCTACTTGGCAGTACATCTACGTATTAGTCATCGCTATTA
CCATGGTGATGCGGTTTTGGCAGTACATCAATGGGCGTGGATAGCGGTTT
GACTCACGGGGATTTCCAAGTCTCCACCCCATTGACGTCAATGGGAGTTT
GTTTTGGCACCAAAATCAACGGGACTTTCCAAAATGTCGTAACAACTCCG
CCCCATTGACGCAAATGGGCGGTAGGCGTGTACGGTGGGAGGTCTATATA
AGCAGAGCTGGTTTAGTGAACCGTCAGATCACTAGTCGACTAGGGATAAC
AGGGCACCCGAGACCGGTACCTC Building block hFUT3 BsaI A
(SEQ ID NO: 38)
GAGGTACCGGTCTCACACCATGGATCCCCTGGGTGCAGCCAAGCCACAAT
GGCCATGGCGCCGCTGTCTGGCCGCACTGCTATTTCAGCTGCTGGTGGCT
GTGTGTTTCTTCTCCTACCTGCGTGTGTCCCGAGACGATGCCACTGGATC
CCCTAGGGCTCCCAGTGGGTCCTCCCGACAGGACACCACTCCCACCCGCC
CCACCCTCCTGATCCTGCTATGGACATGGCCTTTCCACATCCCTGTGGCT
CTGTCCCGCTGTTCAGAGATGGTGCCCGGCACAGCCGACTGCCACATCAC
TGCCGACCGCAAGGTGTACCCACAGGCAGACACGGTCATCGTGCACCACT
GGGATATCATGTCCAACCCTAAGTCACGCCTCCCACCTTCCCCGAGGCCG
CAGGGGCAGCGCTGGATCTGGTTCAACTTGGAGCCACCCCCTAACTGCCA
GCACCTGGAAGCCCTGGACAGATACTTCAATCTCACCATGTCCTACCGCA
GCGACTCCGACATCTTCACGCCCTACGGCTGGCTGGAGCCGTGGTCCGGC
CAGCCTGCCCACCCACCGCTCAACCTCTCGGCCAAGACCGAGCTGGTGGC
CTGGGCGGTGTCCAACTGGAAGCCGGACTCAGCCAGGGTGCGCTACTACC
AGAGCCTGCAGGCTCATCTCAAGGTGGACGTGTACGGACGCTCCCACAAG
CCCCTGCCCAAGGGGACCATGATGGAGACGCTGTCCCGGTACAAGTTCTA
CCTGGCCTTCGAGAACTCCTTGCACCCCGACTACATCACCGAGAAGCTGT
GGAGGAACGCCCTGGAGGCCTGGGCCGTGCCCGTGGTGCTGGGCCCCAGC
AGAAGCAACTACGAGAGGTTCCTGCCACCCGACGCCTTCATCCACGTGGA
CGACTTCCAGAGCCCCAAGGACCTGGCCCGGTACCTGCAGGAGCTGGACA
AGGACCACGCCCGCTACCTGAGCTACTTTCGCTGGCGGGAGACGCTGCGG
CCTCGCTCCTTCAGCTGGGCACTGGATTTCTGCAAGGCCTGCTGGAAACT
GCAGCAGGAATCCAGGTACCAGACGGTGCGCAGCATAGCGGCTTGGTTCA
CCTGATCGAGACCGGTACCTC Building block BGHpA BsaI B
(SEQ ID NO: 39)
GAGGTACCGGTCTCATGATCGACTGTGCCTTCTAGTTGCCAGCCATCTGT

TGTTTGCCCCTCCCCCGTGCCTTCCTTGACCCTGGAAGGTGCCACTCCCA

CTGTCCTTTCCTAATAAAATGAGGAAATTGCATCGCATTGTCTGAGTAGG

TGTCATTCTATTCTGGGGGGTGGGGTGGGGCAGGACAGCAAGGGGGAGGA

TTGGGAGGACAATAGCAGGCATGCTGGGGATGCGGTGGGCTCTATGGCTT

CGCGAGACCGGTACCTC

Building block shB3Galt6 BsaI A
(SEQ ID NO: 40)
GAGGTACCGGTCTCATTCGACAGGGTCGACAAGCTTTTCCAAAAAAAAG

CATGAGGTGCAGTTGCGCCTTTCCTATCTCTTGAATAGGAAAGGCGCAAC

TGCACCTCATGCTGGATCCCGCGTCCTTTCCACAAGATATATAAACCCAA

GAAATCGAAATACTTTCAAGTTACGGTAAGCATATGATAGTCCATTTTAA

AACATAATTTTAAAACTGCAAACTACCCAAGAATTATTACTTTCTACGT

CACGTATTTTGTACTAATATCTTTGTGTTTACAGTCAAATTAATTCTAAT

TATCTCTCTAACAGCCTTGTATCGTATATGCAAATATGAAGGAATCATGG

GAAATAGGCCCTCTTCCTGCCCGACCTTGGCGCGCGCTCGGCGCGCGGTC

ACGCTCCGTCACGTGGTGCGTTTTGTATTCGAGACCGGTACCTC

Vector V1 (SEQ ID NO: 41,
example of a vector of the group V1)
TATTGTAATACGGTTATCCACAGAATCAGGGGATAACGCAGGAAAGAACA

TGTGAGCAAAAGGCCAGCAAAAGGCCAGGAACCGTAAAAAGGCCGCGTTG

CTGGCGTTTTTCCATAGGCTCCGCCCCCCTGACGAGCATCACAAAAATCG

ACGCTCAAGTCAGAGGTGGCGAAACCCGACAGGACTATAAAGATACCAGG

CGTTTCCCCCTGGAAGCTCCCTCGTGCGCTCTCCTGTTCCGACCCTGCCG

CTTACCGGATACCTGTCCGCCTTTCTCCCTTCGGGAAGCGTGGCGCTTTC

TCATAGCTCACGCTGTAGGTATCTCAGTTCGGTGTAGGTCGTTCGCTCCA

AGCTGGGCTGTGTGCACGAACCCCCCGTTCAGCCCGACCGCTGCGCCTTA

TCCGGTAACTATCGTCTTGAGTCCAACCCGGTAAGACACGACTTATCGCC

ACTGGCAGCAGCCACTGGTAACAGGATTAGCAGAGCGAGGTATGTAGGCG

GTGCTACAGAGTTCTTGAAGTGGTGGCCTAACTACGGCTACACTAGAAGA

ACAGTATTTGGTATCTGCGCTCTGCTGAAGCCAGTTACCTTCGGAAAAAG

AGTTGGTAGCTCTTGATCCGGCAAACAAACCACCGCTGGTAGCGGTTTTT

TTGTTTGCAAGCAGCAGATTACGCGCAGAAAAAAAGGATCTCAAGAAGAT

CCTTTGATCTTTTCTACGGGGTCTGACGCTCAGTGGAACGAAAACTCACG

TTAAGGGATTTTGGTCATGAGATTATCAAAAAGGATCTTCACCTAGATCC

TTTTAAATTAAAAATGAAGTTTTAAATCAATCTAAAGTATATATGAGTAA

ACTTGGTCTGACAGTTACCAATGCTTAATCAGTGAGGCACCTATCTCAGC

GATCTGTCTATTTCGTTCATCCATAGTTGCCTGACTCCCCGTCGTGTAGA

TAACTACGATACGGGAGGGCTTACCATCTGGCCCCAGTGCTGCAATGATA

CCGCGTGACCCACGCTCACCGGCTCCAGATTTATCAGCAATAAACCAGCC

AGCCGGAAGGGCCGAGCGCAGAAGTGGTCCTGCAACTTTATCCGCCTCCA

TCCAGTCTATTAATTGTTGCCGGGAAGCTAGAGTAAGTAGTTCGCCAGTT

AATAGTTTGCGCAACGTTGTTGCCATTGCTACAGGCATCGTGGTGTCACG

CTCGTCGTTTGGTATGGCTTCATTCAGCTCCGGTTCCCAACGATCAAGGC

GAGTTACATGATCCCCCATGTGTGCAAAAAAGCGGTTAGCTCCTTCGGT

CCTCCGATCGTTGTCAGAAGTAAGTTGGCCGCAGTGTTATCACTCATGGT

TATGGCAGCACTGCATAATTCTCTTACTGTCATGCCATCCGTAAGATGCT

TTTCTGTGACTGGTGAGTACTCAACCAAGTCATTCTGAGAATAGTGTATG

CGGCGACCGAGTTGCTCTTGCCCGGCGTCAATACGGGATAATACCGCGCC

ACATAGCAGAACTTTAAAAGTGCTCATCATTGGAAAACGTTCTTCGGGGC

GAAAACTCTCAAGGATCTTACCGCTGTTGAGATCCAGTTCGATGTAACCC

ACTCGTGCACCCAACTGATCTTCAGCATCTTTTACTTTCACCAGCGTTTC

TGGGTGAGCAAAAACAGGAAGGCAAAATGCCGCAAAAAAGGGAATAAGGG

CGACACGGAAATGTTGAATACTCATACTCTTCCTTTTTCAATATTATTGA

AGCATTTATCAGGGTTATTGTCTCATGAGCGGATACATATTTGAATGTAT

TTAGAAAAATAAACAAATAGGGGTTCCGCGCACATTTCCCCGAAAAGTGC

CAAGGAACCAATTCAGTCGACTGGATCCTAGTTATTAATAGTAATCAATT

ACGGGGTCATTAGTTCATAGCCCATATATGGAGTTCCGCGTTACATAACT

TACGGTAAATGGCCCGCCTGGCTGACCGCCCAACGACCCCCGCCCATTGA

CGTCAATAATGACGTATGTTCCCATAGTAACGCCAATAGGGACTTTCCAT

TGACGTCAATGGGTGGAGTATTTACGGTAAACTGCCCACTTGGCAGTACA

TCAAGTGTATCATATGCCAAGTACGCCCCCTATTGACGTCAATGACGGTA

AATGGCCCGCCTGGCATTATGCCCAGTACATGACCTTATGGGACTTTCCT

ACTTGGCAGTACATCTACGTATTAGTCATCGCTATTACCATGGTGATGCG

GTTTTGGCAGTACATCAATGGGCGTGGATAGCGGTTTGACTCACGGGGAT

TTCCAAGTCTCCACCCCATTGACGTCAATGGGAGTTTGTTTTGGCACCAA

AATCAACGGGACTTTCCAAAATGTCGTAACAACTCCGCCCCATTGACGCA

AATGGGCGGTAGGCGTGTACGGTGGGAGGTCTATATAAGCAGAGCTGGTT

TAGTGAACCGTCAGATCACTAGTCGACTAGGGATAACAGGGCACCATGGA

TCCCCTGGGTGCAGCCAAGCCACAATGGCCATGGCGCCGCTGTCTGGCCG

CACTGCTATTTCAGCTGCTGGTGGCTGTGTGTTTCTTCTCCTACCTGCGT

GTGTCCCGAGACGATGCCACTGGATCCCCTAGGGCTCCCAGTGGGTCCTC

CCGACAGGACACCACTCCCACCCGCCCCACCCTCCTGATCCTGCTATGGA

CATGGCCTTTCCACATCCCTGTGGCTCTGTCCCGCTGTTCAGAGATGGTG

CCCGGCACAGCCGACTGCCACATCACTGCCGACCGCAAGGTGTACCCACA

GGCAGACACGGTCATCGTGCACCACTGGGATATCATGTCCAACCCTAAGT

CACGCCTCCCACCTTCCCCGAGGCCGCAGGGGCAGCGCTGGATCTGGTTC

AACTTGGAGCCACCCCCTAACTGCCAGCACCTGGAAGCCCTGGACAGATA

CTTCAATCTCACCATGTCCTACCGCAGCGACTCCGACATCTTCACGCCCT

ACGGCTGGCTGGAGCCGTGGTCCGGCCAGCCTGCCCACCCACCGCTCAAC

CTCTCGGCCAAGACCGAGCTGGTGGCCTGGGCGGTGTCCAACTGGAAGCC

GGACTCAGCCAGGGTGCGCTACTACCAGAGCCTGCAGGCTCATCTCAAGG

-continued

TGGACGTGTACGGACGCTCCCACAAGCCCTGCCCAAGGGGACCATGATG

GAGACGCTGTCCCGGTACAAGTTCTACCTGGCCTTCGAGAACTCCTTGCA

CCCCGACTACATCACCGAGAAGCTGTGGAGGAACGCCCTGGAGGCCTGGG

CCGTGCCCGTGGTGCTGGGCCCCAGCAGAAGCAACTACGAGAGGTTCCTG

CCACCCGACGCCTTCATCCACGTGGACGACTTCCAGAGCCCCAAGGACCT

GGCCCGGTACCTGCAGGAGCTGGACAAGGACCACGCCCGCTACCTGAGCT

ACTTTCGCTGGCGGGAGACGCTGCGGCCTCGCTCCTTCAGCTGGGCACTG

GATTTCTGCAAGGCCTGCTGGAAACTGCAGCAGGAATCCAGGTACCAGAC

GGTGCGCAGCATAGCGGCTTGGTTCACCTGATCGACTGTGCCTTCTAGTT

GCCAGCCATCTGTTGTTTGCCCCTCCCCCGTGCCTTCCTTGACCCTGGAA

GGTGCCACTCCCACTGTCCTTTCCTAATAAAATGAGGAAATTGCATCGCA

TTGTCTGAGTAGGTGTCATTCTATTCTGGGGGGTGGGGTGGGGCAGGACA

GCAAGGGGAGGATTGGGAGGACAATAGCAGGCATGCTGGGGATGCGGTG

GGCTCTATGGCTTCGACAGGGTCGACAAGCTTTTCCAAAAAAAAGCATG

AGGTGCAGTTGCGCCTTTCCTATCTCTTGAATAGGAAAGGCGCAACTGCA

CCTCATGCTGGATCCCGCGTCCTTTCCACAAGATATATAAACCCAAGAAA

TCGAAATACTTTCAAGTTACGGTAAGCATATGATAGTCCATTTTAAAACA

TAATTTTAAAACTGCAAACTACCCAAGAAATTATTACTTTCTACGTCACG

TATTTTGTACTAATATCTTTGTGTTTACAGTCAAATTAATTCTAATTATC

TCTCTAACAGCCTTGTATCGTATATGCAAATATGAAGGAATCATGGGAAA

TAGGCCCTCTTCCTGCCCGACCTTGGCGCGCGCTCGGCGCGCGGTCACGC

TCCGTCACGTGGTGCGTTTTG.

The analysis of restriction by triple digestion (structural validation), EcoRV, PvuI, SalI of embodiment 2 is illustrated in FIG. 7.

Functional verification of embodiment 2: Eukaryotic cells (for example: 4T1 mouse breast cancer cells) are transfected with the vector V1 in accordance with a conventional protocol (for example lipotransfection or electroporation). The cells are collected at 24 and 48h after transfection and are lysed so as to extract therefrom the total RNAs and then generate the complementary DNAs (cDNA) by reverse transcription in accordance with a conventional protocol. These cDNAs are then used as matrix for quantitative PCR analysis in accordance with a conventional protocol.

Specific Conditions of the Quantitative PCR:

40 cycles of three subsequent steps are performed: denaturation 94° C.-30s; hybridisation 60° C.-30s; extension 72° C.-30s.

Primers Used:

mB3Galt6
BETA3Galt6ms2-s
(SEQ ID NO: 42)
ACCACTCTGTTGTACCTGGC.

BETA3Galt6ms2-as
(SEQ ID NO: 43)
CACACGTCCTCGGGTCC.

HFUT3
FUT35:
(SEQ ID NO: 44)
CACTAGTCGACTAGGGATAACAGG.

FUT33:
(SEQ ID NO: 45)
ATGTCCATAGCAGGATCAGGAG.

Embodiment 3

Group of Vectors V1.1: Vectors V1 Allowing Selection of the Integration of Transgenes by Non-Homologous Recombination in the Target Genome U1+nxU2a+mxU2b+U3a U1: Bacterial functional unit U2a: Expression functional unit of which the promoter is dependent on RNA polymerase II and of which the expression product is a protein U2b: Expression functional unit of which the promoter is dependent on RNA polymerase III and of which the expression product is a non-coding RNA U3a is a positive selection cassette n≥0, m≥0 and n+m≥2

Example: Vector Allowing the Expression of the Enzyme hFUT3 Whilst Suppressing the Expression of mB3Galt6

| | |
|---|---|
| U1 | ori-Amp |
| U2a | CMV promoter |
| | hFUT3 cDNA |
| | BPA terminator |
| U2b | shRNA mB3Galt6 cassette |
| U3a | hygromycin resistance |

Lists of the building blocks used to construct the vector V1.1 (FIG. 8)

(SEQ ID NO: 36)
Building block Ori-AmpR BsaI B (SEQ ID NO: 37)
Building block pCMV BsaI B (SEQ ID NO: 38)
Building block hFUT3 BsaI A (SEQ ID NO: 39)
Building block BGHpA BsaI B Building block shB3Galt6 BsaI B
(SEQ ID NO: 46)
GAGGTACCGGTCTCATTCGACAGGGTCGACAAGCTTTTCCAAAAAAAAG

CATGAGGTGCAGTTGCGCCTTTCCTATCTCTTGAATAGGAAAGGCGCAAC

TGCACCTCATGCTGGATCCCGCGTCCTTTCCACAAGATATATAAACCCAA

GAAATCGAAATACTTTCAAGTTACGGTAAGCATATGATAGTCCATTTTAA

AACATAATTTTAAAACTGCAAACTACCCAAGAAATTATTACTTTCTACGT

CACGTATTTTGTACTAATATCTTTGTGTTTACAGTCAAATTAATTCTAAT

TATCTCTAACAGCCTTGTATCGTATATGCAAATATGAAGGAATCATGG

GAAATAGGCCCTCTTCCTGCCCGACCTTGGCGCGCGCTCGGCGCGCGGTC

ACGCTCCGTCACGTGGTGCGTTTTGCCAGCGAGACCGGTACCTC

Building block HygroR BsaI B
(SEQ ID NO: 47)
GAGGTACCGGTCTCACCAGCAGGCAGAAGTATGCAAAGCATGCATCTCAA

TTAGTCAGCAACCAGGTGTGGAAAGTCCCCAGGCTCCCCAGCAGGCAGAA

GTATGCAAAGCATGCATCTCAATTAGTCAGCAACCATAGTCCCGCCCCTA

ACTCCGCCCATCCCGCCCCTAACTCCGCCCAGTTCCGCCCATTCTCCGCC

CCATGGCTGACTAATTTTTTTATTTATGCAGAGGCCGAGGCCGCCTCTG

CCTCTGAGCTATTCCAGAAGTAGTGAGGAGGCTTTTTTGGAGGCCTAGGC

TTTTGCAAAAAGCTCCCGGGAGCTTGTATATCCATTTTCGGATCTGATCA

GCACGTGATGAAAAGCCTGAACTCACCGCGACGTCTGTCGAGAAGTTTC

TGATCGAAAAGTTCGACAGCGTGTCCGACCTGATGCAGCTCTCGGAGGGC

GAAGAATCTCGTGCTTTCAGCTTCGATGTAGGAGGGCGTGGATATGTCCT

GCGGGTAAATAGCTGCGCCGATGGTTTCTACAAAGATCGTTATGTTTATC

GGCACTTTGCATCGGCCGCGCTCCCGATTCCGGAAGTGCTTGACATTGGG

GAATTCAGCGAGAGCCTGACCTATTGCATCTCCCGCCGTGCACAGGGTGT

CACGTTGCAAGACTTGCCTGAAACCGAACTGCCCGCTGTTCTGCAGCCGG

TCGCGGAGGCCATGGATGCGATCGCTGCGGCCGATCTTAGCCAGACGAGC

GGGTTCGGCCCATTCGGACCGCAAGGAATCGGTCAATACACTACATGGCG

TGATTTCATATGCGCGATTGCTGATCCCCATGTGTATCACTGGCAAACTG

TGATGGACGACACCGTCAGTGCGTCCGTCGCGCAGGCTCTCGATGAGCTG

ATGCTTTGGGCCGAGGACTGCCCCGAAGTCCGGCACCTCGTGCACGCGGA

TTTCGGCTCCAACAATGTCCTGACGGACAATGGCCGCATAACAGCGGTCA

TTGACTGGAGCGAGGCGATGTTCGGGGATTCCCAATACGAGGTCGCCAAC

ATCTTCTTCTGGAGGCCGTGGTTGGCTTGTATGGAGCAGCAGACGCGCTA

CTTCGAGCGGAGGCATCCGGAGCTTGCAGGATCGCCGCGGCTCCGGGCGT

ATATGCTCCGCATTGGTCTTGACCAACTCTATCAGAGCTTGGTTGACGGC

AATTTCGATGATGCAGCTTGGGCGCAGGGTCGATGCGACGCAATCGTCCG

ATCCGGAGCCGGGACTGTCGGGCGTACACAAATCGCCCGCAGAAGCGCGG

CCGTCTGGACCGATGGCTGTGTAGAAGTACTCGCCGATAGTGGAAACCGA

CGCCCCAGCACTCGTCCGAGGGCAAAGGAATAGCACGTGCTACGAGATTT

CGATTCCACCGCCGCCTTCTATGAAAGGTTGGGCTTCGGAATCGTTTTCC

GGGACGCCGGCTGGATGATCCTCCAGCGCGGGGATCTCATGCTGGAGTTC

TTCGCCCACCCCAACTTGTTTATTGCAGCTTATAATGGTTACAAATAAAG

CAATAGCATCACAAATTTCACAAATAAAGCATTTTTTTCACTGCATTCTA

GTTGTGGTTTGTCCAAACTCATCAATGTATCTATTCGAGACCGGTACCTC

V1.1 (SEQ ID NO: 48,
example of a vector of the group V1.1)
TATTGTAATACGGTTATCCACAGAATCAGGGGATAACGCAGGAAAGAACA

TGTGAGCAAAAGGCCAGCAAAAGGCCAGGAACCGTAAAAAGGCCGCGTTG

CTGGCGTTTTTCCATAGGCTCCGCCCCCCTGACGAGCATCACAAAAATCG

ACGCTCAAGTCAGAGGTGGCGAAACCCGACAGGACTATAAAGATACCAGG

CGTTTCCCCCTGGAAGCTCCCTCGTGCGCTCTCCTGTTCCGACCCTGCCG

CTTACCGGATACCTGTCCGCCTTTCTCCCTTCGGGAAGCGTGGCGCTTTC

TCATAGCTCACGCTGTAGGTATCTCAGTTCGGTGTAGGTCGTTCGCTCCA

AGCTGGGCTGTGTGCACGAACCCCCCGTTCAGCCCGACCGCTGCGCCTTA

TCCGGTAACTATCGTCTTGAGTCCAACCCGGTAAGACACGACTTATCGCC

ACTGGCAGCAGCCACTGGTAACAGGATTAGCAGAGCGAGGTATGTAGGCG

GTGCTACAGAGTTCTTGAAGTGGTGGCCTAACTACGGCTACACTAGAAGA

ACAGTATTTGGTATCTGCGCTCTGCTGAAGCCAGTTACCTTCGGAAAAAG

AGTTGGTAGCTCTTGATCCGGCAAACAAACCACCGCTGGTAGCGGTTTTT

TTGTTTGCAAGCAGCAGATTACGCGCAGAAAAAAAGGATCTCAAGAAGAT

CCTTTGATCTTTTCTACGGGGTCTGACGCTCAGTGGAACGAAAACTCACG

TTAAGGGATTTTGGTCATGAGATTATCAAAAAGGATCTTCACCTAGATCC

TTTTAAATTAAAAATGAAGTTTTAAATCAATCTAAAGTATATATGAGTAA

ACTTGGTCTGACAGTTACCAATGCTTAATCAGTGAGGCACCTATCTCAGC

GATCTGTCTATTTCGTTCATCCATAGTTGCCTGACTCCCCGTCGTGTAGA

TAACTACGATACGGGAGGGCTTACCATCTGGCCCCAGTGCTGCAATGATA

CCGCGTGACCCACGCTCACCGGCTCCAGATTTATCAGCAATAAACCAGCC

AGCCGGAAGGGCCGAGCGCAGAAGTGGTCCTGCAACTTTATCCGCCTCCA

TCCAGTCTATTAATTGTTGCCGGGAAGCTAGAGTAAGTAGTTCGCCAGTT

AATAGTTTGCGCAACGTTGTTGCCATTGCTACAGGCATCGTGGTGTCACG

CTCGTCGTTTGGTATGGCTTCATTCAGCTCCGGTTCCCAACGATCAAGGC

GAGTTACATGATCCCCCATGTTGTGCAAAAAAGCGGTTAGCTCCTTCGGT

CCTCCGATCGTTGTCAGAAGTAAGTTGGCCGCAGTGTTATCACTCATGGT

TATGGCAGCACTGCATAATTCTCTTACTGTCATGCCATCCGTAAGATGCT

TTTCTGTGACTGGTGAGTACTCAACCAAGTCATTCTGAGAATAGTGTATG

CGGCGACCGAGTTGCTCTTGCCCGGCGTCAATACGGGATAATACCGCGCC

ACATAGCAGAACTTTAAAAGTGCTCATCATTGGAAAACGTTCTTCGGGGC

GAAAACTCTCAAGGATCTTACCGCTGTTGAGATCCAGTTCGATGTAACCC

ACTCGTGCACCCAACTGATCTTCAGCATCTTTTACTTTCACCAGCGTTTC

TGGGTGAGCAAAAACAGGAAGGCAAAATGCCGCAAAAAAGGGAATAAGGG

CGACACGGAAATGTTGAATACTCATACTCTTCCTTTTTCAATATTATTGA

AGCATTTATCAGGGTTATTGTCTCATGAGCGGATACATATTTGAATGTAT

TTAGAAAAATAAACAAATAGGGGTTCCGCGCACATTTCCCCGAAAAGTGC

CAAGGAACCAATTCAGTCGACTGGATCCTAGTTATTAATAGTAATCAATT

ACGGGGTCATTAGTTCATAGCCCATATATGGAGTTCCGCGTTACATAACT

TACGGTAAATGGCCCGCCTGGCTGACCGCCCAACGACCCCCGCCCATTGA

CGTCAATAATGACGTATGTTCCCATAGTAACGCCAATAGGGACTTTCCAT

TGACGTCAATGGGTGGAGTATTTACGGTAAACTGCCCACTTGGCAGTACA

TCAAGTGTATCATATGCCAAGTACGCCCCCTATTGACGTCAATGACGGTA

AATGGCCCGCCTGGCATTATGCCCAGTACATGACCTTATGGGACTTTCCT

ACTTGGCAGTACATCTACGTATTAGTCATCGCTATTACCATGGTGATGCG

GTTTTGGCAGTACATCAATGGGCGTGGATAGCGGTTTGACTCACGGGGAT

```
TTCCAAGTCTCCACCCCATTGACGTCAATGGGAGTTTGTTTTGGCACCAA

AATCAACGGGACTTTCCAAAATGTCGTAACAACTCCGCCCCATTGACGCA

AATGGGCGGTAGGCGTGTACGGTGGGAGGTCTATATAAGCAGAGCTGGTT

TAGTGAACCGTCAGATCACTAGTCGACTAGGGATAACAGGGCACCATGGA

TCCCCTGGGTGCAGCCAAGCCACAATGGCCATGGCGCCGCTGTCTGGCCG

CACTGCTATTTCAGCTGCTGGTGGCTGTGTGTTTCTTCTCCTACCTGCGT

GTGTCCCGAGACGATGCCACTGGATCCCCTAGGGCTCCCAGTGGGTCCTC

CCGACAGGACACCACTCCCACCCGCCCCACCCTCCTGATCCTGCTATGGA

CATGGCCTTTCCACATCCCTGTGGCTCTGTCCCGCTGTTCAGAGATGGTG

CCCGGCACAGCCGACTGCCACATCACTGCCGACCGCAAGGTGTACCCACA

GGCAGACACGGTCATCGTGCACCACTGGGATATCATGTCCAACCCTAAGT

CACGCCTCCCACCTTCCCCGAGGCCGCAGGGGCAGCGCTGGATCGGTTC

AACTTGGAGCCACCCCCTAACTGCCAGCACCTGGAAGCCCTGGACAGATA

CTTCAATCTCACCATGTCCTACCGCAGCGACTCCGACATCTTCACGCCCT

ACGGCTGGCTGGAGCCGTGGTCCGGCCAGCCTGCCCACCCACCGCTCAAC

CTCTCGGCCAAGACCGAGCTGGTGGCCTGGGCGGTGTCCAACTGGAAGCC

GGACTCAGCCAGGGTGCGCTACTACCAGAGCCTGCAGGCTCATCTCAAGG

TGGACGTGTACGGACGCTCCCACAAGCCCCTGCCCAAGGGGACCATGATG

GAGACGCTGTCCCGGTACAAGTTCTACCTGGCCTTCGAGAACTCCTTGCA

CCCCGACTACATCACCGAGAAGCTGTGGAGGAACGCCCTGGAGGCCTGGG

CCGTGCCCGTGGTGCTGGGCCCCAGCAGAAGCAACTACGAGAGGTTCCTG

CCACCCGACGCCTTCATCCACGTGGACGACTTCCAGAGCCCCAAGGACCT

GGCCCGGTACCTGCAGGAGCTGGACAAGGACCACGCCCGCTACCTGAGCT

ACTTTCGCTGGCGGGAGACGCTGCGGCCTCGCTCCTTCAGCTGGGCACTG

GATTTCTGCAAGGCCTGCTGGAAACTGCAGCAGGAATCCAGGTACCAGAC

GGTGCGCAGCATAGCGGCTTGGTTCACCTGATCGACTGTGCCTTCTAGTT

GCCAGCCATCTGTTGTTTGCCCCTCCCCCGTGCCTTCCTTGACCCTGGAA

GGTGCCACTCCCACTGTCCTTTCCTAATAAAATGAGGAAATTGCATCGCA

TTGTCTGAGTAGGTGTCATTCTATTCTGGGGGTGGGTGGGGCAGGACA

GCAAGGGGAGGATTGGGAGGACAATAGCAGGCATGCTGGGGATGCGGTG

GGCTCTATGGCTTCGACAGGGTCGACAAGCTTTTCCAAAAAAAAGCATG

AGGTGCAGTTGCGCCTTTCCTATCTCTTGAATAGGAAAGGCGCAACTGCA

CCTCATGCTGGATCCCGCGTCCTTTCCACAAGATATATAAACCCAAGAA

TCGAAATACTTTCAAGTTACGGTAAGCATATGATAGTCCATTTTAAAACA

TAATTTTAAAACTGCAAACTACCCAAGAAATTATTACTTTCTACGTCACG

TATTTTGTACTAATATCTTTGTGTTTACAGTCAAATTAATTCTAATTATC

TCTCTAACAGCCTTGTATCGTATATGCAAATATGAAGGAATCATGGGAAA

TAGGCCCTCTTCCTGCCCGACCTTGGCGCGCGCTCGGCGCGCGGTCACGC

TCCGTCACGTGGTGCGTTTGCCAGCAGGCAGAAGTATGCAAAGCATGCA

TCTCAATTAGTCAGCAACCAGGTGTGGAAAGTCCCCAGGCTCCCCAGCAG

GCAGAAGTATGCAAAGCATGCATCTCAATTAGTCAGCAACCATAGTCCCG

CCCCTAACTCCGCCCATCCCGCCCCTAACTCCGCCCAGTTCCGCCCATTC

TCCGCCCCATGGCTGACTAATTTTTTTTATTTATGCAGAGGCCGAGGCCG

CCTCTGCCTCTGAGCTATTCCAGAAGTAGTGAGGAGGCTTTTTTGGAGGC

CTAGGCTTTTGCAAAAAGCTCCCGGGAGCTTGTATATCCATTTTCGGATC

TGATCAGCACGTGATGAAAAAGCCTGAACTCACCGCGACGTCTGTCGAGA

AGTTTCTGATCGAAAAGTTCGACAGCGTGTCCGACCTGATGCAGCTCTCG

GAGGGCGAAGAATCTCGTGCTTTCAGCTTCGATGTAGGAGGGCGTGGATA

TGTCCTGCGGGTAAATAGCTGCGCCGATGGTTTCTACAAAGATCGTTATG

TTTATCGGCACTTTGCATCGGCCGCGCTCCCGATTCCGGAAGTGCTTGAC

ATTGGGGAATTCAGCGAGAGCCTGACCTATTGCATCTCCCGCCGTGCACA

GGGTGTCACGTTGCAAGACTTGCCTGAAACCGAACTGCCCGCTGTTCTGC

AGCCGGTCGCGGAGGCCATGGATGCGATCGCTGCGGCCGATCTTAGCCAG

ACGAGCGGGTTCGGCCCATTCGGACCGCAAGGAATCGGTCAATACACTAC

ATGGCGTGATTTCATATGCGCGATTGCTGATCCCCATGTGTATCACTGGC

AAACTGTGATGGACGACACCGTCAGTGCGTCCGTCGCGCAGGCTCTCGAT

GAGCTGATGCTTTGGGCCGAGGACTGCCCCGAAGTCCGGCACCTCGTGCA

CGCGGATTTCGGCTCCAACAATGTCCTGACGGACAATGGCCGCATAACAG

CGGTCATTGACTGGAGCGAGGCGATGTTCGGGGATTCCCAATACGAGGTC

GCCAACATCTTCTTCTGGAGGCCGTGGTTGGCTTGTATGGAGCAGCAGAC

GCGCTACTTCGAGCGGAGGCATCCGGAGCTTGCAGGATCGCCGCGGCTCC

GGGCGTATATGCTCCGCATTGGTCTTGACCAACTCTATCAGAGCTTGGTT

GACGGCAATTTCGATGATGCAGCTTGGGCGCAGGGTCGATGCGACGCAAT

CGTCCGATCCGGAGCCGGGACTGTCGGGCGTACACAAATCGCCCGCAGAA

GCGCGGCCGTCTGGACCGATGGCTGTGTAGAAGTACTCGCCGATAGTGGA

AACCGACGCCCCAGCACTCGTCCGAGGGCAAAGGAATAGCACGTGCTACG

AGATTTCGATTCCACCGCCGCCTTCTATGAAAGGTTGGGCTTCGGAATCG

TTTTCCGGGACGCCGGCTGGATGATCCTCCAGCGCGGGGATCTCATGCTG

GAGTTCTTCGCCCACCCCAACTTGTTTATTGCAGCTTATAATGGTTACAA

ATAAAGCAATAGCATCACAAATTTCACAAATAAAGCATTTTTTTCACTGC

ATTCTAGTTGTGGTTTGTCCAAACTCATCAATGTATC
```

The analysis of restriction by triple digestion, EcoRV, PvuI, SalI (1 µg of DNA digested by 10 units of each enzyme 15 at 37° C.) of embodiment 3 is illustrated in FIG. 9.

Functional verification of embodiment 3: Eukaryotic cells (for example: 4T1 mouse breast cancer cells) are transfected with the vector V1.1 in accordance with a conventional protocol (for example lipotransfection or electroporation). After transfection, the cells are treated with hygromycin (50 µg-mL-1 for 7 days). The cells are then collected and lysed so as to extract therefrom the total RNAs and then generate the complementary DNAs (cDNA) by reverse transcription in accordance with a conventional protocol. These cDNAs are then used as matrix for quantitative PCR analysis in accordance with a conventional protocol (FIG. 10).

Specific Conditions of the Quantitative PCR:

40 cycles of three subsequent steps are performed: denaturation 94° C.-30s; hybridisation 60° C.-30s; extension 72° C.-30s.

```
mB3Galt6
BETA3Galt6ms2-s
                                      (SEQ ID NO: 42)
ACCACTCTGTTGTACCTGGC.

BETA3Galt6ms2-as
                                      (SEQ ID NO: 43)
CACACGTCCTCGGGTCC.

hFUT3
FUT35
                                      (SEQ ID NO: 44)
CACTAGTCGACTAGGGATAACAGG.

FUT33
                                      (SEQ ID NO: 45)
ATGTCCATAGCAGGATCAGGAG.
```

Embodiment 4

Group of Vectors V1.2: Vectors V1.1 Allowing Selection of the Simultaneous Integration of Multiple Transgenes by Homologous Recombination in the Target Genome
  U1+U3b+U2+U3a+U3c
  U1: Bacterial functional unit
  U2: nxU2a+mxU2b, n≥0, m≥0 and n+m≥2
  U2a: Expression functional unit of which the promoter is dependent on RNA polymerase II and of which the expression product is a protein
  U2b: Expression functional unit of which the promoter is dependent on RNA polymerase III and of which the expression product is a non-coding RNA
  U3a=positive selection cassette
  U3b=motif 5' of a homologous recombination sequence X
  U3c=motif 3' of a homologous recombination sequence X Example: Vector Allowing the Expression of the Enzyme hFUT3 Whilst Suppressing the Expression of Mb3Galt6

| U1  | ori-Amp |
| --- | --- |
| U3b | Rosa26-5' |
| U2a | CMV promoter |
|     | hFUT3 cDNA |
|     | BPA terminator |
| U2b | shRNA mB3Galt6 cassette |
| U3a | hygromycin resistance |
| U3c | Rosa26-3' |

Lists of the building blocks used for the construction of the vector V1.2 (FIG. 11)

```
                                      (SEQ ID NO: 36)
Building block Ori-AmpR BsaI B Building block rosa26-5 BsaI A
                                      (SEQ ID NO: 49)
GAGGTACCGGTCTCAAGGACCCCGCGGCAGGCCCTCCGAGCGTGGTGGAG

CCGTTCTGTGAGACAGCCGGGTACGAGTCGTGACGCTGGAAGGGGCAAGC

GGGTGGTGGGCAGGAATGCGGTCCGCCCTGCAGCAACCGGAGGGGGAGGG
```

-continued
```
AGAAGGGAGCGGAAAAGTCTCCACCGGACGCGGCCATGGCTCGGGGGGG

GGGGGCAGCGGAGGAGCGCTTCCGGCCGACGTCTCGTCGCTGATTGGCTT

CTTTTCCTCCCGCCGTGTGTGAAAACACAAATGGCGTGTTTTGGTTGGCG

TAAGGCGCCTGTCAGTTAACGGCAGCCGGAGTGCGCAGCCGCCGGCAGCC

TCGCTCTGCCCACTGGGTGGGGCGGGAGGTAGGTGGGGTGAGGCGAGCTG

GACGTGCGGGCGCGGTCGGCCTCTGGCGGGGCGGGGGAGGGGAGGGAGGG

TCAGCGAAAGTAGCTCGCGCGCGAGCGGCCGCCCACCCTCCCCTTCCTCT

GGGGGAGTCGTTTTACCCGCCGCCGGCCGGGCCTCGTCGTCTGATTGGCT

CTCGGGGCCCAGAAAACTGGCCCTTGCCATTGGCTCGTGTTCGTGCAAGT

TGAGTCCATCCGCCGGCCAGCGGGGGCGGCGAGGAGGCGCTCCCAGGTTC

CGGCCCTCCCCTCGGCCCCGCGCCGCAGAGTCTGGCCGCGCGCCCCTGCG

CAACGTGGCAGGAAGCGCGCGCTGGGGGCGGGGACGGGCAGTAGGGCTGA

GCGGCTGCGGGCGGGTGCAAGCACGTTTCCGACTTGAGTTGCCTCAAGA

GGGGCGTGCTGAGCCAGACCTCCATCGCGCACTCCGGGGAGTGGAGGGAA

GGAGCGAGGGCTCAGTTGGGCTGTTTTGGAGGCAGGAAGCACTTGCTCTC

CCAAAGTCGCTCTGAGTTGTTATCAGTAAGGGAGCTGCAGTGGAGTAGGC

GGGGAGAAGGCCGCACCCTTCTCCGGAGGGGGGAGGGGAGTGTTGCAATA

CCTTTCTGGGAGTTCTCTGCTGCCTCCTGGCTTCTGAGGACCGCCCTGGG

CCTGGGAGAATCCCTTGCCCCCTCTTCCCCTCGTGATCTGCAACTCCAGT

CTTACAACGAGACCGGTACCTC

Building block pCMV BsaI C
                                      (SEQ ID NO: 50)
GAGGTACCGGTCTCAACAAACCAATTCAGTCGACTGGATCCTAGTTATTA

ATAGTAATCAATTACGGGGTCATTAGTTCATAGCCCATATATGGAGTTCC

GCGTTACATAACTTACGGTAAATGGCCCGCCTGGCTGACCGCCCAACGAC

CCCCGCCCATTGACGTCAATAATGACGTATGTTCCCATAGTAACGCCAAT

AGGGACTTTCCATTGACGTCAATGGGTGGAGTATTTACGGTAAACTGCCC

ACTTGGCAGTACATCAAGTGTATCATATGCCAAGTACGCCCCCTATTGAC

GTCAATGACGGTAAATGGCCCGCCTGGCATTATGCCCAGTACATGACCTT

ATGGGACTTTCCTACTTGGCAGTACATCTACGTATTAGTCATCGCTATTA

CCATGGTGATGCGGTTTTGGCAGTACATCAATGGGCGTGGATAGCGGTTT

GACTCACGGGGATTTCCAAGTCTCCACCCCATTGACGTCAATGGGAGTTT

GTTTTGGCACCAAAATCAACGGGACTTTCCAAAATGTCGTAACAACTCCG

CCCCATTGACGCAAATGGGCGGTAGGCGTGTACGGTGGGAGGTCTATATA

AGCAGAGCTGGTTTAGTGAACCGTCAGATCACTAGTCGACTAGGGATAAC

AGGGCACCCGAGACCGGTACCTC
```

```
                                      (SEQ ID NO: 38)
Building block hFUT3 BsaI A (SEQ ID NO: 39)
Building block BGHpA BsaI B (SEQ ID NO: 46)
Building block shB3Galt6 BsaI B Building block HygroR BsaI C
```

-continued
(SEQ ID NO: 51)
GAGGTACCGGTCTCACCAGCAGGCAGAAGTATGCAAAGCATGCATCTCAA
TTAGTCAGCAACCAGGTGTGGAAAGTCCCCAGGCTCCCCAGCAGGCAGAA
GTATGCAAAGCATGCATCTCAATTAGTCAGCAACCATAGTCCCGCCCCTA
ACTCCGCCCATCCCGCCCCTAACTCCGCCCAGTTCCGCCCATTCTCCGCC
CCATGGCTGACTAATTTTTTTATTTATGCAGAGGCCGAGGCCGCCTCTG
CCTCTGAGCTATTCCAGAAGTAGTGAGGAGGCTTTTTTGGAGGCCTAGGC
TTTTGCAAAAAGCTCCCGGGAGCTTGTATATCCATTTTCGGATCTGATCA
GCACGTGATGAAAAGCCTGAACTCACCGCGACGTCTGTCGAGAAGTTTC
TGATCGAAAAGTTCGACAGCGTGTCCGACCTGATGCAGCTCTCGGAGGGC
GAAGAATCTCGTGCTTTCAGCTTCGATGTAGGAGGGCGTGGATATGTCCT
GCGGGTAAATAGCTGCGCCGATGGTTTCTACAAAGATCGTTATGTTTATC
GGCACTTTGCATCGGCCGCGCTCCCGATTCCGGAAGTGCTTGACATTGGG
GAATTCAGCGAGAGCCTGACCTATTGCATCTCCCGCCGTGCACAGGGTGT
CACGTTGCAAGACTTGCCTGAAACCGAACTGCCCGCTGTTCTGCAGCCGG
TCGCGGAGGCCATGGATGCGATCGCTGCGGCCGATCTTAGCCAGACGAGC
GGGTTCGGCCCATTCGGACCGCAAGGAATCGGTCAATACACTACATGGCG
TGATTTCATATGCGCGATTGCTGATCCCCATGTGTATCACTGGCAAACTG
TGATGGACGACACCGTCAGTCGTCCGTCGCGCAGGCTCTCGATGAGCTG
ATGCTTTGGGCCGAGGACTGCCCCGAAGTCCGGCACCTCGTGCACGCGGA
TTTCGGCTCCAACAATGTCCTGACGGACAATGGCCGCATAACAGCGGTCA
TTGACTGGAGCGAGGCGATGTTCGGGATTCCCAATACGAGGTCGCCAAC
ATCTTCTTCTGGAGGCCGTGGTTGGCTTGTATGGAGCAGCAGACGCGCTA
CTTCGAGCGGAGGCATCCGGAGCTTGCAGGATCGCCGCGGCTCCGGGCGT
ATATGCTCCGCATTGGTCTTGACCAACTCTATCAGAGCTTGGTTGACGGC
AATTTCGATGATGCAGCTTGGGCGCAGGGTCGATGCGACGCAATCGTCCG
ATCCGGAGCCGGGACTGTCGGCGTACACAAATCGCCCGCAGAAGCGCGG
CCGTCTGGACCGATGGCTGTGTAGAAGTACTCGCCGATAGTGGAAACCGA
CGCCCCAGCACTCGTCCGAGGGCAAAGGAATAGCACGTGCTACGAGATTT
CGATTCCACCGCCGCCTTCTATGAAAGGTTGGGCTTCGGAATCGTTTTCC
GGGACGCCGGCTGGATGATCCTCCAGCGCGGGGATCTCATGCTGGAGTTC
TTCGCCCACCCCAACTTGTTTATTGCAGCTTATAATGGTTACAAATAAAG
CAATAGCATCACAAATTTCACAAATAAAGCATTTTTTTCACTGCATTCTA
GTTGTGGTTTGTCCAAACTCATCAATGTATCGTAGCGAGACCGGTACCTC
Building block rosa26-3 BsaI A
(SEQ ID NO: 52)
GAGGTACCGGTCTCAGTAGAGATGGGCGGGAGTCTTCTGGGCAGGCTTAA
AGGCTAACCTGGTGTGTGGGCGTTGTCCTGCAGGGGAATTGAACAGGTGT
AAAATTGGAGGGACAAGACTTCCCACAGATTTTCGGTTTTGTCGGGAAGT
TTTTTAATAGGGGCAAATAGGAAAATGGAGGATAGGAGTCATCTGGGGTT
TATGCAGCAAAACTACAGGTATATTGCTTGTATCCGCCTCGGAGATTTCC
ATGAGGAGATAAAGACATGTCACCCGAGTTTATACTCTCCTGCTTAGATC -continued
CTACTACAGTATGAAATACAGTGTCGCGAGGTAGACTATGTAAGCAGATT
TAATCATTTTAAAGAGCCCAGTACTTCATATCCATTTCTCCCGCTCCTTC
TGCAGCCTTATCAAAAGGTATTTAGAACACTCATTTTAGCCCCATTTTCA
TTTATTATACTGGCTTATCCAACCCCTAGACAGAGCATTGGCATTTTCCC
TTTCCTGATCTTAGAAGTCTGATGACTCATGAAACCAGACAGATTAGTTA
CATACACCACAAATCGAGGCTGTAGCTGGGGCCTCAACACTGCAGTTCTT
TTATAACTCCTTAGTACACTTTTTGTTGATCCTTTGCCTTGATCCTTAAT
TTTCAGTGTCTATCACCTCTCCCGTCAGGTGGTGTTCCACATTTGGGCCT
ATTCTCAGTCCAGGGAGTTTTACAACAATAGATGTATTGAGAATCCAACC
TAAAGCTTAACTTTCCACTCCCATGAATGCCTCTCTCCTTTTTCTCCATT
ATAACTGAGCTATAACCATTAATGGTTTCAGGTGGATGTCTCCTCCCCCA
ATATACCTGATGTATCTACATATTGCCAGGCTGATATTTTAAGACATAAA
AGGTATATTTCATTATTGAGCCACATGGTATTGATTACTGCTACTAAAAT
TTTGTCATTGTACACATCTGTAAAAGGTGGTTCCTTTTGGAATGCAAAGT
TCAGGTGTTTGTTGTCTTTCCTGACCTAAGGTCTTGTGAGCTTGTATTTT
TTCTATTTAAGCAGTGCTTTCTCTTGGACTGGCTTGACTCATGGCATTCT
ACACGTTATTGCTGGTCTAAATGTGATTTTGCCAAGCTTCTTCAGGACCT
ATAATTTTGCTTGACTTGTAGCCAAACACAAGTAAAATGATTAAGCAACA
AATGTATTTGTGAAGCTTGGTTTTTAGGTTGTTGTGTTGTGTGCTTGT
GCTCTATAATAATACTATCCAGGGGCTGGAGAGGTGGCTCGGAGTTCAAG
AGCACAGACTGCTCTTCCAGAAGTCCTGAGTTCAATTCCCAGCAACCACA
TGGTGGCTCACAACCATCTGTAATGGGATCTGATGCCCTCTTCTGGTGTG
TCTGAAGACCACAAGTGTATTCACATTAAATAAATAATCCTCCTTCTTCT
TCTTTTTTTTTTTTAAAGAGAATACTGTCTCCAGTAGAATTACTGAAGT
AATGAAATACTTTGTGTTTGTTCCAATATGGAAGCCAATAATCAAATACT
CTTAAGCACTGGAAATGTACCAAGGAACTATTTTATTTAAGTGAACTGTG
GACAGAGGAGCCATAACTGCAGACTTGTGGGATACAGAAGACCAATGCAG
ACTTAATGTCTTTTCTCTTACACTAAGCAATAAAGAAATAAAAATTGAAC
TTCTAGTATCCTATTTGTTAAACTGCTAGCTTTACTAACTTTTGTGCTTC
ATCTATACAAAGCTGAAAGCTAAGTCTGCAGCCATTACTAAACATGAAAG
CAAGTAATGATAATTTTGGATTTCAAAAATGTAGGGCCAGAGTTTAGCCA
GCCAGTGGTGGTGCTTGCCTTTATGCCTTAATCCCAGCACTCTGGAGGCA
GAGACAGGCAGATCTCTGAGTTTGAGCCCAGCCTGGTCTACACATCAAGT
TCTATCTAGGATAGCCAGGAATACACACAGAAACCTGTTGGGAGGGGG
GCTCTGAGATTTCATAAAATTATAATTGAAGCATTCCCTAATGAGCCACT
ATGGATGTGGCTAAATCCGTCTACCTTTCTGATGAGATTTGGGTATTATT
TTTTCTGTCTCTGCTGTTGGTTGGGTCTTTTGACACTGTGGGCTTTCTTA
AAGCCTCCTTCCCTGCCATGTGGACTCTTGTTTGCTACTAACTTCCCATG
GCTTAAATGGCATGGCTTTTTGCCTTCTAAGGGCAGCTGCTGAGATTTGC
AGCCTGATTTCCAGGGTGGGGTTGGGAAATCTTTCAAACACTAAAATTGT
CCTTTAATTTTTTTTAAAAAATGGGTTATATAATAAACCTCATAAAATA

GTTATGAGGAGTGAGGTGGACTAATATTAATGAGTCCCTCCCCTATAAAA

GAGCTATTAAGGCTTTTTGTCTTATACTAACTTTTTTTTTAAATGTGGTA

TCTTTAGAACCAAGGGTCTTAGAGTTTTAGTATACAGAAACTGTTGCATC

GCTTAATCAGATTTTCTAGTTTCAAATCCAGAGAATCCAAATTCTTCACA

GCCAAAGTCAAATTAAGAATTTCTGACTTTAATGTTATTTGCTACTGTGA

ATATAAAATGATAGCTTTTCCTGAGGCAGGGTATCACTATGTATCTCTGC

CTGATCTGCAACAAGATATGTAGACTAAAGTTCTGCCTGCTTTTGTCTCC

TGAATACTAAGGTTAAAATGTAGTAATACTTTTGGAACTTGCAGGTCAGA

TTCTTTTATAGGGGACACACTAAGGGAGCTTGGGTGATAGTTGGTAAATG

TGTTTAAGTGATGAAAACTTGAATTATTATCACCGCAACCTACTTTTTAA

AAAAAAAAGCCAGGCCTGTTAGAGCATGCTAAGGGATCCCTAGGACTTGC

TGAGCACACAAGAGTAGTACTTGGCAGGCTCCTGGTGAGAGCATATTTCA

AAAAACAAGGCAGACAACCAAGAAACTACAGTAAGGTTACCTGTCTTTAA

CCATCTGCATATACACAGGGATATTAAAATATTCCAAATAATATTTCATT

CAAGTTTTCCCCCATCAAATTGGGACATGGATTTCTCCGGTGAATAGGCA

GAGTTGGAAACTAAACAAATGTTGGTTTTGTGATTTGTGAAATTGTTTTC

AAGTGATAGTTAAAGCCCATGAGATACAGAACAAAGCTGCTATTTCGAGG

TCACTTGGTTATACTCAGAAGCACTTCTTTGGGTTTCCCTGCACTATCCT

GATCATGTGCTAGGCCTACCTTAGGCTGATTGTTGTTCAAATAACTTAAG

TTTCCTGTCAGGTGATGTCATATGATTTCATATATCAAGGCAAAACATGT

TATATATGTTAAACATTTGGACTTAATGTGAAAGTTAGGTCTTTGTGGGT

TTTGATTTTAATTTCAAAACCTGAGCTAAATAAGTCATTTTACATGTCTT

ACATTTGGTGAATTGTATATTGTGGTTTGCAGGCAAGACTCTCTGACCTA

GTAACCCTCCTATAGAGCACTTTGCTGGGTCACAAGTCTAGGAGTCAAGC

ATTTCACCTTGAAGTTGAGACGTTTTGTTAGTGTATACTAGTTATATGTT

GGAGGACATGTTTATCCAGAAGATATTCAGGACTATTTTTGACTGGGCTA

AGGAATTGATTCTGATTAGCACTGTTAGTGAGCATTGAGTGGCCTTTAGG

CTTGAATTGGAGTCACTTGTATATCTCAAATAATGCTGGCCTTTTTTAAA

AAGCCCTTGTTCTTTATCACCCTGTTTTCTACATAATTTTTGTTCAAAGA

AATACTTGTTTGGATCTCCTTTTGACAACAATAGCATGTTTTCAAGCCAT

ATTTTTTTCCTTTTTTTTTTTTTTGGTTTTTCGAGACAGGGTTTCT

CTGTATAGCCCTGGCTGTCCTGGAACTCACTTTGTAGACCAGGCTGGCCT

CGAACTCAGAAATCCGCCTGCCTCTGCCTCCTGAGTGCCGGGATTAAAGG

CGTGCACCACCACGCCTGGCTAAGTTGGATATTTTGTATATAACTATAAC

CAATACTAACTCCACTGGGTGGATTTTTAATTCAGTCAGTAGTCTTAAGT

GGTCTTTATTGGCCCTTATTAAAATCTACTGTTCACTCTAACAGAGGCTG

TTGGACTAGTGGGACTAAGCAACTTCCTACGGATATACTAGCAGATAAGG

GTCAGGGATAGAAACTAGTCTAGCGTTTTGTATACCTACCAGCTTATACT

ACCTTGTTCTGATAGAAATATTTAGGACATCTAGCTTATCTATTCGAGAC

CGGTACCTC

V1.2 (SEQ ID NO: 53,
example of a vector of the group V1.2)

TATTGTAATACGGTTATCCACAGAATCAGGGGATAACGCAGGAAAGAACA

TGTGAGCAAAAGGCCAGCAAAAGGCCAGGAACCGTAAAAAGGCCGCGTTG

CTGGCGTTTTTCCATAGGCTCCGCCCCCTGACGAGCATCACAAAAATCG

ACGCTCAAGTCAGAGGTGGCGAAACCCGACAGGACTATAAAGATACCAGG

CGTTTCCCCCTGGAAGCTCCCTCGTGCGCTCTCCTGTTCCGACCCTGCCG

CTTACCGGATACCTGTCCGCCTTTCTCCCTTCGGGAAGCGTGGCGCTTTC

TCATAGCTCACGCTGTAGGTATCTCAGTTCGGTGTAGGTCGTTCGCTCCA

AGCTGGGCTGTGTGCACGAACCCCCCGTTCAGCCCGACCGCTGCGCCTTA

TCCGGTAACTATCGTCTTGAGTCCAACCCGGTAAGACACGACTTATCGCC

ACTGGCAGCAGCCACTGGTAACAGGATTAGCAGAGCGAGGTATGTAGGCG

GTGCTACAGAGTTCTTGAAGTGGTGGCCTAACTACGGCTACACTAGAAGA

ACAGTATTTGGTATCTGCGCTCTGCTGAAGCCAGTTACCTTCGGAAAAAG

AGTTGGTAGCTCTTGATCCGGCAAACAAACCACCGCTGGTAGCGGTTTTT

TTGTTTGCAAGCAGCAGATTACGCGCAGAAAAAAAGGATCTCAAGAAGAT

CCTTTGATCTTTTCTACGGGGTCTGACGCTCAGTGGAACGAAAACTCACG

TTAAGGGATTTTGGTCATGAGATTATCAAAAAGGATCTTCACCTAGATCC

TTTTAAATTAAAAATGAAGTTTTAAATCAATCTAAAGTATATATGAGTAA

ACTTGGTCTGACAGTTACCAATGCTTAATCAGTGAGGCACCTATCTCAGC

GATCTGTCTATTTCGTTCATCCATAGTTGCCTGACTCCCCGTCGTGTAGA

TAACTACGATACGGGAGGGCTTACCATCTGGCCCCAGTGCTGCAATGATA

CCGCGTGACCCACGCTCACCGGCTCCAGATTTATCAGCAATAAACCAGCC

AGCCGGAAGGGCCGAGCGCAGAAGTGGTCCTGCAACTTTATCCGCCTCCA

TCCAGTCTATTAATTGTTGCCGGGAAGCTAGAGTAAGTAGTTCGCCAGTT

AATAGTTTGCGCAACGTTGTTGCCATTGCTACAGGCATCGTGGTGTCACG

CTCGTCGTTTGGTATGGCTTCATTCAGCTCCGGTTCCCAACGATCAAGGC

GAGTTACATGATCCCCATGTTGTGCAAAAAAGCGGTTAGCTCCTTCGGT

CCTCCGATCGTTGTCAGAAGTAAGTTGGCCGCAGTGTTATCACTCATGGT

TATGGCAGCACTGCATAATTCTCTTACTGTCATGCCATCCGTAAGATGCT

TTTCTGTGACTGGTGAGTACTCAACCAAGTCATTCTGAGAATAGTGTATG

CGGCGACCGAGTTGCTCTTGCCCGGCGTCAATACGGGATAATACCGCGCC

ACATAGCAGAACTTTAAAAGTGCTCATCATTGGAAAACGTTCTTCGGGGC

GAAAACTCTCAAGGATCTTACCGCTGTTGAGATCCAGTTCGATGTAACCC

ACTCGTGCACCCAACTGATCTTCAGCATCTTTTACTTTCACCAGCGTTTC

TGGGTGAGCAAAAACAGGAAGGCAAAATGCCGCAAAAAAGGGAATAAGGG

CGACACGGAAATGTTGAATACTCATACTCTTCCTTTTTCAATATTATTGA

AGCATTTATCAGGGTTATTGTCTCATGAGCGGATACATATTTGAATGTAT

TTAGAAAAATAAACAAATAGGGGTTCCGCGCACATTTCCCCGAAAAGTGC

CAAGGACCCCGCGGCAGGCCCTCCGAGCGTGGTGGAGCCGTTCTGTGAGA

CAGCCCGGGTACGAGTCGTGACGCTGGAAGGGCAAGCGGGTGGTGGGCAG

GAATGCGGTCCGCCCTGCAGCAACCGGAGGGGGAGGGAGAAGGGAGCGGA

AAAGTCTCCACCGGACGCGGCCATGGCTCGGGGGGGGGGGGCAGCGGAG
GAGCGCTTCCGGCCGACGTCTCGTCGCTGATTGGCTTCTTTTCCTCCCGC
CGTGTGTGAAAACACAAATGGCGTGTTTTGGTTGGCGTAAGGCGCCTGTC
AGTTAACGGCAGCCGGAGTGCGCAGCCGCCGGCAGCCTCGCTCTGCCCAC
TGGGTGGGGCGGGAGGTAGGTGGGGTGAGGCGAGCTGGACGTGCGGGCGC
GGTCGGCCTCTGGCGGGGCGGGGAGGGGAGGGAGGGTCAGCGAAAGTAG
CTCGCGCGCGAGCGGCCGCCCACCCTCCCCTTCCTCTGGGGGAGTCGTTT
TACCCGCCGCCGGCCGGGCCTCGTCGTCTGATTGGCTCTCGGGGCCCAGA
AAACTGGCCCTTGCCATTGGCTCGTGTTCGTGCAAGTTGAGTCCATCCGC
CGGCCAGCGGGGCGGCGAGGAGGCGCTCCCAGGTTCCGGCCCTCCCCTC
GGCCCCGCGCCGCAGAGTCTGGCCGCGCGCCCCTGCGCAACGTGGCAGGA
AGCGCGCGCTGGGGGCGGGGACGGGCAGTAGGGCTGAGCGGCTGCGGGGC
GGGTGCAAGCACGTTTCCGACTTGAGTTGCCTCAAGAGGGGCGTGCTGAG
CCAGACCTCCATCGCGCACTCCGGGGAGTGGAGGGAAGGAGCGAGGGCTC
AGTTGGGCTGTTTTGGAGGCAGGAAGCACTTGCTCTCCCAAAGTCGCTCT
GAGTTGTTATCAGTAAGGGAGCTGCAGTGGAGTAGGCGGGGAGAAGGCCG
CACCCTTCTCCGGAGGGGGAGGGGAGTGTTGCAATACCTTTCTGGGAGT
TCTCTGCTGCCTCCTGGCTTCTGAGGACCGCCCTGGGCCTGGGAGAATCC
CTTGCCCCCTCTTCCCCTCGTGATCTGCAACTCCAGTCTTACAAACCAAT
TCAGTCGACTGGATCCTAGTTATTAATAGTAATCAATTACGGGGTCATTA
GTTCATAGCCCATATATGGAGTTCCGCGTTACATAACTTACGGTAAATGG
CCCGCCTGGCTGACCGCCCAACGACCCCCGCCCATTGACGTCAATAATGA
CGTATGTTCCCATAGTAACGCCAATAGGGACTTTCCATTGACGTCAATGG
GTGGAGTATTTACGGTAAACTGCCCACTTGGCAGTACATCAAGTGTATCA
TATGCCAAGTACGCCCCCTATTGACGTCAATGACGGTAAATGGCCCGCCT
GGCATTATGCCCAGTACATGACCTTATGGGACTTTCCTACTTGGCAGTAC
ATCTACGTATTAGTCATCGCTATTACCATGGTGATGCGGTTTTGGCAGTA
CATCAATGGGCGTGGATAGCGGTTTGACTCACGGGGATTTCCAAGTCTCC
ACCCCATTGACGTCAATGGGAGTTTGTTTTGGCACCAAAATCAACGGGAC
TTTCCAAAATGTCGTAACAACTCCGCCCCATTGACGCAAATGGGCGGTAG
GCGTGTACGGTGGGAGGTCTATATAAGCAGAGCTGGTTTAGTGAACCGTC
AGATCACTAGTCGACTAGGGATAACAGGGCACCATGGATCCCCTGGGTGC
AGCCAAGCCACAATGGCCATGGCGCCGCTGTCTGGCCGCACTGCTATTTC
AGCTGCTGGTGGCTGTGTGTTTCTTCTCCTACCTGCGTGTGTCCCGAGAC
GATGCCACTGGATCCCCTAGGGCTCCCAGTGGGTCCTCCCGACAGGACAC
CACTCCCACCCGCCCCACCCTCCTGATCCTGCTATGGACATGGCCTTTCC
ACATCCCTGTGGCTCTGTCCCGCTGTTCAGAGATGGTGCCCGGCACAGCC
GACTGCCACATCACTGCCGACCGCAAGGTGTACCCACAGGCAGACACGGT
CATCGTGCACCACTGGGATATCATGTCCAACCCTAAGTCACGCCTCCCAC
CTTCCCCGAGGCCGCAGGGGCAGCGCTGGATCTGGTTCAACTTGGAGCCA

CCCCCTAACTGCCAGCACCTGGAAGCCCTGGACAGATACTTCAATCTCAC
CATGTCCTACCGCAGCGACTCCGACATCTTCACGCCCTACGGCTGGCTGG
AGCCGTGGTCCGGCCAGCCTGCCCACCCACCGCTCAACCTCTCGGCCAAG
ACCGAGCTGGTGGCCTGGGCGGTGTCCAACTGGAAGCCGGACTCAGCCAG
GGTGCGCTACTACCAGAGCCTGCAGGCTCATCTCAAGGTGGACGTGTACG
GACGCTCCCACAAGCCCCTGCCCAAGGGGACCATGATGGAGACGCTGTCC
CGGTACAAGTTCTACCTGGCCTTCGAGAACTCCTTGCACCCCGACTACAT
CACCGAGAAGCTGTGGAGGAACGCCCTGGAGGCCTGGGCCGTGCCCGTGG
TGCTGGGCCCCAGCAGAAGCAACTACGAGAGGTTCCTGCCACCCGACGCC
TTCATCCACGTGGACGACTTCCAGAGCCCCAAGGACCTGGCCCGGTACCT
GCAGGAGCTGGACAAGGACCACGCCCGCTACCTGAGCTACTTTCGCTGGC
GGGAGACGCTGCGGCCTCGCTCCTTCAGCTGGGCACTGGATTTCTGCAAG
GCCTGCTGGAAACTGCAGCAGGAATCCAGGTACCAGACGGTGCGCAGCAT
AGCGGCTTGGTTCACCTGATCGACTGTGCCTTCTAGTTGCCAGCCATCTG
TTGTTTGCCCCTCCCCCGTGCCTTCCTTGACCCTGGAAGGTGCCACTCCC
ACTGTCCTTTCCTAATAAAATGAGGAAATTGCATCGCATTGTCTGAGTAG
GTGTCATTCTATTCTGGGGGGTGGGGTGGGGCAGGACAGCAAGGGGGAGG
ATTGGGAGGACAATAGCAGGCATGCTGGGGATGCGGTGGGCTCTATGGCT
TCGACAGGGTCGACAAGCTTTTCCAAAAAAAAAGCATGAGGTGCAGTTGC
GCCTTTCCTATCTCTTGAATAGGAAAGGCGCAACTGCACCTCATGCTGGA
TCCCGCGTCCTTTCCACAAGATATATAAACCCAAGAAATCGAAATACTTT
CAAGTTACGGTAAGCATATGATAGTCCATTTTAAAACATAATTTTAAAAC
TGCAAACTACCCAAGAAATTATTACTTTCTACGTCACGTATTTTGTACTA
ATATCTTTGTGTTTACAGTCAAATTAATTCTAATTATCTCTCTAACAGCC
TTGTATCGTATATGCAAATATGAAGGAATCATGGGAAATAGGCCCTCTTC
CTGCCCGACCTTGGCGCGCGCTCGGCGCGCGGTCACGCTCCGTCACGTGG
TGCGTTTTGCCAGCAGGCAGAAGTATGCAAAGCATGCATCTCAATTAGTC
AGCAACCAGGTGTGGAAAGTCCCCAGGCTCCCCAGCAGGCAGAAGTATGC
AAAGCATGCATCTCAATTAGTCAGCAACCATAGTCCCGCCCCTAACTCCG
CCCATCCCGCCCCTAACTCCGCCCAGTTCCGCCCATTCTCCGCCCCATGG
CTGACTAATTTTTTTTATTTATGCAGAGGCCGAGGCCGCCTCTGCCTCTG
AGCTATTCCAGAAGTAGTGAGGAGGCTTTTTTGGAGGCCTAGGCTTTTGC
AAAAAGCTCCCGGGAGCTTGTATATCCATTTTCGGATCTGATCAGCACGT
GATGAAAAGCCTGAACTCACCGCGACGTCTGTCGAGAAGTTTCTGATCG
AAAAGTTCGACAGCGTGTCCGACCTGATGCAGCTCTCGGAGGGCGAAGAA
TCTCGTGCTTTCAGCTTCGATGTAGGAGGGCGTGGATATGTCCTGCGGGT
AAATAGCTGCGCCGATGGTTTCTACAAAGATCGTTATGTTTATCGGCACT
TTGCATCGGCCGCGCTCCCGATTCCGGAAGTGCTTGACATTGGGGAATTC
AGCGAGAGCCTGACCTATTGCATCTCCCGCCGTGCACAGGGTGTCACGTT
GCAAGACTTGCCTGAAACCGAACTGCCCGCTGTTCTGCAGCCGGTCGCGG
AGGCCATGGATGCGATCGCTGCGGCCGATCTTAGCCAGACGAGCGGGTTC

```
GGCCCATTCGGACCGCAAGGAATCGGTCAATACACTACATGGCGTGATTT
CATATGCGCGATTGCTGATCCCCATGTGTATCACTGGCAAACTGTGATGG
ACGACACCGTCAGTGCGTCCGTCGCGCAGGCTCTCGATGAGCTGATGCTT
TGGGCCGAGGACTGCCCCGAAGTCCGGCACCTCGTGCACGCGGATTTCGG
CTCCAACAATGTCCTGACGGACAATGGCCGCATAACAGCGGTCATTGACT
GGAGCGAGGCGATGTTCGGGGATTCCCAATACGAGGTCGCCAACATCTTC
TTCTGGAGGCCGTGGTTGGCTTGTATGGAGCAGCAGACGCGCTACTTCGA
GCGGAGGCATCCGGAGCTTGCAGGATCGCCGCGGCTCCGGGCGTATATGC
TCCGCATTGGTCTTGACCAACTCTATCAGAGCTTGGTTGACGGCAATTTC
GATGATGCAGCTTGGGCGCAGGGTCGATGCGACGCAATCGTCCGATCCGG
AGCCGGGACTGTCGGGCGTACACAAATCGCCCGCAGAAGCGCGGCCGTCT
GGACCGATGGCTGTGTAGAAGTACTCGCCGATAGTGGAAACCGACGCCCC
AGCACTCGTCCGAGGGCAAAGGAATAGCACGTGCTACGAGATTTCGATTC
CACCGCCGCCTTCTATGAAAGGTTGGGCTTCGGAATCGTTTTCCGGGACG
CCGGCTGGATGATCCTCCAGCGCGGGGATCTCATGCTGGAGTTCTTCGCC
CACCCCAACTTGTTTATTGCAGCTTATAATGGTTACAAATAAAGCAATAG
CATCACAAATTTCACAAATAAAGCATTTTTTTCACTGCATTCTAGTTGTG
GTTTGTCCAAACTCATCAATGTATCGTAGAGATGGGCGGGAGTCTTCTGG
GCAGGCTTAAAGGCTAACCTGGTGTGTGGGCGTTGTCCTGCAGGGGAATT
GAACAGGTGTAAAATTGGAGGGACAAGACTTCCCACAGATTTTCGGTTTT
GTCGGGAAGTTTTTTAATAGGGGCAAATAGGAAAATGGAGGATAGGAGTC
ATCTGGGGTTTATGCAGCAAAACTACAGGTATATTGCTTGTATCCGCCTC
GGAGATTTCCATGAGGAGATAAAGACATGTCACCCGAGTTTATACTCTCC
TGCTTAGATCCTACTACAGTATGAAATACAGTGTCGCGAGGTAGACTATG
TAAGCAGATTTAATCATTTTAAAGAGCCCAGTACTTCATATCCATTTCTC
CCGCTCCTTCTGCAGCCTTATCAAAAGGTATTTAGAACACTCATTTTAGC
CCCATTTTCATTTATTATACTGGCTTATCCAACCCCTAGACAGAGCATTG
GCATTTTCCCTTTCCTGATCTTAGAAGTCTGATGACTCATGAAACCAGAC
AGATTAGTTACATACACCAAATCGAGGCTGTAGCTGGGCCTCAACAC
TGCAGTTCTTTTATAACTCCTTAGTACACTTTTTGTTGATCCTTTGCCTT
GATCCTTAATTTTCAGTGTCTATCACCTCTCCCGTCAGGTGGTGTTCCAC
ATTTGGGCCTATTCTCAGTCCAGGGAGTTTTACAACAATAGATGTATTGA
GAATCCAACCTAAAGCTTAACTTTCCACTCCCATGAATGCCTCTCTCCTT
TTTCTCCATTATAACTGAGCTATAACCATTAATGGTTTCAGGTGGATGTC
TCCTCCCCCAATATACCTGATGTATCTACATATTGCCAGGCTGATATTTT
AAGACATAAAAGGTATATTTCATTATTGAGCCACATGGTATTGATTACTG
CTACTAAAATTTTGTCATTGTACACATCTGTAAAAGGTGGTTCCTTTTGG
AATGCAAAGTTCAGGTGTTTGTTGTCTTTCCTGACCTAAGGTCTTGTGAG
CTTGTATTTTTTCTATTTAAGCAGTGCTTTCTCTTGGACTGGCTTGACTC
ATGGCATTCTACACGTTATTGCTGGTCTAAATGTGATTTTGCCAAGCTTC

TTCAGGACCTATAATTTTGCTTGACTTGTAGCCAAACACAAGTAAAATGA
TTAAGCAACAAATGTATTTGTGAAGCTTGGTTTTTAGGTTGTTGTGTTGT
GTGTGCTTGTGCTCTATAATAATACTATCCAGGGGCTGGAGAGGTGGCTC
GGAGTTCAAGAGCACAGACTGCTCTTCCAGAAGTCCTGAGTTCAATTCCC
AGCAACCACATGGTGGCTCACAACCATCTGTAATGGGATCTGATGCCCTC
TTCTGGTGTGTCTGAAGACCACAAGTGTATTCACATTAAATAAATAATCC
TCCTTCTTCTTCTTTTTTTTTTTTAAAGAGAATACTGTCTCCAGTAGAA
TTACTGAAGTAATGAAATACTTTGTGTTTGTTCCAATATGGAAGCCAATA
ATCAAATACTCTTAAGCACTGGAAATGTACCAAGGAACTATTTTATTTAA
GTGAACTGTGGACAGAGGAGCCATAACTGCAGACTTGTGGGATACAGAAG
ACCAATGCAGACTTAATGTCTTTTCTCTTACACTAAGCAATAAAGAAATA
AAAATTGAACTTCTAGTATCCTATTTGTTAAACTGCTAGCTTTACTAACT
TTTGTGCTTCATCTATACAAAGCTGAAAGCTAAGTCTGCAGCCATTACTA
AACATGAAAGCAAGTAATGATAATTTTGGATTTCAAAAATGTAGGGCCAG
AGTTTAGCCAGCCAGTGGTGGTGCTTGCCTTTATGCCTTAATCCCAGCAC
TCTGGAGGCAGAGACAGGCAGATCTCTGAGTTTGAGCCCAGCCTGGTCTA
CACATCAAGTTCTATCTAGGATAGCCAGGAATACACACAGAAACCCTGTT
GGGGAGGGGGGCTCTGAGATTTCATAAAATTATAATTGAAGCATTCCCTA
ATGAGCCACTATGGATGTGGCTAAATCCGTCTACCTTTCTGATGAGATTT
GGGTATTATTTTTCTGTCTCTGCTGTTGGTTGGGTCTTTTGACACTGTG
GGCTTTCTTAAAGCCTCCTTCCCTGCCATGTGGACTCTTGTTTGCTACTA
ACTTCCCATGGCTTAAATGGCATGGCTTTTTGCCTTCTAAGGGCAGCTGC
TGAGATTTGCAGCCTGATTTCCAGGGTGGGGTTGGGAAATCTTTCAAACA
CTAAAATTGTCCTTTAATTTTTTTTAAAAAATGGGTTATATAATAAACC
TCATAAAATAGTTATGAGGAGTGAGGTGGACTAATATTAATGAGTCCCTC
CCCTATAAAAGAGCTATTAAGGCTTTTTGTCTTATACTAACTTTTTTTTT
AAATGTGGTATCTTTAGAACCAAGGGTCTTAGAGTTTTAGTATACAGAAA
CTGTTGCATCGCTTAATCAGATTTTCTAGTTTCAAATCCAGAGAATCCAA
ATTCTTCACAGCCAAAGTCAAATTAAGAATTTCTGACTTTAATGTTATTT
GCTACTGTGAATATAAAATGATAGCTTTTCCTGAGGCAGGGTATCACTAT
GTATCTCTGCCTGATCTGCAACAAGATATGTAGACTAAAGTTCTGCCTGC
TTTTGTCTCCTGAATACTAAGGTTAAAATGTAGTAATACTTTTGGAACTT
GCAGGTCAGATTCTTTTATAGGGGACACACTAAGGGAGCTTGGGTGATAG
TTGGTAAATGTGTTTAAGTGATGAAAACTTGAATTATTATCACCGCAACC
TACTTTTAAAAAAAAAAGCCAGGCCTGTTAGAGCATGCTAAGGGATCCC
TAGGACTTGCTGAGCACACAAGAGTAGTACTTGGCAGGCTCCTGGTGAGA
GCATATTTCAAAAACAAGGCAGACAACCAAGAAACTACAGTAAGGTTAC
CTGTCTTTAACCATCTGCATATACACAGGGATATTAAAATATTCCAAATA
ATATTTCATTCAAGTTTTCCCCCATCAAATTGGGACATGGATTTCTCCGG
TGAATAGGCAGAGTTGGAAACTAAACAAATGTTGGTTTTGTGATTTGTGA
AATTGTTTTCAAGTGATAGTTAAAGCCCATGAGATACAGAACAAAGCTGC
```

-continued

```
TATTTCGAGGTCACTTGGTTATACTCAGAAGCACTTCTTTGGGTTTCCCT

GCACTATCCTGATCATGTGCTAGGCCTACCTTAGGCTGATTGTTGTTCAA

ATAACTTAAGTTTCCTGTCAGGTGATGTCATATGATTTCATATATCAAGG

CAAAACATGTTATATATGTTAAACATTTGGACTTAATGTGAAAGTTAGGT

CTTTGTGGGTTTTGATTTTAATTTCAAAACCTGAGCTAAATAAGTCATTT

TACATGTCTTACATTTGGTGAATTGTATATTGTGGTTTGCAGGCAAGACT

CTCTGACCTAGTAACCCTCCTATAGAGCACTTTGCTGGGTCACAAGTCTA

GGAGTCAAGCATTTCACCTTGAAGTTGAGACGTTTTGTTAGTGTATACTA

GTTATATGTTGGAGGACATGTTTATCCAGAAGATATTCAGGACTATTTTT

GACTGGGCTAAGGAATTGATTCTGATTAGCACTGTTAGTGAGCATTGAGT

GGCCTTTAGGCTTGAATTGGAGTCACTTGTATATCTCAAATAATGCTGGC

CTTTTTTAAAAAGCCCTTGTTCTTTATCACCCTGTTTTCTACATAATTTT

TGTTCAAAGAAATACTTGTTTGGATCTCCTTTTGACAACAATAGCATGTT

TTCAAGCCATATTTTTTTCCTTTTTTTTTTTTTTTTGGTTTTCGAGA

CAGGGTTTCTCTGTATAGCCCTGGCTGTCCTGGAACTCACTTTGTAGACC

AGGCTGGCCTCGAACTCAGAAATCCGCCTGCCTCTGCCTCCTGAGTGCCG

GGATTAAAGGCGTGCACCACCACGCCTGGCTAAGTTGGATATTTTGTATA

TAACTATAACCAATACTAACTCCACTGGGTGGATTTTTAATTCAGTCAGT

AGTCTTAAGTGGTCTTTATTGGCCCTTATTAAAATCTACTGTTCACTCTA

ACAGAGGCTGTTGGACTAGTGGGACTAAGCAACTTCCTACGGATATACTA

GCAGATAAGGGTCAGGGATAGAAACTAGTCTAGCGTTTTGTATACCTACC

AGCTTATACTACCTTGTTCTGATAGAAATATTTAGGACATCTAGCTTATC
```

The analysis of restriction by triple digestion EcoRV, PvuI, SalI of embodiment 4 is illustrated in FIG. 12.

Functional verification of embodiment 4: Eukaryotic cells (for example: 4T1 mouse breast cancer cells) are transfected with the vector V1.2 in accordance with a conventional protocol (for example lipotransfection or electroporation). After transfection, the cells are treated with hygromycin (50 μg-mL-1 for 7-14 days). The cells are then collected and lysed so as to extract therefrom the total RNAs and then generate the complementary DNAs (cDNA) by reverse transcription in accordance with a conventional protocol. These cDNAs are then used as matrix for quantitative PCR analysis in accordance with a conventional protocol.

Specific Conditions of the Quantitative PCR:

40 cycles of three subsequent steps are performed: denaturation 94° C.-30s; hybridisation 60° C.-30s; extension 72° C.-30s.

Primers used

```
mB3Galt6
BETA3Galt6ms2-s
                                          (SEQ ID NO: 42)
ACCACTCTGTTGTACCTGGC.

BETA3Galt6ms2-as
                                          (SEQ ID NO: 43)
CACACGTCCTCGGGTCC.

hFUT3
FUT35
                                          (SEQ ID NO: 44)
CACTAGTCGACTAGGGATAACAGG.

FUT33
                                          (SEQ ID NO: 45)
ATGTCCATAGCAGGATCAGGAG.
```

Embodiment 5

Group of vectors V1.3: Vectors V1.2 allowing elimination of the host cells having integrated one or more transgenes by non-homologous recombinations U1+U3b+U2+U3a+U3c+U3d U1: Bacterial functional unit U2: nxU2a+mxU2b, n≥0, m≥0 and n+m≥2

U2a: Expression functional unit of which the promoter is dependent on RNA polymerase II and of which the expression product is a protein U2b: Expression functional unit of which the promoter is dependent on RNA polymerase III and of which the expression product is a non-coding RNA U3a=positive selection cassette U3b=motif 5' of a homologous recombination sequence X U3c=motif 3' of a homologous recombination sequence X U3d is a negative selection cassette.

Example: Vector Allowing the Expression of the Enzyme hFUT3 Whilst Suppressing the Expression of Mb3Galt6

| U1 | ori-Amp |
|---|---|
| U3b | Rosa26 5' |
| U2a | CMV promoter |
|  | hFUT3 cDNA |
|  | BPA terminator |
| U2b | shRNA mB3Galt6 cassette |
| U3a | hygromycin resistance |
| U3c | Rosa26 3' |
| U3d | ef1a promoter |
|  | thymidine kinase |
|  | HSV Tk terminator |

List of the building blocks used to construct the vector V1.3 (FIG. 13)

```
                                          (SEQ ID NO: 36)
Building block Ori-AmpR BsaI B (SEQ ID NO: 49)
Building block rosa26-5 BsaI A (SEQ ID NO: 50)
Building block pCMV BsaI C (SEQ ID NO: 38)
Building block hFUT3 BsaI A (SEQ ID NO: 39)
Building block BGHpA BsaI B (SEQ ID NO: 46)
Building block shB3Galt6 BsaI B (SEQ ID NO: 51)
Building block HygroR BsaI C Building block rosa26-3' BsaI B
```

-continued (SEQ ID NO: 54)
GAGGTACCGGTCTCAGTAGAGATGGGCGGGAGTCTTCTGGGCAGGCTTAA

AGGCTAACCTGGTGTGTGGGCGTTGTCCTGCAGGGGAATTGAACAGGTGT

AAAATTGGAGGGACAAGACTTCCCACAGATTTTCGGTTTTGTCGGGAAGT

TTTTTAATAGGGGCAAATAGGAAAATGGAGGATAGGAGTCATCTGGGGTT

TATGCAGCAAAACTACAGGTATATTGCTTGTATCCGCCTCGGAGATTTCC

ATGAGGAGATAAAGACATGTCACCCGAGTTTATACTCTCCTGCTTAGATC

CTACTACAGTATGAAATACAGTGTCGCGAGGTAGACTATGTAAGCAGATT

TAATCATTTTAAAGAGCCCAGTACTTCATATCCATTTCTCCCGCTCCTTC

TGCAGCCTTATCAAAAGGTATTTAGAACACTCATTTTAGCCCCATTTTCA

TTTATTATACTGGCTTATCCAACCCCTAGACAGAGCATTGGCATTTTCCC

TTTCCTGATCTTAGAAGTCTGATGACTCATGAAACCAGACAGATTAGTTA

CATACACCACAAATCGAGGCTGTAGCTGGGGCCTCAACACTGCAGTTCTT

TTATAACTCCTTAGTACACTTTTTGTTGATCCTTTGCCTTGATCCTTAAT

TTTCAGTGTCTATCACCTCTCCCGTCAGGTGGTGTTCCACATTTGGGCCT

ATTCTCAGTCCAGGGAGTTTTACAACAATAGATGTATTGAGAATCCAACC

TAAAGCTTAACTTTCCACTCCCATGAATGCCTCTCTCCTTTTTCTCCATT

ATAACTGAGCTATAACCATTAATGGTTTCAGGTGGATGTCTCCTCCCCCA

ATATACCTGATGTATCTACATATTGCCAGGCTGATATTTTAAGACATAAA

AGGTATATTTCATTATTGAGCCACATGGTATTGATTACTGCTACTAAAAT

TTTGTCATTGTACACATCTGTAAAAGGTGGTTCCTTTTGGAATGCAAAGT

TCAGGTGTTTGTTGTCTTTCCTGACCTAAGGTCTTGTGAGCTTGTATTTT

TTCTATTTAAGCAGTGCTTTCTCTTGGACTGGCTTGACTCATGGCATTCT

ACACGTTATTGCTGGTCTAAATGTGATTTTGCCAAGCTTCTTCAGGACCT

ATAATTTTGCTTGACTTGTAGCCAAACACAAGTAAAATGATTAAGCAACA

AATGTATTTGTGAAGCTTGGTTTTTAGGTTGTTGTGTTGTGTGTGCTTGT

GCTCTATAATAATACTATCCAGGGGCTGGAGAGGTGGCTCGGAGTTCAAG

AGCACAGACTGCTCTTCCAGAAGTCCTGAGTTCAATTCCCAGCAACCACA

TGGTGGCTCACAACCATCTGTAATGGGATCTGATGCCCTCTTCTGGTGTG

TCTGAAGACCACAAGTGTATTCACATTAAATAAATAATCCTCCTTCTTCT

TCTTTTTTTTTTTTAAAGAGAATACTGTCTCCAGTAGAATTACTGAAGT

AATGAAATACTTTGTGTTTGTTCCAATATGGAAGCCAATAATCAAATACT

CTTAAGCACTGGAAATGTACCAAGGAACTATTTTATTTAAGTGAACTGTG

GACAGAGGAGCCATAACTGCAGACTTGTGGGATACAGAAGACCAATGCAG

ACTTAATGTCTTTTCTCTTACACTAAGCAATAAAGAAATAAAAATTGAAC

TTCTAGTATCCTATTTGTTAAACTGCTAGCTTTACTAACTTTTGTGCTTC

ATCTATACAAAGCTGAAAGCTAAGTCTGCAGCCATTACTAAACATGAAAG

CAAGTAATGATAATTTTGGATTTCAAAAATGTAGGGCCAGAGTTTAGCCA

GCCAGTGGTGGTGCTTGCCTTTATGCCTTAATCCCAGCACTCTGGAGGCA

GAGACAGGCAGATCTCTGAGTTTGAGCCCAGCCTGGTCTACACATCAAGT

TCTATCTAGGATAGCCAGGAATACACACAGAAACCCTGTTGGGGAGGGGG

GCTCTGAGATTTCATAAAATTATAATTGAAGCATTCCCTAATGAGCCACT

ATGGATGTGGCTAAATCCGTCTACCTTTCTGATGAGATTGGGTATTATT

TTTTCTGTCTCTGCTGTTGGTTGGGTCTTTTGACACTGTGGGCTTTCTTA

AAGCCTCCTTCCCTGCCATGTGGACTCTTGTTTGCTACTAACTTCCCATG

GCTTAAATGGCATGGCTTTTTGCCTTCTAAGGGCAGCTGCTGAGATTTGC

AGCCTGATTTCCAGGGTGGGGTTGGGAAATCTTTCAAACACTAAAATTGT

CCTTTAATTTTTTTTAAAAAATGGGTTATATAATAAACCTCATAAAATA

GTTATGAGGAGTGAGGTGGACTAATATTAATGAGTCCCTCCCCTATAAAA

GAGCTATTAAGGCTTTTTGTCTTATACTAACTTTTTTTTTAAATGTGGTA

TCTTTAGAACCAAGGGTCTTAGAGTTTTAGTATACAGAAACTGTTGCATC

GCTTAATCAGATTTTCTAGTTTCAAATCCAGAGAATCCAAATTCTTCACA

GCCAAAGTCAAATTAAGAATTTCTGACTTTAATGTTATTTGCTACTGTGA

ATATAAAATGATAGCTTTTCCTGAGGCAGGGTATCACTATGTATCTCTGC

CTGATCTGCAACAAGATATGTAGACTAAAGTTCTGCCTGCTTTTGTCTCC

TGAATACTAAGGTTAAAATGTAGTAATACTTTTGGAACTTGCAGGTCAGA

TTCTTTTATAGGGGACACACTAAGGGAGCTTGGGTGATAGTTGGTAAATG

TGTTTAAGTGATGAAAACTTGAATTATTATCACCGCAACCTACTTTTTAA

AAAAAAAGCCAGGCCTGTTAGAGCATGCTAAGGGATCCCTAGGACTTGC

TGAGCACACAAGAGTAGTACTTGGCAGGCTCCTGGTGAGAGCATATTTCA

AAAAACAAGGCAGACAACCAAGAAACTACAGTAAGGTTACCTGTCTTTAA

CCATCTGCATATACACAGGGATATTAAAATATTCCAAATAATATTTCATT

CAAGTTTTCCCCCATCAAATTGGGACATGGATTTCTCCGGTGAATAGGCA

GAGTTGGAAACTAAACAAATGTTGGTTTTGTGATTTGTGAAATTGTTTTC

AAGTGATAGTTAAAGCCCATGAGATACAGAACAAAGCTGCTATTTCGAGG

TCACTTGGTTATACTCAGAAGCACTTCTTTGGGTTTCCCTGCACTATCCT

GATCATGTGCTAGGCCTACCTTAGGCTGATTGTTGTTCAAATAACTTAAG

TTTCCTGTCAGGTGATGTCATATGATTTCATATATCAAGGCAAAACATGT

TATATATGTTAAACATTTGGACTTAATGTGAAAGTTAGGTCTTTGTGGGT

TTTGATTTAATTTCAAAACCTGAGCTAAATAAGTCATTTTACATGTCTT

ACATTTGGTGAATTGTATATTGTGGTTTGCAGGCAAGACTCTCTGACCTA

GTAACCCTCCTATAGAGCACTTTGCTGGGTCACAAGTCTAGGAGTCAAGC

ATTTCACCTTGAAGTTGAGACGTTTTGTTAGTGTATACTAGTTATATGTT

GGAGGACATGTTTATCCAGAAGATATTCAGGACTATTTTGACTGGGCTA

AGGAATTGATTCTGATTAGCACTGTTAGTGAGCATTGAGTGGCCTTTAGG

CTTGAATTGGAGTCACTTGTATATCTCAAATAATGCTGGCCTTTTTAAA

AAGCCCTTGTTCTTTATCACCCTGTTTTCTACATAATTTTTGTTCAAAGA

AATACTTGTTTGGATCTCCTTTTGACAACAATAGCATGTTTTCAAGCCAT

ATTTTTTTCCTTTTTTTTTTTTTTTGGTTTTCGAGACAGGGTTTCT

CTGTATAGCCCTGGCTGTCCTGGAACTCACTTTGTAGACCAGGCTGGCCT

CGAACTCAGAAATCCGCCTGCCTCTGCCTCCTGAGTGCCGGGATTAAGG

CGTGCACCACCACGCCTGGCTAAGTTGGATATTTTGTATATAACTATAAC

CAATACTAACTCCACTGGGTGGATTTTTAATTCAGTCAGTAGTCTTAAGT

GGTCTTTATTGGCCCTTATTAAAATCTACTGTTCACTCTAACAGAGGCTG

TTGGACTAGTGGGACTAAGCAACTTCCTACGGATATACTAGCAGATAAGG

GTCAGGGATAGAAACTAGTCTAGCGTTTTGTATACCTACCAGCTTATACT

ACCTTGTTCTGATAGAAATATTTAGGACATCTAGCTTATCATGCCGAGAC

CGGTACCTC

Building block pEF1a BsaI A (SEQ ID NO: 55)
GAGGTACCGGTCTCAATGCaaGGAACCAATTCAGTCGACTGGATCCCGAT

GGCTCCGGTGCCCGTCAGTGGGCAGAGCGCACATCGCCCACAGTCCCCGA

GAAGTTGGGGGGAGGGGTCGGCAATTGAACCGGTGCCTAGAGAAGGTGGC

GCGGGGTAAACTGGGAAAGTGATGTCGTGTACTGGCTCCGCCTTTTTCCC

GAGGGTGGGGGAGAACCGTATATAAGTGCAGTAGTCGCCGTGAACGTTCT

TTTTCGCAACGGGTTTGCCGCCAGAACACAGGTCCGCGGCCCCGAACTAG

GCCTAGGCGTCTGATCACTAGTGACTCTAGTCCTAGTCGACTAGGGATAA

CAGGGGCCCCGAGACCGGTACCTC

Building block TK BsaI A (SEQ ID NO: 56)
GAGGTACCGGTCTCAGCCCATGGCTTCGTACCCCTGCCATCAACACGCGT

CTGCGTTCGACCAGGCTGCGCGTTCTCGCGGCCATAGCAACCGACGTACG

GCGTTGCGCCCTCGCCGGCAGCAAGAAGCCACGGAAGTCCGCCTGGAGCA

GAAAATGCCCACGCTACTGCGGGTTTATATAGACGGTCCTCACGGGATGG

GGAAAACCACCACCACGCAACTGCTGGTGCCCTGGGTTCGCGCGACGAT

ATCGTCTACGTACCCGAGCCGATGACTTACTGGCAGGTGCTGGGGGCTTC

CGAGACAATCGCGAACATCTACACCACACAACACCGCCTCGACCAGGGTG

AGATATCGGCCGGGACGCGGCGGTGGTAATGACAAGCGCCCAGATAACA

ATGGGCATGCCTTATGCCGTGACCGACGCCGTTCTGGCTCCTCATATCGG

GGGGGAGGCTGGGAGCTCACATGCCCCGCCCCCGGCCCTCACCCTCATCT

TCGACCGCCATCCCATCGCCGCCCTCCTGTGCTACCCGGCCGCGCGATAC

CTTATGGGCAGCATGACCCCCCAGGCCGTGCTGGCGTTCGTGGCCCTCAT

CCCGCCGACCTTGCCCGGCACAAACATCGTGTTGGGGGCCCTTCCGGAGG

ACAGACACATCGACCGCCTGGCCAAACGCCAGCGCCCCGGCGAGCGGCTT

GACCTGGCTATGCTGGCCGCGATTCGCCGCGTTTACGGGCTGCTTGCCAA

TACGGTGCGGTATCTGCAGGGCGGCGGGTCGTGGCGGGAGGATTGGGGAC

AGCTTTCGGGGACGGCCGTGCCGCCCCAGGGTGCCGAGCCCCAGAGCAAC

GCGGGCCCACGACCCCATATCGGGGACGTTATTTACCCTGTTTCGGGC

CCCCGAGTTGCTGGCCCCCAACGGCGACCTGTACAACGTGTTTGCCTGGG

CCTTGGACGTCTTGGCCAAACGCCTCCGTCCCATGCACGTCTTTATCCTG

GATTACGACCAATCGCCCGCCGGCTGCCGGGACGCCCTGCTGCAACTTAC

CTCCGGGATGGTCCAGACCCACGTCACCACCCCGGCTCCATACCGACGA

TCTGCGACCTGGCGCGCACGTTTGCCCGGGAGATGGGGGAGGCTAACTGA

CCGCCGAGACCGGTACCTC

Building block Tkter BsaI A (SEQ ID NO: 57)
GAGGTACCGGTCTCACCGCGGGGGAGGCTAACTGAAACACGGAAGGAGAC

AATACCGGAAGGAACCCGCGCTATGACGGCAATAAAAAGACAGAATAAAA

CGCACGGTGTTGGGTCGTTTGTTCATAAACGCGGGGTTCGGTCCCAGGGC

TGGCACTCTGTCGATACCCCACCGAGGCCCCATTGGGGCCAATACGCCCG

CGTTTCTTCCTTTTCCCCACCCCACCCCCCAAGTTCGGGTGAAGGCCCAG

GGCTCGCAGCCAACGTCGGGGCGGCAGGCCCTGCCATAGCCTATTCGAGA

CCGGTACCTC

V1.3 (SEQ ID NO: 58,
example of a vector of the group V1.3)
TATTGTAATACGGTTATCCACAGAATCAGGGGATAACGCAGGAAAGAACA

TGTGAGCAAAAGGCCAGCAAAAGGCCAGGAACCGTAAAAAGGCCGCGTTG

CTGGCGTTTTTCCATAGGCTCCGCCCCCCTGACGAGCATCACAAAAATCG

ACGCTCAAGTCAGAGGTGGCGAAACCCGACAGGACTATAAAGATACCAGG

CGTTTCCCCCTGGAAGCTCCCTCGTGCGCTCTCCTGTTCCGACCCTGCCG

CTTACCGGATACCTGTCCGCCTTTCTCCCTTCGGGAAGCGTGGCGCTTTC

TCATAGCTCACGCTGTAGGTATCTCAGTTCGGTGTAGGTCGTTCGCTCCA

AGCTGGGCTGTGTGCACGAACCCCCCGTTCAGCCCGACCGCTGCGCCTTA

TCCGGTAACTATCGTCTTGAGTCCAACCCGGTAAGACACGACTTATCGCC

ACTGGCAGCAGCCACTGGTAACAGGATTAGCAGAGCGAGGTATGTAGGCG

GTGCTACAGAGTTCTTGAAGTGGTGGCCTAACTACGGCTACACTAGAAGA

ACAGTATTTGGTATCTGCGCTCTGCTGAAGCCAGTTACCTTCGGAAAAAG

AGTTGGTAGCTCTTGATCCGGCAAACAAACCACCGCTGGTAGCGGTTTTT

TTGTTTGCAAGCAGCAGATTACGCGCAGAAAAAAAGGATCTCAAGAAGAT

CCTTTGATCTTTTCTACGGGGTCTGACGCTCAGTGGAACGAAAACTCACG

TTAAGGGATTTTGGTCATGAGATTATCAAAAAGGATCTTCACCTAGATCC

TTTTAAATTAAAAATGAAGTTTTAAATCAATCTAAAGTATATATGAGTAA

ACTTGGTCTGACAGTTACCAATGCTTAATCAGTGAGGCACCTATCTCAGC

GATCTGTCTATTTCGTTCATCCATAGTTGCCTGACTCCCCGTCGTGTAGA

TAACTACGATACGGGAGGGCTTACCATCTGGCCCCAGTGCTGCAATGATA

CCGCGTGACCCACGCTCACCGGCTCCAGATTTATCAGCAATAAACCAGCC

AGCCGGAAGGGCCGAGCGCAGAAGTGGTCCTGCAACTTTATCCGCCTCCA

TCCAGTCTATTAATTGTTGCCGGGAAGCTAGAGTAAGTAGTTCGCCAGTT

AATAGTTTGCGCAACGTTGTTGCCATTGCTACAGGCATCGTGGTGTCACG

CTCGTCGTTTGGTATGGCTTCATTCAGCTCCGGTTCCCAACGATCAAGGC

GAGTTACATGATCCCCCATGTTGTGCAAAAAAGCGGTTAGCTCCTTCGGT

CCTCCGATCGTTGTCAGAAGTAAGTTGGCCGCAGTGTTATCACTCATGGT

TATGGCAGCACTGCATAATTCTCTTACTGTCATGCCATCCGTAAGATGCT

TTTCTGTGACTGGTGAGTACTCAACCAAGTCATTCTGAGAATAGTGTATG

CGGCGACCGAGTTGCTCTTGCCCGGCGTCAATACGGGATAATACCGCGCC

ACATAGCAGAACTTTAAAAGTGCTCATCATTGGAAAACGTTCTTCGGGGC

GAAAACTCTCAAGGATCTTACCGCTGTTGAGATCCAGTTCGATGTAACCC

```
ACTCGTGCACCCAACTGATCTTCAGCATCTTTTACTTTCACCAGCGTTTC
TGGGTGAGCAAAAACAGGAAGGCAAAATGCCGCAAAAAAGGGAATAAGGG
CGACACGGAAATGTTGAATACTCATACTCTTCCTTTTTCAATATTATTGA
AGCATTTATCAGGGTTATTGTCTCATGAGCGGATACATATTTGAATGTAT
TTAGAAAAATAAACAAATAGGGGTTCCGCGCACATTTCCCCGAAAAGTGC
CAAGGACCCCGCGGCAGGCCCTCCGAGCGTGGTGGAGCCGTTCTGTGAGA
CAGCCGGGTACGAGTCGTGACGCTGGAAGGGGCAAGCGGGTGGTGGGCAG
GAATGCGGTCCGCCCTGCAGCAACCGGAGGGGAGGGAGAAGGGAGCGGA
AAAGTCTCCACCGGACGCGGCCATGGCTCGGGGGGGGGGGCAGCGGAG
GAGCGCTTCCGCCGACGTCTCGTCGCTGATTGGCTTCTTTTCCTCCCGC
CGTGTGTGAAAACACAAATGGCGTGTTTTGGTTGGCGTAAGGCGCCTGTC
AGTTAACGGCAGCCGGAGTGCGCAGCCGCCGGCAGCCTCGCTCTGCCCAC
TGGGTGGGGCGGGAGGTAGGTGGGGTGAGGCGAGCTGGACGTGCGGGCGC
GGTCGGCCTCTGGCGGGGCGGGGAGGGGAGGGAGGGTCAGCGAAAGTAG
CTCGCGCGCGAGCGGCCGCCCACCCTCCCCTTCCTCTGGGGGAGTCGTTT
TACCCGCCGCCGGCCGGGCCTCGTCGTCTGATTGGCTCTCGGGGCCCAGA
AAACTGGCCCTTGCCATTGGCTCGTGTTCGTGCAAGTTGAGTCCATCCGC
CGGCCAGCGGGGCGGCGAGGAGGCGCTCCCAGGTTCCGGCCCTCCCCTC
GGCCCCGCGCCGCAGAGTCTGGCCGCGCGCCCCTGCGCAACGTGGCAGGA
AGCGCGCGCTGGGGCGGGGACGGGCAGTAGGGCTGAGCGGCTGCGGGGC
GGGTGCAAGCACGTTTCCGACTTGAGTTGCCTCAAGAGGGGCGTGCTGAG
CCAGACCTCCATCGCGCACTCCGGGGAGTGGAGGGAAGGAGCGAGGGCTC
AGTTGGGCTGTTTTGGAGGCAGGAAGCACTTGCTCTCCCAAAGTCGCTCT
GAGTTGTTATCAGTAAGGGAGCTGCAGTGGAGTAGGCGGGGAGAAGGCCG
CACCCTTCTCCGGAGGGGGAGGGGAGTGTTGCAATACCTTTCTGGGAGT
TCTCTGCTGCCTCCTGGCTTCTGAGGACCGCCCTGGGCCTGGGAGAATCC
CTTGCCCCTCTTCCCTCGTGATCTGCAACTCCAGTCTTACAAACCAAT
TCAGTCGACTGGATCCTAGTTATTAATAGTAATCAATTACGGGGTCATTA
GTTCATAGCCCATATATGGAGTTCCGCGTTACATAACTTACGGTAAATGG
CCCGCCTGGCTGACCGCCCAACGACCCCCGCCCATTGACGTCAATAATGA
CGTATGTTCCCATAGTAACGCCAATAGGGACTTTCCATTGACGTCAATGG
GTGGAGTATTTACGGTAAACTGCCCACTTGGCAGTACATCAAGTGTATCA
TATGCCAAGTACGCCCCCTATTGACGTCAATGACGGTAAATGGCCCGCCT
GGCATTATGCCCAGTACATGACCTTATGGGACTTTCCTACTTGGCAGTAC
ATCTACGTATTAGTCATCGCTATTACCATGGTGATGCGGTTTTGGCAGTA
CATCAATGGGCGTGGATAGCGGTTTGACTCACGGGGATTTCCAAGTCTCC
ACCCCATTGACGTCAATGGGAGTTTGTTTTGGCACCAAAATCAACGGGAC
TTTCCAAAATGTCGTAACAACTCCGCCCCATTGACGCAAATGGGCGGTAG
GCGTGTACGGTGGGAGGTCTATATAAGCAGAGCTGGTTTAGTGAACCGTC
AGATCACTAGTCGACTAGGGATAACAGGGCACCATGGATCCCTGGGTGC

AGCCAAGCCACAATGGCCATGGCGCCGCTGTCTGGCCGCACTGCTATTTC
AGCTGCTGGTGGCTGTGTGTTTCTTCTCCTACCTGCGTGTGTCCCGAGAC
GATGCCACTGGATCCCCTAGGGCTCCCAGTGGGTCCTCCCGACAGGACAC
CACTCCCACCCGCCCCACCCTCCTGATCCTGCTATGGACATGGCCTTTCC
ACATCCCTGTGGCTCTGTCCCGCTGTTCAGAGATGGTGCCCGGCACAGCC
GACTGCCACATCACTGCCGACCGCAAGGTGTACCCACAGGCAGACACGGT
CATCGTGCACCACTGGGATATCATGTCCAACCCTAAGTCACGCCTCCCAC
CTTCCCCGAGGCCGCAGGGGCAGCGCTGGATCTGGTTCAACTTGGAGCCA
CCCCCTAACTGCCAGCACCTGGAAGCCCTGGACAGATACTTCAATCTCAC
CATGTCCTACCGCAGCGACTCCGACATCTTCACGCCCTACGGCTGGCTGG
AGCCGTGGTCCGGCCAGCCTGCCCACCCACCGCTCAACCTCTCGGCCAAG
ACCGAGCTGGTGGCCTGGGCGGTGTCCAACTGGAAGCCGGACTCAGCCAG
GGTGCGCTACTACCAGAGCCTGCAGGCTCATCTCAAGGTGGACGTGTACG
GACGCTCCCACAAGCCCCTGCCCAAGGGGACCATGATGGAGACGCTGTCC
CGGTACAAGTTCTACCTGGCCTTCGAGAACTCCTTGCACCCCGACTACAT
CACCGAGAAGCTGTGGAGGAACGCCCTGGAGGCCTGGGCCGTGCCCGTGG
TGCTGGGCCCCAGCAGAAGCAACTACGAGAGGTTCCTGCCACCCGACGCC
TTCATCCACGTGGACGACTTCCAGAGCCCCAAGGACCTGGCCCGGTACCT
GCAGGAGCTGGACAAGGACCACGCCCGCTACCTGAGCTACTTTCGCTGGC
GGGAGACGCTGCGGCCTCGCTCCTTCAGCTGGGCACTGGATTTCTGCAAG
GCCTGCTGGAAACTGCAGCAGGAATCCAGGTACCAGACGGTGCGCAGCAT
AGCGGCTTGGTTCACCTGATCGACTGTGCCTTCTAGTTGCCAGCCATCTG
TTGTTTGCCCCTCCCCCGTGCCTTCCTTGACCCTGGAAGGTGCCACTCCC
ACTGTCCTTTCCTAATAAAATGAGGAAATTGCATCGCATTGTCTGAGTAG
GTGTCATTCTATTCTGGGGGGTGGGTGGGGCAGGACAGCAAGGGGGAGG
ATTGGGAGGACAATAGCAGGCATGCTGGGGATGCGGTGGGCTCTATGGCT
TCGACAGGGTCGACAAGCTTTTCAAAAAAAAAGCATGAGGTGCAGTTGC
GCCTTTCCTATCTCTTGAATAGGAAAGGCGCAACTGCACCTCATGCTGGA
TCCCGCGTCCTTTCCACAAGATATATAAACCCAAGAAATCGAAATACTTT
CAAGTTACGGTAAGCATATGATAGTCCATTTTAAAACATAATTTTAAAAC
TGCAAACTACCCAAGAAATTATTACTTTCTACGTCACGTATTTTGTACTA
ATATCTTTGTGTTTACAGTCAAATTAATTCTAATTATCTCTCTAACAGCC
TTGTATCGTATATGCAAATATGAAGGAATCATGGGAAATAGGCCCTCTTC
CTGCCCGACCTTGGCGCGCGCTCGGCGCGCGGTCACGCTCCGTCACGTGG
TGCGTTTTGCCAGCAGGCAGAAGTATGCAAAGCATGCATCTCAATTAGTC
AGCAACCAGGTGTGGAAAGTCCCCAGGCTCCCCAGCAGGCAGAAGTATGC
AAAGCATGCATCTCAATTAGTCAGCAACCATAGTCCCGCCCCTAACTCCG
CCCATCCCGCCCCTAACTCCGCCCAGTTCCGCCCATTCTCCGCCCCATGG
CTGACTAATTTTTTTTATTTATGCAGAGGCCGAGGCCGCCTCTGCCTCTG
AGCTATTCCAGAAGTAGTGAGGAGGCTTTTTTGGAGGCCTAGGCTTTTGC
AAAAAGCTCCCGGGAGCTTGTATATCCATTTTCGGATCTGATCAGCACGT
```

```
GATGAAAAAGCCTGAACTCACCGCGACGTCTGTCGAGAAGTTTCTGATCG

AAAAGTTCGACAGCGTGTCCGACCTGATGCAGCTCTCGGAGGGCGAAGAA

TCTCGTGCTTTCAGCTTCGATGTAGGAGGGCGTGGATATGTCCTGCGGGT

AAATAGCTGCGCCGATGGTTTCTACAAAGATCGTTATGTTTATCGGCACT

TTGCATCGGCCGCGCTCCCGATTCCGGAAGTGCTTGACATTGGGGAATTC

AGCGAGAGCCTGACCTATTGCATCTCCCGCCGTGCACAGGGTGTCACGTT

GCAAGACTTGCCTGAAACCGAACTGCCCGCTGTTCTGCAGCCGGTCGCGG

AGGCCATGGATGCGATCGCTGCGGCCGATCTTAGCCAGACGAGCGGGTTC

GGCCCATTCGGACCGCAAGGAATCGGTCAATACACTACATGGCGTGATTT

CATATGCGCGATTGCTGATCCCCATGTGTATCACTGGCAAACTGTGATGG

ACGACACCGTCAGTGCGTCCGTCGCGCAGGCTCTCGATGAGCTGATGCTT

TGGGCCGAGGACTGCCCCGAAGTCCGGCACCTCGTGCACGCGGATTTCGG

CTCCAACAATGTCCTGACGGACAATGGCCGCATAACAGCGGTCATTGACT

GGAGCGAGGCGATGTTCGGGGATTCCCAATACGAGGTCGCCAACATCTTC

TTCTGGAGGCCGTGGTTGGCTTGTATGGAGCAGCAGACGCGCTACTTCGA

GCGGAGGCATCCGGAGCTTGCAGGATCGCCGCGGCTCCGGGCGTATATGC

TCCGCATTGGTCTTGACCAACTCTATCAGAGCTTGGTTGACGGCAATTTC

GATGATGCAGCTTGGGCGCAGGGTCGATGCGACGCAATCGTCCGATCCGG

AGCCGGGACTGTCGGGCGTACACAAATCGCCCGCAGAAGCGCGGCCGTCT

GGACCGATGGCTGTGTAGAAGTACTCGCCGATAGTGGAAACCGACGCCCC

AGCACTCGTCCGAGGGCAAAGGAATAGCACGTGCTACGAGATTTCGATTC

CACCGCCGCCTTCTATGAAAGGTTGGGCTTCGGAATCGTTTTCCGGGACG

CCGGCTGGATGATCCTCCAGCGCGGGATCTCATGCTGGAGTTCTTCGCC

CACCCCAACTTGTTTATTGCAGCTTATAATGGTTACAAATAAAGCAATAG

CATCACAAATTTCACAAATAAAGCATTTTTTTCACTGCATTCTAGTTGTG

GTTTGTCCAAACTCATCAATGTATCGTAGAGATGGGCGGAGTCTTCTGG

GCAGGCTTAAAGGCTAACCTGGTGTGTGGGCGTTGTCCTGCAGGGGAATT

GAACAGGTGTAAAATTGGAGGGACAAGACTTCCCACAGATTTTCGGTTTT

GTCGGGAAGTTTTTTAATAGGGGCAAATAGGAAAATGGAGGATAGGAGTC

ATCTGGGGTTTATGCAGCAAAACTACAGGTATATTGCTTGTATCCGCCTC

GGAGATTTCCATGAGGAGATAAAGACATGTCACCCGAGTTTATACTCTCC

TGCTTAGATCCTACTACAGTATGAAATACAGTGTCGCGAGGTAGACTATG

TAAGCAGATTTAATCATTTTAAAGAGCCCAGTACTTCATATCCATTTCTC

CCGCTCCTTCTGCAGCCTTATCAAAAGGTATTTAGAACACTCATTTTAGC

CCCATTTTCATTTATTACTGGCTTATCCAACCCCTAGACAGAGCATTG

GCATTTTCCCTTTCCTGATCTTAGAAGTCTGATGACTCATGAAACCAGAC

AGATTAGTTACATACACCACAAATCGAGGCTGTAGCTGGGGCCTCAACAC

TGCAGTTCTTTTATAACTCCTTAGTACACTTTTTGTTGATCCTTTGCCTT

GATCCTTAATTTTCAGTGTCTATCACCTCTCCCGTCAGGTGGTGTTCCAC

ATTTGGGCCTATTCTCAGTCCAGGGAGTTTTACAACAATAGATGTATTGA

GAATCCAACCTAAAGCTTAACTTTCCACTCCCATGAATGCCTCTCTCCTT

TTTCTCCATTATAACTGAGCTATAACCATTAATGGTTTCAGGTGGATGTC

TCCTCCCCAATATACCTGATGTATCTACATATTGCCAGGCTGATATTTT

AAGACATAAAAGGTATATTTCATTATTGAGCCACATGGTATTGATTACTG

CTACTAAAATTTTGTCATTGTACACATCTGTAAAAGGTGGTTCCTTTTGG

AATGCAAAGTTCAGGTGTTTGTTGTCTTTCCTGACCTAAGGTCTTGTGAG

CTTGTATTTTTTCTATTTAAGCAGTGCTTTCTCTTGGACTGGCTTGACTC

ATGGCATTCTACACGTTATTGCTGGTCTAAATGTGATTTTGCCAAGCTTC

TTCAGGACCTATAATTTTGCTTGACTTGTAGCCAAACACAAGTAAAATGA

TTAAGCAACAAATGTATTTGTGAAGCTTGGTTTTTAGGTTGTTGTGTTGT

GTGTGCTTGTGCTCTATAATAATACTATCCAGGGGCTGGAGAGGTGGCTC

GGAGTTCAAGAGCACAGACTGCTCTTCCAGAAGTCCTGAGTTCAATTCCC

AGCAACCACATGGTGGCTCACAACCATCTGTAATGGGATCTGATGCCCTC

TTCTGGTGTGTCTGAAGACCACAAGTGTATTCACATTAAATAAATAATCC

TCCTTCTTCTTCTTTTTTTTTTTAAAGAGAATACTGTCTCCAGTAGAA

TTACTGAAGTAATGAAATACTTTGTGTTTGTTCCAATATGGAAGCCAATA

ATCAAATACTCTTAAGCACTGGAAATGTACCAAGGAACTATTTTATTTAA

GTGAACTGTGGACAGAGGAGCCATAACTGCAGACTTGTGGGATACAGAAG

ACCAATGCAGACTTAATGTCTTTTCTCTTACACTAAGCAATAAAGAAATA

AAAATTGAACTTCTAGTATCCTATTTGTTAAACTGCTAGCTTTACTAACT

TTTGTGCTTCATCTATACAAAGCTGAAAGCTAAGTCTGCAGCCATTACTA

AACATGAAAGCAAGTAATGATAATTTTGGATTTCAAAAATGTAGGGCCAG

AGTTTAGCCAGCCAGTGGTGGTGCTTGCCTTTATGCCTTAATCCCAGCAC

TCTGGAGGCAGAGACAGGCAGATCTCTGAGTTTGAGCCCAGCCTGGTCTA

CACATCAAGTTCTATCTAGGATAGCCAGGAATACACACAGAAACCCTGTT

GGGGAGGGGGGCTCTGAGATTTCATAAAATTATAATTGAAGCATTCCCTA

ATGAGCCACTATGGATGTGGCTAAATCCGTCTACCTTTCTGATGAGATTT

GGGTATTATTTTTTCTGTCTCTGCTGTTGGTTGGGTCTTTTGACACTGTG

GGCTTTCTTAAAGCCTCCTTCCCTGCCATGTGGACTCTTGTTTGCTACTA

ACTTCCCATGGCTTAAATGGCATGGCTTTTTGCCTTCTAAGGGCAGCTGC

TGAGATTTGCAGCCTGATTTCCAGGGTGGGGTTGGGAAATCTTTCAAACA

CTAAAATTGTCCTTTAATTTTTTTTAAAAAATGGGTTATATAATAAACC

TCATAAAATAGTTATGAGGAGTGAGGTGGACTAATATTAATGAGTCCCTC

CCCTATAAAAGAGCTATTAAGGCTTTTGTCTTATACTAACTTTTTTTTT

AAATGTGGTATCTTTAGAACCAAGGGTCTTAGAGTTTTAGTATACAGAAA

CTGTTGCATCGCTTAATCAGATTTTCTAGTTTCAAATCCAGAGAATCCAA

ATTCTTCACAGCCAAAGTCAAATTAAGAATTTCTGACTTTAATGTTATTT

GCTACTGTGAATATAAAATGATAGCTTTTCCTGAGGCAGGGTATCACTAT

GTATCTCTGCCTGATCTGCAACAAGATATGTAGACTAAAGTTCTGCCTGC

TTTTGTCTCCTGAATACTAAGGTTAAAATGTAGTAATACTTTTGGAACTT

GCAGGTCAGATTCTTTTATAGGGGACACACTAAGGGAGCTTGGGTGATAG
```

-continued

TTGGTAAATGTGTTTAAGTGATGAAAACTTGAATTATTATCACCGCAACC

TACTTTTTAAAAAAAAAAGCCAGGCCTGTTAGAGCATGCTAAGGGATCCC

TAGGACTTGCTGAGCACACAAGAGTAGTACTTGGCAGGCTCCTGGTGAGA

GCATATTTCAAAAAACAAGGCAGACAACCAAGAAACTACAGTAAGGTTAC

CTGTCTTTAACCATCTGCATATACACAGGGATATTAAAATATTCCAAATA

ATATTTCATTCAAGTTTTCCCCCATCAAATTGGGACATGGATTTCTCCGG

TGAATAGGCAGAGTTGGAAACTAAACAAATGTTGGTTTTGTGATTTGTGA

AATTGTTTTCAAGTGATAGTTAAAGCCCATGAGATACAGAACAAAGCTGC

TATTTCGAGGTCACTTGGTTATACTCAGAAGCACTTCTTTGGGTTTCCCT

GCACTATCCTGATCATGTGCTAGGCCTACCTTAGGCTGATTGTTGTTCAA

ATAACTTAAGTTTCCTGTCAGGTGATGTCATATGATTTCATATATCAAGG

CAAAACATGTTATATATGTTAAACATTTGGACTTAATGTGAAAGTTAGGT

CTTTGTGGGTTTTGATTTTAATTTCAAAACCTGAGCTAAATAAGTCATTT

TACATGTCTTACATTTGGTGAATTGTATATTGTGGTTTGCAGGCAAGACT

CTCTGACCTAGTAACCCTCCTATAGAGCACTTTGCTGGGTCACAAGTCTA

GGAGTCAAGCATTTCACCTTGAAGTTGAGACGTTTTGTTAGTGTATACTA

GTTATATGTTGGAGGACATGTTTATCCAGAAGATATTCAGGACTATTTTT

GACTGGGCTAAGGAATTGATTCTGATTAGCACTGTTAGTGAGCATTGAGT

GGCCTTTAGGCTTGAATTGGAGTCACTTGTATATCTCAAATAATGCTGGC

CTTTTTTAAAAAGCCCTTGTTCTTTATCACCCTGTTTTCTACATAATTTT

TGTTCAAAGAAATACTTGTTTGGATCTCCTTTTGACAACAATAGCATGTT

TTCAAGCCATATTTTTTTCCTTTTTTTTTTTTTTGGTTTTCGAGA

CAGGGTTTCTCTGTATAGCCCTGGCTGTCCTGGAACTCACTTTGTAGACC

AGGCTGGCCTCGAACTCAGAAATCCGCCTGCCTCTGCCTCCTGAGTGCCG

GGATTAAAGGCGTGCACCACCACGCCTGGCTAAGTTGGATATTTTGTATA

TAACTATAACCAATACTAACTCCACTGGGTGGATTTTTAATTCAGTCAGT

AGTCTTAAGTGGTCTTTATTGGCCCTTATTAAAATCTACTGTTCACTCTA

ACAGAGGCTGTTGGACTAGTGGGACTAAGCAACTTCCTACGGATATACTA

GCAGATAAGGGTCAGGGATAGAAACTAGTCTAGCGTTTTGTATACCTACC

AGCTTATACTACCTTGTTCTGATAGAAATATTTAGGACATCTAGCTTATC

ATGCAAGGAACCAATTCAGTCGACTGGATCCCGATGGCTCCGGTGCCCGT

CAGTGGGCAGAGCGCACATCGCCCACAGTCCCCGAGAAGTTGGGGGGAGG

GGTCGGCAATTGAACCGGTGCCTAGAGAAGGTGGCGCGGGGTAAACTGGG

AAAGTGATGTCGTGTACTGGCTCCGCCTTTTTCCCGAGGGTGGGGAGAA

CCGTATATAAGTGCAGTAGTCGCCGTGAACGTTCTTTTTCGCAACGGGTT

TGCCGCCAGAACACAGGTCCGCGGCCCCGAACTAGGCCTAGGCGTCTGAT

CACTAGTGACTCTAGTCCTAGTCGACTAGGGATAACAGGGGCCCATGGCT

TCGTACCCCTGCCATCAACACGCGTCTGCGTTCGACCAGGCTGCGCGTTC

TCGCGGCCATAGCAACCGACGTACGGCGTTGCGCCCTCGCCGGCAGCAAG

AAGCCACGGAAGTCCGCCTGGAGCAGAAAATGCCCACGCTACTGCGGGTT

-continued

TATATAGACGGTCCTCACGGGATGGGGAAAACCACCACCACGCAACTGCT

GGTGGCCCTGGGTTCGCGCGACGATATCGTCTACGTACCCGAGCCGATGA

CTTACTGGCAGGTGCTGGGGGCTTCCGAGACAATCGCGAACATCTACACC

ACACAACACCGCCTCGACCAGGGTGAGATATCGGCCGGGACGCGGCGGT

GGTAATGACAAGCGCCCAGATAACAATGGGCATGCCTTATGCCGTGACCG

ACGCCGTTCTGGCTCCTCATATCGGGGGGAGGCTGGGAGCTCACATGCC

CCGCCCCCGGCCCTCACCCTCATCTTCGACCGCCATCCCATCGCCGCCCT

CCTGTGCTACCCGGCCGCGCGATACCTTATGGGCAGCATGACCCCCCAGG

CCGTGCTGGCGTTCGTGGCCCTCATCCCGCCGACCTTGCCCGGCACAAAC

ATCGTGTTGGGGGCCCTTCCGGAGGACAGACACATCGACCGCCTGGCCAA

ACGCCAGCGCCCCGGCGAGCGGCTTGACCTGGCTATGCTGGCCGCGATTC

GCCGCGTTTACGGGCTGCTTGCCAATACGGTGCGGTATCTGCAGGGCGGC

GGGTCGTGGCGGGAGGATTGGGGACAGCTTTCGGGGACGGCCGTGCCGCC

CCAGGGTGCCGAGCCCCAGAGCAACGCGGGCCCACGACCCCATATCGGGG

ACACGTTATTTACCCTGTTTCGGGCCCCCGAGTTGCTGGCCCCCAACGGC

GACCTGTACAACGTGTTTGCCTGGGCCTTGGACGTCTTGGCCAAACGCCT

CCGTCCCATGCACGTCTTTATCCTGGATTACGACCAATCGCCCGCCGGCT

GCCGGGACGCCCTGCTGCAACTTACCTCCGGGATGGTCCAGACCCACGTC

ACCACCCCCGGCTCCATACCGACGATCTGCGACCTGGCGCGCACGTTTGC

CCGGGAGATGGGGGAGGCTAACTGACCGCGGGGGAGGCTAACTGAAACAC

GGAAGGAGACAATACCGGAAGGAACCCGCGCTATGACGGCAATAAAAAGA

CAGAATAAAACGCACGGTGTTGGGTCGTTTGTTCATAAACGCGGGGTTCG

GTCCCAGGGCTGGCACTCTGTCGATACCCCACCGAGGCCCCATTGGGGCC

AATACGCCCGCGTTTCTTCCTTTTCCCCACCCCACCCCCCAAGTTCGGGT

GAAGGCCCAGGGCTCGCAGCCAACGTCGGGGCGGCAGGCCCTGCCATAGC

C

The analysis of restriction by triple digestion EcoRV, PvuI, SalI of embodiment 5 is illustrated in FIG. 14.

Functional verification of embodiment 5: Eukaryotic cells (for example: 4T1 mouse breast cancer cells) are transfected with the vector V1.3 in accordance with a conventional protocol (for example lipotransfection or electroporation). After transfection, the cells are treated with hygromycin (50 µg-mL-1 for 7-14 days), then with Ganciclovir (3-6 days 5-40 µM). The cells are then collected and lysed so as to extract therefrom the total RNAs and then generate the complementary DNAs (cDNA) by reverse transcription in accordance with a conventional protocol. These cDNAs are then used as matrix for quantitative PCR analysis in accordance with a conventional protocol.

Specific Conditions of the Quantitative PCR:

40 cycles of three subsequent steps are performed: denaturation 94° C.-30s; hybridisation 60° C.-30s; extension 72° C.-30s.

mB3Galt6

(SEQ ID NO: 42)

BETA3Galt6ms2-s ACCACTCTGTTGTACCTGGC.

-continued

BETA3Galt6ms2-as CACACGTCCTCGGGTCC. (SEQ ID NO: 43)

hFUT3

FUT35 CACTAGTCGACTAGGGATAACAGG. (SEQ ID NO: 44)

FUT33 ATGTCCATAGCAGGATCAGGAG. (SEQ ID NO: 45)

Embodiment 6

Group of Vectors V2: Vector Allowing Expression of One or More Transgenes in an Inducible Manner.
U1+U2c+nxU2d+mxU2e
U1: Bacterial functional unit
U2c=gene coding a transcriptional transactivator (for example: protein TAT).
U2d=gene(s) of which the promoter is dependent on the transactivator coded by the gene U2c, n≥1
U2e=gene(s) of which the promoter is not dependent on the transactivator coded by the gene U2c, m≥0

Example: Vector Allowing the Inducible Expression of the Enzyme mB3Galt6

| | |
|---|---|
| U1 | ori-Amp |
| U2c | CMV promoter |
| | Teton3G |
| | BPA terminator |
| U2d | TRE3G promoter |
| | mB3Galt6 |
| | HSV Tk terminator |

List of the building blocks used for construction of the vector V2 (FIG. 15)

```
Building block Ori-AmpR BsaI B
                                                    (SEQ ID NO: 36)

Building block pCMV BsaI B
                                                    (SEQ ID NO: 37)

Building block TO3G BsaI A
                                                    (SEQ ID NO: 59)
GAGGTACCGGTCTCACACCATGTCTAGACTGGACAAGAGCAAAGTCATAAACTCTGCTCTGGAATTACTCAATGGA

GTCGGTATCGAAGGCCTGACGACAAGGAAACTCGCTCAAAAGCTGGGAGTTGAGCAGCCTACCCTGTACTGGCAC

GTGAAGAACAAGCGGGCCCTGCTCGATGCCCTGCCAATCGAGATGCTGGACAGGCATCATACCCACTCCTGCCCCC

TGGAAGGCGAGTCATGGCAAGACTTTCTGCGGAACAACGCCAAGTCATACCGCTGTGCTCTCCTCTCACATCGCGA

CGGGGCTAAAGTGCATCTCGGCACCCGCCCAACAGAGAAACAGTACGAAACCCTGGAAAATCAGCTCGCGTTCCT

GTGTCAGCAAGGCTTCTCCCTGGAGAACGCACTGTACGCTCTGTCCGCCGTGGGCCACTTTACACTGGGCTGCGTA

TTGGAGGAACAGGAGCATCAAGTAGCAAAAGAGGAAAGAGAGACACCTACCACCGATTCTATGCCCCCACTTCTG

AAACAAGCAATTGAGCTGTTCGACCGGCAGGGAGCCGAACCTGCCTTCCTTTTCGGCCTGGAACTAATCATATGTG

GCCTGGAGAAACAGCTAAAGTGCGAAAGCGGCGGGCCGACCGACGCCCTTGACGATTTTGACTTAGACATGCTCC

CAGCCGATGCCCTTGACGACTTTGACCTTGATATGCTGCCTGCTGACGCTCTTGACGATTTTGACCTTGACATGCTCC

CCGGGTAATGATCGAGACCGGTACCTC

Building block BGHpA BsaI B
                                                    (SEQ ID NO: 39)

Building block pTRE3G BsaI A
                                                    (SEQ ID NO: 60)
GAGGTACCGGTCTCATTCGCTTTCGTCTTCAAGAATTCCTGGAGTTTACTCCCTATCAGTGATAGAGAACGTATGAA

GAGTTTACTCCCTATCAGTGATAGAGAACGTATGCAGACTTTACTCCCTATCAGTGATAGAGAACGTATAAGGAGT

TTACTCCCTATCAGTGATAGAGAACGTATGACCAGTTTACTCCCTATCAGTGATAGAGAACGTATCTACAGTTTACT

CCCTATCAGTGATAGAGAACGTATATCCAGTTTACTCCCTATCAGTGATAGAGAACGTATAAGCTTTAGGCGTGTAC

GGTGGGCGCCTATAAAAGCAGAGCTCGTTTAGTGAACCGTCAGATCGCCTGGAGCAATTCCACAACACTTTTGTCT

TATACCAACTTTCCGTACCACTTCCTACCCTCGTAAACCAGCGAGACCGGTACCTC

Building block mB3Galt6 BsaI A
                                                    (SEQ ID NO: 61)
CCAGATGAAGGTATTCCGGCGCGCTTGGCGGCACCGGGTGGCGCTGGGCCTAGGCGGCCTGGCGTTCTGCGGCA

CCACTCTGTTGTACCTGGCGCGCTGCGCTTCCGAGGGCGAGACGCCCTCCGCTTCCGGAGCCGCTCGGCCCCGCGC

TAAGGCCTTCCTGGCGGTGCTGGTGGCCAGTGCGCCCCGCGCGGTCGAGCGCCGCACCGCAGTGCGCAGCACGTG

GCTGGCACCGGAGAGGCGTGGCGGACCCGAGGACGTGTGGGCGCGCTTCGCCGTGGGCACTGGCGGCTTAGGCT
```

-continued

CGGAGGAGCGGCGCGCTCTTGAGCTCGAGCAGGCGCAGCACGGGGACCTGCTGCTGCTGCCCGCCCTGCGCGAC

GCCTACGAGAACCTCACGGCCAAGGTCCTGGCCATGCTGACCTGGCTGGATGAGCGCGTGGACTTCGAGTTCGTG

CTCAAGGCGGACGACGACTCCTTTGCGCGCCTGGACGCTATCCTGGTGGACCTACGCGCACGGGAGCCCGCACGC

CGCCGGCGCCTCTACTGGGGCTTCTTTTCCGGGCGCGGGCGCGTCAAGCCGGGAGGTCGCTGGCGAGAAGCAGCC

TGGCAACTCTGCGACTACTACCTGCCCTACGCGTTGGGCGGTGGCTATGTCCTTTCTGCGGACCTGGTGCATTACCT

GCGCCTCAGCCGCGAGTACCTGCGCGCGTGGCACAGTGAAGACGTATCGCTGGGCACCTGGCTGGCACCAGTGGA

TGTGCAACGGGAGCACGACCCACGCTTCGACACGGAGTACAAATCTCGAGGCTGCAACAATCAGTATCTGGTGAC

ACACAAGCAAAGCCCAGAGGACATGTTGGAGAAGCAACAGATGTTGCTGCATGAGGGCCGGTTGTGCAAGCATG

AGGTGCAGTTGCGCCTTTCCTATGTCTATGACTGGTCAGCTCCACCCTCCCAGTGCTGCCAGCGCAAGGAGGGCGT

TCCCTGACCGC

Building block Tkter BsaI A (SEQ ID NO: 57)

V2 (SEQ ID NO: 62, example of a vector of the group V2)
TATTGTAATACGGTTATCCACAGAATCAGGGGATAACGCAGGAAAGAACATGTGAGCAAAAGGCCAGCAAAAGG

CCAGGAACCGTAAAAAGGCCGCGTTGCTGGCGTTTTTCCATAGGCTCCGCCCCCCTGACGAGCATCACAAAAATCG

ACGCTCAAGTCAGAGGTGGCGAAACCCGACAGGACTATAAAGATACCAGGCGTTTCCCCCTGGAAGCTCCCTCGT

GCGCTCTCCTGTTCCGACCCTGCCGCTTACCGGATACCTGTCCGCCTTTCTCCCTTCGGGAAGCGTGGCGCTTTCTCA

TAGCTCACGCTGTAGGTATCTCAGTTCGGTGTAGGTCGTTCGCTCCAAGCTGGGCTGTGTGCACGAACCCCCCGTTC

AGCCCGACCGCTGCGCCTTATCCGGTAACTATCGTCTTGAGTCCAACCCGGTAAGACACGACTTATCGCCACTGGC

AGCAGCCACTGGTAACAGGATTAGCAGAGCGAGGTATGTAGGCGGTGCTACAGAGTTCTTGAAGTGGTGGCCTAA

CTACGGCTACACTAGAAGAACAGTATTTGGTATCTGCGCTCTGCTGAAGCCAGTTACCTTCGGAAAAAGAGTTGGT

AGCTCTTGATCCGGCAAACAAACCACCGCTGGTAGCGGTTTTTTTGTTTGCAAGCAGCAGATTACGCGCAGAAAAA

AAGGATCTCAAGAAGATCCTTTGATCTTTTCTACGGGGTCTGACGCTCAGTGGAACGAAAACTCACGTTAAGGGAT

TTTGGTCATGAGATTATCAAAAAGGATCTTCACCTAGATCCTTTTAAATTAAAAATGAAGTTTTAAATCAATCTAAAG

TATATATGAGTAAACTTGGTCTGACAGTTACCAATGCTTAATCAGTGAGGCACCTATCTCAGCGATCTGTCTATTTC

GTTCATCCATAGTTGCCTGACTCCCCGTCGTGTAGATAACTACGATACGGGAGGGCTTACCATCTGGCCCCAGTGCT

GCAATGATACCGCGTGACCCACGCTCACCGGCTCCAGATTTATCAGCAATAAACCAGCCAGCCGGAAGGGCCGAG

CGCAGAAGTGGTCCTGCAACTTTATCCGCCTCCATCCAGTCTATTAATTGTTGCCGGGAAGCTAGAGTAAGTAGTTC

GCCAGTTAATAGTTTGCGCAACGTTGTTGCCATTGCTACAGGCATCGTGGTGTCACGCTCGTCGTTTGGTATGGCTT

CATTCAGCTCCGGTTCCCAACGATCAAGGCGAGTTACATGATCCCCCATGTTGTGCAAAAAAGCGGTTAGCTCCTTC

GGTCCTCCGATCGTTGTCAGAAGTAAGTTGGCCGCAGTGTTATCACTCATGGTTATGGCAGCACTGCATAATTCTCT

TACTGTCATGCCATCCGTAAGATGCTTTTCTGTGACTGGTGAGTACTCAACCAAGTCATTCTGAGAATAGTGTATGC

GGCGACCGAGTTGCTCTTGCCCGGCGTCAATACGGGATAATACCGCGCCACATAGCAGAACTTTAAAAGTGCTCAT

CATTGGAAAACGTTCTTCGGGGCGAAAACTCTCAAGGATCTTACCGCTGTTGAGATCCAGTTCGATGTAACCCACTC

GTGCACCCAACTGATCTTCAGCATCTTTTACTTTCACCAGCGTTTCTGGGTGAGCAAAAACAGGAAGGCAAAATGC

CGCAAAAAAGGGAATAAGGGCGACACGGAAATGTTGAATACTCATACTCTTCCTTTTTCAATATTATTGAAGCATTT

ATCAGGGTTATTGTCTCATGAGCGGATACATATTTGAATGTATTTAGAAAAATAAACAAATAGGGGTTCCGCGCAC

ATTTCCCCGAAAAGTGCCAAGGAACCAATTCAGTCGACTGGATCCTAGTTATTAATAGTAATCAATTACGGGGTCAT

TAGTTCATAGCCCATATATGGAGTTCCGCGTTACATAACTTACGGTAAATGGCCCGCCTGGCTGACCGCCCAACGA

CCCCCGCCCATTGACGTCAATAATGACGTATGTTCCCATAGTAACGCCAATAGGGACTTTCCATTGACGTCAATGGG

TGGAGTATTTACGGTAAACTGCCCACTTGGCAGTACATCAAGTGTATCATATGCCAAGTACGCCCCCTATTGACGTC

AATGACGGTAAATGGCCCGCCTGGCATTATGCCCAGTACATGACCTTATGGGACTTTCCTACTTGGCAGTACATCTA

-continued

```
CGTATTAGTCATCGCTATTACCATGGTGATGCGGTTTTGGCAGTACATCAATGGGCGTGGATAGCGGTTTGACTCA
CGGGGATTTCCAAGTCTCCACCCCATTGACGTCAATGGGAGTTTGTTTTGGCACCAAAATCAACGGGACTTTCCAAA
ATGTCGTAACAACTCCGCCCCATTGACGCAAATGGGCGGTAGGCGTGTACGGTGGGAGGTCTATATAAGCAGAGC
TGGTTTAGTGAACCGTCAGATCACTAGTCGACTAGGGATAACAGGGCACCATGTCTAGACTGGACAAGAGCAAAG
TCATAAACTCTGCTCTGGAATTACTCAATGGAGTCGGTATCGAAGGCCTGACGACAAGGAAACTCGCTCAAAAGCT
GGGAGTTGAGCAGCCTACCCTGTACTGGCACGTGAAGAACAAGCGGGCCCTGCTCGATGCCCTGCCAATCGAGAT
GCTGGACAGGCATCATACCCACTCCTGCCCCCTGGAAGGCGAGTCATGGCAAGACTTTCTGCGGAACAACGCCAA
GTCATACCGCTGTGCTCTCCTCTCACATCGCGACGGGGCTAAAGTGCATCTCGGCACCCGCCCAACAGAGAAACAG
TACGAAACCCTGGAAAATCAGCTCGCGTTCCTGTGTCAGCAAGGCTTCTCCCTGGAGAACGCACTGTACGCTCTGT
CCGCCGTGGGCCACTTTACACTGGGCTGCGTATTGGAGGAACAGGAGCATCAAGTAGCAAAAGAGGAAAGAGAG
ACACCTACCACCGATTCTATGCCCCCACTTCTGAAACAAGCAATTGAGCTGTTCGACCGGCAGGGAGCCGAACCTG
CCTTCCTTTTCGGCCTGGAACTAATCATATGTGGCCTGGAGAAACAGCTAAAGTGCGAAAGCGGCGGGCCGACCG
ACGCCCTTGACGATTTTGACTTAGACATGCTCCCAGCCGATGCCCTTGACGACTTTGACCTTGATATGCTGCCTGCT
GACGCTCTTGACGATTTTGACCTTGACATGCTCCCCGGGTAATGATCGACTGTGCCTTCTAGTTGCCAGCCATCTGT
TGTTTGCCCCTCCCCCGTGCCTTCCTTGACCCTGGAAGGTGCCACTCCCACTGTCCTTTCCTAATAAAATGAGGAAAT
TGCATCGCATTGTCTGAGTAGGTGTCATTCTATTCTGGGGGGTGGGGTGGGGCAGGACAGCAAGGGGGAGGATT
GGGAGGACAATAGCAGGCATGCTGGGGATGCGGTGGGCTCTATGGCTTCGCTTTCGTCTTCAAGAATTCCTGGAG
TTTACTCCCTATCAGTGATAGAGAACGTATGAAGAGTTTACTCCCTATCAGTGATAGAGAACGTATGCAGACTTTAC
TCCCTATCAGTGATAGAGAACGTATAAGGAGTTTACTCCCTATCAGTGATAGAGAACGTATGACCAGTTTACTCCCT
ATCAGTGATAGAGAACGTATCTACAGTTTACTCCCTATCAGTGATAGAGAACGTATATCCAGTTTACTCCCTATCAG
TGATAGAGAACGTATAAGCTTTAGGCGTGTACGGTGGGCGCCTATAAAAGCAGAGCTCGTTTAGTGAACCGTCAG
ATCGCCTGGAGCAATTCCACAACACTTTTGTCTTATACCAACTTTCCGTACCACTTCCTACCCTCGTAAACCAGAGCA
TGAAGGTATTCCGGCGCGCTTGGCGGCACCGGGTGGCGCTGGGCCTAGGCGGCCTGGCGTTCTGCGGCACCACTC
TGTTGTACCTGGCGCGCTGCGCTTCCGAGGGCGAGACGCCCTCCGCTTCCGGAGCCGCTCGGCCCCGCGCTAAGG
CCTTCCTGGCGGTGCTGGTGGCCAGTGCGCCCCGCGCGGTCGAGCGCCGCACCGCAGTGCGCAGCACGTGGCTGG
CACCGGAGAGGCGTGGCGGACCCGAGGACGTGTGGGCGCGCTTCGCCGTGGGCACTGCCGGCTTAGGCTCGGAG
GAGCGGCGCGCTCTTGAGCTCGAGCAGGCGCAGCACGGGGACCTGCTGCTGCTGCCCGCCCTGCGCGACGCCTAC
GAGAACCTCACGGCCAAGGTCCTGGCCATGCTGACCTGGCTGGATGAGCGCGTGGACTTCGAGTTCGTGCTCAAG
GCGGACGACGACTCCTTTGCGCGCCTGGACGCTATCCTGGTGGACCTACGCGCACGGGAGCCCGCACGCCGCCGG
CGCCTCTACTGGGGCTTCTTTTCCGGGCGCGGGCGCGTCAAGCCGGGAGGTCGCTGGCGAGAAGCAGCCTGGCAA
CTCTGCGACTACTACCTGCCCTACGCGTTGGGCGGTGGCTATGTCCTTTCTGCGGACCTGGTGCATTACCTGCGCCT
CAGCCGCGAGTACCTGCGCGCGTGGCACAGTGAAGACGTATCGCTGGGCACCTGGCTGGCACCAGTGGATGTGCA
ACGGGAGCACGACCCACGCTTCGACACGGAGTACAAATCTCGAGGCTGCAACAATCAGTATCTGGTGACACACAA
GCAAAGCCCAGAGGACATGTTGGAGAAGCAACAGATGTTGCTGCATGAGGGCCGGTTGTGCAAGCATGAGGTGC
AACTTCGCCTTTCCTATGTCTATGACTGGTCAGCTCCACCCTCCCAGTGCTGCCAGCGCAAGGAGGGCGTTCCCTGA
TGTCACCGCGGGGAGGCTAACTGAAACACGGAAGGAGACAATACCGGAAGGAACCCGCGCTATGACGGCAATA
AAAAGACAGAATAAAACGCACGGTGTTGGGTCGTTTGTTCATAAACGCGGGGTTCGGTCCCAGGGCTGGCACTCT
GTCGATACCCCACCGAGGCCCCATTGGGGCCAATACGCCCGCGTTTCTTCCTTTTCCCCACCCCACCCCCCAAGTTC
GGGTGAAGGCCCAGGGCTCGCAGCCAACGTCGGGGCGGCAGGCCCTGCCATAGCC
```

The analysis of restriction by triple digestion NdeI, SalI, XhoI of embodiment 6 is illustrated in FIG. 16.

Functional verification of embodiment 6: Eukaryotic cells (for example: 4T1 mouse breast cancer cells) are transfected with the vector V2 in accordance with a conventional protocol (for example lipotransfection or electroporation). After transfection, the cells are treated with 100-1000 ng·mL$^{-1}$ of doxycycline for 24 to 48 hours. The cells are then collected and lysed so as to extract therefrom the total RNAs and then generate the complementary DNAs (cDNA) by reverse transcription in accordance with a conventional protocol. These cDNAs are then used as matrix for quantitative PCR analysis in accordance with a conventional protocol.

Specific Conditions of the Quantitative PCR:

40 cycles of three subsequent steps are performed: denaturation 94° C.-30s; hybridisation 60° C.-30s; extension 72° C.-30s.

Primers Used:

```
                                          (SEQ ID NO: 42)
BETA3Galt6ms2-s ACCACTCTGTTGTACCTGGC.

(SEQ ID NO: 43)
BETA3Galt6ms2-as CACACGTCCTCGGGTCC.
```

Embodiment 7

Group of vectors V3: Vector allowing execution of the genetic complementation under inducible control.

U1+U2f+U2c+U2g

U1: Bacterial functional unit

U2f=gene of which the promoter is an RNA polymerase III promoter and of which the expression product is a short hairpin RNA (shRNA) precursor of a small interfering RNA targeting a gene X.

U2c=gene coding a transcriptional transactivator (example: protein TAT of VIH-1 or -2).

U2g=gene of which the promoter is dependent on the transactivator coded by the gene U2c and of which the expression product is a mutated version of the product of the gene X so as to be insensitive to the product of the gene U2f Example: Vector allowing suppression of the expression of the enzyme mB3Galt6 whilst overexpressing the expression of this enzyme in an inducible manner (possible complementation).

| U1  | ori-Amp |
| U2c | CMV promoter |
|     | Teton3G |
|     | BPA terminator |
| U2g | TRE3G promoter |
|     | mB3Galt6 - mutated |
|     | HSV Tk terminator |
| U2f | shRNA mB3GALT6 cassette |

List of the building blocks used for construction of the vector V3 (FIG. 17)

Building block Ori-AmpR BsaI B (SEQ ID NO: 36)

Building block pCMV BsaI B (SEQ ID NO: 37)

Building block TO3G BsaI A (SEQ ID NO: 59)

Building block BGHpA BsaI B (SEQ ID NO: 39)

Building block pTRE3G BsaI A (SEQ ID NO: 60)

Building block mB3Galt6 BsaI B (SEQ ID NO: 63)

GAGGTACCGGTCTCACCAGAGCATGAAGGTATTCCGGCGCGCTTGGCGGCACCGGGTGGCGCTGGGCCTAGGCG

GCCTGGCGTTCTGCGGCACCACTCTGTTGTACCTGGCGCGCTGCGCTTCCGAGGGCGAGACGCCCTCCGCTTCCGG

AGCCGCTCGGCCCCGCGCTAAGGCCTTCCTGGCGGTGCTGGTGGCCAGTGCGCCCCGCGCGGTCGAGCGCCGCAC

CGCAGTGCGCAGCACGTGGCTGGCACCGGAGAGGCGTGGCGGACCCGAGGACGTGTGGGCGCGCTTCGCCGTG

GGCACTGGCGGCTTAGGCTCGGAGGAGCGGCGCGCTCTTGAGCTCGAGCAGGCGCAGCACGGGGACCTGCTGCT

GCTGCCCGCCCTGCGCGACGCCTACGAGAACCTCACGGCCAAGGTCCTGGCCATGCTGACCTGGCTGGATGAGCG

CGTGGACTTCGAGTTCGTGCTCAAGGCGGACGACGACTCCTTTGCGCGCCTGGACGCTATCCTGGTGGACCTACGC

GCACGGGAGCCCGCACGCCGCCGGCGCCTCTACTGGGGCTTCTTTTCCGGGCGCGGGCGCGTCAAGCCGGGAGGT

CGCTGGCGAGAAGCAGCCTGGCAACTCTGCGACTACTACCTGCCCTACGCGTTGGGCGGTGGCTATGTCCTTTCTG

CGGACCTGGTGCATTACCTGCGCCTCAGCCGCGAGTACCTGCGCGCGTGGCACAGTGAAGACGTATCGCTGGGCA

CCTGGCTGGCACCAGTGGATGTGCAACGGGAGCACGACCCACGCTTCGACACGGAGTACAAATCTCGAGGCTGCA

ACAATCAGTATCTGGTGACACACAAGCAAAGCCCAGAGGACATGTTGGAGAAGCAACAGATGTTGCTGCATGAGG

```
GCCGGTTGTGCAAGCATGAGGTGCAACTTCGCCTTTCCTATGTCTATGACTGGTCAGCTCCACCCTCCCAGTGCTGC

CAGCGCAAGGAGGGCGTTCCCTGATGTCACCGCCGAGACCGGTACCTC
```

Building block Tkter BsaI B (SEQ ID NO: 64)
```
GAGGTACCGGTCTCACCGCGGGGGAGGCTAACTGAAACACGGAAGGAGACAATACCGGAAGGAACCCGCGCTAT

GACGGCAATAAAAAGACAGAATAAAACGCACGGTGTTGGGTCGTTTGTTCATAAACGCGGGGTTCGGTCCCAGGG

CTGGCACTCTGTCGATACCCCACCGAGGCCCCATTGGGGCCAATACGCCCGCGTTTCTTCCTTTTCCCCACCCCACCC

CCCAAGTTCGGGTGAAGGCCCAGGGCTCGCAGCCAACGTCGGGGCGGCAGGCCCTGCCATAGCCACAACGAGAC

CGGTACCTC
```

Building block shB3Galt6 BsaI C (SEQ ID NO: 65)
```
GAGGTACCGGTCTCAACAAACAGGGTCGACAAGCTTTTCCAAAAAAAAAGCATGAGGTGCAGTTGCGCCTTTCCTA

TCTCTTGAATAGGAAAGGCGCAACTGCACCTCATGCTGGATCCCGCGTCCTTTCCACAAGATATATAAACCCAAGAA

ATCGAAATACTTTCAAGTTACGGTAAGCATATGATAGTCCATTTTAAAACATAATTTTAAAACTGCAAACTACCCAA

GAAATTATTACTTTCTACGTCACGTATTTTGTACTAATATCTTTGTGTTTACAGTCAAATTAATTCTAATTATCTCTCTA

ACAGCCTTGTATCGTATATGCAAATATGAAGGAATCATGGGAAATAGGCCCTCTTCCTGCCCGACCTTGGCGCGCG

CTCGGCGCGCGGTCACGCTCCGTCACGTGGTGCGTTTTGTATTCGAGACCGGTACCTC
```

V3 (SEQ ID NO: 66, example of a vector of the group V3)
```
TATTGTAATACGGTTATCCACAGAATCAGGGGATAACGCAGGAAAGAACATGTGAGCAAAAGGCCAGCAAAAGGC

CAGGAACCGTAAAAAGGCCGCGTTGCTGGCGTTTTTCCATAGGCTCCGCCCCCCTGACGAGCATCACAAAAATCGAC

GCTCAAGTCAGAGGTGGCGAAACCCGACAGGACTATAAAGATACCAGGCGTTTCCCCCTGGAAGCTCCCTCGTGCG

CTCTCCTGTTCCGACCCTGCCGCTTACCGGATACCTGTCCGCCTTTCTCCCTTCGGGAAGCGTGGCGCTTTCTCATAGC

TCACGCTGTAGGTATCTCAGTTCGGTGTAGGTCGTTCGCTCCAAGCTGGGCTGTGTGCACGAACCCCCCGTTCAGCC

CGACCGCTGCGCCTTATCCGGTAACTATCGTCTTGAGTCCAACCCGGTAAGACACGACTTATCGCCACTGGCAGCAG

CCACTGGTAACAGGATTAGCAGAGCGAGGTATGTAGGCGGTGCTACAGAGTTCTTGAAGTGGTGGCCTAACTACGG

CTACACTAGAAGAACAGTATTTGGTATCTGCGCTCTGCTGAAGCCAGTTACCTTCGGAAAAAGAGTTGGTAGCTCTT

GATCCGGCAAACAAACCACCGCTGGTAGCGGTTTTTTTGTTTGCAAGCAGCAGATTACGCGCAGAAAAAAAGGATC

TCAAGAAGATCCTTTGATCTTTTCTACGGGGTCTGACGCTCAGTGGAACGAAAACTCACGTTAAGGGATTTTGGTCA

TGAGATTATCAAAAAGGATCTTCACCTAGATCCTTTTAAATTAAAAATGAAGTTTTAAATCAATCTAAAGTATATATG

AGTAAACTTGGTCTGACAGTTACCAATGCTTAATCAGTGAGGCACCTATCTCAGCGATCTGTCTATTTCGTTCATCCA

TAGTTGCCTGACTCCCCGTCGTGTAGATAACTACGATACGGGAGGGCTTACCATCTGGCCCCAGTGCTGCAATGATA

CCGCGTGACCCACGCTCACCGGCTCCAGATTTATCAGCAATAAACCAGCCAGCCGGAAGGGCCGAGCGCAGAAGTG

GTCCTGCAACTTTATCCGCCTCCATCCAGTCTATTAATTGTTGCCGGGAAGCTAGAGTAAGTAGTTCGCCAGTTAATA

GTTTGCGCAACGTTGTTGCCATTGCTACAGGCATCGTGGTGTCACGCTCGTCGTTTGGTATGGCTTCATTCAGCTCCG

GTTCCCAACGATCAAGGCGAGTTACATGATCCCCCATGTTGTGCAAAAAAGCGGTTAGCTCCTTCGGTCCTCCGATC

GTTGTCAGAAGTAAGTTGGCCGCAGTGTTATCACTCATGGTTATGGCAGCACTGCATAATTCTCTTACTGTCATGCCA

TCCGTAAGATGCTTTTCTGTGACTGGTGAGTACTCAACCAAGTCATTCTGAGAATAGTGTATGCGGCGACCGAGTTG

CTCTTGCCCGGCGTCAATACGGGATAATACCGCGCCACATAGCAGAACTTTAAAAGTGCTCATCATTGGAAAACGTT

CTTCGGGGCGAAAACTCTCAAGGATCTTACCGCTGTTGAGATCCAGTTCGATGTAACCCACTCGTGCACCCAACTGA

TCTTCAGCATCTTTTACTTTCACCAGCGTTTCTGGGTGAGCAAAAACAGGAAGGCAAAATGCCGCAAAAAAGGGAAT

AAGGGCGACACGGAAATGTTGAATACTCATACTCTTCCTTTTTCAATATTATTGAAGCATTTATCAGGGTTATTGTCTC

ATGAGCGGATACATATTTGAATGTATTTAGAAAAATAAACAAATAGGGGTTCCGCGCACATTTCCCCGAAAAGTGCC

AAGGAACCAATTCAGTCGACTGGATCCTAGTTATTAATAGTAATCAATTACGGGGTCATTAGTTCATAGCCCATATAT
```

-continued

```
GGAGTTCCGCGTTACATAACTTACGGTAAATGGCCCGCCTGGCTGACCGCCCAACGACCCCCGCCCATTGACGTCAA
TAATGACGTATGTTCCCATAGTAACGCCAATAGGGACTTTCCATTGACGTCAATGGGTGGAGTATTTACGGTAAACT
GCCCACTTGGCAGTACATCAAGTGTATCATATGCCAAGTACGCCCCCTATTGACGTCAATGACGGTAAATGGCCCGC
CTGGCATTATGCCCAGTACATGACCTTATGGGACTTTCCTACTTGGCAGTACATCTACGTATTAGTCATCGCTATTACC
ATGGTGATGCGGTTTTGGCAGTACATCAATGGGCGTGGATAGCGGTTTGACTCACGGGGATTTCCAAGTCTCCACCC
CATTGACGTCAATGGGAGTTTGTTTTGGCACCAAAATCAACGGGACTTTCCAAAATGTCGTAACAACTCCGCCCCATT
GACGCAAATGGGCGGTAGGCGTGTACGGTGGGAGGTCTATATAAGCAGAGCTGGTTTAGTGAACCGTCAGATCAC
TAGTCGACTAGGGATAACAGGGCACCATGTCTAGACTGGACAAGAGCAAAGTCATAAACTCTGCTCTGGAATTACTC
AATGGAGTCGGTATCGAAGGCCTGACGACAAGGAAACTCGCTCAAAAGCTGGGAGTTGAGCAGCCTACCCTGTACT
GGCACGTGAAGAACAAGCGGGCCCTGCTCGATGCCCTGCCAATCGAGATGCTGGACAGGCATCATACCCACTCCTG
CCCCCTGGAAGGCGAGTCATGGCAAGACTTTCTGCGGAACAACGCCAAGTCATACCGCTGTGCTCTCCTCTCACATC
GCGACGGGGCTAAAGTGCATCTCGGCACCCGCCCAACAGAGAAACAGTACGAAACCCTGGAAAATCAGCTCGCGTT
CCTGTGTCAGCAAGGCTTCTCCCTGGAGAACGCACTGTACGCTCTGTCCGCCGTGGGCCACTTTACACTGGGCTGCG
TATTGGAGGAACAGGAGCATCAAGTAGCAAAAGAGGAAAGAGAGACACCTACCACCGATTCTATGCCCCACTTCT
GAAACAAGCAATTGAGCTGTTCGACCGGCAGGGAGCCGAACCTGCCTTCCTTTTCGGCCTGGAACTAATCATATGTG
GCCTGGAGAAACAGCTAAAGTGCGAAAGCGGCGGGCCGACCGACGCCCTTGACGATTTTGACTTAGACATGCTCCC
AGCCGATGCCCTTGACGACTTTGACCTTGATATGCTGCCTGCTGACGCTCTTGACGATTTTGACCTTGACATGCTCCC
CGGGTAATGATCGACTGTGCCTTCTAGTTGCCAGCCATCTGTTGTTTGCCCCTCCCCCGTGCCTTCCTTGACCCTGGA
AGGTGCCACTCCCACTGTCCTTTCCTAATAAAATGAGGAAATTGCATCGCATTGTCTGAGTAGGTGTCATTCTATTCT
GGGGGGTGGGGTGGGGCAGGACAGCAAGGGGGAGGATTGGGAGGACAATAGCAGGCATGCTGGGGATGCGGT
GGGCTCTATGGCTTCGCTTTCGTCTTCAAGAATTCCTGGAGTTTACTCCCTATCAGTGATAGAGAACGTATGAAGAGT
TTACTCCCTATCAGTGATAGAGAACGTATGCAGACTTTACTCCCTATCAGTGATAGAGAACGTATAAGGAGTTTACTC
CCTATCAGTGATAGAGAACGTATGACCAGTTTACTCCCTATCAGTGATAGAGAACGTATCTACAGTTTACTCCCTATC
AGTGATAGAGAACGTATATCCAGTTTACTCCCTATCAGTGATAGAGAACGTATAAGCTTTAGGCGTGTACGGTGGGC
GCCTATAAAAGCAGAGCTCGTTTAGTGAACCGTCAGATCGCCTGGAGCAATTCCACAACACTTTTGTCTTATACCAAC
TTTCCGTACCACTTCCTACCCTCGTAAACCAGAGCATGAAGGTATTCCGGCGCGCTTGGCGGCACCGGGTGGCGCTG
GGCCTAGGCGGCCTGGCGTTCTGCGGCACCACTCTGTTGTACCTGGCGCGCTGCGCTTCCGAGGGCGAGACGCCCT
CCGCTTCCGGAGCCGCTCGGCCCCGCGCTAAGGCCTTCCTGGCGGTGCTGGTGGCCAGTGCGCCCCGCGCGGTCGA
GCGCCGCACCGCAGTGCGCAGCACGTGGCTGGCACCGGAGAGGCGTGGCGGACCCGAGGACGTGTGGGCGCGCT
TCGCCGTGGGCACTGGCGGCTTAGGCTCGGAGGAGCGGCGCGCTCTTGAGCTCGAGCAGGCGCAGCACGGGGACC
TGCTGCTGCTGCCCGCCCTGCGCGACGCCTACGAGAACCTCACGGCCAAGGTCCTGGCCATGCTGACCTGGCTGGAT
GAGCGCGTGGACTTCGAGTTCGTGCTCAAGGCGGACGACGACTCCTTTGCGCGCCTGGACGCTATCCTGGTGGACC
TACGCGCACGGGAGCCCGCACGCCGCCGGCGCCTCTACTGGGGCTTCTTTTCCGGGCGCGGGCGCGTCAAGCCGGG
AGGTCGCTGGCGAGAAGCAGCCTGGCAACTCTGCGACTACTACCTGCCCTACGCGTTGGGCGGTGGCTATGTCCTTT
CTGCGGACCTGGTGCATTACCTGCGCCTCAGCCGCGAGTACCTGCGCGCGTGGCACAGTGAAGACGTATCGCTGGG
CACCTGGCTGGCACCAGTGGATGTGCAACGGGAGCACGACCCACGCTTCGACACGGAGTACAAATCTCGAGGCTGC
AACAATCAGTATCTGGTGACACACAAGCAAAGCCCAGAGGACATGTTGGAGAAGCAACAGATGTTGCTGCATGAG
GGCCGGTTGTGCAAGCATGAGGTGCAACTTCGCCTTTCCTATGTCTATGACTGGTCAGCTCCACCCTCCCAGTGCTGC
CAGCGCAAGGAGGGCGTTCCCTATGTCACCGCGGGGAGGCTAACTGAAACACGGAAGGAGACAATACCGGAA
GGAACCCGCGCTATGACGGCAATAAAAAGACAGAATAAAACGCACGGTGTTGGGTCGTTTGTTCATAAACGCGGG
```

```
-continued
GTTCGGTCCCAGGGCTGGCACTCTGTCGATACCCCACCGAGGCCCCATTGGGGCCAATACGCCCGCGTTTCTTCCTTT

TCCCCACCCCACCCCCCAAGTTCGGGTGAAGGCCCAGGGCTCGCAGCCAACGTCGGGGCGGCAGGCCCTGCCATAG

CCACAAACAGGGTCGACAAGCTTTTCCAAAAAAAAAGCATGAGGTGCAGTTGCGCCTTTCCTATCTCTTGAATAGGA

AAGGCGCAACTGCACCTCATGCTGGATCCCGCGTCCTTTCCACAAGATATATAAACCCAAGAAATCGAAATACTTTCA

AGTTACGGTAAGCATATGATAGTCCATTTTAAAACATAATTTTAAAACTGCAAACTACCCAAGAAATTATTACTTTCTA

CGTCACGTATTTTGTACTAATATCTTTGTGTTTACAGTCAAATTAATTCTAATTATCTCTCTAACAGCCTTGTATCGTAT

ATGCAAATATGAAGGAATCATGGGAAATAGGCCCTCTTCCTGCCCGACCTTGGCGCGCGCTCGGCGCGCGGTCACG

CTCCGTCACGTGGTGCGTTTTG
```

The analysis of restriction by triple digestion NdeI, SalI, XhoI of embodiment 7 is illustrated in FIG. 18.

Functional verification of construction N°7: Eukaryotic cells (for example: 4T1 mouse breast cancer cells) are transfected with the vector V3 in accordance with a conventional protocol (for example lipotransfection or electroporation). After transfection, the cells are treated, or not, with 100-1000 ng·ml$^{-1}$ of doxycycline for 24 to 48 hours. The cells are then collected and lysed so as to extract therefrom the total RNAs and then generate the complementary DNAs (cDNA) by reverse transcription in accordance with a conventional protocol. These cDNAs are then used as matrix for quantitative PCR analysis in accordance with a conventional protocol.

Specific Conditions of the Quantitative PCR:

40 cycles of three subsequent steps are performed: denaturation 94° C.-30s; hybridisation 60° C.-30s; extension 72° C.-30s.

Primers Used:

```
                                          (SEQ ID NO: 42)
BETA3Galt6ms2-s ACCACTCTGTTGTACCTGGC.

(SEQ ID NO: 43)
BETA3Galt6ms2-as CACACGTCCTCGGGTCC.
```

Embodiment 8

V2b (Belonging to the Group of Vectors V2): Vector Allowing Expression of One or More Transgenes in an Inducible Manner. V2b is Distinguished from V2 by the Structuring of its Bacterial Functional Unit in Two Building Blocks Instead of One.

U1+U2c+nxU2d+mxU2e

U1: Bacterial functional unit

U2c=gene coding a transcriptional transactivator.

U2d=gene(s) of which the promoter is dependent on the transactivator coded by the gene U2c, n≥1

U2e=gene(s) of which the promoter is not dependent on the transactivator coded by the gene U2c, m≥0

Example: Vector Allowing Inducible Expression of the Enzyme mB3Galt6

| | |
|---|---|
| U1 | ori-Amp |
| U2c | CMV promoter |
| | Teton3G |
| | BPA terminator |
| U2d | TRE3G promoter |
| | mB3Galt6 |
| | HSV Tk terminator |

List of the building blocks used for construction of the vector V2b (FIG. 19)

```
Building block Ori BsaI A
                                                  (SEQ ID NO: 104)
GAGGTACCGGTCTCATATTGTAATACGGTTATCCACAGAATCAGGGGATAACGCAGGAAAGAACATGTGAGCAAA

AGGCCAGCAAAAGGCCAGGAACCGTAAAAAGGCCGCGTTGCTGGCGTTTTTCCATAGGCTCCGCCCCCCTGACGA

GCATCACAAAAATCGACGCTCAAGTCAGAGGTGGCGAAACCCGACAGGACTATAAAGATACCAGGCGTTTCCCCC

TGGAAGCTCCCTCGTGCGCTCTCCTGTTCCGACCCTGCCGCTTACCGGATACCTGTCCGCCTTTCTCCCTTCGGGAA

GCGTGGCGCTTTCTCATAGCTCACGCTGTAGGTATCTCAGTTCGGTGTAGGTCGTTCGCTCCAAGCTGGGCTGTGT

GCACGAACCCCCCGTTCAGCCCGACCGCTGCGCCTTATCCGGTAACTATCGTCTTGAGTCCAACCCGGTAAGACAC

GACTTATCGCCACTGGCAGCAGCCACTGGTAACAGGATTAGCAGAGCGAGGTATGTAGGCGGTGCTACAGAGTTC

TTGAAGTGGTGGCCTAACTACGGCTACACTAGAAGAACAGTATTTGGTATCTGCGCTCTGCTGAAGCCAGTTACCT

TCGGAAAAGAGTTGGTAGCTCTTGATCCGGCAAACAAACCACCGCTGGTAGCGGTTTTTTTGTTTGCAAGCAGCA

GATTACGCGCAGAAAAAAGGATCTCAAGAAGATCCTTTGATCTTTTCTACGGGGTCTGACGCTCAGTGGAACGAA

AACTCACGTTAAGGGATTTTGGTCATGAGATTATCAAAAAGGATCTTCACCTAGATCCTTTTAAATTAAAAATGAAG

TTTTAAATCAATCTAAAGTATATATGAGTTTTATGAGACCGGTACCTC
```

-continued

Building block AmpR BsaI A (SEQ ID NO: 105)
GAGGTACCGGTCTCTTTTATTGGTCTGACAGTTACCAATGCTTAATCAGTGAGGCACCTATCTCAGCGATCTGTCTA

TTTCGTTCATCCATAGTTGCCTGACTCCCCGTCGTGTAGATAACTACGATACGGGAGGGCTTACCATCTGGCCCCAG

TGCTGCAATGATACCGCGTGACCCACGCTCACCGGCTCCAGATTTATCAGCAATAAACCAGCCAGCCGGAAGGGCC

GAGCGCAGAAGTGGTCCTGCAACTTTATCCGCCTCCATCCAGTCTATTAATTGTTGCCGGGAAGCTAGAGTAAGTA

GTTCGCCAGTTAATAGTTTGCGCAACGTTGTTGCCATTGCTACAGGCATCGTGGTGTCACGCTCGTCGTTTGGTATG

GCTTCATTCAGCTCCGGTTCCCAACGATCAAGGCGAGTTACATGATCCCCCATGTTGTGCAAAAAAGCGGTTAGCTC

CTTCGGTCCTCCGATCGTTGTCAGAAGTAAGTTGGCCGCAGTGTTATCACTCATGGTTATGGCAGCACTGCATAATT

CTCTTACTGTCATGCCATCCGTAAGATGCTTTTCTGTGACTGGTGAGTACTCAACCAAGTCATTCTGAGAATAGTGT

ATGCGGCGACCGAGTTGCTCTTGCCCGGCGTCAATACGGGATAATACCGCGCCACATAGCAGAACTTTAAAAGTGC

TCATCATTGGAAAACGTTCTTCGGGGCGAAAACTCTCAAGGATCTTACCGCTGTTGAGATCCAGTTCGATGTAACCC

ACTCGTGCACCCAACTGATCTTCAGCATCTTTTACTTTCACCAGCGTTTCTGGGTGAGCAAAAACAGGAAGGCAAAA

TGCCGCAAAAAAGGGAATAAGGGCGACACGGAAATGTTGAATACTCATACTCTTCCTTTTTCAATATTATTGAAGC

ATTTATCAGGGTTATTGTCTCATGAGCGGATACATATTTGAATGTATTTAGAAAAATAAACAAATAGGGGTTCCGC

GCACATTTCCCCGAAAAGTGCCAAGGACGAGACCGGTACCTC

Building block pCMV BsaI B (SEQ ID NO: 37)

Building block TO3G BsaI A (SEQ ID NO: 59)

Building block BGHpA BsaI B (SEQ ID NO: 39)

Building block pTRE3G BsaI A (SEQ ID NO: 60)

Building block mb3Galt6 BsaI B (SEQ ID NO: 63)

Building block Tkter BsaI A (SEQ ID NO: 57)

Vector V2b (SEQ ID NO: 149, example of a vector of the group V2)
TATTGTAATACGGTTATCCACAGAATCAGGGGATAACGCAGGAAAGAACATGTGAGCAAAAGGCCAGCAAAAGG

CCAGGAACCGTAAAAAGGCCGCGTTGCTGGCGTTTTTCCATAGGCTCCGCCCCCCTGACGAGCATCACAAAAATCG

ACGCTCAAGTCAGAGGTGGCGAAACCCGACAGGACTATAAAGATACCAGGCGTTTCCCCCTGGAAGCTCCCTCGT

GCGCTCTCCTGTTCCGACCCTGCCGCTTACCGGATACCTGTCCGCCTTTCTCCCTTCGGGAAGCGTGGCGCTTTCTCA

TAGCTCACGCTGTAGGTATCTCAGTTCGGTGTAGGTCGTTCGCTCCAAGCTGGGCTGTGTGCACGAACCCCCCGTTC

AGCCCGACCGCTGCGCCTTATCCGGTAACTATCGTCTTGAGTCCAACCCGGTAAGACACGACTTATCGCCACTGGC

AGCAGCCACTGGTAACAGGATTAGCAGAGCGAGGTATGTAGGCGGTGCTACAGAGTTCTTGAAGTGGTGGCCTAA

CTACGGCTACACTAGAAGAACAGTATTTGGTATCTGCGCTCTGCTGAAGCCAGTTACCTTCGGAAAAAGAGTTGGT

AGCTCTTGATCCGGCAAACAAACCACCGCTGGTAGCGGTTTTTTTGTTTGCAAGCAGCAGATTACGCGCAGAAAAA

AAGGATCTCAAGAAGATCCTTTGATCTTTTCTACGGGGTCTGACGCTCAGTGGAACGAAAACTCACGTTAAGGGAT

TTTGGTCATGAGATTATCAAAAAGGATCTTCACCTAGATCCTTTTAAATTAAAAATGAAGTTTTAAATCAATCTAAAG

TATATATGAGTTTTATTGGTCTGACAGTTACCAATGCTTAATCAGTGAGGCACCTATCTCAGCGATCTGTCTATTTCG

TTCATCCATAGTTGCCTGACTCCCCGTCGTGTAGATAACTACGATACGGGAGGGCTTACCATCTGGCCCCAGTGCTG

CAATGATACCGCGTGACCCACGCTCACCGGCTCCAGATTTATCAGCAATAAACCAGCCAGCCGGAAGGGCCGAGC

GCAGAAGTGGTCCTGCAACTTTATCCGCCTCCATCCAGTCTATTAATTGTTGCCGGGAAGCTAGAGTAAGTAGTTCG

CCAGTTAATAGTTTGCGCAACGTTGTTGCCATTGCTACAGGCATCGTGGTGTCACGCTCGTCGTTTGGTATGGCTTC

-continued

```
ATTCAGCTCCGGTTCCCAACGATCAAGGCGAGTTACATGATCCCCCATGTTGTGCAAAAAAGCGGTTAGCTCCTTCG
GTCCTCCGATCGTTGTCAGAAGTAAGTTGGCCGCAGTGTTATCACTCATGGTTATGCAGCACTGCATAATTCTCTT
ACTGTCATGCCATCCGTAAGATGCTTTTCTGTGACTGGTGAGTACTCAACCAAGTCATTCTGAGAATAGTGTATGCG
GCGACCGAGTTGCTCTTGCCCGGCGTCAATACGGGATAATACCGCGCCACATAGCAGAACTTTAAAAGTGCTCATC
ATTGGAAAACGTTCTTCGGGGCGAAAACTCTCAAGGATCTTACCGCTGTTGAGATCCAGTTCGATGTAACCCACTC
GTGCACCCAACTGATCTTCAGCATCTTTTACTTTCACCAGCGTTTCTGGGTGAGCAAAAACAGGAAGGCAAAATGC
CGCAAAAAAGGGAATAAGGGCGACACGGAAATGTTGAATACTCATACTCTTCCTTTTTCAATATTATTGAAGCATTT
ATCAGGGTTATTGTCTCATGAGCGGATACATATTTGAATGTATTTAGAAAAATAAACAAATAGGGGTTCCGCGCAC
ATTTCCCCGAAAAGTGCCAAGGAACCAATTCAGTCGACTGGATCCTAGTTATTAATAGTAATCAATTACGGGGTCAT
TAGTTCATAGCCCATATATGGAGTTCCGCGTTACATAACTTACGGTAAATGGCCCGCCTGGCTGACCGCCCAACGA
CCCCCGCCCATTGACGTCAATAATGACGTATGTTCCCATAGTAACGCCAATAGGGACTTTCCATTGACGTCAATGGG
TGGAGTATTTACGGTAAACTGCCCACTTGGCAGTACATCAAGTGTATCATATGCCAAGTACGCCCCCTATTGACGTC
AATGACGGTAAATGGCCCGCCTGGCATTATGCCCAGTACATGACCTTATGGGACTTTCCTACTTGGCAGTACATCTA
CGTATTAGTCATCGCTATTACCATGGTGATGCGGTTTTGGCAGTACATCAATGGGCGTGGATAGCGGTTTGACTCA
CGGGGATTTCCAAGTCTCCACCCCATTGACGTCAATGGGAGTTTGTTTTGGCACCAAAATCAACGGGACTTTCCAAA
ATGTCGTAACAACTCCGCCCCATTGACGCAAATGGGCGGTAGGCGTGTACGGTGGGAGGTCTATATAAGCAGAGC
TGGTTTAGTGAACCGTCAGATCACTAGTCGACTAGGGATAACAGGGCACCATGTCTAGACTGGACAAGAGCAAAG
TCATAAACTCTGCTCTGGAATTACTCAATGGAGTCGGTATCGAAGGCCTGACGCACAAGGAAACTCGCTCAAAAGCT
GGGAGTTGAGCAGCCTACCCTGTACTGGCACGTGAAGAACAAGCGGGCCCTGCTCGATGCCCTGCCAATCGAGAT
GCTGGACAGGCATCATACCCACTCCTGCCCCCTGGAAGGCGAGTCATGGCAAGACTTTCTGCGGAACAACGCCAA
GTCATACCGCTGTGCTCTCCTCTCACATCGCGACGGGGCTAAAGTGCATCTCGGCACCCGCCCAACAGAGAAACAG
TACGAAACCCTGGAAAATCAGCTCGCGTTCCTGTGTCAGCAAGGCTTCTCCCTGGAGAACGCACTGTACGCTCTGT
CCGCCGTGGGCCACTTTACACTGGGCTGCGTATTGGAGGAACAGGAGCATCAAGTAGCAAAAGAGGAAAGAGAG
ACACCTACCACCGATTCTATGCCCCCACTTCTGAAACAAGCAATTGAGCTGTTCGACCGGCAGGGAGCCGAACCTG
CCTTCCTTTTCGGCCTGGAACTAATCATATGTGGCCTGGAGAAACAGCTAAAGTGCGAAAGCGGCGGGCCGACCG
ACGCCCTTGACGATTTTGACTTAGACATGCTCCCAGCCGATGCCCTTGACGACTTTGACCTTGATATGCTGCCTGCT
GACGCTCTTGACGATTTTGACCTTGACATGCTCCCCGGGTAATGATCGACTGTGCCTTCTAGTTGCCAGCCATCTGT
TGTTTGCCCCTCCCCCGTGCCTTCCTTGACCCTGGAAGGTGCCACTCCCACTGTCCTTTCCTAATAAAATGAGGAAAT
TGCATCGCATTGTCTGAGTAGGTGTCATTCTATTCTGGGGGGTGGGGTGGGGCAGGACAGCAAGGGGGAGGATT
GGGAGGACAATAGCAGGCATGCTGGGGATGCGGTGGGCTCTATGGCTTCGCTTTCGTCTTCAAGAATTCCTGGAG
TTTACTCCCTATCAGTGATAGAGAACGTATGAAGAGTTTACTCCCTATCAGTGATAGAGAACGTATGCAGACTTTAC
TCCCTATCAGTGATAGAGAACGTATAAGGAGTTTACTCCCTATCAGTGATAGAGAACGTATGACCAGTTTACTCCCT
ATCAGTGATAGAGAACGTATCTACAGTTTACTCCCTATCAGTGATAGAGAACGTATATCCAGTTTACTCCCTATCAG
TGATAGAGAACGTATAAGCTTTAGGCGTGTACGGTGGGCGCCTATAAAAGCAGAGCTCGTTTAGTGAACCGTCAG
ATCGCCTGGAGCAATTCCACAACACTTTTGTCTTATACCAACTTTCCGTACCACTTCCTACCCTCGTAAACCAGAGCA
TGAAGGTATTCCGGCGCGCTTGGCGGCACCGGGTGGCGCTGGGCCTAGGCGGCCTGGCGTTCTGCGGCACCACTC
TGTTGTACCTGGCGCGCTGCGCTTCCGAGGGCGAGACGCCCTCCGCTTCCGGAGCCGCTCGGCCCCGCGCTAAGG
CCTTCCTGGCGGTGCTGGTGGCCAGTGCGCCCCGCGCGGTCGAGCGCCGCACCGCAGTGCGCAGCACGTGGCTGG
CACCGGAGAGGCGTGGCGGACCCGAGGACGTGTGGGCGCGCTTCGCCGTGGGCACTGGCGGCTTAGGCTCGGAG
GAGCGGCGCGCTCTTGAGCTCGAGCAGGCGCAGCACGGGACCTGCTGCTGCTGCCCGCCCTGCGCGACGCCTAC
```

-continued
```
GAGAACCTCACGGCCAAGGTCCTGGCCATGCTGACCTGGCTGGATGAGCGCGTGGACTTCGAGTTCGTGCTCAAG

GCGGACGACGACTCCTTTGCGCGCCTGGACGCTATCCTGGTGGACCTACGCGCACGGGAGCCCGCACGCCGCCGG

CGCCTCTACTGGGGCTTCTTTTCCGGGCGCGGGCGCGTCAAGCCGGGAGGTCGCTGGCGAGAAGCAGCCTGGCAA

CTCTGCGACTACTACCTGCCCTACGCGTTGGGCGGTGGCTATGTCCTTTCTGCGGACCTGGTGCATTACCTGCCT

CAGCCGCGAGTACCTGCGCGCGTGGCACAGTGAAGACGTATCGCTGGGCACCTGGCTGGCACCAGTGGATGTGCA

ACGGGAGCACGACCCACGCTTCGACACGGAGTACAAATCTCGAGGCTGCAACAATCAGTATCTGGTGACACACAA

GCAAAGCCCAGAGGACATGTTGGAGAAGCAACAGATGTTGCTGCATGAGGGCCGGTTGTGCAAGCATGAGGTGC

AACTTCGCCTTTCCTATGTCTATGACTGGTCAGCTCCACCCTCCCAGTGCTGCCAGCGCAAGGAGGGCGTTCCCTGA

TGTCACCGCGGGGGAGGCTAACTGAAACACGGAAGGAGACAATACCGGAAGGAACCCGCGCTATGACGGCAATA

AAAAGACAGAATAAAACGCACGGTGTTGGGTCGTTTGTTCATAAACGCGGGGTTCGGTCCCAGGGCTGGCACTCT

GTCGATACCCCACCGAGGCCCCATTGGGGCCAATACGCCCGCGTTTCTTCCTTTTCCCCACCCCACCCCCCAAGTTC

GGGTGAAGGCCCAGGGCTCGCAGCCAACGTCGGGGCGGCAGGCCCTGCCATAGCC
```

The restriction fingerprint by triple digestion (structural validation), NdeI, SalI, XhoI, of embodiment 8 is illustrated in FIG. 20.

Functional verification of embodiment 8: Eukaryotic cells (for example: 4T1 mouse breast cancer cells) are transfected with the vector V2b in accordance with a conventional protocol (for example lipotransfection or electroporation). After transfection, the cells are treated with 100-1000 ng·mL$^{-1}$ of doxycycline for 24 to 48 hours. The cells are then collected and lysed so as to extract therefrom the total RNAs and then generate the complementary DNAs (cDNA) by reverse transcription in accordance with a conventional protocol. These cDNAs are then used as matrix for quantitative PCR analysis in accordance with a conventional protocol. (FIG. 21)

The experiment shows that the expression of the transcript mB3Galt6, coded by the vector V2b, is increased in the 4T1 cell solely in the presence of doxycycline, demonstrating the concomitant presences of an inducible transgene and its co-activator in the vector V2b.

Specific Conditions of the Quantitative PCR:

40 cycles of three subsequent steps are performed: denaturation 94° C.-30s; hybridisation 60° C.-30s; extension 72° C.-30s.

Primers Used:

```
                                         (SEQ ID NO: 42)
BETA3Galt6ms2-s ACCACTCTGTTGTACCTGGC.

(SEQ ID NO: 43)
BETA3Galt6ms2-as CACACGTCCTCGGGTCC.
```

Embodiment 9

V3b: (Belonging to the Group of Vectors V3) Vector Allowing Execution of the Genetic Complementation Under Inducible Control. V3b is Distinguished from V3 by the Structuring of its Bacterial Functional Unit in Two Building Blocks Instead of One.

U1+U2f+U2c+U2g

U1: Bacterial functional unit

U2f=gene of which the promoter is an RNA polymerase III promoter and of which the expression product is a short hairpin RNA (shRNA) precursor of a small interfering RNA targeting a gene X.

U2c=gene coding a transcriptional transactivator (example: protein TAT of VIH-1 or -2).

U2g=gene of which the promoter is dependent of the transactivator coded by the gene U2c and of which the expression product is a mutated version of the product of the gene X so as to be insensitive to the product of the gene U2f Example: Vector allowing suppression of the expression of the enzyme mB3Galt6 whilst overexpressing the expression of this enzyme in an inducible manner (possible complementation).

| U1 | Ori AmpR |
|---|---|
| U2c | CMV promoter |
| | Teton3G |
| | BPA terminator |
| U2g | TRE3G promoter |
| | mB3Galt6 - mutated |
| | HSV Tk terminator |
| U2f | shRNA mB3Galt6 cassette |

List of the building blocks used for construction of the vector V3b (FIG. 22)

```
Building block Ori Bsal A
                                        (SEQ ID NO: 104)

Building block AmpR Bsal A
                                        (SEQ ID NO: 105)

Building block pCMV Bsal B
                                        (SEQ ID NO: 37)

Building block TO3G Bsal A
                                        (SEQ ID NO: 59)
```

-continued

Building block BGHpA BsaI B
(SEQ ID NO: 39)

Building block pTRE3G BsaI A
(SEQ ID NO: 60)

Building block mb3Galt6 BsaI B
(SEQ ID NO: 63)

Building block Tkter BsaI B
(SEQ ID NO: 64)

Building block shB3Galt6 BsaI C
(SEQ ID NO: 65)

Vector V3b (SEQ ID NO: 150, example of a vector of the group V3)
TATTGTAATACGGTTATCCACAGAATCAGGGGATAACGCAGGAAAGAACATGTGAGCAAAAGGCCAGCAAAAGG

CCAGGAACCGTAAAAAGGCCGCGTTGCTGGCGTTTTTCCATAGGCTCCGCCCCCCTGACGAGCATCACAAAAATCG

ACGCTCAAGTCAGAGGTGGCGAAACCCGACAGGACTATAAAGATACCAGGCGTTTCCCCCTGGAAGCTCCCTCGT

GCGCTCTCCTGTTCCGACCCTGCCGCTTACCGGATACCTGTCCGCCTTTCTCCCTTCGGGAAGCGTGGCGCTTTCTCA

TAGCTCACGCTGTAGGTATCTCAGTTCGGTGTAGGTCGTTCGCTCCAAGCTGGGCTGTGTGCACGAACCCCCCGTTC

AGCCCGACCGCTGCGCCTTATCCGGTAACTATCGTCTTGAGTCCAACCCGGTAAGACACGACTTATCGCCACTGGC

AGCAGCCACTGGTAACAGGATTAGCAGAGCGAGGTATGTAGGCGGTGCTACAGAGTTCTTGAAGTGGTGGCCTAA

CTACGGCTACACTAGAAGAACAGTATTTGGTATCTGCGCTCTGCTGAAGCCAGTTACCTTCGGAAAAAGAGTTGGT

AGCTCTTGATCCGGCAAACAAACCACCGCTGGTAGCGGTTTTTTTGTTTGCAAGCAGCAGATTACGCGCAGAAAAA

AAGGATCTCAAGAAGATCCTTTGATCTTTTCTACGGGGTCTGACGCTCAGTGGAACGAAAACTCACGTTAAGGGAT

TTTGGTCATGAGATTATCAAAAAGGATCTTCACCTAGATCCTTTTAAATTAAAAATGAAGTTTTAAATCAATCTAAAG

TATATATGAGTTTTATTGGTCTGACAGTTACCAATGCTTAATCAGTGAGGCACCTATCTCAGCGATCTGTCTATTTCG

TTCATCCATAGTTGCCTGACTCCCCGTCGTGTAGATAACTACGATACGGGAGGGCTTACCATCTGGCCCCAGTGCTG

CAATGATACCGCGTGACCCACGCTCACCGGCTCCAGATTTATCAGCAATAAACCAGCCAGCCGGAAGGGCCGAGC

GCAGAAGTGGTCCTGCAACTTTATCCGCCTCCATCCAGTCTATTAATTGTTGCCGGGAAGCTAGAGTAAGTAGTTCG

CCAGTTAATAGTTTGCGCAACGTTGTTGCCATTGCTACAGGCATCGTGGTGTCACGCTCGTCGTTTGGTATGGCTTC

ATTCAGCTCCGGTTCCCAACGATCAAGGCGAGTTACATGATCCCCCATGTTGTGCAAAAAAGCGGTTAGCTCCTTCG

GTCCTCCGATCGTTGTCAGAAGTAAGTTGGCCGCAGTGTTATCACTCATGGTTATGGCAGCACTGCATAATTCTCTT

ACTGTCATGCCATCCGTAAGATGCTTTTCTGTGACTGGTGAGTACTCAACCAAGTCATTCTGAGAATAGTGTATGCG

GCGACCGAGTTGCTCTTGCCCGGCGTCAATACGGGATAATACCGCGCCACATAGCAGAACTTTAAAAGTGCTCATC

ATTGGAAAACGTTCTTCGGGGCGAAAACTCTCAAGGATCTTACCGCTGTTGAGATCCAGTTCGATGTAACCCACTC

GTGCACCCAACTGATCTTCAGCATCTTTTACTTTCACCAGCGTTTCTGGGTGAGCAAAAACAGGAAGGCAAAATGC

CGCAAAAAAGGGAATAAGGGCGACACGGAAATGTTGAATACTCATACTCTTCCTTTTTCAATATTATTGAAGCATTT

ATCAGGGTTATTGTCTCATGAGCGGATACATATTTGAATGTATTTAGAAAAATAAACAAATAGGGGTTCCGCGCAC

ATTTCCCCGAAAAGTGCCAAGGAACCAATTCAGTCGACTGGATCCTAGTTATTAATAGTAATCAATTACGGGGTCAT

TAGTTCATAGCCCATATATGGAGTTCCGCGTTACATAACTTACGGTAAATGGCCCGCCTGGCTGACCGCCCAACGA

CCCCCGCCCATTGACGTCAATAATGACGTATGTTCCCATAGTAACGCCAATAGGGACTTTCCATTGACGTCAATGGG

TGGAGTATTTACGGTAAACTGCCCACTTGGCAGTACATCAAGTGTATCATATGCCAAGTACGCCCCCTATTGACGTC

AATGACGGTAAATGGCCCGCCTGGCATTATGCCCAGTACATGACCTTATGGGACTTTCCTACTTGGCAGTACATCTA

CGTATTAGTCATCGCTATTACCATGGTGATGCGGTTTTGGCAGTACATCAATGGGCGTGGATAGCGGTTTGACTCA

CGGGGATTTCCAAGTCTCCACCCCATTGACGTCAATGGGAGTTTGTTTTGGCACCAAAATCAACGGGACTTTCCAAA

ATGTCGTAACAACTCCGCCCCATTGACGCAAATGGGCGGTAGGCGTGTACGGTGGGAGGTCTATATAAGCAGAGC

```
TGGTTTAGTGAACCGTCAGATCACTAGTCGACTAGGGATAACAGGGCACCATGTCTAGACTGGACAAGAGCAAAG
TCATAAACTCTGCTCTGGAATTACTCAATGGAGTCGGTATCGAAGGCCTGACGACAAGGAAACTCGCTCAAAAGCT
GGGAGTTGAGCAGCCTACCCTGTACTGGCACGTGAAGAACAAGCGGGCCCTGCTCGATGCCCTGCCAATCGAGAT
GCTGGACAGGCATCATACCCACTCCTGCCCCCTGGAAGGCGAGTCATGGCAAGACTTTCTGCGGAACAACGCCAA
GTCATACCGCTGTGCTCTCCTCTCACATCGCGACGGGGCTAAAGTGCATCTCGGCACCCGCCCAACAGAGAAACAG
TACGAAACCCTGGAAAATCAGCTCGCGTTCCTGTGTCAGCAAGGCTTCTCCCTGGAGAACGCACTGTACGCTCTGT
CCGCCGTGGGCCACTTTACACTGGGCTGCGTATTGGAGGAACAGGAGCATCAAGTAGCAAAAGAGGAAAGAGAG
ACACCTACCACCGATTCTATGCCCCCACTTCTGAAACAAGCAATTGAGCTGTTCGACCGGCAGGGAGCCGAACCTG
CCTTCCTTTTCGGCCTGGAACTAATCATATGTGGCCTGGAGAAACAGCTAAAGTGCGAAAGCGGCGGGCCGACCG
ACGCCCTTGACGATTTTGACTTAGACATGCTCCCAGCCGATGCCCTTGACGACTTTGACCTTGATATGCTGCCTGCT
GACGCTCTTGACGATTTTGACCTTGACATGCTCCCCGGGTAATGATCGACTGTGCCTTCTAGTTGCCAGCCATCTGT
TGTTTGCCCCTCCCCCGTGCCTTCCTTGACCCTGGAAGGTGCCACTCCCACTGTCCTTTCCTAATAAAATGAGGAAAT
TGCATCGCATTGTCTGAGTAGGTGTCATTCTATTCTGGGGGGTGGGGTGGGGCAGGACAGCAAGGGGGAGGATT
GGGAGGACAATAGCAGGCATGCTGGGGATGCGGTGGGCTCTATGGCTTCGCTTTCGTCTTCAAGAATTCCTGGAG
TTTACTCCCTATCAGTGATAGAGAACGTATGAAGAGTTTACTCCCTATCAGTGATAGAGAACGTATGCAGACTTTAC
TCCCTATCAGTGATAGAGAACGTATAAGGAGTTTACTCCCTATCAGTGATAGAGAACGTATGACCAGTTTACTCCCT
ATCAGTGATAGAGAACGTATCTACAGTTTACTCCCTATCAGTGATAGAGAACGTATATCCAGTTTACTCCCTATCAG
TGATAGAGAACGTATAAGCTTTAGGCGTGTACGGTGGGCGCCTATAAAAGCAGAGCTCGTTTAGTGAACCGTCAG
ATCGCCTGGAGCAATTCCACAACACTTTTGTCTTATACCAACTTTCCGTACCACTTCCTACCCTCGTAAACCAGAGCA
TGAAGGTATTCCGGCGCGCTTGGCGGCACCGGGTGGCGCTGGGCCTAGGCGGCCTGGCGTTCTGCGGCACCACTC
TGTTGTACCTGGCGCGCTGCGCTTCCGAGGGCGAGACGCCCTCCGCTTCCGGAGCCGCTCGGCCCCGCGCTAAGG
CCTTCCTGGCGGTGCTGGTGGCCAGTGCGCCCCGCGCGGTCGAGCGCCGCACCGCAGTGCGCAGCACGTGGCTGG
CACCGGAGAGGCGTGGCGGACCCGAGGACGTGTGGGCGCGCTTCGCCGTGGGCACTGGCGGCTTAGGCTCGGAG
GAGCGGCGCGCTCTTGAGCTCGAGCAGGCGCAGCACGGGGACCTGCTGCTGCTGCCCGCCCTGCGCGACGCCTAC
GAGAACCTCACGGCCAAGGTCCTGGCCATGCTGACCTGGCTGGATGAGCGCGTGGACTTCGAGTTCGTGCTCAAG
GCGGACGACGACTCCTTTGCGCGCCTGGACGCTATCCTGGTGGACCTACGCGCACGGGAGCCCGCACGCCGCCGG
CGCCTCTACTGGGCGCTTCTTTTCCGGGCGCGGGCGCGTCAAGCCGGGAGGTCGCTGGCGAGAAGCAGCCTGGCAA
CTCTGCGACTACTACCTGCCCTACGCGTTGGGCGGTGGCTATGTCCTTTCTGCGGACCTGGTGCATTACCTGCGCCT
CAGCCGCGAGTACCTGCGCGCGTGGCACAGTGAAGACGTATCGCTGGGCACCTGGCTGGCACCAGTGGATGTGCA
ACGGGAGCACGACCCACGCTTCGACACGGAGTACAAATCTCGAGGCTGCAACAATCAGTATCTGGTGACACACAA
GCAAAGCCCAGAGGACATGTTGGAGAAGCAACAGATGTTGCTGCATGAGGGCCGGTTGTGCAAGCATGAGGTGC
AACTTCGCCTTTCCTATGTCTATGACTGGTCAGCTCCACCCTCCCAGTGCTGCCAGCGCAAGGAGGGCGTTCCCTGA
TGTCACCGCGGGGGAGGCTAACTGAAACACGGAAGGAGACAATACCGGAAGGAACCCGCGCTATGACGGCAATA
AAAAGACAGAATAAAACGCACGGTGTTGGGTCGTTTGTTCATAAACGCGGGGTTCGGTCCCAGGGCTGGCACTCT
GTCGATACCCCACCGAGGCCCCATTGGGGCCAATACGCCCGCGTTTCTTCCTTTTCCCCACCCCACCCCCCAAGTTC
GGGTGAAGGCCCAGGGCTCGCAGCCAACGTCGGGGCGGCAGGCCCTGCCATAGCCACAAACAGGGTCGACAAGC
TTTTCCAAAAAAAAAGCATGAGGTGCAGTTGCGCCTTTCCTATCTCTTGAATAGGAAAGGCGCAACTGCACCTCAT
GCTGGATCCCGCGTCCTTTCCACAAGATATATAAACCCAAGAAATCGAAATACTTTCAAGTTACGGTAAGCATATGA
TAGTCCATTTTAAAACATAATTTTAAAACTGCAAACTACCCAAGAAATTATTACTTTCTACGTCACGTATTTTGTACTA
```

```
ATATCTTTGTGTTTACAGTCAAATTAATTCTAATTATCTCTCTAACAGCCTTGTATCGTATATGCAAATATGAAGGAA

TCATGGGAAATAGGCCCTCTTCCTGCCCGACCTTGGCGCGCGCTCGGCGCGCGGTCACGCTCCGTCACGTGGTGCG

TTTTG
```

The restriction fingerprint by triple digestion (structural validation), NdeI, SalI, XhoI, of embodiment 9 is illustrated in FIG. 23.

Embodiment 10

V1.1b: (Belonging to the Group of Vectors V1.1) Vector Allowing Selection of the Integration of Transgenes by Non-Homologous Recombination in the Target Genome. This Vector is Distinguished from the Vector V1.1 by the Structuring of its Bacterial Functional Unit in Two Building Blocks Instead of One.

U1+U2+U3a
- U1: Bacterial functional unit
- U2: nxU2a+mxU2b, n≥0, m≥0 and n+m≥2
- U2a: Expression functional unit of which the promoter is dependent on RNA polymerase II and of which the expression product is a protein U3a: positive selection cassette Example: Vector allowing expression of two fusion proteins formed of a fluorescent domain and a specific cell compartment-addressing domain (here, cell membrane and Golgi apparatus).

| | |
|---|---|
| U1 | Ori AmpR |
| U2a-1 | EF1alpha promoter |
| | fusion protein EGFP-CAAX |
| | BPA terminator |
| U2a-2 | CMV promoter |
| | N-terminal domain of fusion protein: SiaT |
| | C-terminal domain of fusion protein: mCherry |
| | HSV-TK terminator |
| U3a | hygromycin resistance |

List of the building blocks used for construction of the vector V1.1b (FIG. 24)

```
Building block Ori BsaI B
                                                           (SEQ ID NO: 106)
GAGGTACCGGTCTCTATTACGGTAATACGGTTATCCACAGAATCAGGGGATAACGCAGGAAAGAACATGTGAGCA

AAAGGCCAGCAAAAGGCCAGGAACCGTAAAAAGGCCGCGTTGCTGGCGTTTTTCCATAGGCTCCGCCCCCCTGAC

GAGCATCACAAAAATCGACGCTCAAGTCAGAGGTGGCGAAACCCGACAGGACTATAAAGATACCAGGCGTTTCCC

CCTGGAAGCTCCCTCGTGCGCTCTCCTGTTCCGACCCTGCCGCTTACCGGATACCTGTCCGCCTTTCTCCCTTCGGGA

AGCGTGGCGCTTTCTCATAGCTCACGCTGTAGGTATCTCAGTTCGGTGTAGGTCGTTCGCTCCAAGCTGGGCTGTG

TGCACGAACCCCCCGTTCAGCCCGACCGCTGCGCCTTATCCGGTAACTATCGTCTTGAGTCCAACCCGGTAAGACAC

GACTTATCGCCACTGGCAGCAGCCACTGGTAACAGGATTAGCAGAGCGAGGTATGTAGGCGGTGCTACAGAGTTC

TTGAAGTGGTGGCCTAACTACGGCTACACTAGAAGAACAGTATTTGGTATCTGCGCTCTGCTGAAGCCAGTTACCT

TCGGAAAAAGAGTTGGTAGCTCTTGATCCGGCAAACAAACCACCGCTGGTAGCGGTTTTTTTGTTTGCAAGCAGCA

GATTACGCGCAGAAAAAAAGGATCTCAAGAAGATCCTTTGATCTTTTCTACGGGGTCTGACGCTCAGTGGAACGAA

AACTCACGTTAAGGGATTTTGGTCATGAGATTATCAAAAAGGATCTTCACCTAGATCCTTTTAAATTAAAAATGAAG

TTTTAAATCAATCTAAAGTATATATGAGTAAACCGAGACCGGTACCTC

Building block AmpR BsaI B
                                                           (SEQ ID NO: 107)
GAGGTACCGGTCTCAAAACTTGGTCTGACAGTTACCAATGCTTAATCAGTGAGGCACCTATCTCAGCGATCTGTCTA

TTTCGTTCATCCATAGTTGCCTGACTCCCCGTCGTGTAGATAACTACGATACGGGAGGGCTTACCATCTGGCCCCAG

TGCTGCAATGATACCGCGTGACCCACGCTCACCGGCTCCAGATTTATCAGCAATAAACCAGCCAGCCGGAAGGGCC

GAGCGCAGAAGTGGTCCTGCAACTTTATCCGCCTCCATCCAGTCTATTAATTGTTGCCGGGAAGCTAGAGTAAGTA

GTTCGCCAGTTAATAGTTTGCGCAACGTTGTTGCCATTGCTACAGGCATCGTGGTGTCACGCTCGTCGTTTGGTATG

GCTTCATTCAGCTCCGGTTCCCAACGATCAAGGCGAGTTACATGATCCCCCATGTTGTGCAAAAAGCGGTTAGCTC

CTTCGGTCCTCCGATCGTTGTCAGAAGTAAGTTGGCCGCAGTGTTATCACTCATGGTTATGGCAGCACTGCATAATT

CTCTTACTGTCATGCCATCCGTAAGATGCTTTTCTGTGACTGGTGAGTACTCAACCAAGTCATTCTGAGAATAGTGT

ATGCGGCGACCGAGTTGCTCTTGCCCGGCGTCAATACGGGATAATACCGCGCCACATAGCAGAACTTTAAAAGTGC

TCATCATTGGAAAACGTTCTTCGGGGCGAAAACTCTCAAGGATCTTACCGCTGTTGAGATCCAGTTCGATGTAACCC
```

-continued

ACTCGTGCACCCAACTGATCTTCAGCATCTTTTACTTTCACCAGCGTTTCTGGGTGAGCAAAAACAGGAAGGCAAAA

TGCCGCAAAAAAGGGAATAAGGGCGACACGGAAATGTTGAATACTCATACTCTTCCTTTTTCAATATTATTGAAGC

ATTTATCAGGGTTATTGTCTCATGAGCGGATACATATTTGAATGTATTTAGAAAAATAAACAAATAGGGGTTCCGC

GCACATTTCCCCGAAAAGTGCCAATGCTGAGACCGGTACCTC

Building block pEF1aL BsaI B (SEQ ID NO: 108)

GAGGTACCGGTCTCAATGCGTGAGGCTCCGGTGCCCGTCAGTGGGCAGAGCGCACATCGCCCACAGTCCCCGAGA

AGTTGGGGGGAGGGGTCGGCAATTGAACCGGTGCCTAGAGAAGGTGGCGCGGGGTAAACTGGGAAAGTGATGT

CGTGTACTGGCTCCGCCTTTTTCCCGAGGGTGGGGGAGAACCGTATATAAGTGCAGTAGTCGCCGTGAACGTTCTT

TTTCGCAACGGGTTTGCCGCCAGAACACAGGTAAGTGCCGTGTGTGGTTCCCGCGGGCCTGGCCTCTTTACGGGTT

ATGGCCCTTGCGTGCCTTGAATTACTTCCACCTGGCTGCAGTACGTGATTCTTGATCCCGAGCTTCGGGTTGGAAGT

GGGTGGGAGAGTTCGAGGCCTTGCGCTTAAGGAGCCCCTTCGCCTCGTGCTTGAGTTGAGGCCTGGCCTGGGCGC

TGGGGCCGCCGCGTGCGAATCTGGTGGCACCTTCGCGCCTGTCTCGCTGCTTTCGATAAGTCTCTAGCCATTTAAAA

TTTTTGATGACCTGCTGCGACGCTTTTTTTCTGGCAAGATAGTCTTGTAAATGCGGGCCAAGATCTGCACACTGGTA

TTTCGGTTTTTGGGGCCGCGGGCGGCGACGGGGCCCGTGCGTCCCAGCGCACATGTTCGGCGAGGCGGGGCCTG

CGAGCGCGGCCACCGAGAATCGGACGGGGGTAGTCTCAAGCTGGCCGGCCTGCTCTGGTGCCTGGCCTCGCGCCG

CCGTGTATCGCCCCGCCCTGGGCGGCAAGGCTGGCCCGGTCGGCACCAGTTGCGTGAGCGGAAAGATGGCCGCTT

CCCGGCCCTGCTGCAGGGAGCTCAAAATGGAGGACGCGGCGCTCGGGAGAGCGGGCGGGTGAGTCACCCACACA

AAGGAAAAGGGCCTTTCCGTCCTCAGCCGTCGCTTCATGTGACTCCACGGAGTACCGGGCGCCGTCCAGGCACCTC

GATTAGTTCTCGAGCTTTTGGAGTACGTCGTCTTTAGGTTGGGGGGAGGGGTTTTATGCGATGGAGTTTCCCCACA

CTGAGTGGGTGGAGACTGAAGTTAGGCCAGCTTGGCACTTGATGTAATTCTCCTTGGAATTTGCCCTTTTTGAGTTT

GGATCTTGGTTCATTCTCAAGCCTCAGACAGTGGTTCAAAGTTTTTTTCTTCCATTTCAGGTGTCGTGATATCCGAGA

CCGGTACCTC

Building block EGFP-CAAX BsaI A (SEQ ID NO: 109)

GAGGTACCGGTCTCCTATCATGGTGAGCAAGGGCGAGGAGCTGTTCACCGGGGTGGTGCCCATCCTGGTCGAGCT

GGACGGCGACGTAAACGGCCACAAGTTCAGCGTGTCCGGCGAGGGCGAGGGCGATGCCACCTACGGCAAGCTGA

CCCTGAAGTTCATCTGCACCACCGGCAAGCTGCCCGTGCCCTGGCCCACCCTCGTGACCACCCTGACCTACGGCGT

GCAGTGCTTCAGCCGCTACCCCGACCACATGAAGCAGCACGACTTCTTCAAGTCCGCCATGCCCGAAGGCTACGTC

CAGGAGCGCACCATCTTCTTCAAGGACGACGGCAACTACAAGACCCGCGCCGAGGTGAAGTTCGAGGGCGACACC

CTGGTGAACCGCATCGAGCTGAAGGGCATCGACTTCAAGGAGGACGGCAACATCCTGGGGCACAAGCTGGAGTA

CAACTACAACAGCCACAACGTCTATATCATGGCCGACAAGCAGAAGAACGGCATCAAGGTGAACTTCAAGATCCG

CCACAACATCGAGGACGGCAGCGTGCAGCTCGCCGACCACTACCAGCAGAACACCCCCATCGGCGACGGCCCCGT

GCTGCTGCCCGACAACCACTACCTGAGCACCCAGTCCGCCCTGAGCAAAGACCCCAACGAGAAGCGCGATCACAT

GGTCCTGCTGGAGTTCGTGACCGCCGCCGGGATCACTCTCGGCATGGACGAGCTGTACAAGAAGAAGAAAAAGAA

GTCAAAGACAAAGTGTGTAATTATGTAAGAGTGGAGACCGGTACCTC

Building block BGHpA BsaI C (SEQ ID NO: 110)

GAGGTACCGGTCTCAGAGTCGACTGTGCCTTCTAGTTGCCAGCCATCTGTTGTTTGCCCCTCCCCCGTGCCTTCCTTG

ACCCTGGAAGGTGCCACTCCCACTGTCCTTTCCTAATAAAATGAGGAAATTGCATCGCATTGTCTGAGTAGGTGTCA

TTCTATTCTGGGGGGTGGGGTGGGGCAGGACAGCAAGGGGGAGGATTGGGAGGACAATAGCAGGCATGCTGGG

GATGCGGTGGGCTCTATGGGTAGCGAGACCGGTACCTC

-continued

Building block pCMV BsaI D (SEQ ID NO: 111)
GAGGTACCGGTCTCAGTAGTTATTAATAGTAATCAATTACGGGGTCATTAGTTCATAGCCCATATATGGAGTTCCGC

GTTACATAACTTACGGTAAATGGCCCGCCTGGCTGACCGCCCAACGACCCCCGCCCATTGACGTCAATAATGACGT

ATGTTCCCATAGTAACGCCAATAGGGACTTTCCATTGACGTCAATGGGTGGAGTATTTACGGTAAACTGCCCACTTG

GCAGTACATCAAGTGTATCATATGCCAAGTACGCCCCCTATTGACGTCAATGACGGTAAATGGCCCGCCTGGCATT

ATGCCCAGTACATGACCTTATGGGACTTTCCTACTTGGCAGTACATCTACGTATTAGTCATCGCTATTACCATGGTG

ATGCGGTTTTGGCAGTACATCAATGGGCGTGGATAGCGGTTTGACTCACGGGGATTTCCAAGTCTCCACCCCATTG

ACGTCAATGGGAGTTTGTTTTGGCACCAAAATCAACGGGACTTTCCAAAATGTCGTAACAACTCCGCCCCATTGAC

GCAAATGGGCGGTAGGCGTGTACGGTGGGAGGTCTATATAAGCAGAGCTGGTTTAGTGAACCGTCAGATCTTCGC

GAGACCGGTACCTC

Building block SiaT BsaI B (SEQ ID NO: 112)
GAGGTACCGGTCTCCTTCGATGATTCACACCAACCTGAAGAAAAAGTTCAGCTGCTGCGTCCTGGTCTTTCTTCTGT

TTGCAGTCATCTGTGTGTGGAAGGAAAAGAAGAAAGGGAGTTACTATGATTCCTTTAAATTGCAAACCAAGGAATT

CCAGGTGTTAAAGAGTCTGGGGAAATTGGCCATGGGGTCTGATTCCCAGTCTGTATCCTCAAGCAGCACCCAGGAC

CCCCACAGGGGCCGCCAGACCCTCGGCAGTCTCAGAGGCCTAGCCAAGGCCAAACCAGAGGCCTCCTTCCAGGTG

TGGAACAAGGACAGCTCTTCCAAAAACCTTATCCCTAGGCTGCAAAAGGGGTCGGGGGTGATGAGACCGGTACCTC

Building block mCherry BsaI B (SEQ ID NO: 113)
GAGGTACCGGTCTCAGTGAGCAAGGGCGAGGAGGATAACATGGCCATCATCAAGGAGTTCATGCGCTTCAAGGT

GCACATGGAGGGCTCCGTGAACGGCCACGAGTTCGAGATCGAGGGCGAGGGCGAGGGCCGCCCCTACGAGGGC

ACCCAGACCGCCAAGCTGAAGGTGACCAAGGGTGGCCCCCTGCCCTTCGCCTGGGACATCCTGTCCCCTCAGTTCA

TGTACGGCTCCAAGGCCTACGTGAAGCACCCCGCCGACATCCCCGACTACTTGAAGCTGTCCTTCCCCGAGGGCTT

CAAGTGGGAGCGCGTGATGAACTTCGAGGACGGCGGCGTGGTGACCGTGACCCAGGACTCCTCCCTGCAGGACG

GCGAGTTCATCTACAAGGTGAAGCTGCGCGGCACCAACTTCCCCTCCGACGGCCCCGTAATGCAGAAGAAAACCAT

GGGCTGGGAGGCCTCCTCCGAGCGGATGTACCCCGAGGACGGCGCCCTGAAGGGCGAGATCAAGCAGAGGCTGA

AGCTGAAGGACGGCGGCCACTACGACGCTGAGGTCAAGACCACCTACAAGGCCAAGAAGCCCGTGCAGCTGCCC

GGCGCCTACAACGTCAACATCAAGTTGGACATCACCTCCCACAACGAGGACTACACCATCGTGGAACAGTACGAAC

GCGCCGAGGGCCGCCACTCCACCGGCGGCATGGACGAGCTGTACAAGTAACCGCTGAGACCGGTACCTC

Building block TKter BsaI B (SEQ ID NO: 64)

Building block HygroR BsaI D (SEQ ID NO: 114)
GAGGTACCGGTCTCAACAACAGGCAGAAGTATGCAAAGCATGCATCTCAATTAGTCAGCAACCAGGTGTGGAAAG

TCCCCAGGCTCCCCAGCAGGCAGAAGTATGCAAAGCATGCATCTCAATTAGTCAGCAACCATAGTCCCGCCCCTAA

CTCCGCCCATCCCGCCCCTAACTCCGCCCAGTTCCGCCCATTCTCCGCCCCATGGCTGACTAATTTTTTTTATTTATGC

AGAGGCCGAGGCCGCCTCTGCCTCTGAGCTATTCCAGAAGTAGTGAGGAGGCTTTTTTGGAGGCCTAGGCTTTTGC

AAAAAGCTCCCGGGAGCTTGTATATCCATTTTCGGATCTGATCAGCACGTGATGAAAAGCCTGAACTCACCGCGA

CGTCTGTCGAGAAGTTTCTGATCGAAAAGTTCGACAGCGTGTCCGACCTGATGCAGCTCTCGGAGGGCGAAGAAT

CTCGTGCTTTCAGCTTCGATGTAGGAGGGCGTGGATATGTCCTGCGGGTAAATAGCTGCGCCGATGGTTTCTACAA

AGATCGTTATGTTTATCGGCACTTTGCATCGGCCGCGCTCCCGATTCCGGAAGTGCTTGACATTGGGGAATTCAGC

GAGAGCCTGACCTATTGCATCTCCCGCCGTGCACAGGGTGTCACGTTGCAAGACTTGCCTGAAACCGAACTGCCCG

CTGTTCTGCAGCCGGTCGCGGAGGCCATGGATGCGATCGCTGCGGCCGATCTTAGCCAGACGAGCGGGTTCGGCC

CATTCGGACCGCAAGGAATCGGTCAATACACTACATGGCGTGATTTCATATGCGCGATTGCTGATCCCCATGTGTAT

-continued

```
CACTGGCAAACTGTGATGGACGACACCGTCAGTGCGTCCGTCGCGCAGGCTCTCGATGAGCTGATGCTTTGGGCC

GAGGACTGCCCCGAAGTCCGGCACCTCGTGCACGCGGATTTCGGCTCCAACAATGTCCTGACGGACAATGGCCGC

ATAACAGCGGTCATTGACTGGAGCGAGGCGATGTTCGGGGATTCCCAATACGAGGTCGCCAACATCTTCTTCTGGA

GGCCGTGGTTGGCTTGTATGGAGCAGCAGACGCGCTACTTCGAGCGGAGGCATCCGGAGCTTGCAGGATCGCCGC

GGCTCCGGGCGTATATGCTCCGCATTGGTCTTGACCAACTCTATCAGAGCTTGGTTGACGGCAATTTCGATGATGC

AGCTTGGGCGCAGGGTCGATGCGACGCAATCGTCCGATCCGGAGCCGGGACTGTCGGGCGTACACAAATCGCCC

GCAGAAGCGCGGCCGTCTGGACCGATGGCTGTGTAGAAGTACTCGCCGATAGTGGAAACCGACGCCCCAGCACTC

GTCCGAGGGCAAAGGAATAGCACGTGCTACGAGATTTCGATTCCACCGCCGCCTTCTATGAAAGGTTGGGCTTCG

GAATCGTTTTCCGGGACGCCGGCTGGATGATCCTCCAGCGCGGGATCTCATGCTGGAGTTCTTCGCCCACCCCAA

CTTGTTTATTGCAGCTTATAATGGTTACAAATAAAGCAATAGCATCACAAATTTCACAAATAAAGCATTTTTTTCACT

GCATTCTAGTTGTGGTTTGTCCAAACTCATCAATGTATCATTACGAGACCGGTACCTC

V1.1b (SEQ ID NO: 151, example of a vector of the group V1.1)
CGGTAATACGGTTATCCACAGAATCAGGGGATAACGCAGGAAAGAACATGTGAGCAAAAGGCCAGCAAAAGGCC

AGGAACCGTAAAAAGGCCGCGTTGCTGGCGTTTTTCCATAGGCTCCGCCCCCCTGACGAGCATCACAAAAATCGAC

GCTCAAGTCAGAGGTGGCGAAACCCGACAGGACTATAAAGATACCAGGCGTTTCCCCCTGGAAGCTCCCTCGTGC

GCTCTCCTGTTCCGACCCTGCCGCTTACCGGATACCTGTCCGCCTTTCTCCCTTCGGGAAGCGTGGCGCTTTCTCATA

GCTCACGCTGTAGGTATCTCAGTTCGGTGTAGGTCGTTCGCTCCAAGCTGGGCTGTGTGCACGAACCCCCCGTTCA

GCCCGACCGCTGCGCCTTATCCGGTAACTATCGTCTTGAGTCCAACCCGGTAAGACACGACTTATCGCCACTGGCA

GCAGCCACTGGTAACAGGATTAGCAGAGCGAGGTATGTAGGCGGTGCTACAGAGTTCTTGAAGTGGTGGCCTAAC

TACGGCTACACTAGAAGAACAGTATTTGGTATCTGCGCTCTGCTGAAGCCAGTTACCTTCGGAAAAAGAGTTGGTA

GCTCTTGATCCGGCAAACAAACCACCGCTGGTAGCGGTTTTTTGTTTGCAAGCAGCAGATTACGCGCAGAAAAAA

AGGATCTCAAGAAGATCCTTTGATCTTTTCTACGGGGTCTGACGCTCAGTGGAACGAAAACTCACGTTAAGGGATT

TTGGTCATGAGATTATCAAAAGGATCTTCACCTAGATCCTTTTAAATTAAAAATGAAGTTTTAAATCAATCTAAAGT

ATATATGAGTAAACTTGGTCTGACAGTTACCAATGCTTAATCAGTGAGGCACCTATCTCAGCGATCTGTCTATTTCG

TTCATCCATAGTTGCCTGACTCCCCGTCGTGTAGATAACTACGATACGGGAGGGCTTACCATCTGGCCCCAGTGCTG

CAATGATACCGCGTGACCCACGCTCACCGGCTCCAGATTTATCAGCAATAAACCAGCCAGCCGGAAGGGCCGAGC

GCAGAAGTGGTCCTGCAACTTTATCCGCCTCCATCCAGTCTATTAATTGTTGCCGGGAAGCTAGAGTAAGTAGTTCG

CCAGTTAATAGTTTGCGCAACGTTGTTGCCATTGCTACAGGCATCGTGGTGTCACGCTCGTCGTTTGGTATGGCTTC

ATTCAGCTCCGGTTCCCAACGATCAAGGCGAGTTACATGATCCCCCATGTTGTGCAAAAAAGCGGTTAGCTCCTTCG

GTCCTCCGATCGTTGTCAGAAGTAAGTTGGCCGCAGTGTTATCACTCATGGTTATGGCAGCACTGCATAATTCTCTT

ACTGTCATGCCATCCGTAAGATGCTTTTCTGTGACTGGTGAGTACTCAACCAAGTCATTCTGAGAATAGTGTATGCG

GCGACCGAGTTGCTCTTGCCCGGCGTCAATACGGGATAATACCGCGCCACATAGCAGAACTTTAAAAGTGCTCATC

ATTGGAAAACGTTCTTCGGGGCGAAAACTCTCAAGGATCTTACCGCTGTTGAGATCCAGTTCGATGTAACCCACTC

GTGCACCCAACTGATCTTCAGCATCTTTTACTTTCACCAGCGTTTCTGGGTGAGCAAAAACAGGAAGGCAAAATGC

CGCAAAAAAGGGAATAAGGGCGACACGGAAATGTTGAATACTCATACTCTTCCTTTTTCAATATTATTGAAGCATTT

ATCAGGGTTATTGTCTCATGAGCGGATACATATTTGAATGTATTTAGAAAAATAAACAAATAGGGGTTCCGCGCAC

ATTTCCCCGAAAAGTGCCAATGCGTGAGGCTCCGGTGCCCGTCAGTGGGCAGAGCGCACATCGCCCACAGTCCCC

GAGAAGTTGGGGGGAGGGGTCGGCAATTGAACCGGTGCCTAGAGAAGGTGGCGCGGGGTAAACTGGGAAAGTG

ATGTCGTGTACTGGCTCCGCCTTTTTCCCGAGGGTGGGGGAGAACCGTATATAAGTGCAGTAGTCGCCGTGAACGT

TCTTTTTTCGCAACGGGTTTGCCGCCAGAACACAGGTAAGTGCCGTGTGTGGTTCCCGCGGGCCTGGCCTCTTTACG

GGTTATGGCCCTTGCGTGCCTTGAATTACTTCCACCTGGCTGCAGTACGTGATTCTTGATCCCGAGCTTCGGGTTGG
```

-continued

```
AAGTGGGTGGGAGAGTTCGAGGCCTTGCGCTTAAGGAGCCCCTTCGCCTCGTGCTTGAGTTGAGGCCTGGCCTGG

GCGCTGGGGCCGCCGCGTGCGAATCTGGTGGCACCTTCGCGCCTGTCTCGCTGCTTTCGATAAGTCTCTAGCCATTT

AAAATTTTTGATGACCTGCTGCGACGCTTTTTTTCTGGCAAGATAGTCTTGTAAATGCGGGCCAAGATCTGCACACT

GGTATTTCGGTTTTTGGGGCCGCGGGCGGCGACGGGGCCCGTGCGTCCCAGCGCACATGTTCGGCGAGGCGGGG

CCTGCGAGCGCGGCCACCGAGAATCGGACGGGGGTAGTCTCAAGCTGGCCGGCCTGCTCTGGTGCCTGGCCTCGC

GCCGCCGTGTATCGCCCCGCCCTGGGCGGCAAGGCTGGCCCGGTCGGCACCAGTTGCGTGAGCGGAAAGATGGC

CGCTTCCCGGCCCTGCTGCAGGGAGCTCAAAATGGAGGACGCGGCGCTCGGGAGAGCGGGCGGGTGAGTCACCC

ACACAAAGGAAAAGGGCCTTTCCGTCCTCAGCCGTCGCTTCATGTGACTCCACGGAGTACCGGGCGCCGTCCAGGC

ACCTCGATTAGTTCTCGAGCTTTTGGAGTACGTCGTCTTTAGGTTGGGGGAGGGGTTTTATGCGATGGAGTTTCC

CCACACTGAGTGGGTGGAGACTGAAGTTAGGCCAGCTTGGCACTTGATGTAATTCTCCTTGGAATTTGCCCTTTTTG

AGTTTGGATCTTGGTTCATTCTCAAGCCTCAGACAGTGGTTCAAAGTTTTTTCTTCCATTTCAGGTGTCGTGATATC

ATGGTGAGCAAGGGCGAGGAGCTGTTCACCGGGGTGGTGCCCATCCTGGTCGAGCTGGACGGCGACGTAAACGG

CCACAAGTTCAGCGTGTCCGGCGAGGGCGAGGGCGATGCCACCTACGGCAAGCTGACCCTGAAGTTCATCTGCAC

CACCGGCAAGCTGCCCGTGCCCTGGCCCACCCTCGTGACCACCCTGACCTACGGCGTGCAGTGCTTCAGCCGCTAC

CCCGACCACATGAAGCAGCACGACTTCTTCAAGTCCGCCATGCCCGAAGGCTACGTCCAGGAGCGCACCATCTTCT

TCAAGGACGACGGCAACTACAAGACCCGCGCCGAGGTGAAGTTCGAGGGCGACACCCTGGTGAACCGCATCGAG

CTGAAGGGCATCGACTTCAAGGAGGACGGCAACATCCTGGGGCACAAGCTGGAGTACAACTACAACAGCCACAAC

GTCTATATCATGGCCGACAAGCAGAAGAACGGCATCAAGGTGAACTTCAAGATCCGCCACAACATCGAGGACGGC

AGCGTGCAGCTCGCCGACCACTACCAGCAGAACACCCCCATCGGCGACGGCCCCGTGCTGCTGCCCGACAACCACT

ACCTGAGCACCCAGTCCGCCCTGAGCAAAGACCCCAACGAGAAGCGCGATCACATGGTCCTGCTGGAGTTCGTGA

CCGCCGCCGGGATCACTCTCGGCATGGACGAGCTGTACAAGAAGAAGAAAAAGAAGTCAAAGACAAAGTGTGTA

ATTATGTAAGAGTCGACTGTGCCTTCAGTTGCCAGCCATCTGTTGTTTGCCCCTCCCCCGTGCCTTCCTTGACCCTG

GAAGGTGCCACTCCCACTGTCCTTTCCTAATAAAATGAGGAAATTGCATCGCATTGTCTGAGTAGGTGTCATTCTAT

TCTGGGGGGTGGGGTGGGGCAGGACAGCAAGGGGGAGGATTGGGAGGACAATAGCAGGCATGCTGGGGATGC

GGTGGGCTCTATGGGTAGTTATTAATAGTAATCAATTACGGGGTCATTAGTTCATAGCCCATATATGGAGTTCCGC

GTTACATAACTTACGGTAAATGGCCCGCCTGGCTGACCGCCCAACGACCCCCGCCCATTGACGTCAATAATGACGT

ATGTTCCCATAGTAACGCCAATAGGGACTTTCCATTGACGTCAATGGGTGGAGTATTTACGGTAAACTGCCCACTTG

GCAGTACATCAAGTGTATCATATGCCAAGTACGCCCCCTATTGACGTCAATGACGGTAAATGGCCCGCCTGGCATT

ATGCCCAGTACATGACCTTATGGGACTTTCCTACTTGGCAGTACATCTACGTATTAGTCATCGCTATTACCATGGTG

ATGCGGTTTTGGCAGTACATCAATGGGCGTGGATAGCGGTTTGACTCACGGGGATTTCCAAGTCTCCACCCCATTG

ACGTCAATGGGAGTTTGTTTTGGCACCAAAATCAACGGGACTTTCCAAAATGTCGTAACAACTCCGCCCCATTGAC

GCAAATGGGCGGTAGGCGTGTACGGTGGGAGGTCTATATAAGCAGAGCTGGTTTAGTGAACCGTCAGATCTTCGA

TGATTCACACCAACCTGAAGAAAAAGTTCAGCTGCTGCGTCCTGGTCTTTCTTCTGTTTGCAGTCATCTGTGTGTGG

AAGGAAAAGAAGAAAGGGAGTTACTATGATTCCTTTAAATTGCAAACCAAGGAATTCCAGGTGTTAAAGAGTCTG

GGGAAATTGGCCATGGGGTCTGATTCCCAGTCTGTATCCTCAAGCAGCACCCAGGACCCCCACAGGGGCCGCCAG

ACCCTCGGCAGTCTCAGAGGCCTAGCCAAGGCCAAACCAGAGGCCTCCTTCCAGGTGTGGAACAAGGACAGCTCT

TCCAAAAACCTTATCCCTAGGCTGCAAAAGGGGTCGGGGGTGAGCAAGGGCGAGGAGGATAACATGGCCATCAT

CAAGGAGTTCATGCGCTTCAAGGTGCACATGGAGGGCTCCGTGAACGGCCACGAGTTCGAGATCGAGGGCGAGG

GCGAGGGCCGCCCCTACGAGGGCACCCAGACCGCCAAGCTGAAGGTGACCAAGGGTGGCCCCCTGCCCTTCGCCT

GGGACATCCTGTCCCCTCAGTTCATGTACGGCTCCAAGGCCTACGTGAAGCACCCCGCCGACATCCCCGACTACTTG
```

-continued

```
AAGCTGTCCTTCCCCGAGGGCTTCAAGTGGGAGCGCGTGATGAACTTCGAGGACGGCGGCGTGGTGACCGTGACC

CAGGACTCCTCCCTGCAGGACGGCGAGTTCATCTACAAGGTGAAGCTGCGCGGCACCAACTTCCCCTCCGACGGCC

CCGTAATGCAGAAGAAAACCATGGGCTGGGAGGCCTCCTCCGAGCGGATGTACCCCGAGGACGGCGCCCTGAAG

GGCGAGATCAAGCAGAGGCTGAAGCTGAAGGACGGCGGCCACTACGACGCTGAGGTCAAGACCACCTACAAGGC

CAAGAAGCCCGTGCAGCTGCCCGGCGCCTACAACGTCAACATCAAGTTGGACATCACCTCCCACAACGAGGACTAC

ACCATCGTGGAACAGTACGAACGCGCCGAGGGCCGCCACTCCACCGGCGGCATGGACGAGCTGTACAAGTAACCG

CGGGGGAGGCTAACTGAAACACGGAAGGAGACAATACCGGAAGGAACCCGCGCTATGACGGCAATAAAAAGACA

GAATAAAACGCACGGTGTTGGGTCGTTTGTTCATAAACGCGGGGTTCGGTCCCAGGGCTGGCACTCTGTCGATACC

CCACCGAGGCCCCATTGGGGCCAATACGCCCGCGTTTCTTCCTTTTCCCCACCCCACCCCCCAAGTTCGGGTGAAGG

CCCAGGGCTCGCAGCCAACGTCGGGGCGGCAGGCCCTGCCATAGACAACAGGCAGAAGTATGCAAAGCATGCAT

CTCAATTAGTCAGCAACCAGGTGTGGAAAGTCCCCAGGCTCCCCAGCAGGCAGAAGTATGCAAAGCATGCATCTCA

ATTAGTCAGCAACCATAGTCCCGCCCCTAACTCCGCCCATCCCGCCCCTAACTCCGCCCAGTTCCGCCCATTCTCCGC

CCCATGGCTGACTAATTTTTTTTATTTATGCAGAGGCCGAGGCCGCCTCTGCCTCTGAGCTATTCCAGAAGTAGTGA

GGAGGCTTTTTGGAGGCCTAGGCTTTTGCAAAAAGCTCCCGGGAGCTTGTATATCCATTTTCGGATCTGATCAGCA

CGTGATGAAAAGCCTGAACTCACCGCGACGTCTGTCGAGAAGTTTCTGATCGAAAAGTTCGACAGCGTGTCCGAC

CTGATGCAGCTCTCGGAGGGCGAAGAATCTCGTGCTTTCAGCTTCGATGTAGGAGGGCGTGGATATGTCCTGCGG

GTAAATAGCTGCGCCGATGGTTTCTACAAAGATCGTTATGTTTATCGGCACTTTGCATCGGCCGCGCTCCCGATTCC

GGAAGTGCTTGACATTGGGGAATTCAGCGAGAGCCTGACCTATTGCATCTCCCGCCGTGCACAGGGTGTCACGTTG

CAAGACTTGCCTGAAACCGAACTGCCCGCTGTTCTGCAGCCGGTCGCGGAGGCCATGGATGCGATCGCTGCGGCC

GATCTTAGCCAGACGAGCGGGTTCGGCCCATTCGGACCGCAAGGAATCGGTCAATACACTACATGGCGTGATTTCA

TATGCGCGATTGCTGATCCCCATGTGTATCACTGGCAAACTGTGATGGACGACACCGTCAGTGCGTCCGTCGCGCA

GGCTCTCGATGAGCTGATGCTTTGGGCCGAGGACTGCCCCGAAGTCCGGCACCTCGTGCACGCGGATTTCGGCTCC

AACAATGTCCTGACGGACAATGGCCGCATAACAGCGGTCATTGACTGGAGCGAGGCGATGTTCGGGGATTCCCAA

TACGAGGTCGCCAACATCTTCTTCTGGAGGCCGTGGTTGGCTTGTATGGAGCAGCAGACGCGCTACTTCGAGCGG

AGGCATCCGGAGCTTGCAGGATCGCCGCGGCTCCGGGCGTATATGCTCCGCATTGGTCTTGACCAACTCTATCAGA

GCTTGGTTGACGGCAATTTCGATGATGCAGCTTGGGCGCAGGGTCGATGCGACGCAATCGTCCGATCCGGAGCCG

GGACTGTCGGGCGTACACAAATCGCCCGCAGAAGCGCGGCCGTCTGGACCGATGGCTGTGTAGAAGTACTCGCCG

ATAGTGGAAACCGACGCCCCAGCACTCGTCCGAGGGCAAAGGAATAGCACGTGCTACGAGATTTCGATTCCACCG

CCGCCTTCTATGAAAGGTTGGGCTTCGGAATCGTTTTCCGGGACGCCGGCTGGATGATCCTCCAGCGCGGGGATCT

CATGCTGGAGTTCTTCGCCCACCCCAACTTGTTTATTGCAGCTTATAATGGTTACAAATAAAGCAATAGCATCACAA

ATTTCACAAATAAAGCATTTTTTTCACTGCATTCTAGTTGTGGTTTGTCCAAACTCATCAATGTATCATTA
```

The restriction fingerprint by triple digestion (structural validation), EcoRV, PstI, ScaI, of embodiment 10 is illustrated in FIG. 25.

Functional verification of embodiment 10: Eukaryotic cells (for example: 4T1 mouse breast cancer cells) are transfected with the vector V1.1b in accordance with a conventional protocol (for example lipotransfection or electroporation). Twenty-four hours after transfection, the cells are observed using an optical microscope under white light and fluorescence. (FIG. 26)

The cells visible under GFP fluorescence show a marking outlining the membrane contours of each cell. The cells visible under mCherry fluorescence show a dotted marking, corresponding to the Golgi apparatus. When the GFP and mCherry markings are superimposed, all of the visible cells express the two markings simultaneously, the non-fluorescent cells being cells which have not received a vector following the electroporation. This shows well the co-expression of two fluorescent markers correctly expressed in the separate cell compartments following the introduction of a single vector into the cells.

Embodiment 11

Group of vectors V4: Vectors allowing selection of cells of which the genome has been edited by targeted homologous recombination.

U1+U3b+U3a+U3c

U1: Bacterial functional unit

U3a=positive selection cassette

U3b=motif 5' of a homologous recombination sequence X
U3c=motif 3' of the homologous recombination sequence X Example: Vector Allowing Selection of a Yeast Strain *S. cerevisiae* of which the Gene MNN10 has been Deleted

| U1 | Ori AmpR |
| U3b | MNN10-left |
| U3a | Kanamycin resistance KanMX4 |
| U3c | MNN10-right |

List of building blocks used to construct the vector V4 (FIG. 27)

Building block Ori-2 BsaI C
(SEQ ID NO: 115)
GAGGTACCGGTCTCTGGGGCGGTAATACGGTTATCCACAGAATCAGGGGA
TAACGCAGGAAAGAACATGTGAGCAAAAGGCCAGCAAAAGGCCAGGAACC
GTAAAAAGGCCGCGTTGCTGGCGTTTTTCCATAGGCTCCGCCCCCCTGAC
GAGCATCACAAAAATCGACGCTCAAGTCAGAGGTGGCGAAACCCGACAGG
ACTATAAAGATACCAGGCGTTTCCCCCTGGAAGCTCCCTCGTGCGCTCTC
CTGTTCCGACCCTGCCGCTTACCGGATACCTGTCCGCCTTTCTCCCTTCG
GGAAGCGTGGCGCTTTCTCATAGCTCACGCTGTAGGTATCTCAGTTCGGT
GTAGGTCGTTCGCTCCAAGCTGGGCTGTGTGCACGAACCCCCCGTTCAGC
CCGACCGCTGCGCCTTATCCGGTAACTATCGTCTTGAGTCCAACCCGGTA
AGACACGACTTATCGCCACTGGCAGCAGCCACTGGTAACAGGATTAGCAG
AGCGAGGTATGTAGGCGGTGCTACAGAGTTCTTGAAGTGGTGGCCTAACT
ACGGCTACACTAGAAGAACAGTATTTGGTATCTGCGCTCTGCTGAAGCCA
GTTACCTTCGGAAAAAGAGTTGGTAGCTCTTGATCCGGCAAACAAACCAC
CGCTGGTAGCGGTTTTTTTGTTTGCAAGCAGCAGATTACGCGCAGAAAAA
AAGGATCTCAAGAAGATCCTTTGATCTTTTCTACGGGGTCTGACGCTCAG
TGGAACGAAAACTCACGTTAAGGGATTTTGGTCATGAGATTATCAAAAAG
GATCTTCACCTAGATCCTTTTAAATTAAAAATGAAGTTTTAAATCAATCT
AAAGTATATATGAGTTTAAACTGAGACCGGTACCTC Building block AmpR BsaI C
(SEQ ID NO: 116)
GAGGTACCGGTCTCAAAACTTGGTCTGACAGTTACCAATGCTTAATCAGT
GAGGCACCTATCTCAGCGATCTGTCTATTTCGTTCATCCATAGTTGCCTG
ACTCCCCGTCGTGTAGATAACTACGATACGGGAGGGCTTACCATCTGGCC
CCAGTGCTGCAATGATACCGCGTGACCCACGCTCACCGGCTCCAGATTTA
TCAGCAATAAACCAGCCAGCCGGAAGGGCCGAGCGCAGAAGTGGTCCTGC
AACTTTATCCGCCTCCATCCAGTCTATTAATTGTTGCCGGGAAGCTAGAG
TAAGTAGTTCGCCAGTTAATAGTTTGCGCAACGTTGTTGCCATTGCTACA
GGCATCGTGGTGTCACGCTCGTCGTTTGGTATGGCTTCATTCAGCTCCGG
TTCCCAACGATCAAGGCGAGTTACATGATCCCCCATGTTGTGCAAAAAAG
CGGTTAGCTCCTTCGGTCCTCCGATCGTTGTCAGAAGTAAGTTGGCCGCA GTGTTATCACTCATGGTTATGGCAGCACTGCATAATTCTCTTACTGTCAT
GCCATCCGTAAGATGCTTTTCTGTGACTGGTGAGTACTCAACCAAGTCAT
TCTGAGAATAGTGTATGCGGCGACCGAGTTGCTCTTGCCCGGCGTCAATA
CGGGATAATACCGCGCCACATAGCAGAACTTTAAAAGTGCTCATCATTGG
AAAACGTTCTTCGGGGCGAAAACTCTCAAGGATCTTACCGCTGTTGAGAT
CCAGTTCGATGTAACCCACTCGTGCACCCAACTGATCTTCAGCATCTTTT
ACTTTCACCAGCGTTTCTGGGTGAGCAAAAACAGGAAGGCAAAATGCCGC
AAAAAAGGGAATAAGGGCGACACGGAAATGTTGAATACTCATACTCTTCC
TTTTTCAATATTATTGAAGCATTTATCAGGGTTATTGTCTCATGAGCGGA
TACATATTTGAATGTATTTAGAAAAATAAACAAATAGGGGTTCCGCGCAC
ATTTCCCCGAAAAGTGCCAGTGATGAGACCGGTACCTC Building block MNN10-Lrec BsaI A
(SEQ ID NO: 117)
GAGGTACCGGTCTCTGTGAGTTTAAACATGCATTCAAAGGTCATAATTGC
TGCTCTATTTACAGTCGTCCATAATGACATTTCTCTTTGATTATTTTCTT
GTTTTTTCGCTCTTCTCAAGTGGATGTTACATAACAAACAAAACAGAAAA
AATTGTTTAAATATAAAGTTTAAAAGTTATCTTTGATTCCGCACCTGAAT
TTTTGGATTGAAGGCCAAAGGAGGTTTATCAGGGAGAGAAAAGCTCTCTA
TTTATTTTTATAAGGAATAATTGTGCATGTACAACTATACAATTGCGTGA
GACCGGTACCTC Building block KanMX BsaI A
(SEQ ID NO: 119)
GAGGTACCGGTCTCGTGCGGTACGCTGCAGGTCGACAACCCTTAATATAA
CTTCGTATAATGTATGCTATACGAAGTTATTAGGTCTAGAGATCTGTTTA
GCTTGCCTCGTCCCCGCCGGGTCACCCGGCCAGCGACATGGAGGCCCAGA
ATACCCTCCTTGACAGTCTTGACGTGCGCAGCTCAGGGGCATGATGTGAC
TGTCGCCCGTACATTTAGCCCATACATCCCCATGTATAATCATTTGCATC
CATACATTTTGATGGCCGCACGGCGCGAAGCAAAAATTACGGCTCCTCGC
TGCAGACCTGCGAGCAGGGAAACGCTCCCCTCACAGACGCGTTGAATTGT
CCCCACGCCGCGCCCCTGTAGAGAAATATAAAAGGTTAGGATTTGCCACT
GAGGTTCTTCTTTCATATACTTCCTTTTAAAATCTTGCTAGGATACAGTT
CTCACATCACATCCGAACATAAACAACCATGGGTAAGGAAAAGACTCACG
TTTCGAGGCCGCGATTAAATTCCAACATGGATGCTGATTTATATGGGTAT
AAATGGGCTCGCGATAATGTCGGGCAATCAGGTGCGACAATCTATCGATT
GTATGGGAAGCCCGATGCGCCAGAGTTGTTTCTGAAACATGGCAAAGGTA
GCGTTGCCAATGATGTTACAGATGAGATGGTCAGACTAAACTGGCTGACG
GAATTTATGCCTCTTCCGACCATCAAGCATTTTATCCGTACTCCTGATGA
TGCATGGTTACTCACCACTGCGATCCCCGGCAAAACAGCATTCCAGGTAT
TAGAAGAATATCCTGATTCAGGTGAAAATATTGTTGATGCGCTGGCAGTG
TTCCTGCGCCGGTTGCATTCGATTCCTGTTTGTAATTGTCCTTTTAACAG
CGATCGCGTATTTCGTCTCGCTCAGGCGCAATCACGAATGAATAACGGTT
TGGTTGATGCGAGTGATTTTGATGACGAGCGTAATGGCTGGCCTGTTGAA

```
CAAGTCTGGAAAGAAATGCATAAGCTTTTGCCATTCTCACCGGATTCAGT

CGTCACTCATGGTGATTTCTCACTTGATAACCTTATTTTTGACGAGGGGA

AATTAATAGGTTGTATTGATGTTGGACGAGTCGGAATCGCAGACCGATAC

CAGGATCTTGCCATCCTATGGAACTGCCTCGGTGAGTTTTCTCCTTCATT

ACAGAAACGGCTTTTTCAAAAATATGGTATTGATAATCCTGATATGAATA

AATTGCAGTTTCATTTGATGCTCGATGAGTTTTTCTAATCAGTACTGACA

ATAAAAAGATTCTTGTTTTCAAGAACTTGTCATTTGTATAGTTTTTTTAT

ATTGTAGTTGTTCTATTTTAATCAAATGTTAGCGTGATTTATATTTTTTT

TCGCCTCGACATCATCTGCCCAGATGCGAAGTTAAGTGCGCAGAAAGTAA

TATCATGCGTCAATCGTATGTGAATGCTGGTCGCTATACTGCTGTCGATT

CGATACTAACGCCGCCATCCAGTGTCGAAAACGAGCTCTCGAGAACCCTT

AATATAACTTCGTATAATGTATGCTATACGAAGTTATTAGGTGATATCAG

ATCCACTAGTGTCGTAGAGACCGGTACCTC

Building block MNN10-Rrec BsaI A
                                           (SEQ ID NO: 118)
GAGGTACCGGTCTCTTCGTAATGGAAGTTATCAATATTGTAAAGAGAAGC

ATTTACAAGCTTTTATTTTTCTTTTTAATTTCCACTACTGGTTCTGCTTT

AAAATGTTGTTTTATAATTTATGTACATTTAGGCCTATAGAAGATTCTTT

CAATAATATGCTACACATTCTTTTATTTTTCCATCATATGTTGGAGTTTA

TGCCTCCTCGGCAGGAGTTGGGCGGTGCGAAGAGAAGAAAAAGAGTGAAA

CTAAAAAAGGAATCTGCCTTTGCATAAGTTCAAAAGTGCAATTTTAGTG

TTGGATTTAAACGGGAAAAATTGAAATGGCCATCGAAACAATACTTGTAA

TAAACAAATCAGGCGGACTAATCTATCAGCGGAATTTTACCAACGACGAA

CAGAAATTGAACAGCAATGAATACTTAATTCTTGCTAGTACACTGCACGG

TGTATTCGCCATCGCGAGCCAGCTGACTCCGAAGGCATTACAGCTAACTC

AACAAACGAACATCGAAAATACCATCCCATATATACCTTACGTGGGCATG

TCCAGCAATAGGAGCGATACAAGAAATGGAGGTGGCAATAACAACAAACA

CACTAATAATGAAAACTGGGCAGTTTAAACGGGGAGAGACCGGTACCTC

Vector V4
    (SEQ ID NO: 152, example of a vector of group V4)
CGGTAATACGGTTATCCACAGAATCAGGGGATAACGCAGGAAAGAACATG

TGAGCAAAAGGCCAGCAAAAGGCCAGGAACCGTAAAAAGGCCGCGTTGCT

GGCGTTTTTCCATAGGCTCCGCCCCCCTGACGAGCATCACAAAAATCGAC

GCTCAAGTCAGAGGTGGCGAAACCCGACAGGACTATAAAGATACCAGGCG

TTTCCCCCTGGAAGCTCCCTCGTGCGCTCTCCTGTTCCGACCCTGCCGCT

TACCGGATACCTGTCCGCCTTTCTCCCTTCGGGAAGCGTGGCGCTTTCTC

ATAGCTCACGCTGTAGGTATCTCAGTTCGGTGTAGGTCGTTCGCTCCAAG

CTGGGCTGTGTGCACGAACCCCCCGTTCAGCCCGACCGCTGCGCCTTATC

CGGTAACTATCGTCTTGAGTCCAACCCGGTAAGACACGACTTATCGCCAC

TGGCAGCAGCCACTGGTAACAGGATTAGCAGAGCGAGGTATGTAGGCGGT

GCTACAGAGTTCTTGAAGTGGTGGCCTAACTACGGCTACACTAGAAGAAC

AGTATTTGGTATCTGCGCTCTGCTGAAGCCAGTTACCTTCGGAAAAAGAG

TTGGTAGCTCTTGATCCGGCAAACAAACCACCGCTGGTAGCGGTTTTTTT

GTTTGCAAGCAGCAGATTACGCGCAGAAAAAAAGGATCTCAAGAAGATCC

TTTGATCTTTTCTACGGGGTCTGACGCTCAGTGGAACGAAAACTCACGTT

AAGGGATTTTGGTCATGAGATTATCAAAAAGGATCTTCACCTAGATCCTT

TTAAATTAAAAATGAAGTTTTAAATCAATCTAAAGTATATATGAGTTAAA

ACTTGGTCTGACAGTTACCAATGCTTAATCAGTGAGGCACCTATCTCAGC

GATCTGTCTATTTCGTTCATCCATAGTTGCCTGACTCCCCGTCGTGTAGA

TAACTACGATACGGGAGGGCTTACCATCTGGCCCCAGTGCTGCAATGATA

CCGCGTGACCCACGCTCACCGGCTCCAGATTTATCAGCAATAAACCAGCC

AGCCGGAAGGGCCGAGCGCAGAAGTGGTCCTGCAACTTTATCCGCCTCCA

TCCAGTCTATTAATTGTTGCCGGGAAGCTAGAGTAAGTAGTTCGCCAGTT

AATAGTTTGCGCAACGTTGTTGCCATTGCTACAGGCATCGTGGTGTCACG

CTCGTCGTTTGGTATGGCTTCATTCAGCTCCGGTTCCCAACGATCAAGGC

GAGTTACATGATCCCCCATGTTGTGCAAAAAAGCGGTTAGCTCCTTCGGT

CCTCCGATCGTTGTCAGAAGTAAGTTGGCCGCAGTGTTATCACTCATGGT

TATGGCAGCACTGCATAATTCTCTTACTGTCATGCCATCCGTAAGATGCT

TTTCTGTGACTGGTGAGTACTCAACCAAGTCATTCTGAGAATAGTGTATG

CGGCGACCGAGTTGCTCTTGCCCGGCGTCAATACGGGATAATACCGCGCC

ACATAGCAGAACTTTAAAAGTGCTCATCATTGGAAAACGTTCTTCGGGGC

GAAAACTCTCAAGGATCTTACCGCTGTTGAGATCCAGTTCGATGTAACCC

ACTCGTGCACCCAACTGATCTTCAGCATCTTTTACTTTCACCAGCGTTTC

TGGGTGAGCAAAAACAGGAAGGCAAAATGCCGCAAAAAAGGGAATAAGGG

CGACACGGAAATGTTGAATACTCATACTCTTCCTTTTTCAATATTATTGA

AGCATTTATCAGGGTTATTGTCTCATGAGCGGATACATATTTGAATGTAT

TTAGAAAAATAAACAAATAGGGGTTCCGCGCACATTTCCCCGAAAAGTGC

CAGTGAGTTTAAACATGCATTCAAAGGTCATAATTGCTGCTCTATTTACA

GTCGTCCATAATGACATTTCTCTTTGATTATTTTCTTGTTTTTTCGCTCT

TCTCAAGTGGATGTTACATAACAAACAAAACAGAAAAATTGTTTAAATA

TAAAGTTTAAAAGTTATCTTTGATTCCGCACCTGAATTTTTGGATTGAAG

GCCAAAGGAGGTTTATCAGGGAGAGAAAAGCTCTCTATTTATTTTTATAA

GGAATAATTGTGCATGTACAACTATACAATTGCGGTACGCTGCAGGTCGA

CAACCCTTAATATAACTTCGTATAATGTATGCTATACGAAGTTATTAGGT

CTAGAGATCTGTTTAGCTTGCCTCGTCCCCGCCGGGTCACCCGGCCAGCG

ACATGGAGGCCCAGAATACCCTCCTTGACAGTCTTGACGTGCGCAGCTCA

GGGGCATGATGTGACTGTCGCCCGTACATTTAGCCCATACATCCCCATGT

ATAATCATTTGCATCCATACATTTTGATGGCCGCACGGCGCGAAGCAAAA

ATTACGGCTCCTCGCTGCAGACCTGCGAGCAGGGAAACGCTCCCCTCACA

GACGCGTTGAATTGTCCCCACGCCGCGCCCCTGTAGAGAAATATAAAAGG

TTAGGATTTGCCACTGAGGTTCTTCTTTCATATACTTCCTTTTAAAATCT

TGCTAGGATACAGTTCTCACATCACATCCGAACATAAACAACCATGGGTA

AGGAAAAGACTCACGTTTCGAGGCCGCGATTAAATTCCAACATGGATGCT
```

```
GATTTATATGGGTATAAATGGGCTCGCGATAATGTCGGGCAATCAGGTGC

GACAATCTATCGATTGTATGGGAAGCCCGATGCGCCAGAGTTGTTTCTGA

AACATGGCAAAGGTAGCGTTGCCAATGATGTTACAGATGAGATGGTCAGA

CTAAACTGGCTGACGGAATTTATGCCTCTTCCGACCATCAAGCATTTTAT

CCGTACTCCTGATGATGCATGGTTACTCACCACTGCGATCCCCGGCAAAA

CAGCATTCCAGGTATTAGAAGAATATCCTGATTCAGGTGAAAATATTGTT

GATGCGCTGGCAGTGTTCCTGCGCCGGTTGCATTCGATTCCTGTTTGTAA

TTGTCCTTTTAACAGCGATCGCGTATTTCGTCTCGCTCAGGCGCAATCAC

GAATGAATAACGGTTTGGTTGATGCGAGTGATTTTGATGACGAGCGTAAT

GGCTGGCCTGTTGAACAAGTCTGGAAAGAAATGCATAAGCTTTTGCCATT

CTCACCGGATTCAGTCGTCACTCATGGTGATTTCTCACTTGATAACCTTA

TTTTTGACGAGGGGAAATTAATAGGTTGTATTGATGTTGGACGAGTCGGA

ATCGCAGACCGATACCAGGATCTTGCCATCCTATGGAACTGCCTCGGTGA

GTTTTCTCCTTCATTACAGAAACGGCTTTTTCAAAAATATGGTATTGATA

ATCCTGATATGAATAAATTGCAGTTTCATTTGATGCTCGATGAGTTTTTC

TAATCAGTACTGACAATAAAAAGATTCTTGTTTTCAAGAACTTGTCATTT

GTATAGTTTTTTTATATTGTAGTTGTTCTATTTTAATCAAATGTTAGCGT

GATTTATATTTTTTTCGCCTCGACATCATCTGCCCAGATGCGAAGTTAA

GTGCGCAGAAAGTAATATCATGCGTCAATCGTATGTGAATGCTGGTCGCT

ATACTGCTGTCGATTCGATACTAACGCCGCCATCCAGTGTCGAAAACGAG

CTCTCGAGAACCCTTAATATAACTTCGTATAATGTATGCTATACGAAGTT

ATTAGGTGATATCAGATCCACTAGTGTCGTAATGGAAGTTATCAATATTG

TAAAGAGAAGCATTTACAAGCTTTTATTTTTCTTTTTAATTTCCACTACT

GGTTCTGCTTTAAAATGTTGTTTTATAATTTATGTACATTTAGGCCTATA

GAAGATTCTTTCAATAATATGCTACACATTCTTTTATTTTTCCATCATAT

GTTGGAGTTTATGCCTCCTCGGCAGGAGTTGGGCGGTGCGAAGAGAAGAA

AAAGAGTGAAACTAAAAAAAGGAATCTGCCTTTGCATAAGTTCAAAAGTG

CAATTTTAGTGTTGGATTTAAACGGGAAAAATTGAAATGGCCATCGAAAC

AATACTTGTAATAAACAAATCAGGCGGACTAATCTATCAGCGGAATTTTA

CCAACGACGAACAGAAATTGAACAGCAATGAATACTTAATTCTTGCTAGT

ACACTGCACGGTGTATTCGCCATCGCGAGCCAGCTGACTCCGAAGGCATT

ACAGCTAACTCAACAAACGAACATCGAAAATACCATCCCATATATACCTT

ACGTGGGCATGTCCAGCAATAGGAGCGATACAAGAAATGGAGGTGGCAAT

AACAACAAACACACTAATAATGAAAAACTGGGCAGTTTAAACGGGG
```

The restriction fingerprint by double digestion (structural validation), HindIII and PmeI of embodiment 11 is illustrated in FIG. 28.

Functional verification of embodiment 11: The vector V4 was used to inactivate the yeast gene MNN10 by homologous recombination. For this, the deletion cassette of the vector was released by digestion with the enzyme PmeI and transformed into a yeast strain BY4741. Colonies obtained after 72h growth on selective medium containing G418 were transplanted and the invalidation of the gene MNN10 was verified by PCR. In order to validate the functionality of the construction, the profile of migration on native gel of the invertase of the MNN10 mutant thus obtained was analysed and compared with that of a wild-type strain and with that of a mutant strain pmr1, presenting a severe lack of glycosylation.

As shown in FIG. 29, the profile of migration of the invertase of the MNN10 mutant (trail C) is clearly different from the profile of migration of the invertase of the wild-type strain (trail B), revealing a lack of glycosylation of the enzyme in the MNN10 mutant. This lack of glycosylation is not as severe as that observed for the mutant pmr1 (trail A), corresponding to that which is known of the role of the products of these genes in N-glycosylation.

Sequences of Matrices Used to Produce Different Building Blocks of the Invention.

Matrix eZ-Ori-AmpR
(SEQ ID NO: 153)
```
GCGTCTTCTAGGGTTAAGGTTAGTGTAGAGAAGCAACCGAAGATTGAGAA

GACATGGCGGTAATACGGTTATCCACAGAATCAGGGGATAACGCAGGAAA

GAACATGTGAGCAAAAGGCCAGCAAAAGGCCAGGAACCGTAAAAAGGCCG

CGTTGCTGGCGTTTTTCCATAGGCTCCGCCCCCTGACGAGCATCACAAA

AATCGACGCTCAAGTCAGAGGTGGCGAAACCCGACAGGACTATAAAGATA

CCAGGCGTTTCCCCCTGGAAGCTCCCTCGTGCGCTCTCCTGTTCCGACCC

TGCCGCTTACCGGATACCTGTCCGCCTTTCTCCCTTCGGGAAGCGTGGCG

CTTTCTCATAGCTCACGCTGTAGGTATCTCAGTTCGGTGTAGGTCGTTCG

CTCCAAGCTGGGCTGTGTGCACGAACCCCCCGTTCAGCCCGACCGCTGCG

CCTTATCCGGTAACTATCGTCTTGAGTCCAACCCGGTAAGACACGACTTA

TCGCCACTGGCAGCAGCCACTGGTAACAGGATTAGCAGAGCGAGGTATGT

AGGCGGTGCTACAGAGTTCTTGAAGTGGTGGCCTAACTACGGCTACACTA

GAAGAACAGTATTTGGTATCTGCGCTCTGCTGAAGCCAGTTACCTTCGGA

AAAAGAGTTGGTAGCTCTTGATCCGGCAAACAAACCACCGCTGGTAGCGG

TTTTTTTGTTTGCAAGCAGCAGATTACGCGCAGAAAAAAAGGATCTCAAG

AAGATCCTTTGATCTTTTCTACGGGGTCTGACGCTCAGTGGAACGAAAAC

TCACGTTAAGGGATTTTGGTCATGAGATTATCAAAAAGGATCTTCACCTA

GATCCTTTTAAATTAAAAATGAAGTTTTAAATCAATCTAAAGTATATATG

AGTAAACTTGGTCTGACAGTTACCAATGCTTAATCAGTGAGGCACCTATC

TCAGCGATCTGTCTATTTCGTTCATCCATAGTTGCCTGACTCCCCGTCGT

GTAGATAACTACGATACGGGAGGGCTTACCATCTGGCCCCAGTGCTGCAA

TGATACCGCGTGACCCACGCTCACCGGCTCCAGATTTATCAGCAATAAAC

CAGCCAGCCGGAAGGGCCGAGCGCAGAAGTGGTCCTGCAACTTTATCCGC

CTCCATCCAGTCTATTAATTGTTGCCGGGAAGCTAGAGTAAGTAGTTCGC

CAGTTAATAGTTTGCGCAACGTTGTTGCCATTGCTACAGGCATCGTGGTG

TCACGCTCGTCGTTTGGTATGGCTTCATTCAGCTCCGGTTCCCAACGATC

AAGGCGAGTTACATGATCCCCCATGTTGTGCAAAAAAGCGGTTAGCTCCT

TCGGTCCTCCGATCGTTGTCAGAAGTAAGTTGGCCGCAGTGTTATCACTC

ATGGTTATGGCAGCACTGCATAATTCTCTTACTGTCATGCCATCCGTAAG

ATGCTTTTCTGTGACTGGTGAGTACTCAACCAAGTCATTCTGAGAATAGT
```

```
GTATGCGGCGACCGAGTTGCTCTTGCCCGGCGTCAATACGGGATAATACC

GCGCCACATAGCAGAACTTTAAAAGTGCTCATCATTGGAAAACGTTCTTC

GGGGCGAAAACTCTCAAGGATCTTACCGCTGTTGAGATCCAGTTCGATGT

AACCCACTCGTGCACCCAACTGATCTTCAGCATCTTTTACTTTCACCAGC

GTTTCTGGGTGAGCAAAAACAGGAAGGCAAAATGCCGCAAAAAAGGGAAT

AAGGGCGACACGGAAATGTTGAATACTCATACTCTTCCTTTTTCAATATT

ATTGAAGCATTTATCAGGGTTATTGTCTCATGAGCGGATACATATTTGAA

TGTATTTAGAAAAATAAACAAATAGGGGTTCCGCGCACATTTCCCCGAAA

AGTGCCACCTATGAGACGTGAGGCTAGGGATAGGACGAGAGCATCGGAA

CGAGGACTAGCGTCTCA
```

Matrix BGH polyA
(SEQ ID NO: 154):
```
TCGACTGTGCCTTCTAGTTGCCAGCCATCTGTTGTTTGCCCCTCCCCGT

GCCTTCCTTGACCCTGGAAGGTGCCACTCCCACTGTCCTTTCCTAATAAA

ATGAGGAAATTGCATCGCATTGTCTGAGTAGGTGTCATTCTATTCTGGGG

GGTGGGGTGGGGCAGGACAGCAAGGGGGAGGATTGGGAAGACAATAGCAG

GCATGCTGGGGATGCGGTGGGCTCTATGGCTTCTG
```

Matrix eZ-E1GFP
(SEQ ID NO: 155)
```
ATGGTGAGCAAGGGCGAGGAGCTGTTCACCGGGGTGGTGCCCATCCTGGT

CGAGCTGGACGGCGACGTAAACGGCCACAAGTTCAGCGTGTCCGGCGAGG

GCGAGGGCGATGCCACCTACGGCAAGCTGACCCTGAAGTTCATCTGCACC

ACCGGCAAGCTGCCCGTGCCCTGGCCCACCCTCGTGACCACCCTGTCCTA

CGGCGTGCAGTGCTTCAGCCGCTACCCCGACCACATGAAGCAGCACGACT

TCTTCAAGTCCGCCATGCCCGAAGGCTACGTCCAGGAGCGCACCATCTTC

TTCAAGGACGACGGCAACTACAAGACCCGCGCCGAGGTGAAGTTCGAGGG

CGACACCCTGGTGAACCGCATCGAGCTGAAGGGCATCGACTTCAAGGAGG

ACGGCAACATCCTGGGGCACAAGCTGGAGTACAACTACAACAGCCACAAC

GTCTATATCATGGCCGACAAGCAGAAGAACGGCATCAAGGTGAACTTCAA

GATCCGCCACAACATCGAGGACGGCAGCGTGCAGCTCGCCGACCACTACC

AGCAGAACACCCCCATCGGCGACGGCCCCGTGCTGCTGCCCGACAACCAC

TACCTGAGCTACCAGTCCGCCCTGAGCAAAGACCCCAACGAGAAGCGCGA

TCACATGGTCCTGCTGGAGTTCGTGACCGCCGCCGGGATCACTCTCGGCA

TGGACGAGCTGTACAAGTAA
```

Matrix EGFP
(SEQ ID NO: 156)
```
ATGGTGAGCAAGGGCGAGGAGCTGTTCACCGGGGTGGTGCCCATCCTGGT

CGAGCTGGACGGCGACGTAAACGGCCACAAGTTCAGCGTGTCCGGCGAGG

GCGAGGGCGATGCCACCTACGGCAAGCTGACCCTGAAGTTCATCTGCACC

ACCGGCAAGCTGCCCGTGCCCTGGCCCACCCTCGTGACCACCCTGACCTA

CGGCGTGCAGTGCTTCAGCCGCTACCCCGACCACATGAAGCAGCACGACT

TCTTCAAGTCCGCCATGCCCGAAGGCTACGTCCAGGAGCGCACCATCTTC

TTCAAGGACGACGGCAACTACAAGACCCGCGCCGAGGTGAAGTTCGAGGG

CGACACCCTGGTGAACCGCATCGAGCTGAAGGGCATCGACTTCAAGGAGG

ACGGCAACATCCTGGGGCACAAGCTGGAGTACAACTACAACAGCCACAAC

GTCTATATCATGGCCGACAAGCAGAAGAACGGCATCAAGGTGAACTTCAA

GATCCGCCACAACATCGAGGACGGCAGCGTGCAGCTCGCCGACCACTACC

AGCAGAACACCCCCATCGGCGACGGCCCCGTGCTGCTGCCCGACAACCAC

TACCTGAGCACCCAGTCCGCCCTGAGCAAAGACCCCAACGAGAAGCGCGA

TCACATGGTCCTGCTGGAGTTCGTGACCGCCGCCGGGATCACTCTCGGCA

TGGACGAGCTGTACAAGTAA
```

Matrix ECFP
(SEQ ID NO: 157)
```
ATGGTGAGCAAGGGCGAGGAGCTGTTCACCGGGGTGGTGCCCATCCTGGT

CGAGCTGGACGGCGACGTAAACGGCCACAAGTTCAGCGTGTCCGGCGAGG

GCGAGGGCGATGCCACCTACGGCAAGCTGACCCTGAAGTTCATCTGCACC

ACCGGCAAGCTGCCCGTGCCCTGGCCCACCCTCGTGACCACCCTGACCTG

GGGCGTGCAGTGCTTCAGCCGCTACCCCGACCACATGAAGCAGCACGACT

TCTTCAAGTCCGCCATGCCCGAAGGCTACGTCCAGGAGCGCACCATCTTC

TTCAAGGACGACGGCAACTACAAGACCCGCGCCGAGGTGAAGTTCGAGGG

CGACACCCTGGTGAACCGCATCGAGCTGAAGGGCATCGACTTCAAGGAGG

ACGGCAACATCCTGGGGCACAAGCTGGAGTACAACTACATCAGCCACAAC

GTCTATATCACCGCCGACAAGCAGAAGAACGGCATCAAGGCCAACTTCAA

GATCCGCCACAACATCGAGGACGGCAGCGTGCAGCTCGCCGACCACTACC

AGCAGAACACCCCCATCGGCGACGGCCCCGTGCTGCTGCCCGACAACCAC

TACCTGAGCACCCAGTCCGCCCTGAGCAAAGACCCCAACGAGAAGCGCGA

TCACATGGTCCTGCTGGAGTTCGTGACCGCCGCCGGGATCACTCTCGGCA

TGGACGAGCTGTACAAGTCC
```

Matrix EYFP
(SEQ ID NO: 158)
```
ATGGTGAGCAAGGGCGAGGAGCTGTTCACCGGGGTGGTGCCCATCCTGGT

CGAGCTGGACGGCGACGTAAACGGCCACAAGTTCAGCGTGTCCGGCGAGG

GCGAGGGCGATGCCACCTACGGCAAGCTGACCCTGAAGTTCATCTGCACC

ACCGGCAAGCTGCCCGTGCCCTGGCCCACCCTCGTGACCACCTTCGGCTA

CGGCCTGCAGTGCTTCGCCCGCTACCCCGACCACATGAAGCAGCACGACT

TCTTCAAGTCCGCCATGCCCGAAGGCTACGTCCAGGAGCGCACCATCTTC

TTCAAGGACGACGGCAACTACAAGACCCGCGCCGAGGTGAAGTTCGAGGG

CGACACCCTGGTGAACCGCATCGAGCTGAAGGGCATCGACTTCAAGGAGG

ACGGCAACATCCTGGGGCACAAGCTGGAGTACAACTACAACAGCCACAAC

GTCTATATCATGGCCGACAAGCAGAAGAACGGCATCAAGGTGAACTTCAA

GATCCGCCACAACATCGAGGACGGCAGCGTGCAGCTCGCCGACCACTACC

AGCAGAACACCCCCATCGGCGACGGCCCCGTGCTGCTGCCCGACAACCAC

TACCTGAGCTACCAGTCCGCCCTGAGCAAAGACCCCAACGAGAAGCGCGA

TCACATGGTCCTGCTGGAGTTCGTGACCGCCGCCGGGATCACTCTCGGCA

TGGACGAGCTGTAC
```

Matrix mCherry (SEQ ID NO: 159)
ATGGTCGGGGGTGAGCAAGGGCGAGGAGGATAACATGGCCATCATCAAGG

AGTTCATGCGCTTCAAGGTGCACATGGAGGGCTCCGTGAACGGCCACGAG

TTCGAGATCGAGGGCGAGGGCGAGGGCCGCCCCTACGAGGGCACCCAGAC

CGCCAAGCTGAAGGTGACCAAGGGTGGCCCCCTGCCCTTCGCCTGGGACA

TCCTGTCCCCTCAGTTCATGTACGGCTCCAAGGCCTACGTGAAGCACCCC

GCCGACATCCCCGACTACTTGAAGCTGTCCTTCCCCGAGGGCTTCAAGTG

GGAGCGCGTGATGAACTTCGAGGACGGCGGCGTGGTGACCGTGACCCAGG

ACTCCTCCCTGCAGGACGGCGAGTTCATCTACAAGGTGAAGCTGCGCGGC

ACCAACTTCCCCTCCGACGGCCCCGTAATGCAGAAGAAAACCATGGGCTG

GGAGGCCTCCTCCGAGCGGATGTACCCCGAGGACGGCGCCCTGAAGGGCG

AGATCAAGCAGAGGCTGAAGCTGAAGGACGGCGGCCACTACGACGCTGAG

GTCAAGACCACCTACAAGGCCAAGAAGCCCGTGCAGCTGCCCGGCGCCTA

CAACGTCAACATCAAGTTGGACATCACCTCCCACAACGAGGACTACACCA

TCGTGGAACAGTACGAACGCGCCGAGGGCCGCCACTCCACCGGCGGCATG

GACGAGCTGTACAAGTGA

Matrix hFUT3 cDNA (SEQ ID NO: 160)
ATGGATCCCCTGGGTGCAGCCAAGCCACAATGGCCATGGCGCCGCTGTCT

GGCCGCACTGCTATTTCAGCTGCTGGTGGCTGTGTGTTTCTTCTCCTACC

TGCGTGTGTCCCGAGACGATGCCACTGGATCCCCTAGGGCTCCCAGTGGG

TCCTCCCGACAGGACACCACTCCCACCCGCCCCACCCTCCTGATCCTGCT

ATGGACATGGCCTTTCCACATCCCTGTGGCTCTGTCCCGCTGTTCAGAGA

TGGTGCCCGGCACAGCCGACTGCCACATCACTGCCGACCGCAAGGTGTAC

CCACAGGCAGACACGGTCATCGTGCACCACTGGGATATCATGTCCAACCC

TAAGTCACGCCTCCCACCTTCCCCGAGGCCGCAGGGGCAGCGCTGGATCT

GGTTCAACTTGGAGCCACCCCCTAACTGCCAGCACCTGGAAGCCCTGGAC

AGATACTTCAATCTCACCATGTCCTACCGCAGCGACTCCGACATCTTCAC

GCCCTACGGCTGGCTGGAGCCGTGGTCCGGCCAGCCTGCCCACCCACCGC

TCAACCTCTCGGCCAAGACCGAGCTGGTGGCCTGGGCGGTGTCCAACTGG

AAGCCGGACTCAGCCAGGGTGCGCTACTACCAGAGCCTGCAGGCTCATCT

CAAGGTGGACGTGTACGGACGCTCCCACAAGCCCCTGCCCAAGGGGACCA

TGATGGAGACGCTGTCCCGGTACAAGTTCTACCTGGCCTTCGAGAACTCC

TTGCACCCCGACTACATCACCGAGAAGCTGTGGAGGAACGCCCTGGAGGC

CTGGGCCGTGCCCGTGGTGCTGGGCCCCAGCAGAAGCAACTACGAGAGGT

TCCTGCCACCCGACGCCTTCATCCACGTGGACGACTTCCAGAGCCCCAAG

GACCTGGCCCGGTACCTGCAGGAGCTGGACAAGGACCACGCCCGCTACCT

GAGCTACTTTCGCTGGCGGGAGACGCTGCGGCCTCGCTCCTTCAGCTGGG

CACTGGATTTCTGCAAGGCCTGCTGGAAACTGCAGCAGGAATCCAGGTAC

CAGACGGTGCGCAGCATAGCGGCTTGGTTCACCTGA

Matrix eZ-hygromycinR K7

(SEQ ID NO: 161)
CAGGCAGAAGTATGCAAAGCATGCATCTCAATTAGTCAGCAACCAGGTGT

GGAAAGTCCCCAGGCTCCCCAGCAGGCAGAAGTATGCAAAGCATGCATCT

CAATTAGTCAGCAACCATAGTCCCGCCCCTAACTCCGCCCATCCCGCCCC

TAACTCCGCCCAGTTCCGCCCATTCTCCGCCCCATGGCTGACTAATTTTT

TTTATTTATGCAGAGGCCGAGGCCGCCTCTGCCTCTGAGCTATTCCAGAA

GTAGTGAGGAGGCTTTTTTGGAGGCCTAGGCTTTTGCAAAAAGCTCCCGG

GAGCTTGTATATCCATTTTCGGATCTGATCAGCACGTGATGAAAAAGCCT

GAACTCACCGCGACGTCTGTCGAGAAGTTTCTGATCGAAAAGTTCGACAG

CGTGTCCGACCTGATGCAGCTCTCGGAGGGCGAAGAATCTCGTGCTTTCA

GCTTCGATGTAGGAGGGCGTGGATATGTCCTGCGGGTAAATAGCTGCGCC

GATGGTTTCTACAAAGATCGTTATGTTTATCGGCACTTTGCATCGGCCGC

GCTCCCGATTCCGGAAGTGCTTGACATTGGGGAATTCAGCGAGAGCCTGA

CCTATTGCATCTCCCGCCGTGCACAGGGTGTCACGTTGCAAGACTTGCCT

GAAACCGAACTGCCCGCTGTTCTGCAGCCGGTCGCGGAGGCCATGGATGC

GATCGCTGCGGCCGATCTTAGCCAGACGAGCGGGTTCGGCCCATTCGGAC

CGCAAGGAATCGGTCAATACACTACATGGCGTGATTTCATATGCGCGATT

GCTGATCCCCATGTGTATCACTGGCAAACTGTGATGGACGACACCGTCAG

TGCGTCCGTCGCGCAGGCTCTCGATGAGCTGATGCTTTGGGCCGAGGACT

GCCCCGAAGTCCGGCACCTCGTGCACGCGGATTTCGGCTCCAACAATGTC

CTGACGGACAATGGCCGCATAACAGCGGTCATTGACTGGAGCGAGGCGAT

GTTCGGGGATTCCCAATACGAGGTCGCCAACATCTTCTTCTGGAGGCCGT

GGTTGGCTTGTATGGAGCAGCAGACGCGCTACTTCGAGCGGAGGCATCCG

GAGCTTGCAGGATCGCCGCGGCTCCGGGCGTATATGCTCCGCATTGGTCT

TGACCAACTCTATCAGAGCTTGGTTGACGGCAATTTCGATGATGCAGCTT

GGGCGCAGGGTCGATGCGACGCAATCGTCCGATCCGGAGCCGGGACTGTC

GGGCGTACACAAATCGCCCGCAGAAGCGCGGCCGTCTGGACCGATGGCTG

TGTAGAAGTACTCGCCGATAGTGGAAACCGACGCCCCAGCACTCGTCCGA

GGGCAAAGGAATAGCACGTGCTACGAGATTTCGATTCCACCGCCGCCTTC

TATGAAAGGTTGGGCTTCGGAATCGTTTTCCGGGACGCCGGCTGGATGAT

CCTCCAGCGCGGGGATCTCATGCTGGAGTTCTTCGCCCACCCCAACTTGT

TTATTGCAGCTTATAATGGTTACAAATAAAGCAATAGCATCACAAATTTC

ACAAATAAAGCATTTTTTTCACTGCATTCTAGTTGTGGTTTGTCCAAACT

CATCAATGTATC

Matrix KanMX4 K7

(SEQ ID NO: 162)
GTACGCTGCAGGTCGACAACCCTTAATATAACTTCGTATAATGTATGCTA

TACGAAGTTATTAGGTCTAGAGATCTGTTTAGCTTGCCTCGTCCCCGCCG

GGTCACCCGGCCAGCGACATGGAGGCCCAGAATACCCTCCTTGACAGTCT

TGACGTGCGCAGCTCAGGGGCATGATGTGACTGTCGCCCGTACATTTAGC

CCATACATCCCCATGTATAATCATTTGCATCCATACATTTTGATGGCCGC

-continued
```
ACGGCGCGAAGCAAAAATTACGGCTCCTCGCTGCAGACCTGCGAGCAGGG
AAACGCTCCCCTCACAGACGCGTTGAATTGTCCCCACGCCGCGCCCCTGT
AGAGAAATATAAAAGGTTAGGATTTGCCACTGAGGTTCTTCTTTCATATA
CTTCCTTTTAAAATCTTGCTAGGATACAGTTCTCACATCACATCCGAACA
TAAACAACCATGGGTAAGGAAAAGACTCACGTTTCGAGGCCGCGATTAAA
TTCCAACATGGATGCTGATTTATATGGGTATAAATGGGCTCGCGATAATG
TCGGGCAATCAGGTGCGACAATCTATCGATTGTATGGGAAGCCCGATGCG
CCAGAGTTGTTTCTGAAACATGGCAAAGGTAGCGTTGCCAATGATGTTAC
AGATGAGATGGTCAGACTAAACTGGCTGACGGAATTTATGCCTCTTCCGA
CCATCAAGCATTTTATCCGTACTCCTGATGATGCATGGTTACTCACCACT
GCGATCCCCGGCAAAACAGCATTCCAGGTATTAGAAGAATATCCTGATTC
AGGTGAAAATATTGTTGATGCGCTGGCAGTGTTCCTGCGCCGGTTGCATT
CGATTCCTGTTTGTAATTGTCCTTTTAACAGCGATCGCGTATTTCGTCTC
GCTCAGGCGCAATCACGAATGAATAACGGTTTGGTTGATGCGAGTGATTT
TGATGACGAGCGTAATGGCTGGCCTGTGAACAAGTCTGGAAAGAAATGC
ATAAGCTTTTGCCATTCTCACCGGATTCAGTCGTCACTCATGGTGATTTC
TCACTTGATAACCTTATTTTTGACGAGGGGAAATTAATAGGTTGTATTGA
TGTTGGACGAGTCGGAATCGCAGACCGATACCAGGATCTTGCCATCCTAT
GGAACTGCCTCGGTGAGTTTTCTCCTTCATTACGAAACGGCTTTTTCAA
AAATATGGTATTGATAATCCTGATATGAATAAATTGCAGTTTCATTTGAT
GCTCGATGAGTTTTTCTAATCAGTACTGACAATAAAAAGATTCTTGTTTT
CAAGAACTTGTCATTTGTATAGTTTTTTTATATTGTAGTTGTTCTATTTT
AATCAAATGTTAGCGTGATTTATATTTTTTTTCGCCTCGACATCATCTGC
CCAGATGCGAAGTTAAGTGCGCAGAAAGTAATATCATGCGTCAATCGTAT
GTGAATGCTGGTCGCTATACTGCTGTCGATTCGATACTAACGCCGCCATC
CAGTGTCGAAAACGAGCTCTCGAGAACCCTTAATATAACTTCGTATAATG
TATGCTATACGAAGTTATTAGGTGATATCAGATCCACTAGTG
```
Matrix LacZα
(SEQ ID NO: 163)
```
GCCCAATACGCAAACCGCCTCTCCCCGCGCGTTGGCCGATTCATTAATGC
AGCTGGCACGACAGGTTTCCCGACTGGAAAGCGGGCAGTGAGCGCAACGC
AATTAATGTGAGTTAGCTCACTCATTAGGCACCCCAGGCTTTACACTTTA
TGCTTCCGGCTCGTATGTTGTGTGGAATTGTGAGCGGATAACAATTTCAC
ACAGGAAACAGCTATGACCATGATTACGGACAGCCTGGCCGTCGTTTTAC
AACGTCGTGACTGGGAAAACCCTGGCGTTACCCAACTTAATCGCCTTGCA
GCACATCCCCCTTTCGCCAGCTGGCGTAATAGCGAAGAGGCCCGCACCGA
TCGCCCTTCCCAACAGTTGCGCAGCCTGAATGGCGAATGGCGCCTGATGC
GGTATTTTCTCCTTACGCATCTGTGCGGTATTTCACACCGCATATGGTGC
ACTCTCAGTACAATCTGCTCTGATGCCGCATAGAC
```
Matrix mB3Galt6 cDNA
(SEQ ID NO: 164)
```
ATGAAGGTATTCCGGCGCGCTTGGCGGCACCGGGTGGCGCTGGGCCTAGG
CGGCCTGGCGTTCTGCGGCACCACTCTGTTGTACCTGGCGCGCTGCGCTT
CCGAGGGCGAGACGCCCTCCGCTTCCGGAGCCGCTCGGCCCCGCGCTAAG
GCCTTCCTGGCGGTGCTGGTGGCCAGTGCGCCCCGCGCGGTCGAGCGCCG
CACCGCAGTGCGCAGCACGTGGCTGGCACCGGAGAGGCGTGGCGGACCCG
AGGACGTGTGGGCGCGCTTCGCCGTGGGCACTGGCGGCTTAGGCTCGGAG
GAGCGGCGCGCTCTTGAGCTCGAGCAGGCGCAGCACGGGGACCTGCTGCT
GCTGCCCGCCCTGCGCGACGCCTACGAGAACCTCACGGCCAAGGTCCTGG
CCATGCTGACCTGGCTGGATGAGCGCGTGGACTTCGAGTTCGTGCTCAAG
GCGGACGACGACTCCTTTGCGCGCCTGGACGCTATCCTGGTGGACCTACG
CGCACGGGAGCCCGCACGCCGCCGGCGCCTCTACTGGGGCTTCTTTTCCG
GGCGCGGGCGCGTCAAGCCGGGAGGTCGCTGGCGAGAAGCAGCCTGGCAA
CTCTGCGACTACTACCTGCCCTACGCGTTGGGCGGTGGCTATGTCCTTTC
TGCGGACCTGGTGCATTACCTGCGCCTCAGCCGCGAGTACCTGCGCGCGT
GGCACAGTGAAGACGTATCGCTGGGCACCTGGCTGGCACCAGTGGATGTG
CAACGGAGCACGACCCACGCTTCGACACGGAGTACAAATCTCGAGGCTG
CAACAATCAGTATCTGGTGACACACAAGCAAAGCCCAGAGGACATGTTGG
AGAAGCAACAGATGTTGCTGCATGAGGGCCGGTTGTGCAAGCATGAGGTG
CAGTTGCGCCTTTCCTATGTCTATGACTGGTCAGCTCCACCCTCCCAGTG
CTGCCAGCGCAAGGAGGGCGTTCCCTGATGTCA
```
eZ-mB3Galt6 cDNA matrix promoter, shRNA insensitive
(SEQ ID NO: 165)
```
ATGAAGGTATTCCGGCGCGCTTGGCGGCACCGGGTGGCGCTGGGCCTAGG
CGGCCTGGCGTTCTGCGGCACCACTCTGTTGTACCTGGCGCGCTGCGCTT
CCGAGGGCGAGACGCCCTCCGCTTCCGGAGCCGCTCGGCCCCGCGCTAAG
GCCTTCCTGGCGGTGCTGGTGGCCAGTGCGCCCCGCGCGGTCGAGCGCCG
CACCGCAGTGCGCAGCACGTGGCTGGCACCGGAGAGGCGTGGCGGACCCG
AGGACGTGTGGGCGCGCTTCGCCGTGGGCACTGGCGGCTTAGGCTCGGAG
GAGCGGCGCGCTCTTGAGCTCGAGCAGGCGCAGCACGGGGACCTGCTGCT
GCTGCCCGCCCTGCGCGACGCCTACGAGAACCTCACGGCCAAGGTCCTGG
CCATGCTGACCTGGCTGGATGAGCGCGTGGACTTCGAGTTCGTGCTCAAG
GCGGACGACGACTCCTTTGCGCGCCTGGACGCTATCCTGGTGGACCTACG
CGCACGGGAGCCCGCACGCCGCCGGCGCCTCTACTGGGGCTTCTTTTCCG
GGCGCGGGCGCGTCAAGCCGGGAGGTCGCTGGCGAGAAGCAGCCTGGCAA
CTCTGCGACTACTACCTGCCCTACGCGTTGGGCGGTGGCTATGTCCTTTC
TGCGGACCTGGTGCATTACCTGCGCCTCAGCCGCGAGTACCTGCGCGCGT
GGCACAGTGAAGACGTATCGCTGGGCACCTGGCTGGCACCAGTGGATGTG
CAACGGAGCACGACCCACGCTTCGACACGGAGTACAAATCTCGAGGCTG
CAACAATCAGTATCTGGTGACACACAAGCAAAGCCCAGAGGACATGTTGG
AGAAGCAACAGATGTTGCTGCATGAGGGCCGGTTGTGCAAGCATGAGGTG
CAACTTCGCCTTTCCTATGTCTATGACTGGTCAGCTCCACCCTCCCAGTG
CTGCCAGCGCAAGGAGGGCGTTCCCTGATGTCA
```

Yeast S. cerevisiae MNN10 gene matrix
(SEQ ID NO: 166)
AAACATGCATTCAAAGGTCATAATTGCTGCTCTATTTACAGTCGTCCATA

ATGACATTTCTCTTTGATTATTTTCTTGTTTTTTCGCTCTTCTCAAGTGG

ATGTTACATAACAAACAAAACAGAAAAAATTGTTTAAATATAAAGTTTAA

AAGTTATCTTTGATTCCGCACCTGAATTTTTGGATTGAAGGCCAAAGGAG

GTTTATCAGGGAGAGAAAAGCTCTCTATTTATTTTTATAAGGAATAATTG

TGCATGTACAACTATACAATATGTCTAGTGTACCTTATAATTCCCAACTT

CCTATATCCAACCATCTAGAGTACGATGAAGATGAAAAGAAGAGCAGAGG

CTCAAAACTAGGCCTGAAATATAAAATGATATACTGGAGGAAAACTTTAT

GCAGTTCGCTAGCGAGATGGAGAAAGCTAATACTATTAATATCTTTAGCT

TTGTTTTTATTCATATGGATAAGCGATTCCACCATAAGCAGAAATCCATC

TACCACAAGTTTTCAAGGCCAAAATAGTAACGATAATAAGTTGAGTAATA

CTGGTTCTAGCATCAACTCCAAAAGATATGTACCACCATATTCTAAGAGA

TCAAGATGGTCGTTTTGGAATCAAGATCCTAGGATTGTCATTATATTAGC

GGCAAACGAAGGTGGTGGTGTATTGAGGTGGAAAAATGAGCAAGAATGGG

CTATCGAAGGCATATCAATAGAAATAAGAAGGCCTATGCAAGAGACAT

GGATATGCGTTGACTATCAAGGATTTGACAACGTCCAAAAGATACTCTCA

CGAATACAGAGAGGGTTGGCAAAAAGTAGATATATTGAGACAGACGTTCA

GGGAGTTTCCTAATGCAGAATGGTTCTGGTGGTTGGACCTGGATACTATG

ATAATGGAGCCTTCTAAATCATTAGAAGAACATATTTTCGACAGATTGGA

AACTCTGGCTGACAGAGAATTGAAAAGTTTTAATCCCCTAAACCTAAGAG

ACGACATACCCTATGTCGATTATTCAGAGGAAATGGAGTTTCTAATAACA

CAAGATTGTGGAGGCTTCAATTTGGGCTCATTTCTGATAAAAAATAGCGA

ATGGTCTAAGCTGCTTCTAGATATGTGGTGGGACCCCGTTCTGTATGAAC

AAAAACATATGGTTTGGGAACATAGAGAACAAGATGCGTTAGAGGCATTA

TATGAAAACGAACCGTGGATTCGTTCGAGAATAGGATTTTTGCCCTTAAG

AACGATCAATGCATTCCCACCGGGAGCATGCTCTGAATACAGTGGTGACT

CAAGATACTTTTACAGTGAGAAAGACCATGATTTTGTTGTGAATATGGCC

GGATGCAATTTTGGCAGAGATTGCTGGGGCGAGATGCAGTACTACACCAC

TTTAATGGAAAAACTGAATAGGAAATGGTACACGAGATTTTTCTTCCCAT

AAAATGGAAGTTATCAATATTGTAAAGAGAAGCATTTACAAGCTTTTATT

TTTCTTTTTAATTTCCACTACTGGTTCTGCTTTAAAATGTTGTTTTATAA

TTTATGTACATTTAGGCCTATAGAAGATTCTTTCAATAATATGCTACACA

TTCTTTTATTTTTCCATCATATGTTGGAGTTTATGCCTCCTCGGCAGGAG

TTGGGCGGTGCAAGAGAAGAAAAAGAGTGAAACTAAAAAAAGGAATCTG

CCTTTGCATAAGTTCAAAAGTGCAATTTTAGTGTTGGATTTAAACGGGAA

AAATTGAAATGGCCATCGAAACAATACTTGTAATAAACAAATCAGGCGGA

CTAATCTATCAGCGGAATTTTACCAACGACGAACAGAAATTGAACAGCAA

TGAATACTTAATTCTTGCTAGTACACTGCACGGTGTATTCGCCATCGCGA

GCCAGCTGACTCCGAAGGCATTACAGCTAACTCAACAAACGAACATCGAA

AATACCATCCCATATATACCTTACGTGGGCATGTCCAGCAATAGGAGCGA

TACAAGAAATGGAGGTGGCAATAACAACAAACACACTAATAATGAAAAAC

TGGGCAGTTT

CMV matrix promoter
(SEQ ID NO: 167)
ACCAATTCAGTCGACTGGATCCTAGTTATTAATAGTAATCAATTACGGGG

TCATTAGTTCATAGCCCATATATGGAGTTCCGCGTTACATAACTTACGGT

AAATGGCCCGCCTGGCTGACCGCCCAACGACCCCCGCCCATTGACGTCAA

TAATGACGTATGTTCCCATAGTAACGCCAATAGGGACTTTCCATTGACGT

CAATGGGTGGAGTATTTACGGTAAACTGCCCACTTGGCAGTACATCAAGT

GTATCATATGCCAAGTACGCCCCCTATTGACGTCAATGACGGTAAATGGC

CCGCCTGGCATTATGCCCAGTACATGACCTTATGGGACTTTCCTACTTGG

CAGTACATCTACGTATTAGTCATCGCTATTACCATGGTGATGCGGTTTTG

GCAGTACATCAATGGGCGTGGATAGCGGTTTGACTCACGGGGATTTCCAA

GTCTCCACCCCATTGACGTCAATGGGAGTTTGTTTTGGCACCAAAATCAA

CGGGACTTTCCAAAATGTCGTAACAACTCCGCCCCATTGACGCAAATGGG

CGGTAGGCGTGTACGGTGGGAGGTCTATATAAGCAGAGCTGGTTTAGTGA

ACCGTCAGATCACTAGTCGACTAGGGATAACAGGGCCGC

EF1alpha matrix promoter, short version
(SEQ ID NO: 168)
AGGAACCAATTCAGTCGACTGGATCCCGATGGCTCCGGTGCCCGTCAGTG

GGCAGAGCGCACATCGCCCACAGTCCCCGAGAAGTTGGGGGGAGGGGTCG

GCAATTGAACCGGTGCCTAGAGAAGGTGGCGCGGGGTAAACTGGGAAAGT

GATGTCGTGTACTGGCTCCGCCTTTTTCCCGAGGGTGGGGGAGAACCGTA

TATAAGTGCAGTAGTCGCCGTGAACGTTCTTTTTCGCAACGGGTTTGCCG

CCAGAACACAGGTCCGCGGCCCCGAACTAGGCCTAGGCGTCTGATCACTA

GTGACTCTAGTCCTAGTCGACTAGGGATAACAGGG

EF1alpha matrix promoter
(SEQ ID NO: 169)
GTGAGGCTCCGGTGCCCGTCAGTGGGCAGAGCGCACATCGCCCACAGTCC

CCGAGAAGTTGGGGGGAGGGGTCGGCAATTGAACCGGTGCCTAGAGAAGG

TGGCGCGGGGTAAACTGGGAAAGTGATGTCGTGTACTGGCTCCGCCTTTT

TCCCGAGGGTGGGGAGAACCGTATATAAGTGCAGTAGTCGCCGTGAACG

TTCTTTTTCGCAACGGGTTTGCCGCCAGAACACAGGTAAGTGCCGTGTGT

GGTTCCCGCGGGCCTGGCCTCTTTACGGGTTATGGCCCTTGCGTGCCTTG

AATTACTTCCACCTGGCTGCAGTACGTGATTCTTGATCCCGAGCTTCGGG

TTGGAAGTGGGTGGGAGAGTTCGAGGCCTTGCGCTTAAGGAGCCCCTTCG

CCTCGTGCTTGAGTTGAGGCCTGGCCTGGGCGCTGGGGCCGCCGCGTGCG

AATCTGGTGGCACCTTCGCGCCTGTCTCGCTGCTTTCGATAAGTCTCTAG

CCATTTAAAATTTTTGATGACCTGCTGCGACGCTTTTTTTCTGGCAAGAT

AGTCTTGTAAATGCGGGCCAAGATCTGCACACTGGTATTTCGGTTTTTGG

GGCCGCGGGCGGCGACGGGGCCCGTGCGTCCCAGCGCACATGTTCGGCGA

GGCGGGGCCTGCGAGCGCGGCCACCGAGAATCGGACGGGGGTAGTCTCAA

GCTGGCCGGCCTGCTCTGGTGCCTGGCCTCGCGCCGCCGTGTATCGCCCC

GCCCTGGGCGGCAAGGCTGGCCCGGTCGGCACCAGTTGCGTGAGCGGAAA

GATGGCCGCTTCCCGGCCCTGCTGCAGGGAGCTCAAAATGGAGGACGCGG

CGCTCGGGAGAGCGGGCGGGTGAGTCACCCACACAAAGGAAAAGGGCCTT

TCCGTCCTCAGCCGTCGCTTCATGTGACTCCACGGAGTACCGGGCGCCGT

CCAGGCACCTCGATTAGTTCTCGAGCTTTTGGAGTACGTCGTCTTTAGGT

TGGGGGGAGGGGTTTTATGCGATGGAGTTTCCCCACACTGAGTGGGTGGA

GACTGAAGTTAGGCCAGCTTGGCACTTGATGTAATTCTCCTTGGAATTTG

CCCTTTTTGAGTTTGGATCTTGGTTCATTCTCAAGCCTCAGACAGTGGTT

CAAAGTTTTTTTCTTCCATTTCAGGTGTCGTGA

TRE3G matrix promoter (SEQ ID NO: 170)

CTTTCGTCTTCAAGAATTCCTGGAGTTTACTCCCTATCAGTGATAGAGAA

CGTATGAAGAGTTTACTCCCTATCAGTGATAGAGAACGTATGCAGACTTT

ACTCCCTATCAGTGATAGAGAACGTATAAGGAGTTTACTCCCTATCAGTG

ATAGAGAACGTATGACCAGTTTACTCCCTATCAGTGATAGAGAACGTATC

TACAGTTTACTCCCTATCAGTGATAGAGAACGTATATCCAGTTTACTCCC

TATCAGTGATAGAGAACGTATAAGCTTTAGGCGTGTACGGTGGGCGCCTA

TAAAAGCAGAGCTCGTTTAGTGAACCGTCAGATCGCCTGGAGCAATTCCA

CAACACTTTTGTCTTATACCAACTTTCCGTACCACTTCCTACCCTCGTAA

A

Matrix eZ-Rosa26-3'

(SEQ ID NO: 171)

AGATGGGCGGGAGTCTTCTGGGCAGGCTTAAAGGCTAACCTGGTGTGTGG

GCGTTGTCCTGCAGGGGAATTGAACAGGTGTAAAATTGGAGGGACAAGAC

TTCCCACAGATTTTCGGTTTTGTCGGGAAGTTTTTTAATAGGGGCAAATA

GGAAAATGGAGGATAGGAGTCATCTGGGGTTTATGCAGCAAAACTACAGG

TATATTGCTTGTATCCGCCTCGGAGATTTCCATGAGGAGATAAAGACATG

TCACCCGAGTTTATACTCTCCTGCTTAGATCCTACTACAGTATGAAATAC

AGTGTCGCGAGGTAGACTATGTAAGCAGATTTAATCATTTTAAAGAGCCC

AGTACTTCATATCCATTTCTCCCGCTCCTTCTGCAGCCTTATCAAAAGGT

ATTTAGAACACTCATTTTAGCCCCATTTTCATTTATTATACTGGCTTATC

CAACCCCTAGACAGAGCATTGGCATTTTCCCTTTCCTGATCTTAGAAGTC

TGATGACTCATGAAACCAGACAGATTAGTTACATACACCACAAATCGAGG

CTGTAGCTGGGGCCTCAACACTGCAGTTCTTTTATAACTCCTTAGTACAC

TTTTTGTTGATCCTTTGCCTTGATCCTTAATTTTCAGTGTCTATCACCTC

TCCCGTCAGGTGGTGTTCCACATTTGGGCCTATTCTCAGTCCAGGGAGTT

TTACAACAATAGATGTATTGAGAATCCAACCTAAAGCTTAACTTTCCACT

CCCATGAATGCCTCTCTCCTTTTTCTCCATTATAACTGAGCTATAACCAT

TAATGGTTTCAGGTGGATGTCTCCTCCCCCAATATACCTGATGTATCTAC

ATATTGCCAGGCTGATATTTTAAGACATAAAAGGTATATTTCATTATTGA

GCCACATGGTATTGATTACTGCTACTAAAATTTTGTCATTGTACACATCT

GTAAAAGGTGGTTCCTTTTGGAATGCAAAGTTCAGGTGTTTGTTGTCTTT

CCTGACCTAAGGTCTTGTGAGCTTGTATTTTTTCTATTTAAGCAGTGCTT

TCTCTTGGACTGGCTTGACTCATGGCATTCTACACGTTATTGCTGGTCTA

AATGTGATTTTGCCAAGCTTCTTCAGGACCTATAATTTTGCTTGACTTGT

AGCCAAACACAAGTAAAATGATTAAGCAACAAATGTATTTGTGAAGCTTG

GTTTTTAGGTTGTTGTGTTGTGTGTGCTTGTGCTCTATAATAATACTATC

CAGGGGCTGGAGAGGTGGCTCGGAGTTCAAGAGCACAGACTGCTCTTCCA

GAAGTCCTGAGTTCAATTCCCAGCAACCACATGGTGGCTCACAACCATCT

GTAATGGGATCTGATGCCCTCTTCTGGTGTGTCTGAAGACCACAAGTGTA

TTCACATTAAATAAATAATCCTCCTTCTTCTTCTTTTTTTTTTTTTAAAG

AGAATACTGTCTCCAGTAGAATTACTGAAGTAATGAAATACTTTGTGTTT

GTTCCAATATGGAAGCCAATAATCAAATACTCTTAAGCACTGGAAATGTA

CCAAGGAACTATTTTATTTAAGTGAACTGTGGACAGAGGAGCCATAACTG

CAGACTTGTGGGATACAGAAGACCAATGCAGACTTAATGTCTTTTCTCTT

ACACTAAGCAATAAAGAAATAAAAATTGAACTTCTAGTATCCTATTTGTT

AAACTGCTAGCTTTACTAACTTTTGTGCTTCATCTATACAAAGCTGAAAG

CTAAGTCTGCAGCCATTACTAAACATGAAAGCAAGTAATGATAATTTTGG

ATTTCAAAAATGTAGGGCCAGAGTTTAGCCAGCCAGTGGTGGTGCTTGCC

TTTATGCCTTAATCCCAGCACTCTGGAGGCAGAGACAGGCAGATCTCTGA

GTTTGAGCCCAGCCTGGTCTACACATCAAGTTCTATCTAGGATAGCCAGG

AATACACACAGAAACCCTGTTGGGAGGGGGGCTCTGAGATTTCATAAAA

TTATAATTGAAGCATTCCCTAATGAGCCACTATGGATGTGGCTAAATCCG

TCTACCTTTCTGATGAGATTTGGGTATTATTTTTTCTGTCTCTGCTGTTG

GTTGGGTCTTTTGACACTGTGGGCTTTCTTAAAGCCTCCTTCCCTGCCAT

GTGGACTCTTGTTTGCTACTAACTTCCCATGGCTTAAATGGCATGGCTTTT

TTGCCTTCTAAGGGCAGCTGCTGAGATTTGCAGCCTGATTTCCAGGGTGG

GGTTGGGAAATCTTTCAAACACTAAAATTGTCCTTTAATTTTTTTTTAAA

AAATGGGTTATATAATAAACCTCATAAAATAGTTATGAGGAGTGAGGTGG

ACTAATATTAATGAGTCCCTCCCCTATAAAAGAGCTATTAAGGCTTTTTG

TCTTATACTAACTTTTTTTTAAATGTGGTATCTTTAGAACCAAGGGTCT

TAGAGTTTTAGTATACAGAAACTGTTGCATCGCTTAATCAGATTTTCTAG

TTTCAAATCCAGAGAATCCAAATTCTTCACAGCCAAAGTCAAATTAAGAA

TTTCTGACTTTAATGTTATTTGCTACTGTGAATATAAAATGATAGCTTTT

CCTGAGGCAGGGTATCACTATGTATCTCTGCCTGATCTGCAACAAGATAT

GTAGACTAAAGTTCTGCCTGCTTTTGTCTCCTGAATACTAAGGTTAAAAT

GTAGTAATACTTTTGGAACTTGCAGGTCAGATTCTTTTATAGGGGACACA

CTAAGGGAGCTTGGGTGATAGTTGGTAAATGTGTTTAAGTGATGAAAACT

TGAATTATTATCACCGCAACCTACTTTTTAAAAAAAAAAGCCAGGCCTGT

TAGAGCATGCTAAGGGATCCCTAGGACTTGCTGAGCACACAAGAGTAGTA

CTTGGCAGGCTCCTGGTGAGAGCATATTTCAAAAAACAAGGCAGACAACC

AAGAAACTACAGTAAGGTTACCTGTCTTTAACCATCTGCATATACACAGG

GATATTAAAATATTCCAAATAATATTTCATTCAAGTTTTCCCCCATCAAA

TTGGGACATGGATTTCTCCGGTGAATAGGCAGAGTTGGAAACTAAACAAA

TGTTGGTTTTGTGATTTGTGAAATTGTTTTCAAGTGATAGTTAAAGCCCA

TGAGATACAGAACAAAGCTGCTATTTCGAGGTCACTTGGTTATACTCAGA

AGCACTTCTTTGGGTTTCCCTGCACTATCCTGATCATGTGCTAGGCCTAC

CTTAGGCTGATTGTTGTTCAAATAACTTAAGTTTCCTGTCAGGTGATGTC

ATATGATTTCATATATCAAGGCAAAACATGTTATATATGTTAAACATTTG

GACTTAATGTGAAAGTTAGGTCTTTGTGGGTTTTGATTTTAATTTCAAAA

CCTGAGCTAAATAAGTCATTTTACATGTCTTACATTTGGTGAATTGTATA

TTGTGGTTTGCAGGCAAGACTCTCTGACCTAGTAACCCTCCTATAGAGCA

CTTTGCTGGGTCACAAGTCTAGGAGTCAAGCATTTCACCTTGAAGTTGAG

ACGTTTTGTTAGTGTATACTAGTTATATGTTGGAGGACATGTTTATCCAG

AAGATATTCAGGACTATTTTTGACTGGGCTAAGGAATTGATTCTGATTAG

CACTGTTAGTGAGCATTGAGTGGCCTTTAGGCTTGAATTGGAGTCACTTG

TATATCTCAAATAATGCTGGCCTTTTTAAAAAGCCCTTGTTCTTTATCA

CCCTGTTTTCTACATAATTTTTGTTCAAAGAAATACTTGTTTGGATCTCC

TTTTGACAACAATAGCATGTTTTCAAGCCATATTTTTTTCCTTTTTTTT

TTTTTTTTGGTTTTTCGAGACAGGGTTTCTCTGTATAGCCCTGGCTGTC

CTGGAACTCACTTTGTAGACCAGGCTGGCCTCGAACTCAGAAATCCGCCT

GCCTCTGCCTCCTGAGTGCCGGGATTAAAGGCGTGCACCACCACGCCTGG

CTAAGTTGGATATTTTGTATATAACTATAACCAATACTAACTCCACTGGG

TGGATTTTTAATTCAGTCAGTAGTCTTAAGTGGTCTTTATTGGCCCTTAT

TAAAATCTACTGTTCACTCTAACAGAGGCTGTTGGACTAGTGGGACTAAG

CAACTTCCTACGGATATACTAGCAGATAAGGGTCAGGGATAGAAACTAGT

CTAGCGTTTTGTATACCTACCAGCTTATACTACCTTGTTCTGATAGAAAT

ATTTAGGACATCTAGCTTATC

Matrix eZ-Rosa26-5'
(SEQ ID NO: 172)
CCCCGCGGCAGGCCCTCCGAGCGTGGTGGAGCCGTTCTGTGAGACAGCCG

GGTACGAGTCGTGACGCTGGAAGGGGCAAGCGGGTGGTGGGCAGGAATGC

GGTCCGCCCTGCAGCAACCGGAGGGGGAGGGAGAAGGGAGCGGAAAAGTC

TCCACCGGACGCGGCCATGGCTCGGGGGGGGGGGGCAGCGGAGGAGCGC

TTCCGGCCGACGTCTCGTCGCTGATTGGCTTCTTTTTCCTCCCGCCGTGTG

TGAAAACACAAATGGCGTGTTTTGGTTGGCGTAAGGCGCCTGTCAGTTAA

CGGCAGCCGAGTGCGCAGCCGCCGGCAGCCTCGCTCTGCCCACTGGGTG

GGGCGGGAGGTAGGTGGGGTGAGGCGAGCTGGACGTGCGGGCGCGGTCGG

CCTCTGGCGGGGCGGGGAGGGGAGGGAGGGTCAGCGAAAGTAGCTCGCG

CGCGAGCGGCCGCCCACCCTCCCCTTCCTCTGGGGGAGTCGTTTTACCCG

CCGCCGGCCGGGCCTCGTCGTCTGATTGGCTCTCGGGGCCCAGAAACTG

GCCCTTGCCATTGGCTCGTGTTCGTGCAAGTTGAGTCCATCCGCCGGCCA

GCGGGGGCGGCGAGGAGGCGCTCCCAGGTTCCGGCCCTCCCCTCGGCCCC

GCGCCGCAGAGTCTGGCCGCGCGCCCCTGCGCAACGTGGCAGGAAGCGCG

CGCTGGGGGCGGGGACGGGCAGTAGGGCTGAGCGGCTGCGGGGCGGGTGC

AAGCACGTTTCCGACTTGAGTTGCCTCAAGAGGGGCGTGCTGAGCCAGAC

CTCCATCGCGCACTCCGGGGAGTGGAGGGAAGGAGCGAGGGCTCAGTTGG

GCTGTTTTGGAGGCAGGAAGCACTTGCTCTCCCAAAGTCGCTCTGAGTTG

TTATCAGTAAGGGAGCTGCAGTGGAGTAGGCGGGGAGAAGGCCGCACCCT

TCTCCGGAGGGGGAGGGGAGTGTTGCAATACCTTTCTGGGAGTTCTCTG

CTGCCTCCTGGCTTCTGAGGACCGCCCTGGGCCTGGGAGAATCCCTTGCC

CCCTCTTCCCCTCGTGATCTGCAACTCCAGTCTT

Matrix mB3Galt6 shRNA TR506016D
(SEQ ID NO: 173)
ACAGGGTCGACAAGCTTTTCCAAAAAAAAAGCATGAGGTGCAGTTGCGCC

TTTCCTATCTCTTGAATAGGAAAGGCGCAACTGCACCTCATGCTGGATCC

CGCGTCCTTTCCACAAGATATATAAACCCAAGAAATCGAAATACTTTCAA

GTTACGGTAAGCATATGATAGTCCATTTTAAAACATAATTTTAAAACTGC

AAACTACCCAAGAAATTATTACTTTCTACGTCACGTATTTTGTACTAATA

TCTTTGTGTTTACAGTCAAATTAATTCTAATTATCTCTAACAGCCTTG

TATCGTATATGCAAATATGAAGGAATCATGGGAAATAGGCCCTCTTCCTG

CCCGACCTTGGCGCGCGCTCGGCGCGCGGTCACGCTCCGTCACGTGGTGC

GTTTTG

Matrix eZ-SiaT-TGS-Hook
(SEQ ID NO: 174)
ATGATTCACACCAACCTGAAGAAAAAGTTCAGCTGCTGCGTCCTGGTCTT

TCTTCTGTTTGCAGTCATCTGTGTGTGGAAGGAAAAGAAGAAAGGGAGTT

ACTATGATTCCTTTAAATTGCAAACCAAGGAATTCCAGGTGTTAAAGAGT

CTGGGGAAATTGGCCATGGGGTCTGATTCCCAGTCTGTATCCTCAAGCAG

CACCCAGGACCCCCACAGGGGCCGCCAGACCCTCGGCAGTCTCAGAGGCC

TAGCCAAGGCCAAACCAGAGGCCTCCTTCCAGGTGTGGAACAAGGACAGC

TCTTCCAAAAACCTTATCCCTAGGCTGCAAAAGGGGTCGGGG

Matrix TagBFP
(SEQ ID NO: 175)
ATGTCGGGGAGCGAGCTGATTAAGGAGAACATGCACATGAAGCTGTACAT

GGAGGGCACCGTGGACAACCATCACTTCAAGTGCACATCCGAGGGCGAAG

GCAAGCCCTACGAGGGCACCCAGACCATGAGAATCAAGGTGGTCGAGGGC

GGCCCTCTCCCCTTCGCCTTCGACATCCTGGCTACTAGCTTCCTCTACGG

CAGCAAGACCTTCATCAACCACACCCAGGGCATCCCCGACTTCTTCAAGC

AGTCCTTCCCTGAGGGCTTCACATGGGAGAGAGTCACCACATACGAGGAC

GGGGGCGTGCTGACCGCTACCCAGGACACCAGCCTCCAGGACGGCTGCCT

CATCTACAACGTCAAGATCAGAGGGGTGAACTTCACATCCAACGGCCCTG

TGATGCAGAAGAAAACACTCGGCTGGGAGGCCTTCACCGAAACGCTGTAC

CCCGCTGACGGCGGCCTGGAAGGCAGAAACGACATGGCCCTGAAGCTCGT

GGGCGGGAGCCATCTGATCGCAAACATCAAGACCACATATAGATCCAAGA

AACCCGCTAAGAACCTCAAGATGCCTGGCGTCTACTATGTGGACTACAGA

CTGGAAAGAATCAAGGAGGCCAACAACGAAACCTACGTCGAGCAGCACGA

GGTGGCAGTGGCCAGATACTGCGACCTCCCTAGCAAACTGGGGCACAAGC

TTAATTCCGGATGA

Matrix thymidine kinase cDNA (SEQ ID NO: 176)

ATGGCTTCGTACCCTGCCATCAACACGCGTCTGCGTTCGACCAGGCTGC

GCGTTCTCGCGGCCATAGCAACCGACGTACGGCGTTGCGCCCTCGCCGGC

AGCAAGAAGCCACGGAAGTCCGCCTGGAGCAGAAAATGCCCACGCTACTG

CGGGTTTATATAGACGGTCCTCACGGGATGGGGAAAACCACCACCACGCA

ACTGCTGGTGGCCCTGGGTTCGCGCGACGATATCGTCTACGTACCCGAGC

CGATGACTTACTGGCAGGTGCTGGGGGCTTCCGAGACAATCGCGAACATC

TACACCACACAACACCGCCTCGACCAGGGTGAGATATCGGCCGGGACGC

GGCGGTGGTAATGACAAGCGCCCAGATAACAATGGGCATGCCTTATGCCG

TGACCGACGCCGTTCTGGCTCCTCATATCGGGGGGAGGCTGGGAGCTCA

CATGCCCCGCCCCCGGCCCTCACCCTCATCTTCGACCGCCATCCCATCGC

CGCCCTCCTGTGCTACCCGGCCGCGCGATACCTTATGGGCAGCATGACCC

CCCAGGCCGTGCTGGCGTTCGTGGCCCTCATCCCGCCGACCTTGCCCGGC

ACAAACATCGTGTTGGGGGCCCTTCCGGAGGACAGACACATCGACCGCCT

GGCCAAACGCCAGCGCCCCGGCGAGCGGCTTGACCTGGCTATGCTGGCCG

CGATTCGCCGCGTTTACGGGCTGCTTGCCAATACGGTGCGGTATCTGCAG

GGCGGCGGGTCGTGGCGGGAGGATTGGGGACAGCTTTCGGGGACGGCCGT

GCCGCCCCAGGGTGCCGAGCCCAGAGCAACGCGGGCCCACGACCCCATA

TCGGGGACACGTTATTTACCCTGTTTCGGCCCCCGAGTTGCTGGCCCCC

AACGGCGACCTGTACAACGTGTTTGCCTGGGCCTTGGACGTCTTGGCCAA

ACGCCTCCGTCCCATGCACGTCTTTATCCTGGATTACGACCAATCGCCCG

CCGGCTGCCGGGACGCCCTGCTGCAACTTACCTCCGGGATGGTCCAGACC

CACGTCACCACCCCCGGCTCCATACCGACGATCTGCGACCTGGCGCGCAC

GTTTGCCCGGGAGATGGGGGAGGCTAACTGA

Matrix TK term (SEQ ID NO: 177)

GGGGGAGGCTAACTGAAACACGGAAGGAGACAATACCGGAAGGAACCCGC

GCTATGACGGCAATAAAAAGACAGAATAAAACGCACGGTGTTGGGTCGTT

TGTTCATAAACGCGGGGTTCGGTCCCAGGGCTGGCACTCTGTCGATACCC

CACCGAGGCCCCATTGGGGCCAATACGCCCGCGTTTCTTCCTTTTCCCCA

CCCCACCCCCCAAGTTCGGGTGAAGGCCCAGGGCTCGCAGCCAACGTCGG

GGCGGCAGGCCCTGCCATAGCC

Matrix TetON-3G cDNA (SEQ ID NO: 178)

ATGTCTAGACTGGACAAGAGCAAAGTCATAAACTCTGCTCTGGAATTACT

CAATGGAGTCGGTATCGAAGGCCTGACGACAAGGAAACTCGCTCAAAAGC

TGGGAGTTGAGCAGCCTACCCTGTACTGGCACGTGAAGAACAAGCGGGCC

CTGCTCGATGCCCTGCCAATCGAGATGCTGGACAGGCATCATACCCACTC

CTGCCCCCTGGAAGGCGAGTCATGGCAAGACTTTCTGCGGAACAACGCCA

AGTCATACCGCTGTGCTCTCCTCTCACATCGCGACGGGGCTAAAGTGCAT

CTCGGCACCCGCCCAACAGAGAAACAGTACGAAACCCTGGAAAATCAGCT

CGCGTTCCTGTGTCAGCAAGGCTTCTCCCTGGAGAACGCACTGTACGCTC

TGTCCGCCGTGGGCCACTTTACACTGGGCTGCGTATTGGAGGAACAGGAG

CATCAAGTAGCAAAAGAGGAAAGAGAGACACCTACCACCGATTCTATGCC

CCCACTTCTGAAACAAGCAATTGAGCTGTTCGACCGGCAGGGAGCCGAAC

CTGCCTTCCTTTTCGGCCTGGAACTAATCATATGTGGCCTGGAGAAACAG

CTAAAGTGCGAAAGCGGCGGGCCGACCGACGCCCTTGACGATTTTGACTT

AGACATGCTCCCAGCCGATGCCCTTGACGACTTTGACCTTGATATGCTGC

CTGCTGACGCTCTTGACGATTTTGACCTTGACATGCTCCCCGGGTAA

The invention claimed is:

1. A method for producing a circular double-stranded DNA vector comprising at least six sequences of interest, said method consisting of:

(a) a step of simultaneously contacting at equimolar ratio at least six molecular building blocks, which are different from one another, in the presence of a single type IIs restriction enzyme and a ligase, each molecular building block consisting of an isolated linear double-stranded DNA molecule and containing:
- (i) a sequence of interest with no specific recognition site of the aforementioned type IIs restriction enzyme,
- (ii) two double-stranded DNA adapters, flanked upstream and downstream of said sequence of interest, each double-stranded DNA adapter comprising a sequence of at least 12 nucleotides, which sequence contains:

a single and only recognition site of the aforementioned type IIs restriction enzyme, the recognition site of the aforementioned type IIs restriction enzyme of the adapter upstream of said sequence of interest and the recognition site of the aforementioned type IIs restriction enzyme of the adapter downstream of said specific sequence being convergent, (b) a step of incubation of the mixture obtained in step a) at a temperature ranging from 20° C. to a temperature of 55° C., during a period ranging from 2 minutes to a period of 30 minutes, which step leads:

to the elimination by cleaving of the recognition sites of the type IIs restriction enzyme used, to the formation of a cohesive single-stranded suture of at least 2 nucleotides at each of the ends of said sequence of interest, said cohesive single-stranded suture of at least 2 nucleotides upstream of one of the at least six sequences of interest being complementary to said cohesive single-stranded suture of at least 2 nucleotides downstream of another sequence of interest, to the pairing by nucleotide complementarity of the aforementioned cohesive single-stranded sutures of at least 2 nucleotides, and to the positioning of the sequences of interest contiguously with one another in an order and a single and defined direction, said cohesive single-stranded suture of at least 2 nucleotides upstream and downstream of the sequence of interest is selected for assembly using a scoring matrix where each pairing of two sequences of four non-palindromic nucleotides is attributed a score ranging from 0 to 10, where 0 corresponds to a total absence of complementarity (0%) and 10 indicates total complementarity (100%) and each suture selected has a score of complementarity equal to 0, 1 or 2 compared to other sutures selected for assembly, (c) a step of ligation of said selected cohesive single-stranded sutures of at least 2 nucleotides, said step being performed at a temperature ranging from 10° C. to a temperature of 40° C. during a period ranging from 2 min to a period of 30 min to obtain a circular double-stranded DNA vector said step (b) and (c) being repeated from 1 to 49 times, said method also comprising:

(d) at least one step of incubation at a temperature from 41 to 60° C. during a period ranging from 0.5 to 15 min; and wherein said steps (a), (b), (c) and (d) are performed in the same reaction mixture.

2. The method according to claim 1, in which the type IIs restriction enzyme is a type IIs restriction enzyme selected from BsaI, Eco31I, BbsI, BpiI, BsmBI, Esp3I, BspMI, BfuAI and BveI.

3. The method according to claim 1, in which the double-stranded DNA adapter, downstream or upstream of said sequence of interest, further comprises at least one recognition site of a type IIp restriction enzyme.

4. The method according to claim 1, in which the double-stranded DNA adapters upstream and downstream of said sequence of interest do not have a site of recognition of a type IIs restriction enzyme other than that of the type IIs restriction enzyme present in the step of simultaneously contacting at least six molecular building blocks, which are different from one another.

5. The method according to claim 1, in which the cohesive single-stranded suture of at least 2 nucleotides at each of the ends upstream and downstream of the sequence of interest comprises 2 to 10 nucleotides.

6. The method according to claim 1, in which each cohesive single-stranded suture of at least 2 nucleotides produced from a molecular building block pairs with a cohesive single-stranded suture of at least 2 nucleotides produced from another molecular building block.

7. The method according to claim 1, in which the cohesive single-stranded suture of at least 2 nucleotides produced at each of the ends downstream and upstream of the sequence of interest comprises a sequence of 42 possible combinations excluding the z*z combinations which result in a DNA palindrome, in which z is between 2 and 10 and z is the number of nucleotides of the single-stranded suture.

8. The method according to claim 1, in which the cohesive single-stranded suture of at least 2 nucleotides upstream and downstream of the sequence of interest is designed with the aid of a scoring matrix.

9. The method according to claim 1, in which said type IIs restriction enzyme cleaves the DNA at a distance ranging from 2 to 15 nucleotides, 2 to 14, 2 to 13, 2 to 12, 2 to 11, 2 to 10, 2 to 9, 2 to 8, 2 to 7, 2 to 6, 2 to 5, 2 to 4 or 2 to 3 nucleotides from the specific recognition site of said type IIs enzyme.

10. The method according to claim 1, comprising, before the step of simultaneously contacting at least six molecular building blocks, a step of preparing each of the molecular building blocks by chemical synthesis or by a step of amplification by PCR of the sequence of interest contained in a building block with the aid of a forward primer comprising, from 5' to 3', a sequence corresponding to the sequence of the adapter and at least 14 nucleotides of the sequence of interest, and a reverse primer comprising, from 5' to 3', at least 14 nucleotides of the sequence of interest and at least one sequence corresponding to the sequence of the adapter.

11. The method according to claim 1, which further comprises a step (e) of incubation at a temperature from 61 to 90° C. during a period ranging from 0.5 to 15 minutes.

12. The method according to claim 3, wherein the double-stranded DNA adapter, downstream or upstream of said sequence of interest, further comprises two recognition sites of restriction enzymes selected from KpnI and AgeI, EcoRI and BstBI, SalI and MluI.

13. The method according to claim 5, in which the cohesive single-stranded suture of at least 2 nucleotides at each of the ends upstream and downstream of the sequence of interest comprises 2 to 5 nucleotides.

14. The method according to claim 1, wherein step (a) comprises the simultaneously contacting of an equimolar ratio of at least eight molecular building blocks.

* * * * *

SEQUENCE LISTING

<160> NUMBER OF SEQ ID NOS: 178

<210> SEQ ID NO 1
<211> LENGTH: 40
<212> TYPE: DNA
<213> ORGANISM: Artificial sequence
<220> FEATURE:
<223> OTHER INFORMATION: BGHpA TGAT BsaI CW

<400> SEQUENCE: 1
gaggtaccgg tctcatgatc gactgtgcct tctagttgcc                40

<210> SEQ ID NO 2
<211> LENGTH: 36
<212> TYPE: DNA
<213> ORGANISM: Artificial sequence
<220> FEATURE:
<223> OTHER INFORMATION: BGHpA AGAA BsaI CCW

<400> SEQUENCE: 2
gaggtaccgg tctccagaag ccatagagcc caccgc                36

<210> SEQ ID NO 3
<211> LENGTH: 50
<212> TYPE: DNA
<213> ORGANISM: Artificial sequence
<220> FEATURE:
<223> OTHER INFORMATION: lacZ-up TTCT BsaI CW

<400> SEQUENCE: 3
gaggtaccgg tctcgttctc cctgcaggtg cgcccaatac gcaaaccgcc                50

<210> SEQ ID NO 4
<211> LENGTH: 44
<212> TYPE: DNA
<213> ORGANISM: Artificial sequence
<220> FEATURE:
<223> OTHER INFORMATION: lacZ-up TGTC BsaI CCW

<400> SEQUENCE: 4
gaggtaccgg tctcctgtcc gtaatcatgg tcatagctgt ttcc                      44

<210> SEQ ID NO 5
<211> LENGTH: 41
<212> TYPE: DNA
<213> ORGANISM: Artificial sequence
<220> FEATURE:
<223> OTHER INFORMATION: lacZ-down GACA BsaI CW

<400> SEQUENCE: 5
gaggtaccgg tctcggacag cctggccgtc gttttacaac g                         41

<210> SEQ ID NO 6
<211> LENGTH: 55
<212> TYPE: DNA
<213> ORGANISM: Artificial sequence
<220> FEATURE:
<223> OTHER INFORMATION: lacZ-down CTGG BsaI CCW

<400> SEQUENCE: 6
gaggtaccgg tctcactggc cctgcaggtc tatgcggcat cagagcagat tgtac          55

<210> SEQ ID NO 7
<211> LENGTH: 39
<212> TYPE: DNA
<213> ORGANISM: Artificial sequence
<220> FEATURE:
<223> OTHER INFORMATION: SV40pori CCAG BsaI CW

<400> SEQUENCE: 7
gaggtaccgg tctccccagc aggcagaagt atgcaaagc                            39

<210> SEQ ID NO 8
<211> LENGTH: 40
<212> TYPE: DNA
<213> ORGANISM: Artificial sequence
<220> FEATURE:
<223> OTHER INFORMATION: SV40term ATAA BsaI CCW

<400> SEQUENCE: 8
gaggtaccgg tctcgataag atacattgat gagtttggac                           40

<210> SEQ ID NO 9
<211> LENGTH: 58
<212> TYPE: DNA
<213> ORGANISM: Artificial sequence
<220> FEATURE:

-continued

<223> OTHER INFORMATION: ColE1-ori TTAT BsaI CW

<400> SEQUENCE: 9
gaggtaccgg tctcattatg cgtcttctag ggttaaggtt agtgtagaga agcaaccg        58

<210> SEQ ID NO 10
<211> LENGTH: 59
<212> TYPE: DNA
<213> ORGANISM: Artificial sequence
<220> FEATURE:
<223> OTHER INFORMATION: AmpR TCCT BsaI CCW

<400> SEQUENCE: 10
gaggtaccgg tctcgtcctt gagacgctag tcctcgttcc cgatgctctc gtcctatcc       59

<210> SEQ ID NO 11
<211> LENGTH: 37
<212> TYPE: DNA
<213> ORGANISM: Artificial sequence
<220> FEATURE:
<223> OTHER INFORMATION: pENprom AGGA BsaI CW

<400> SEQUENCE: 11
gaggtaccgg tctcaaggaa ccaattcagt cgactgg                               37

<210> SEQ ID NO 12
<211> LENGTH: 46
<212> TYPE: DNA
<213> ORGANISM: Artificial sequence
<220> FEATURE:
<223> OTHER INFORMATION: pENprom GGTG BsaI CCW

<400> SEQUENCE: 12
gaggtaccgg tctcaggtgg cggccctgtt atccctagtc gactag                     46

<210> SEQ ID NO 13
<211> LENGTH: 40
<212> TYPE: DNA
<213> ORGANISM: Artificial sequence
<220> FEATURE:
<223> OTHER INFORMATION: SiaT CACC BsaI CW

<400> SEQUENCE: 13
gaggtaccgg tctcccacca tgattcacac caacctgaag                            40

<210> SEQ ID NO 14
<211> LENGTH: 40
<212> TYPE: DNA
<213> ORGANISM: Artificial sequence
<220> FEATURE:
<223> OTHER INFORMATION: SiaT CCCC BsaI CCW

<400> SEQUENCE: 14
gaggtaccgg tctcaccccct tttgcagcct agggataagg                           40

<210> SEQ ID NO 15
<211> LENGTH: 43
<212> TYPE: DNA
<213> ORGANISM: Artificial sequence
<220> FEATURE:
<223> OTHER INFORMATION: XFP-Ctag GGGG BsaI CW

<400> SEQUENCE: 15
gaggtaccgg tctccggggt cggggtgag caagggcgag gag                         43

<210> SEQ ID NO 16
<211> LENGTH: 39
<212> TYPE: DNA
<213> ORGANISM: Artificial sequence
<220> FEATURE:
<223> OTHER INFORMATION: XFP-Ctag ATCA BsaI CCW

<400> SEQUENCE: 16
gaggtaccgg tctccatcac ttgtacagct cgtccatgc                              39

<210> SEQ ID NO 17
<211> LENGTH: 2005
<212> TYPE: DNA
<213> ORGANISM: Artificial sequence
<220> FEATURE:
<223> OTHER INFORMATION: Ori-AmpR BsaI A

<400> SEQUENCE: 17

| | |
|---|---|
| gaggtaccgg tctcattatg cgtcttctag ggttaaggtt agtgtagaga agcaaccgaa | 60 |
| gattgagaag acatggcggt aatacggtta ccacagaat caggggataa cgcaggaaag | 120 |
| aacatgtgag caaaaggcca gcaaaaggcc aggaaccgta aaaaggccgc gttgctggcg | 180 |
| ttttttccata ggctccgccc ccctgacgag catcacaaaa atcgacgctc aagtcagagg | 240 |
| tggcgaaacc cgacaggact ataaagatac caggcgtttc ccctggaag ctccctcgtg | 300 |
| cgctctcctg ttccgaccct gccgcttacc ggatacctgt ccgcctttct cccttcggga | 360 |
| agcgtggcgc tttctcatag ctcacgctgt aggtatctca gttcggtgta ggtcgttcgc | 420 |
| tccaagctgg gctgtgtgca cgaaccccc gttcagcccg accgctgcgc cttatccggt | 480 |
| aactatcgtc ttgagtccaa cccggtaaga cacgacttat cgccactggc agcagccact | 540 |
| ggtaacagga ttagcagagc gaggtatgta ggcggtgcta cagagttctt gaagtggtgg | 600 |
| cctaactacg gctacactag aagaacagta tttggtatct gcgctctgct gaagccagtt | 660 |
| accttcggaa aaagagttgg tagctcttga tccggcaaac aaaccaccgc tggtagcggt | 720 |
| ttttttgttt gcaagcagca gattacgcgc agaaaaaaag gatctcaaga agatcctttg | 780 |
| atcttttcta cggggtctga cgctcagtgg aacgaaaact cacgttaagg gattttggtc | 840 |
| atgagattat caaaaaggat cttcacctag atcctttta attaaaaatg aagttttaaa | 900 |
| tcaatctaaa gtatatatga gtaaacttgg tctgacagtt accaatgctt aatcagtgag | 960 |
| gcacctatct cagcgatctg tctatttcgt tcatccatag ttgcctgact ccccgtcgtg | 1020 |
| tagataacta cgatacggga gggcttacca tctggcccca gtgctgcaat gataccgcgt | 1080 |
| gacccacgct caccggctcc agatttatca gcaataaacc agccagccgg aagggccgag | 1140 |
| cgcagaagtg gtcctgcaac tttatccgcc tccatccagt ctattaattg ttgccgggaa | 1200 |
| gctagagtaa gtagttcgcc agttaatagt ttgcgcaacg ttgttgccat tgctacaggc | 1260 |
| atcgtggtgt cacgctcgtc gtttggtatg gcttcattca gctccggttc ccaacgatca | 1320 |
| aggcgagtta catgatcccc catgttgtgc aaaaaagcgg ttagctcctt cggtcctccg | 1380 |
| atcgttgtca gaagtaagtt ggccgcagtg ttatcactca tggttatggc agcactgcat | 1440 |
| aattctctta ctgtcatgcc atccgtaaga tgcttttctg tgactggtga gtactcaacc | 1500 |
| aagtcattct gagaatagtg tatgcggcga ccgagttgct cttgcccggc gtcaatacgg | 1560 |
| gataataccg cgccacatag cagaacttta aaagtgctca tcattggaaa acgttcttcg | 1620 |
| gggcgaaaac tctcaaggat cttaccgctg ttgagatcca gttcgatgta acccactcgt | 1680 |
| gcacccaact gatcttcagc atcttttact ttcaccagcg tttctgggtg agcaaaaaca | 1740 |

```
ggaaggcaaa atgccgcaaa aaagggaata agggcgacac ggaaatgttg aatactcata      1800
ctcttccttt ttcaatatta ttgaagcatt tatcagggtt attgtctcat gagcggatac      1860
atatttgaat gtatttagaa aaataaacaa ataggggttc cgcgcacatt tccccgaaaa      1920
gtgccaccta tgagacgtga ggctagggat aggacgagag catcgggaac gaggactagc      1980
gtctcaagga cgagaccggt acctc                                            2005

<210> SEQ ID NO 18
<211> LENGTH: 677
<212> TYPE: DNA
<213> ORGANISM: Artificial sequence
<220> FEATURE:
<223> OTHER INFORMATION: pCMV BsaI A

<400> SEQUENCE: 18
gaggtaccgg tctcaaggaa ccaattcagt cgactggatc ctagttatta atagtaatca       60
attacggggt cattagttca tagcccatat atggagttcc gcgttacata acttacggta      120
aatggcccgc ctggctgacc gcccaacgac ccccgcccat tgacgtcaat aatgacgtat      180
gttcccatag taacgccaat agggactttc cattgacgtc aatgggtgga gtatttacgg      240
taaactgccc acttggcagt acatcaagtg tatcatatgc caagtacgcc ccctattgac      300
gtcaatgacg gtaaatggcc cgcctggcat tatgcccagt acatgacctt atgggacttt      360
cctacttggc agtacatcta cgtattagtc atcgctatta ccatggtgat gcggttttgg      420
cagtacatca atgggcgtgg atagcggttt gactcacggg gatttccaag tctccacccc      480
attgacgtca atgggagttt gttttggcac caaaatcaac gggactttcc aaaatgtcgt      540
aacaactccg ccccattgac gcaaatgggc ggtaggcgtg tacggtggga ggtctatata      600
agcagagctg gtttagtgaa ccgtcagatc actagtcgac tagggataac agggccgcca      660
cctgagaccg gtacctc                                                    677

<210> SEQ ID NO 19
<211> LENGTH: 370
<212> TYPE: DNA
<213> ORGANISM: Artificial sequence
<220> FEATURE:
<223> OTHER INFORMATION: SiaT BsaI A

<400> SEQUENCE: 19
gaggtaccgg tctcccacca tgattcacac caacctgaag aaaaagttca gctgctgcgt       60
cctggtcttt cttctgtttg cagtcatctg tgtgtggaag gaaaagaaga agggagtta      120 ctatgattcc tttaaattgc aaaccaagga attccaggtg ttaaagagtc tggggaaatt      180
ggccatgggg tctgattccc agtctgtatc ctcaagcagc acccaggacc ccacaggggg      240
ccgccagacc ctcggcagtc tcagaggcct agccaaggcc aaaccagagg cctccttcca      300
ggtgtggaac aaggacagct cttccaaaaa ccttatccct aggctgcaaa aggggtgaga      360
ccggtacctc                                                            370

<210> SEQ ID NO 20
<211> LENGTH: 758
<212> TYPE: DNA
<213> ORGANISM: Artificial sequence
<220> FEATURE:
<223> OTHER INFORMATION: E1GFP BsaI A

<400> SEQUENCE: 20
gaggtaccgg tctccggggt cggggggtgag caagggcgag gagctgttca ccggggtggt       60
```

```
gcccatcctg gtcgagctgg acggcgacgt aaacggccac aagttcagcg tgtccggcga      120
gggcgagggc gatgccacct acggcaagct gaccctgaag ttcatctgca ccaccggcaa      180
gctgcccgtg ccctggccca ccctcgtgac caccctgtcc tacggcgtgc agtgcttcag      240
ccgctacccc gaccacatga agcagcacga cttcttcaag tccgccatgc ccgaaggcta      300
cgtccaggag cgcaccatct tcttcaagga cgacggcaac tacaagaccc gcgccgaggt      360
gaagttcgag ggcgacaccc tggtgaaccg catcgagctg aagggcatcg acttcaagga      420
ggacggcaac atcctggggc acaagctgga gtacaactac aacagccaca cgtctatat       480 catggccgac aagcagaaga acggcatcaa ggtgaacttc aagatccgcc acaacatcga      540
ggacggcagc gtgcagctcg ccgaccacta ccagcagaac ccccatcg gcgacggccc        600 cgtgctgctg cccgacaacc actacctgag ctaccagtcc gccctgagca agacccccaa      660
cgagaagcgc gatcacatgg tcctgctgga gttcgtgacc gccgccggga tcactctcgg      720
catggacgag ctgtacaagt gatggagacc ggtacctc                              758

<210> SEQ ID NO 21
<211> LENGTH: 758
<212> TYPE: DNA
<213> ORGANISM: Artificial sequence
<220> FEATURE:
<223> OTHER INFORMATION: EGFP BsaI A

<400> SEQUENCE: 21
gaggtaccgg tctccggggt cggggtgag caagggcgag gagctgttca ccggggtggt       60
gcccatcctg gtcgagctgg acggcgacgt aaacggccac aagttcagcg tgtccggcga      120
gggcgagggc gatgccacct acggcaagct gaccctgaag ttcatctgca ccaccggcaa      180
gctgcccgtg ccctggccca ccctcgtgac caccctgacc tacggcgtgc agtgcttcag      240
ccgctacccc gaccacatga agcagcacga cttcttcaag tccgccatgc ccgaaggcta      300
cgtccaggag cgcaccatct tcttcaagga cgacggcaac tacaagaccc gcgccgaggt      360
gaagttcgag ggcgacaccc tggtgaaccg catcgagctg aagggcatcg acttcaagga      420
ggacggcaac atcctggggc acaagctgga gtacaactac aacagccaca cgtctatat       480 catggccgac aagcagaaga acggcatcaa ggtgaacttc aagatccgcc acaacatcga      540
ggacggcagc gtgcagctcg ccgaccacta ccagcagaac ccccatcg gcgacggccc        600 cgtgctgctg cccgacaacc actacctgag cacccagtcc gccctgagca agacccccaa      660
cgagaagcgc gatcacatgg tcctgctgga gttcgtgacc gccgccggga tcactctcgg      720
catggacgag ctgtacaagt gatggagacc ggtacctc                              758

<210> SEQ ID NO 22
<211> LENGTH: 758
<212> TYPE: DNA
<213> ORGANISM: Artificial sequence
<220> FEATURE:
<223> OTHER INFORMATION: ECFP BsaI A

<400> SEQUENCE: 22
gaggtaccgg tctccggggt cggggtgag caagggcgag gagctgttca ccggggtggt       60
gcccatcctg gtcgagctgg acggcgacgt aaacggccac aagttcagcg tgtccggcga      120
gggcgagggc gatgccacct acggcaagct gaccctgaag ttcatctgca ccaccggcaa      180
gctgcccgtg ccctggccca ccctcgtgac caccctgacc tggggcgtgc agtgcttcag      240
```

| | |
|---|---|
| ccgctacccc gaccacatga agcagcacga cttcttcaag tccgccatgc ccgaaggcta | 300 |
| cgtccaggag cgcaccatct tcttcaagga cgacggcaac tacaagaccc gcgccgaggt | 360 |
| gaagttcgag ggcgacaccc tggtgaaccg catcgagctg aagggcatcg acttcaagga | 420 |
| ggacggcaac atcctggggc acaagctgga gtacaactac atcagccaca acgtctatat | 480 |
| caccgccgac aagcagaaga acggcatcaa ggccaacttc aagatccgcc acaacatcga | 540 |
| ggacggcagc gtgcagctcg ccgaccacta ccagcagaac ccccatcg gcgacggccc | 600 |
| cgtgctgctg cccgacaacc actacctgag cacccagtcc gccctgagca agacccccaa | 660 |
| cgagaagcgc gatcacatgg tcctgctgga gttcgtgacc gccgccggga tcactctcgg | 720 |
| catggacgag ctgtacaagt gatggagacc ggtacctc | 758 |

<210> SEQ ID NO 23
<211> LENGTH: 758
<212> TYPE: DNA
<213> ORGANISM: Artificial sequence
<220> FEATURE:
<223> OTHER INFORMATION: EYFP BsaI A

<400> SEQUENCE: 23

| | |
|---|---|
| gaggtaccgg tctccggggt cggggtgag caagggcgag gagctgttca ccggggtggt | 60 |
| gcccatcctg gtcgagctgg acggcgacgt aaacggccac aagttcagcg tgtccggcga | 120 |
| gggcgagggc gatgccacct acggcaagct gaccctgaag ttcatctgca ccaccggcaa | 180 |
| gctgcccgtg ccctggccca cccttcgtgac caccttcggc tacggcctgc agtgcttcgc | 240 |
| ccgctacccc gaccacatga agcagcacga cttcttcaag tccgccatgc ccgaaggcta | 300 |
| cgtccaggag cgcaccatct tcttcaagga cgacggcaac tacaagaccc gcgccgaggt | 360 |
| gaagttcgag ggcgacaccc tggtgaaccg catcgagctg aagggcatcg acttcaagga | 420 |
| ggacggcaac atcctggggc acaagctgga gtacaactac aacagccaca cgtctatat | 480 |
| catgccgac aagcagaaga acggcatcaa ggtgaacttc aagatccgcc acaacatcga | 540 |
| ggacggcagc gtgcagctcg ccgaccacta ccagcagaac ccccatcg gcgacggccc | 600 |
| cgtgctgctg cccgacaacc actacctgag ctaccagtcc gccctgagca agacccccaa | 660 |
| cgagaagcgc gatcacatgg tcctgctgga gttcgtgacc gccgccggga tcactctcgg | 720 |
| catggacgag ctgtacaagt gatggagacc ggtacctc | 758 |

<210> SEQ ID NO 24
<211> LENGTH: 746
<212> TYPE: DNA
<213> ORGANISM: Artificial sequence
<220> FEATURE:
<223> OTHER INFORMATION: mCherry BsaI A

<400> SEQUENCE: 24

| | |
|---|---|
| gaggtaccgg tctccggggt cggggagcga gctgattaag gagaacatgc acatgaagct | 60 |
| gtacatggag ggcaccgtgg acaaccatca cttcaagtgc acatccgagg gcgaaggcaa | 120 |
| gccctacgag ggcacccaga ccatgagaat caaggtggtc gagggcggcc ctctccccctt | 180 |
| cgccttcgac atcctggcta ctagcttcct ctacggcagc aagaccttca tcaaccacac | 240 |
| ccagggcatc ccgacttct tcaagcagtc cttccctgag ggcttcacat gggagagagt | 300 |
| caccacatac gaggacgggg gcgtgctgac cgctacccag gacaccagcc tccaggacgg | 360 |
| ctgcctcatc tacaacgtca agatcagagg ggtgaacttc acatccaacg ccctgtgat | 420 |
| gcagaagaaa acactcggct gggaggcctt caccgaaacg ctgtaccccg ctgacggcgg | 480 |

```
cctggaaggc agaaacgaca tggccctgaa gctcgtgggc gggagccatc tgatcgcaaa    540
catcaagacc acatatagat ccaagaaacc cgctaagaac ctcaagatgc ctggcgtcta    600
ctatgtggac tacagactgg aaagaatcaa ggaggccaac aacgaaacct acgtcgagca    660
gcacgaggtg gcagtggcca gatactgcga cctccctagc aaactggggc acaagcttaa    720
ttccggatga tggagaccgg tacctc                                        746
```

```
<210> SEQ ID NO 25
<211> LENGTH: 746
<212> TYPE: DNA
<213> ORGANISM: Artificial sequence
<220> FEATURE:
<223> OTHER INFORMATION: TagBFP BsaI A

<400> SEQUENCE: 25
gaggtaccgg tctccggggt cggggagcga gctgattaag gagaacatgc acatgaagct    60
gtacatggag ggcaccgtgg acaaccatca cttcaagtgc acatccgagg gcgaaggcaa    120
gccctacgag ggcacccaga ccatgagaat caaggtggtc gagggcggcc ctctcccctt    180
cgccttcgac atcctggcta ctagcttcct ctacggcagc aagaccttca tcaaccacac    240
ccagggcatc cccgacttct tcaagcagtc cttccctgag ggcttcacat gggagagagt    300
caccacatac gaggacgggg gcgtgctgac cgctacccag gacaccagcc tccaggacgg    360
ctgcctcatc tacaacgtca agatcagagg ggtgaacttc acatccaacg ccctgtgat    420 gcagaagaaa acactcggct gggaggcctt caccgaaacg ctgtacccg ctgacgcgg    480 cctggaaggc agaaacgaca tggccctgaa gctcgtgggc gggagccatc tgatcgcaaa    540
catcaagacc acatatagat ccaagaaacc cgctaagaac ctcaagatgc ctggcgtcta    600
ctatgtggac tacagactgg aaagaatcaa ggaggccaac aacgaaacct acgtcgagca    660
gcacgaggtg gcagtggcca gatactgcga cctccctagc aaactggggc acaagcttaa    720
ttccggatga tggagaccgg tacctc                                        746
```

```
<210> SEQ ID NO 26
<211> LENGTH: 267
<212> TYPE: DNA
<213> ORGANISM: Artificial sequence
<220> FEATURE:
<223> OTHER INFORMATION: BGHpA BsaI A

<400> SEQUENCE: 26
gaggtaccgg tctcatgatc gactgtgcct tctagttgcc agccatctgt tgtttgcccc    60
tcccccgtgc cttccttgac cctggaaggt gccactccca ctgtcctttc ctaataaaat    120
gaggaaattg catcgcattg tctgagtagg tgtcattcta ttctgggggg tggggtgggg    180
caggacagca agggggagga ttgggaggac aatagcaggc atgctgggga tgcggtgggc    240
tctatggctt ctggagaccg gtacctc                                       267
```

```
<210> SEQ ID NO 27
<211> LENGTH: 278
<212> TYPE: DNA
<213> ORGANISM: Artificial sequence
<220> FEATURE:
<223> OTHER INFORMATION: LacZ-up BsaI A

<400> SEQUENCE: 27
gaggtaccgg tctcgttctc cctgcaggtg cgcccaatac gcaaaccgcc tctccccgcg    60
```

| | |
|---|---|
| cgttggccga ttcattaatg cagctggcac gacaggtttc ccgactggaa agcgggcagt | 120 |
| gagcgcaacg caattaatgt gagttagctc actcattagg cacccccaggc tttacactttt | 180 |
| atgcttccgg ctcgtatgtt gtgtggaatt gtgagcggat aacaatttca cacaggaaac | 240 |
| agctatgacc atgattacgg acaggagacc ggtacctc | 278 |

<210> SEQ ID NO 28
<211> LENGTH: 299
<212> TYPE: DNA
<213> ORGANISM: Artificial sequence
<220> FEATURE:
<223> OTHER INFORMATION: LacZ-down BsaI A

<400> SEQUENCE: 28

| | |
|---|---|
| gaggtaccgg tctcggacag cctggccgtc gttttacaac gtcgtgactg ggaaaaccct | 60 |
| ggcgttaccc aacttaatcg ccttgcagca catccccctt tcgccagctg gcgtaatagc | 120 |
| gaagaggccc gcaccgatcg cccttcccaa cagttgcgca gcctgaatgg cgaatggcgc | 180 |
| ctgatgcggt attttctcct tacgcatctg tgcggtattt cacaccgcat atggtgcact | 240 |
| ctcagtacaa tctgctctga tgccgcatag acctgcaggg ccagtgagac cggtacctc | 299 |

<210> SEQ ID NO 29
<211> LENGTH: 1650
<212> TYPE: DNA
<213> ORGANISM: Artificial sequence
<220> FEATURE:
<223> OTHER INFORMATION: HygroR BsaI A

<400> SEQUENCE: 29

| | |
|---|---|
| gaggtaccgg tctccccagc aggcagaagt atgcaaagca tgcatctcaa ttagtcagca | 60 |
| accaggtgtg gaaagtcccc aggctcccca gcaggcagaa gtatgcaaag catgcatctc | 120 |
| aattagtcag caaccatagt cccgccccta actccgccca tcccgcccct aactccgccc | 180 |
| agttccgccc attctccgcc ccatggctga ctaattttttt ttatttatgc agaggccgag | 240 |
| gccgcctctg cctctgagct attccagaag tagtgaggag gcttttttgg aggcctaggc | 300 |
| ttttgcaaaa agctcccggg agcttgtata tccattttcg gatctgatca gcacgtgatg | 360 |
| aaaaagcctg aactcaccgc gacgtctgtc gagaagtttc tgatcgaaaa gttcgacagc | 420 |
| gtgtccgacc tgatgcagct ctcggagggc gaagaatctc gtgctttcag cttcgatgta | 480 |
| ggagggcgtg gatatgtcct gcgggtaaat agctgcgccg atggtttcta caaagatcgt | 540 |
| tatgtttatc ggcactttgc atcggccgcg ctcccgattc cggaagtgct tgacattggg | 600 |
| gaattcagcg agagcctgac ctattgcatc tcccgccgtg cacagggtgt cacgttgcaa | 660 |
| gacttgcctg aaaccgaact gcccgctgtt ctgcagccgg tcgcggaggc catggatgcg | 720 |
| atcgctgcgg ccgatcttag ccagacgagc gggttcggcc cattcggacc gcaaggaatc | 780 |
| ggtcaataca ctacatggcg tgatttcata tgcgcgattg ctgatcccca tgtgtatcac | 840 |
| tggcaaactg tgatggacga caccgtcagt gcgtccgtcg cgcaggctct cgatgagctg | 900 |
| atgctttggg ccgaggactg ccccgaagtc cggcacctcg tgcacgcgga tttcggctcc | 960 |
| aacaatgtcc tgacggacaa tggccgcata acagcggtca ttgactggag cgaggcgatg | 1020 |
| ttcggggatt cccaatacga ggtcgccaac atcttcttct ggaggccgtg gttggcttgt | 1080 |
| atggagcagc agacgcgcta cttcgagcgg aggcatccgg agcttgcagg atcgccgcgg | 1140 |
| ctccgggcgt atatgctccg cattggtctt gaccaactct atcagagctt ggttgacggc | 1200 |
| aatttcgatg atgcagcttg ggcgcagggt cgatgcgacg caatcgtccg atccggagcc | 1260 |

```
gggactgtcg ggcgtacaca aatcgcccgc agaagcgcgg ccgtctggac cgatggctgt   1320
gtagaagtac tcgccgatag tggaaaccga cgccccagca ctcgtccgag ggcaaaggaa   1380
tagcacgtgc tacgagattt cgattccacc gccgccttct atgaaaggtt gggcttcgga   1440
atcgttttcc gggacgccgg ctggatgatc ctccagcgcg gggatctcat gctggagttc   1500
ttcgcccacc ccaacttgtt tattgcagct tataatggtt acaaataaag caatagcatc   1560
acaaatttca caaataaagc atttttttca ctgcattcta gttgtggttt gtccaaactc   1620
atcaatgtat cttatcgaga ccggtacctc                                     1650
```

<210> SEQ ID NO 30
<211> LENGTH: 6032
<212> TYPE: DNA
<213> ORGANISM: Artificial sequence
<220> FEATURE:
<223> OTHER INFORMATION: pHCsiaT-E1GFP

<400> SEQUENCE: 30

```
tgaggctagg gataggacga gagcatcggg aacgaggact agcgtctcaa ggaaccaatt     60
cagtcgactg gatcctagtt attaatagta atcaattacg gggtcattag ttcatagccc    120
atatatggag ttccgcgtta cataacttac ggtaaatggc ccgcctggct gaccgcccaa    180 cgaccccgc ccattgacgt caataatgac gtatgttccc atagtaacgc caatagggac    240
tttccattga cgtcaatggg tggagtattt acggtaaact gcccacttgg cagtacatca    300
agtgtatcat atgccaagta cgccccctat tgacgtcaat gacggtaaat ggcccgcctg    360
gcattatgcc cagtacatga ccttatggga ctttcctact tggcagtaca tctacgtatt    420
agtcatcgct attaccatgg tgatgcggtt ttggcagtac atcaatgggc gtggatagcg    480
gtttgactca cggggatttc caagtctcca ccccattgac gtcaatggga gtttgttttg    540
gcaccaaaat caacgggact ttccaaaatg tcgtaacaac tccgccccat tgacgcaaat    600
gggcggtagg cgtgtacggt gggaggtcta taagcaga gctggtttag tgaaccgtca     660
gatcactagt cgactaggga taacagggcc gccaccatga ttcacaccaa cctgaagaaa    720
aagttcagct gctgcgtcct ggtctttctt ctgtttgcag tcatctgtgt gtggaaggaa    780
aagaagaaag ggagttacta tgattccttt aaattgcaaa ccaaggagtt ccaggtgtta    840
aagagtctgg ggaaattggc catggggtct gattcccagt ctgtatcctc aagcagcacc    900 caggacccc acaggggccg ccagaccctc ggcagtctca gaggcctagc caaggccaaa    960
ccagaggcct ccttccaggt gtggaacaag acagctctt ccaaaaacct tatccctagg   1020
ctgcaaaagg ggtcgggggt gagcaagggc gaggagctgt tcaccggggt ggtgcccatc   1080
ctggtcgagc tggacggcga cgtaaacggc cacaagttca gcgtgtccgg cgagggcgag   1140
ggcgatgcca cctacggcaa gctgaccctg aagttcatct gcaccaccgg caagctgccc   1200
gtgccctggc ccaccctcgt gaccaccctg tcctacggcg tgcagtgctt cagccgctac   1260
cccgaccaca tgaagcagca cgacttcttc aagtccgcca tgcccgaagg ctacgtccag   1320
gagcgcacca tcttcttcaa ggacgacggc aactacaaga cccgcgccga ggtgaagttc   1380
gagggcgaca ccctggtgaa ccgcatcgag ctgaagggca tcgacttcaa ggaggacggc   1440
aacatcctgg ggcacaagct ggagtacaac tacaacagcc acaacgtcta tatcatggcc   1500
gacaagcaga agaacggcat caaggtgaac ttcaagatcc gccacaacat cgaggacggc   1560
agcgtgcagc tcgccgacca ctaccagcag aacacccca tcggcgacgg ccccgtgctg   1620
```

```
ctgcccgaca accactacct gagctaccag tccgccctga gcaaagaccc caacgagaag    1680
cgcgatcaca tggtcctgct ggagttcgtg accgccgccg ggatcactct cggcatggac    1740
gagctgtaca agtgatcgac tgtgccttct agttgccagc catctgttgt ttgcccctcc    1800
cccgtgcctt ccttgaccct ggaaggtgcc actcccactg tcctttccta ataaaatgag    1860
gaaattgcat cgcattgtct gagtaggtgt cattctattc tggggggtgg ggtggggcag    1920
gacagcaagg gggaggattg ggaggacaat agcaggcatg ctgggatgcg gtgggctct     1980
atggcttctc cctgcaggtg cgcccaatac gcaaaccgcc tctccccgcg cgttggccga    2040
ttcattaatg cagctggcac gacaggtttc ccgactggaa agcgggcagt gagcgcaacg    2100
caattaatgt gagttagctc actcattagg cacccccagc tttacacttt atgcttccgg    2160
ctcgtatgtt gtgtggaatt gtgagcggat aacaatttca cacaggaaac agctatgacc    2220
atgattacgg acagcctggc cgtcgtttta caacgtcgtg actgggaaaa ccctggcgtt    2280
acccaactta tcgccttgc  agcacatccc cctttcgcca gctggcgtaa tagcgaagag    2340
gcccgcaccg atcgcccttc ccaacagttg cgcagcctga atggcgaatg cgcctgatg     2400
cggtattttc tccttacgca tctgtgcggt atttcacacc gcatatggtg cactctcagt    2460
acaatctgct ctgatgccgc atagacctgc agggccagca ggcagaagta tgcaaagcat    2520
gcatctcaat tagtcagcaa ccaggtgtgg aaagtcccca ggctccccag caggcagaag    2580
tatgcaaagc atgcatctca attagtcagc aaccatagtc ccgcccctaa ctccgcccat    2640
cccgccccta actccgccca gttccgccca ttctccgccc catggctgac taatttttt     2700
tatttatgca gaggccgagg ccgcctctgc ctctgagcta ttccagaagt agtgaggagg    2760
cttttttgga ggcctaggct tttgcaaaaa gctcccggga gcttgtatat ccattttcgg    2820
atctgatcag cacgtgatga aaaagcctga actcaccgcg acgtctgtcg agaagtttct    2880
gatcgaaaag ttcgacagcg tgtccgacct gatgcagctc tcggagggcg aagaatctcg    2940
tgctttcagc ttcgatgtag gagggcgtgg atatgtcctg cgggtaaata gctgcgccga    3000
tggtttctac aaagatcgtt atgtttatcg gcactttgca tcggccgcgc tcccgattcc    3060
ggaagtgctt gacattgggg aattcagcga gagcctgacc tattgcatct cccgccgtgc    3120
acagggtgtc acgttgcaag acttgcctga accgaactgc ccgctgttc  tgcagccggt    3180
cgcggaggcc atggatgcga tcgctgcggc cgatcttagc cagacgagcg ggttcggccc    3240
attcggaccg caaggaatcg gtcaatacac tacatggcgt gatttcatat gcgcgattgc    3300
tgatccccat gtgtatcact ggcaaactgt gatggacgac accgtcagtg cgtccgtcgc    3360
gcaggctctc gatgagctga tgctttgggc cgaggactgc cccgaagtcc ggcacctcgt    3420
gcacgcggat ttcggctcca caatgtcct  gacggacaat ggccgcataa cagcggtcat    3480
tgactggagc gaggcgatgt cggggattc  ccaatacgag gtcgccaaca tcttcttctg    3540
gaggccgtgg ttggcttgta tggagcagca gacgcgctac ttcgagcgga ggcatccgga    3600
gcttgcagga tcgccgcggc tccgggcgta tatgctccgc attggtcttg accaactcta    3660
tcagagcttg gttgacggca atttcgatga tgcagcttgg gcgcagggtc gatgcgacgc    3720
aatcgtccga tccggagccg ggactgtcgg gcgtacacaa atcgcccgca gaagcgcggc    3780
cgtctggacc gatggctgtg tagaagtact cgccgatagt ggaaaccgac gccccagcac    3840
tcgtccgagg gcaaaggaat agcacgtgct acgagatttc gattccaccg ccgccttcta    3900
tgaaaggttg gcttcggaa  tcgttttccg ggacgccggc tggatgatcc tccagcgcgg    3960
ggatctcatg ctggagttct tcgcccaccc caacttgttt attgcagctt ataatggtta    4020
```

```
caaataaagc aataqcatca caaatttcac aaataaagca ttttttttcac tgcattctag    4080
ttgtggtttg tccaaactca tcaatgtatc ttatgcgtct tctagggtta aggttagtgt    4140
agagaagcaa ccgaagattg agaagacatg gcggtaatac ggttatccac agaatcaggg    4200
gataacgcag gaaagaacat gtgagcaaaa ggccagcaaa aggccaggaa ccgtaaaaag    4260
gccgcgttgc tggcgttttt ccataggctc cgcccccctg acgagcatca caaaaatcga    4320
cgctcaagtc agaggtggcg aaacccgaca ggactataaa gataccaggc gtttccccct    4380
ggaagctccc tcgtgcgctc tcctgttccg accctgccgc ttaccggata cctgtccgcc    4440
tttctccctt cgggaagcgt ggcgctttct catagctcac gctgtaggta tctcagttcg    4500
gtgtaggtcg ttcgctccaa gctgggctgt gtgcacgaac cccccgttca gcccgaccgc    4560
tgcgccttat ccggtaacta tcgtcttgag tccaacccgg taagacacga cttatcgcca    4620
ctggcagcag ccactggtaa caggattagc agagcgaggt atgtaggcgg tgctacagag    4680
ttcttgaagt ggtggcctaa ctacggctac actagaagaa cagtatttgg tatctgcgct    4740
ctgctgaagc cagttacctt cggaaaaaga gttggtagct cttgatccgg caaacaaacc    4800
accgctggta gcggtttttt tgtttgcaag cagcagatta cgcgcagaaa aaaggatct    4860
caagaagatc ctttgatctt ttctacgggg tctgacgctc agtggaacga aaactcacgt    4920
taagggattt tggtcatgag attatcaaaa aggatcttca cctagatcct tttaaattaa    4980
aaatgaagtt ttaaatcaat ctaaagtata tatgagtaaa cttggtctga cagttaccaa    5040
tgcttaatca gtgaggcacc tatctcagcg atctgtctat ttcgttcatc catagttgcc    5100
tgactccccg tcgtgtagat aactacgata cgggagggct taccatctgg ccccagtgct    5160
gcaatgatac cgcgtgaccc acgctcaccg gctccagatt tatcagcaat aaaccagcca    5220
gccggaaggg ccgagcgcag aagtggtcct gcaactttat ccgcctccat ccagtctatt    5280
aattgttgcc gggaagctag agtaagtagt tcgccagtta atagtttgcg caacgttgtt    5340
gccattgcta caggcatcgt ggtgtcacgc tcgtcgtttg gtatggcttc attcagctcc    5400
ggttcccaac gatcaaggcg agttacatga tcccccatgt tgtgcaaaaa agcggttagc    5460
tccttcggtc ctccgatcgt tgtcagaagt aagttggccg cagtgttatc actcatggtt    5520
atggcagcac tgcataattc tcttactgtc atgccatccg taagatgctt ttctgtgact    5580
ggtgagtact caaccaagtc attctgagaa tagtgtatgc ggcgaccgag ttgctcttgc    5640
ccggcgtcaa tacgggataa taccgcgcca catagcagaa ctttaaaagt gctcatcatt    5700
ggaaaacgtt cttcggggcg aaaactctca aggatcttac cgctgttgag atccagttcg    5760
atgtaaccca ctcgtgcacc caactgatct tcagcatctt ttactttcac cagcgtttct    5820
gggtgagcaa aaacaggaag gcaaaatgcc gcaaaaaagg gaataagggc gacacggaaa    5880
tgttgaatac tcatactctt cctttttcaa tattattgaa gcatttatca gggttattgt    5940
ctcatgagcg gatacatatt tgaatgtatt tagaaaaata aacaaatagg ggttccgcgc    6000
acatttcccc gaaaagtgcc acctatgaga cg                                  6032
```

<210> SEQ ID NO 31
<211> LENGTH: 6032
<212> TYPE: DNA
<213> ORGANISM: Artificial sequence
<220> FEATURE:
<223> OTHER INFORMATION: pHCsiaT-EGFP

<400> SEQUENCE: 31

-continued

```
tgaggctagg gataggacga gagcatcggg aacgaggact agcgtctcaa ggaaccaatt      60
cagtcgactg gatcctagtt attaatagta atcaattacg gggtcattag ttcatagccc     120
atatatggag ttccgcgtta cataacttac ggtaaatggc ccgcctggct gaccgcccaa     180 cgaccccgc ccattgacgt caataatgac gtatgttccc atagtaacgc caatagggac      240
tttccattga cgtcaatggg tggagtattt acggtaaact gcccacttgg cagtacatca     300
agtgtatcat atgccaagta cgccccctat tgacgtcaat gacggtaaat ggcccgcctg     360
gcattatgcc cagtacatga ccttatggga ctttcctact tggcagtaca tctacgtatt     420
agtcatcgct attaccatgg tgatgcggtt ttggcagtac atcaatgggc gtggatagcg     480
gtttgactca cggggatttc caagtctcca ccccattgac gtcaatggga gtttgttttg     540
gcaccaaaat caacgggact ttccaaaatg tcgtaacaac tccgccccat tgacgcaaat     600
gggcggtagg cgtgtacggt gggaggtcta taagcaga gctggtttag tgaaccgtca      660
gatcactagt cgactaggga taacagggcc gccaccatga ttcacaccaa cctgaagaaa     720
aagttcagct gctgcgtcct ggtctttctt ctgtttgcag tcatctgtgt gtggaaggaa     780
aagaagaaag ggagttacta tgattccttt aaattgcaaa ccaaggaatt ccaggtgtta     840
aagagtctgg ggaaattggc catggggtct gattcccagt ctgtatcctc aagcagcacc     900
caggaccccc acaggggccg ccagaccctc ggcagtctca gaggcctagc caaggccaaa     960
ccagaggcct ccttccaggt gtggaacaag acagctctt ccaaaaacct tatccctagg    1020
ctgcaaaagg ggtcgggggt gagcaagggc gaggagctgt tcaccggggt ggtgcccatc    1080
ctggtcgagc tggacggcga cgtaaacggc cacaagttca gcgtgtccgg cgagggcgag    1140
ggcgatgcca cctacggcaa gctgaccctg aagttcatct gcaccaccgg caagctgccc    1200
gtgccctggc ccaccctcgt gaccaccctg acctacggcg tgcagtgctt cagccgctac    1260
cccgaccaca tgaagcagca cgacttcttc aagtccgcca tgcccgaagg ctacgtccag    1320
gagcgcacca tcttcttcaa ggacgacggc aactacaaga cccgcgccga ggtgaagttc    1380
gagggcgaca ccctggtgaa ccgcatcgag ctgaagggca tcgacttcaa ggaggacggc    1440
aacatcctgg ggcacaagct ggagtacaac tacaacagcc acaacgtcta tatcatggcc    1500
gacaagcaga agaacggcat caaggtgaac ttcaagatcc gccacaacat cgaggacggc    1560
agcgtgcagc tcgccgacca ctaccagcag aacacccca tcggcgacgg ccccgtgctg    1620
ctgcccgaca ccactacct gagcacccag tccgccctga gcaaagaccc caacgagaag    1680
cgcgatcaca tggtcctgct ggagttcgtg accgccgccg ggatcactct cggcatggac    1740
gagctgtaca agtgatcgac tgtgccttct agttgccagc catctgttgt ttgcccctcc    1800
cccgtgcctt ccttgaccct ggaaggtgcc actcccactg tcctttccta taaaatgag    1860 gaaattgcat cgcattgtct gagtaggtgt cattctattc tggggggtgg ggtggggcag    1920
gacagcaagg gggaggattg ggaggacaat agcaggcatg ctgggggatgc ggtgggctct    1980 atggcttctc cctgcaggtg cgcccaatac gcaaaccgcc tctccccgcg cgttggccga    2040
ttcattaatg cagctggcac gacaggtttc ccgactggaa agcgggcagt gagcgcaacg    2100
caattaatgt gagttagctc actcattagg caccccagge tttacacttt atgcttccgg    2160
ctcgtatgtt gtgtggaatt gtgagcggat aacaatttca cacaggaaac agctatgacc    2220
atgattacgg acagcctggc cgtcgtttta caacgtcgtg actgggaaaa ccctggcgtt    2280
acccaactta atcgccttgc agcacatccc cctttcgcca gctggcgtaa tagcgaagag    2340
gcccgcaccg atcgcccttc ccaacagttg cgcagcctga atggcgaatg gcgcctgatg    2400
```

-continued

```
cggtattttc tccttacgca tctgtgcggt atttcacacc gcatatggtg cactctcagt   2460
acaatctgct ctgatgccgc atagacctgc agggccagca ggcagaagta tgcaaagcat   2520
gcatctcaat tagtcagcaa ccaggtgtgg aaagtcccca ggctcccag caggcagaag   2580 tatgcaaagc atgcatctca attagtcagc aaccatagtc ccgcccctaa ctccgcccat   2640 cccgcccta actccgccca gttccgccca ttctccgccc catggctgac taatttttt   2700 tatttatgca gaggccgagg ccgcctctgc ctctgagcta ttccagaagt agtgaggagg   2760
cttttttgga ggcctaggct tttgcaaaaa gctcccggga gcttgtatat ccattttcgg   2820
atctgatcag cacgtgatga aaaagcctga actcaccgcg acgtctgtcg agaagtttct   2880
gatcgaaaag ttcgacagcg tgtccgacct gatgcagctc tcggagggcg aagaatctcg   2940
tgctttcagc ttcgatgtag gagggcgtgg atatgtcctg cgggtaaata gctgcgccga   3000
tggtttctac aaagatcgtt atgtttatcg gcactttgca tcggccgcgc tcccgattcc   3060
ggaagtgctt gacattgggg aattcagcga gagcctgacc tattgcatct cccgccgtgc   3120
acagggtgtc acgttgcaag acttgcctga accgaactg cccgctgttc tgcagccggt   3180
cgcggaggcc atggatgcga tcgctgcggc cgatcttagc cagacgagcg ggttcggccc   3240
attcggaccg caaggaatcg gtcaatacac tacatggcgt gatttcatat gcgcgattgc   3300
tgatccccat gtgtatcact ggcaaactgt gatggacgac accgtcagtg cgtccgtcgc   3360
gcaggctctc gatgagctga tgctttgggc cgaggactgc cccgaagtcc ggcacctcgt   3420
gcacgcggat ttcggctcca acaatgtcct gacggacaat ggccgcataa cagcggtcat   3480
tgactggagc gaggcgatgt tcggggattc ccaatacgag gtcgccaaca tcttcttctg   3540
gaggccgtgg ttggcttgta tggagcagca cgcgctac ttcgagcgga ggcatccgga   3600
gcttgcagga tcgccgcggc tccgggcgta tatgctccgc attggtcttg accaactcta   3660
tcagagcttg gttgacggca atttcgatga tgcagcttgg gcgcagggtc gatgcgacgc   3720
aatcgtccga tccggagccg ggactgtcgg gcgtacacaa atcgcccgca gaagcgcggc   3780
cgtctggacc gatggctgtg tagaagtact cgccgatagt ggaaaccgac gccccagcac   3840
tcgtccgagg gcaaaggaat agcacgtgct acgagatttc gattccaccg ccgccttcta   3900
tgaaaggttg ggcttcggaa tcgttttccg ggacgccggc tggatgatcc tccagcgcgg   3960
ggatctcatg ctggagttct cgcccaccc caacttgttt attgcagctt ataatggtta   4020
caaataaagc aatagcatca caaatttcac aaataaagca ttttttttcac tgcattctag   4080 ttgtggtttg tccaaactca tcaatgtatc ttatgcgtct tctagggtta aggttagtgt   4140
agagaagcaa ccgaagattg agaagacatg gcggtaatac ggttatccac agaatcaggg   4200
gataacgcag gaaagaacat gtgagcaaaa ggccagcaaa aggccaggaa ccgtaaaaag   4260
gccgcgttgc tggcgttttt ccataggctc cgccccctg acgagcatca caaaaatcga   4320
cgctcaagtc agaggtggcg aaacccgaca ggactataaa gataccaggc gtttccccct   4380
ggaagctccc tcgtgcgctc tcctgttccg accctgccgc ttaccggata cctgtccgcc   4440
tttctccctt cgggaagcgt ggcgctttct catagctcac gctgtaggta tctcagttcg   4500
gtgtaggtcg ttcgctccaa gctgggctgt gtgcacgaac cccccgttca gcccgaccgc   4560
tgcgccttat ccggtaacta tcgtcttgag tccaacccgg taagacacga cttatcgcca   4620
ctggcagcag ccactggtaa caggattagc agagcgaggt atgtaggcgg tgctacagag   4680
ttcttgaagt ggtggcctaa ctacggctac actagaagaa cagtatttgg tatctgcgct   4740
```

```
ctgctgaagc cagttacctt cggaaaaaga gttggtagct cttgatccgg caaacaaacc    4800
accgctggta gcggttttttt tgtttgcaag cagcagatta cgcgcagaaa aaaggatct    4860 caagaagatc ctttgatctt ttctacgggg tctgacgctc agtggaacga aaactcacgt    4920 taagggatttt tggtcatgag attatcaaaa aggatcttca cctagatcct tttaaattaa    4980
aaatgaagtt ttaaatcaat ctaaagtata tatgagtaaa cttggtctga cagttaccaa    5040
tgcttaatca gtgaggcacc tatctcagcg atctgtctat ttcgttcatc catagttgcc    5100
tgactccccg tcgtgtagat aactacgata cgggagggct taccatctgg ccccagtgct    5160
gcaatgatac cgcgtgaccc acgctcaccg gctccagatt tatcagcaat aaaccagcca    5220
gccggaaggg ccgagcgcag aagtggtcct gcaactttat ccgcctccat ccagtctatt    5280
aattgttgcc gggaagctag agtaagtagt tcgccagtta atagtttgcg caacgttgtt    5340
gccattgcta caggcatcgt ggtgtcacgc tcgtcgtttg gtatggcttc attcagctcc    5400
ggttcccaac gatcaaggcg agttacatga tcccccatgt tgtgcaaaaa agcggttagc    5460
tccttcggtc ctccgatcgt tgtcagaagt aagttggccg cagtgttatc actcatggtt    5520
atggcagcac tgcataattc tcttactgtc atgccatccg taagatgctt ttctgtgact    5580
ggtgagtact caaccaagtc attctgagaa tagtgtatgc ggcgaccgag ttgctcttgc    5640
ccggcgtcaa tacgggataa taccgcgcca catagcagaa ctttaaaagt gctcatcatt    5700
ggaaaacgtt cttcggggcg aaaactctca aggatcttac cgctgttgag atccagttcg    5760
atgtaaccca ctcgtgcacc caactgatct tcagcatctt ttactttcac cagcgtttct    5820
gggtgagcaa aaacaggaag gcaaaatgcc gcaaaaaagg gaataagggc gacacggaaa    5880
tgttgaatac tcatactctt ccttttcaa tattattgaa gcatttatca gggttattgt    5940
ctcatgagcg gatacatatt tgaatgtatt tagaaaaata acaaataggg gttccgcgc    6000 acatttcccc gaaaagtgcc acctatgaga cg                                  6032
```

<210> SEQ ID NO 32
<211> LENGTH: 6032
<212> TYPE: DNA
<213> ORGANISM: Artificial sequence
<220> FEATURE:
<223> OTHER INFORMATION: pHCsiaT-ECFP

<400> SEQUENCE: 32

```
tgaggctagg gataggacga gagcatcggg aacgaggact agcgtctcaa ggaaccaatt      60
cagtcgactg gatcctagtt attaatagta atcaattacg gggtcattag ttcatagccc     120
atatatggag ttccgcgtta cataacttac ggtaaatggc ccgcctggct gaccgcccaa     180
cgacccccgc ccattgacgt caataatgac gtatgttccc atagtaacgc caatagggac     240
tttccattga cgtcaatggg tggagtattt acggtaaact gcccacttgg cagtacatca     300
agtgtatcat atgccaagta cgccccctat tgacgtcaat gacggtaaat ggcccgcctg     360
gcattatgcc cagtacatga ccttatggga ctttcctact tggcagtaca tctacgtatt     420
agtcatcgct attaccatgg tgatgcggtt ttggcagtac atcaatgggc gtggatagcg     480
gtttgactca cggggatttc caagtctcca ccccattgac gtcaatggga gtttgttttg     540
gcaccaaaat caacgggact ttccaaaatg tcgtaacaac tccgccccat tgacgcaaat     600
gggcggtagg cgtgtacggt gggaggtcta tataagcaga gctggtttag tgaaccgtca     660
gatcactagt cgactaggga taacagggcc gccaccatga ttcacaccaa cctgaagaaa     720
aagttcagct gctgcgtcct ggtctttctt ctgtttgcag tcatctgtgt gtggaaggaa     780
```

```
aagaagaaag ggagttacta tgattccttt aaattgcaaa ccaaggaatt ccaggtgtta      840
aagagtctgg ggaaattggc catggggtct gattcccagt ctgtatcctc aagcagcacc      900
caggaccccc acaggggccg ccagaccctc ggcagtctca gaggcctagc caaggccaaa      960
ccagaggcct ccttccaggt gtggaacaag gacagctctt ccaaaaacct tatccctagg     1020
ctgcaaaagg ggtcgggggt gagcaagggc gaggagctgt tcaccggggt ggtgcccatc     1080
ctggtcgagc tggacggcga cgtaaacggc cacaagttca gcgtgtccgg cgagggcgag     1140
ggcgatgcca cctacggcaa gctgaccctg aagttcatct gcaccaccgg caagctgccc     1200
gtgcccggc ccaccctcgt gaccaccctg acctggggcg tgcagtgctt cagccgctac      1260
cccgaccaca tgaagcagca cgacttcttc aagtccgcca tgcccgaagg ctacgtccag     1320
gagcgcacca tcttcttcaa ggacgacggc aactacaaga cccgcgccga ggtgaagttc     1380
gagggcgaca ccctggtgaa ccgcatcgag ctgaagggca tcgacttcaa ggaggacggc     1440
aacatcctgg ggcacaagct ggagtacaac tacatcagcc acaacgtcta tatcaccgcc     1500
gacaagcaga agaacggcat caaggccaac ttcaagatcc gccacaacat cgaggacggc     1560
agcgtgcagc tcgccgacca ctaccagcag aacaccccca tcggcgacgg ccccgtgctg     1620
ctgcccgaca ccactacct gagcacccag tccgccctga gcaaagaccc caacgagaag      1680
cgcgatcaca tggtcctgct ggagttcgtg accgccgccg ggatcactct cggcatggac     1740
gagctgtaca agtgatcgac tgtgccttct agttgccagc catctgttgt ttgcccctcc     1800
cccgtgcctt ccttgaccct ggaaggtgcc actcccactg tccttttccta ataaaatgag    1860
gaaattgcat cgcattgtct gagtaggtgt cattctattc tggggggtgg ggtggggcag     1920
gacagcaagg gggaggattg ggaggacaat agcaggcatg ctggggatgc ggtgggctct     1980
atggcttctc cctgcaggtg cgcccaatac gcaaaccgcc tctccccgcg cgttggccga    2040
ttcattaatg cagctggcac gacaggtttc ccgactggaa agcgggcagt gagcgcaacg    2100
caattaatgt gagttagctc actcattagg caccccaggc tttacacttt atgcttccgg    2160
ctcgtatgtt gtgtggaatt gtgagcggat aacaatttca cacaggaaac agctatgacc    2220
atgattacgg acagcctggc cgtcgtttta caacgtcgtg actgggaaaa ccctggcgtt    2280
acccaactta atcgccttgc agcacatccc cctttcgcca gctggcgtaa tagcgaagag    2340
gcccgcaccg atcgcccttc ccaacagttg cgcagcctga atggcgaatg cgcctgatg    2400
cggtattttc tccttacgca tctgtgcggt atttcacacc gcatatggtg cactctcagt    2460
acaatctgct ctgatgccgc atagacctgc agggccagca ggcagaagta tgcaaagcat    2520
gcatctcaat tagtcagcaa ccaggtgtgg aaagtcccca ggctcccag caggcagaag    2580
tatgcaaagc atgcatctca attagtcagc aaccatagtc cgcccctaa ctccgcccat     2640
cccgccccta actccgccca gttccgccca ttctccgccc catggctgac taatttttt     2700
tatttatgca gaggccgagg ccgcctctgc ctctgagcta ttccagaagt agtgaggagg    2760
cttttttgga ggcctaggct tttgcaaaaa gctcccggga gcttgtatat ccatttttcgg   2820
atctgatcag cacgtgatga aaagcctga actcaccgcg acgtctgtcg agaagtttct    2880
gatcgaaaag ttcgacagcg tgtccgacct gatgcagctc tcggagggcg aagaatctcg    2940
tgctttcagc ttcgatgtag gagggcgtgg atatgtcctg cgggtaaata gctgcgccga   3000
tggtttctac aaagatcgtt atgtttatcg gcactttgca tcggccgcgc tcccgattcc    3060
ggaagtgctt gacattgggg aattcagcga gagcctgacc tattgcatct cccgccgtgc    3120
```

```
acagggtgtc acgttgcaag acttgcctga aaccgaactg cccgctgttc tgcagccggt   3180
cgcggaggcc atggatgcga tcgctgcggc cgatcttagc cagacgagcg ggttcggccc   3240
attcggaccg caaggaatcg gtcaatacac tacatggcgt gatttcatat gcgcgattgc   3300
tgatccccat gtgtatcact ggcaaactgt gatggacgac accgtcagtg cgtccgtcgc   3360
gcaggctctc gatgagctga tgctttgggc cgaggactgc cccgaagtcc ggcacctcgt   3420
gcacgcggat ttcggctcca acaatgtcct gacggacaat ggccgcataa cagcggtcat   3480
tgactggagc gaggcgatgt tcggggattc ccaatacgag gtcgccaaca tcttcttctg   3540
gaggccgtgg ttggcttgta tggagcagca gacgcgctac ttcgagcgga ggcatccgga   3600
gcttgcagga tcgccgcggc tccgggcgta tatgctccgc attggtcttg accaactcta   3660
tcagagcttg gttgacggca atttcgatga tgcagcttgg gcgcagggtc gatgcgacgc   3720
aatcgtccga tccggagccg ggactgtcgg gcgtacacaa atcgcccgca gaagcgcggc   3780
cgtctggacc gatggctgtg tagaagtact cgccgatagt ggaaaccgac gccccagcac   3840
tcgtccgagg gcaaaggaat agcacgtgct acgagatttc gattccaccg ccgccttcta   3900
tgaaaggttg ggcttcggaa tcgttttccg ggacgccggc tggatgatcc tccagcgcgg   3960
ggatctcatg ctggagttct tcgcccaccc caacttgttt attgcagctt ataatggtta   4020
caaataaagc aatagcatca caaatttcac aaataaagca ttttttttcac tgcattctag   4080
ttgtggtttg tccaaactca tcaatgtatc ttatgcgtct tctagggtta aggttagtgt   4140
agagaagcaa ccgaagattg agaagacatg gcggtaatac ggttatccac agaatcaggg   4200
gataacgcag gaaagaacat gtgagcaaaa ggccagcaaa aggccaggaa ccgtaaaaag   4260
gccgcgttgc tggcgttttt ccataggctc cgcccccctg acgagcatca caaaaatcga   4320
cgctcaagtc agaggtggcg aaacccgaca ggactataaa gataccaggc gtttccccct   4380
ggaagctccc tcgtgcgctc tcctgttccg accctgccgc ttaccggata cctgtccgcc   4440
tttctccctt cgggaagcgt ggcgctttct catagctcac gctgtaggta tctcagttcg   4500
gtgtaggtcg ttcgctccaa gctgggctgt gtgcacgaac cccccgttca gcccgaccgc   4560
tgcgccttat ccggtaacta tcgtcttgag tccaacccgg taagacacga cttatcgcca   4620
ctggcagcag ccactggtaa caggattagc agagcgaggt atgtaggcgg tgctacagag   4680
ttcttgaagt ggtggcctaa ctacggctac actagaagaa cagtatttgg tatctgcgct   4740
ctgctgaagc cagttacctt cggaaaaaga gttggtagct cttgatccgg caaacaaacc   4800
accgctggta gcggtttttt tgtttgcaag cagcagatta cgcgcagaaa aaaggatct   4860
caagaagatc ctttgatctt ttctacgggg tctgacgctc agtggaacga aaactcacgt   4920
taagggattt tggtcatgag attatcaaaa aggatcttca cctagatcct ttttaaattaa   4980
aaatgaagtt ttaaatcaat ctaaagtata tatgagtaaa cttggtctga cagttaccaa   5040
tgcttaatca gtgaggcacc tatctcagcg atctgtctat ttcgttcatc catagttgcc   5100
tgactccccg tcgtgtagat aactacgata cgggagggct taccatctgg ccccagtgct   5160
gcaatgatac cgcgtgaccc acgctcaccg gctccagatt tatcagcaat aaaccagcca   5220
gccgaagggg ccgagcgcag aagtggtcct gcaactttat ccgcctccat ccagtctatt   5280
aattgttgcc gggaagctag agtaagtagt tcgccagtta atagtttgcg caacgttgtt   5340
gccattgcta caggcatcgt ggtgtcacgc tcgtcgtttg gtatggcttc attcagctcc   5400
ggttcccaac gatcaaggcg agttacatga tcccccatgt tgtgcaaaaa agcggttagc   5460
tccttcggtc ctccgatcgt tgtcagaagt aagttggccg cagtgttatc actcatggtt   5520
```

| | |
|---|---|
| atggcagcac tgcataattc tcttactgtc atgccatccg taagatgctt ttctgtgact | 5580 |
| ggtgagtact caaccaagtc attctgagaa tagtgtatgc ggcgaccgag ttgctcttgc | 5640 |
| ccggcgtcaa tacgggataa taccgcgcca catagcagaa ctttaaaagt gctcatcatt | 5700 |
| ggaaaacgtt cttcggggcg aaaactctca aggatcttac cgctgttgag atccagttcg | 5760 |
| atgtaaccca ctcgtgcacc caactgatct tcagcatctt ttactttcac cagcgtttct | 5820 |
| gggtgagcaa aaacaggaag gcaaaatgcc gcaaaaaagg gaataagggc gacacggaaa | 5880 |
| tgttgaatac tcatactctt ccttttttcaa tattattgaa gcatttatca gggttattgt | 5940 |
| ctcatgagcg gatacatatt tgaatgtatt tagaaaaata aacaaatagg ggttccgcgc | 6000 |
| acatttcccc gaaaagtgcc acctatgaga cg | 6032 |

<210> SEQ ID NO 33
<211> LENGTH: 6032
<212> TYPE: DNA
<213> ORGANISM: Artificial sequence
<220> FEATURE:
<223> OTHER INFORMATION: pHCsiaT-EYFP

<400> SEQUENCE: 33

| | |
|---|---|
| tgaggctagg gataggacga gagcatcggg aacgaggact agcgtctcaa ggaaccaatt | 60 |
| cagtcgactg gatcctagtt attaatagta atcaattacg gggtcattag ttcatagccc | 120 |
| atatatggag ttccgcgtta cataacttac ggtaaatggc ccgcctggct gaccgcccaa | 180 |
| cgacccccgc ccattgacgt caataatgac gtatgttccc atagtaacgc caatagggac | 240 |
| tttccattga cgtcaatggg tggagtattt acggtaaact gcccacttgg cagtacatca | 300 |
| agtgtatcat atgccaagta cgccccctat tgacgtcaat gacggtaaat ggcccgcctg | 360 |
| gcattatgcc cagtacatga ccttatggga ctttcctact tggcagtaca tctacgtatt | 420 |
| agtcatcgct attaccatgg tgatgcggtt ttggcagtac atcaatgggc gtggatagcg | 480 |
| gtttgactca cggggatttc caagtctcca ccccattgac gtcaatggga gtttgttttg | 540 |
| gcaccaaaat caacgggact ttccaaaatg tcgtaacaac tccgccccat tgacgcaaat | 600 |
| gggcggtagg cgtgtacggt gggaggtcta taagcaga gctggtttag tgaaccgtca | 660 |
| gatcactagt cgactaggga taacagggcc gccaccatga ttcacaccaa cctgaagaaa | 720 |
| aagttcagct gctgcgtcct ggtctttctt ctgtttgcag tcatctgtgt gtggaaggaa | 780 |
| aagaagaaag ggagttacta tgattccttt aaattgcaaa ccaaggaatt ccaggtgtta | 840 |
| aagagtctgg ggaaattggc catggggtct gattcccagt ctgtatcctc aagcagcacc | 900 |
| caggaccccc acaggggccg ccagaccctc ggcagtctca gaggcctagc caaggccaaa | 960 |
| ccagaggcct ccttccaggt gtggaacaag gacagctctt ccaaaaacct tatccctagg | 1020 |
| ctgcaaaagg ggtcgggggt gagcaagggc gaggagctgt tcaccggggt ggtgcccatc | 1080 |
| ctggtcgagc tggacggcga cgtaaacggc cacaagttca gcgtgtccgg cgagggcgag | 1140 |
| ggcgatgcca cctacggcaa gctgaccctg aagttcatct gcaccaccgg caagctgccc | 1200 |
| gtgccctggc ccaccctcgt gaccaccttc ggctacggcc tgcagtgctt cgcccgctac | 1260 |
| cccgaccaca tgaagcagca cgacttcttc aagtccgcca tgcccgaagg ctacgtccag | 1320 |
| gagcgcacca tcttcttcaa ggacgacggc aactacaaga cccgcgccga ggtgaagttc | 1380 |
| gagggcgaca ccctggtgaa ccgcatcgag ctgaagggca tcgacttcaa ggaggacggc | 1440 |
| aacatcctgg ggcacaagct ggagtacaac tacaacagcc acaacgtcta tatcatggcc | 1500 |

-continued

| | |
|---|---|
| gacaagcaga agaacggcat caaggtgaac ttcaagatcc gccacaacat cgaggacggc | 1560 |
| agcgtgcagc tcgccgacca ctaccagcag aacaccccca tcggcgacgg ccccgtgctg | 1620 |
| ctgcccgaca ccactacct gagctaccag tccgccctga gcaaagaccc caacgagaag | 1680 |
| cgcgatcaca tggtcctgct ggagttcgtg accgccgccg ggatcactct cggcatggac | 1740 |
| gagctgtaca agtgatcgac tgtgccttct agttgccagc catctgttgt ttgcccctcc | 1800 |
| cccgtgcctt ccttgaccct ggaaggtgcc actcccactg tcctttccta ataaaatgag | 1860 |
| gaaattgcat cgcattgtct gagtaggtgt cattctattc tggggggtgg ggtggggcag | 1920 |
| gacagcaagg gggaggattg ggaggacaat agcaggcatg ctgggatgc ggtgggctct | 1980 |
| atggcttctc cctgcaggtg cgcccaatac gcaaaccgcc tctccccgcg cgttggccga | 2040 |
| ttcattaatg cagctggcac gacaggtttc ccgactggaa agcgggcagt gagcgcaacg | 2100 |
| caattaatgt gagttagctc actcattagg cacccccaggc tttacacttt atgcttccgg | 2160 |
| ctcgtatgtt gtgtggaatt gtgagcggat aacaatttca cacaggaaac agctatgacc | 2220 |
| atgattacgg acagcctggc cgtcgtttta caacgtcgtg actgggaaaa ccctggcgtt | 2280 |
| acccaactta atcgccttgc agcacatccc cctttcgcca gctggcgtaa tagcgaagag | 2340 |
| gcccgcaccg atcgcccttc ccaacagttg cgcagcctga atggcgaatg cgcctgatg | 2400 |
| cggtattttc tccttacgca tctgtgcggt atttcacacc gcatatggtg cactctcagt | 2460 |
| acaatctgct ctgatgccgc atagacctgc agggccagca ggcagaagta tgcaaagcat | 2520 |
| gcatctcaat tagtcagcaa ccaggtgtgg aaagtcccca ggctcccag caggcagaag | 2580 |
| tatgcaaagc atgcatctca attagtcagc aaccatagtc ccgcccctaa ctccgcccat | 2640 |
| cccgccccta actccgccca gttccgccca ttctccgccc catggctgac taattttttt | 2700 |
| tatttatgca gaggccgagg ccgcctctgc ctctgagcta ttccagaagt agtgaggagg | 2760 |
| cttttttgga ggcctaggct tttgcaaaaa gctcccggga gcttgtatat ccattttcgg | 2820 |
| atctgatcag cacgtgatga aaagcctga actcaccgcg acgtctgtcg agaagtttct | 2880 |
| gatcgaaaag ttcgacagcg tgtccgacct gatgcagctc tcggagggcg aagaatctcg | 2940 |
| tgctttcagc ttcgatgtag gagggcgtgg atatgtcctg cgggtaaata gctgcgccga | 3000 |
| tggtttctac aaagatcgtt atgtttatcg gcactttgca tcggccgcgc tcccgattcc | 3060 |
| ggaagtgctt gacattgggg aattcagcga gagcctgacc tattgcatct cccgccgtgc | 3120 |
| acagggtgtc acgttgcaag acttgcctga accgaactg cccgctgttc tgcagccggt | 3180 |
| cgcggaggcc atggatgcga tcgctgcggc cgatcttagc cagacgagcg ggttcggccc | 3240 |
| attcggaccg caaggaatcg gtcaatacac tacatggcgt gatttcatat gcgcgattgc | 3300 |
| tgatccccat gtgtatcact ggcaaactgt gatggacgac accgtcagtg cgtccgtcgc | 3360 |
| gcaggctctc gatgagctga tgctttgggc cgaggactgc cccgaagtcc ggcacctcgt | 3420 |
| gcacgcggat ttcggctcca acaatgtcct gacggacaat ggccgcataa cagcggtcat | 3480 |
| tgactggagc gaggcgatgt tcggggattc ccaatacgag gtcgccaaca tcttcttctg | 3540 |
| gaggccgtgg ttggcttgta tggagcagca gacgcgctac ttcgagcgga ggcatccgga | 3600 |
| gcttgcagga tcgccgcggc tccgggcgta tatgctccgc attggtcttg accaactcta | 3660 |
| tcagagcttg gttgacggca atttcgatga tgcagcttgg gcgcagggtc gatgcgacgc | 3720 |
| aatcgtccga tccggagccg ggactgtcgg gcgtacacaa atcgcccgca gaagcgcggc | 3780 |
| cgtctggacc gatggctgtg tagaagtact cgccgatagt ggaaaccgac gccccagcac | 3840 |
| tcgtccgagg gcaaaggaat agcacgtgct acgagatttc gattccaccg ccgccttcta | 3900 |

```
tgaaaggttg ggcttcggaa tcgttttccg ggacgccggc tggatgatcc tccagcgcgg    3960
ggatctcatg ctggagttct tcgcccaccc caacttgttt attgcagctt ataatggtta    4020
caaataaagc aatagcatca caaatttcac aaataaagca ttttttttcac tgcattctag    4080 ttgtggtttg tccaaactca tcaatgtatc ttatgcgtct tctagggtta aggttagtgt    4140
agagaagcaa ccgaagattg agaagacatg gcggtaatac ggttatccac agaatcaggg    4200
gataacgcag gaaagaacat gtgagcaaaa ggccagcaaa aggccaggaa ccgtaaaaag    4260
gccgcgttgc tggcgttttt ccataggctc cgcccccctg acgagcatca caaaaatcga    4320
cgctcaagtc agaggtggcg aaacccgaca ggactataaa gataccaggc gtttccccct    4380
ggaagctccc tcgtgcgctc tcctgttccg accctgccgc ttaccggata cctgtccgcc    4440
tttctccctt cgggaagcgt ggcgctttct catagctcac gctgtaggta tctcagttcg    4500
gtgtaggtcg ttcgctccaa gctgggctgt gtgcacgaac cccccgttca gcccgaccgc    4560
tgcgccttat ccggtaacta tcgtcttgag tccaacccgg taagacacga cttatcgcca    4620
ctggcagcag ccactggtaa caggattagc agagcgaggt atgtaggcgg tgctacagag    4680
ttcttgaagt ggtggcctaa ctacggctac actagaagaa cagtatttgg tatctgcgct    4740
ctgctgaagc cagttacctt cggaaaaaga gttggtagct cttgatccgg caaacaaacc    4800
accgctggta gcggtttttt tgtttgcaag cagcagatta cgcgcagaaa aaaggatct    4860 caagaagatc ctttgatctt ttctacgggg tctgacgctc agtggaacga aaactcacgt    4920
taagggattt tggtcatgag attatcaaaa aggatcttca cctagatcct tttaaattaa    4980
aaatgaagtt ttaaatcaat ctaaagtata tatgagtaaa cttggtctga cagttaccaa    5040
tgcttaatca gtgaggcacc tatctcagcg atctgtctat ttcgttcatc catagttgcc    5100
tgactccccg tcgtgtagat aactacgata cgggagggct taccatctgg ccccagtgct    5160
gcaatgatac cgcgtgaccc acgctcaccg gctccagatt tatcagcaat aaaccagcca    5220
gccggaaggg ccgagcgcag aagtggtcct gcaactttat ccgcctccat ccagtctatt    5280
aattgttgcc gggaagctag agtaagtagt tcgccagtta atagtttgcg caacgttgtt    5340
gccattgcta caggcatcgt ggtgtcacgc tcgtcgtttg gtatggcttc attcagctcc    5400
ggttcccaac gatcaaggcg agttacatga tcccccatgt tgtgcaaaaa agcggttagc    5460
tccttcggtc ctccgatcgt tgtcagaagt aagttggccg cagtgttatc actcatggtt    5520
atggcagcac tgcataattc tcttactgtc atgccatccg taagatgctt ttctgtgact    5580
ggtgagtact caaccaagtc attctgagaa tagtgtatgc ggcgaccgag ttgctcttgc    5640
ccggcgtcaa tacgggataa taccgcgcca catagcagaa ctttaaaagt gctcatcatt    5700
ggaaaacgtt cttcggggcg aaaactctca aggatcttac cgctgttgag atccagttcg    5760
atgtaaccca ctcgtgcacc caactgatct tcagcatctt ttactttcac cagcgtttct    5820
gggtgagcaa aaacaggaag gcaaaatgcc gcaaaaaagg gaataagggc gacacgaaa    5880 tgttgaatac tcatactctt ccttttcaa tattattgaa gcatttatca gggttattgt    5940
ctcatgagcg gatacatatt tgaatgtatt tagaaaaata acaaataggg ggttccgcgc    6000
acatttcccc gaaaagtgcc acctatgaga cg                                  6032
```

<210> SEQ ID NO 34
<211> LENGTH: 6023
<212> TYPE: DNA
<213> ORGANISM: Artificial sequence
<220> FEATURE:

<223> OTHER INFORMATION: pHCsiaT-mCherry

<400> SEQUENCE: 34

```
tgaggctagg ataggacga gagcatcggg aacgaggact agcgtctcaa ggaaccaatt    60
cagtcgactg gatcctagtt attaatagta atcaattacg gggtcattag ttcatagccc   120
atatatggag ttccgcgtta cataacttac ggtaaatggc ccgcctggct gaccgcccaa   180
cgacccccgc ccattgacgt caataatgac gtatgttccc atagtaacgc caatagggac   240
tttccattga cgtcaatggg tggagtattt acggtaaact gcccacttgg cagtacatca   300
agtgtatcat atgccaagta cgccccctat tgacgtcaat gacggtaaat ggcccgcctg   360
gcattatgcc cagtacatga ccttatggga ctttcctact tggcagtaca tctacgtatt   420
agtcatcgct attaccatgg tgatgcggtt ttggcagtac atcaatgggc gtggatagcg   480
gtttgactca cggggatttc caagtctcca ccccattgac gtcaatggga gtttgttttg   540
gcaccaaaat caacgggact ttccaaaatg tcgtaacaac tccgccccat tgacgcaaat   600
gggcggtagg cgtgtacggt gggaggtcta taagcaga gctggtttag tgaaccgtca    660
gatcactagt cgactaggga taacaggggc gccaccatga ttcacaccaa cctgaagaaa   720
aagttcagct gctgcgtcct ggtctttctt ctgtttgcag tcatctgtgt gtggaaggaa   780
agaagaaag ggagttacta tgattccttt aaattgcaaa ccaaggaatt ccaggtgtta    840
aagagtctgg ggaaattggc catggggtct gattcccagt ctgtatcctc aagcagcacc   900
caggaccccc acaggggccg ccagaccctc ggcagtctca gaggcctagc caaggccaaa   960
ccagaggcct ccttccaggt gtggaacaag acagctctt ccaaaaacct tatccctagg    1020
ctgcaaaagg ggtcggggt gagcaagggc gaggaggata acatggccat catcaaggag    1080
ttcatgcgct tcaaggtgca catggagggc tccgtgaacg gccacgagtt cgagatcgag   1140
ggcgagggcg agggccgccc ctacgagggc acccagaccg ccaagctgaa ggtgaccaag   1200
ggtggcccc tgcccttcgc ctgggacatc ctgtcccctc agttcatgta cggctccaag    1260
gcctacgtga agcaccccgc cgacatcccc gactacttga agctgtcctt ccccgagggc   1320
ttcaagtggg agcgcgtgat gaacttcgag gacggcggcg tggtgaccgt gacccaggac   1380
tcctccctgc aggacggcga gttcatctac aaggtgaagc tgcgcggcac caacttcccc   1440
tccgacggcc ccgtaatgca gaagaaaacc atgggctggg aggcctcctc cgagcggatg   1500
taccccgagg acggcgccct gaagggcgag atcaagcaga ggctgaagct gaaggacggc   1560
ggccactacg acgctgaggt caagaccacc tacaaggcca agaagcccgt gcagctgccc   1620
ggcgcctaca acgtcaacat caagttggac atcacctccc acaacgagga ctacaccatc   1680
gtggaacagt acgaacgcgc cgagggccgc cactccaccg gcggcatgga cgagctgtac   1740
aagtgatcga ctgtgccttc tagttgccag ccatctgttg tttgcccctc ccccgtgcct   1800
tccttgaccc tggaaggtgc cactcccact gtcctttcct aataaaatga ggaaattgca   1860
tcgcattgtc tgagtaggtg tcattctatt ctggggggtg ggtgggca ggacagcaag    1920
ggggaggatt gggaggacaa tagcaggcat gctgggatg cggtgggctc tatggcttct    1980
ccctgcaggt gcgcccaata cgcaaaccgc ctctccccgc gcgttggccg attcattaat   2040
gcagctggca cgacaggttt cccgactgga aagcgggcag tgagcgcaac gcaattaatg   2100
tgagttagct cactcattag gcaccccagg ctttacactt tatgcttccg gctcgtatgt   2160
tgtgtggaat tgtgagcgga taacaatttc acacaggaaa cagctatgac catgattacg   2220
gacagcctgg ccgtcgtttt acaacgtcgt gactgggaaa accctggcgt tacccaactt   2280
```

```
aatcgccttg cagcacatcc cccttccgcc agctggcgta atagcgaaga ggcccgcacc    2340
gatcgcccct cccaacagtt gcgcagcctg aatggcgaat ggcgcctgat gcggtatttt    2400
ctccttacgc atctgtgcgg tatttcacac cgcatatggt gcactctcag tacaatctgc    2460
tctgatgccg catagacctg cagggccagc aggcagaagt atgcaaagca tgcatctcaa    2520
ttagtcagca accaggtgtg aaagtcccc  aggctcccca gcaggcagaa gtatgcaaag    2580
catgcatctc aattagtcag caaccatagt cccgcccta  actccgccca tcccgccct     2640 aactccgccc agttccgccc attctccgcc ccatggctga ctaattttt  ttatttatgc    2700 agaggccgag gccgcctctg cctctgagct attccagaag tagtgaggag gcttttttgg    2760
aggcctaggc ttttgcaaaa agctcccggg agcttgtata tccattttcg atctgatca     2820 gcacgtgatg aaaaagcctg aactcaccgc gacgtctgtc gagaagtttc tgatcgaaaa    2880
gttcgacagc gtgtccgacc tgatgcagct ctcggagggc gaagaatctc gtgctttcag    2940
cttcgatgta ggagggcgtg gatatgtcct gcgggtaaat agctgcgccg atggtttcta    3000
caaagatcgt tatgtttatc ggcactttgc atcgccgcg  ctcccgattc cggaagtgct    3060
tgacattggg gaattcagcg agagcctgac ctattgcatc tcccgccgtg cacagggtgt    3120
cacgttgcaa gacttgcctg aaaccgaact gcccgctgtt ctgcagccgg tcgcggaggc    3180
catggatgcg atcgctgcgg ccgatcttag ccagacgagc gggttcggcc cattcggacc    3240
gcaaggaatc ggtcaataca ctacatggcg tgatttcata tgcgcgattg ctgatcccca    3300
tgtgtatcac tggcaaactg tgatggacga caccgtcagt gcgtccgtcg cgcaggctct    3360
cgatgagctg atgctttggg ccgaggactg ccccgaagtc cggcacctcg tgcacgcgga    3420
tttcggctcc aacaatgtcc tgacggacaa tggccgcata acagcggtca ttgactggag    3480
cgaggcgatg ttcggggatt cccaatacga ggtcgccaac atcttcttct ggaggccgtg    3540
gttggcttgt atggagcagc agacgcgcta cttcgagcgg aggcatccgg agcttgcagg    3600
atcgccgcgg ctccgggcgt atatgctccg cattggtctt gaccaactct atcagagctt    3660
ggttgacggc aatttcgatg atgcagcttg ggcgcagggt cgatgcgacg caatcgtccg    3720
atccggagcc gggactgtcg ggcgtacaca atcgccccgc agaagcgcgg ccgtctggac    3780
cgatggctgt gtagaagtac tcgccgatag tggaaaccga cgccccagca ctcgtccgag    3840
ggcaaaggaa tagcacgtgc tacgagattt cgattccacc gccgccttct atgaaaggtt    3900
gggcttcgga atcgttttcc gggacgccgg ctggatgatc ctccagcgcg gggatctcat    3960
gctggagttc ttcgcccacc ccaacttgtt tattgcagct tataatggtt acaaataaag    4020
caatagcatc acaaatttca caaataaagc attttttca  ctgcattcta gttgtggttt    4080
gtccaaactc atcaatgtat cttatgcgtc ttctagggtt aaggttagtg tagagaagca    4140
accgaagatt gagaagacat ggcggtaata cggttatcca cagaatcagg ggataacgca    4200
ggaaagaaca tgtgagcaaa aggccagcaa aaggccagga accgtaaaaa ggccgcgttg    4260
ctggcgtttt tccataggct ccgcccccct gacgagcatc acaaaaatcg acgctcaagt    4320
cagaggtggc gaaacccgac aggactataa agataccagg cgtttccccc tggaagctcc    4380
ctcgtgcgct ctcctgttcc gaccctgccg cttaccggat acctgtccgc ctttctccct    4440
tcgggaagcg tggcgctttc tcatagctca cgctgtaggt atctcagttc ggtgtaggtc    4500
gttcgctcca agctgggctg tgtgcacgaa ccccccgttc agcccgaccg ctgcgcctta    4560
tccggtaact atcgtcttga gtccaacccg gtaagacacg acttatcgcc actggcagca    4620
```

```
gccactggta acaggattag cagagcgagg tatgtaggcg gtgctacaga gttcttgaag    4680
tggtggccta actacggcta cactagaaga acagtatttg gtatctgcgc tctgctgaag    4740
ccagttacct tcggaaaaag agttggtagc tcttgatccg gcaaacaaac caccgctggt    4800
agcggttttt ttgtttgcaa gcagcagatt acgcgcagaa aaaaaggatc tcaagaagat    4860
cctttgatct tttctacggg gtctgacgct cagtggaacg aaaactcacg ttaagggatt    4920
ttggtcatga gattatcaaa aaggatcttc acctagatcc ttttaaatta aaaatgaagt    4980
tttaaatcaa tctaaagtat atatgagtaa acttggtctg acagttacca atgcttaatc    5040
agtgaggcac ctatctcagc gatctgtcta tttcgttcat ccatagttgc ctgactcccc    5100
gtcgtgtaga taactacgat acgggagggc ttaccatctg gccccagtgc tgcaatgata    5160
ccgcgtgacc cacgctcacc ggctccagat ttatcagcaa taaaccagcc agccggaagg    5220
gccgagcgca gaagtggtcc tgcaacttta tccgcctcca tccagtctat taattgttgc    5280
cgggaagcta gagtaagtag ttcgccagtt aatagtttgc gcaacgttgt tgccattgct    5340
acaggcatcg tggtgtcacg ctcgtcgttt ggtatggctt cattcagctc cggttcccaa    5400
cgatcaaggc gagttacatg atcccccatg ttgtgcaaaa aagcggttag ctccttcggt    5460
cctccgatcg ttgtcagaag taagttggcc gcagtgttat cactcatggt tatggcagca    5520
ctgcataatt ctcttactgt catgccatcc gtaagatgct tttctgtgac tggtgagtac    5580
tcaaccaagt cattctgaga atagtgtatg cggcgaccga gttgctcttg cccggcgtca    5640
atacgggata taccgcgcc acatagcaga actttaaaag tgctcatcat tggaaaacgt    5700
tcttcggggc gaaaactctc aaggatctta ccgctgttga tccagttc gatgtaaccc    5760
actcgtgcac ccaactgatc ttcagcatct tttactttca ccagcgtttc tgggtgagca    5820
aaaacaggaa ggcaaaatgc cgcaaaaaag ggaataaggg cgacacggaa atgttgaata    5880
ctcatactct tcctttttca atattattga agcatttatc agggttattg tctcatgagc    5940
ggatacatat ttgaatgtat ttagaaaaat aaacaaatag gggttccgcg cacatttccc    6000
cgaaaagtgc cacctatgag acg                                            6023
```

<210> SEQ ID NO 35
<211> LENGTH: 6020
<212> TYPE: DNA
<213> ORGANISM: Artificial sequence
<220> FEATURE:
<223> OTHER INFORMATION: pHCsiaT-TagBFP

<400> SEQUENCE: 35

```
tgaggctagg gataggacga gagcatcggg aacgaggact agcgtctcaa ggaaccaatt      60
cagtcgactg gatcctagtt attaatagta atcaattacg gggtcattag ttcatagccc     120
atatatggag ttccgcgtta cataacttac ggtaaatggc ccgcctggct gaccgcccaa     180
cgacccccgc ccattgacgt caataatgac gtatgttccc atagtaacgc caatagggac     240
tttccattga cgtcaatggg tggagtattt acggtaaact gcccacttgg cagtacatca     300
agtgtatcat atgccaagta cgccccctat tgacgtcaat gacggtaaat ggcccgcctg     360
gcattatgcc cagtacatga ccttatggga ctttcctact tggcagtaca tctacgtatt     420
agtcatcgct attaccatgg tgatgcggtt ttggcagtac atcaatgggc gtggatagcg     480
gtttgactca cggggatttc caagtctcca ccccattgac gtcaatggga gtttgttttg     540
gcaccaaaat caacgggact ttccaaaatg tcgtaacaac tccgccccat tgacgcaaat     600
gggcggtagg cgtgtacggt gggaggtcta tataagcaga gctggtttag tgaaccgtca     660
```

-continued

```
gatcactagt cgactaggga taacagggcc gccaccatga ttcacaccaa cctgaagaaa      720
aagttcagct gctgcgtcct ggtctttctt ctgtttgcag tcatctgtgt gtggaaggaa      780
aagaagaaag ggagttacta tgattccttt aaattgcaaa ccaaggaatt ccaggtgtta      840
aagagtctgg ggaaattggc catggggtct gattcccagt ctgtatcctc aagcagcacc      900
caggaccccc acaggggccg ccagaccctc ggcagtctca gaggcctagc caaggccaaa      960
ccagaggcct ccttccaggt gtggaacaag gacagctctt ccaaaaacct tatccctagg     1020
ctgcaaaagg ggtcggggag cgagctgatt aaggagaaca tgcacatgaa gctgtacatg     1080
gagggcaccg tggacaacca tcacttcaag tgcacatccg agggcgaagg caagccctac     1140
gagggcaccc agaccatgag aatcaaggtg gtcgagggcg ccctctcccc cttcgccttc     1200
gacatcctgg ctactagctt cctctacggc agcaagacct tcatcaacca cacccagggc     1260
atccccgact tcttcaagca gtccttccct gagggcttca catgggagag agtcaccaca     1320
tacgaggacg gggcgtgct gaccgctacc caggacacca gcctccagga cggctgcctc     1380
atctacaacg tcaagatcag agggggtgaac ttcacatcca acggccctgt gatgcagaag     1440
aaaacactcg gctgggaggc cttcaccgaa acgctgtacc ccgctgacgg cggcctggaa     1500
ggcagaaacg acatggccct gaagctcgtg ggcgggagcc atctgatcgc aaacatcaag     1560
accacatata gatccaagaa acccgctaag aacctcaaga tgcctggcgt ctactatgtg     1620
gactacagac tggaaagaat caaggaggcc aacaacgaaa cctacgtcga gcagcacgag     1680
gtggcagtgg ccagatactg cgacctccct agcaaactgg ggcacaagct taattccgga     1740
tgatcgactg tgccttctag ttgccagcca tctgttgttt gcccctcccc cgtgccttcc     1800
ttgaccctgg aagtgccac tcccactgtc ctttcctaat aaaatgagga aattgcatcg     1860
cattgtctga gtaggtgtca ttctattctg gggggtgggg tgggcagga cagcaagggg     1920 gaggattggg aggacaatag caggcatgct ggggatgcgg tgggctctat ggcttctccc     1980
tgcaggtgcg cccaatacgc aaaccgcctc tccccgcgcg ttggccgatt cattaatgca     2040
gctggcacga caggtttccc gactggaaag cgggcagtga gcgcaacgca attaatgtga     2100
gttagctcac tcattaggca ccccaggctt tacactttat gcttccggct cgtatgttgt     2160
gtggaattgt gagcggataa caatttcaca caggaaacag ctatgaccat gattacggac     2220
agcctggccg tcgttttaca acgtcgtgac tgggaaaacc ctggcgttac ccaacttaat     2280
cgccttgcag cacatccccc tttcgccagc tggcgtaata gcgaagaggc ccgcaccgat     2340
cgcccttccc aacagttgcg cagcctgaat ggcgaatggc gcctgatgcg gtattttctc     2400
cttacgcatc tgtgcggtat ttcacaccgc atatggtgca ctctcagtac aatctgctct     2460
gatgccgcat agacctgcag ggccagcagg cagaagtatg caaagcatgc atctcaatta     2520
gtcagcaacc aggtgtggaa agtccccagg ctccccagca ggcagaagta tgcaaagcat     2580
gcatctcaat tagtcagcaa ccatagtccc gcccctaact ccgcccatcc cgcccctaac     2640
tccgcccagt tccgcccatt ctccgcccca tggctgacta attttttta tttatgcaga     2700 ggccgaggcc gcctctgcct ctgagctatt ccagaagtag tgaggaggct ttttggagg     2760 cctaggcttt tgcaaaaagc tcccgggagc ttgtatatcc attttcggat ctgatcagca     2820
cgtgatgaaa aagcctgaac tcaccgcgac gtctgtcgag aagtttctga tcgaaaagtt     2880
cgacagcgtg tccgacctga tgcagctctc ggagggcgaa gaatctcgtg ctttcagctt     2940
cgatgtagga gggcgtggat atgtcctgcg ggtaaatagc tgcgccgatg gtttctacaa     3000
```

```
agatcgttat gtttatcggc actttgcatc ggccgcgctc ccgattccgg aagtgcttga    3060
cattggggaa ttcagcgaga gcctgaccta ttgcatctcc cgccgtgcac agggtgtcac    3120
gttgcaagac ttgcctgaaa ccgaactgcc cgctgttctg cagccggtcg cggaggccat    3180
ggatgcgatc gctgcggccg atcttagcca gacgagcggg ttcggcccat tcggaccgca    3240
aggaatcggt caatacacta catggcgtga tttcatatgc gcgattgctg atccccatgt    3300
gtatcactgg caaactgtga tggacgcacac cgtcagtgcg tccgtcgcgc aggctctcga    3360
tgagctgatg ctttgggccg aggactgccc cgaagtccgg cacctcgtgc acgcggattt    3420
cggctccaac aatgtcctga cggacaatgg ccgcataaca gcggtcattg actggagcga    3480
ggcgatgttc ggggattccc aatacgaggt cgccaacatc ttcttctgga ggccgtggtt    3540
ggcttgtatg gagcagcaga cgcgctactt cgagcggagg catccggagc ttgcaggatc    3600
gccgcggctc cggcgtata tgctccgcat tggtcttgac caactctatc agagcttggt    3660
tgacggcaat ttcgatgatg cagcttgggc gcagggtcga tgcgacgcaa tcgtccgatc    3720
cggagccggg actgtcgggc gtacacaaat cgcccgcaga agcgcggccg tctgaccga    3780
tggctgtgta aagtactcg ccgatagtgg aaaccgacgc cccagcactc gtccgagggc    3840
aaaggaatag cacgtgctac gagatttcga ttccaccgcc gccttctatg aaaggttggg    3900
cttcggaatc gttttccggg acgccggctg gatgatcctc cagcgcgggg atctcatgct    3960
ggagttcttc gcccacccca acttgtttat tgcagcttat aatggttaca ataaagcaa    4020
tagcatcaca aatttcacaa ataaagcatt ttttcactg cattctagtt gtggtttgtc    4080
caaactcatc aatgtatctt atgcgtcttc tagggttaag gttagtgtag agaagcaacc    4140
gaagattgag aagacatggc ggtaatacgg ttatccacag aatcagggga taacgcagga    4200
aagaacatgt gagcaaaagg ccagcaaaag gccaggaacc gtaaaaaggc cgcgttgctg    4260
gcgttttcc ataggctccg ccccctgac gagcatcaca aaatcgacg ctcaagtcag    4320
aggtggcgaa acccgacagg actataaaga taccaggcgt ttccccctgg aagctccctc    4380
gtgcgctctc ctgttccgac cctgccgctt accggatacc tgtccgcctt tctcccttcg    4440
ggaagcgtgg cgctttctca tagctcacgc tgtaggtatc tcagttcggt gtaggtcgtt    4500
cgctccaagc tgggctgtgt gcacgaaccc cccgttcagc ccgaccgctg cgccttatcc    4560
ggtaactatc gtcttgagtc aacccggta agacacgact tatcgccact ggcagcagcc    4620
actggtaaca ggattagcag agcgaggtat gtaggcggtg ctacagagtt cttgaagtgg    4680
tggcctaact acggctacac tagaagaaca gtatttggta tctgcgctct gctgaagcca    4740
gttaccttcg gaaaaagagt tggtagctct tgatccggca acaaaccac cgctggtagc    4800
ggttttttg tttgcaagca gcagattacg cgcagaaaaa aaggatctca agaagatcct    4860
ttgatctttt ctacggggtc tgacgctcag tggaacgaaa actcacgtta agggattttg    4920
gtcatgagat tatcaaaaag gatcttcacc tagatccttt taaattaaaa atgaagtttt    4980
aaatcaatct aaagtatata tgagtaaact tggtctgaca gttaccaatg cttaatcagt    5040
gaggcaccta tctcagcgat ctgtctattt cgttcatcca tagttgcctg actccccgtc    5100
gtgtagataa ctacgatacg ggagggctta ccatctggcc ccagtgctgc aatgataccg    5160
cgtgacccac gctcaccggc tccagattta tcagcaataa accagccagc cggaagggcc    5220
gagcgcagaa gtggtcctgc aactttatcc gcctccatcc agtctattaa ttgttgccgg    5280
gaagctagag taagtagttc gccagttaat agtttgcgca acgttgttgc cattgctaca    5340
ggcatcgtgg tgtcacgctc gtcgtttggt atggcttcat tcagctccgg ttcccaacga    5400
```

```
tcaaggcgag ttacatgatc ccccatgttg tgcaaaaaag cggttagctc cttcggtcct    5460
ccgatcgttg tcagaagtaa gttggccgca gtgttatcac tcatggttat ggcagcactg    5520
cataattctc ttactgtcat gccatccgta agatgctttt ctgtgactgg tgagtactca    5580
accaagtcat tctgagaata gtgtatgcgg cgaccgagtt gctcttgccc ggcgtcaata    5640
cgggataata ccgcgccaca tagcagaact ttaaaagtgc tcatcattgg aaaacgttct    5700
tcggggcgaa aactctcaag gatcttaccg ctgttgagat ccagttcgat gtaacccact    5760
cgtgcaccca actgatcttc agcatctttt actttcacca gcgtttctgg gtgagcaaaa    5820
acaggaaggc aaaatgccgc aaaaaaggga taagggcga cacggaaatg ttgaatactc    5880
atactcttcc ttttcaata ttattgaagc atttatcagg gttattgtct catgagcgga    5940
tacatatttg aatgtattta gaaaaataaa caaataggg ttccgcgcac atttccccga    6000
aaagtgccac ctatgagacg                                                 6020
```

<210> SEQ ID NO 36
<211> LENGTH: 1886
<212> TYPE: DNA
<213> ORGANISM: Artificial sequence
<220> FEATURE:
<223> OTHER INFORMATION: Ori-AmpR BsaI B

<400> SEQUENCE: 36

```
gaggtaccgg tctcatattg taatacggtt atccacagaa tcaggggata acgcaggaaa      60
gaacatgtga gcaaaaggcc agcaaaaggc caggaaccgt aaaaaggccg cgttgctggc     120 gttttccat aggctccgcc cccctgacga gcatcacaaa aatcgacgct caagtcagag     180
gtggcgaaac ccgacaggac tataaagata ccaggcgttt ccccctggaa gctccctcgt     240
gcgctctcct gttccgaccc tgccgcttac cggatacctg tccgcctttc tcccttcggg     300
aagcgtggcg ctttctcata gctcacgctg taggtatctc agttcggtgt aggtcgttcg     360
ctccaagctg ggctgtgtgc acgaacccccc gttcagccc gaccgctgcg ccttatccgg     420
taactatcgt cttgagtcca acccggtaag acacgactta tcgccactgg cagcagccac     480
tggtaacagg attagcagag cgaggtatgt aggcggtgct acagagttct tgaagtggtg     540
gcctaactac ggctacacta agaacagt atttggtatc tgcgctctgc tgaagccagt     600
taccttcgga aaaagagttg gtagctcttg atccggcaaa caaaccaccg ctggtagcgg     660 ttttttgtt tgcaagcagc agattacgcg cagaaaaaaa ggatctcaag aagatccttt     720
gatcttttct acggggtctg acgctcagtg gaacgaaaac tcacgttaag ggattttggt     780
catgagatta tcaaaaagga tcttcaccta gatccttta aattaaaaat gaagttttaa     840
atcaatctaa agtatatatg agtaaacttg gtctgacagt taccaatgct taatcagtga     900
ggcacctatc tcagcgatct gtctatttcg ttcatccata gttgcctgac tccccgtcgt     960
gtagataact acgatacggg agggcttacc atctggcccc agtgctgcaa tgataccgcg    1020
tgacccacgc tcaccggctc cagatttatc agcaataaac cagccagccg aagggccga    1080 gcgcagaagt ggtcctgcaa ctttatccgc ctccatccag tctattaatt gttgccggga    1140
agctagagta agtagttcgc cagttaatag tttgcgcaac gttgttgcca ttgctacagg    1200
catcgtggtg tcacgctcgt cgtttggtat ggcttcattc agctccggtt cccaacgatc    1260
aaggcgagtt acatgatccc ccatgttgtg caaaaagcg ttagctcct tcggtcctcc    1320 gatcgttgtc agaagtaagt tggccgcagt gttatcactc atggttatgg cagcactgca    1380
```

```
taattctctt actgtcatgc catccgtaag atgctttcct gtgactggtg agtactcaac   1440
caagtcattc tgagaatagt gtatgcggcg accgagttgc tcttgcccgg cgtcaatacg   1500
ggataatacc gcgccacata gcagaacttt aaaagtgctc atcattggaa aacgttcttc   1560
ggggcgaaaa ctctcaagga tcttaccgct gttgagatcc agttcgatgt aacccactcg   1620
tgcacccaac tgatcttcag catcttttac tttcaccagc gtttctgggt gagcaaaaac   1680
aggaaggcaa aatgccgcaa aaaagggaat aagggcgaca cggaaatgtt gaatactcat   1740
actcttcctt tttcaatatt attgaagcat ttatcagggt tattgtctca tgagcggata   1800
catatttgaa tgtatttaga aaaataaaca ataggggtt ccgcgcacat ttccccgaaa   1860
agtgccaagg acgagaccgg tacctc                                        1886
```

<210> SEQ ID NO 37
<211> LENGTH: 673
<212> TYPE: DNA
<213> ORGANISM: Artificial sequence
<220> FEATURE:
<223> OTHER INFORMATION: pCMV BsaI B

<400> SEQUENCE: 37

```
gaggtaccgg tctcaaggaa ccaattcagt cgactggatc ctagttatta atagtaatca    60
attacggggt cattagttca tagcccatat atggagttcc gcgttacata acttacggta   120
aatggcccgc ctggctgacc gcccaacgac ccccgcccat tgacgtcaat aatgacgtat   180
gttcccatag taacgccaat agggactttc cattgacgtc aatgggtgga gtatttacgg   240
taaactgccc acttggcagt acatcaagtg tatcatatgc caagtacgcc ccctattgac   300
gtcaatgacg gtaaatggcc cgcctggcat tatgcccagt acatgacctt atgggacttt   360
cctacttggc agtacatcta cgtattagtc atcgctatta ccatggtgat gcggttttgg   420
cagtacatca atgggcgtgg atagcggttt gactcacggg gatttccaag tctccacccc   480
attgacgtca atgggagttt gttttggcac caaaatcaac gggactttcc aaaatgtcgt   540
aacaactccg ccccattgac gcaaatgggc ggtaggcgtg tacggtggga ggtctatata   600
agcagagctg gtttagtgaa ccgtcagatc actagtcgac tagggataac agggcacccg   660
agaccggtac ctc                                                      673
```

<210> SEQ ID NO 38
<211> LENGTH: 1121
<212> TYPE: DNA
<213> ORGANISM: Artificial sequence
<220> FEATURE:
<223> OTHER INFORMATION: hFUT3 BsaI A

<400> SEQUENCE: 38

```
gaggtaccgg tctcacacca tggatcccct gggtgcagcc aagccacaat ggccatggcg    60
ccgctgtctg gccgcactgc tatttcagct gctggtggcc gtgtgtttct tctcctacct   120
gcgtgtgtcc cgagacgatg ccactggatc ccctagggct cccagtgggt cctcccgaca   180
ggacaccact cccacccgcc ccaccctcct gatcctgcta tggacatggc ctttccacat   240
ccctgtggct ctgtcccgct gttcagagat ggtgcccggc acagccgact gccacatcac   300
tgccgaccgc aaggtgtacc cacaggcaga cacggtcatc gtgcaccact gggatatcat   360
gtccaaccct aagtcacgcc tcccaccttc cccgaggccg caggggcagc gctggatctg   420
gttcaacttg gagccacccc ctaactgcca gcacctggaa gccctggaca gatacttcaa   480
tctcaccatg tcctaccgca gcgactccga catcttcacg ccctacggct ggctggagcc   540
```

```
gtggtccggc cagcctgccc acccaccgct caacctctcg gccaagaccg agctggtggc    600
ctgggcggtg tccaactgga agccggactc agccagggtg cgctactacc agagcctgca    660
ggctcatctc aaggtggacg tgtacggacg ctcccacaag ccctgccca agggaccat      720 gatggagacg ctgtcccggt acaagttcta cctggccttc gagaactcct tgcaccccga    780
ctacatcacc gagaagctgt ggaggaacgc cctggaggcc tgggccgtgc ccgtggtgct    840
gggccccagc agaagcaact acgagaggtt cctgccaccc gacgccttca tccacgtgga    900
cgacttccag agccccaagg acctggcccg gtacctgcag gagctggaca aggaccacgc    960
ccgctacctg agctactttc gctggcggga gacgctgcgg cctcgctcct tcagctgggc   1020
actggatttc tgcaaggcct gctggaaact gcagcaggaa tccaggtacc agacggtgcg   1080
cagcatagcg gcttggttca cctgatcgag accggtacct c                        1121
```

<210> SEQ ID NO 39  
<211> LENGTH: 267  
<212> TYPE: DNA  
<213> ORGANISM: Artificial sequence  
<220> FEATURE:  
<223> OTHER INFORMATION: BGHpA BsaI B

<400> SEQUENCE: 39

```
gaggtaccgg tctcatgatc gactgtgcct tctagttgcc agccatctgt tgtttgcccc     60
tcccccgtgc cttccttgac cctggaaggt gccactccca ctgtcctttc ctaataaaat   120
gaggaaattg catcgcattg tctgagtagg tgtcattcta ttctgggggg tggggtgggg   180
caggacagca agggggagga ttgggaggac aatagcaggc atgctgggga tgcggtgggc   240
tctatggctt cgcgagaccg gtacctc                                        267
```

<210> SEQ ID NO 40  
<211> LENGTH: 444  
<212> TYPE: DNA  
<213> ORGANISM: Artificial sequence  
<220> FEATURE:  
<223> OTHER INFORMATION: shB3Galt6 BsaI A

<400> SEQUENCE: 40

```
gaggtaccgg tctcattcga cagggtcgac aagcttttcc aaaaaaaaag catgaggtgc     60
agttgcgcct ttcctatctc ttgaatagga aaggcgcaac tgcacctcat gctggatccc   120
gcgtcctttc cacaagatat ataaacccaa gaaatcgaaa tactttcaag ttacggtaag   180
catatgatag tccatttaa aacataattt taaaactgca aactacccaa gaaattatta    240 cttctctacgt cacgtatttt gtactaatat ctttgtgttt acagtcaaat taattctaat   300
tatctctcta acagccttgt atcgtatatg caaatatgaa ggaatcatgg gaaataggcc    360
ctcttcctgc ccgaccttgg cgcgcgctcg gcgcgcggtc acgctccgtc acgtggtgcg    420
ttttgtattc gagaccggta cctc                                           444
```

<210> SEQ ID NO 41  
<211> LENGTH: 4221  
<212> TYPE: DNA  
<213> ORGANISM: Artificial sequence  
<220> FEATURE:  
<223> OTHER INFORMATION: V1

<400> SEQUENCE: 41

```
tattgtaata cggttatcca cagaatcagg ggataacgca ggaaagaaca tgtgagcaaa     60
```

-continued

```
aggccagcaa aaggccagga accgtaaaaa ggccgcgttg ctggcgtttt tccataggct     120
ccgcccccct gacgagcatc acaaaaatcg acgctcaagt cagaggtggc gaaacccgac     180
aggactataa agataccagg cgtttccccc tggaagctcc ctcgtgcgct ctcctgttcc     240
gaccctgccg cttaccggat acctgtccgc ctttctccct tcgggaagcg tggcgctttc     300
tcatagctca cgctgtaggt atctcagttc ggtgtaggtc gttcgctcca agctgggctg     360
tgtgcacgaa ccccccgttc agcccgaccg ctgcgcctta tccggtaact atcgtcttga     420
gtccaacccg gtaagacacg acttatcgcc actggcagca gccactggta acaggattag     480
cagagcgagg tatgtaggcg gtgctacaga gttcttgaag tggtggccta actacggcta     540
cactagaaga acagtatttg gtatctgcgc tctgctgaag ccagttacct tcggaaaaag     600
agttggtagc tcttgatccg gcaaacaaac caccgctggt agcggttttt ttgtttgcaa     660
gcagcagatt acgcgcagaa aaaaggatc tcaagaagat cctttgatct tttctacggg     720
gtctgacgct cagtggaacg aaaactcacg ttaagggatt ttggtcatga gattatcaaa     780
aaggatcttc acctagatcc ttttaaatta aaaatgaagt tttaaatcaa tctaaagtat     840
atatgagtaa acttggtctg acagttacca atgcttaatc agtgaggcac ctatctcagc     900
gatctgtcta tttcgttcat ccatagttgc ctgactcccc gtcgtgtaga taactacgat     960
acgggagggc ttaccatctg gccccagtgc tgcaatgata ccgcgtgacc cacgctcacc    1020
ggctccagat ttatcagcaa taaaccagcc agccggaagg gccgagcgca gaagtggtcc    1080
tgcaacttta tccgcctcca tccagtctat taattgttgc cgggaagcta gagtaagtag    1140
ttcgccagtt aatagtttgc gcaacgttgt tgccattgct acaggcatcg tggtgtcacg    1200
ctcgtcgttt ggtatggctt cattcagctc cggttcccaa cgatcaaggc gagttacatg    1260
atcccccatg ttgtgcaaaa aagcggttag ctccttcggt cctccgatcg ttgtcagaag    1320
taagttggcc gcagtgttat cactcatggt tatggcagca ctgcataatt ctcttactgt    1380
catgccatcc gtaagatgct tttctgtgac tggtgagtac tcaaccaagt cattctgaga    1440
atagtgtatg cggcgaccga gttgctcttg cccggcgtca atacgggata taccgcgcc     1500 acatagcaga actttaaaag tgctcatcat tggaaaacgt tcttcgggc gaaaactctc    1560 aaggatctta ccgctgttga tccagttc gatgtaaccc actcgtgcac ccaactgatc     1620
ttcagcatct tttactttca ccagcgtttc tgggtgagca aaaacaggaa ggcaaaatgc    1680
cgcaaaaaag ggaataaggg cgacacggaa atgttgaata ctcatactct tccttttca    1740 atattattga agcatttatc agggttattg tctcatgagc ggatacatat ttgaatgtat    1800
ttagaaaaat aaacaaatag gggttccgcg cacatttccc cgaaaagtgc caaggaacca    1860
attcagtcga ctggatccta gttattaata gtaatcaatt acgggtcat tagttcatag    1920 cccatatatg gagttccgcg ttacataact tacggtaaat ggcccgcctg gctgaccgcc    1980
caacgacccc cgcccattga cgtcaataat gacgtatgtt cccatagtaa cgccaatagg    2040
gactttccat tgacgtcaat gggtggagta tttacggtaa actgcccact tggcagtaca    2100
tcaagtgtat catatgccaa gtacgccccc tattgacgtc aatgacggta aatggcccgc    2160
ctggcattat gcccagtaca tgaccttatg gactttcct acttggcagt acatctacgt    2220
attagtcatc gctattacca tggtgatgcg gttttggcag tacatcaatg ggcgtggata    2280
gcggtttgac tcacggggat ttccaagtct ccaccccatt gacgtcaatg ggagtttgtt    2340
ttggcaccaa aatcaacggg actttccaaa atgtcgtaac aactccgccc cattgacgca    2400
aatgggcggt aggcgtgtac ggtgggaggt ctatataagc agagctggtt tagtgaaccg    2460
```

```
tcagatcact agtcgactag ggataacagg gcaccatgga tccctgggt gcagccaagc   2520
cacaatggcc atggcgccgc tgtctggccg cactgctatt tcagctgctg gtggctgtgt   2580
gtttcttctc ctacctgcgt gtgtcccgag acgatgccac tggatccct agggctccca   2640
gtgggtcctc ccgacaggac accactccca cccgccccac cctcctgatc ctgctatgga   2700
catggccttt ccacatccct gtggctctgt cccgctgttc agagatggtg cccggcacag   2760
ccgactgcca catcactgcc gaccgcaagg tgtacccaca ggcagacacg gtcatcgtgc   2820
accactggga tatcatgtcc aaccctaagt cacgcctccc accttccccg aggccgcagg   2880
ggcagcgctg gatctggttc aacttggagc accccctaa ctgccagcac ctggaagccc   2940
tggacagata cttcaatctc accatgtcct accgcagcga ctccgacatc ttcacgccct   3000
acggctggct ggagccgtgg tccggccagc ctgcccaccc accgctcaac ctctcggcca   3060
agaccgagct ggtggcctgg gcggtgtcca actggaagcc ggactcagcc agggtgcgct   3120
actaccagag cctgcaggct catctcaagg tggacgtgta cggacgctcc cacaagcccc   3180
tgcccaaggg gaccatgatg gagacgctgt cccggtacaa gttctacctg gccttcgaga   3240
actccttgca ccccgactac atcaccgaga agctgtggag gaacgccctg gaggcctggg   3300
ccgtgcccgt ggtgctgggc cccagcagaa gcaactacga gaggttcctg ccacccgacg   3360
ccttcatcca cgtggacgac ttccagagcc ccaaggacct ggcccggtac ctgcaggagc   3420
tggacaagga ccacgcccgc tacctgagct actttcgctg gcgggagacg ctgcggcctc   3480
gctccttcag ctgggcactg gatttctgca aggcctgctg gaaactgcag caggaatcca   3540
ggtaccagac ggtgcgcagc atagcggctt ggttcacctg atcgactgtg ccttctagtt   3600
gccagccatc tgttgtttgc cctccccg tgccttcctt gacccctggaa ggtgccactc   3660
ccactgtcct ttcctaataa aatgaggaaa ttgcatcgca ttgtctgagt aggtgtcatt   3720
ctattctggg gggtggggtg gggcaggaca gcaaggggga ggattgggag gacaatagca   3780
ggcatgctgg ggatgcggtg ggctctatgg cttcgacagg gtcgacaagc ttttccaaaa   3840
aaaaagcatg aggtgcagtt gcgccttttc tatctcttga ataggaaagg cgcaactgca   3900
cctcatgctg gatcccgcgt cctttccaca agatatataa acccaagaaa tcgaaatact   3960
ttcaagttac ggtaagcata tgatagtcca ttttaaaaca taattttaaa actgcaaact   4020
acccaagaaa ttattacttt ctacgtcacg tattttgtac taatatcttt gtgtttacag   4080
tcaaattaat tctaattatc tctctaacag ccttgtatcg tatatgcaaa tatgaaggaa   4140
tcatgggaaa taggccctct tcctgcccga ccttggcgcg cgctcggcgc gcggtcacgc   4200
tccgtcacgt ggtgcgtttt g                                              4221
```

<210> SEQ ID NO 42
<211> LENGTH: 20
<212> TYPE: DNA
<213> ORGANISM: Artificial sequence
<220> FEATURE:
<223> OTHER INFORMATION: BETA3Galt6ms2-s

<400> SEQUENCE: 42

```
accactctgt tgtacctggc                                                20
```

<210> SEQ ID NO 43
<211> LENGTH: 17
<212> TYPE: DNA
<213> ORGANISM: Artificial sequence
<220> FEATURE:

<223> OTHER INFORMATION: BETA3Galt6ms2-as

<400> SEQUENCE: 43
cacacgtcct cgggtcc                                                  17

<210> SEQ ID NO 44
<211> LENGTH: 24
<212> TYPE: DNA
<213> ORGANISM: Artificial sequence
<220> FEATURE:
<223> OTHER INFORMATION: FUT35

<400> SEQUENCE: 44
cactagtcga ctagggataa cagg                                          24

<210> SEQ ID NO 45
<211> LENGTH: 22
<212> TYPE: DNA
<213> ORGANISM: Artificial sequence
<220> FEATURE:
<223> OTHER INFORMATION: FUT33

<400> SEQUENCE: 45
atgtccatag caggatcagg ag                                            22

<210> SEQ ID NO 46
<211> LENGTH: 444
<212> TYPE: DNA
<213> ORGANISM: Artificial sequence
<220> FEATURE:
<223> OTHER INFORMATION: shB3Galt6 BsaI B

<400> SEQUENCE: 46
gaggtaccgg tctcattcga cagggtcgac aagcttttcc aaaaaaaaag catgaggtgc    60
agttgcgcct ttcctatctc ttgaatagga aaggcgcaac tgcacctcat gctggatccc   120
gcgtcctttc cacaagatat ataaacccaa gaaatcgaaa tactttcaag ttacggtaag   180
catatgatag tccattttaa aacataattt taaaactgca aactacccaa gaaattatta   240 cttttctacgt cacgtatttt gtactaatat ctttgtgttt acagtcaaat taattctaat   300
tatctctcta acagccttgt atcgtatatg caaatatgaa ggaatcatgg gaaataggcc   360
ctcttcctgc ccgaccttgg cgcgcgctcg gcgcgcggtc acgctccgtc acgtggtgcg   420
ttttgccagc gagaccggta cctc                                         444

<210> SEQ ID NO 47
<211> LENGTH: 1650
<212> TYPE: DNA
<213> ORGANISM: Artificial sequence
<220> FEATURE:
<223> OTHER INFORMATION: HygroR BsaI B

<400> SEQUENCE: 47
gaggtaccgg tctcaccagc aggcagaagt atgcaaagca tgcatctcaa ttagtcagca    60
accaggtgtg gaaagtcccc aggctcccca gcaggcagaa gtatgcaaag catgcatctc   120
aattagtcag caaccatagt cccgccccta actccgccca tcccgcccct aactccgccc   180
agttccgccc attctccgcc ccatggctga ctaattttt ttatttatgc agaggccgag   240
gccgcctctg cctctgagct attccagaag tagtgaggag gcttttttgg aggcctaggc   300
ttttgcaaaa agctcccggg agcttgtata tccattttcg gatctgatca gcacgtgatg   360
aaaaagcctg aactcaccgc gacgtctgtc gagaagtttc tgatcgaaaa gttcgacagc   420

```
gtgtccgacc tgatgcagct ctcggagggc gaagaatctc gtgctttcag cttcgatgta    480
ggagggcgtg atatgtcct gcgggtaaat agctgcgccg atggtttcta caaagatcgt    540 tatgttatc ggcactttgc atcggccgcg ctcccgattc cggaagtgct tgacattggg    600
gaattcagcg agagcctgac ctattgcatc tcccgccgtg cacagggtgt cacgttgcaa    660
gacttgcctg aaaccgaact gcccgctgtt ctgcagccgg tcgcggaggc catggatgcg    720
atcgctgcgg ccgatcttag ccagacgagc gggttcggcc cattcggacc gcaaggaatc    780
ggtcaataca ctacatggcg tgatttcata tgcgcgattg ctgatcccca tgtgtatcac    840
tggcaaactg tgatggacga caccgtcagt gcgtccgtcg cgcaggctct cgatgagctg    900
atgctttggg ccgaggactg ccccgaagtc cggcacctcg tgcacgcgga tttcggctcc    960
aacaatgtcc tgacggacaa tggccgcata acagcggtca ttgactggag cgaggcgatg   1020
ttcggggatt cccaatacga ggtcgccaac atcttcttct ggaggccgtg gttggcttgt   1080
atggagcagc agacgcgcta cttgagcgg aggcatccgg agcttgcagg atcgccgcgg   1140
ctccgggcgt atatgctccg cattggtctt gaccaactct atcagagctt ggttgacggc   1200
aatttcgatg atgcagcttg ggcgcagggt cgatgcgacg caatcgtccg atccggagcc   1260
gggactgtcg ggcgtacaca aatcgcccgc agaagcgcgg ccgtctggac cgatggctgt   1320
gtagaagtac tcgccgatag tggaaaccga cgccccagca ctcgtccgag ggcaaaggaa   1380
tagcacgtgc tacgagattt cgattccacc gccgccttct atgaaaggtt gggcttcgga   1440 atcgtttttcc gggacgccgg ctggatgatc ctccagcgcg gggatctcat gctggagttc   1500
ttcgcccacc ccaacttgtt tattgcagct tataatggtt acaaataaag caatagcatc   1560
acaaatttca caaataaagc attttttttca ctgcattcta gttgtggttt gtccaaactc   1620
atcaatgtat ctattcgaga ccggtacctc                                    1650

<210> SEQ ID NO 48
<211> LENGTH: 5837
<212> TYPE: DNA
<213> ORGANISM: Artificial sequence
<220> FEATURE:
<223> OTHER INFORMATION: V1.1

<400> SEQUENCE: 48
tattgtaata cggttatcca cagaatcagg ggataacgca ggaaagaaca tgtgagcaaa     60
aggccagcaa aaggccagga accgtaaaaa ggccgcgttg ctggcgtttt tccataggct    120 ccgccccct gacgagcatc acaaaaatcg acgctcaagt cagaggtggc gaaacccgac    180
aggactataa agataccagg cgtttccccc tggaagctcc ctcgtgcgct ctcctgttcc    240
gaccctgccg cttaccggat acctgtccgc ctttctccct tcgggaagcg tggcgctttc    300
tcatagctca cgctgtaggt atctcagttc ggtgtaggtc gttcgctcca agctgggctg    360
tgtgcacgaa ccccccgttc agcccgaccg ctgcgcctta ccggtaact atcgtcttga    420 gtccaacccg gtaagacacg acttatcgcc actggcagca gccactggta acaggattag    480
cagagcgagg tatgtaggcg gtgctacaga gttcttgaag tggtggccta actacggcta    540
cactagaaga acagtatttg gtatctgcgc tctgctgaag ccagttacct tcggaaaaag    600
agttggtagc tcttgatccg gcaaacaaac caccgctggt agcggttttt tgtttgcaa    660 gcagcagatt acgcgcagaa aaaaaggatc tcaagaagat cctttgatct tttctacggg    720
gtctgacgct cagtggaacg aaaactcacg ttaagggatt ttggtcatga gattatcaaa    780
```

-continued

| | |
|---|---|
| aaggatcttc acctagatcc tttaaaatta aaaatgaagt tttaaatcaa tctaaagtat | 840 |
| atatgagtaa acttggtctg acagttacca atgcttaatc agtgaggcac ctatctcagc | 900 |
| gatctgtcta tttcgttcat ccatagttgc ctgactcccc gtcgtgtaga taactacgat | 960 |
| acgggagggc ttaccatctg gccccagtgc tgcaatgata ccgcgtgacc cacgctcacc | 1020 |
| ggctccagat ttatcagcaa taaaccagcc agccggaagg gccgagcgca gaagtggtcc | 1080 |
| tgcaacttta tccgcctcca tccagtctat taattgttgc cgggaagcta gagtaagtag | 1140 |
| ttcgccagtt aatagtttgc gcaacgttgt tgccattgct acaggcatcg tggtgtcacg | 1200 |
| ctcgtcgttt ggtatggctt cattcagctc cggttcccaa cgatcaaggc gagttacatg | 1260 |
| atcccccatg ttgtgcaaaa aagcggttag ctccttcggt cctccgatcg ttgtcagaag | 1320 |
| taagttggcc gcagtgttat cactcatggt tatggcagca ctgcataatt ctcttactgt | 1380 |
| catgccatcc gtaagatgct tttctgtgac tggtgagtac tcaaccaagt cattctgaga | 1440 |
| atagtgtatg cggcgaccga gttgctcttg cccggcgtca atacgggata ataccgcgcc | 1500 |
| acatagcaga actttaaaag tgctcatcat tggaaaacgt tcttcggggc gaaaactctc | 1560 |
| aaggatctta ccgctgttga gatccagttc gatgtaaccc actcgtgcac ccaactgatc | 1620 |
| ttcagcatct tttactttca ccagcgtttc tgggtgagca aaaacaggaa ggcaaaatgc | 1680 |
| cgcaaaaaag gaataagggc gacacggaaa tgttgaata ctcatactct tccttttca | 1740 |
| atattattga agcatttatc agggttattg tctcatgagc ggatacatat ttgaatgtat | 1800 |
| ttagaaaaat aaacaaatag gggttccgcg cacatttccc cgaaaagtgc caaggaacca | 1860 |
| attcagtcga ctggatccta gttattaata gtaatcaatt acgggtcat tagttcatag | 1920 |
| cccatatatg gagttccgcg ttacataact tacggtaaat ggcccgcctg gctgaccgcc | 1980 |
| caacgacccc cgcccattga cgtcaataat gacgtatgtt cccatagtaa cgccaatagg | 2040 |
| gactttccat tgacgtcaat gggtggagta tttacggtaa actgcccact tggcagtaca | 2100 |
| tcaagtgtat catatgccaa gtacgccccc tattgacgtc aatgacggta atggcccgc | 2160 |
| ctggcattat gcccagtaca tgaccttatg ggactttcct acttggcagt acatctacgt | 2220 |
| attagtcatc gctattacca tggtgatgcg gttttggcag tacatcaatg ggcgtggata | 2280 |
| gcggtttgac tcacggggat ttccaagtct ccaccccatt gacgtcaatg ggagtttgtt | 2340 |
| ttggcaccaa aatcaacggg actttccaaa atgtcgtaac aactccgccc cattgacgca | 2400 |
| aatgggcggt aggcgtgtac ggtgggaggt ctatataagc agagctggtt tagtgaaccg | 2460 |
| tcagatcact agtcgactag ggataacagg gcaccatgga tcccctgggt gcagccaagc | 2520 |
| cacaatggcc atggcgccgc tgtctggccg cactgctatt tcagctgctg gtggctgtgt | 2580 |
| gtttcttctc ctacctgcgt gtgtcccgag acgatgccac tggatcccct agggctccca | 2640 |
| gtgggtcctc ccgacaggac accactccca cccgccccac cctcctgatc ctgctatgga | 2700 |
| catggccttt ccacatccct gtggctctgt ccgctgttc agagatggtg cccggcacag | 2760 |
| ccgactgcca catcactgcc gaccgcaagg tgtacccaca ggcagacacg gtcatcgtgc | 2820 |
| accactggga tatcatgtcc aaccctaagt cacgcctccc accttccccg aggccgcagg | 2880 |
| ggcagcgctg gatctggttc aacttggagc caccccctaa ctgccagcac ctggaagccc | 2940 |
| tggacagata cttcaatctc accatgtcct accgcagcga ctccgacatc ttcacgccct | 3000 |
| acggctggct ggagccgtgg tccggccagc ctgcccaccc accgctcaac ctctcggcca | 3060 |
| agaccgagct ggtggcctgg gcggtgtcca actggaagcc ggactcagcc agggtgcgct | 3120 |
| actaccagag cctgcaggct catctcaagg tggacgtgta cggacgctcc cacaagcccc | 3180 |

```
tgcccaaggg gaccatgatg gagacgctgt cccggtacaa gttctacctg gccttcgaga   3240
actccttgca ccccgactac atcaccgaga agctgtggag gaacgccctg gaggcctggg   3300
ccgtgcccgt ggtgctgggc cccagcagaa gcaactacga gaggttcctg ccacccgacg   3360
ccttcatcca cgtggacgac ttccagagcc ccaaggacct ggcccggtac ctgcaggagc   3420
tggacaagga ccacgcccgc tacctgagct actttcgctg gcgggagacg ctgcggcctc   3480
gctccttcag ctgggcactg gatttctgca aggcctgctg gaaactgcag caggaatcca   3540
ggtaccagac ggtgcgcagc atagcggctt ggttcacctg atcgactgtg ccttctagtt   3600
gccagccatc tgttgtttgc ccctcccccg tgccttcctt gaccctggaa ggtgccactc   3660
ccactgtcct ttcctaataa aatgaggaaa ttgcatcgca ttgtctgagt aggtgtcatt   3720
ctattctggg gggtggggtg gggcaggaca gcaaggggga ggattgggag gacaatagca   3780
ggcatgctgg ggatgcggtg ggctctatgg cttcgacagg gtcgacaagc ttttccaaaa   3840
aaaaagcatg aggtgcagtt gcgccttttc ctatctcttga ataggaaagg cgcaactgca   3900
cctcatgctg gatcccgcgt cctttccaca agatatataa acccaagaaa tcgaaatact   3960
ttcaagttac ggtaagcata tgatagtcca ttttaaaaca taattttaaa actgcaaact   4020
acccaagaaa ttattacttt ctacgtcacg tattttgtac taatatcttt gtgtttacag   4080
tcaaattaat tctaattatc tctctaacag ccttgtatcg tatatgcaaa tatgaaggaa   4140
tcatgggaaa taggccctct tcctgcccga ccttggcgcg cgctcggcgc gcggtcacgc   4200
tccgtcacgt ggtgcgtttt gccagcaggc agaagtatgc aaagcatgca tctcaattag   4260
tcagcaacca ggtgtggaaa gtccccaggc tccccagcag gcagaagtat gcaaagcatg   4320
catctcaatt agtcagcaac catagtcccg cccctaactc cgcccatccc gcccctaact   4380
ccgcccagtt ccgcccattc tccgcccat ggctgactaa ttttttttat ttatgcagag   4440
gccgaggccg cctctgcctc tgagctattc cagaagtagt gaggaggctt ttttggaggc   4500
ctaggctttt gcaaaaagct cccgggagct tgtatatcca ttttcggatc tgatcagcac   4560
gtgatgaaaa agcctgaact caccgcgacg tctgtcgaga gtttctgat cgaaaagttc    4620 gacagcgtgt ccgacctgat gcagctctcg gagggcgaag aatctcgtgc tttcagcttc   4680
gatgtaggag ggcgtggata tgtcctgcgg gtaaatagct gcgccgatgg tttctacaaa   4740
gatcgttatg tttatcggca ctttgcatcg gccgcgctcc cgattccgga agtgcttgac   4800
attggggaat tcagcgagag cctgacctat tgcatctccc gccgtgcaca gggtgtcacg   4860
ttgcaagact gcctgaaaac cgaactgccc gctgttctgc agccggtcgc ggaggccatg   4920
gatgcgatcg ctgcggccga tcttagccag acgagcgggt tcggcccatt cggaccgcaa   4980
ggaatcggtc aatacactac atggcgtgat ttcatatgcg cgattgctga tccccatgtg   5040
tatcactggc aaactgtgat ggacgacacc gtcagtgcgt ccgtcgcgca ggctctcgat   5100
gagctgatgc tttgggccga ggactgcccc gaagtccggc acctcgtgca cgcggatttc   5160
ggctccaaca atgtcctgac ggacaatggc cgcataacag cggtcattga ctggagcgag   5220
gcgatgttcg gggattccca atacgaggtc gccaacatct tcttctggag gccgtggttg   5280
gcttgtatgg agcagcagac gcgctacttc gagcggaggc atccggagct tgcaggatcg   5340
ccgcggctcc gggcgtatat gctccgcatt ggtcttgacc aactctatca gagcttggtt   5400
gacggcaatt tcgatgatgc agcttgggcg cagggtcgat gcgacgcaat cgtccgatcc   5460
ggagccggga ctgtcgggcg tacacaaatc gcccgcagaa gcgcggccgt ctggaccgat   5520
```

| | |
|---|---|
| ggctgtgtag aagtactcgc cgatagtgga aaccgacgcc ccagcactcg tccgagggca | 5580 |
| aaggaatagc acgtgctacg agatttcgat tccaccgccg ccttctatga aaggttgggc | 5640 |
| ttcggaatcg ttttccggga cgccggctgg atgatcctcc agcgcgggga tctcatgctg | 5700 |
| gagttcttcg cccaccccaa cttgtttatt gcagcttata atggttacaa ataaagcaat | 5760 |
| agcatcacaa atttcacaaa taaagcattt ttttcactgc attctagttg tggtttgtcc | 5820 |
| aaactcatca atgtatc | 5837 |

<210> SEQ ID NO 49
<211> LENGTH: 1122
<212> TYPE: DNA
<213> ORGANISM: Artificial sequence
<220> FEATURE:
<223> OTHER INFORMATION: rosa26-5' BsaI A

<400> SEQUENCE: 49

| | |
|---|---|
| gaggtaccgg tctcaaggac cccgcggcag gccctccgag cgtggtggag ccgttctgtg | 60 |
| agacagccgt gtacgagtcg tgacgctgga aggggcaagc gggtggtggg caggaatgcg | 120 |
| gtccgccctg cagcaaccgg agggggaggg agaagggagc ggaaaagtct ccaccggacg | 180 |
| cggccatggc tcggggggg gggggcagcg gaggagcgct tccggccgac gtctcgtcgc | 240 |
| tgattggctt cttttcctcc cgccgtgtgt gaaaacacaa atggcgtgtt ttggttggcg | 300 |
| taaggcgcct gtcagttaac ggcagccgga gtgcgcagcc gccggcagcc tcgctctgcc | 360 |
| cactgggtgg ggcgggaggt aggtggggtg aggcgagctg gacgtgcggg cgcggtcggc | 420 |
| ctctggcggg gcggggagg ggagggaggg tcagcgaaag tagctcgcgc gcgagcggcc | 480 |
| gcccaccctc cccttcctct gggggagtcg ttttacccgc cgccggccgg gcctcgtcgt | 540 |
| ctgattggct ctcggggccc agaaaactgg cccttgccat ggctcgtgt tcgtgcaagt | 600 |
| tgagtccatc cgccggccag cggggcggc gaggaggcgc tcccaggttc cggccctccc | 660 |
| ctcggccccg cgccgcagag tctggccgcg cgccccctgcg caacgtggca ggaagcgcgc | 720 |
| gctgggggcg gggacgggca gtagggctga gcggctgcgg ggcgggtgca agcacgtttc | 780 |
| cgacttgagt tgcctcaaga ggggcgtgct gagccagacc tccatcgcgc actccgggga | 840 |
| gtggagggaa ggagcgaggg ctcagttggg ctgttttgga ggcaggaagc acttgctctc | 900 |
| ccaaagtcgc tctgagttgt tatcagtaag ggagctgcag tggagtaggc ggggagaagg | 960 |
| ccgcaccctt ctccggaggg gggagggggag tgttgcaata cctttctggg agttctctgc | 1020 |
| tgcctcctgg cttctgagga ccgccctggg cctgggagaa tcccttgccc cctcttcccc | 1080 |
| tcgtgatctg caactccagt cttacaacga gaccggtacc tc | 1122 |

<210> SEQ ID NO 50
<211> LENGTH: 673
<212> TYPE: DNA
<213> ORGANISM: Artificial sequence
<220> FEATURE:
<223> OTHER INFORMATION: pCMV BsaI C

<400> SEQUENCE: 50

| | |
|---|---|
| gaggtaccgg tctcaacaaa ccaattcagt cgactggatc ctagttatta atagtaatca | 60 |
| attacggggt cattagttca tagcccatat atggagttcc gcgttacata acttacggta | 120 |
| aatggcccgc ctggctgacc gcccaacgac ccccgcccat tgacgtcaat aatgacgtat | 180 |
| gttcccatag taacgccaat agggactttc cattgacgtc aatgggtgga gtatttacgg | 240 |
| taaactgccc acttggcagt acatcaagtg tatcatatgc caagtacgcc ccctattgac | 300 |

```
gtcaatgacg gtaaatggcc cgcctggcat tatgcccagt acatgacctt atgggacttt      360
cctacttggc agtacatcta cgtattagtc atcgctatta ccatggtgat gcggttttgg      420
cagtacatca atgggcgtgg atagcggttt gactcacggg gatttccaag tctccacccc      480
attgacgtca atgggagttt gttttggcac caaaatcaac gggactttcc aaaatgtcgt      540
aacaactccg ccccattgac gcaaatgggc ggtaggcgtg tacggtggga ggtctatata      600
agcagagctg gtttagtgaa ccgtcagatc actagtcgac tagggataac agggcacccg      660
agaccggtac ctc                                                          673
```

```
<210> SEQ ID NO 51
<211> LENGTH: 1650
<212> TYPE: DNA
<213> ORGANISM: Artificial sequence
<220> FEATURE:
<223> OTHER INFORMATION: HygroR BsaI C

<400> SEQUENCE: 51
```

```
gaggtaccgg tctcaccagc aggcagaagt atgcaaagca tgcatctcaa ttagtcagca       60
accaggtgtg gaaagtcccc aggctcccca gcaggcagaa gtatgcaaag catgcatctc      120
aattagtcag caaccatagt cccgccccta actccgccca tcccgcccct aactccgccc      180
agttccgccc attctccgcc ccatggctga ctaatttttt ttatttatgc agaggccgag      240
gccgcctctg cctctgagct attccagaag tagtgaggag gcttttttgg aggcctaggc      300
ttttgcaaaa agctcccggg agcttgtata tccattttcg gatctgatca gcacgtgatg      360
aaaaagcctg aactcaccgc gacgtctgtc gagaagtttc tgatcgaaaa gttcgacagc      420
gtgtccgacc tgatgcagct ctcggagggc gaagaatctc gtgctttcag cttcgatgta      480
ggagggcgtg gatatgtcct gcgggtaaat agctgcgccg atggtttcta caaagatcgt      540
tatgtttatc ggcactttgc atcggccgcg ctcccgattc cggaagtgct tgacattggg      600
gaattcagcg agagcctgac ctattgcatc tcccgccgtg cacagggtgt cacgttgcaa      660
gacttgcctg aaaccgaact gcccgctgtt ctgcagccgg tcgcggaggc catggatgcg      720
atcgctgcgg ccgatcttag ccagacgagc gggttcggcc cattcggacc gcaaggaatc      780
ggtcaataca ctacatggcg tgatttcata tgcgcgattg ctgatcccca tgtgtatcac      840
tggcaaactg tgatggacga caccgtcagt gcgtccgtcg cgcaggctct cgatgagctg      900
atgctttggg ccgaggactg ccccgaagtc cggcacctcg tgcacgcgga tttcggctcc      960
aacaatgtcc tgacggacaa tggccgcata acagcggtca ttgactggag cgaggcgatg     1020
ttcggggatt cccaatacga ggtcgccaac atcttcttct ggaggccgtg gttggcttgt     1080
atggagcagc agacgcgcta cttcgagcgg aggcatccgg agcttgcagg atcgccgcgg     1140
ctccgggcgt atatgctccg cattggtctt gaccaactct atcagagctt ggttgacggc     1200
aatttcgatg atgcagcttg ggcgcagggt cgatgcgacg caatcgtccg atccggagcc     1260
gggactgtcg ggcgtacaca atcgcccgc agaagcgcgg ccgtctggac cgatggctgt     1320
gtagaagtac tcgccgatag tggaaaccga cgccccagca ctcgtccgag ggcaaaggaa     1380
tagcacgtgc tacgagattt cgattccacc gccgccttct atgaaaggtt gggcttcgga     1440
atcgttttcc gggacgccgg ctggatgatc ctccagcgcg gggatctcat gctggagttc     1500
ttcgcccacc ccaacttgtt tattgcagct tataatggtt acaaataaag caatagcatc     1560
acaaatttca caaataaagc atttttttca ctgcattcta gttgtggttt gtccaaactc     1620
```

```
atcaatgtat cgtagcgaga ccggtacctc                                     1650
```

<210> SEQ ID NO 52
<211> LENGTH: 4309
<212> TYPE: DNA
<213> ORGANISM: Artificial sequence
<220> FEATURE:
<223> OTHER INFORMATION: rosa26-3' BsaI A

<400> SEQUENCE: 52

```
gaggtaccgg tctcagtaga gatgggcggg agtcttctgg gcaggcttaa aggctaacct     60
ggtgtgtggg cgttgtcctg caggggaatt gaacaggtgt aaaattggag ggacaagact    120
tcccacagat tttcggtttt gtcgggaagt ttttaatag gggcaaatag gaaaatggag     180
gataggagtc atctgggtt tatgcagcaa aactacaggt atattgcttg tatccgcctc     240
ggagatttcc atgaggagat aaagacatgt cacccgagtt tatactctcc tgcttagatc    300
ctactacagt atgaaataca gtgtcgcgag gtagactatg taagcagatt taatcatttt    360
aaagagccca gtacttcata tccattttctc ccgctccttc tgcagcctta tcaaaaggta   420
tttagaacac tcattttagc cccatttttca tttattatac tggcttatcc aaccccctaga 480
cagagcattg gcatttttccc tttcctgatc ttagaagtct gatgactcat gaaaccagac   540
agattagtta catacaccac aaatcgaggc tgtagctggg gcctcaacac tgcagttctt   600
ttataactcc ttagtacact ttttgttgat cctttgcctt gatccttaat tttcagtgtc    660
tatcacctct cccgtcaggt ggtgttccac atttgggcct attctcagtc cagggagttt   720
tacaacaata gatgtattga gaatccaacc taaagcttaa ctttccactc ccatgaatgc    780
ctctctcctt tttctccatt ataactgagc tataaccatt aatggtttca ggtggatgtc    840
tcctccccca atatacctga tgtatctaca tattgccagg ctgatatttt aagacataaa    900
aggtatattt cattattgag ccacatggta ttgattactg ctactaaaat tttgtcattg    960
tacacatctg taaaaggtgg ttccttttgg aatgcaaagt tcaggtgttt gttgtctttc   1020
ctgacctaag gtcttgtgag cttgtatttt ttctatttaa gcagtgcttt ctcttggact   1080
ggcttgactc atggcattct acacgttatt gctggtctaa atgtgatttt gccaagcttc   1140
ttcaggacct ataattttgc ttgacttgta gccaaacaca agtaaaatga ttaagcaaca    1200
aatgtatttg tgaagcttgg ttttttaggtt gttgtgttgt gtgtgcttgt gctctataat   1260
aatactatcc aggggctgga gaggtggctc ggagttcaag agcacagact gctcttccag    1320
aagtcctgag ttcaattccc agcaaccaca tggtggctca caaccatctg taatgggatc   1380
tgatgccctc ttctggtgtg tctgaagacc acaagtgtat tcacattaaa taaataatcc   1440
tccttcttct tctttttttt ttttaaaga gaatactgtc tccagtagaa ttactgaagt    1500
aatgaaatac tttgtgtttg ttccaatatg gaagccaata atcaaatact cttaagcact   1560
ggaaatgtac caaggaacta ttttatttaa gtgaactgtg gacagaggag ccataactgc   1620
agacttgtgg gatacagaag accaatgcag acttaatgtc ttttctctta cactaagcaa    1680
taaagaaata aaaattgaac ttctagtatc ctatttgtta aactgctagc tttactaact   1740
tttgtgcttc atctatacaa agctgaaagc taagtctgca gccattacta acatgaaag    1800
caagtaatga taattttgga tttcaaaaat gtagggccag agtttagcca gccagtggtg   1860
gtgcttgcct ttatgcctta atcccagcac tctggaggca gagacaggca gatctctgag   1920
tttgagccca gcctggtcta cacatcaagt tctatctagg atagccagga atacacacag   1980
aaaccctgtt ggggaggggg gctctgagat ttcataaaat tataattgaa gcattcccta   2040
```

```
atgagccact atggatgtgg ctaaatccgt ctacctttct gatgagattt gggtattatt    2100
ttttctgtct ctgctgttgg ttgggtcttt tgacactgtg ggctttctta aagcctcctt    2160
ccctgccatg tggactcttg tttgctacta acttcccatg gcttaaatgg catggctttt    2220
tgccttctaa gggcagctgc tgagatttgc agcctgattt ccagggtggg gttgggaaat    2280
ctttcaaaca ctaaaattgt cctttaattt tttttttaaa aatgggttat ataataaacc    2340
tcataaaata gttatgagga gtgaggtgga ctaatattaa tgagtccctc ccctataaaa    2400
gagctattaa ggcttttgt cttatactaa cttttttttt aaatgtggta tctttagaac     2460
caagggtctt agagtttag tatacagaaa ctgttgcatc gcttaatcag attttctagt     2520
ttcaaatcca gagaatccaa attcttcaca gccaaagtca aattaagaat ttctgacttt    2580
aatgttattt gctactgtga atataaaatg atagcttttc ctgaggcagg gtatcactat    2640
gtatctctgc ctgatctgca acaagatatg tagactaaag ttctgcctgc ttttgtctcc    2700
tgaatactaa ggttaaaatg tagtaatact tttggaactt gcaggtcaga ttcttttata    2760
ggggacacac taagggagct tgggtgatag ttggtaaatg tgtttaagtg atgaaaactt    2820
gaattattat caccgcaacc tacttttttaa aaaaaaaagc caggcctgtt agagcatgct    2880
aagggatccc taggacttgc tgagcacaca agagtagtac ttggcaggct cctggtgaga    2940
gcatatttca aaaacaagg cagacaacca agaaactaca gtaaggttac ctgtctttaa     3000
ccatctgcat atacacaggg atattaaaat attccaaata atatttcatt caagttttcc    3060
cccatcaaat tgggacatgg atttctccgg tgaataggca gagttggaaa ctaaacaaat    3120
gttggttttg tgatttgtga aattgttttc aagtgatagt taaagcccat gagatacaga    3180
acaaagctgc tatttcgagg tcacttggtt atactcagaa gcacttcttt gggtttccct    3240
gcactatcct gatcatgtgc taggcctacc ttaggctgat tgttgttcaa ataacttaag    3300
tttcctgtca ggtgatgtca tatgatttca tatatcaagg caaaacatgt tatatatgtt    3360
aaacatttgg acttaatgtg aaagttaggt ctttgtgggt tttgatttta atttcaaaac    3420
ctgagctaaa taagtcattt tacatgtctt acatttggtg aattgtatat tgtggtttgc    3480
aggcaagact ctctgaccta gtaaccctcc tatagagcac tttgctgggt cacaagtcta    3540
ggagtcaagc atttcacctt gaagttgaga cgttttgtta gtgtatacta gttatatgtt    3600
ggaggacatg tttatccaga agatattcag gactattttt gactgggcta aggaattgat    3660
tctgattagc actgttagtg agcattgagt ggcctttagg cttgaattgg agtcacttgt    3720
atatctcaaa taatgctggc cttttttaaa aagcccttgt tctttatcac cctgttttct    3780
acataatttt tgttcaaaga aatacttgtt tggatctcct tttgacaaca atagcatgtt    3840
ttcaagccat attttttttc ctttttttttt ttttttttgg ttttcgaga cagggttct     3900
ctgtatagcc ctggctgtcc tggaactcac tttgtagacc aggctggcct cgaactcaga    3960
aatccgcctg cctctgcctc ctgagtgccg ggattaaagg cgtgcaccac cacgcctggc    4020
taagttggat attttgtata taactataac caatactaac tccactgggt ggatttttaa    4080
ttcagtcagt agtcttaagt ggtctttatt ggcccttatt aaaatctact gttcactcta    4140
acagaggctg ttggactagt gggactaagc aacttcctac ggatatacta gcagataagg    4200
gtcagggata gaaactagtc tagcgttttg tatacctacc agcttatact accttgttct    4260
gatagaaata tttaggacat ctagcttatc tattcgagac cggtaccctc               4309
```

<210> SEQ ID NO 53

<211> LENGTH: 11200
<212> TYPE: DNA
<213> ORGANISM: Artificial sequence
<220> FEATURE:
<223> OTHER INFORMATION: V1.2

<400> SEQUENCE: 53

| | |
|---|---|
| gtaatacggt tatccacaga atcaggggat aacgcaggaa agaacatgtg agcaaaaggc | 60 |
| cagcaaaagg ccaggaaccg taaaaaggcc gcgttgctgg cgttttttcca taggctccgc | 120 |
| cccccctgacg agcatcacaa aaatcgacgc tcaagtcaga ggtggcgaaa cccgacagga | 180 |
| ctataaagat accaggcgtt ccccctgga agctccctcg tgcgctctcc tgttccgacc | 240 |
| ctgccgctta ccggatacct gtccgccttt ctcccttcgg gaagcgtggc gctttctcat | 300 |
| agctcacgct gtaggtatct cagttcggtg taggtcgttc gctccaagct gggctgtgtg | 360 |
| cacgaacccc ccgttcagcc cgaccgctgc gccttatccg gtaactatcg tcttgagtcc | 420 |
| aacccggtaa gacacgactt atcgccactg gcagcagcca ctggtaacag gattagcaga | 480 |
| gcgaggtatg taggcggtgc tacagagttc ttgaagtggt ggcctaacta cggctacact | 540 |
| agaagaacag tatttggtat ctgcgctctg ctgaagccag ttaccttcgg aaaaagagtt | 600 |
| ggtagctctt gatccggcaa acaaaccacc gctggtagcg gttttttttgt ttgcaagcag | 660 |
| cagattacgc gcagaaaaaa aggatctcaa gaagatcctt tgatcttttc tacggggtct | 720 |
| gacgctcagt ggaacgaaaa ctcacgttaa gggattttgg tcatgagatt atcaaaaagg | 780 |
| atcttcacct agatcctttt aaattaaaaa tgaagtttta aatcaatcta agtatatat | 840 |
| gagtaaactt ggtctgacag ttaccaatgc ttaatcagtg aggcacctat ctcagcgatc | 900 |
| tgtctatttc gttcatccat agttgcctga ctccccgtcg tgtagataac tacgatacgg | 960 |
| gagggcttac catctggccc cagtgctgca atgataccgc gtgacccacg ctcaccggct | 1020 |
| ccagatttat cagcaataaa ccagccagcc ggaagggccg agcgcagaag tggtcctgca | 1080 |
| actttatccg cctccatcca gtctattaat tgttgccggg aagctagagt aagtagttcg | 1140 |
| ccagttaata gtttgcgcaa cgttgttgcc attgctacag gcatcgtggt gtcacgctcg | 1200 |
| tcgtttggta tggcttcatt cagctccggt tcccaacgat caaggcgagt tacatgatcc | 1260 |
| cccatgttgt gcaaaaaagc ggttagctcc ttcggtcctc cgatcgttgt cagaagtaag | 1320 |
| ttggccgcag tgttatcact catggttatg gcagcactgc ataattctct tactgtcatg | 1380 |
| ccatccgtaa gatgcttttc tgtgactggt gagtactcaa ccaagtcatt ctgagaatag | 1440 |
| tgtatgcggc gaccgagttg ctcttgcccg gcgtcaatac gggataatac cgcgccacat | 1500 |
| agcagaactt taaaagtgct catcattgga aaacgttctt cggggcgaaa actctcaagg | 1560 |
| atcttaccgc tgttgagatc cagttcgatg taacccactc gtgcacccaa ctgatcttca | 1620 |
| gcatctttta ctttcaccag cgtttctggg tgagcaaaaa caggaaggca aaatgccgca | 1680 |
| aaaaagggaa taagggcgac acggaaatgt tgaatactca tactcttcct ttttcaatat | 1740 |
| tattgaagca tttatcaggg ttattgtctc atgagcggat acatatttga atgtatttag | 1800 |
| aaaaataaac aaatagggt tccgcgcaca tttccccgaa aagtgccaag gaccccgcgg | 1860 |
| caggccctcc gagcgtggtg gagccgttct gtgagacagc cgggtacgag tcgtgacgct | 1920 |
| ggaaggggca agcgggtggt gggcaggaat gcggtccgcc ctgcagcaac cggagggga | 1980 |
| gggagaaggg agcggaaaag tctccaccgg acgcggccat ggctcggggg ggggggggca | 2040 |
| gcggaggagc gcttccggcc gacgtctcgt cgctgattgg cttctttttcc tcccgccgtg | 2100 |
| tgtgaaaaca caaatggcgt gttttggttg gcgtaaggcg cctgtcagtt aacggcagcc | 2160 |

```
ggagtgcgca gccgccggca gcctcgctct gcccactggg tggggcggga ggtaggtggg    2220
gtgaggcgag ctggacgtgc gggcgcggtc ggcctctggc ggggcggggg aggggaggga    2280
gggtcagcga aagtagctcg cgcgcgagcg gccgcccacc ctccccttcc tctggggggag   2340 tcgttttacc cgccgccggc cgggcctcgt cgtctgattg gctctcgggg cccagaaaac    2400
tggcccttgc cattggctcg tgttcgtgca agttgagtcc atccgccggc cagcgggggc    2460
ggcgaggagg cgctcccagg ttccggccct cccctcggcc ccgcgccgca gagtctggcc    2520
gcgcgcccct gcgcaacgtg gcaggaagcg cgcgctgggg gcggggacgg gcagtagggc    2580
tgagcggctg cggggcgggt gcaagcacgt ttccgacttg agttgcctca agagggcgt     2640 gctgagccag acctccatcg cgcactccgg ggagtggagg gaaggagcga gggctcagtt    2700
gggctgtttt ggaggcagga agcacttgct ctcccaaagt cgctctgagt tgttatcagt    2760
aagggagctg cagtggagta ggcggggaga aggccgcacc cttctccgga gggggagggg   2820
gagtgttgca ataccttct gggagttctc tgctgcctcc tggcttctga ggaccgccct     2880
gggcctggga gaatcccttg cccctcttc ccctcgtgat ctgcaactcc agtcttacaa     2940
accaattcag tcgactggat cctagttatt aatagtaatc aattacgggg tcattagttc    3000
atagcccata tatggagttc cgcgttacat aacttacggt aaatggcccg cctggctgac    3060
cgcccaacga ccccgccca ttgacgtcaa taatgacgta tgttcccata gtaacgccaa     3120
tagggacttt ccattgacgt caatgggtgg agtatttacg gtaaactgcc cacttggcag    3180
tacatcaagt gtatcatatg ccaagtacgc cccctattga cgtcaatgac ggtaaatggc    3240
ccgcctggca ttatgcccag tacatgacct tatgggactt tcctacttgg cagtacatct    3300
acgtattagt catcgctatt accatggtga tgcggttttg gcagtacatc aatgggcgtg    3360
gatagcggtt tgactcacgg ggatttccaa gtctccaccc cattgacgtc aatgggagtt    3420
tgttttggca ccaaaatcaa cgggactttc caaaatgtcg taacaactcc gccccattga    3480
cgcaaatggg cggtaggcgt gtacggtggg aggtctatat aagcagagct ggtttagtga    3540
accgtcagat cactagtcga ctagggataa cagggcacca tggatcccct gggtgcagcc    3600
aagccacaat ggccatggcg ccgctgtctg gccgcactgc tatttcagct gctggtggct    3660
gtgtgtttct tctcctacct gcgtgtgtcc cgagacgatg ccactggatc ccctagggct    3720
cccagtgggt cctcccgaca ggacaccact cccacccgcc ccaccctcct gatcctgcta    3780
tggacatggc cttccacat ccctgtggct ctgtcccgct gttcagagat ggtgcccggc      3840
acagccgact gccacatcac tgccgaccgc aaggtgtacc cacaggcaga cacggtcatc    3900
gtgcaccact gggatatcat gtccaaccct aagtcacgcc tcccaccttc cccgaggccg    3960
caggggcagc gctggatctg gttcaacttg gagccacccc ctaactgcca gcacctggaa    4020
gccctggaca gatacttcaa tctcaccatg tcctaccgca gcgactccga catcttcacg    4080
ccctacggct ggctggagcc gtggtccggc cagcctgccc acccaccgct caacctctcg    4140
gccaagaccg agctggtggc ctgggcggtg tccaactgga gccggactc agccagggtg     4200 cgctactacc agagcctgca ggctcatctc aaggtggacg tgtacggacg ctcccacaag    4260
cccctgccca aggggaccat gatggagacg ctgtcccggt acaagttcta cctggccttc    4320
gagaactcct tgcaccccga ctacatcacc gagaagctgt ggaggaacgc cctggaggcc    4380
tgggccgtgc ccgtggtgct gggcccagc agaagcaact acgagaggtt cctgccaccc    4440
gacgccttca tccacgtgga cgacttccag agccccaagg acctggcccg gtacctgcag    4500
```

```
gagctggaca aggaccacgc ccgctacctg agctactttc gctggcggga gacgctgcgg    4560
cctcgctcct tcagctgggc actggatttc tgcaaggcct gctggaaact gcagcaggaa    4620
tccaggtacc agacggtgcg cagcatagcg gcttggttca cctgatcgac tgtgccttct    4680
agttgccagc catctgttgt ttgcccctcc ccgtgccttc cttgaccct ggaaggtgcc     4740 actcccactg tcctttccta ataaaatgag gaaattgcat cgcattgtct gagtaggtgt    4800
cattctattc tggggggtgg ggtggggcag gacagcaagg gggaggattg ggaggacaat    4860
agcaggcatg ctggggatgc ggtgggctct atggcttcga cagggtcgac aagcttttcc    4920
aaaaaaaaag catgaggtgc agttgcgcct ttcctatctc ttgaatagga aaggcgcaac    4980
tgcacctcat gctggatccc gcgtcctttc cacaagatat ataaacccaa gaaatcgaaa    5040
tactttcaag ttacggtaag catatgatag tccattttaa aacataattt taaaactgca    5100
aactacccaa gaaattatta ctttctacgt cacgtatttt gtactaatat ctttgtgttt    5160
acagtcaaat taattctaat tatctctcta acagccttgt atcgtatatg caaatatgaa    5220
ggaatcatgg gaaataggcc ctcttcctgc ccgaccttgg cgcgcgctcg gcgcgcggtc    5280
acgctccgtc acgtggtgcg ttttgccagc aggcagaagt atgcaaagca tgcatctcaa    5340
ttagtcagca accaggtgtg gaaagtcccc aggctcccca gcaggcagaa gtatgcaaag    5400
catgcatctc aattagtcag caaccatagt cccgccccta actccgccca tcccgcccct    5460
aactccgccc agttccgccc attctccgcc ccatggctga ctaattttt ttatttatgc     5520 agaggccgag gccgcctctg cctctgagct attccagaag tagtgaggag gcttttttgg    5580
aggcctaggc ttttgcaaaa agctcccggg agcttgtata tccattttcg gatctgatca    5640
gcacgtgatg aaaagcctg aactcaccgc gacgtctgtc gagaagtttc tgatcgaaaa      5700
gttcgacagc gtgtccgacc tgatgcagct ctcggagggc gaagaatctc gtgctttcag    5760
cttcgatgta ggagggcgtg gatatgtcct gcgggtaaat agctgcgccg atggtttcta    5820
caaagatcgt tatgtttatc ggcactttgc atcggccgcg ctcccgattc cggaagtgct    5880
tgacattggg gaattcagcg agagcctgac ctattgcatc tcccgccgtg cacagggtgt    5940
cacgttgcaa gacttgcctg aaaccgaact gcccgctgtt ctgcagccgg tcgcggaggc    6000
catggatgcg atcgctgcgg ccgatcttag ccagacgagc gggttcggcc cattcggacc    6060
gcaaggaatc ggtcaataca ctacatggcg tgatttcata tgcgcgattg ctgatcccca    6120
tgtgtatcac tggcaaactg tgatggacga caccgtcagt gcgtccgtcg cgcaggctct    6180
cgatgagctg atgctttggg ccgaggactg ccccgaagtc cggcacctcg tgcacgcgga    6240
tttcggctcc aacaatgtcc tgacggacaa tggccgcata acagcggtca ttgactggag    6300
cgaggcgatg ttcggggatt cccaatacga ggtcgccaac atcttcttct ggaggccgtg    6360
gttggcttgt atggagcagc agacgcgcta cttcgagcgg aggcatccgg agcttgcagg    6420
atcgccgcgg ctccgggcgt atatgctccg cattggtctt gaccaactct atcagagctt    6480
ggttgacggc aatttcgatg atgcagcttg gcgcagggt cgatgcgacg caatcgtccg     6540
atccggagcc gggactgtcg ggcgtacaca atcgcccgc agaagcgcgg ccgtctggac     6600
cgatggctgt gtagaagtac tcgccgatag tggaaaccga cgcccagca ctcgtccgag     6660 ggcaaaggaa tagcacgtgc tacgagattt cgattccacc gccgccttct atgaaaggtt    6720
gggcttcgga atcgttttcc gggacgccgg ctggatgatc ctccagcgcg ggatctcat    6780 gctggagttc ttcgcccacc ccaacttgtt tattgcagct tataatggtt acaaataaag    6840
caatagcatc acaaatttca caaataaagc atttttttca ctgcattcta gttgtggttt    6900
```

```
gtccaaactc atcaatgtat cgtagagatg ggcgggagtc ttctgggcag gcttaaaggc    6960
taacctggtg tgtgggcgtt gtcctgcagg ggaattgaac aggtgtaaaa ttggagggac    7020
aagacttccc acagattttc ggttttgtcg ggaagttttt taatagggc aaataggaaa     7080 atggaggata ggagtcatct gggtttatg cagcaaaact acaggtatat tgcttgtatc     7140
cgcctcggag atttccatga ggagataaag acatgtcacc cgagtttata ctctcctgct    7200
tagatcctac tacagtatga atacagtgt cgcgaggtag actatgtaag cagatttaat     7260
cattttaaag agcccagtac ttcatatcca tttctcccgc tccttctgca gccttatcaa    7320
aaggtattta gaacactcat tttagcccca ttttcattta ttatactggc ttatccaacc    7380
cctagacaga gcattggcat tttccctttc ctgatcttag aagtctgatg actcatgaaa    7440
ccagacagat tagttacata caccacaaat cgaggctgta gctggggcct caacactgca    7500 gttctttat aactccttag tacacttttt gttgatcctt tgccttgatc cttaattttc      7560
agtgtctatc acctctcccg tcaggtggtg ttccacattt gggcctattc tcagtccagg    7620
gagttttaca acaatagatg tattgagaat ccaacctaaa gcttaacttt ccactcccat    7680
gaatgcctct ctccttttc tccattataa ctgagctata accattaatg gtttcaggtg     7740
gatgtctcct cccccaatat acctgatgta tctacatatt gccaggctga tattttaaga    7800 cataaaggt atatttcatt attgagccac atggtattga ttactgctac taaaattttg     7860
tcattgtaca catctgtaaa aggtggttcc ttttggaatg caaagttcag gtgtttgttg    7920
tctttcctga cctaaggtct tgtgagcttg tatttttct atttaagcag tgctttctct     7980
tggactggct tgactcatgg cattctacac gttattgctg gtctaaatgt gattttgcca    8040
agcttcttca ggacctataa ttttgcttga cttgtagcca aacacaagta aaatgattaa    8100
gcaacaaatg tatttgtgaa gcttggtttt taggttgttg tgttgtgtgt gcttgtgctc    8160
tataataata ctatccaggg gctggagagg tggctcggag ttcaagagca cagactgctc    8220
ttccagaagt cctgagttca attcccagca accacatggt ggctcacaac catctgtaat    8280
gggatctgat gccctcttct ggtgtgtctg aagaccacaa gtgtattcac attaaataaa    8340
taatcctcct tcttcttctt ttttttttt taaagagaat actgtctcca gtagaattac     8400
tgaagtaatg aaatactttg tgtttgttcc aatatggaag ccaataatca aatactctta    8460
agcactggaa atgtaccaag gaactatttt atttaagtga actgtggaca gaggagccat    8520
aactgcagac ttgtgggata cagaagacca atgcagactt aatgtctttt ctcttacact    8580
aagcaataaa gaaataaaaa ttgaacttct agtatcctat ttgttaaact gctagcttta    8640 ctaactttg tgcttcatct atacaaagct gaaagctaag tctgcagcca ttactaaaca     8700
tgaaagcaag taatgataat tttggatttc aaaaatgtag ggccagagtt tagccagcca    8760
gtggtggtgc ttgccttat gccttaatcc cagcactctg gaggcagaga caggcagatc     8820
tctgagtttg agcccagcct ggtctacaca tcaagttcta tctaggatag ccaggaatac    8880
acacagaaac cctgttgggg aggggggctc tgagatttca taaaattata attgaagcat    8940
tccctaatga gccactatgg atgtggctaa atccgtctac ctttctgatg agatttgggt    9000 attattttt ctgtctctgc tgttggttgg gtcttttgac actgtgggct ttcttaaagc     9060
ctccttccct gccatgtgga ctcttgtttg ctactaactt cccatggctt aaatggcatg    9120 gcttttgcc ttctaagggc agctgctgag atttgcagcc tgatttccag ggtgggttg      9180 ggaaatcttt caaacactaa aattgtcctt taattttttt ttaaaaaatg ggttatataa    9240
```

```
taaacctcat aaaatagtta tgaggagtga ggtggactaa tattaatgag tccctcccct    9300
ataaaagagc tattaaggct ttttgtctta tactaacttt ttttttaaat gtggtatctt    9360
tagaaccaag ggtcttagag ttttagtata cagaaactgt tgcatcgctt aatcagattt    9420
tctagtttca aatccagaga atccaaattc ttcacagcca aagtcaaatt aagaatttct    9480
gactttaatg ttatttgcta ctgtgaatat aaaatgatag cttttcctga ggcagggtat    9540
cactatgtat ctctgcctga tctgcaacaa gatatgtaga ctaaagttct gcctgctttt    9600
gtctcctgaa tactaaggtt aaaatgtagt aatacttttg gaacttgcag gtcagattct    9660
tttatagggg acacactaag ggagcttggg tgatagttgg taaatgtgtt taagtgatga    9720
aaacttgaat tattatcacc gcaacctact ttttaaaaaa aaaagccagg cctgttagag    9780
catgctaagg gatccctagg acttgctgag cacacaagag tagtacttgg caggctcctg    9840
gtgagagcat atttcaaaaa acaaggcaga caaccaagaa actacagtaa ggttacctgt    9900 cttttaaccat ctgcatatac acagggatat taaaatattc caaataatat ttcattcaag    9960
ttttccccca tcaaattggg acatggattt ctccggtgaa taggcagagt tggaaactaa   10020
acaaatgttg gttttgtgat ttgtgaaatt gttttcaagt gatagttaaa gcccatgaga   10080
tacagaacaa agctgctatt tcgaggtcac ttggttatac tcagaagcac ttctttgggt   10140
ttccctgcac tatcctgatc atgtgctagg cctaccttag gctgattgtt gttcaaataa   10200
cttaagtttc ctgtcaggtg atgtcatatg atttcatata tcaaggcaaa acatgttata   10260
tatgttaaac atttggactt aatgtgaaag ttaggtcttt gtgggttttg atttaatt    10320 caaaacctga gctaaataag tcattttaca tgtcttacat ttggtgaatt gtatattgtg   10380
gtttgcaggc aagactctct gacctagtaa ccctcctata gagcactttg ctgggtcaca   10440
agtctaggag tcaagcattt caccttgaag ttgagacgtt ttgttagtgt atactagtta   10500
tatgttggag gacatgttta tccagaagat attcaggact atttttgact gggctaagga   10560
attgattctg attagcactg ttagtgagca ttgagtggcc tttaggcttg aattggagtc   10620
acttgtatat ctcaaataat gctggccttt tttaaaaagc ccttgttctt tatcaccctg   10680
ttttctacat aattttttgtt caagaaaata cttgttggga tctccttttg acaacaatag   10740
catgttttca agccatattt tttttccttt tttttttttt ttttggtttt tcgagacagg   10800
gtttctctgt atagccctgg ctgtcctgga actcactttg tagaccaggc tggcctcgaa   10860
ctcagaaatc cgcctgcctc tgcctcctga gtgccgggat taaaggcgtg caccaccacg   10920
cctggctaag ttggatattt tgtatataac tataaccaat actaactcca ctgggtggat   10980
ttttaattca gtcagtagtc ttaagtggtc tttattggcc cttattaaaa tctactgttc   11040
actctaacag aggctgttgg actagtggga ctaagcaact tcctacggat atactagcag   11100
ataagggtca gggatagaaa ctagtctagc gttttgtata cctaccagct tatactacct   11160
tgttctgata gaaatattta ggacatctag cttatctatt                         11200
```

<210> SEQ ID NO 54
<211> LENGTH: 4309
<212> TYPE: DNA
<213> ORGANISM: Artificial sequence
<220> FEATURE:
<223> OTHER INFORMATION: rosa26-3' BsaI B

<400> SEQUENCE: 54

```
gaggtaccgg tctcagtaga gatgggcggg agtcttctgg gcaggcttaa aggctaacct      60
ggtgtgtggg cgttgtcctg caggggaatt gaacaggtgt aaaattggag ggacaagact     120
```

```
tcccacagat tttcggtttt gtcgggaagt tttttaatag gggcaaatag gaaaatggag      180
gataggagtc atctggggtt tatgcagcaa aactacaggt atattgcttg tatccgcctc      240
ggagatttcc atgaggagat aaagacatgt cacccgagtt tatactctcc tgcttagatc      300
ctactacagt atgaaataca gtgtcgcgag gtagactatg taagcagatt taatcatttt      360
aaagagccca gtacttcata tccatttctc ccgctccttc tgcagcctta tcaaaaggta      420
tttagaacac tcatttttagc cccatttttca tttattatac tggcttatcc aaccccctaga    480 cagagcattg gcattttccc tttcctgatc ttagaagtct gatgactcat gaaaccagac      540
agattagtta catacaccac aaatcgaggc tgtagctggg gcctcaacac tgcagttctt      600
ttataactcc ttagtacact ttttgttgat cctttgcctt gatccttaat tttcagtgtc      660
tatcacctct cccgtcaggt ggtgttccac atttgggcct attctcagtc cagggagttt      720
tacaacaata gatgtattga gaatccaacc taaagcttaa ctttccactc ccatgaatgc      780
ctctctcctt tttctccatt ataactgagc tataaccatt aatggtttca ggtggatgtc      840
tcctccccca atatacctga tgtatctaca tattgccagg ctgatatttt aagacataaa      900
aggtatattt cattattgag ccacatggta ttgattactg ctactaaaat tttgtcattg      960
tacacatctg taaaaggtgg ttccttttgg aatgcaaagt tcaggtgttt gttgtctttc     1020
ctgacctaag gtcttgtgag cttgtatttt ttctatttaa gcagtgcttt ctcttggact     1080
ggcttgactc atggcattct acacgttatt gctggtctaa atgtgatttt gccaagcttc     1140
ttcaggacct ataattttgc ttgacttgta gccaaacaca agtaaaatga ttaagcaaca     1200
aatgtatttg tgaagcttgg ttttttaggtt gttgtgttgt gtgtgcttgt gctctataat   1260
aatactatcc aggggctgga gaggtggctc ggagttcaag agcacagact gctcttccag     1320
aagtcctgag ttcaattccc agcaaccaca tggtggctca caaccatctg taatgggatc     1380
tgatgccctc ttctggtgtg tctgaagacc acaagtgtat tcacattaaa taaataatcc     1440
tccttcttct tcttttttttt tttttaaaga gaatactgtc tccagtagaa ttactgaagt     1500
aatgaaatac tttgtgtttg ttccaatatg gaagccaata atcaaatact cttaagcact     1560
ggaaatgtac caaggaacta ttttatttaa gtgaactgtg gacagaggag ccataactgc     1620
agacttgtgg gatacagaag accaatgcag acttaatgtc ttttctctta cactaagcaa     1680
taaagaaata aaaattgaac ttctagtatc ctatttgtta aactgctagc tttactaact     1740
tttgtgcttc atctatacaa agctgaaagc taagtctgca gccattacta aacatgaaag     1800
caagtaatga taatttttgga tttcaaaaat gtagggccag agtttagcca gccagtggtg     1860
gtgcttgcct ttatgcctta atcccagcac tctggaggca gagacaggca gatctctgag     1920
tttgagccca gcctggtcta cacatcaagt tctatctagg atagccagga atacacacag     1980
aaaccctgtt ggggagggg gctctgagat ttcataaaat tataattgaa gcattcccta     2040
atgagccact atggatgtgg ctaaatccgt ctacctttct gatgagattt gggtattatt     2100
ttttctgtct ctgctgttgg ttgggtcttt tgacactgtg ggctttctta aagcctcctt     2160
ccctgccatg tggactcttg tttgctacta acttcccatg gcttaaatgg catggctttt     2220
tgccttctaa gggcagctgc tgagatttgc agcctgattt ccagggtggg gttgggaaat     2280
ctttcaaaca ctaaaattgt cctttaattt tttttttaaaa aatgggttat ataataaacc     2340
tcataaaata gttatgagga gtgaggtgga ctaatattaa tgagtccctc ccctataaaa     2400
gagctattaa ggcttttttgt cttatactaa ctttttttttt aaatgtggta tctttagaac     2460
```

```
caagggtctt agagttttag tatacagaaa ctgttgcatc gcttaatcag attttctagt    2520
ttcaaatcca gagaatccaa attcttcaca gccaaagtca aattaagaat ttctgacttt    2580
aatgttattt gctactgtga atataaaatg atagcttttc ctgaggcagg gtatcactat    2640
gtatctctgc ctgatctgca acaagatatg tagactaaag ttctgcctgc ttttgtctcc    2700
tgaatactaa ggttaaaatg tagtaatact tttggaactt gcaggtcaga ttcttttata    2760
ggggacacac taagggagct tgggtgatag ttggtaaatg tgtttaagtg atgaaaactt    2820
gaattattat caccgcaacc tacttttaa aaaaaaagc caggcctgtt agagcatgct     2880
aagggatccc taggacttgc tgagcacaca agagtagtac ttggcaggct cctggtgaga    2940
gcatatttca aaaacaagg cagacaacca agaaactaca gtaaggttac ctgtctttaa    3000
ccatctgcat atacacaggg atattaaaat attccaaata atatttcatt caagttttcc    3060
cccatcaaat tgggacatgg atttctccgg tgaataggca gagttggaaa ctaaacaaat    3120
gttggttttg tgatttgtga aattgttttc aagtgatagt taaagcccat gagatacaga    3180
acaaagctgc tatttcgagg tcacttggtt atactcagaa gcacttcttt gggtttccct    3240
gcactatcct gatcatgtgc taggcctacc ttaggctgat tgttgttcaa ataacttaag    3300
tttcctgtca ggtgatgtca tatgatttca tatatcaagg caaaacatgt tatatatgtt    3360
aaacatttgg acttaatgtg aaagttaggt ctttgtgggt tttgatttta atttcaaaac    3420
ctgagctaaa taagtcattt tacatgtctt acatttggtg aattgtatat tgtggtttgc    3480
aggcaagact ctctgaccta gtaaccctcc tatagagcac tttgctgggt cacaagtcta    3540
ggagtcaagc atttcacctt gaagttgaga cgttttgtta gtgtatacta gttatatgtt    3600
ggaggacatg tttatccaga agatattcag gactattttt gactgggcta aggaattgat    3660
tctgattagc actgttagtg agcattgagt ggcctttagg cttgaattgg agtcacttgt    3720
atatctcaaa taatgctggc ctttttaaa aagcccttgt tctttatcac cctgttttct     3780
acataatttt tgttcaaaga aatacttgtt tggatctcct tttgacaaca atagcatgtt    3840
ttcaagccat attttttttc ctttttttt tttttttgg ttttttcgaga cagggtttct      3900 ctgtatagcc ctggctgtcc tggaactcac tttgtagacc aggctggcct cgaactcaga    3960
aatccgcctg cctctgcctc ctgagtgccg ggattaaagg cgtgcaccac cacgcctggc    4020
taagttggat attttgtata taactataac caatactaac tccactgggt ggattttaa     4080 ttcagtcagt agtcttaagt ggtctttatt ggcccttatt aaaatctact gttcactcta    4140
acagaggctg ttggactagt gggactaagc aacttcctac ggatatacta gcagataagg    4200
gtcagggata gaaactagtc tagcgttttg tatacctacc agcttatact accttgttct    4260
gatagaaata tttaggacat ctagcttatc atgccgagac cggtacctc               4309
```

<210> SEQ ID NO 55
<211> LENGTH: 374
<212> TYPE: DNA
<213> ORGANISM: Artificial sequence
<220> FEATURE:
<223> OTHER INFORMATION: pEF1a BsaI A

<400> SEQUENCE: 55

```
gaggtaccgg tctcaatgca aggaaccaat tcagtcgact ggatcccgat ggctccggtg     60
cccgtcagtg ggcagagcgc acatcgccca cagtccccga aagttgggg ggaggggtcg     120 gcaattgaac cggtgcctag agaaggtggc gcggggtaaa ctgggaaagt gatgtcgtgt    180
actggctccg ccttttttccc gagggtgggg gagaaccgta tataagtgca gtagtcgccg    240
```

| | |
|---|---|
| tgaacgttct ttttcgcaac gggtttgccg ccagaacaca ggtccgcggc cccgaactag | 300 |
| gcctaggcgt ctgatcacta gtgactctag tcctagtcga ctaggataa cagggggcccc | 360 |
| gagaccggta cctc | 374 |

<210> SEQ ID NO 56
<211> LENGTH: 1169
<212> TYPE: DNA
<213> ORGANISM: Artificial sequence
<220> FEATURE:
<223> OTHER INFORMATION: TK BsaI A

<400> SEQUENCE: 56

| | |
|---|---|
| gaggtaccgg tctcagccca tggcttcgta ccctgccat caacacgcgt ctgcgttcga | 60 |
| ccaggctgcg cgttctcgcg gccatagcaa ccgacgtacg gcgttgcgcc ctcgccggca | 120 |
| gcaagaagcc acggaagtcc gcctggagca gaaaatgccc acgctactgc gggtttatat | 180 |
| agacggtcct cacgggatgg ggaaaaccac caccacgcaa ctgctggtgg ccctgggttc | 240 |
| gcgcgacgat atcgtctacg tacccgagcc gatgacttac tggcaggtgc tgggggcttc | 300 |
| cgagacaatc gcgaacatct acaccacaca acaccgcctc gaccagggtg agatatcggc | 360 |
| cggggacgcg gcggtggtaa tgacaagcgc ccagataaca atgggcatgc cttatgccgt | 420 |
| gaccgacgcc gttctggctc tcatatcggg ggggaggct gggagctcac atgccccgcc | 480 |
| cccggccctc accctcatct cgaccgcca tcccatcgcc gccctcctgt gctacccggc | 540 |
| cgcgcgatac cttatgggca gcatgacccc ccaggccgtg ctggcgttcg tggccctcat | 600 |
| cccgccgacc ttgccggca caaacatcgt gttggggggcc cttccggagg acagacacat | 660 |
| cgaccgcctg gccaaacgcc agcgcccgg cgagcggctt gacctggcta tgctggccgc | 720 |
| gattcgccgc gtttacgggc tgcttgccaa tacggtgcgg tatctgcagg gcggcgggtc | 780 |
| gtggcgggag gattgggggac agcttttcggg gacggccgtg ccgccccagg gtgccgagcc | 840 |
| ccagagcaac gcgggcccac gaccccatat cggggacacg ttatttaccc tgtttcgggc | 900 |
| ccccgagttg ctggccccca acggcgacct gtacaacgtg tttgcctggg ccttggacgt | 960 |
| cttggccaaa cgcctccgtc ccatgcacgt ctttatcctg gattacgacc aatcgcccgc | 1020 |
| cggctgccgg gacgccctgc tgcaacttac ctccgggatg gtccagaccc acgtcaccac | 1080 |
| ccccggctcc ataccgacga tctgcgacct ggcgcgcacg tttgcccggg agatggggga | 1140 |
| ggctaactga ccgccgagac cggtacctc | 1169 |

<210> SEQ ID NO 57
<211> LENGTH: 310
<212> TYPE: DNA
<213> ORGANISM: Artificial sequence
<220> FEATURE:
<223> OTHER INFORMATION: Tkter BsaI A

<400> SEQUENCE: 57

| | |
|---|---|
| gaggtaccgg tctcaccgcg ggggaggcta actgaaacac ggaaggagac aataccggaa | 60 |
| ggaacccgcg ctatgacggc aataaaaaga cagaataaaa cgcacggtgt tgggtcgttt | 120 |
| gttcataaac gcggggttcg gtcccagggc tggcactctg tcgataccc accgaggccc | 180 |
| cattggggcc aatacgcccg cgtttcttcc ttttccccac cccacccccc aagttcgggt | 240 |
| gaaggcccag ggctcgcagc caacgtcggg gcggcaggcc ctgccatagc ctattcgaga | 300 |
| ccggtacctc | 310 |

<210> SEQ ID NO 58
<211> LENGTH: 12951
<212> TYPE: DNA
<213> ORGANISM: Artificial sequence
<220> FEATURE:
<223> OTHER INFORMATION: V1.3

<400> SEQUENCE: 58

| | | | | | |
|---|---|---|---|---|---|
| tattgtaata | cggttatcca | cagaatcagg | ggataacgca | ggaaagaaca | tgtgagcaaa | 60 |
| aggccagcaa | aaggccagga | accgtaaaaa | ggccgcgttg | ctggcgtttt | tccataggct | 120 |
| ccgcccccct | gacgagcatc | acaaaaatcg | acgctcaagt | cagaggtggc | gaaacccgac | 180 |
| aggactataa | agataccagg | cgtttccccc | tggaagctcc | ctcgtgcgct | ctcctgttcc | 240 |
| gaccctgccg | cttaccggat | acctgtccgc | ctttctccct | tcgggaagcg | tggcgctttc | 300 |
| tcatagctca | cgctgtaggt | atctcagttc | ggtgtaggtc | gttcgctcca | agctgggctg | 360 |
| tgtgcacgaa | ccccccgttc | agcccgaccg | ctgcgcctta | tccggtaact | atcgtcttga | 420 |
| gtccaacccg | gtaagacacg | acttatcgcc | actggcagca | gccactggta | acaggattag | 480 |
| cagagcgagg | tatgtaggcg | gtgctacaga | gttcttgaag | tggtggccta | actacggcta | 540 |
| cactagaaga | acagtatttg | gtatctgcgc | tctgctgaag | ccagttacct | tcggaaaaag | 600 |
| agttggtagc | tcttgatccg | gcaaacaaac | caccgctggt | agcggttttt | ttgtttgcaa | 660 |
| gcagcagatt | acgcgcagaa | aaaaaggatc | tcaagaagat | cctttgatct | tttctacggg | 720 |
| gtctgacgct | cagtggaacg | aaaactcacg | ttaagggatt | ttggtcatga | gattatcaaa | 780 |
| aaggatcttc | acctagatcc | ttttaaatta | aaaatgaagt | tttaaatcaa | tctaaagtat | 840 |
| atatgagtaa | acttggtctg | acagttacca | atgcttaatc | agtgaggcac | ctatctcagc | 900 |
| gatctgtcta | tttcgttcat | ccatagttgc | ctgactcccc | gtcgtgtaga | taactacgat | 960 |
| acgggagggc | ttaccatctg | gccccagtgc | tgcaatgata | ccgcgtgacc | cacgctcacc | 1020 |
| ggctccagat | ttatcagcaa | taaaccagcc | agccggaagg | gccgagcgca | gaagtggtcc | 1080 |
| tgcaacttta | tccgcctcca | tccagtctat | taattgttgc | cgggaagcta | gagtaagtag | 1140 |
| ttcgccagtt | aatagtttgc | gcaacgttgt | tgccattgct | acaggcatcg | tggtgtcacg | 1200 |
| ctcgtcgttt | ggtatggctt | cattcagctc | cggttcccaa | cgatcaaggc | gagttacatg | 1260 |
| atcccccatg | ttgtgcaaaa | aagcggttag | ctccttcggt | cctccgatcg | ttgtcagaag | 1320 |
| taagttggcc | gcagtgttat | cactcatggt | tatggcagca | ctgcataatt | ctcttactgt | 1380 |
| catgccatcc | gtaagatgct | tttctgtgac | tggtgagtac | tcaaccaagt | cattctgaga | 1440 |
| atagtgtatg | cggcgaccga | gttgctcttg | cccggcgtca | atacgggata | ataccgcgcc | 1500 |
| acatagcaga | actttaaaag | tgctcatcat | tggaaaacgt | tcttcgggggc | gaaaactctc | 1560 |
| aaggatctta | ccgctgttga | gatccagttc | gatgtaaccc | actcgtgcac | ccaactgatc | 1620 |
| ttcagcatct | tttactttca | ccagcgtttc | tgggtgagca | aaaacaggaa | ggcaaaatgc | 1680 |
| cgcaaaaaag | ggaataaggg | cgacacggaa | atgttgaata | ctcatactct | tcctttttca | 1740 |
| atattattga | agcatttatc | agggttattg | tctcatgagc | ggatacatat | ttgaatgtat | 1800 |
| ttagaaaaat | aaacaaatag | gggttccgcg | cacatttccc | cgaaaagtgc | caaggacccc | 1860 |
| gcggcaggcc | ctccgagcgt | ggtggagccg | ttctgtgaga | cagccgggta | cgagtcgtga | 1920 |
| cgctggaagg | ggcaagcggg | tggtgggcag | gaatgcggtc | cgccctgcag | caaccggagg | 1980 |
| gggagggaga | agggagcgga | aaagtctcca | ccggacgcgg | ccatggctcg | ggggggggg | 2040 |
| ggcagcggag | gagcgcttcc | ggccgacgtc | tcgtcgctga | ttggcttctt | ttcctcccgc | 2100 |

```
cgtgtgtgaa acacaaatg gcgtgttttg gttggcgtaa ggcgcctgtc agttaacggc    2160
agccggagtg cgcagccgcc ggcagcctcg ctctgcccac tgggtggggc gggaggtagg    2220
tggggtgagg cgagctggac gtgcgggcgc ggtcggcctc tggcggggcg ggggagggga    2280
gggagggtca gcgaaagtag ctcgcgcgcg agcggccgcc caccctcccc ttcctctggg    2340
ggagtcgttt tacccgccgc cggccgggcc tcgtcgtctg attggctctc ggggcccaga    2400
aaactggccc ttgccattgg ctcgtgttcg tgcaagttga gtccatccgc cggccagcgg    2460
gggcggcgag gaggcgctcc caggttccgg ccctcccctc ggccccgcgc cgcagagtct    2520
ggccgcgcgc ccctgcgcaa cgtggcagga agcgcgcgct gggggcgggg acgggcagta    2580
gggctgagcg gctgcggggc gggtgcaagc acgtttccga cttgagttgc ctcaagaggg    2640
gcgtgctgag ccagacctcc atcgcgcact ccggggagtg gagggaagga gcgagggctc    2700
agttgggctg ttttggaggc aggaagcact tgctctccca aagtcgctct gagttgttat    2760
cagtaaggga gctgcagtgg agtaggcggg gagaaggccg cacccttctc cggaggggggg   2820 aggggagtgt tgcaatacct ttctgggagt tctctgctgc ctcctggctt ctgaggaccg    2880
ccctgggcct gggagaatcc cttgcccct cttcccctcg tgatctgcaa ctccagtctt    2940
acaaaccaat tcagtcgact ggatcctagt tattaatagt aatcaattac ggggtcatta    3000
gttcatagcc catatatgga gttccgcgtt acataactta cggtaaatgg cccgcctggc    3060
tgaccgccca acgaccccccg cccattgacg tcaataatga cgtatgttcc catagtaacg    3120
ccaataggga ctttccattg acgtcaatgg gtggagtatt tacggtaaac tgcccacttg    3180
gcagtacatc aagtgtatca tatgccaagt acgcccccta ttgacgtcaa tgacggtaaa    3240
tggcccgcct ggcattatgc ccagtacatg accttatggg actttcctac ttggcagtac    3300
atctacgtat tagtcatcgc tattaccatg gtgatgcggt tttggcagta catcaatggg    3360
cgtggatagc ggtttgactc acggggattt ccaagtctcc accccattga cgtcaatggg    3420
agtttgtttt ggcaccaaaa tcaacgggac tttccaaaat gtcgtaacaa ctccgcccca    3480
ttgacgcaaa tgggcggtag gcgtgtacgg tgggaggtct atataagcag agctggttta    3540
gtgaaccgtc agatcactag tcgactaggg ataacagggc accatggatc ccctgggtgc    3600
agccaagcca caatggccat ggcgccgctg tctggccgca ctgctatttc agctgctggt    3660
ggctgtgtgt ttcttctcct acctgcgtgt gtcccgagac gatgccactg gatccctag    3720 ggctcccagt gggtcctccc gacaggacac cactcccacc cgccccaccc tcctgatcct    3780
gctatggaca tggccttttcc acatccctgt ggctctgtcc cgctgttcag agatggtgcc    3840
cggcacagcc gactgccaca tcactgccga ccgcaaggtg tacccacagg cagacacggt    3900
catcgtgcac cactgggata tcatgtccaa ccctaagtca cgcctccac cttccccgag    3960 gccgcagggg cagcgctgga tctggttcaa cttggagcca cccctaact gccagcacct    4020 ggaagccctg gacagatact tcaatctcac catgtcctac cgcagcgact ccgacatctt    4080
cacgccctac ggctggctgg agccgtggtc cggccagcct gcccacccac cgctcaacct    4140
ctcggccaag accgagctgg tggcctgggc ggtgtccaac tggaagccgg actcagccag    4200
ggtgcgctac taccagagcc tgcaggctca tctcaaggtg gacgtgtacg gacgctccca    4260
caagcccctg cccaagggga ccatgatgga gacgctgtcc cggtacaagt tctacctggc    4320
cttcgagaac tccttgcacc ccgactacat caccgagaag ctgtgtgagga acgcctgga    4380 ggcctgggcc gtgcccgtgg tgctgggccc cagcagaagc aactacgaga ggttcctgcc    4440
```

```
acccgacgcc ttcatccacg tggacgactt ccagagcccc aaggacctgg cccggtacct    4500
gcaggagctg gacaaggacc acgcccgcta cctgagctac tttcgctggc gggagacgct    4560
gcggcctcgc tccttcagct gggcactgga tttctgcaag gcctgctgga aactgcagca    4620
ggaatccagg taccagacgg tgcgcagcat agcggcttgg ttcacctgat cgactgtgcc    4680
ttctagttgc cagccatctg ttgtttgccc ctcccccgtg ccttccttga ccctggaagg    4740
tgccactccc actgtccttt cctaataaaa tgaggaaatt gcatcgcatt gtctgagtag    4800
gtgtcattct attctggggg gtggggtggg gcaggacagc aaggggagg attgggagga     4860 caatagcagg catgctgggg atgcggtggg ctctatggct tcgacagggt cgacaagctt    4920
ttccaaaaaa aaagcatgag gtgcagttgc gcctttccta tctcttgaat aggaaaggcg    4980
caactgcacc tcatgctgga tcccgcgtcc tttccacaag atatataaac ccaagaaatc    5040
gaaatacttt caagttacgg taagcatatg atagtccatt ttaaaacata attttaaaac    5100
tgcaaactac ccaagaaatt attactttct acgtcacgta ttttgtacta atatctttgt    5160
gtttacagtc aaattaattc taattatctc tctaacagcc ttgtatcgta tatgcaaata    5220
tgaaggaatc atgggaaata ggccctcttc ctgcccgacc ttggcgcgcg ctcggcgcgc    5280
ggtcacgctc cgtcacgtgg tgcgttttgc cagcaggcag aagtatgcaa agcatgcatc    5340
tcaattagtc agcaaccagg tgtggaaagt ccccaggctc cccagcaggc agaagtatgc    5400
aaagcatgca tctcaattag tcagcaacca tagtcccgcc cctaactccg cccatcccgc    5460
ccctaactcc gcccagttcc gcccattctc cgccccatgg ctgactaatt ttttttattt    5520
atgcagaggc cgaggccgcc tctgcctctg agctattcca gaagtagtga ggaggctttt    5580
ttggaggcct aggcttttgc aaaaagctcc cgggagcttg tatatccatt ttcggatctg    5640
atcagcacgt gatgaaaaag cctgaactca ccgcgacgtc tgtcgagaag tttctgatcg    5700
aaaagttcga cagcgtgtcc gacctgatgc agctctcgga gggcgaagaa tctcgtgctt    5760
tcagcttcga tgtaggaggg cgtggatatg tcctgcgggt aaatagctgc gccgatggtt    5820
tctacaaaga tcgttatgtt tatcggcact ttgcatcggc cgcgctcccg attccggaag    5880
tgcttgacat tggggaattc agcgagagcc tgacctattg catctcccgc cgtgcacagg    5940
gtgtcacgtt gcaagacttg cctgaaaccg aactgcccgc tgttctgcag ccggtcgcgg    6000
aggccatgga tgcgatcgct gcggccgatc ttagccagac gagcgggttc ggcccattcg    6060
gaccgcaagg aatcggtcaa tacactacat ggcgtgattt catatgcgcg attgctgatc    6120
cccatgtgta tcactggcaa actgtgatgg acgacaccgt cagtgcgtcc gtcgcgcagg    6180
ctctcgatga gctgatgctt tgggccgagg actgccccga agtccggcac ctcgtgcacg    6240
cggatttcgg ctccaacaat gtcctgacgg acaatggccg cataacagcg gtcattgact    6300
ggagcgaggc gatgttcggg gattcccaat acgaggtcgc caacatcttc ttctggaggc    6360
cgtggttggc ttgtatggag cagcagacgc gctacttcga gcggaggcat ccggagcttg    6420
caggatcgcc gcggctccgg gcgtatatgc tccgcattgg tcttgaccaa ctctatcaga    6480
gcttggttga cggcaatttc gatgatgcag cttgggcgca gggtcgatgc gacgcaatcg    6540
tccgatccgg agccgggact gtcgggcgta cacaaatcgc ccgcagaagc gcggccgtct    6600
ggaccgatgg ctgtgtagaa gtactcgccg atagtggaaa ccgacgcccc agcactcgtc    6660
cgagggcaaa ggaatagcac gtgctacgag atttcgattc caccgccgcc ttctatgaaa    6720
ggttgggctt cggaatcgtt ttccgggacg ccggctggat gatcctccag cgcgggatc     6780 tcatgctgga gttcttcgcc caccccaact tgtttattgc agcttataat ggttacaaat    6840
```

```
aaagcaatag catcacaaat ttcacaaata aagcattttt ttcactgcat tctagttgtg    6900
gtttgtccaa actcatcaat gtatcgtaga gatgggcggg agtcttctgg gcaggcttaa    6960
aggctaacct ggtgtgtggg cgttgtcctg caggggaatt gaacaggtgt aaaattggag    7020
ggacaagact tcccacagat tttcggtttt gtcgggaagt tttttaatag gggcaaatag    7080
gaaaatggag gataggagtc atctggggtt tatgcagcaa aactacaggt atattgcttg    7140
tatccgcctc ggagatttcc atgaggagat aaagacatgt cacccgagtt tatactctcc    7200
tgcttagatc ctactacagt atgaaataca gtgtcgcgag gtagactatg taagcagatt    7260
taatcatttt aaagagccca gtacttcata tccatttctc ccgctccttc tgcagcctta    7320
tcaaaaggta tttagaacac tcattttagc cccatttttca tttattatac tggcttatcc    7380 aaccctaga cagagcattg gcatttttccc tttcctgatc ttagaagtct gatgactcat    7440
gaaaccagac agattagtta catacaccac aaatcgaggc tgtagctggg gcctcaacac    7500
tgcagttctt ttataactcc ttagtacact ttttgttgat cctttgcctt gatccttaat    7560
tttcagtgtc tatcacctct cccgtcaggt ggtgttccac atttgggcct attctcagtc    7620
cagggagttt tacaacaata gatgtattga gaatccaacc taaagcttaa ctttccactc    7680
ccatgaatgc ctctctcctt tttctccatt ataactgagc tataaccatt aatggtttca    7740
ggtggatgtc tcctccccca atatacctga tgtatctaca tattgccagg ctgatatttt    7800
aagacataaa aggtatattt cattattgag ccacatggta ttgattactg ctactaaaat    7860
tttgtcattg tacacatctg taaaaggtgg ttccttttgg aatgcaaagt tcaggtgttt    7920
gttgtctttc ctgacctaag gtcttgtgag cttgtatttt ttctatttaa gcagtgcttt    7980
ctcttggact ggcttgactc atggcattct acacgttatt gctggtctaa atgtgatttt    8040
gccaagcttc ttcaggacct ataattttgc ttgacttgta gccaaacaca agtaaaatga    8100
ttaagcaaca aatgtatttg tgaagcttgg ttttttaggtt gttgtgttgt gtgtgcttgt    8160
gctctataat aatactatcc aggggctgga gaggtggctc ggagttcaag agcacagact    8220
gctcttccag aagtcctgag ttcaattccc agcaaccaca tggtggctca caaccatctg    8280
taatgggatc tgatgccctc ttctggtgtg tctgaagacc acaagtgtat tcacattaaa    8340
taaataatcc tccttcttct tcttttttttt ttttttaaaga gaatactgtc tccagtagaa    8400
ttactgaagt aatgaaatac tttgtgtttg ttccaatatg gaagccaata atcaaatact    8460
cttaagcact ggaaatgtac caaggaacta tttttatttaa gtgaactgtg gacagaggag    8520
ccataactgc agacttgtgg gatacagaag accaatgcag acttaatgtc tttttctctta    8580 cactaagcaa taaagaaata aaaattgaac ttctagtatc ctatttgtta aactgctagc    8640
tttactaact tttgtgcttc atctatacaa agctgaaagc taagtctgca gccattacta    8700
aacatgaaag caagtaatga taattttgga tttcaaaaat gtagggccag agtttagcca    8760
gccagtggtg gtgcttgcct ttatgcctta atcccagcac tctggaggca gagacaggca    8820
gatctctgag tttgagccca gcctggtcta cacatcaagt tctatctagg atagccagga    8880
atacacacag aaaccctgtt ggggaggggg gctctgagat ttcataaaat tataattgaa    8940
gcattcccta atgagccact atggatgtgg ctaaatccgt ctacctttct gatgagattt    9000
gggtattatt ttttctgtct ctgctgttgg ttgggtcttt tgacactgtg ggctttctta    9060
aagcctcctt ccctgccatg tggactcttg tttgctacta acttcccatg gcttaaatgg    9120
catggctttt tgccttctaa gggcagctgc tgagatttgc agcctgattt ccagggtggg    9180
```

```
gttgggaaat ctttcaaaca ctaaaattgt cctttaattt ttttttaaaa aatgggttat    9240
ataataaacc tcataaaata gttatgagga gtgaggtgga ctaatattaa tgagtccctc    9300
ccctataaaa gagctattaa ggcttttttgt cttatactaa ctttttttttt aaatgtggta  9360 tctttagaac caagggtctt agagttttag tatacagaaa ctgttgcatc gcttaatcag    9420
attttctagt ttcaaatcca gagaatccaa attcttcaca gccaaagtca aattaagaat    9480
ttctgacttt aatgttattt gctactgtga atataaaatg atagcttttc ctgaggcagg    9540
gtatcactat gtatctctgc ctgatctgca acaagatatg tagactaaag ttctgcctgc    9600
ttttgtctcc tgaatactaa ggttaaaatg tagtaatact tttggaactt gcaggtcaga    9660 ttctttttata ggggacacac taagggagct tgggtgatag ttggtaaatg tgtttaagtg   9720
atgaaaactt gaattattat caccgcaacc tactttttaa aaaaaaaagc caggcctgtt    9780
agagcatgct aagggatccc taggacttgc tgagcacaca agagtagtac ttggcaggct    9840
cctggtgaga gcatatttca aaaacaagg cagacaacca agaaactaca gtaaggttac     9900
ctgtctttaa ccatctgcat atacacaggg atattaaaat attccaaata atatttcatt    9960
caagttttcc cccatcaaat tgggacatgg atttctccgg tgaataggca gagttggaaa   10020
ctaaacaaat gttggttttg tgatttgtga aattgttttc aagtgatagt taaagcccat   10080
gagatacaga acaaagctgc tatttcgagg tcacttggtt atactcagaa gcacttcttt   10140
gggtttccct gcactatcct gatcatgtgc taggcctacc ttaggctgat tgttgttcaa   10200
ataacttaag tttcctgtca ggtgatgtca tatgatttca tatatcaagg caaaacatgt   10260
tatatatgtt aaacatttgg acttaatgtg aaagttaggt ctttgtgggt tttgatttta   10320
atttcaaaac ctgagctaaa taagtcattt tacatgtctt acatttggtg aattgtatat   10380
tgtggtttgc aggcaagact ctctgaccta gtaaccctcc tatagagcac tttgctgggt   10440
cacaagtcta ggagtcaagc atttcacctt gaagttgaga cgttttgtta gtgtatacta   10500
gttatatgtt ggaggacatg tttatccaga agatattcag gactattttt gactgggcta   10560
aggaattgat tctgattagc actgttagtg agcattgagt ggcctttagg cttgaattgg   10620
agtcacttgt atatctcaaa taatgctggc cttttttaaa aagcccttgt tctttatcac   10680
cctgttttct acataatttt tgttcaaaga atacttgtt tggatctcct tttgacaaca    10740
atagcatgtt ttcaagccat attttttttc ctttttttttt ttttttttgg tttttcgaga  10800
cagggtttct ctgtatagcc ctggctgtcc tggaactcac tttgtagacc aggctggcct   10860
cgaactcaga atccgcctg cctctgcctc tgagtgccg ggattaaagg cgtgcaccac     10920
cacgcctggc taagttggat attttgtata taactataac caatactaac tccactgggt   10980 ggattttttaa ttcagtcagt agtcttaagt ggtctttatt ggcccttatt aaaatctact  11040
gttcactcta acagaggctg ttggactagt gggactaagc aacttcctac ggatatacta   11100
gcagataagg gtcagggata gaaactagtc tagcgttttg tatacctacc agcttatact   11160
accttgttct gatagaaata tttaggacat ctagcttatc atgcaaggaa ccaattcagt   11220
cgactggatc ccgatggctc cggtgcccgt cagtgggcag agcgcacatc gcccacagtc   11280
cccgagaagt tgggggagg ggtcggcaat tgaaccggtg cctagagaag gtggcgcggg    11340
gtaaactggg aaagtgatgt cgtgtactgg ctccgccttt ttcccgaggg tggggagaa    11400 ccgtatataa gtgcagtagt cgccgtgaac gttcttttttc gcaacgggtt tgccgccaga  11460
acacaggtcc gcggccccga actaggccta ggcgtctgat cactagtgac tctagtccta   11520
gtcgactagg gataacaggg gcccatggct tcgtacccct gccatcaaca cgcgtctgcg   11580
```

```
ttcgaccagg ctgcgcgttc tcgcggccat agcaaccgac gtacggcgtt gcgccctcgc    11640
cggcagcaag aagccacgga agtccgcctg gagcagaaaa tgcccacgct actgcgggtt    11700
tatatagacg gtcctcacgg gatggggaaa accaccacca cgcaactgct ggtggccctg    11760
ggttcgcgcg acgatatcgt ctacgtaccc gagccgatga cttactggca ggtgctgggg    11820
gcttccgaga caatcgcgaa catctacacc acacaacacc gcctcgacca gggtgagata    11880
tcggccgggg acgcggcgt ggtaatgaca agcgcccaga taacaatggg catgccttat    11940
gccgtgaccg acgccgttct ggctcctcat atcgggggg aggctgggag ctcacatgcc    12000
ccgcccccgg ccctcaccct catcttcgac cgccatccca tcgccgccct cctgtgctac    12060
ccggccgcgc gataccttat gggcagcatg acccccagg ccgtgctggc gttcgtggcc    12120
ctcatcccgc cgaccttgcc cggcacaaac atcgtgttgg gggcccttcc ggaggacaga    12180
cacatcgacc gcctggccaa acgccagcgc cccggcgagc ggcttgacct ggctatgctg    12240
gccgcgattc gccgcgtta cgggctgctt gccaatacgg tgcggtatct gcagggcggc    12300
gggtcgtggc gggaggattg ggacagctt tcggggacgg ccgtgccgcc ccagggtgcc    12360
gagccccaga gcaacgcggg cccacgaccc catatcgggg acacgttatt taccctgttt    12420
cgggcccccg agttgctggc ccccaacggc gacctgtaca acgtgtttgc ctgggccttg    12480
gacgtcttgg ccaaacgcct ccgtcccatg cacgtcttta tcctggatta cgaccaatcg    12540
cccgccggct gccgggacgc cctgctgcaa cttacctccg ggatggtcca gacccacgtc    12600 accaccccg gctccatacc gacgatctgc gacctggcgc gcacgtttgc ccgggagatg    12660
ggggaggcta actgaccgcg ggggaggcta actgaaacac ggaaggagac aataccggaa    12720
ggaacccgcg ctatgacggc aataaaaaga cagaataaaa cgcacggtgt tgggtcgttt    12780
gttcataaac gcggggttcg gtcccagggc tggcactctg tcgataccc accgaggccc    12840 cattggggcc aatacgcccg cgtttcttcc ttttccccac cccacccccc aagttcgggt    12900
gaaggcccag ggctcgcagc caacgtcggg gcggcaggcc ctgccatagc c             12951
```

<210> SEQ ID NO 59
<211> LENGTH: 785
<212> TYPE: DNA
<213> ORGANISM: Artificial sequence
<220> FEATURE:
<223> OTHER INFORMATION: TO3G BsaI A

<400> SEQUENCE: 59

```
gaggtaccgg tctcacacca tgtctagact ggacaagagc aaagtcataa actctgctct      60
ggaattactc aatggagtcg gtatcgaagg cctgacgaca aggaaactcg ctcaaaagct     120
gggagttgag cagcctaccc tgtactgcca cgtgaagaac aagcgggccc tgctcgatgc     180
cctgccaatc gagatgctgg acaggcatca tacccactcc tgcccctgg aaggcgagtc     240 atggcaagac tttctgcgga caacgccaa gtcataccgc tgtgctctcc tctcacatcg     300
cgacggggct aaagtgcatc tcggcacccg cccaacagag aaacagtacg aaaccctgga     360
aaatcagctc gcgttcctgt gtcagcaagg cttctccctg gagaacgcac tgtacgctct     420
gtccgccgtg ggccactttta cactgggctg cgtattggag gaacaggagc atcaagtagc     480
aaaagaggaa agagagacac ctaccaccga ttctatgccc ccacttctga acaagcaat     540 tgagctgttc gaccggcagg gagccgaacc tgccttcctt ttcggcctgg aactaatcat     600
atgtggcctg gagaaacagc taaagtgcga aagcggcggg ccgaccgacg cccttgacga     660
```

```
tttgactta gacatgctcc cagccgatgc ccttgacgac tttgaccttg atatgctgcc    720
tgctgacgct cttgacgatt ttgaccttga catgctcccc gggtaatgat cgagaccggt    780
acctc                                                                785

<210> SEQ ID NO 60
<211> LENGTH: 439
<212> TYPE: DNA
<213> ORGANISM: Artificial sequence
<220> FEATURE:
<223> OTHER INFORMATION: pTRE3G BsaI A

<400> SEQUENCE: 60
gaggtaccgg tctcattcgc tttcgtcttc aagaattcct ggagtttact ccctatcagt     60
gatagagaac gtatgaagag tttactccct atcagtgata gagaacgtat gcagacttta   120
ctccctatca gtgatagaga acgtataagg agtttactcc ctatcagtga tagagaacgt   180
atgaccagtt tactccctat cagtgataga gaacgtatct acagtttact ccctatcagt   240
gatagagaac gtatatccag tttactccct atcagtgata gagaacgtat aagctttagg   300
cgtgtacggt gggcgcctat aaaagcagag ctcgtttagt gaaccgtcag atcgcctgga   360
gcaattccac aacactttg tcttataccaa actttccgta ccacttccta ccctcgtaaa    420
ccagcgagac cggtacctc                                                 439

<210> SEQ ID NO 61
<211> LENGTH: 986
<212> TYPE: DNA
<213> ORGANISM: Artificial sequence
<220> FEATURE:
<223> OTHER INFORMATION: mB3Galt6 BsaI A

<400> SEQUENCE: 61
ccagatgaag gtattccggc gcgcttggcg gcaccgggtg gcgctgggcc taggcggcct     60
ggcgttctgc ggcaccactc tgttgtacct ggcgcgctgc gcttccgagg gcagacgcc    120 ctccgcttcc ggagccgctc ggccccgcgc taaggccttc ctggcggtgc tggtggccag   180
tgcgccccgc gcggtcgagc gccgcaccgc agtgcgcagc acgtggctgg caccggagag   240
gcgtggcgga cccgaggacg tgtgggcgcg cttcgccgtg ggcactggcg gcttaggctc   300
ggaggagcgg cgcgctcttg agctcgagca ggcgcagcac ggggacctgc tgctgctgcc   360
cgccctgcgc gacgcctacg agaacctcac ggccaaggtc ctggccatgc tgacctggct   420
ggatgagcgc gtggacttcg agttcgtgct caaggcggac gacgactcct tgcgcgcct   480 ggacgctatc ctggtggacc tacgcgcacg ggagcccgca cgccgccggc gcctctactg    540
gggcttcttt tccgggcgcg ggcgcgtcaa gccgggaggt cgctggcgag aagcagcctg   600
gcaactctgc gactactacc tgccctacgc gttgggcggt ggctatgtcc tttctgcgga   660
cctggtgcat tacctgcgcc tcagccgcga gtacctgcgc gcgtggcaca gtgaagacgt   720
atcgctgggc acctggctgg caccagtgga tgtgcaacgg gagcacgacc cacgcttcga   780
cacggagtac aaatctcgag gctgcaacaa tcagtatctg gtgacacaca gcaaagccc    840 agaggacatg ttggagaagc aacagatgtt gctgcatgag ggccggttgt gcaagcatga   900
ggtgcagttg cgcctttcct atgtctatga ctggtcagct ccaccctccc agtgctgcca   960
gcgcaaggag ggcgttccct gaccgc                                        986

<210> SEQ ID NO 62
<211> LENGTH: 5146
```

```
<212> TYPE: DNA
<213> ORGANISM: Artificial sequence
<220> FEATURE:
<223> OTHER INFORMATION: V2

<400> SEQUENCE: 62
tattgtaata cggttatcca cagaatcagg ggataacgca ggaaagaaca tgtgagcaaa    60
aggccagcaa aaggccagga accgtaaaaa ggccgcgttg ctggcgtttt tccataggct   120
ccgcccccct gacgagcatc acaaaaatcg acgctcaagt cagaggtggc gaaacccgac   180
aggactataa agataccagg cgtttccccc tggaagctcc ctcgtgcgct cctgttcc     240
gaccctgccg cttaccggat acctgtccgc ctttctccct tcgggaagcg tggcgctttc   300
tcatagctca cgctgtaggt atctcagttc ggtgtaggtc gttcgctcca agctgggctg   360
tgtgcacgaa ccccccgttc agcccgaccg ctgcgcctta ccggtaact atcgtcttga    420
gtccaacccg gtaagacacg acttatcgcc actggcagca gccactggta acaggattag   480
cagagcgagg tatgtaggcg gtgctacaga gttcttgaag tggtggccta actacggcta   540
cactagaaga acagtatttg gtatctgcgc tctgctgaag ccagttacct tcggaaaaag   600
agttggtagc tcttgatccg gcaaacaaac caccgctggt agcggttttt ttgtttgcaa   660
gcagcagatt acgcgcagaa aaaaggatc tcaagaagat cctttgatct tttctacggg    720
gtctgacgct cagtggaacg aaaactcacg ttaagggatt ttggtcatga gattatcaaa   780
aaggatcttc acctagatcc ttttaaatta aaatgaagt tttaaatcaa tctaaagtat    840
atatgagtaa acttggtctg acagttacca atgcttaatc agtgaggcac ctatctcagc   900
gatctgtcta tttcgttcat ccatagttgc ctgactcccc gtcgtgtaga taactacgat   960
acgggagggc ttaccatctg gccccagtgc tgcaatgata ccgcgtgacc cacgctcacc  1020
ggctccagat ttatcagcaa taaaccagcc agccggaagg gccgagcgca gaagtggtcc  1080
tgcaacttta tccgcctcca tccagtctat taattgttgc cgggaagcta gagtaagtag  1140
ttcgccagtt aatagtttgc gcaacgttgt tgccattgct acaggcatcg tggtgtcacg  1200
ctcgtcgttt ggtatggctt cattcagctc cggttcccaa cgatcaaggc gagttacatg  1260
atcccccatg ttgtgcaaaa aagcggttag ctccttcggt cctccgatcg ttgtcagaag  1320
taagttggcc gcagtgttat cactcatggt tatggcagca ctgcataatt ctcttactgt  1380
catgccatcc gtaagatgct tttctgtgac tggtgagtac tcaaccaagt cattctgaga  1440
atagtgtatg cggcgaccga gttgctcttg cccggcgtca atacgggata ataccgcgcc  1500
acatagcaga actttaaaag tgctcatcat tggaaaacgt tcttcgggc gaaaactctc    1560
aaggatctta ccgctgttga tccagttc gatgtaaccc actcgtgcac ccaactgatc    1620
ttcagcatct tttactttca ccagcgtttc tgggtgagca aaaacaggaa ggcaaaatgc  1680
cgcaaaaaag ggaataaggg cgacacggaa atgttgaata ctcatactct ccttttttca  1740
atattattga agcatttatc agggttattg tctcatgagc ggatacatat ttgaatgtat  1800
ttagaaaaat aaacaaatag gggttccgcg cacatttccc cgaaaagtgc caaggaacca  1860
attcagtcga ctggatccta gttattaata gtaatcaatt acgggtcat tagttcatag   1920
cccatatatg gagttccgcg ttacataact acggtaaat ggcccgcctg gctgaccgcc    1980
caacgacccc cgcccattga cgtcaataat gacgtatgtt cccatagtaa cgccaatagg  2040
gactttccat tgacgtcaat gggtggagta tttacggtaa actgcccact ggcagtaca   2100
tcaagtgtat catatgccaa gtacgccccc tattgacgtc aatgacggta aatggcccgc  2160
```

```
ctggcattat gcccagtaca tgaccttatg ggactttcct acttggcagt acatctacgt    2220
attagtcatc gctattacca tggtgatgcg gtttttggcag tacatcaatg ggcgtggata   2280
gcggtttgac tcacggggat ttccaagtct ccaccccatt gacgtcaatg ggagtttgtt   2340
ttggcaccaa aatcaacggg actttccaaa atgtcgtaac aactccgccc cattgacgca   2400
aatgggcggt aggcgtgtac ggtgggaggt ctatataagc agagctggtt tagtgaaccg   2460
tcagatcact agtcgactag gataacagg gcaccatgtc tagactggac aagagcaaag    2520
tcataaactc tgctctggaa ttactcaatg gagtcggtat cgaaggcctg acgacaagga   2580
aactcgctca aaagctggga gttgagcagc ctaccctgta ctggcacgtg aagaacaagc   2640
gggccctgct cgatgccctg ccaatcgaga tgctggacag gcatcatacc cactcctgcc   2700
ccctggaagg cgagtcatgg caagactttc tgcggaacaa cgccaagtca taccgctgtg   2760
ctctcctctc acatcgcgac ggggctaaag tgcatctcgg caccccgccca acagagaaac  2820 agtacgaaac cctggaaaat cagctcgcgt tcctgtgtca gcaaggcttc tccctggaga   2880
acgcactgta cgctctgtcc gccgtgggcc actttacact gggctgcgta ttggaggaac   2940
aggagcatca agtagcaaaa gaggaaagag agacacctac caccgattct atgcccccac   3000
ttctgaaaca agcaattgag ctgttcgacc ggcaggagc cgaacctgcc ttccttttcg     3060
gcctggaact aatcatatgt ggcctggaga acagctaaa gtgcgaaagc ggcgggccga    3120 ccgacgcct tgacgatttt gacttagaca tgctcccagc cgatgccctt gacgactttg    3180
accttgatat gctgcctgct gacgctcttg acgattttga ccttgacatg ctccccgggt   3240
aatgatcgac tgtgccttct agttgccagc catctgttgt ttgcccctcc ccgtgcctt    3300 ccttgaccct ggaaggtgcc actcccactg tcctttccta ataaaatgag gaaattgcat   3360
cgcattgtct gagtaggtgt cattctattc tggggggtgg ggtggggcag gacagcaagg   3420
gggaggattg ggaggacaat agcaggcatg ctggggatgc ggtgggctct atggcttcgc   3480
tttcgtcttc aagaattcct ggagtttact ccctatcagt gatagagaac gtatgaagag   3540
tttactccct atcagtgata gagaacgtat gcagacttta ctccctatca gtgatagaga   3600
acgtataagg agtttactcc ctatcagtga tagagaacgt atgaccagtt tactccctat   3660
cagtgataga gaacgtatct acagtttact ccctatcagt gatagagaac gtatatccag   3720
tttactccct atcagtgata gagaacgtat aagcttagg cgtgtacggt gggcgcctat    3780
aaaagcagag ctcgtttagt gaaccgtcag atcgcctgga gcaattccac aacacttttg   3840
tcttatacca actttccgta ccacttccta ccctcgtaaa ccagagcatg aaggtattcc   3900
ggcgcgcttg gcggcaccgg gtggcgctgg gcctaggcgg cctggcgttc tgcggcacca   3960
ctctgttgta cctggcgcgc tgcgcttccg agggcgagac gccctccgct tccgagccg    4020 ctcggccccg cgctaaggcc ttcctggcgg tgctggtggc cagtgcgccc cgcgcggtcg   4080
agcgccgcac cgcagtgcgc agcacgtggc tggcaccgga gaggcgtggc ggacccgagg   4140
acgtgtgggc gcgcttcgcc gtgggcactg gcggcttagg ctcggaggag cggcgcgctc   4200
ttgagctcga gcaggcgcag cacggggacc tgctgctgct gcccgccctg cgcgacgcct   4260
acgagaacct cacggccaag gtcctggcca tgctgacctg gctggatgag cgcgtggact   4320
tcgagttcgt gctcaaggcg gacgacgact cctttgcgcg cctggacgct atcctggtgg   4380
acctacgcgc acgggagccc gcacgccgcc ggcgcctcta ctgggcttc ttttccgggc    4440 gcgggcgcgt caagccggga ggtcgctggc gagaagcagc ctggcaactc tgcgactact   4500
acctgcccta cgcgttgggc ggtggctatg tcctttctgc ggacctggtg cattacctgc   4560
```

```
gcctcagccg cgagtacctg cgcgcgtggc acagtgaaga cgtatcgctg ggcacctggc    4620
tggcaccagt ggatgtgcaa cgggagcacg acccacgctt cgacacggag tacaaatctc    4680
gaggctgcaa caatcagtat ctggtgacac acaagcaaag cccagaggac atgttggaga    4740
agcaacagat gttgctgcat gagggccggt tgtgcaagca tgaggtgcaa cttcgccttt    4800
cctatgtcta tgactggtca gctccaccct cccagtgctg ccagcgcaag gagggcgttc    4860
cctgatgtca ccgcggggga ggctaactga aacacggaag gagacaatac cggaaggaac    4920
ccgcgctatg acggcaataa aaagacagaa taaaacgcac ggtgttgggt cgtttgttca    4980
taaacgcggg gttcggtccc agggctggca ctctgtcgat accccaccga gggccccattg    5040 gggccaatac gcccgcgttt cttccttttc cccaccccac cccccaagtt cgggtgaagg    5100
cccagggctc gcagccaacg tcgggcggc aggccctgcc atagcc                    5146
```

<210> SEQ ID NO 63
<211> LENGTH: 1024
<212> TYPE: DNA
<213> ORGANISM: Artificial sequence
<220> FEATURE:
<223> OTHER INFORMATION: mB3Galt6 BsaI B

<400> SEQUENCE: 63

```
gaggtaccgg tctcaccaga gcatgaaggt attccggcgc gcttggcggc accgggtggc      60
gctgggccta ggcggcctgg cgttctgcgg caccactctg ttgtacctgg cgcgctgcgc     120 ttccagggc gagacgccct ccgcttccgg agccgctcgg ccccgcgcta aggccttcct     180
ggcggtgctg gtggccagtg cgccccgcgc ggtcgagcgc cgcaccgcag tgcgcagcac     240
gtggctggca ccggagaggc gtggcggacc cgaggacgtg tgggcgcgct cgccgtggg      300 cactggcggc ttaggctcgg aggagcggcg cgctcttgag ctcgagcagg cgcagcacgg     360
ggacctgctg ctgctgcccg ccctgcgcga cgcctacgag aacctcacgg ccaaggtcct     420
ggccatgctg acctggctgg atgagcgcgt ggacttcgag ttcgtgctca aggcggacga     480
cgactccttt gcgcgcctgg acgctatcct ggtggaccta cgcgcacggg agcccgcacg     540
ccgccggcgc ctctactggg gcttcttttc cgggcgcggg cgcgtcaagc cgggaggtcg     600
ctggcgagaa gcagcctggc aactctgcga ctactacctg ccctacgcgt gggcggtgg      660 ctatgtcctt tctgcggacc tggtgcatta cctgcgcctc agccgcgagt acctgcgcgc     720
gtggcacagt gaagacgtat cgctgggcac ctggctggca ccagtggatg tgcaacggga     780
gcacgaccca cgcttcgaca cggagtacaa atctcgaggc tgcaacaatc agtatctggt     840
gacacacaag caaagcccag aggacatgtt ggagaagcaa cagatgttgc tgcatgaggg     900
ccggttgtgc aagcatgagg tgcaacttcg ccttcctat gtctatgact ggtcagctcc     960
accctcccag tgctgccagc gcaaggaggg cgttccctga tgtcaccgcc gagaccggta    1020
cctc                                                                1024
```

<210> SEQ ID NO 64
<211> LENGTH: 310
<212> TYPE: DNA
<213> ORGANISM: Artificial sequence
<220> FEATURE:
<223> OTHER INFORMATION: Tkter BsaI B

<400> SEQUENCE: 64

```
gaggtaccgg tctcaccgcg ggggaggcta actgaaacac ggaaggagac aataccggaa      60
```

| ggaacccgcg ctatgacggc aataaaaaga cagaataaaa cgcacggtgt tgggtcgttt | 120 |
| gttcataaac gcggggttcg gtcccagggc tggcactctg tcgataccc accgaggccc | 180 |
| cattggggcc aatacgcccg cgtttcttcc ttttccccac ccaccccc aagttcgggt | 240 |
| gaaggcccag ggctcgcagc caacgtcggg gcggcaggcc ctgccatagc cacaacgaga | 300 |
| ccggtacctc | 310 |

<210> SEQ ID NO 65
<211> LENGTH: 444
<212> TYPE: DNA
<213> ORGANISM: Artificial sequence
<220> FEATURE:
<223> OTHER INFORMATION: shB3Galt6 BsaI C

<400> SEQUENCE: 65

| gaggtaccgg tctcaacaaa cagggtcgac aagcttttcc aaaaaaaaag catgaggtgc | 60 |
| agttgcgcct ttcctatctc ttgaatagga aggcgcaac tgcacctcat gctggatccc | 120 |
| gcgtcctttc cacaagatat ataaacccaa gaaatcgaaa tactttcaag ttacggtaag | 180 |
| catatgatag tccatttaa aacataattt taaaactgca aactacccaa gaaattatta | 240 |
| cttctacgt cacgtatttt gtactaatat ctttgtgttt acagtcaaat taattctaat | 300 |
| tatctctcta acagccttgt atcgtatatg caaatatgaa ggaatcatgg gaaataggcc | 360 |
| ctcttcctgc ccgaccttgg cgcgcgctcg gcgcgcggtc acgctccgtc acgtggtgcg | 420 |
| ttttgtattc gagaccggta cctc | 444 |

<210> SEQ ID NO 66
<211> LENGTH: 5556
<212> TYPE: DNA
<213> ORGANISM: Artificial sequence
<220> FEATURE:
<223> OTHER INFORMATION: V3

<400> SEQUENCE: 66

| tattgtaata cggttatcca cagaatcagg ggataacgca ggaaagaaca tgtgagcaaa | 60 |
| aggccagcaa aaggccagga accgtaaaaa ggccgcgttg ctggcgtttt tccataggct | 120 |
| ccgcccccct gacgagcatc acaaaaatcg acgctcaagt cagaggtggc gaaacccgac | 180 |
| aggactataa agataccagg cgtttccccc tggaagctcc ctcgtgcgct ctcctgttcc | 240 |
| gaccctgccg cttaccggat acctgtccgc ctttctccct tcgggaagcg tggcgctttc | 300 |
| tcatagctca cgctgtaggt atctcagttc ggtgtaggtc gttcgctcca agctgggctg | 360 |
| tgtgcacgaa ccccccgttc agcccgaccg ctgcgcctta ccggtaact atcgtcttga | 420 |
| gtccaacccg gtaagacacg acttatcgcc actggcagca gccactggta acaggattag | 480 |
| cagagcgagg tatgtaggcg gtgctacaga gttcttgaag tggtggccta actacggcta | 540 |
| cactagaaga acagtatttg gtatctgcgc tctgctgaag ccagttacct tcggaaaaag | 600 |
| agttggtagc tcttgatccg gcaaacaaac caccgctggt agcggttttt ttgtttgcaa | 660 |
| gcagcagatt acgcgcagaa aaaaaggatc tcaagaagat cctttgatct tttctacggg | 720 |
| gtctgacgct cagtggaacg aaaactcacg ttaagggatt ttggtcatga gattatcaaa | 780 |
| aaggatcttc acctagatcc ttttaaatta aaaatgaagt tttaaatcaa tctaaagtat | 840 |
| atatgagtaa acttggtctg acagttacca atgcttaatc agtgaggcac ctatctcagc | 900 |
| gatctgtcta tttcgttcat ccatagttgc ctgactcccc gtcgtgtaga taactacgat | 960 |
| acgggagggc ttaccatctg gccccagtgc tgcaatgata ccgcgtgacc cacgctcacc | 1020 |

```
ggctccagat ttatcagcaa taaaccagcc agccggaagg gccgagcgca gaagtggtcc   1080
tgcaacttta tccgcctcca tccagtctat taattgttgc cgggaagcta gagtaagtag   1140
ttcgccagtt aatagtttgc gcaacgttgt tgccattgct acaggcatcg tggtgtcacg   1200
ctcgtcgttt ggtatggctt cattcagctc cggttcccaa cgatcaaggc gagttacatg   1260
atcccccatg ttgtgcaaaa aagcggttag ctccttcggt cctccgatcg ttgtcagaag   1320
taagttggcc gcagtgttat cactcatggt tatggcagca ctgcataatt ctcttactgt   1380
catgccatcc gtaagatgct tttctgtgac tggtgagtac tcaaccaagt cattctgaga   1440
atagtgtatg cggcgaccga gttgctcttg cccggcgtca atcgggata ataccgcgcc   1500
acatagcaga actttaaaag tgctcatcat tggaaaacgt tcttcggggc gaaaactctc   1560
aaggatctta ccgctgttga gatccagttc gatgtaaccc actcgtgcac ccaactgatc   1620
ttcagcatct tttactttca ccagcgtttc tgggtgagca aaaacaggaa ggcaaaatgc   1680
cgcaaaaaag gaataaaggg cgacacggaa atgttgaata ctcatactct tcctttttca   1740
atattattga agcatttatc agggttattg tctcatgagc ggatacatat ttgaatgtat   1800
ttagaaaaat aaacaaatag gggttccgcg cacatttccc cgaaaagtgc caaggaacca   1860
attcagtcga ctggatccta gttattaata gtaatcaatt acgggtcat tagttcatag   1920
cccatatatg gagttccgcg ttacataact tacggtaaat ggcccgcctg gctgaccgcc   1980
caacgacccc cgcccattga cgtcaataat gacgtatgtt cccatagtaa cgccaatagg   2040
gactttccat tgacgtcaat gggtggagta tttacggtaa actgcccact tggcagtaca   2100
tcaagtgtat catatgccaa gtacgccccc tattgacgtc aatgacggta aatggcccgc   2160
ctggcattat gcccagtaca tgaccttatg gactttcct acttggcagt acatctacgt   2220
attagtcatc gctattacca tggtgatgcg gttttggcag tacatcaatg ggcgtggata   2280
gcggtttgac tcacggggat ttccaagtct ccaccccatt gacgtcaatg ggagtttgtt   2340
ttggcaccaa aatcaacggg actttccaaa atgtcgtaac aactccgccc cattgacgca   2400
aatgggcggt aggcgtgtac ggtgggaggt ctatataagc agagctggtt tagtgaaccg   2460
tcagatcact agtcgactag gataacagg gcaccatgtc tagactggac aagagcaaag   2520
tcataaactc tgctctggaa ttactcaatg gagtcggtat cgaaggcctg acgacaagga   2580
aactcgctca aaagctggga gttgagcagc ctaccctgta ctggcacgtg aagaacaagc   2640
gggccctgct cgatgccctg ccaatcgaga tgctggacag gcatcatacc cactcctgcc   2700
ccctggaagg cgagtcatgg caagactttc tgcggaacaa cgccaagtca taccgctgtg   2760
ctctcctctc acatcgcgac ggggctaaag tgcatctcgg caccgccca acagagaaac   2820
agtacgaaac cctggaaaat cagctcgcgt tcctgtgtca gcaaggcttc ccctggaga   2880
acgcactgta cgctctgtcc gccgtgggcc actttacact gggctgcgta ttggaggaac   2940
aggagcatca gtagcaaaa gaggaaagag agacacctac caccgattct atgccccac   3000
ttctgaaaca agcaattgag ctgttcgacc ggcagggagc cgaacctgcc ttcctttccg   3060
gcctggaact aatcatatgt ggcctggaga aacagctaaa gtgcgaaagc ggcgggccga   3120
ccgacgccct tgacgatttt gacttagaca tgctcccagc cgatgccctt gacgactttg   3180
accttgatat gctgcctgct gacgctcttg acgattttga ccttgacatg ctccccgggt   3240
aatgatcgac tgtgccttct agttgccagc catctgttgt ttgcccctcc cccgtgcctt   3300
ccttgaccct ggaaggtgcc actcccactg tcctttccta ataaaatgag gaaattgcat   3360
```

| | |
|---|---:|
| cgcattgtct gagtaggtgt cattctattc tgggggtgg ggtggggcag gacagcaagg | 3420 |
| gggaggattg ggaggacaat agcaggcatg ctggggatgc ggtgggctct atggcttcgc | 3480 |
| tttcgtcttc aagaattcct ggagtttact ccctatcagt gatagagaac gtatgaagag | 3540 |
| tttactccct atcagtgata gagaacgtat gcagacttta ctccctatca gtgatagaga | 3600 |
| acgtataagg agtttactcc ctatcagtga tagagaacgt atgaccagtt tactccctat | 3660 |
| cagtgataga gaacgtatct acagtttact ccctatcagt gatagagaac gtatatccag | 3720 |
| tttactccct atcagtgata gagaacgtat aagctttagg cgtgtacggt gggcgcctat | 3780 |
| aaaagcagag ctcgtttagt gaaccgtcag atcgcctgga gcaattccac aacactttg | 3840 |
| tcttatacca actttccgta ccacttccta ccctcgtaaa ccagagcatg aaggtattcc | 3900 |
| ggcgcgcttg gcggcaccgg gtggcgctgg gcctaggcgg cctggcgttc tgcggcacca | 3960 |
| ctctgttgta cctggcgcgc tgcgcttccg agggcgagac gccctccgct tccggagccg | 4020 |
| ctcggccccg cgctaaggcc ttcctggcgg tgctggtggc cagtgcgccc cgcgcggtcg | 4080 |
| agcgccgcac cgcagtgcgc agcacgtggc tggcaccgga gaggcgtggc ggacccgagg | 4140 |
| acgtgtgggc gcgcttcgcc gtgggcactg gcggcttagg ctcggaggag cggcgcgctc | 4200 |
| ttgagctcga gcaggcgcag cacggggacc tgctgctgct gcccgccctg cgcgacgcct | 4260 |
| acgagaacct cacggccaag gtcctggcca tgctgacctg gctggatgag cgcgtggact | 4320 |
| tcgagttcgt gctcaaggcg gacgacgact cctttgcgcg cctggacgct atcctggtgg | 4380 |
| acctacgcgc acgggagccc gcacgccgcc ggcgcctcta ctgggcttc ttttccgggc | 4440 |
| gcgggcgcgt caagccggga ggtcgctggc gagaagcagc ctggcaactc tgcgactact | 4500 |
| acctgcccta cgcgttgggc ggtggctatg tcctttctgc ggacctggtg cattacctgc | 4560 |
| gcctcagccg cgagtacctg cgcgcgtggc acagtgaaga cgtatcgctg ggcacctggc | 4620 |
| tggcaccagt ggatgtgcaa cgggagcacg acccacgctt cgacacggag tacaaatctc | 4680 |
| gaggctgcaa caatcagtat ctggtgacac acaagcaaag cccagaggac atgttggaga | 4740 |
| agcaacagat gttgctgcat gagggccggt tgtgcaagca tgaggtgcaa cttcgccttt | 4800 |
| cctatgtcta tgactggtca gctccaccct cccagtgctg ccagcgcaag gagggcgttc | 4860 |
| cctgatgtca ccgcggggga ggctaactga acacggaag gagacaatac cggaaggaac | 4920 |
| ccgcgctatg acggcaataa aaagacagaa taaaacgcac ggtgttgggt cgtttgttca | 4980 |
| taaacgcggg gttcggtccc agggctggca ctctgtcgat accccaccga ggccccattg | 5040 |
| gggccaatac gcccgcgttt cttccttttc cccaccccac cccccaagtt cgggtgaagg | 5100 |
| cccagggctc gcagccaacg tcgggcggc aggccctgcc atagccacaa acagggtcga | 5160 |
| caagcttttc caaaaaaaaa gcatgaggtg cagttgcgcc tttcctatct cttgaatagg | 5220 |
| aaaggcgcaa ctgcacctca tgctggatcc cgcgtccttt ccacaagata tataaaccca | 5280 |
| agaaatcgaa atactttcaa gttacggtaa gcatatgata gtccatttta aaacataatt | 5340 |
| ttaaaactgc aaactaccca agaaattatt actttctacg tcacgtattt tgtactaata | 5400 |
| tctttgtgtt tacagtcaaa ttaattctaa ttatctctct aacagccttg tatcgtatat | 5460 |
| gcaaatatga aggaatcatg ggaaataggc cctcttcctg cccgaccttg gcgcgcgctc | 5520 |
| ggcgcgcggt cacgctccgt cacgtggtgc gttttg | 5556 |

<210> SEQ ID NO 67
<211> LENGTH: 34
<212> TYPE: DNA
<213> ORGANISM: Artificial sequence

```
<220> FEATURE:
<223> OTHER INFORMATION: LoxP1
<220> FEATURE:
<221> NAME/KEY: misc_feature
<222> LOCATION: (14)..(16)
<223> OTHER INFORMATION: n = a, t, c or g
<220> FEATURE:
<221> NAME/KEY: misc_feature
<222> LOCATION: (19)..(21)
<223> OTHER INFORMATION: n = a, t, c or g

<400> SEQUENCE: 67
ataacttcgt atannntann ntatacgaag ttat                           34

<210> SEQ ID NO 68
<211> LENGTH: 34
<212> TYPE: DNA
<213> ORGANISM: Artificial sequence
<220> FEATURE:
<223> OTHER INFORMATION: FRT Flp-FRT

<400> SEQUENCE: 68
gaagttccta ttctctagaa agtataggaa cttc                           34

<210> SEQ ID NO 69
<211> LENGTH: 50
<212> TYPE: DNA
<213> ORGANISM: Artificial sequence
<220> FEATURE:
<223> OTHER INFORMATION: tagBFP-Ctag GGGG BsaI CW

<400> SEQUENCE: 69
gaggtaccgg tctccggggt cggggagcga gctgattaag gagaacatgc          50

<210> SEQ ID NO 70
<211> LENGTH: 43
<212> TYPE: DNA
<213> ORGANISM: Artificial sequence
<220> FEATURE:
<223> OTHER INFORMATION: tagBFP-Ctag ATCA BsaI CCW

<400> SEQUENCE: 70
gaggtaccgg tctccatcat ccggaattaa gcttgtgccc cag                 43

<210> SEQ ID NO 71
<211> LENGTH: 45
<212> TYPE: DNA
<213> ORGANISM: Artificial sequence
<220> FEATURE:
<223> OTHER INFORMATION: ColE1-ori-2 TATT BsaI CW

<400> SEQUENCE: 71
gaggtaccgg tctcgtattg taatacggtt atccacagaa tcagg               45

<210> SEQ ID NO 72
<211> LENGTH: 42
<212> TYPE: DNA
<213> ORGANISM: Artificial sequence
<220> FEATURE:
<223> OTHER INFORMATION: AmpR-2 TCCT BsaI CCW

<400> SEQUENCE: 72
gaggtaccgg tctcgtcctt ggcactttc ggggaaatgt gc                   42

<210> SEQ ID NO 73
<211> LENGTH: 37
<212> TYPE: DNA
```

```
<213> ORGANISM: Artificial sequence
<220> FEATURE:
<223> OTHER INFORMATION: CMVp AGGA BsaI CW

<400> SEQUENCE: 73
gaggtaccgg tctcaaggaa ccaattcagt cgactgg                                37

<210> SEQ ID NO 74
<211> LENGTH: 42
<212> TYPE: DNA
<213> ORGANISM: Artificial sequence
<220> FEATURE:
<223> OTHER INFORMATION: CMVp GGTG BsaI CCW

<400> SEQUENCE: 74
gaggtaccgg tctcgggtgc cctgttatcc ctagtcgact ag                          42

<210> SEQ ID NO 75
<211> LENGTH: 39
<212> TYPE: DNA
<213> ORGANISM: Artificial sequence
<220> FEATURE:
<223> OTHER INFORMATION: hFUT3 CACC BsaI CW

<400> SEQUENCE: 75
gaggtaccgg tctcacacca tggatcccct gggtgcagc                              39

<210> SEQ ID NO 76
<211> LENGTH: 41
<212> TYPE: DNA
<213> ORGANISM: Artificial sequence
<220> FEATURE:
<223> OTHER INFORMATION: hFUT3 ATCA BsaI CCW

<400> SEQUENCE: 76
gaggtaccgg tctcgatcag gtgaaccaag ccgctatgct g                           41

<210> SEQ ID NO 77
<211> LENGTH: 36
<212> TYPE: DNA
<213> ORGANISM: Artificial sequence
<220> FEATURE:
<223> OTHER INFORMATION: BGH polyA CGAA BsaI CCW

<400> SEQUENCE: 77
gaggtaccgg tctcgcgaag ccatagagcc caccgc                                 36

<210> SEQ ID NO 78
<211> LENGTH: 40
<212> TYPE: DNA
<213> ORGANISM: Artificial sequence
<220> FEATURE:
<223> OTHER INFORMATION: shB3Galt6 TTCG BsaI CW

<400> SEQUENCE: 78
gaggtaccgg tctcattcga cagggtcgac aagcttttcc                             40

<210> SEQ ID NO 79
<211> LENGTH: 38
<212> TYPE: DNA
<213> ORGANISM: Artificial sequence
<220> FEATURE:
<223> OTHER INFORMATION: shB3Galt6 AATA BsaI CCW

<400> SEQUENCE: 79
gaggtaccgg tctcgaatac aaaacgcacc acgtgacg                               38
```

<210> SEQ ID NO 80
<211> LENGTH: 38
<212> TYPE: DNA
<213> ORGANISM: Artificial sequence
<220> FEATURE:
<223> OTHER INFORMATION: shB3Galt6 CTGG BsaI CCW

<400> SEQUENCE: 80
gaggtaccgg tctcgctggc aaaacgcacc acgtgacg                    38

<210> SEQ ID NO 81
<211> LENGTH: 39
<212> TYPE: DNA
<213> ORGANISM: Artificial sequence
<220> FEATURE:
<223> OTHER INFORMATION: Hygro CCAG BsaI CW

<400> SEQUENCE: 81
gaggtaccgg tctcaccagc aggcagaagt atgcaaagc                   39

<210> SEQ ID NO 82
<211> LENGTH: 47
<212> TYPE: DNA
<213> ORGANISM: Artificial sequence
<220> FEATURE:
<223> OTHER INFORMATION: Hygro AATA BsaI CCW

<400> SEQUENCE: 82
gaggtaccgg tctcgaatag atacattgat gagtttggac aaaccac          47

<210> SEQ ID NO 83
<211> LENGTH: 37
<212> TYPE: DNA
<213> ORGANISM: Artificial sequence
<220> FEATURE:
<223> OTHER INFORMATION: rosa26-5' AGGA BsaI CW

<400> SEQUENCE: 83
gaggtaccgg tctcaaggac cccgcggcag gccctcc                     37

<210> SEQ ID NO 84
<211> LENGTH: 43
<212> TYPE: DNA
<213> ORGANISM: Artificial sequence
<220> FEATURE:
<223> OTHER INFORMATION: rosa26-5' TTGT BsaI CCW

<400> SEQUENCE: 84
gaggtaccgg tctcgttgta agactggagt tgcagatcac gag              43

<210> SEQ ID NO 85
<211> LENGTH: 37
<212> TYPE: DNA
<213> ORGANISM: Artificial sequence
<220> FEATURE:
<223> OTHER INFORMATION: CMVp ACAA BsaI CW

<400> SEQUENCE: 85
gaggtaccgg tctcaacaaa ccaattcagt cgactgg                     37

<210> SEQ ID NO 86
<211> LENGTH: 47
<212> TYPE: DNA
<213> ORGANISM: Artificial sequence
<220> FEATURE:

```
<223> OTHER INFORMATION: Hygro CTAC BsaI CCW

<400> SEQUENCE: 86
gaggtaccgg tctcgctacg atacattgat gagtttggac aaaccac        47

<210> SEQ ID NO 87
<211> LENGTH: 39
<212> TYPE: DNA
<213> ORGANISM: Artificial sequence
<220> FEATURE:
<223> OTHER INFORMATION: rosa26-3' GTAG BsaI CW

<400> SEQUENCE: 87
gaggtaccgg tctcagtaga gatgggcggg agtcttctg                 39

<210> SEQ ID NO 88
<211> LENGTH: 49
<212> TYPE: DNA
<213> ORGANISM: Artificial sequence
<220> FEATURE:
<223> OTHER INFORMATION: rosa26-3' AATA BsaI CCW

<400> SEQUENCE: 88
gaggtaccgg tctcgaatag ataagctaga tgtcctaaat atttctatc      49

<210> SEQ ID NO 89
<211> LENGTH: 49
<212> TYPE: DNA
<213> ORGANISM: Artificial sequence
<220> FEATURE:
<223> OTHER INFORMATION: rosa26-3' GCAT BsaI CCW

<400> SEQUENCE: 89
gaggtaccgg tctcggcatg ataagctaga tgtcctaaat atttctatc      49

<210> SEQ ID NO 90
<211> LENGTH: 45
<212> TYPE: DNA
<213> ORGANISM: Artificial sequence
<220> FEATURE:
<223> OTHER INFORMATION: EF1a ATGC BsaI CW

<400> SEQUENCE: 90
gaggtaccgg tctcaatgca aggaaccaat tcagtcgact ggatc          45

<210> SEQ ID NO 91
<211> LENGTH: 42
<212> TYPE: DNA
<213> ORGANISM: Artificial sequence
<220> FEATURE:
<223> OTHER INFORMATION: EF1a GGGC BsaI CCW

<400> SEQUENCE: 91
gaggtaccgg tctcggggcc cctgttatcc ctagtcgact ag             42

<210> SEQ ID NO 92
<211> LENGTH: 37
<212> TYPE: DNA
<213> ORGANISM: Artificial sequence
<220> FEATURE:
<223> OTHER INFORMATION: TK GCCC BsaI CW

<400> SEQUENCE: 92
gaggtaccgg tctcagccca tggcttcgta cccctgc                   37
```

```
<210> SEQ ID NO 93
<211> LENGTH: 41
<212> TYPE: DNA
<213> ORGANISM: Artificial sequence
<220> FEATURE:
<223> OTHER INFORMATION: TK GCGG BsaI CCW

<400> SEQUENCE: 93
gaggtaccgg tctcggcggt cagttagcct cccccatctc c        41

<210> SEQ ID NO 94
<211> LENGTH: 40
<212> TYPE: DNA
<213> ORGANISM: Artificial sequence
<220> FEATURE:
<223> OTHER INFORMATION: HSVTKterm CCGC BsaI CW

<400> SEQUENCE: 94
gaggtaccgg tctcaccgcg ggggaggcta actgaaacac          40

<210> SEQ ID NO 95
<211> LENGTH: 37
<212> TYPE: DNA
<213> ORGANISM: Artificial sequence
<220> FEATURE:
<223> OTHER INFORMATION: HSVTKterm AATA BsaI CCW

<400> SEQUENCE: 95
gaggtaccgg tctcgaatag gctatggcag ggcctgc             37

<210> SEQ ID NO 96
<211> LENGTH: 44
<212> TYPE: DNA
<213> ORGANISM: Artificial sequence
<220> FEATURE:
<223> OTHER INFORMATION: TetOn3G CACC BsaI CW

<400> SEQUENCE: 96
gaggtaccgg tctcacacca tgtctagact ggacaagagc aaag     44

<210> SEQ ID NO 97
<211> LENGTH: 40
<212> TYPE: DNA
<213> ORGANISM: Artificial sequence
<220> FEATURE:
<223> OTHER INFORMATION: TetOn3G ATCA BsaI CCW

<400> SEQUENCE: 97
gaggtaccgg tctcaatcat tacccgggga gcatgtcaag          40

<210> SEQ ID NO 98
<211> LENGTH: 46
<212> TYPE: DNA
<213> ORGANISM: Artificial sequence
<220> FEATURE:
<223> OTHER INFORMATION: pTet3G TTCG BsaI CW

<400> SEQUENCE: 98
gaggtaccgg tctcattcgt cttcaagaat tcctcgagtt tactcc   46

<210> SEQ ID NO 99
<211> LENGTH: 43
<212> TYPE: DNA
<213> ORGANISM: Artificial sequence
<220> FEATURE:
<223> OTHER INFORMATION: pTet3G CTGG BsaI CCW
```

<400> SEQUENCE: 99
gaggtaccgg tctcgctggt ttacgagggt aggaagtggt acg         43

<210> SEQ ID NO 100
<211> LENGTH: 45
<212> TYPE: DNA
<213> ORGANISM: Artificial sequence
<220> FEATURE:
<223> OTHER INFORMATION: mB3Galt6 CCAG BsaI CW

<400> SEQUENCE: 100
gaggtaccgg tctcaccaga gcatgaaggt attccggcgc gcttg       45

<210> SEQ ID NO 101
<211> LENGTH: 43
<212> TYPE: DNA
<213> ORGANISM: Artificial sequence
<220> FEATURE:
<223> OTHER INFORMATION: mB3Galt6 GCGG BsaI CCW

<400> SEQUENCE: 101
gaggtaccgg tctcggcggt gacatcaggg aacgccctcc ttg         43

<210> SEQ ID NO 102
<211> LENGTH: 37
<212> TYPE: DNA
<213> ORGANISM: Artificial sequence
<220> FEATURE:
<223> OTHER INFORMATION: HSVTKterm TTGT BsaI CCW

<400> SEQUENCE: 102
gaggtaccgg tctcgttgtg gctatggcag ggcctgc               37

<210> SEQ ID NO 103
<211> LENGTH: 40
<212> TYPE: DNA
<213> ORGANISM: Artificial sequence
<220> FEATURE:
<223> OTHER INFORMATION: shB3Galt6 ACAA BsaI CW

<400> SEQUENCE: 103
gaggtaccgg tctcaacaaa cagggtcgac aagcttttcc            40

<210> SEQ ID NO 104
<211> LENGTH: 882
<212> TYPE: DNA
<213> ORGANISM: Artificial sequence
<220> FEATURE:
<223> OTHER INFORMATION: Ori BsaI A

<400> SEQUENCE: 104
gaggtaccgg tctcatattg taatacggtt atccacagaa tcaggggata acgcaggaaa    60
gaacatgtga gcaaaaggcc agcaaaaggc caggaaccgt aaaaaggccg cgttgctggc   120 gttttccat aggctccgcc cccctgacga gcatcacaaa aatcgacgct caagtcagag   180
gtggcgaaac ccgacaggac tataaagata ccaggcgttt ccccctggaa gctccctcgt   240
gcgctctcct gttccgaccc tgccgcttac cggatacctg tccgcctttc tcccttcggg   300
aagcgtggcg ctttctcata gctcacgctg taggtatctc agttcggtgt aggtcgttcg   360
ctccaagctg ggctgtgtgc acgaaccccc cgttcagccc gaccgctgcg ccttatccgg   420
taactatcgt cttgagtcca acccggtaag acacgactta tcgccactgg cagcagccac   480
tggtaacagg attagcagag cgaggtatgt aggcggtgct acagagttct tgaagtggtg   540

```
gcctaactac ggctacacta gaagaacagt atttggtatc tgcgctctgc tgaagccagt        600
taccttcgga aaaagagttg gtagctcttg atccggcaaa caaaccaccg ctggtagcgg        660
ttttttgttt tgcaagcagc agattacgcg cagaaaaaaa ggatctcaag aagatccttt        720
gatcttttct acgggtctg acgctcagtg aacgaaaac tcacgttaag ggattttggt        780
catgagatta tcaaaaagga tcttcaccta gatccttta aattaaaaat gaagttttaa        840
atcaatctaa agtatatatg agtttttatga gaccggtacc tc                         882

<210> SEQ ID NO 105
<211> LENGTH: 1038
<212> TYPE: DNA
<213> ORGANISM: Artificial sequence
<220> FEATURE:
<223> OTHER INFORMATION: AmpR BsaI A

<400> SEQUENCE: 105
gaggtaccgg tctcttttat tggtctgaca gttaccaatg cttaatcagt gaggcaccta         60
tctcagcgat ctgtctattt cgttcatcca tagttgcctg actccccgtc gtgtagataa        120
ctacgatacg ggagggctta ccatctggcc ccagtgctgc aatgatacccg cgtgacccac        180 gctcaccggc tccagattta tcagcaataa accagccagc cggaagggcc gagcgcagaa        240
gtggtcctgc aactttatcc gcctccatcc agtctattaa ttgttgccgg gaagctagag        300
taagtagttc gccagttaat agtttgcgca acgttgttgc cattgctaca ggcatcgtgg        360
tgtcacgctc gtcgtttggt atggcttcat tcagctccgg ttcccaacga tcaaggcgag        420
ttacatgatc ccccatgttg tgcaaaaaag cggttagctc cttcggtcct ccgatcgttg        480
tcagaagtaa gttggccgca gtgttatcac tcatggttat ggcagcactg cataattctc        540
ttactgtcat gccatccgta agatgctttt ctgtgactgg tgagtactca accaagtcat        600
tctgagaata gtgtatgcgg cgaccgagtt gctcttgccc ggcgtcaata cgggataata        660
ccgcgccaca tagcagaact ttaaaagtgc tcatcattgg aaaacgttct cggggcgaa        720 aactctcaag gatcttaccg ctgttgagat ccagttcgat gtaacccact cgtgcaccca        780
actgatcttc agcatctttt actttcacca gcgtttctgg gtgagcaaaa acaggaaggc        840
aaaatgccgc aaaaaaggga ataagggcga cacggaaatg ttgaatactc atactcttcc        900
tttttcaata ttattgaagc atttatcagg gttattgtct catgagcgga tacatatttg        960
aatgtattta gaaaaataaa caaatagggg ttccgcgcac atttccccga aaagtgccaa       1020
ggacgagacc ggtacctc                                                     1038

<210> SEQ ID NO 106
<211> LENGTH: 884
<212> TYPE: DNA
<213> ORGANISM: Artificial sequence
<220> FEATURE:
<223> OTHER INFORMATION: Ori BsaI B

<400> SEQUENCE: 106
gaggtaccgg tctctattac ggtaatacgg ttatccacag aatcagggga taacgcagga         60
aagaacatgt gagcaaaagg ccagcaaaag gccaggaacc gtaaaaaggc cgcgttgctg        120 gcgttttttcc ataggctccg ccccccctgac gagcatcaca aaaatcgacg ctcaagtcag        180
aggtggcgaa acccgacagg actataaaga taccaggcgt ttccccctgg aagctccctc        240
gtgcgctctc ctgttccgac cctgccgctt accggatacc tgtccgcctt tctcccttcg        300
```

| | |
|---|---|
| ggaagcgtgg cgctttctca tagctcacgc tgtaggtatc tcagttcggt gtaggtcgtt | 360 |
| cgctccaagc tgggctgtgt gcacgaaccc ccgttcagc ccgaccgctg cgccttatcc | 420 |
| ggtaactatc gtcttgagtc aacccggta agacacgact tatcgccact ggcagcagcc | 480 |
| actggtaaca ggattagcag agcgaggtat gtaggcggtg ctacagagtt cttgaagtgg | 540 |
| tggcctaact acggctacac tagaagaaca gtatttggta tctgcgctct gctgaagcca | 600 |
| gttaccttcg gaaaaagagt tggtagctct tgatccggca aacaaaccac cgctggtagc | 660 |
| ggtttttttg tttgcaagca gcagattacg cgcagaaaaa aaggatctca agaagatcct | 720 |
| ttgatctttt ctacggggtc tgacgctcag tggaacgaaa actcacgtta agggattttg | 780 |
| gtcatgagat tatcaaaaag gatcttcacc tagatccttt taaattaaaa atgaagtttt | 840 |
| aaatcaatct aaagtatata tgagtaaacc gagaccggta cctc | 884 |

<210> SEQ ID NO 107
<211> LENGTH: 1038
<212> TYPE: DNA
<213> ORGANISM: Artificial sequence
<220> FEATURE:
<223> OTHER INFORMATION: AmpR BsaI B

<400> SEQUENCE: 107

| | |
|---|---|
| gaggtaccgg tctcaaaact tggtctgaca gttaccaatg cttaatcagt gaggcaccta | 60 |
| tctcagcgat ctgtctattt cgttcatcca tagttgcctg actccccgtc gtgtagataa | 120 |
| ctacgatacg ggagggctta ccatctggcc ccagtgctgc aatgataccg cgtgacccac | 180 |
| gctcaccggc tccagattta tcagcaataa accagccagc cggaagggcc gagcgcagaa | 240 |
| gtggtcctgc aactttatcc gcctccatcc agtctattaa ttgttgccgg gaagctagag | 300 |
| taagtagttc gccagttaat agtttgcgca acgttgttgc cattgctaca ggcatcgtgg | 360 |
| tgtcacgctc gtcgtttggt atggcttcat tcagctccgg ttcccaacga tcaaggcgag | 420 |
| ttacatgatc ccccatgttg tgcaaaaaag cggttagctc cttcggtcct ccgatcgttg | 480 |
| tcagaagtaa gttggccgca gtgttatcac tcatggttat ggcagcactg cataattctc | 540 |
| ttactgtcat gccatccgta agatgctttt ctgtgactgg tgagtactca accaagtcat | 600 |
| tctgagaata gtgtatgcgg cgaccgagtt gctcttgccc ggcgtcaata cgggataata | 660 |
| ccgcgccaca tagcagaact ttaaaagtgc tcatcattgg aaaacgttct cggggcgaa | 720 |
| aactctcaag gatcttaccg ctgttgagat ccagttcgat gtaacccact cgtgcaccca | 780 |
| actgatcttc agcatctttt actttcacca gcgtttctgg gtgagcaaaa acaggaaggc | 840 |
| aaaatgccgc aaaaaaggga ataagggcga cacggaaatg ttgaatactc atactcttcc | 900 |
| tttttcaata ttattgaagc atttatcagg gttattgtct catgagcgga tacatatttg | 960 |
| aatgtattta gaaaaataaa caaataggg ttccgcgcac atttccccga aaagtgccaa | 1020 |
| tgctgagacc ggtacctc | 1038 |

<210> SEQ ID NO 108
<211> LENGTH: 1221
<212> TYPE: DNA
<213> ORGANISM: Artificial sequence
<220> FEATURE:
<223> OTHER INFORMATION: pEF1aL BsaI B

<400> SEQUENCE: 108

| | |
|---|---|
| gaggtaccgg tctcaatgcg tgaggctccg gtgcccgtca gtgggcagag cgcacatcgc | 60 |
| ccacagtccc cgagaagttg gggggagggg tcggcaattg aaccggtgcc tagagaaggt | 120 |

| | |
|---|---|
| ggcgcgggt aaactgggaa agtgatgtcg tgtactggct ccgcctttt cccgagggtg | 180 |
| ggggagaacc gtatataagt gcagtagtcg ccgtgaacgt tcttttcgc aacgggtttg | 240 |
| ccgccagaac acaggtaagt gccgtgtgtg gttcccgcgg gcctggcctc tttacgggtt | 300 |
| atggcccttg cgtgccttga attacttcca cctggctgca gtacgtgatt cttgatcccg | 360 |
| agcttcgggt tggaagtggg tgggagagtt cgaggccttg cgcttaagga gccccttcgc | 420 |
| ctcgtgcttg agttgaggcc tggcctgggc gctggggccg ccgcgtgcga atctggtggc | 480 |
| accttcgcgc ctgtctcgct gctttcgata agtctctagc catttaaaat ttttgatgac | 540 |
| ctgctgcgac gcttttttc tggcaagata gtcttgtaaa tgcgggccaa gatctgcaca | 600 |
| ctggtatttc ggttttggg gccgcgggcg gcgacggggc ccgtgcgtcc cagcgcacat | 660 |
| gttcggcgag gcggggcctg cgagcgcggc caccgagaat cggacggggg tagtctcaag | 720 |
| ctggccggcc tgctctggtg cctggcctcg cgccgccgtg tatcgccccg ccctgggcgg | 780 |
| caaggctggc ccgtcggca ccagttgcgt gagcggaaag atggccgctt ccggccctg | 840 |
| ctgcagggag ctcaaaatgg aggacgcggc gctcgggaga gcgggcgggt gagtcaccca | 900 |
| cacaaaggaa aagggccttt ccgtcctcag ccgtcgcttc atgtgactcc acggagtacc | 960 |
| gggcgccgtc caggcacctc gattagttct cgagcttttg gagtacgtcg tctttaggtt | 1020 |
| gggggagggg gttttatgcg atggagtttc cccacactga gtgggtggag actgaagtta | 1080 |
| ggccagcttg gcacttgatg taattctcct tggaatttgc ccttttgag tttggatctt | 1140 |
| ggttcattct caagcctcag acagtggttc aaagttttt tcttccattt caggtgtcgt | 1200 |
| gatatccgag accggtacct c | 1221 |

<210> SEQ ID NO 109
<211> LENGTH: 797
<212> TYPE: DNA
<213> ORGANISM: Artificial sequence
<220> FEATURE:
<223> OTHER INFORMATION: EGFP-CAAX BsaI A

<400> SEQUENCE: 109

| | |
|---|---|
| gaggtaccgg tctcctatca tggtgagcaa gggcgaggag ctgttcaccg gggtggtgcc | 60 |
| catcctggtc gagctggacg gcgacgtaaa cggccacaag ttcagcgtgt ccggcgaggg | 120 |
| cgagggcgat gccacctacg gcaagctgac cctgaagttc atctgcacca ccggcaagct | 180 |
| gcccgtgccc tggcccaccc tcgtgaccac cctgacctac ggcgtgcagt gcttcagccg | 240 |
| ctaccccgac cacatgaagc agcacgactt cttcaagtcc gccatgcccg aaggctacgt | 300 |
| ccaggagcgc accatcttct tcaaggacga cggcaactac aagacccgcg ccgaggtgaa | 360 |
| gttcgagggc gacaccctgg tgaaccgcat cgagctgaag ggcatcgact tcaaggagga | 420 |
| cggcaacatc ctggggcaca gctggagta caactacaac agccacaacg tctatatcat | 480 |
| ggccgacaag cagaagaacg gcatcaaggt gaacttcaag atccgccaca acatcgagga | 540 |
| cggcagcgtg cagctcgccg accactacca gcagaacacc cccatcggcg acggccccgt | 600 |
| gctgctgccc gacaaccact acctgagcac ccagtccgcc ctgagcaaag accccaacga | 660 |
| gaagcgcgat cacatggtcc tgctggagtt cgtgaccgcc gccgggatca ctctcggcat | 720 |
| ggacgagctg tacaagaaga agaaaaagaa gtcaaagaca aagtgtgtaa ttatgtaaga | 780 |
| gtggagaccg gtacctc | 797 |

<210> SEQ ID NO 110

<211> LENGTH: 266
<212> TYPE: DNA
<213> ORGANISM: Artificial sequence
<220> FEATURE:
<223> OTHER INFORMATION: BGHpA BsaI C

<400> SEQUENCE: 110

```
gaggtaccgg tctcagagtc gactgtgcct tctagttgcc agccatctgt tgtttgcccc      60
tcccccgtgc cttccttgac cctggaaggt gccactccca ctgtcctttc ctaataaaat    120
gaggaaattg catcgcattg tctgagtagg tgtcattcta ttctgggggg tggggtgggg    180
caggacagca aggggagga ttggaggac aatagcaggc atgctgggga tgcggtgggc      240
tctatgggta gcgagaccgg tacctc                                          266
```

<210> SEQ ID NO 111
<211> LENGTH: 624
<212> TYPE: DNA
<213> ORGANISM: Artificial sequence
<220> FEATURE:
<223> OTHER INFORMATION: pCMV BsaI D

<400> SEQUENCE: 111

```
gaggtaccgg tctcagtagt tattaatagt aatcaattac ggggtcatta gttcatagcc      60
catatatgga gttccgcgtt acataactta cggtaaatgg cccgcctggc tgaccgccca    120
acgacccccg cccattgacg tcaataatga cgtatgttcc catagtaacg ccaatgggga    180
ctttccattg acgtcaatgg gtggagtatt tacggtaaac tgcccacttg gcagtacatc    240
aagtgtatca tatgccaagt acgccccta ttgacgtcaa tgacggtaaa tggcccgcct     300
ggcattatgc ccagtacatg accttatggg actttcctac ttggcagtac atctacgtat    360
tagtcatcgc tattaccatg gtgatgcggt tttggcagta catcaatggg cgtggatagc    420
ggtttgactc acggggattt ccaagtctcc accccattga cgtcaatggg agtttgtttt    480
ggcaccaaaa tcaacgggac tttccaaaat gtcgtaacaa ctccgcccca ttgacgcaaa    540
tgggcggtag gcgtgtacgg tgggaggtct atataagcag agctggttta gtgaaccgtc    600
agatcttcgc gagaccggta cctc                                            624
```

<210> SEQ ID NO 112
<211> LENGTH: 380
<212> TYPE: DNA
<213> ORGANISM: Artificial sequence
<220> FEATURE:
<223> OTHER INFORMATION: SiaT BsaI B

<400> SEQUENCE: 112

```
gaggtaccgg tctccttcga tgattcacac caacctgaag aaaaagttca gctgctgcgt      60
cctggtcttt cttctgtttg cagtcatctg tgtgtggaag gaaaagaaga aagggagtta    120
ctatgattcc tttaaattgc aaaccaagga attccaggtg ttaaagagtc tggggaaatt    180
ggccatgggg tctgattccc agtctgtatc ctcaagcagc acccaggacc ccacagggga    240
ccgccagacc ctcggcagtc tcagaggcct agccaaggcc aaaccagagg cctccttcca    300
ggtgtggaac aaggacagct cttccaaaaa ccttatccct aggctgcaaa aggggtcggg    360
ggtgatgaga ccggtacctc                                                 380
```

<210> SEQ ID NO 113
<211> LENGTH: 742
<212> TYPE: DNA
<213> ORGANISM: Artificial sequence
<220> FEATURE:
<223> OTHER INFORMATION: mCherry BsaI B

<400> SEQUENCE: 113

```
gaggtaccgg tctcagtgag caagggcgag gaggataaca tggccatcat caaggagttc      60
atgcgcttca aggtgcacat ggagggctcc gtgaacggcc acgagttcga gatcgagggc     120
gagggcgagg ccgcccta cgagggcacc cagaccgcca agctgaaggt gaccaagggt      180
ggccccctgc ccttcgcctg ggacatcctg tcccctcagt tcatgtacgg ctccaaggcc     240
tacgtgaagc accccgccga catccccgac tacttgaagc tgtccttccc cgagggcttc     300
aagtgggagc gcgtgatgaa cttcgaggac ggcggcgtgg tgaccgtgac ccaggactcc     360
tccctgcagg acggcgagtt catctacaag gtgaagctgc gcggcaccaa cttcccctcc     420
gacggccccg taatgcagaa gaaaaccatg ggctgggagg cctcctccga gcggatgtac     480
cccgaggacg gcgccctgaa gggcgagatc aagcagaggc tgaagctgaa ggacggcggc     540
cactacgacg ctgaggtcaa gaccacctac aaggccaaga gcccgtgca gctgcccggc      600
gcctacaacg tcaacatcaa gttggacatc acctcccaca acgaggacta caccatcgtg     660
gaacagtacg aacgcgccga gggccgccac tccaccggcg gcatggacga gctgtacaag     720
taaccgctga gaccggtacc tc                                               742
```

<210> SEQ ID NO 114
<211> LENGTH: 1650
<212> TYPE: DNA
<213> ORGANISM: Artificial sequence
<220> FEATURE:
<223> OTHER INFORMATION: HygroR BsaI D

<400> SEQUENCE: 114

```
gaggtaccgg tctcaacaac aggcagaagt atgcaaagca tgcatctcaa ttagtcagca      60
accaggtgtg aaagtcccc aggctcccca gcaggcagaa gtatgcaaag catgcatctc      120
aattagtcag caaccatagt cccgccccta actccgccca tcccgcccct aactccgccc     180
agttccgccc attctccgcc ccatggctga ctaatttttt ttatttatgc agaggccgag     240
gccgcctctg cctctgagct attccagaag tagtgaggag gcttttttgg aggcctaggc     300
ttttgcaaaa agctcccggg agcttgtata tccattttcg gatctgatca gcacgtgatg     360
aaaaagcctg aactcaccgc gacgtctgtc gagaagtttc tgatcgaaaa gttcgacagc     420
gtgtccgacc tgatgcagct ctcggagggc gaagaatctc gtgctttcag cttcgatgta     480
ggagggcgtg gatatgtcct gcgggtaaat agctgcgccg atggtttcta caaagatcgt     540
tatgtttatc ggcactttgc atcggccgcg ctcccgattc cggaagtgct tgacattggg     600
gaattcagcg agagcctgac ctattgcatc tcccgccgtg cacagggtgt cacgttgcaa     660
gacttgcctg aaaccgaact gcccgctgtt ctgcagccgg tcgcggaggc catggatgcg     720
atcgctgcgg ccgatcttag ccagacgagc gggttcggcc cattcggacc gcaaggaatc     780
ggtcaataca ctacatggcg tgatttcata tgcgcgattg ctgatcccca tgtgtatcac     840
tggcaaactg tgatggacga caccgtcagt gcgtccgtcg cgcaggctct cgatgagctg     900
atgctttggg ccgaggactg ccccgaagtc cggcacctcg tgcacgcgga tttcggctcc     960
aacaatgtcc tgacggacaa tggccgcata acagcggtca ttgactggag cgaggcgatg    1020
ttcgggatt cccaatacga ggtcgccaac atcttcttct ggaggccgtg gttggcttgt    1080
atggagcagc agacgcgcta cttcgagcgg aggcatccgg agcttgcagg atcgccgcgg    1140
```

```
ctccgggcgt atatgctccg cattggtctt gaccaactct atcagagctt ggttgacggc    1200
aatttcgatg atgcagcttg ggcgcagggt cgatgcgacg caatcgtccg atccggagcc    1260
gggactgtcg ggcgtacaca aatcgcccgc agaagcgcgg ccgtctggac cgatggctgt    1320
gtagaagtac tcgccgatag tggaaaccga cgccccagca ctcgtccgag ggcaaaggaa    1380
tagcacgtgc tacgagattt cgattccacc gccgccttct atgaaaggtt gggcttcgga    1440
atcgttttcc gggacgccgg ctggatgatc ctccagcgcg gggatctcat gctggagttc    1500
ttcgcccacc ccaacttgtt tattgcagct tataatggtt acaaataaag caatagcatc    1560
acaaatttca caaataaagc attttttca ctgcattcta gttgtggttt gtccaaactc    1620
atcaatgtat cattacgaga ccggtacctc                                     1650
```

<210> SEQ ID NO 115
<211> LENGTH: 886
<212> TYPE: DNA
<213> ORGANISM: Artificial sequence
<220> FEATURE:
<223> OTHER INFORMATION: Ori-2 BsaI C

<400> SEQUENCE: 115

```
gaggtaccgg tctctggggc ggtaatacgg ttatccacag aatcagggga taacgcagga     60
aagaacatgt gagcaaaagg ccagcaaaag gccaggaacc gtaaaaaggc cgcgttgctg    120
gcgtttttcc ataggctccg ccccctgac gagcatcaca aaaatcgacg ctcaagtcag    180
aggtggcgaa acccgacagg actataaaga taccaggcgt ttccccctgg aagctccctc    240
gtgcgctctc ctgttccgac cctgccgctt accggatacc tgtccgcctt tctcccttcg    300
ggaagcgtgg cgctttctca tagctcacgc tgtaggtatc tcagttcggt gtaggtcgtt    360
cgctccaagc tgggctgtgt gcacgaaccc ccgttcagc ccgaccgctg cgccttatcc    420
ggtaactatc gtcttgagtc aacccggta agacacgact tatcgccact ggcagcagcc    480
actggtaaca ggattagcag agcgaggtat gtaggcggtg ctacagagtt cttgaagtgg    540
tggcctaact acggctacac tagaagaaca gtatttggta tctgcgctct gctgaagcca    600
gttaccttcg aaaaagagt tggtagctct tgatccggca acaaaccac cgctggtagc    660 ggttttttg tttgcaagca gcagattacg cgcagaaaaa aaggatctca agaagatcct    720
ttgatctttt ctacggggtc tgacgctcag tggaacgaaa actcacgtta agggattttg    780
gtcatgagat tatcaaaaag gatcttcacc tagatccttt taaattaaaa atgaagtttt    840
aaatcaatct aaagtatata tgagtttaaa ctgagaccgg tacctc                   886
```

<210> SEQ ID NO 116
<211> LENGTH: 1038
<212> TYPE: DNA
<213> ORGANISM: Artificial sequence
<220> FEATURE:
<223> OTHER INFORMATION: AmpR BsaI C

<400> SEQUENCE: 116

```
gaggtaccgg tctcaaaact ggtctgaca gttaccaatg cttaatcagt gaggcaccta     60
tctcagcgat ctgtctattt cgttcatcca tagttgcctg actccccgtc gtgtagataa    120
ctacgatacg ggagggctta ccatctggcc ccagtgctgc aatgataccg cgtgacccac    180
gctcaccggc tccagattta tcagcaataa accagccagc cggaagggcc gagcgcagaa    240
gtggtcctgc aactttatcc gcctccatcc agtctattaa ttgttgccgg gaagctagag    300
taagtagttc gccagttaat agtttgcgca acgttgttgc cattgctaca ggcatcgtgg    360
```

```
tgtcacgctc gtcgtttggt atggcttcat tcagctccgg ttcccaacga tcaaggcgag    420
ttacatgatc ccccatgttg tgcaaaaaag cggttagctc cttcggtcct ccgatcgttg    480
tcagaagtaa gttggccgca gtgttatcac tcatggttat ggcagcactg cataattctc    540
ttactgtcat gccatccgta agatgctttt ctgtgactgg tgagtactca accaagtcat    600
tctgagaata gtgtatgcgg cgaccgagtt gctcttgccc ggcgtcaata cgggataata    660
ccgcgccaca tagcagaact taaaagtgc tcatcattgg aaaacgttct tcggggcgaa     720
aactctcaag gatcttaccg ctgttgagat ccagttcgat gtaacccact cgtgcaccca    780
actgatcttc agcatctttt actttcacca gcgtttctgg gtgagcaaaa acaggaaggc    840
aaaatgccgc aaaaaaggga taagggcga cacggaaatg ttgaatactc atactcttcc     900
tttttcaata ttattgaagc atttatcagg gttattgtct catgagcgga tacatatttg    960
aatgtattta gaaaaataaa caaatagggg ttccgcgcac atttccccga aaagtgccag   1020
tgatgagacc ggtacctc                                                 1038

<210> SEQ ID NO 117
<211> LENGTH: 312
<212> TYPE: DNA
<213> ORGANISM: Artificial sequence
<220> FEATURE:
<223> OTHER INFORMATION: MNN10-Lrec BsaI A

<400> SEQUENCE: 117
gaggtaccgg tctctgtgag tttaaacatg cattcaaagg tcataattgc tgctctattt     60
acagtcgtcc ataatgacat ttctctttga ttattttctt gttttttcgc tcttctcaag    120
tggatgttac ataacaaaca aaacagaaaa aattgtttaa atataaagtt taaaagttat    180
ctttgattcc gcacctgaat ttttggattg aaggccaaag gaggtttatc agggagagaa    240
aagctctcta tttatttttta taaggaataa ttgtgcatgt acaactatac aattgcgtga    300
gaccggtacc tc                                                        312

<210> SEQ ID NO 118
<211> LENGTH: 650
<212> TYPE: DNA
<213> ORGANISM: Artificial sequence
<220> FEATURE:
<223> OTHER INFORMATION: MNN10-Rrec BsaI A

<400> SEQUENCE: 118
gaggtaccgg tctcttcgta atggaagtta tcaatattgt aaagagaagc atttacaagc     60
ttttattttt cttttttaatt tccactactg gttctgcttt aaaatgttgt tttataattt    120
atgtacattt aggcctatag aagattcttt caataatatg ctacacattc ttttattttt    180
ccatcatatg ttggagttta tgcctcctcg gcaggagttg ggcggtgcga agagaagaaa    240
aagagtgaaa ctaaaaaaag gaatctgcct ttgcataagt tcaaagtgc aattttagtg     300 ttggatttaa acgggaaaaa ttgaaatggc catcgaaaca atacttgtaa taaacaaatc    360
aggcggacta atctatcagc ggaattttac caacgacgaa cagaaattga acagcaatga    420
atacttaatt cttgctagta cactgcacgg tgtattcgcc atcgcgagcc agctgactcc    480
gaaggcatta cagctaactc aacaaacgaa catcgaaaat accatcccat atatacctta    540
cgtgggcatg tccagcaata ggagcgatac aagaaatgga ggtggcaata acaacaaaca    600
cactaataat gaaaaactgg gcagtttaaa cggggagaga ccggtacctc                650
```

<210> SEQ ID NO 119
<211> LENGTH: 1630
<212> TYPE: DNA
<213> ORGANISM: Artificial sequence
<220> FEATURE:
<223> OTHER INFORMATION: KanMX BsaI A

<400> SEQUENCE: 119

```
gaggtaccgg tctcgtgcgg tacgctgcag gtcgacaacc cttaatataa cttcgtataa     60
tgtatgctat acgaagttat taggtctaga gatctgttta gcttgcctcg tccccgccgg    120
gtcacccggc cagcgacatg gaggcccaga ataccctcct tgacagtctt gacgtgcgca    180
gctcaggggc atgatgtgac tgtcgcccgt acatttagcc catacatccc catgtataat    240
catttgcatc catacatttt gatggccgca cggcgcgaag caaaaattac ggctcctcgc    300
tgcagacctg cgagcaggga aacgctcccc tcacagacgc gttgaattgt ccccacgccg    360
cgccctgta gagaaatata aaaggttagg atttgccact gaggttcttc tttcatatac    420
ttccttttaa aatcttgcta ggatacagtt ctcacatcac atccgaacat aaacaaccat    480
gggtaaggaa aagactcacg tttcgaggcc gcgattaaat tccaacatgg atgctgattt    540
atatgggtat aaatgggctc gcgataatgt cgggcaatca ggtgcgacaa tctatcgatt    600
gtatgggaag cccgatgcgc cagagttgtt tctgaaacat ggcaaaggta gcgttgccaa    660
tgatgttaca gatgagatgg tcagactaaa ctggctgacg gaatttatgc ctcttccgac    720
catcaagcat tttatccgta ctcctgatga tgcatggtta ctcaccactg cgatccccgg    780
caaaacagca ttccaggtat tagaagaata tcctgattca ggtgaaaata ttgttgatgc    840
gctggcagtg ttcctgcgcc ggttgcattc gattcctgtt tgtaattgtc cttttaacag    900
cgatcgcgta tttcgtctcg ctcaggcgca atcacgaatg aataacggtt tggttgatgc    960
gagtgatttt gatgacgagc gtaatggctg gcctgttgaa caagtctgga agaaatgca   1020
taagcttttg ccattctcac cggattcagt cgtcactcat ggtgatttct cacttgataa   1080
ccttattttt gacgagggga attaataggt tgtattgat gttggacgag tcggaatcgc   1140
agaccgatac caggatcttg ccatcctatg gaactgcctc ggtgagtttt ctccttcatt   1200
acagaaacgg ctttttcaaa aatatggtat tgataatcct gatatgaata aattgcagtt   1260
tcatttgatg ctcgatgagt ttttctaatc agtactgaca ataaaaagat tcttgttttc   1320
aagaacttgt catttgtata gttttttat attgtagttg ttctatttta atcaaatgtt   1380
agcgtgattt atatttttt tcgcctcgac atcatctgcc cagatgcgaa gttaagtgcg   1440
cagaaagtaa tatcatgcgt caatcgtatg tgaatgctgg tcgctatact gctgtcgatt   1500
cgatactaac gccgccatcc agtgtcgaaa acgagctctc gagaacccctt aatataactt   1560
cgtataatgt atgctatacg aagttattag gtgatatcag atccactagt gtcgtagaga   1620
ccggtacctc                                                         1630
```

<210> SEQ ID NO 120
<211> LENGTH: 49
<212> TYPE: DNA
<213> ORGANISM: Artificial sequence
<220> FEATURE:
<223> OTHER INFORMATION: ColE1-ori TAAA BsaI CCW

<400> SEQUENCE: 120

```
gaggtaccgg tctcataaaa ctcatatata ctttagattg atttaaaac                49
```

```
<210> SEQ ID NO 121
<211> LENGTH: 47
<212> TYPE: DNA
<213> ORGANISM: Artificial sequence
<220> FEATURE:
<223> OTHER INFORMATION: AmpR TTTA BsaI CW

<400> SEQUENCE: 121
gaggtaccgg tctcttttat tggtctgaca gttaccaatg cttaatc         47

<210> SEQ ID NO 122
<211> LENGTH: 49
<212> TYPE: DNA
<213> ORGANISM: Artificial sequence
<220> FEATURE:
<223> OTHER INFORMATION: ColE1-ori GTTT BsaI CCW

<400> SEQUENCE: 122
gaggtaccgg tctcggttta ctcatatata ctttagattg atttaaaac       49

<210> SEQ ID NO 123
<211> LENGTH: 40
<212> TYPE: DNA
<213> ORGANISM: Artificial sequence
<220> FEATURE:
<223> OTHER INFORMATION: ColE1-ori 2 ATTA BsaI CW

<400> SEQUENCE: 123
gaggtaccgg tctctattac ggtaatacgg ttatccacag                 40

<210> SEQ ID NO 124
<211> LENGTH: 42
<212> TYPE: DNA
<213> ORGANISM: Artificial sequence
<220> FEATURE:
<223> OTHER INFORMATION: AmpR 2 GCAT BsaI CCW

<400> SEQUENCE: 124
gaggtaccgg tctcagcatt ggcactttc ggggaaatgt gc               42

<210> SEQ ID NO 125
<211> LENGTH: 47
<212> TYPE: DNA
<213> ORGANISM: Artificial sequence
<220> FEATURE:
<223> OTHER INFORMATION: AmpR AAAC BsaI CW

<400> SEQUENCE: 125
gaggtaccgg tctcaaaact tggtctgaca gttaccaatg cttaatc         47

<210> SEQ ID NO 126
<211> LENGTH: 40
<212> TYPE: DNA
<213> ORGANISM: Artificial sequence
<220> FEATURE:
<223> OTHER INFORMATION: EF1ap GATA BsaI CCW

<400> SEQUENCE: 126
gaggtaccgg tctcggatat cacgacacct gaaatggaag                 40

<210> SEQ ID NO 127
<211> LENGTH: 39
<212> TYPE: DNA
<213> ORGANISM: Artificial sequence
<220> FEATURE:
<223> OTHER INFORMATION: EF1apL ATGC BsaI CW
```

```
<400> SEQUENCE: 127
gaggtaccgg tctcaatgcg tgaggctccg gtgcccgtc                                 39

<210> SEQ ID NO 128
<211> LENGTH: 81
<212> TYPE: DNA
<213> ORGANISM: Artificial sequence
<220> FEATURE:
<223> OTHER INFORMATION: EGFP-CAAX ACTC BsaI CCW

<400> SEQUENCE: 128
gaggtaccgg tctccactct tacataatta cacactttgt ctttgacttc ttttcttct           60 tcttgtacag ctcgtccatg c                                                   81

<210> SEQ ID NO 129
<211> LENGTH: 38
<212> TYPE: DNA
<213> ORGANISM: Artificial sequence
<220> FEATURE:
<223> OTHER INFORMATION: EGFP TATC BsaI CW

<400> SEQUENCE: 129
gaggtaccgg tctcctatca tggtgagcaa gggcgagg                                 38

<210> SEQ ID NO 130
<211> LENGTH: 39
<212> TYPE: DNA
<213> ORGANISM: Artificial sequence
<220> FEATURE:
<223> OTHER INFORMATION: BGHpA CTAC BsaI CCW 2

<400> SEQUENCE: 130
gaggtaccgg tctcgctacc catagagccc accgcatcc                                39

<210> SEQ ID NO 131
<211> LENGTH: 40
<212> TYPE: DNA
<213> ORGANISM: Artificial sequence
<220> FEATURE:
<223> OTHER INFORMATION: BGHpA GAGT BsaI CW

<400> SEQUENCE: 131
gaggtaccgg tctcagagtc gactgtgcct tctagttgcc                               40

<210> SEQ ID NO 132
<211> LENGTH: 42
<212> TYPE: DNA
<213> ORGANISM: Artificial sequence
<220> FEATURE:
<223> OTHER INFORMATION: CMVp CGAA BsaI CCW

<400> SEQUENCE: 132
gaggtaccgg tctcgcgaag atctgacggt tcactaaacc ag                            42

<210> SEQ ID NO 133
<211> LENGTH: 46
<212> TYPE: DNA
<213> ORGANISM: Artificial sequence
<220> FEATURE:
<223> OTHER INFORMATION: CMVp GTAG BsaI CW

<400> SEQUENCE: 133
gaggtaccgg tctcagtagt tattaatagt aatcaattac ggggtc                        46
```

-continued

```
<210> SEQ ID NO 134
<211> LENGTH: 37
<212> TYPE: DNA
<213> ORGANISM: Artificial sequence
<220> FEATURE:
<223> OTHER INFORMATION: SiaT TCAC BsaI CCW

<400> SEQUENCE: 134
gaggtaccgg tctcatcacc cccgacccct tttgcag                    37

<210> SEQ ID NO 135
<211> LENGTH: 46
<212> TYPE: DNA
<213> ORGANISM: Artificial sequence
<220> FEATURE:
<223> OTHER INFORMATION: SiaT TTCG BsaI CW

<400> SEQUENCE: 135
gaggtaccgg tctccttcga tgattcacac caacctgaag aaaaag         46

<210> SEQ ID NO 136
<211> LENGTH: 42
<212> TYPE: DNA
<213> ORGANISM: Artificial sequence
<220> FEATURE:
<223> OTHER INFORMATION: XFP-Ctag GCGG BsaI CCW

<400> SEQUENCE: 136
gaggtaccgg tctcagcggt tacttgtaca gctcgtccat gc              42

<210> SEQ ID NO 137
<211> LENGTH: 33
<212> TYPE: DNA
<213> ORGANISM: Artificial sequence
<220> FEATURE:
<223> OTHER INFORMATION: XFP-Ctag GTGA BsaI CW

<400> SEQUENCE: 137
gaggtaccgg tctcagtgag caagggcgag gag                        33

<210> SEQ ID NO 138
<211> LENGTH: 47
<212> TYPE: DNA
<213> ORGANISM: Artificial sequence
<220> FEATURE:
<223> OTHER INFORMATION: Hygro TAAT BsaI CCW

<400> SEQUENCE: 138
gaggtaccgg tctcgtaatg atacattgat gagtttggac aaaccac         47

<210> SEQ ID NO 139
<211> LENGTH: 39
<212> TYPE: DNA
<213> ORGANISM: Artificial sequence
<220> FEATURE:
<223> OTHER INFORMATION: Hygro ACAA BsaI CW

<400> SEQUENCE: 139
gaggtaccgg tctcaacaac aggcagaagt atgcaaagc                  39

<210> SEQ ID NO 140
<211> LENGTH: 51
<212> TYPE: DNA
<213> ORGANISM: Artificial sequence
<220> FEATURE:
<223> OTHER INFORMATION: ColE1-ori 2 GTTT BsaI CCW
```

<400> SEQUENCE: 140
gaggtaccgg tctcagttta aactcatata tactttagat tgatttaaaa c        51

<210> SEQ ID NO 141
<211> LENGTH: 40
<212> TYPE: DNA
<213> ORGANISM: Artificial sequence
<220> FEATURE:
<223> OTHER INFORMATION: ColE1-ori 2 GGGG BsaI CW

<400> SEQUENCE: 141
gaggtaccgg tctctggggc ggtaatacgg ttatccacag        40

<210> SEQ ID NO 142
<211> LENGTH: 42
<212> TYPE: DNA
<213> ORGANISM: Artificial sequence
<220> FEATURE:
<223> OTHER INFORMATION: AmpR 2 TCAC BsaI CCW

<400> SEQUENCE: 142
gaggtaccgg tctcatcact ggcactttc ggggaaatgt gc        42

<210> SEQ ID NO 143
<211> LENGTH: 49
<212> TYPE: DNA
<213> ORGANISM: Artificial sequence
<220> FEATURE:
<223> OTHER INFORMATION: MNN10Lrec CGCA BsaI CCW

<400> SEQUENCE: 143
gaggtaccgg tctcacgcaa ttgtatagtt gtacatgcac aattattcc        49

<210> SEQ ID NO 144
<211> LENGTH: 52
<212> TYPE: DNA
<213> ORGANISM: Artificial sequence
<220> FEATURE:
<223> OTHER INFORMATION: MNN10Lrec GTGA BsaI CW

<400> SEQUENCE: 144
gaggtaccgg tctctgtgag tttaaacatg cattcaaagg tcataattgc tg        52

<210> SEQ ID NO 145
<211> LENGTH: 52
<212> TYPE: DNA
<213> ORGANISM: Artificial sequence
<220> FEATURE:
<223> OTHER INFORMATION: MNN10Rrec CCCC BsaI CCW

<400> SEQUENCE: 145
gaggtaccgg tctctccccg tttaaactgc ccagttttc attattagtg tg        52

<210> SEQ ID NO 146
<211> LENGTH: 50
<212> TYPE: DNA
<213> ORGANISM: Artificial sequence
<220> FEATURE:
<223> OTHER INFORMATION: MNN10Rrec TCGT BsaI CW

<400> SEQUENCE: 146
gaggtaccgg tctcttcgta atggaagtta tcaatattgt aaagagaagc        50

<210> SEQ ID NO 147
<211> LENGTH: 41

```
<212> TYPE: DNA
<213> ORGANISM: Artificial sequence
<220> FEATURE:
<223> OTHER INFORMATION: KanMX ACGA BsaI  CCW

<400> SEQUENCE: 147
gaggtaccgg tctctacgac actagtggat ctgatatcac c                    41

<210> SEQ ID NO 148
<211> LENGTH: 40
<212> TYPE: DNA
<213> ORGANISM: Artificial sequence
<220> FEATURE:
<223> OTHER INFORMATION: KanMX TGCG BsaI  CW

<400> SEQUENCE: 148
gaggtaccgg tctcgtgcgg tacgctgcag gtcgacaacc                      40

<210> SEQ ID NO 149
<211> LENGTH: 5146
<212> TYPE: DNA
<213> ORGANISM: Artificial sequence
<220> FEATURE:
<223> OTHER INFORMATION: V2b

<400> SEQUENCE: 149
tattgtaata cggttatcca cagaatcagg ggataacgca ggaaagaaca tgtgagcaaa    60
aggccagcaa aaggccagga accgtaaaaa ggccgcgttg ctggcgtttt tccataggct   120
ccgcccccct gacgagcatc acaaaaatcg acgctcaagt cagaggtggc gaaacccgac   180
aggactataa agataccagg cgtttccccc tggaagctcc ctcgtgcgct ctcctgttcc   240
gaccctgccg cttaccggat acctgtccgc ctttctccct tcgggaagcg tggcgctttc   300
tcatagctca cgctgtaggt atctcagttc ggtgtaggtc gttcgctcca agctgggctg   360
tgtgcacgaa ccccccgttc agcccgaccg ctgcgcctta tccggtaact atcgtcttga   420
gtccaacccg gtaagacacg acttatcgcc actggcagca gccactggta acaggattag   480
cagagcgagg tatgtaggcg gtgctacaga gttcttgaag tggtggccta actacggcta   540
cactagaaga acagtatttg gtatctgcgc tctgctgaag ccagttacct tcggaaaaag   600
agttggtagc tcttgatccg gcaaacaaac caccgctggt agcggttttt tgtttgcaa   660 gcagcagatt acgcgcagaa aaaaaggatc tcaagaagat cctttgatct tttctacggg   720
gtctgacgct cagtggaacg aaaactcacg ttaagggatt ttggtcatga gattatcaaa   780
aaggatcttc acctagatcc ttttaaatta aaaatgaagt tttaaatcaa tctaaagtat   840
atatgagttt tattggtctg acagttacca atgcttaatc agtgaggcac ctatctcagc   900
gatctgtcta tttcgttcat ccatagttgc ctgactcccc gtcgtgtaga taactacgat   960
acgggagggc ttaccatctg gccccagtgc tgcaatgata ccgcgtgacc cacgctcacc  1020
ggctccagat ttatcagcaa taaaccagcc agccggaagg gccgagcgca gaagtggtcc  1080
tgcaacttta tccgcctcca tccagtctat taattgttgc cgggaagcta gagtaagtag  1140
ttcgccagtt aatagtttgc gcaacgttgt tgccattgct acaggcatcg tggtgtcacg  1200
ctcgtcgttt ggtatggctt cattcagctc cggttcccaa cgatcaaggc gagttacatg  1260
atcccccatg ttgtgcaaaa aagcggttag ctccttcggt cctccgatcg ttgtcagaag  1320
taagttggcc gcagtgttat cactcatggt tatggcagca ctgcataatt ctcttactgt  1380
catgccatcc gtaagatgct tttctgtgac tggtgagtac tcaaccaagt cattctgaga  1440
```

```
atagtgtatg cggcgaccga gttgctcttg cccggcgtca atacgggata ataccgcgcc    1500
acatagcaga actttaaaag tgctcatcat tggaaaacgt tcttcgggcc gaaaactctc    1560
aaggatctta ccgctgttga gatccagttc gatgtaaccc actcgtgcac ccaactgatc    1620
ttcagcatct tttactttca ccagcgtttc tgggtgagca aaaacaggaa ggcaaaatgc    1680
cgcaaaaaag ggaataaggg cgacacggaa atgttgaata ctcatactct tccttttcca    1740
atattattga agcatttatc agggttattg tctcatgagc ggatacatat ttgaatgtat    1800
ttagaaaaat aaacaaatag gggttccgcg cacatttccc cgaaaagtgc caaggaacca    1860
attcagtcga ctggatccta gttattaata gtaatcaatt acgggtcat tagttcatag    1920 cccatatatg gagttccgcg ttacataact tacggtaaat ggcccgcctg gctgaccgcc    1980
caacgacccc cgcccattga cgtcaataat gacgtatgtt cccatagtaa cgccaatagg    2040
gactttccat tgacgtcaat gggtggagta tttacggtaa actgcccact tggcagtaca    2100
tcaagtgtat catatgccaa gtacgccccc tattgacgtc aatgacggta atggcccgc     2160 ctggcattat gcccagtaca tgaccttatg gactttcct acttggcagt acatctacgt    2220
attagtcatc gctattacca tggtgatgcg gttttggcag tacatcaatg ggcgtggata    2280
gcggtttgac tcacggggat ttccaagtct ccacccatt gacgtcaatg ggagtttgtt    2340
ttggcaccaa aatcaacggg actttccaaa atgtcgtaac aactccgccc cattgacgca    2400
aatgggcggt aggcgtgtac ggtgggaggt ctatataagc agagctggtt tagtgaaccg    2460
tcagatcact agtcgactag gataacagg gcaccatgtc tagactggac aagagcaaag    2520
tcataaactc tgctctggaa ttactcaatg gagtcggtat cgaaggcctg acgacaagga    2580
aactcgctca aaagctggga gttgagcagc ctaccctgta ctggcacgtg aagaacaagc    2640
gggccctgct cgatgccctg ccaatcgaga tgctggacag gcatcatacc cactcctgcc    2700
ccctggaagg cgagtcatgg caagactttc tgcggaacaa cgccaagtca taccgctgtg    2760
ctctcctctc acatcgcgac ggggctaaag tgcatctcgg cacccgccca acagagaaac    2820
agtacgaaac cctggaaaat cagctcgcgt tcctgtgtca gcaaggcttc tccctggaga    2880
acgcactgta cgctctgtcc gccgtgggcc actttacact gggctgcgta ttggaggaac    2940
aggagcatca agtagcaaaa gaggaaagag agacacctac caccgattct atgccccac    3000 ttctgaaaca agcaattgag ctgttcgacc ggcagggagc cgaacctgcc ttcctttcg     3060 gcctggaact aatcatatgt ggcctggaga aacagctaaa gtgcgaaagc ggcgggccga    3120
ccgacgccct tgacgatttt gacttagaca tgctcccagc cgatgccctt gacgactttg    3180
accttgatat gctgcctgct gacgctcttg acgattttga ccttgacatg ctccccgggt    3240
aatgatcgac tgtgccttct agttgccagc catctgttgt ttgcccctcc cccgtgcctt    3300
ccttgaccct ggaaggtgcc actcccactg tccttttccta ataaaatgag gaaattgcat    3360
cgcattgtct gagtaggtgt cattctattc tggggggtgg ggtggggcag gacagcaagg    3420
gggaggattg ggaggacaat agcaggcatg ctggggatgc ggtgggctct atggcttcgc    3480
tttcgtcttc aagaattcct ggagtttact ccctatcagt gatagagaac gtatgaagag    3540
tttactccct atcagtgata gagaacgtat gcagacttta ctccctatca gtgatagaga    3600
acgtataagg agtttactcc ctatcagtga tagagaacgt atgaccagtt tactccctat    3660
cagtgataga gaacgtatct acagtttact ccctatcagt gatagagaac gtatatccag    3720
tttactccct atcagtgata gagaacgtat aagcttagg cgtgtacggt gggcgcctat     3780
aaaagcagag ctcgtttagt gaaccgtcag atcgcctgga gcaattccac aacacttttg    3840
```

```
tcttatacca actttccgta ccacttccta ccctcgtaaa ccagagcatg aaggtattcc    3900
ggcgcgcttg gcggcaccgg gtggcgctgg gcctaggcgg cctggcgttc tgcggcacca    3960
ctctgttgta cctggcgcgc tgcgcttccg agggcgagac gccctccgct tccggagccg    4020
ctcggccccg cgctaaggcc ttcctggcgg tgctggtggc cagtgcgccc cgcgcggtcg    4080
agcgccgcac cgcagtgcgc agcacgtggc tggcaccgga gaggcgtggc ggacccgagg    4140
acgtgtgggc gcgcttcgcc gtgggcactg gcggcttagg ctcggaggag cggcgcgctc    4200
ttgagctcga gcaggcgcag cacggggacc tgctgctgct gcccgccctg cgcgacgcct    4260
acgagaacct cacggccaag gtcctggcca tgctgacctg gctggatgag cgcgtggact    4320
tcgagttcgt gctcaaggcg gacgacgact cctttgcgcg cctggacgct atcctggtgg    4380
acctacgcgc acgggagccc gcacgccgcc ggcgcctcta ctggggcttc ttttccgggc    4440
gcgggcgcgt caagccggga ggtcgctggc gagaagcagc ctggcaactc tgcgactact    4500
acctgcccta cgcgttgggc ggtggctatg tcctttctgc ggacctggtg cattacctgc    4560
gcctcagccg cgagtacctg cgcgcgtggc acagtgaaga cgtatcgctg ggcacctggc    4620
tggcaccagt ggatgtgcaa cgggagcacg acccacgctt cgacacggag tacaaatctc    4680
gaggctgcaa caatcagtat ctggtgacac acaagcaaag cccagaggac atgttggaga    4740
agcaacagat gttgctgcat gagggccggt tgtgcaagca tgaggtgcaa cttcgccttt    4800
cctatgtcta tgactggtca gctccaccct cccagtgctg ccagcgcaag gagggcgttc    4860
cctgatgtca ccgcggggga ggctaactga aacacggaag gagacaatac cggaaggaac    4920
ccgcgctatg acggcaataa aaagacagaa taaaacgcac ggtgttgggt cgtttgttca    4980
taaacgcggg gttcggtccc agggctggca ctctgtcgat accccaccga ggccccattg    5040
gggccaatac gcccgcgttt cttccttttc cccaccccac cccccaagtt cgggtgaagg    5100
cccagggctc gcagccaacg tcgggcggc aggccctgcc atagcc    5146
```

<210> SEQ ID NO 150
<211> LENGTH: 5556
<212> TYPE: DNA
<213> ORGANISM: Artificial sequence
<220> FEATURE:
<223> OTHER INFORMATION: V3b

<400> SEQUENCE: 150

```
tattgtaata cggttatcca cagaatcagg ggataacgca ggaaagaaca tgtgagcaaa      60
aggccagcaa aaggccagga accgtaaaaa ggccgcgttg ctggcgtttt tccataggct     120
ccgcccccct gacgagcatc acaaaaatcg acgctcaagt cagaggtggc gaaacccgac     180
aggactataa agataccagg cgtttccccc tggaagctcc ctcgtgcgct ctcctgttcc     240
gaccctgccg cttaccggat acctgtccgc ctttctccct tcgggaagcg tggcgctttc     300
tcatagctca cgctgtaggt atctcagttc ggtgtaggtc gttcgctcca agctgggctg     360
tgtgcacgaa ccccccgttc agcccgaccg ctgcgcctta ccggtaact atcgtcttga     420 gtccaacccg gtaagacacg acttatcgcc actggcagca gccactggta acaggattag     480
cagagcgagg tatgtaggcg gtgctacaga gttcttgaag tggtggccta actacggcta     540
cactagaaga acagtatttg gtatctgcgc tctgctgaag ccagttacct tcggaaaaag     600
agttggtagc tcttgatccg gcaaacaaac caccgctggt agcggttttt ttgtttgcaa     660
gcagcagatt acgcgcagaa aaaaggatc tcaagaagat cctttgatct tttctacggg     720
```

```
gtctgacgct cagtggaacg aaaactcacg ttaagggatt ttggtcatga gattatcaaa    780
aaggatcttc acctagatcc tttttaaatta aaaatgaagt tttaaatcaa tctaaagtat    840
atatgagttt tattggtctg acagttacca atgcttaatc agtgaggcac ctatctcagc    900
gatctgtcta tttcgttcat ccatagttgc ctgactcccc gtcgtgtaga taactacgat    960
acgggagggc ttaccatctg gccccagtgc tgcaatgata ccgcgtgacc cacgctcacc   1020
ggctccagat ttatcagcaa taaaccagcc agccggaagg gccgagcgca gaagtggtcc   1080
tgcaactttta tccgcctcca tccagtctat taattgttgc cgggaagcta gagtaagtag   1140
ttcgccagtt aatagtttgc gcaacgttgt tgccattgct acaggcatcg tggtgtcacg   1200
ctcgtcgttt ggtatggctt cattcagctc cggttcccaa cgatcaaggc gagttacatg   1260
atcccccatg ttgtgcaaaa aagcggttag ctccttcggt cctccgatcg ttgtcagaag   1320
taagttggcc gcagtgttat cactcatggt tatggcagca ctgcataatt ctcttactgt   1380
catgccatcc gtaagatgct tttctgtgac tggtgagtac tcaaccaagt cattctgaga   1440
atagtgtatg cggcgaccga gttgctcttg cccggcgtca atacgggata taccgcgcc    1500
acatagcaga actttaaaag tgctcatcat tggaaaacgt tcttcggggc gaaaactctc   1560
aaggatctta ccgctgttga tccagttc gatgtaaccc actcgtgcac ccaactgatc    1620
ttcagcatct tttactttca ccagcgtttc tgggtgagca aaaacaggaa ggcaaaatgc   1680
cgcaaaaaag ggaataaggg cgacacggaa atgttgaata ctcatactct tcctttttca   1740
atattattga agcatttatc agggttattg tctcatgagc ggatacatat ttgaatgtat   1800
ttagaaaaat aaacaaatag gggttccgcg cacatttccc cgaaaagtgc caaggaacca   1860
attcagtcga ctggatccta gttattaata gtaatcaatt acggggtcat tagttcatag   1920
cccatatatg gagttccgcg ttacataact tacggtaaat ggcccgcctg gctgaccgcc   1980
caacgacccc cgcccattga cgtcaataat gacgtatgtt cccatagtaa cgccaatagg   2040
gactttccat tgacgtcaat gggtggagta tttacggtaa actgcccact ggcagtaca    2100
tcaagtgtat catatgccaa gtacgccccc tattgacgtc aatgacggta aatggcccgc   2160
ctggcattat gcccagtaca tgaccttatg gactttcct acttggcagt acatctacgt    2220
attagtcatc gctattacca tggtgatgcg gttttggcag tacatcaatg ggcgtggata   2280
gcggtttgac tcacggggat ttccaagtct ccacccatt gacgtcaatg ggagtttgtt    2340
ttggcaccaa aatcaacggg actttccaaa atgtcgtaac aactccgccc cattgacgca   2400
aatgggcggt aggcgtgtac ggtgggaggt ctatataagc agagctggtt tagtgaaccg   2460
tcagatcact agtcgactag ggataacagg gcaccatgtc tagactggac aagagcaaag   2520
tcataaactc tgctctggaa ttactcaatg gagtcggtat cgaaggcctg acgacaagga   2580
aactcgctca aaagctggga gttgagcagc ctaccctgta ctggcacgtg aagaacaagc   2640
gggccctgct cgatgccctg ccaatcgaga tgctggacag gcatcatacc cactcctgcc   2700
ccctggaagg cgagtcatgg caagactttc tgcggaacaa cgccaagtca taccgctgtg   2760
ctctcctctc acatcgcgac ggggctaaag tgcatctcgg cacccgccca acagagaaac   2820
agtacgaaac cctggaaaat cagctcgcgt tcctgtgtca gcaaggcttc tccctggaga   2880
acgcactgta cgctctgtcc gccgtgggcc actttacact gggctgcgta ttggaggaac   2940
aggagcatca gtagcaaaaa gaggaaagag agacacctac caccgattct atgcccccac   3000
ttctgaaaca agcaattgag ctgttcgacc ggcagggagc cgaacctgcc ttccttttcg   3060
gcctggaact aatcatatgt ggcctggaga aacagctaaa gtgcgaaagc ggcgggccga   3120
```

```
ccgacgccct tgacgatttt gacttagaca tgctcccagc cgatgccctt gacgactttg   3180
accttgatat gctgcctgct gacgctcttg acgattttga ccttgacatg ctccccgggt   3240
aatgatcgac tgtgccttct agttgccagc catctgttgt ttgcccctcc ccgtgcctt    3300 ccttgaccct ggaaggtgcc actcccactg tcctttccta ataaaatgag gaaattgcat   3360
cgcattgtct gagtaggtgt cattctattc tggggggtgg ggtggggcag gacagcaagg   3420
gggaggattg ggaggacaat agcaggcatg ctggggatgc ggtgggctct atggcttcgc   3480
tttcgtcttc aagaattcct ggagtttact ccctatcagt gatagagaac gtatgaagag   3540
tttactccct atcagtgata gagaacgtat gcagactttta ctccctatca gtgatagaga   3600
acgtataagg agtttactcc ctatcagtga tagagaacgt atgaccagtt tactccctat   3660
cagtgataga gaacgtatct acagtttact ccctatcagt gatagagaac gtatatccag   3720
tttactccct atcagtgata gagaacgtat aagctttagg cgtgtacggt gggcgcctat   3780
aaaagcagag ctcgtttagt gaaccgtcag atcgcctgga gcaattccac aacacttttg   3840
tcttatacca actttccgta ccacttccta ccctcgtaaa ccagagcatg aaggtattcc   3900
ggcgcgcttg gcggcaccgg gtggcgctgg gcctaggcgg cctggcgttc tgcggcacca   3960
ctctgttgta cctggcgcgc tgcgcttccg agggcgagac gccctccgct tccggagccg   4020
ctcggccccg cgctaaggcc ttcctggcgg tgctggtggc cagtgcgccc gcgcggtcg    4080 agcgccgcac cgcagtgcgc agcacgtggc tggcaccgga gaggcgtggc ggacccgagg   4140
acgtgtgggc gcgcttcgcc gtgggcactg gcggcttagg ctcggaggag cggcgcgctc   4200
ttgagctcga gcaggcgcag cacggggacc tgctgctgct gcccgccctg cgcgacgcct   4260
acgagaacct cacggccaag gtcctggcca tgctgacctg gctggatgag cgcgtggact   4320
tcgagttcgt gctcaaggcg gacgacgact cctttgcgcg cctggacgct atcctggtgg   4380
acctacgcgc acgggagccc gcacgccgcc ggcgcctcta ctgggcttc tttttccgggc   4440 gcgggcgcgt caagccggga ggtcgctggc gagaagcagc ctggcaactc tgcgactact   4500
acctgcccta cgcgttgggc ggtggctatg tcctttctgc ggacctggtg cattacctgc   4560
gcctcagccg cgagtacctg cgcgcgtggc acagtgaaga cgtatcgctg ggcacctggc   4620
tggcaccagt ggatgtgcaa cgggagcacg acccacgctt cgacacggag tacaaatctc   4680
gaggctgcaa caatcagtat ctggtgacac acaagcaaag cccagaggac atgttggaga   4740
agcaacagat gttgctgcat gagggccggt tgtgcaagca tgaggtgcaa cttcgccttt   4800
cctatgtcta tgactggtca gctccaccct cccagtgctg ccagcgcaag gagggcgttc   4860
cctgatgtca ccgcggggga ggctaactga acacggaag gagacaatac cggaaggaac   4920
ccgcgctatg acggcaataa aaagacagaa taaaacgcac ggtgttgggt cgtttgttca   4980
taaacgcggg gttcggtccc agggctggca ctctgtcgat accccaccga ggccccattg   5040
gggccaatac gcccgcgttt cttccttttc cccacccac cccccaagtt cgggtgaagg    5100
cccagggctc gcagccaacg tcgggcggc aggccctgcc atagccacaa acagggtcga    5160
caagcttttc caaaaaaaaa gcatgaggtg cagttgcgcc tttcctatct cttgaatagg   5220
aaaggcgcaa ctgcacctca tgctggatcc cgcgtccttt ccacaagata tataaaccca   5280
agaaatcgaa atactttcaa gttacggtaa gcatatgata gtccatttta aaacataatt   5340
ttaaaactgc aaactaccca agaaattatt actttctacg tcacgtattt tgtactaata   5400
tctttgtgtt tacagtcaaa ttaattctaa ttatctctct aacagccttg tatcgtatat   5460
```

```
gcaaatatga aggaatcatg ggaaataggc cctcttcctg cccgaccttg gcgcgcgctc    5520
ggcgcgcggt cacgctccgt cacgtggtgc gttttg                              5556

<210> SEQ ID NO 151
<211> LENGTH: 7570
<212> TYPE: DNA
<213> ORGANISM: Artificial sequence
<220> FEATURE:
<223> OTHER INFORMATION: V1.1b

<400> SEQUENCE: 151
cggtaatacg gttatccaca gaatcagggg ataacgcagg aaagaacatg tgagcaaaag      60
gccagcaaaa ggccaggaac cgtaaaaagg ccgcgttgct ggcgtttttc cataggctcc     120
gcccccctga cgagcatcac aaaaatcgac gctcaagtca gaggtggcga acccgacag      180 gactataaag ataccaggcg tttccccctg gaagctccct cgtgcgctct cctgttccga     240
ccctgccgct taccggatac ctgtccgcct ttctcccttc gggaagcgtg gcgctttctc     300
atagctcacg ctgtaggtat ctcagttcgg tgtaggtcgt tcgctccaag ctgggctgtg     360
tgcacgaacc cccgttcag cccgaccgct gcgccttatc cggtaactat cgtcttgagt     420
ccaacccggt aagacacgac ttatcgccac tggcagcagc cactggtaac aggattagca     480
gagcgaggta tgtaggcggt gctacagagt tcttgaagtg gtggcctaac tacggctaca     540
ctagaagaac agtatttggt atctgcgctc tgctgaagcc agttaccttc ggaaaaagag     600
ttggtagctc ttgatccggc aaacaaacca ccgctggtag cggttttttt gtttgcaagc     660
agcagattac gcgcagaaaa aaaggatctc aagaagatcc tttgatcttt tctacggggt     720
ctgacgctca gtggaacgaa aactcacgtt aagggatttt ggtcatgaga ttatcaaaaa     780
ggatcttcac ctagatcctt ttaaattaaa aatgaagttt aaatcaatc taaagtatat     840 atgagtaaac ttggtctgac agttaccaat gcttaatcag tgaggcacct atctcagcga     900
tctgtctatt tcgttcatcc atagttgcct gactccccgt cgtgtagata actacgatac     960
gggagggctt accatctggc cccagtgctg caatgatacc gcgtgaccca cgctcaccgg    1020
ctccagattt atcagcaata aaccagccag ccggaagggc cgagcgcaga agtggtcctg    1080
caactttatc cgcctccatc cagtctatta attgttgccg ggaagctaga gtaagtagtt    1140
cgccagttaa tagtttgcgc aacgttgttg ccattgctac aggcatcgtg gtgtcacgct    1200
cgtcgtttgg tatggcttca ttcagctccg gttcccaacg atcaaggcga gttacatgat    1260
cccccatgtt gtgcaaaaaa gcggttagct ccttcggtcc tccgatcgtt gtcagaagta    1320
agttggccgc agtgttatca ctcatggtta tggcagcact gcataattct cttactgtca    1380
tgccatccgt aagatgcttt tctgtgactg gtgagtactc aaccaagtca ttctgagaat    1440
agtgtatgcg gcgaccgagt tgctcttgcc cggcgtcaat acgggataat accgcgccac    1500
atagcagaac tttaaaagtg ctcatcattg gaaaacgttc ttcggggcga aaactctcaa    1560
ggatcttacc gctgttgaga tccagttcga tgtaacccac tcgtgcaccc aactgatctt    1620
cagcatcttt tactttcacc agcgtttctg ggtgagcaaa acaggaagg caaaatgccg    1680 caaaaaaggg aataagggcg acacggaaat gttgaatact catactcttc cttttcaat    1740 attattgaag catttatcag ggttattgtc tcatgagcgg atacatattt gaatgtattt    1800
agaaaaataa acaaataggg gttccgcgca catttccccg aaaagtgcca atgcgtgagg    1860
ctccggtgcc cgtcagtggg cagagcgcac atcgcccaca gtccccgaga agttgggggg    1920
aggggtcggc aattgaaccg gtgcctagag aaggtggcgc ggggtaaact gggaaagtga    1980
```

```
tgtcgtgtac tggctccgcc ttttttcccga gggtggggga gaaccgtata taagtgcagt   2040
agtcgccgtg aacgttcttt ttcgcaacgg gtttgccgcc agaacacagg taagtgccgt   2100
gtgtggttcc cgcgggcctg gcctctttac gggttatggc ccttgcgtgc cttgaattac   2160
ttccacctgg ctgcagtacg tgattcttga tcccgagctt cgggttggaa gtgggtggga   2220
gagttcgagg ccttgcgctt aaggagcccc ttcgcctcgt gcttgagttg aggcctggcc   2280
tgggcgctgg ggccgccgcg tgcgaatctg gtggcacctt cgcgcctgtc tcgctgcttt   2340
cgataagtct ctagccattt aaaattttg atgacctgct gcgacgcttt ttttctggca   2400
agatagtctt gtaaatgcgg gccaagatct gcacactggt atttcggttt ttggggccgc   2460
gggcggcgac ggggcccgtg cgtcccagcg cacatgttcg gcgaggcggg gcctgcgagc   2520
gcggccaccg agaatcggac gggggtagtc tcaagctggc cggcctgctc tggtgcctgg   2580
cctcgcgccg ccgtgtatcg ccccgccctg gcggcaagg ctggcccggt cggcaccagt   2640
tgcgtgagcg gaaagatggc cgcttccgg ccctgctgca gggagctcaa aatggaggac   2700
gcggcgctcg ggagagcggg cgggtgagtc acccacacaa aggaaaaggg cctttccgtc   2760
ctcagccgtc gcttcatgtg actccacgga gtaccgggcg ccgtccaggc acctcgatta   2820
gttctcgagc ttttggagta cgtcgtcttt aggttggggg gaggggtttt atgcgatgga   2880
gtttccccac actgagtggg tggagactga agttaggcca gcttggcact tgatgtaatt   2940
ctccttggaa tttgcccttt ttgagtttgg atcttggttc attctcaagc ctcagacagt   3000
ggttcaaagt tttttcttc catttcaggt gtcgtgatat catggtgagc aagggcgagg   3060
agctgttcac cggggtggtg cccatcctgg tcgagctgga cggcgacgta aacggccaca   3120
agttcagcgt gtccggcgag ggcgagggcg atgccaccta cggcaagctg accctgaagt   3180
tcatctgcac caccggcaag ctgcccgtgc cctggcccac cctcgtgacc accctgacct   3240
acggcgtgca gtgcttcagc cgctaccccg accacatgaa gcagcacgac ttcttcaagt   3300
ccgccatgcc cgaaggctac gtccaggagc gcaccatctt cttcaaggac gacggcaact   3360
acaagacccg cgccgaggtg aagttcgagg gcgacaccct ggtgaaccgc atcgagctga   3420
agggcatcga cttcaaggag gacggcaaca tcctggggca caagctggag tacaactaca   3480
acagccacaa cgtctatatc atggccgaca agcagaagaa cggcatcaag gtgaacttca   3540
agatccgcca caacatcgag gacggcagcg tgcagctcgc cgaccactac cagcagaaca   3600
cccccatcgg cgacggcccc gtgctgctgc ccgacaacca ctacctgagc acccagtccg   3660
ccctgagcaa agacccccaac gagaagcgcg atcacatggt cctgctggag ttcgtgaccg   3720
ccgccgggat cactctcggc atggacgagc tgtacaagaa gaagaaaag aagtcaaaga   3780
caaagtgtgt aattatgtaa gagtcgactg tgccttctag ttgccagcca tctgttgttt   3840
gcccctcccc cgtgccttcc ttgaccctgg aaggtgccac tcccactgtc ctttcctaat   3900
aaaatgagga aattgcatcg cattgtctga gtaggtgtca ttctattctg ggggtgggg   3960
tggggcagga cagcaagggg gaggattggg aggacaatag caggcatgct ggggatgcgg   4020
tgggctctat gggtagttat taatagtaat caattacggg gtcattagtt catagcccat   4080
atatggagtt ccgcgttaca taacttacgg taaatggccc gcctggctga ccgcccaacg   4140
acccccgccc attgacgtca ataatgacgt atgttcccat agtaacgcca atagggactt   4200
tccattgacg tcaatgggtg gagtatttac ggtaaactgc ccacttggca gtacatcaag   4260
tgtatcatat gccaagtacg ccccctattg acgtcaatga cggtaaatgg cccgcctggc   4320
```

```
attatgccca gtacatgacc ttatgggact ttcctacttg gcagtacatc tacgtattag    4380
tcatcgctat taccatggtg atgcggtttt ggcagtacat caatgggcgt ggatagcggt    4440
ttgactcacg gggatttcca agtctccacc ccattgacgt caatgggagt ttgttttggc    4500
accaaaatca acgggacttt ccaaaatgtc gtaacaactc cgccccattg acgcaaatgg    4560
gcggtaggcg tgtacggtgg gaggtctata taagcagagc tggtttagtg aaccgtcaga    4620
tcttcgatga ttcacaccaa cctgaagaaa aagttcagct gctgcgtcct ggtctttctt    4680
ctgtttgcag tcatctgtgt gtggaaggaa aagaagaaag ggagttacta tgattccttt    4740
aaattgcaaa ccaaggaatt ccaggtgtta aagagtctgg ggaaattggc catggggtct    4800
gattcccagt ctgtatcctc aagcagcacc caggaccccc acaggggccg ccagaccctc    4860
ggcagtctca gaggcctagc caaggccaaa ccagaggcct ccttccaggt gtggaacaag    4920
gacagctctt ccaaaaacct tatccctagg ctgcaaaagg ggtcgggggt gagcaagggc    4980
gaggaggata acatggccat catcaaggag ttcatgcgct tcaaggtgca catggagggc    5040
tccgtgaacg gccacgagtt cgagatcgag ggcgagggcg agggccgccc ctacgagggc    5100
acccagaccg ccaagctgaa ggtgaccaag ggtggccccc tgcccttcgc ctgggacatc    5160
ctgtcccctc agttcatgta cggctccaag gcctacgtga agcaccccgc cgacatcccc    5220
gactacttga agctgtcctt ccccgagggc ttcaagtggg agcgcgtgat gaacttcgag    5280
gacggcggcg tggtgaccgt gacccaggac tcctccctgc aggacggcga gttcatctac    5340
aaggtgaagc tgcgcggcac caacttcccc tccgacggcc ccgtaatgca gaagaaaacc    5400
atgggctggg aggcctcctc cgagcggatg taccccgagg acggcgccct gaagggcgag    5460
atcaagcaga ggctgaagct gaaggacggc ggccactacg acgctgaggt caagaccacc    5520
tacaaggcca gaagcccgt gcagctgccc ggcgcctaca cgtcaacat caagttggac    5580 atcacctccc acaacgagga ctacaccatc gtggaacagt acgaacgcgc cgagggccgc    5640
cactccaccg gcggcatgga cgagctgtac aagtaaccgc gggggaggct aactgaaaca    5700
cggaaggaga caataccgga aggaacccgc gctatgacgg caataaaaag acagaataaa    5760
acgcacggtg ttgggtcgtt tgttcataaa cgcggggttc ggtcccaggg ctggcactct    5820
gtcgataccc caccgaggcc ccattgggc caatacgccc gcgtttcttc cttttcccca    5880 ccccacccccc aagttcgggg tgaaggccca gggctcgcag ccaacgtcgg ggcggcaggc    5940
cctgccatag acaacaggca gaagtatgca aagcatgcat ctcaattagt cagcaaccag    6000
gtgtggaaag tccccaggct ccccagcagg cagaagtatg caaagcatgc atctcaatta    6060
gtcagcaacc atagtcccgc ccctaactcc gcccatcccg cccctaactc cgcccagttc    6120
cgcccattct ccgcccatg gctgactaat ttttttatt tatgcagagg ccgaggccgc    6180
ctctgcctct gagctattcc agaagtagtg aggaggcttt tttggaggcc taggcttttg    6240
caaaaagctc ccgggagctt gtatatccat tttcggatct gatcagcacg tgatgaaaaa    6300
gcctgaactc accgcgacgt ctgtcgagaa gtttctgatc gaaaagttcg acagcgtgtc    6360
cgacctgatg cagctctcgg agggcgaaga atctcgtgct ttcagcttcg atgtaggagg    6420
gcgtggatat gtcctgcggg taaatagctg cgccgatggt ttctacaaag atcgttatgt    6480
ttatcggcac tttgcatcgg ccgcgctccc gattccggaa gtgcttgaca ttggggaatt    6540
cagcgagagc ctgacctatt gcatctcccg ccgtgcacag ggtgtcacgt tgcaagactt    6600
gcctgaaacc gaactgcccg ctgttctgca gccggtcgcg gaggccatgg atgcgatcgc    6660
tgcggccgat cttagccaga cgagcgggtt cggcccattc ggaccgcaag gaatcggtca    6720
```

| | | | | |
|---|---|---|---|---|
| atacactaca | tggcgtgatt | tcatatgcgc | gattgctgat | ccccatgtgt | atcactggca | 6780 |
| aactgtgatg | gacgacaccg | tcagtgcgtc | cgtcgcgcag | gctctcgatg | agctgatgct | 6840 |
| ttgggccgag | gactgccccg | aagtccggca | cctcgtgcac | gcggatttcg | gctccaacaa | 6900 |
| tgtcctgacg | gacaatggcc | gcataacagc | ggtcattgac | tggagcgagg | cgatgttcgg | 6960 |
| ggattcccaa | tacgaggtcg | ccaacatctt | cttctggagg | ccgtggttgg | cttgtatgga | 7020 |
| gcagcagacg | cgctacttcg | agcggaggca | tccggagctt | gcaggatcgc | cgcggctccg | 7080 |
| ggcgtatatg | ctccgcattg | gtcttgacca | actctatcag | agcttggttg | acggcaattt | 7140 |
| cgatgatgca | gcttgggcgc | agggtcgatg | cgacgcaatc | gtccgatccg | gagccgggac | 7200 |
| tgtcgggcgt | acacaaatcg | cccgcagaag | cgcggccgtc | tggaccgatg | gctgtgtaga | 7260 |
| agtactcgcc | gatagtggaa | accgacgccc | cagcactcgt | ccgagggcaa | aggaatagca | 7320 |
| cgtgctacga | gatttcgatt | ccaccgccgc | cttctatgaa | aggttgggct | tcggaatcgt | 7380 |
| tttccgggac | gccggctgga | tgatcctcca | gcgcggggat | ctcatgctgg | agttcttcgc | 7440 |
| ccaccccaac | ttgtttattg | cagcttataa | tggttacaaa | taaagcaata | gcatcacaaa | 7500 |
| tttcacaaat | aaagcatttt | tttcactgca | ttctagttgt | ggtttgtcca | aactcatcaa | 7560 |
| tgtatcatta | | | | | 7570 |

<210> SEQ ID NO 152
<211> LENGTH: 4346
<212> TYPE: DNA
<213> ORGANISM: Artificial sequence
<220> FEATURE:
<223> OTHER INFORMATION: V4

<400> SEQUENCE: 152

| | | | | | | |
|---|---|---|---|---|---|---|
| cggtaatacg | gttatccaca | gaatcagggg | ataacgcagg | aaagaacatg | tgagcaaaag | 60 |
| gccagcaaaa | ggccaggaac | cgtaaaaagg | ccgcgttgct | ggcgtttttc | cataggctcc | 120 |
| gcccccctga | cgagcatcac | aaaaatcgac | gctcaagtca | gaggtggcga | aacccgacag | 180 |
| gactataaag | ataccaggcg | tttccccctg | gaagctccct | cgtgcgctct | cctgttccga | 240 |
| ccctgccgct | taccggatac | ctgtccgcct | ttctcccttc | gggaagcgtg | gcgctttctc | 300 |
| atagctcacg | ctgtaggtat | ctcagttcgg | tgtaggtcgt | tcgctccaag | ctgggctgtg | 360 |
| tgcacgaacc | ccccgttcag | cccgaccgct | gcgccttatc | cggtaactat | cgtcttgagt | 420 |
| ccaacccggt | aagacacgac | ttatcgccac | tggcagcagc | cactggtaac | aggattagca | 480 |
| gagcgaggta | tgtaggcggt | gctacagagt | tcttgaagtg | gtggcctaac | tacggctaca | 540 |
| ctagaagaac | agtatttggt | atctgcgctc | tgctgaagcc | agttaccttc | ggaaaaagag | 600 |
| ttggtagctc | ttgatccggc | aaacaaacca | ccgctggtag | cggtttttt | gtttgcaagc | 660 |
| agcagattac | gcgcagaaaa | aaaggatctc | aagaagatcc | tttgatcttt | tctacggggt | 720 |
| ctgacgctca | gtggaacgaa | aactcacgtt | aagggatttt | ggtcatgaga | ttatcaaaaa | 780 |
| ggatcttcac | ctagatcctt | ttaaattaaa | aatgaagttt | taaatcaatc | taaagtatat | 840 |
| atgagttaaa | acttggtctg | acagttacca | atgcttaatc | agtgaggcac | ctatctcagc | 900 |
| gatctgtcta | tttcgttcat | ccatagttgc | ctgactcccc | gtcgtgtaga | taactacgat | 960 |
| acgggagggc | ttaccatctg | gccccagtgc | tgcaatgata | ccgcgtgacc | cacgctcacc | 1020 |
| ggctccagat | ttatcagcaa | taaaccagcc | agccggaagg | gccgagcgca | gaagtggtcc | 1080 |
| tgcaacttta | tccgcctcca | tccagtctat | taattgttgc | cgggaagcta | gagtaagtag | 1140 |

```
ttcgccagtt aatagtttgc gcaacgttgt tgccattgct acaggcatcg tggtgtcacg      1200
ctcgtcgttt ggtatggctt cattcagctc cggttcccaa cgatcaaggc gagttacatg      1260
atcccccatg ttgtgcaaaa aagcggttag ctccttcggt cctccgatcg ttgtcagaag      1320
taagttggcc gcagtgttat cactcatggt tatggcagca ctgcataatt ctcttactgt      1380
catgccatcc gtaagatgct tttctgtgac tggtgagtac tcaaccaagt cattctgaga      1440
atagtgtatg cggcgaccga gttgctcttg cccggcgtca atacgggata ataccgcgcc      1500
acatagcaga actttaaaag tgctcatcat tggaaaacgt tcttcggggc gaaaactctc      1560
aaggatctta ccgctgttga gatccagttc gatgtaaccc actcgtgcac ccaactgatc      1620
ttcagcatct tttactttca ccagcgtttc tgggtgagca aaaacaggaa ggcaaaatgc      1680
cgcaaaaaag ggaataaggg cgacacggaa atgttgaata ctcatactct tcctttttca      1740
atattattga agcatttatc agggttattg tctcatgagc ggatacatat ttgaatgtat      1800
ttagaaaaat aaacaaatag gggttccgcg cacatttccc cgaaaagtgc cagtgagttt      1860
aaacatgcat tcaaaggtca taattgctgc tctatttaca gtcgtccata atgacatttc      1920
tctttgatta ttttcttgtt tttcgctct tctcaagtgg atgttacata acaaacaaaa      1980
cagaaaaaat tgtttaaata taaagtttaa aagttatctt tgattccgca cctgaatttt      2040
tggattgaag gccaaaggag gtttatcagg gagagaaaag ctctctattt atttttataa      2100 ggataattg tgcatgtaca actatacaat tgcggtacgc tgcaggtcga caacccttaa      2160
tataacttcg tataatgtat gctatacgaa gttattaggt ctagagatct gtttagcttg      2220
cctcgtcccc gccgggtcac ccggccagcg acatggaggc ccagaatacc ctccttgaca      2280
gtcttgacgt gcgcagctca ggggcatgat gtgactgtcg cccgtacatt tagcccatac      2340
atccccatgt ataatcattt gcatccatac attttgatgg ccgcacggcg cgaagcaaaa      2400
attacggctc ctcgctgcag acctgcgagc agggaaacgc tcccctcaca gacgcgttga      2460
attgtcccca cgccgcgccc ctgtagagaa atataaaagg ttaggatttg ccactgaggt      2520
tcttctttca tatacttcct tttaaaatct tgctaggata cagttctcac atcacatccg      2580
aacataaaca accatgggta aggaaaagac tcacgtttcg aggccgcgat taaattccaa      2640
catggatgct gatttatatg ggtataaatg ggctcgcgat aatgtcgggc aatcaggtgc      2700
gacaatctat cgattgtatg ggaagcccga tgcgccagag ttgtttctga acatggcaa      2760 aggtagcgtt gccaatgatg ttacagatga gatggtcaga ctaaactggc tgacggaatt      2820
tatgcctctt ccgaccatca agcattttat ccgtactcct gatgatgcat ggttactcac      2880
cactgcgatc cccggcaaaa cagcattcca ggtattagaa gaatatcctg attcaggtga      2940
aaatattgtt gatgcgctgg cagtgttcct gcgccggttg cattcgattc ctgtttgtaa      3000
ttgtcctttt aacagcgatc gcgtatttcg tctcgctcag gcgcaatcac gaatgaataa      3060
cggtttggtt gatgcgagtg attttgatga cgagcgtaat ggctggcctg ttgaacaagt      3120
ctggaaagaa atgcataagc ttttgccatt ctcaccggat tcagtcgtca ctcatggtga      3180
tttctcactt gataacctta ttttgacga ggggaaatta ataggttgta ttgatgttgg      3240
acgagtcgga atcgcagacc gataccagga tcttgccatc ctatggaact gcctcggtga      3300
gttttctcct tcattacaga aacggctttt tcaaaaatat ggtattgata atcctgatat      3360
gaataaattg cagtttcatt tgatgctcga tgagttttc taatcagtac tgacaataaa      3420
aagattcttg ttttcaagaa cttgtcattt gtatagtttt tttatattgt agttgttcta      3480
ttttaatcaa atgttagcgt gatttatatt ttttttcgcc tcgacatcat ctgcccagat      3540
```

```
gcgaagttaa gtgcgcagaa agtaatatca tgcgtcaatc gtatgtgaat gctggtcgct    3600
atactgctgt cgattcgata ctaacgccgc catccagtgt cgaaaacgag ctctcgagaa    3660
cccttaatat aacttcgtat aatgtatgct atacgaagtt attaggtgat atcagatcca    3720
ctagtgtcgt aatggaagtt atcaatattg taaagagaag catttacaag ctttttatttt   3780 tctttttaat ttccactact ggttctgctt taaaatgttg tttttataatt tatgtacatt    3840 taggcctata gaagattctt tcaataatat gctacacatt cttttatttt tccatcatat    3900
gttggagttt atgcctcctc ggcaggagtt gggcggtgcg aagagaagaa aaagagtgaa    3960
actaaaaaaa ggaatctgcc tttgcataag ttcaaaagtg caattttagt gttggattta    4020
aacgggaaaa attgaaatgg ccatcgaaac aatacttgta ataaacaaat caggcggact    4080
aatctatcag cggaattta ccaacgacga acagaaattg aacagcaatg aatacttaat     4140
tcttgctagt acactgcacg gtgtattcgc catcgcgagc cagctgactc cgaaggcatt    4200
acagctaact caacaaacga acatcgaaaa taccatccca tatataccctt acgtgggcat   4260 gtccagcaat aggagcgata caagaaatgg aggtggcaat aacaacaaac acactaataa    4320
tgaaaaactg ggcagtttaa acgggg                                          4346
```

<210> SEQ ID NO 153
<211> LENGTH: 1967
<212> TYPE: DNA
<213> ORGANISM: Artificial sequence
<220> FEATURE:
<223> OTHER INFORMATION: Matrice eZ-Ori-AmpR

<400> SEQUENCE: 153

```
gcgtcttcta gggttaaggt tagtgtagag aagcaaccga agattgagaa gacatggcgg      60
taatacggtt atccacagaa tcaggggata acgcaggaaa gaacatgtga gcaaaaggcc     120
agcaaaaggc caggaaccgt aaaaaggccg cgttgctggc gttttcccat aggctccgcc     180
cccctgacga gcatcacaaa aatcgacgct caagtcagag gtggcgaaac ccgacaggac    240
tataaagata ccaggcgttt ccccctggaa gctccctcgt gcgctctcct gttccgaccc     300
tgccgcttac cggatacctg tccgcctttc tcccttcggg aagcgtggcg ctttctcata     360
gctcacgctg taggtatctc agttcggtgt aggtcgttcg ctccaagctg ggctgtgtgc    420
acgaaccccc cgttcagccc gaccgctgcg ccttatccgg taactatcgt cttgagtcca    480
acccggtaag acacgactta tcgccactgg cagcagccac tggtaacagg attagcagag    540
cgaggtatgt aggcggtgct acagagttct tgaagtggtg gcctaactac ggctacacta    600
gaagaacagt atttggtatc tgcgctctgc tgaagccagt taccttcgga aaaagagttg    660
gtagctcttg atccggcaaa caaaccaccg ctggtagcgg ttttttttgtt tgcaagcagc    720 agattacgcg cagaaaaaaa ggatctcaag aagatccttt gatcttttct acggggtctg    780
acgctcagtg gaacgaaaac tcacgttaag ggattttggt catgagatta tcaaaaagga    840
tcttcaccta gatccttta aattaaaaat gaagttttaa atcaatctaa agtatatatg      900
agtaaacttg gtctgacagt taccaatgct taatcagtga ggcacctatc tcagcgatct     960
gtctatttcg ttcatccata gttgcctgac tccccgtcgt gtagataact acgatacggg    1020
agggcttacc atctggcccc agtgctgcaa tgataccgcg tgacccacgc tcaccggctc    1080
cagatttatc agcaataaac cagccagccg gaagggccga gcgcagaagt ggtcctgcaa    1140
ctttatccgc ctccatccag tctattaatt gttgccggga agctagagta agtagttcgc    1200
```

```
cagttaatag tttgcgcaac gttgttgcca ttgctacagg catcgtggtg tcacgctcgt    1260
cgtttggtat ggcttcattc agctccggtt cccaacgatc aaggcgagtt acatgatccc    1320
ccatgttgtg caaaaaagcg gttagctcct tcggtcctcc gatcgttgtc agaagtaagt    1380
tggccgcagt gttatcactc atggttatgg cagcactgca taattctctt actgtcatgc    1440
catccgtaag atgcttttct gtgactggtg agtactcaac caagtcattc tgagaatagt    1500
gtatgcggcg accgagttgc tcttgcccgg cgtcaatacg ggataatacc gcgccacata    1560
gcagaacttt aaaagtgctc atcattggaa aacgttcttc ggggcgaaaa ctctcaagga    1620
tcttaccgct gttgagatcc agttcgatgt aacccactcg tgcacccaac tgatcttcag    1680 catctttac tttcaccagc gtttctgggt gagcaaaaac aggaaggcaa aatgccgcaa    1740
aaaagggaat aagggcgaca cggaaatgtt gaatactcat actcttcctt tttcaatatt    1800
attgaagcat ttatcagggt tattgtctca tgagcggata catatttgaa tgtatttaga    1860
aaaataaaca aataggggtt ccgcgcacat ttccccgaaa agtgccacct atgagacgtg    1920
aggctaggga taggacgaga gcatcgggaa cgaggactag cgtctca                  1967

<210> SEQ ID NO 154
<211> LENGTH: 235
<212> TYPE: DNA
<213> ORGANISM: Artificial sequence
<220> FEATURE:
<223> OTHER INFORMATION: Matrice BGH polyA

<400> SEQUENCE: 154
tcgactgtgc cttctagttg ccagccatct gttgtttgcc cctccccgt gccttccttg       60 accctggaag gtgccactcc cactgtcctt tcctaataaa atgaggaaat tgcatcgcat     120
tgtctgagta ggtgtcattc tattctgggg ggtggggtgg ggcaggacag caaggggag     180 gattgggagg acaatagcag gcatgctggg gatgcggtgg gctctatggc ttctg         235

<210> SEQ ID NO 155
<211> LENGTH: 720
<212> TYPE: DNA
<213> ORGANISM: Artificial sequence
<220> FEATURE:
<223> OTHER INFORMATION: Matrice eZ-E1GFP

<400> SEQUENCE: 155
atggtgagca agggcgagga gctgttcacc ggggtggtgc ccatcctggt cgagctggac       60
ggcgacgtaa acggccacaa gttcagcgtg tccggcgagg gcgagggcga tgccacctac     120
ggcaagctga ccctgaagtt catctgcacc accggcaagc tgcccgtgcc ctggcccacc     180
ctcgtgacca cctgtcta cggcgtgcag tgcttcagcc gctacccga ccacatgaag      240 cagcacgact tcttcaagtc cgccatgccc gaaggctacg tccaggagcg caccatcttc     300
ttcaaggacg acggcaacta caagacccgc gccgaggtga agttcgaggg cgacaccctg     360
gtgaaccgca tcgagctgaa gggcatcgac ttcaaggagg acggcaacat cctggggcac     420
aagctggagt acaactacaa cagccacaac gtctatatca tggccgacaa gcagaagaac     480
ggcatcaagg tgaacttcaa gatccgccac aacatcgagg acggcagcgt gcagctcgcc     540
gaccactacc agcagaacac ccccatcggc gacggccccg tgctgctgcc cgacaaccac     600
tacctgagct accagtccgc cctgagcaaa gaccccaacg agaagcgcga tcacatggtc     660
ctgctggagt tcgtgaccgc cgccgggatc actctcggca tggacgagct gtacaagtaa     720
```

<210> SEQ ID NO 156
<211> LENGTH: 720
<212> TYPE: DNA
<213> ORGANISM: Artificial sequence
<220> FEATURE:
<223> OTHER INFORMATION: Matrice EGFP

<400> SEQUENCE: 156

```
atggtgagca agggcgagga gctgttcacc ggggtggtgc ccatcctggt cgagctggac      60
ggcgacgtaa acggccacaa gttcagcgtg tccggcgagg gcgagggcga tgccacctac     120
ggcaagctga ccctgaagtt catctgcacc accggcaagc tgcccgtgcc ctggcccacc     180
ctcgtgacca ccctgaccta cggcgtgcag tgcttcagcc gctaccccga ccacatgaag     240
cagcacgact tcttcaagtc cgccatgccc gaaggctacg tccaggagcg caccatcttc     300
ttcaaggacg acggcaacta caagacccgc gccgaggtga agttcgaggg cgacaccctg     360
gtgaaccgca tcgagctgaa gggcatcgac ttcaaggagg acggcaacat cctggggcac     420
aagctggagt acaactacaa cagccacaac gtctatatca tggccgacaa gcagaagaac     480
ggcatcaagg tgaacttcaa gatccgccac aacatcgagg acggcagcgt gcagctcgcc     540
gaccactacc agcagaacac ccccatcggc gacggccccg tgctgctgcc cgacaaccac     600
tacctgagca cccagtccgc cctgagcaaa gaccccaacg agaagcgcga tcacatggtc     660
ctgctggagt tcgtgaccgc cgccgggatc actctcggca tggacgagct gtacaagtaa     720
```

<210> SEQ ID NO 157
<211> LENGTH: 720
<212> TYPE: DNA
<213> ORGANISM: Artificial sequence
<220> FEATURE:
<223> OTHER INFORMATION: Matrice ECFP

<400> SEQUENCE: 157

```
atggtgagca agggcgagga gctgttcacc ggggtggtgc ccatcctggt cgagctggac      60
ggcgacgtaa acggccacaa gttcagcgtg tccggcgagg gcgagggcga tgccacctac     120
ggcaagctga ccctgaagtt catctgcacc accggcaagc tgcccgtgcc ctggcccacc     180
ctcgtgacca ccctgacctg gggcgtgcag tgcttcagcc gctaccccga ccacatgaag     240
cagcacgact tcttcaagtc cgccatgccc gaaggctacg tccaggagcg caccatcttc     300
ttcaaggacg acggcaacta caagacccgc gccgaggtga agttcgaggg cgacaccctg     360
gtgaaccgca tcgagctgaa gggcatcgac ttcaaggagg acggcaacat cctggggcac     420
aagctggagt acaactacat cagccacaac gtctatatca ccgccgacaa gcagaagaac     480
ggcatcaagg ccaacttcaa gatccgccac aacatcgagg acggcagcgt gcagctcgcc     540
gaccactacc agcagaacac ccccatcggc gacggccccg tgctgctgcc cgacaaccac     600
tacctgagca cccagtccgc cctgagcaaa gaccccaacg agaagcgcga tcacatggtc     660
ctgctggagt tcgtgaccgc cgccgggatc actctcggca tggacgagct gtacaagtcc     720
```

<210> SEQ ID NO 158
<211> LENGTH: 714
<212> TYPE: DNA
<213> ORGANISM: Artificial sequence
<220> FEATURE:
<223> OTHER INFORMATION: Matrice EYFP

<400> SEQUENCE: 158

```
atggtgagca agggcgagga gctgttcacc ggggtggtgc ccatcctggt cgagctggac      60
```

| | |
|---|---|
| ggcgacgtaa acggccacaa gttcagcgtg tccggcgagg gcgagggcga tgccacctac | 120 |
| ggcaagctga ccctgaagtt catctgcacc accggcaagc tgcccgtgcc ctggcccacc | 180 |
| ctcgtgacca ccttcggcta cggcctgcag tgcttcgccc gctaccccga ccacatgaag | 240 |
| cagcacgact tcttcaagtc cgccatgccc gaaggctacg tccaggagcg caccatcttc | 300 |
| ttcaaggacg acggcaacta caagacccgc gccgaggtga agttcgaggg cgacaccctg | 360 |
| gtgaaccgca tcgagctgaa gggcatcgac ttcaaggagg acggcaacat cctggggcac | 420 |
| aagctggagt acaactacaa cagccacaac gtctatatca tggccgacaa gcagaagaac | 480 |
| ggcatcaagg tgaacttcaa gatccgccac aacatcgagg acggcagcgt gcagctcgcc | 540 |
| gaccactacc agcagaacac ccccatcggc gacggccccg tgctgctgcc cgacaaccac | 600 |
| tacctgagct accagtccgc cctgagcaaa gaccccaacg agaagcgcga tcacatggtc | 660 |
| ctgctggagt tcgtgaccgc cgccgggatc actctcggca tggacgagct gtac | 714 |

<210> SEQ ID NO 159
<211> LENGTH: 718
<212> TYPE: DNA
<213> ORGANISM: Artificial sequence
<220> FEATURE:
<223> OTHER INFORMATION: Matrice mCherry

<400> SEQUENCE: 159

| | |
|---|---|
| atggtcgggg gtgagcaagg gcgaggagga taacatggcc atcatcaagg agttcatgcg | 60 |
| cttcaaggtg cacatggagg gctccgtgaa cggccacgag ttcgagatcg agggcgaggg | 120 |
| cgagggccgc ccctacgagg gcacccgac cgccaagctg aaggtgacca agggtggccc | 180 |
| cctgcccttc gcctgggaca tcctgtcccc tcagttcatg tacggctcca aggcctacgt | 240 |
| gaagcacccc gccgacatcc ccgactactt gaagctgtcc ttccccgagg gcttcaagtg | 300 |
| ggagcgcgtg atgaacttcg aggacggcgg cgtggtgacc gtgacccagg actcctccct | 360 |
| gcaggacggc gagttcatct acaaggtgaa gctgcgcggc accaacttcc cctccgacgg | 420 |
| ccccgtaatg cagaagaaaa ccatgggctg ggaggcctcc tccgagcgga tgtaccccga | 480 |
| ggacggcgcc ctgaagggcg agatcaagca gaggctgaag ctgaaggacg gcggccacta | 540 |
| cgacgctgag gtcaagacca cctacaaggc caagaagccc gtgcagctgc ccggcgccta | 600 |
| caacgtcaac atcaagttgg acatcacctc ccacaacgag gactacacca tcgtggaaca | 660 |
| gtacgaacgc gccgagggcc gccactccac cggcggcatg gacgagctgt acaagtga | 718 |

<210> SEQ ID NO 160
<211> LENGTH: 1086
<212> TYPE: DNA
<213> ORGANISM: Artificial sequence
<220> FEATURE:
<223> OTHER INFORMATION: Matrice hFUT3 cDNA

<400> SEQUENCE: 160

| | |
|---|---|
| atggatcccc tgggtgcagc caagccacaa tggccatggc ccgctgtct ggccgcactg | 60 |
| ctatttcagc tgctggtggc tgtgtgtttc ttctcctacc tgcgtgtgtc ccgagacgat | 120 |
| gccactggat cccctagggc tcccagtggg tcctcccgac aggacaccac tcccacccgc | 180 |
| cccacccctcc tgatcctgct atggacatgg cctttccaca tccctgtggc tctgtcccgc | 240 |
| tgttcagaga tggtgcccgg cacagccgac tgccacatca ctgccgaccg caaggtgtac | 300 |
| ccacaggcag acacggtcat cgtgcaccac tgggatatca tgtccaaccc taagtcacgc | 360 |
| ctcccacctt ccccgaggcc gcaggggcag cgctggatct ggttcaactt ggagccaccc | 420 |

```
cctaactgcc agcacctgga agccctggac agatacttca atctcaccat gtcctaccgc    480
agcgactccg acatcttcac gccctacggc tggctggagc cgtggtccgg ccagcctgcc    540
cacccaccgc tcaacctctc ggccaagacc gagctggtgg cctgggcggt gtccaactgg    600
aagccggact cagccagggt gcgctactac cagagcctgc aggctcatct caaggtggac    660
gtgtacggac gctcccacaa gcccctgccc aaggggacca tgatggagac gctgtcccgg    720
tacaagttct acctggcctt cgagaactcc ttgcaccccg actacatcac cgagaagctg    780
tggaggaacg ccctggaggc ctgggccgtg cccgtggtgc tgggcccag cagaagcaac     840 tacgagaggt tcctgccacc cgacgccttc atccacgtgg acgacttcca gagccccaag    900
gacctggccc ggtacctgca ggagctggac aaggaccacg cccgctacct gagctacttt    960
cgctggcggg agacgctgcg gcctcgctcc ttcagctggg cactggattt ctgcaaggcc   1020
tgctggaaac tgcagcagga atccaggtac cagacggtgc gcagcatagc ggcttggttc   1080
acctga                                                                1086

<210> SEQ ID NO 161
<211> LENGTH: 1612
<212> TYPE: DNA
<213> ORGANISM: Artificial sequence
<220> FEATURE:
<223> OTHER INFORMATION: Matrice eZ-HygromycinR K7

<400> SEQUENCE: 161
caggcagaag tatgcaaagc atgcatctca attagtcagc aaccaggtgt ggaaagtccc      60
caggctcccc agcaggcaga agtatgcaaa gcatgcatct caattagtca gcaaccatag    120
tcccgcccct aactccgccc atcccgccc taactccgcc cagttccgcc cattctccgc     180
cccatggctg actaattttt tttatttatg cagaggccga ggccgcctct gcctctgagc    240
tattccagaa gtagtgagga ggcttttttg gaggcctagg cttttgcaaa aagctcccgg    300
gagcttgtat atccattttc ggatctgatc agcacgtgat gaaaaagcct gaactcaccg    360
cgacgtctgt cgagaagttt ctgatcgaaa agttcgacag cgtgtccgac ctgatgcagc    420
tctcggaggg cgaagaatct cgtgctttca gcttcgatgt aggagggcgt ggatatgtcc    480
tgcgggtaaa tagctgcgcc gatggtttct acaaagatcg ttatgtttat cggcactttg    540
catcggccgc gctcccgatt ccggaagtgc ttgacattgg ggaattcagc gagagcctga    600
cctattgcat ctcccgccgt gcacagggtg tcacgttgca agacttgcct gaaaccgaac    660
tgcccgctgt tctgcagccg gtcgcggagg ccatggatga tcgctgcg ccgatctta     720 gccagacgag cgggttcggc ccattcggac cgcaaggaat cggtcaatac actacatggc    780
gtgatttcat atgcgcgatt gctgatcccc atgtgtatca ctggcaaact gtgatggacg    840
acaccgtcag tgcgtccgtc gcgcaggctc tcgatgagct gatgctttgg gccgaggact    900
gccccgaagt ccggcacctc gtgcacgcgg atttcggctc caacaatgtc ctgacggaca    960
atggccgcat aacagcggtc attgactgga gcgaggcgat gttcggggat tcccaatacg   1020
aggtcgccaa catcttcttc tggaggccgt ggttggcttg tatggagcag cagacgcgct   1080
acttcgagcg gaggcatccg gagcttgcag atcgccgcg gctccgggcg tatatgctcc   1140
gcattggtct tgaccaactc tatcagagct tggttgacgg caatttcgat gatgcagctt   1200
gggcgcaggg tcgatgcgac gcaatcgtcc gatccggagc cgggactgtc gggcgtacac   1260
aaatcgcccg cagaagcgcg gccgtctgga ccgatggctg tgtagaagta ctcgccgata   1320
```

```
gtggaaaccg acgccccagc actcgtccga gggcaaagga atagcacgtg ctacgagatt    1380
tcgattccac cgccgccttc tatgaaaggt tgggcttcgg aatcgttttc cgggacgccg    1440
gctggatgat cctccagcgc ggggatctca tgctggagtt cttcgcccac cccaacttgt    1500
ttattgcagc ttataatggt tacaaataaa gcaatagcat cacaaatttc acaaataaag    1560 cattttttc actgcattct agttgtggtt tgtccaaact catcaatgta tc            1612
```

<210> SEQ ID NO 162
<211> LENGTH: 1592
<212> TYPE: DNA
<213> ORGANISM: Artificial sequence
<220> FEATURE:
<223> OTHER INFORMATION: Matrice KanMX4 K7

<400> SEQUENCE: 162

```
gtacgctgca ggtcgacaac ccttaatata acttcgtata atgtatgcta tacgaagtta     60
ttaggtctag agatctgttt agcttgcctc gtccccgccg ggtcacccgg ccagcgacat    120
ggaggcccag aatacccctcc ttgacagtct tgacgtgcgc agctcagggg catgatgtga   180
ctgtcgcccg tacatttagc ccatacatcc ccatgtataa tcatttgcat ccatacattt    240
tgatggccgc acggcgcgaa gcaaaaatta cggctcctcg ctgcagacct gcgagcaggg    300
aaacgctccc ctcacagacg cgttgaattg tccccacgcc gcgcccctgt agagaaatat    360
aaaaggttag gatttgccac tgaggttctt ctttcatata cttccttta aaatcttgct    420 aggatacagt tctcacatca catccgaaca taaacaacca tgggtaagga aaagactcac    480
gtttcgaggc cgcgattaaa ttccaacatg gatgctgatt tatatgggta taaatgggct    540
cgcgataatg tcgggcaatc aggtgcgaca atctatcgat tgtatgggaa gcccgatgcg    600
ccagagttgt ttctgaaaca tggcaaaggt agcgttgcca atgatgttac agatgagatg    660
gtcagactaa actggctgac ggaatttatg cctcttccga ccatcaagca ttttatccgt    720
actcctgatg atgcatggtt actcaccact gcgatccccg gcaaaacagc attccaggta    780
ttagaagaat atcctgattc aggtgaaaat attgttgatg cgctggcagt gttcctgcgc    840
cggttgcatt cgattcctgt ttgtaattgt cctttaaca gcgatcgcgt atttcgtctc    900
gctcaggcgc aatcacgaat gaataacggt ttggttgatg cgagtgattt tgatgacgag    960
cgtaatggct ggcctgttga acaagtctgg aaagaaatgc ataagctttt gccattctca   1020
ccggattcag tcgtcactca tggtgatttc tcacttgata accttatttt tgacgagggg   1080
aaattaatag gttgtattga tgttggacga gtcggaatcg cagaccgata ccaggatctt   1140
gccatcctat ggaactgcct cggtgagttt tctccttcat tacagaaacg ctttttcaa   1200 aaatatggta ttgataatcc tgatatgaat aaattgcagt ttcatttgat gctcgatgag   1260
tttttctaat cagtactgac aataaaaaga ttcttgtttt caagaacttg tcatttgtat   1320
agttttttta tattgtagtt gttctatttt aatcaaatgt tagcgtgatt tatattttt   1380 ttcgcctcga catcatctgc ccagatgcga agttaagtgc gcagaaagta atatcatgcg   1440
tcaatcgtat gtgaatgctg gtcgctatac tgctgtcgat tcgatactaa cgccgccatc   1500
cagtgtcgaa aacgagctct cgagaaccct aatataact tcgtataatg tatgctatac   1560
gaagttatta ggtgatatca gatccactag tg                                 1592
```

<210> SEQ ID NO 163
<211> LENGTH: 485
<212> TYPE: DNA
<213> ORGANISM: Artificial sequence
<220> FEATURE:
<223> OTHER INFORMATION: Matrice LacZ

<400> SEQUENCE: 163

| | |
|---|---|
| gcccaatacg caaaccgcct ctccccgcgc gttggccgat tcattaatgc agctggcacg | 60 |
| acaggtttcc cgactggaaa gcgggcagtg agcgcaacgc aattaatgtg agttagctca | 120 |
| ctcattaggc accccaggct ttacacttta tgcttccggc tcgtatgttg tgtggaattg | 180 |
| tgagcggata caatttcac acaggaaaca gctatgacca tgattacgga cagcctggcc | 240 |
| gtcgttttac aacgtcgtga ctgggaaaac cctggcgtta cccaacttaa tcgccttgca | 300 |
| gcacatcccc ctttcgccag ctggcgtaat agcgaagagg cccgcaccga tcgcccttcc | 360 |
| caacagttgc gcagcctgaa tggcgaatgg cgcctgatgc ggtattttct ccttacgcat | 420 |
| ctgtgcggta tttcacaccg catatggtgc actctcagta caatctgctc tgatgccgca | 480 |
| tagac | 485 |

<210> SEQ ID NO 164
<211> LENGTH: 983
<212> TYPE: DNA
<213> ORGANISM: Artificial sequence
<220> FEATURE:
<223> OTHER INFORMATION: Matrice mB3Galt6 cDNA

<400> SEQUENCE: 164

| | |
|---|---|
| atgaaggtat tccggcgcgc ttggcggcac cgggtggcgc tgggcctagg cggcctggcg | 60 |
| ttctgcggca ccactctgtt gtacctggcg cgctgcgctt ccgagggcga cgcgcctcc | 120 |
| gcttccggag ccgctcggcc ccgcgctaag gccttcctgg cggtgctggt ggccagtgcg | 180 |
| ccccgcgcgg tcgagcgccg caccgcagtg cgcagcacgt ggctggcacc ggagaggcgt | 240 |
| ggcggacccg aggacgtgtg ggcgcgcttc gccgtgggca ctggcggctt aggctcggag | 300 |
| gagcggcgcg ctcttgagct cgagcaggcg cagcacgggg acctgctgct gctgcccgcc | 360 |
| ctgcgcgacg cctacgagaa cctcacggcc aaggtcctgg ccatgctgac ctggctggat | 420 |
| gagcgcgtgg acttcgagtt cgtgctcaag gcggacgacg actcctttgc gcgcctggac | 480 |
| gctatcctgg tggacctacg cgcacgggag cccgcacgcc gccggcgcct ctactgggc | 540 |
| ttcttttccg ggcgcgggcg cgtcaagccg ggaggtcgct ggcgagaagc agcctggcaa | 600 |
| ctctgcgact actacctgcc ctacgcgttg ggcggtggct atgtcctttc tgcggacctg | 660 |
| gtgcattacc tgcgcctcag ccgcgagtac ctgcgcgcgt ggcacagtga agacgtatcg | 720 |
| ctgggcacct ggctggcacc agtggatgtg caacgggagc acgacccacg cttcgacacg | 780 |
| gagtacaaat ctcgaggctg caacaatcag tatctggtga cacacaagca aagcccagag | 840 |
| gacatgttgg agaagcaaca gatgttgctg catgagggcc ggttgtgcaa gcatgaggtg | 900 |
| cagttgcgcc tttcctatgt ctatgactgg tcagctccac cctcccagtg ctgccagcgc | 960 |
| aaggagggcg ttccctgatg tca | 983 |

<210> SEQ ID NO 165
<211> LENGTH: 983
<212> TYPE: DNA
<213> ORGANISM: Artificial sequence
<220> FEATURE:
<223> OTHER INFORMATION: Matrice eZ-mB3Galt6 cDNA shRNA insensible

<400> SEQUENCE: 165

| | |
|---|---|
| atgaaggtat tccggcgcgc ttggcggcac cgggtggcgc tgggcctagg cggcctggcg | 60 |

```
ttctgcggca ccactctgtt gtacctggcg cgctgcgctt ccgagggcga gacgccctcc    120
gcttccggag ccgctcggcc ccgcgctaag gccttcctgg cggtgctggt ggccagtgcg    180
ccccgcgcgg tcgagcgccg caccgcagtg cgcagcacgt ggctggcacc ggagaggcgt    240
ggcggacccg aggacgtgtg ggcgcgcttc gccgtgggca ctggcggctt aggctcggag    300
gagcggcgcg ctcttgagct cgagcaggcg cagcacgggg acctgctgct gctgcccgcc    360
ctgcgcgacg cctacgagaa cctcacggcc aaggtcctgg ccatgctgac ctggctggat    420
gagcgcgtgg acttcgagtt cgtgctcaag gcggacgacg actcctttgc gcgcctggac    480
gctatcctgg tggacctacg cgcacggag cccgcacgcc gccggcgcct ctactggggc    540
ttcttttccg ggcgcgggcg cgtcaagccg ggaggtcgct ggcgagaagc agcctggcaa    600
ctctgcgact actacctgcc ctacgcgttg ggcggtggct atgtcctttc tgcggacctg    660
gtgcattacc tgcgcctcag ccgcgagtac ctgcgcgcgt ggcacagtga agacgtatcg    720
ctgggcacct ggctggcacc agtggatgtg caacgggagc acgacccacg cttcgacacg    780
gagtacaaat ctcgaggctg caacaatcag tatctggtga cacacaagca aagcccagag    840
gacatgttgg agaagcaaca gatgttgctg catgagggcc ggttgtgcaa gcatgaggtg    900
caacttcgcc tttcctatgt ctatgactgg tcagctccac cctcccagtg ctgccagcgc    960
aaggagggcg ttccctgatg tca                                            983
```

<210> SEQ ID NO 166
<211> LENGTH: 2060
<212> TYPE: DNA
<213> ORGANISM: Artificial sequence
<220> FEATURE:
<223> OTHER INFORMATION: Matrice Yeast S.cerevisiae MNN10 gene

<400> SEQUENCE: 166

```
aaacatgcat tcaaaggtca taattgctgc tctatttaca gtcgtccata atgacatttc     60
tctttgatta ttttcttgtt tttcgctct tctcaagtgg atgttacata acaaacaaaa    120
cagaaaaaat tgtttaaata taaagtttaa aagttatctt tgattccgca cctgaatttt    180
tggattgaag gccaaaggag gtttatcagg gagagaaaag ctctctattt attttttataa   240 ggataattg tgcatgtaca actatacaat atgtctagtg taccttataa ttcccaactt    300
cctatatcca accatctaga gtacgatgaa gatgaaaaga gagcagagg ctcaaaacta    360 ggcctgaaat ataaaatgat atactggagg aaaactttat gcagttcgct agcgagatgg    420
agaaagctaa tactattaat atctttagct ttgttttat tcatatggat aagcgattcc    480
accataagca gaaatccatc taccacaagt tttcaaggcc aaaatagtaa cgataataag    540
ttgagtaata ctggttctag catcaactcc aaaagatatg taccaccata ttctaagaga    600
tcaagatggt cgttttggaa tcaagatcct aggattgtca ttatattagc ggcaaacgaa    660
ggtggtggtg tattgaggtg gaaaaatgag caagaatggg ctatcgaagg catatcaata    720
gaaaataaga aggcctatgc gaagagacat ggatatgcgt tgactatcaa ggatttgaca    780
acgtccaaaa gatactctca cgaatacaga gagggttggc aaaaagtaga tatattgaga    840
cagacgttca gggagtttcc taatgcagaa tggttctggt ggttggacct ggatactatg    900
ataatggagc cttctaaatc attagaagaa catattttcg acagattgga aactctggct    960
gacagagaat tgaaaagttt taatccccta aacctaagag acgacatacc ctatgtcgat   1020
tattcagagg aaatggagtt tctaataaca caagattgtg gaggcttcaa tttgggctca   1080
tttctgataa aaaatagcga atggtctaag ctgcttctag atatgtggtg ggaccccgtt   1140
```

```
ctgtatgaac aaaaacatat ggtttgggaa catagagaac aagatgcgtt agaggcatta    1200
tatgaaaacg aaccgtggat tcgttcgaga ataggatttt tgcccttaag aacgatcaat    1260
gcattcccac cgggagcatg ctctgaatac agtggtgact caagatactt ttacagtgag    1320
aaagaccatg attttgttgt gaatatggcc ggatgcaatt ttggcagaga ttgctggggc    1380
gagatgcagt actacaccac tttaatggaa aaactgaata ggaaatggta cacgagattt    1440
ttcttcccat aaaatggaag ttatcaatat tgtaaagaga agcatttaca agctttatt     1500 tttcttttta atttccacta ctggttctgc tttaaaatgt tgttttataa tttatgtaca    1560
tttaggccta tagaagattc tttcaataat atgctacaca ttcttttatt tttccatcat    1620
atgttggagt ttatgcctcc tcggcaggag ttgggcggtg cgaagagaag aaaaagagtg    1680
aaactaaaaa aaggaatctg cctttgcata agttcaaaag tgcaattta gtgttggatt     1740 taaacgggaa aaattgaaat ggccatcgaa acaatacttg taataaacaa atcaggcgga    1800
ctaatctatc agcggaattt taccaacgac gaacagaaat tgaacagcaa tgaatactta    1860
attcttgcta gtacactgca cggtgtattc gccatcgcga gccagctgac tccgaaggca    1920
ttacagctaa ctcaacaaac gaacatcgaa ataccatcc catatatacc ttacgtgggc      1980
atgtccagca ataggagcga tacaagaaat ggaggtggca ataacaacaa acacactaat    2040
aatgaaaaac tgggcagttt                                                 2060

<210> SEQ ID NO 167
<211> LENGTH: 639
<212> TYPE: DNA
<213> ORGANISM: Artificial sequence
<220> FEATURE:
<223> OTHER INFORMATION: Matrice promoteur CMV

<400> SEQUENCE: 167
accaattcag tcgactggat cctagttatt aatagtaatc aattacgggg tcattagttc      60
atagcccata tatggagttc cgcgttacat aacttacggt aaatggcccg cctggctgac    120
cgcccaacga cccccgccca ttgacgtcaa taatgacgta tgttcccata gtaacgccaa    180
tagggacttt ccattgacgt caatgggtgg agtatttacg gtaaactgcc cacttggcag    240
tacatcaagt gtatcatatg ccaagtacgc ccctattga cgtcaatgac ggtaaatggc      300
ccgcctggca ttatgcccag tacatgacct tatgggactt tcctacttgg cagtacatct    360
acgtattagt catcgctatt accatggtga tgcggttttg gcagtacatc aatgggcgtg    420
gatagcggtt tgactcacgg ggatttccaa gtctccaccc cattgacgtc aatgggagtt    480
tgttttggca ccaaaatcaa cgggactttc caaaatgtcg taacaactcc gccccattga    540
cgcaaatggg cggtaggcgt gtacggtggg aggtctatat aagcagagct ggtttagtga    600
accgtcagat cactagtcga ctagggataa cagggccgc                            639

<210> SEQ ID NO 168
<211> LENGTH: 335
<212> TYPE: DNA
<213> ORGANISM: Artificial sequence
<220> FEATURE:
<223> OTHER INFORMATION: Matrice promoteur EF1alpha, version courte

<400> SEQUENCE: 168
aggaaccaat tcagtcgact ggatcccgat ggctccggtg cccgtcagtg ggcagagcgc      60
acatcgccca cagtccccga aagttgggg ggaggggtcg gcaattgaac cggtgcctag     120
```

```
agaaggtggc gcggggtaaa ctgggaaagt gatgtcgtgt actggctccg ccttttttccc    180 gagggtgggg gagaaccgta tataagtgca gtagtcgccg tgaacgttct ttttcgcaac    240
gggtttgccg ccagaacaca ggtccgcggc cccgaactag gcctaggcgt ctgatcacta    300
gtgactctag tcctagtcga ctagggataa caggg                               335
```

<210> SEQ ID NO 169
<211> LENGTH: 1183
<212> TYPE: DNA
<213> ORGANISM: Artificial sequence
<220> FEATURE:
<223> OTHER INFORMATION: Matrice promoteur EF1alpha

<400> SEQUENCE: 169

```
gtgaggctcc ggtgcccgtc agtgggcaga gcgcacatcg cccacagtcc ccgagaagtt     60 gggggggaggg gtcggcaatt gaaccggtgc ctagagaagg tggcgcgggg taaactggga    120
aagtgatgtc gtgtactggc tccgcctttt tcccgagggt gggggagaac cgtatataag    180
tgcagtagtc gccgtgaacg ttcttttttcg caacgggttt gccgcagaa cacaggtaag    240 tgccgtgtgt ggttcccgcg ggcctggcct ctttacgggt tatggccctt gcgtgccttg    300
aattacttcc acctggctgc agtacgtgat tcttgatccc gagcttcggg ttggaagtgg    360
gtgggagagt tcgaggcctt gcgcttaagg agccccttcg cctcgtgctt gagttgaggc    420
ctggcctggg cgctggggcc gccgcgtgcg aatctggtgg caccttcgcg cctgtctcgc    480
tgctttcgat aagtctctag ccatttaaaa ttttgatga cctgctgcga cgcttttttt    540
ctggcaagat agtcttgtaa atgcgggcca agatctgcac actggtattt cggttttgg     600 ggccgcgggc ggcgacgggg cccgtgcgtc ccagcgcaca tgttcggcga ggcggggcct    660
gcgagcgcgc ccaccgagaa tcggacgggg gtagtctcaa gctggccggc ctgctctggt    720
gcctggcctc gcgccgccgt gtatcgcccc gccctgggcg gcaaggctgg cccggtcggc    780
accagttgcg tgagcggaaa gatggccgct cccggccct gctgcaggga gctcaaaatg     840
gaggacgcgg cgctcgggag agcgggcggg tgagtcaccc acacaaagga aaagggcctt    900
tccgtcctca gccgtcgctt catgtgactc acggagtac cggcgccgt ccaggcacct     960 cgattagttc tcgagctttt ggagtacgtc gtctttaggt tggggggagg ggttttatgc    1020
gatggagttt ccccacactg agtgggtgga gactgaagtt aggccagctt ggcacttgat    1080
gtaattctcc ttggaatttg ccctttttga gtttggatct tggttcattc tcaagcctca    1140
gacagtggtt caaagttttt ttcttccatt tcaggtgtcg tga                      1183
```

<210> SEQ ID NO 170
<211> LENGTH: 401
<212> TYPE: DNA
<213> ORGANISM: Artificial sequence
<220> FEATURE:
<223> OTHER INFORMATION: Matrice promoteur TRE3G

<400> SEQUENCE: 170

```
ctttcgtctt caagaattcc tggagtttac tccctatcag tgatagagaa cgtatgaaga     60
gtttactccc tatcagtgat agagaacgta tgcagacttt actccctatc agtgatagag    120
aacgtataag gagtttactc cctatcagtg atagagaacg tatgaccagt ttactcccta    180
tcagtgatag agaacgtatc tacagtttac tccctatcag tgatagagaa cgtatatcca    240
gtttactccc tatcagtgat agagaacgta taagctttag gcgtgtacgg tgggcgccta    300
taaaagcaga gctcgtttag tgaaccgtca gatcgcctgg agcaattcca caacactttt    360
```
gtcttatacc aactttccgt accacttcct accctcgtaa a             401

<210> SEQ ID NO 171
<211> LENGTH: 4271
<212> TYPE: DNA
<213> ORGANISM: Artificial sequence
<220> FEATURE:
<223> OTHER INFORMATION: Matrice eZ-Rosa26-3'

<400> SEQUENCE: 171

```
agatgggcgg gagtcttctg gcaggcttaa aaggctaacc tggtgtgtgg gcgttgtcct     60
gcagggggaat tgaacaggtg taaaattgga gggacaagac ttcccacaga ttttcggttt   120
tgtcgggaag ttttttaata ggggcaaata ggaaaatgga ggataggagt catctggggt   180
ttatgcagca aaactacagg tatattgctt gtatccgcct cggagatttc catgaggaga   240
taaagacatg tcacccgagt ttatactctc ctgcttagat cctactacag tatgaaatac   300
agtgtcgcga ggtagactat gtaagcagat ttaatcattt taaagagccc agtacttcat   360
atccatttct cccgctcctt ctgcagcctt atcaaaaggt atttagaaca ctcatttag    420
ccccatttc atttattata ctggcttatc caaccctag acagagcatt ggcatttcc     480
cttcctgat cttagaagtc tgatgactca tgaaaccaga cagattagtt acatacacca   540
caaatcgagg ctgtagctgg ggcctcaaca ctgcagttct tttataactc cttagtacac   600
ttttttgttga tcctttgcct tgatccttaa ttttcagtgt ctatcacctc tcccgtcagg   660
tggtgttcca catttgggcc tattctcagt ccagggagtt ttacaacaat agatgtattg   720
agaatccaac ctaaagctta actttccact cccatgaatg cctctctcct ttttctccat   780
tataactgag ctataaccat taatggtttc aggtggatgt ctcctcccc aatatacctg   840
atgtatctac atattgccag gctgatattt taagacataa aaggtatatt tcattattga   900
gccacatggt attgattact gctactaaaa ttttgtcatt gtacacatct gtaaaaggtg   960
gttccttttg gaatgcaaag ttcaggtgtt tgttgtcttt cctgacctaa ggtcttgtga  1020
gcttgtattt tttctattta agcagtgctt tctcttggac tggcttgact catggcattc  1080
tacacgttat tgctggtcta aatgtgattt tgccaagctt cttcaggacc tataattttg  1140
cttgacttgt agccaaacac aagtaaaatg attaagcaac aaatgtattt gtgaagcttg  1200
gttttaggt tgttgtgttg tgtgtgcttg tgctctataa taatactatc caggggctgg  1260
agaggtggct cggagttcaa gagcacagac tgctcttcca gaagtcctga gttcaattcc  1320
cagcaaccac atggtggctc acaaccatct gtaatgggat ctgatgccct cttctggtgt  1380
gtctgaagac cacaagtgta ttcacattaa ataaataatc ctccttcttc ttctttttt   1440
tttttaaag agaatactgt ctccagtaga attactgaag taatgaaata ctttgtgttt   1500
gttccaatat ggaagccaat aatcaaatac tcttaagcac tggaaatgta ccaaggaact  1560
atttatttta agtgaactgt ggacagagga gccataactg cagacttgtg ggatacagaa  1620
gaccaatgca gacttaatgt ctttttctctt acactaagca ataaagaaat aaaaattgaa  1680
cttctagtat cctatttgtt aaactgctag ctttactaac ttttgtgctt catctataca  1740
aagctgaaag ctaagtctgc agccattact aaacatgaaa gcaagtaatg ataatttgg   1800
atttcaaaaa tgtagggcca gagtttagcc agccagtggt ggtgcttgcc tttatgcctt  1860
aatcccagca ctctggaggc agagacaggc agatctctga gtttgagccc agcctggtct  1920
acacatcaag ttctatctag gatagccagg aatacacaca gaaaccctgt tggggagggg  1980
```

-continued

```
ggctctgaga tttcataaaa ttataattga agcattccct aatgagccac tatggatgtg    2040
gctaaatccg tctaccttc tgatgagatt tgggtattat tttttctgtc tctgctgttg     2100
gttgggtctt ttgacactgt gggctttctt aaagcctcct tccctgccat gtggactctt    2160
gtttgctact aacttccat ggcttaaatg catggctttt tgccttcta agggcagctg      2220 ctgagatttg cagcctgatt tccagggtgg ggttgggaaa tctttcaaac actaaaattg    2280
tcctttaatt ttttttaaa aaatgggtta tataataaac ctcataaaat agttatgagg     2340
agtgaggtgg actaatatta atgagtccct ccctataaa agagctatta aggcttttg      2400 tcttatacta actttttttt taaatgtggt atctttagaa ccaagggtct tagagttta     2460 gtatacagaa actgttgcat cgcttaatca gattttctag tttcaaatcc agagaatcca   2520
aattcttcac agccaaagtc aaattaagaa tttctgactt taatgttatt tgctactgtg   2580
aatataaaat gatagctttt cctgaggcag ggtatcacta tgtatctctg cctgatctgc   2640
aacaagatat gtagactaaa gttctgcctg cttttgtctc ctgaatacta aggttaaaat   2700
gtagtaatac ttttggaact tgcaggtcag attctttat aggggacaca ctaagggagc     2760
ttgggtgata gttggtaaat gtgtttaagt gatgaaaact tgaattatta tcaccgcaac    2820 ctactttta aaaaaaaaag ccaggcctgt tagagcatgc taagggatcc ctaggacttg     2880
ctgagcacac aagagtagta cttggcaggc tcctggtgag agcatatttc aaaaaacaag    2940
gcagacaacc aagaaactac agtaaggtta cctgtcttta accatctgca tatacacagg    3000
gatattaaaa tattccaaat aatatttcat tcaagtttc ccccatcaaa ttgggacatg      3060
gatttctccg gtgaataggc agagttggaa actaaacaaa tgttggtttt gtgatttgtg    3120
aaattgtttt caagtgatag ttaaagccca tgagatacag aacaaagctg ctatttcgag    3180
gtcacttggt tatactcaga agcacttctt tgggtttccc tgcactatcc tgatcatgtg    3240
ctaggcctac cttaggctga ttgttgttca aataacttaa gtttcctgtc aggtgatgtc    3300
atatgatttc atatatcaag gcaaaacatg ttatatatgt taaacatttg gacttaatgt    3360
gaaagttagg tctttgtggg ttttgatttt aatttcaaaa cctgagctaa ataagtcatt    3420
ttacatgtct tacatttggt gaattgtata ttgtggtttg caggcaagac tctctgacct    3480
agtaaccctc ctatagagca ctttgctggg tcacaagtct aggagtcaag catttcacct    3540
tgaagttgag acgttttgtt agtgtatact agttatatgt tggaggacat gtttatccag    3600
aagatattca ggactatttt tgactgggct aaggaattga ttctgattag cactgttagt    3660
gagcattgag tggcctttag gcttgaattg gagtcacttg tatatctcaa ataatgctgg    3720 cctttttaa aaagcccttg ttctttatca ccctgttttc tacataattt ttgttcaaag     3780
aaatacttgt ttggatctcc ttttgacaac aatagcatgt tttcaagcca tatttttttt   3840
cctttttttt tttttttttg gttttcgag acagggtttc tctgtatagc cctggctgtc     3900
ctggaactca ctttgtagac caggctggcc tcgaactcag aaatccgcct gcctctgcct    3960
cctgagtgcc gggattaaag gcgtgcacca ccacgcctgg ctaagttgga tattttgtat    4020
ataactataa ccaatactaa ctccactggg tggattttta attcagtcag tagtcttaag    4080
tggtctttat tggcccttat taaaatctac tgttcactct aacagaggct gttgactag     4140 tgggactaag caacttccta cggatatact agcagataag ggtcagggat agaaactagt    4200
ctagcgtttt gtatacctac cagcttatac taccttgttc tgatagaaat atttaggaca    4260
tctagcttat c                                                         4271
```

<210> SEQ ID NO 172
<211> LENGTH: 1084
<212> TYPE: DNA
<213> ORGANISM: Artificial sequence
<220> FEATURE:
<223> OTHER INFORMATION: Matrice eZ-Rosa26-5'

<400> SEQUENCE: 172

```
ccccgcggca ggccctccga gcgtggtgga gccgttctgt gagacagccg ggtacgagtc      60
gtgacgctgg aaggggcaag cgggtggtgg caggaatgc ggtccgccct gcagcaaccg      120
gaggggagg gagaagggag cggaaaagtc tccaccggac gcggccatgg ctcgggggg      180
ggggggcagc ggaggagcgc ttccggccga cgtctcgtcg ctgattggct tcttttcctc    240
ccgccgtgtg tgaaaacaca aatggcgtgt tttggttggc gtaaggcgcc tgtcagttaa    300
cggcagccgg agtgcgcagc cgccggcagc ctcgctctgc ccactgggtg gggcggggag    360
taggtggggt gaggcgagct ggacgtgcgg gcgcggtcgg cctctggcgg ggcggggag    420
gggagggagg gtcagcgaaa gtagctcgcg cgcgagcggc cgcccaccct ccccttcctc    480
tgggggagtc gttttacccg ccgccggccg ggcctcgtcg tctgattggc tctcggggcc    540
cagaaaactg gcccttgcca ttggctcgtg ttcgtgcaag ttgagtccat ccgccggcca    600
gcggggcgg cgaggaggcg ctcccaggtt ccggccctcc cctcggcccc gcgccgcaga    660
gtctggccgc gcgcccctgc gcaacgtggc aggaagcgcg cgctgggggc ggggacgggc    720
agtagggctg agcggctgcg gggcgggtgc aagcacgttt ccgacttgag ttgcctcaag    780
aggggcgtgc tgagccagac ctccatcgcg cactccgggg agtggaggga aggagcgagg    840
gctcagttgg gctgttttgg aggcaggaag cacttgctct cccaaagtcg ctctgagttg    900
ttatcagtaa gggagctgca gtggagtagg cggggagaag gccgcaccct tctccggagg    960
ggggagggga gtgttgcaat acctttctgg gagttctctg ctgcctcctg gcttctgagg    1020
accgccctgg gctgggaga atcccttgcc ccctcttccc ctcgtgatct gcaactccag    1080
tctt                                                                 1084
```

<210> SEQ ID NO 173
<211> LENGTH: 406
<212> TYPE: DNA
<213> ORGANISM: Artificial sequence
<220> FEATURE:
<223> OTHER INFORMATION: mB3Galt6 shRNA TR506016D

<400> SEQUENCE: 173

```
acagggtcga caagcttttc caaaaaaaaa gcatgaggtg cagttgcgcc tttcctatct      60
cttgaatagg aaaggcgcaa ctgcacctca tgctggatcc cgcgtccttt ccacaagata    120
tataaaccca agaaatcgaa atactttcaa gttacggtaa gcatatgata gtccatttta    180
aaacataatt ttaaaactgc aaactaccca agaaattatt actttctacg tcacgtattt    240
tgtactaata tctttgtgtt tacagtcaaa ttaattctaa ttatctctct aacagccttg    300
tatcgtatat gcaaatatga aggaatcatg ggaaataggc cctcttcctg cccgaccttg    360
gcgcgcgctc ggcgcgcggt cacgctccgt cacgtggtgc gttttg                   406
```

<210> SEQ ID NO 174
<211> LENGTH: 342
<212> TYPE: DNA
<213> ORGANISM: Artificial sequence
<220> FEATURE:
<223> OTHER INFORMATION: Matrice eZ-SiaT-TGS-Hook

<400> SEQUENCE: 174

```
atgattcaca ccaacctgaa gaaaaagttc agctgctgcg tcctggtctt tcttctgttt      60
gcagtcatct gtgtgtggaa ggaaaagaag aaagggagtt actatgattc ctttaaattg     120
caaaccaagg aattccaggt gttaaagagt ctggggaaat tggccatggg gtctgattcc     180
cagtctgtat cctcaagcag cacccaggac ccccacaggg gccgccagac cctcggcagt     240
ctcagaggcc tagccaaggc caaaccagag gcctccttcc aggtgtggaa caaggacagc     300
tcttccaaaa accttatccc taggctgcaa aaggggtcgg gg                        342
```

<210> SEQ ID NO 175
<211> LENGTH: 714
<212> TYPE: DNA
<213> ORGANISM: Artificial sequence
<220> FEATURE:
<223> OTHER INFORMATION: Matrice TagBFP

<400> SEQUENCE: 175

```
atgtcgggga gcgagctgat taaggagaac atgcacatga agctgtacat ggagggcacc      60
gtggacaacc atcacttcaa gtgcacatcc gagggcgaag gcaagcccta cgagggcacc     120
cagaccatga gaatcaaggt ggtcgagggc ggccctctcc ccttcgcctt cgacatcctg     180
gctactagct tcctctacgg cagcaagacc ttcatcaacc acacccaggg catccccgac     240
ttcttcaagc agtccttccc tgagggcttc acatgggaga gagtcaccac atacgaggac     300
gggggcgtgc tgaccgctac ccaggacacc agcctccagg acggctgcct catctacaac     360
gtcaagatca gaggggtgaa cttcacatcc aacggccctg tgatgcagaa gaaaacactc     420
ggctgggagg ccttcaccga aacgctgtac cccgctgacg gcggcctgga aggcagaaac     480
gacatggccc tgaagctcgt gggcgggagc catctgatcg caaacatcaa gaccacatat     540
agatccaaga aacccgctaa gaacctcaag atgcctggcg tctactatgt ggactacaga     600
ctggaaagaa tcaaggaggc caacaacgaa acctacgtcg agcagcacga ggtggcagtg     660
gccagatact gcgacctccc tagcaaactg ggcacaagc ttaattccgg atga            714
```

<210> SEQ ID NO 176
<211> LENGTH: 1131
<212> TYPE: DNA
<213> ORGANISM: Artificial sequence
<220> FEATURE:
<223> OTHER INFORMATION: Matrice Thymidine Kinase cDNA

<400> SEQUENCE: 176

```
atggcttcgt accccctgcca tcaacacgcg tctgcgttcg accaggctgc gcgttctcgc      60
ggccatagca accgacgtac ggcgttgcgc cctcgccggc agcaagaagc cacgaagtc     120
cgcctggagc agaaaatgcc cacgctactg cgggtttata tagacggtcc tcacgggatg     180
gggaaaacca ccaccacgca actgctggtg gccctgggtt cgcgcgacga tatcgtctac     240
gtacccgagc cgatgactta ctggcaggtg ctggggcttt ccgagacaat cgcgaacatc     300
tacaccacac aacaccgcct cgaccagggt gagatatcgg ccggggacgc ggcggtggta     360
atgacaagcg cccagataac aatgggcatg ccttatgccg tgaccgacgc cgttctggct     420
cctcatatcg gggggaggc tgggagctca catgccccgc cccggccct caccctcatc     480
ttcgaccgcc atcccatcgc cgcccttcctg tgctacccgg ccgcgcgata ccttatgggc     540
agcatgaccc ccaggccgt gctggcgttc gtggccctca tcccgccgac cttgccggc     600
acaaacatcg tgttggggc ccttccggag gacagacaca tcgaccgcct ggccaaacgc     660
```

```
cagcgccccg gcgagcggct tgacctggct atgctggccg cgattcgccg cgtttacggg      720
ctgcttgcca atacggtgcg gtatctgcag ggcggcgggt cgtggcggga ggattgggga      780
cagctttcgg ggacggccgt gccgccccag ggtgccgagc cccagagcaa cgcgggccca      840
cgaccccata tcggggacac gttatttacc ctgtttcggg cccccgagtt gctggccccc      900
aacggcgacc tgtacaacgt gtttgcctgg gccttggacg tcttggccaa acgcctccgt      960
cccatgcacg tctttatcct ggattacgac caatcgcccg ccggctgccg ggacgccctg     1020
ctgcaactta cctccgggat ggtccagacc cacgtcacca cccccggctc cataccgacg     1080
atctgcgacc tggcgcgcac gtttgcccgg gagatggggg aggctaactg a              1131

<210> SEQ ID NO 177
<211> LENGTH: 272
<212> TYPE: DNA
<213> ORGANISM: Artificial sequence
<220> FEATURE:
<223> OTHER INFORMATION: Matrice TK term

<400> SEQUENCE: 177
gggggaggct aactgaaaca cggaaggaga caataccgga aggaacccgc gctatgacgg       60
caataaaaag acagaataaa acgcacggtg ttgggtcgtt tgttcataaa cgcggggttc      120
ggtcccaggg ctggcactct gtcgataccc caccgaggcc ccattggggc caatacgccc      180
gcgtttcttc cttttcccca ccccacccc caagttcggg tgaaggccca gggctcgcag      240
ccaacgtcgg ggcggcaggc cctgccatag cc                                   272

<210> SEQ ID NO 178
<211> LENGTH: 747
<212> TYPE: DNA
<213> ORGANISM: Artificial sequence
<220> FEATURE:
<223> OTHER INFORMATION: Matrice TetON-3G cDNA

<400> SEQUENCE: 178
atgtctagac tggacaagag caaagtcata aactctgctc tggaattact caatggagtc       60
ggtatcgaag gcctgacgac aaggaaactc gctcaaaagc tgggagttga gcagcctacc      120
ctgtactggc acgtgaagaa caagcgggcc ctgctcgatg ccctgccaat cgagatgctg      180
gacaggcatc atacccactc ctgcccctg gaaggcgagt catggcaaga ctttctgcgg      240
aacaacgcca agtcataccg ctgtgctctc ctctcacatc gcgacggggc taaagtgcat      300
ctcggcaccc gcccaacaga gaaacagtac gaaaccctgg aaaatcagct cgcgttcctg      360
tgtcagcaag gcttctccct ggagaacgca ctgtacgctc tgtccgccgt gggccacttt      420
acactgggct gcgtattgga ggaacaggag catcaagtag caaaagagga aagagagaca      480
cctaccaccg attctatgcc cccacttctg aaacaagcaa ttgagctgtt cgaccggcag      540
ggagccgaac ctgccttcct tttcggcctg gaactaatca tatgtggcct ggagaaacag      600
ctaaagtgcg aaagcggcgg gccgaccgac gcccttgacg atttttgactt agacatgctc      660 ccagccgatg cccttgacga ctttgacctt gatatgctgc ctgctgacgc tcttgacgat      720
tttgaccttg acatgctccc cgggtaa                                         747
```